(12) United States Patent
Degn et al.

(10) Patent No.: US 9,469,848 B2
(45) Date of Patent: *Oct. 18, 2016

(54) VARIANTS OF GLUCOAMYLASE

(75) Inventors: Peter Edvard Degn, Egå (DK);
Richard R. Bott, Burlingame, CA
(US); Casper Willem Vroemen, Palo
Alto, CA (US); **Martijn Silvan
Scheffers, Leiden (NL); Wolfgang
Aehle, Zwingenberg (DE); Elin
Petersen**, Skanderborg (DK)

(73) Assignee: DUPONT NUTRITION BIOSCIENCES APS (DK)

( * ) Notice: Subject to any disclaimer, the term of this patent is extended or adjusted under 35 U.S.C. 154(b) by 310 days.

This patent is subject to a terminal disclaimer.

(21) Appl. No.: 13/806,398

(22) PCT Filed: Jun. 30, 2011

(86) PCT No.: PCT/EP2011/061082
§ 371 (c)(1),
(2), (4) Date: Dec. 21, 2012

(87) PCT Pub. No.: WO2012/001139
PCT Pub. Date: Jan. 5, 2012

(65) Prior Publication Data
US 2013/0102035 A1 Apr. 25, 2013
US 2013/0309726 A9 Nov. 21, 2013

Related U.S. Application Data

(60) Provisional application No. 61/360,891, filed on Jul. 1, 2010, provisional application No. 61/444,481, filed on Feb. 18, 2011.

(30) Foreign Application Priority Data

Jul. 15, 2010 (DK) .......................... PA 201070337
Aug. 18, 2010 (WO) ...................... PCT/EP10/62035

(51) Int. Cl.
| | | |
|---|---|---|
| *C12P 19/20* | (2006.01) | |
| *C12N 9/34* | (2006.01) | |
| *C07H 21/04* | (2006.01) | |
| *C07K 1/00* | (2006.01) | |
| *C12N 9/26* | (2006.01) | |
| *A23L 1/09* | (2006.01) | |
| *C12C 5/00* | (2006.01) | |
| *C12C 7/04* | (2006.01) | |
| *C12P 19/02* | (2006.01) | |
| *C13K 1/06* | (2006.01) | |

(52) U.S. Cl.
CPC ............... *C12N 9/26* (2013.01); *A23L 1/095* (2013.01); *C12C 5/004* (2013.01); *C12C 7/04* (2013.01); *C12N 9/2408* (2013.01); *C12N 9/2428* (2013.01); *C12P 19/02* (2013.01); *C12P 19/20* (2013.01); *C12Y 302/01003* (2013.01); *C13K 1/06* (2013.01); *Y02P 20/52* (2015.11)

(58) Field of Classification Search
CPC ......... A23L 1/095; C12C 5/004; C12C 7/04; C12N 9/2428; C12N 9/2408; C12N 9/26; C12P 19/02; C12P 19/20; Y02P 20/52; C13K 1/06; C12Y 302/01003
USPC .................... 435/96, 205; 536/23.2; 530/350
See application file for complete search history.

(56) References Cited

U.S. PATENT DOCUMENTS

| | | | |
|---|---|---|---|
| 7,037,704 B2 * | 5/2006 | Dunn-Coleman et al. | ... 435/202 |
| 8,058,033 B2 | 11/2011 | Aehle et al. | |
| 8,809,023 B2 * | 8/2014 | Degn et al. ................ | 435/91.53 |
| 2006/0154342 A1 | 7/2006 | Clarkson et al. | |
| 2007/0031928 A1 | 2/2007 | Nielsen et al. | |

FOREIGN PATENT DOCUMENTS

| | | |
|---|---|---|
| EP | 1 914 306 A2 | 4/2008 |
| WO | WO 2008/045489 A2 | 4/2008 |
| WO | WO 2009/048487 A1 | 4/2009 |
| WO | WO 2009/048488 A1 | 4/2009 |
| WO | WO 2009/067218 A2 | 5/2009 |
| WO | WO 2011/022465 A1 | 2/2011 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Shiraishi, F., et al., "Kinetics of Condensation of Glucose into Maltose and Isomaltose in Hydrolysis of Starch by Glucoamylase," *Biotechnology and Bioengineering*, 1985, vol. XXVII, pp. 498-502.

* cited by examiner

*Primary Examiner* — Ganapathirama Raghu

(57) ABSTRACT

The present invention relates to combinatorial variants of a parent glucoamylase that have altered properties for reducing the synthesis of condensation products during hydrolysis of starch. Accordingly, the variants of a parent glucoamylase are suitable such as for use within brewing and glucose syrup production. Also disclosed are DNA constructs encoding the variants and methods of producing the glucoamylase variants in host cells.

14 Claims, 22 Drawing Sheets

TrGA parent protein (632 amino acids) (SEQ ID NO: 1)

```
  1 MHVLSTAVLL GSVAVQKVLG RPGSSGLSDV TKRSVDDFIS TETPIALNNL
 51 LCNVGPDGCR AFGTSAGAVI ASPSTIDPDY YYMWTRDSAL VFKNLIDRFT
101 ETYDAGLQRR IEQYITAQVT LQGLSNPSGS LADGSGLGEP KFELTLKPFT
151 GNWGRPQRDG PALRAIALIG YSKWLINNNY QSTVSNVIWP IVRNDLNYVA
201 QYWNQTGFDL WEEVNGSSFF TVANQHRALV EGATLAATLG QSGSAYSSVA
251 PQVLCFLQRF WVSSGGYVDS NINTNEGRTG KDVNSVLTSI HTFDPNLGCD
301 AGTFQPCSDK ALSNLKVVVD SFRSIYGVNK GIPAGAAVAI GRYAEDVYYN
351 GNPWYLATFA AAEQLYDAIY VWKKTGSITV TATSLAFFQE LVPGVTAGTY
401 SSSSSTFTNI INAVSTYADG FLSEAAKYVP ADGSLAEQFD RNSGTPLSAL
451 HLTWSYASFL TATARRAGIV PPSWANSSAS TIPSTCSGAS VVGSYSRPTA
501 TSFPPSQTPK PGVPSGTPYT PLPCATPTSV AVTFHELVST QFGQTVKVAG
551 NAAALGNWST SAAVALDAVN YADNHPLWIG TVNLEAGDVV EYKYINVGQD
601 GSVTWESDPN HTYTVPAVAC VTQVVKEDTW QS
```

*FIG. 1A*

DNA coding sequence of TrGA (1899 bp) (SEQ ID NO: 4)

```
   1 ATGCACGTCC TGTCGACTGC GGTGCTGCTC GGCTCCGTTG CCGTTCAAAA
  51 GGTCCTGGGA AGACCAGGAT CAAGCGGTCT GTCCGACGTC ACCAAGAGGT
 101 CTGTTGACGA CTTCATCAGC ACCGAGACGC CTATTGCACT GAACAATCTT
 151 CTTTGCAATG TTGGTCCTGA TGGATGCCGT GCATTCGGCA CATCAGCTGG
 201 TGCGGTGATT GCATCTCCA GCACAATTGA CCCGGACTAC TATTACATGT
 251 GGACGCGAGA TAGCGCTCTT GTCTTCAAGA ACCTCATCGA CCGCTTCACC
 301 GAAACGTACG ATGCGGGCCT GCAGCGCCGC ATCGAGCAGT ACATTACTGC
 351 CCAGGTCACT CTCCAGGGCC TCTCTAACCC CTCGGGCTCC CTCGCGGACG
 401 GCTCTGGTCT CGGCGAGCCC AAGTTTGAGT TGACCCTGAA GCCTTTCACC
 451 GGCAACTGGG GTCGACCGCA GCGGGATGGC CCAGCTCTGC GAGCCATTGC
 501 CTTGATTGGA TACTCAAAGT GGCTCATCAA CAACAACTAT CAGTCGACTG
 551 TGTCCAACGT CATCTGGCCT ATTGTGCGCA ACGACCTCAA CTATGTTGCC
 601 CAGTACTGGA ACCAAACCGG CTTTGACCTC TGGGAAGAAG TCAATGGGAG
 651 CTCATTCTTT ACTGTTGCCA ACCAGCACCG AGCACTTGTC GAGGGCGCCA
 701 CTCTTGCTGC CACTCTTGGC CAGTCGGGAA GCGCTTATTC ATCTGTTGCT
 751 CCCCAGGTTT TGTGCTTTCT CCAACGATTC TGGGTGTCGT CTGGTGGATA
 801 CGTCGACTCC AACATCAACA CCAACGAGGG CAGGACTGGC AAGGATGTCA
 851 ACTCCGTCCT GACTTCCATC CACACCTTCG ATCCCAACCT TGGCTGTGAC
 901 GCAGGCACCT TCCAGCCATG CAGTGACAAA GCGCTCTCCA ACCTCAAGGT
 951 TGTTGTCGAC TCCTTCCGCT CCATCTACGG CGTGAACAAG GGCATTCCTG
1001 CCGGTGCTGC CGTCGCCATT GGCCGGTATG CAGAGGATGT GTACTACAAC
1051 GGCAACCCTT GGTATCTTGC TACATTTGCT GCTGCCGAGC AGCTGTACGA
1101 TGCCATCTAC GTCTGGAAGA AGACGGGCTC CATCACGGTG ACCGCCACCT
1151 CCCTGGCCTT CTTCCAGGAG CTTGTTCCTG GCGTGACGGC CGGGACCTAC
1201 TCCAGCAGCT CTTCGACCTT TACCAACATC ATCAACGCCG TCTCGACATA
1251 CGCCGATGGC TTCCTCAGCG AGGCTGCCAA GTACGTCCCC GCCGACGGTT
1301 CGCTGGCCGA GCAGTTTGAC CGCAACAGCG GCACTCCGCT GTCTGCGCTT
1351 CACCTGACGT GGTCGTACGC CTCGTTCTTG ACAGCCACGG CCCGTCGGGC
1401 TGGCATCGTG CCCCCCTCGT GGGCCAACAG CAGCGCTAGC ACGATCCCCT
1451 CGACGTGCTC CGGCGCGTCC GTGGTCGGAT CCTACTCGCG TCCCACCGCC
1501 ACGTCATTCC CTCCGTCGCA GACGCCCAAG CCTGGCGTGC CTTCCGGTAC
1551 TCCCTACACG CCCCTGCCCT GCGCGACCCC AACCTCCGTG GCCGTCACCT
1601 TCCACGAGCT CGTGTCGACA CAGTTTGGCC AGACGGTCAA GGTGGCGGGC
1651 AACGCCGCGG CCCTGGGCAA CTGGAGCACG AGCGCCGCCG TGGCTCTGGA
1701 CGCCGTCAAC TATGCCGATA ACCACCCCCT GTGGATTGGG ACGGTCAACC
1751 TCGAGGCTGG AGACGTCGTG GAGTACAAGT ACATCAATGT GGGCCAAGAT
1801 GGCTCCGTGA CCTGGGAGAG TGATCCCAAC CACACTTACA CGGTTCCTGC
1851 GGTGGCTTGT GTGACGCAGG TTGTCAAGGA GGACACCTGG CAGTCGTAA
```

*FIG. 1B*

```
AaGA    (1)   -ATLDSWLSNEATVARTAILNNIGADGAWVSGADSGIVVASPSTDNPDYF
AnGA    (1)   -ATLDSWLSNEATVARTAILNNIGADGAWVSGADSGIVVASPSTDNPDYF
AoGA    (1)   QSDLNAFIEAQTPIAKQGYLNNIGADGKLVEGAAAGIVYASPSKSNPDYF
HgGA    (1)   -AAVDTFINTEKPIAWNKLLANIGPNGKAAPGAAAGVVIASPSRTDPPYF
HvGA    (1)   --SVDDFINTQTPIALNNLLCNVGPDGCRAFGTSAGAVIASPSTTDPDYY
TrGA    (1)   --SVDDFISTETPIALNNLLCNVGPDGCRAFGTSAGAVIASPSTIDPDYY
                  *   *    *      *  * **** * *

AaGA    (50)  YTWTRDSGLVIKTLVDLFRNGDTD-LLSTIENYISSQAIVQGISNPSGDL
AnGA    (50)  YTWTRDSGLVLKTLVDLFRNGDTS-LLSTIENYISAQAIVQGISNPSGDL
AoGA    (51)  YTWTRDAGLTMEEYIEQFIGGDAT-LESTIQNYVDSQANEQAVSNPSGGL
HgGA    (50)  FTWTPDAALVLTGIIESLGHNYNT---------------TLQQVSNPSGTF
HvGA    (49)  YMWTRDSALVFKNIVDRFTQQYDAGLQRRIEQYISAQVTLQGISNPSGSL
TrGA    (49)  YMWTRDSALVFKNLIDRFTETYDAGLQRRIEQYITAQVTLQGLSNPSGSL
              ** *  *                              *  *****

AaGA    (99)  SSGG-LGEPKFNVDETAYTGSWGRPQRDGPALRATAMIGFRQWLLDNGYT
AnGA    (99)  SSGAGLGEPKFNVDETAYTGSWGRPQRDGPALRATAMIGFGQWLLDNGYT
AoGA    (100) SDGSGLAEPKFYYNISQFTDSWGRPQRDGPALRASALIAYGNSLISSDKQ
HgGA    (86)  ADGSGLGEAKFNVDLTAFTGEWGRPQRDGPPLRAIALIQYAKWLIANGYK
HvGA    (99)  SDGSGLGEPKFELTLSQFTGNWGRPQRDGPALRAIALIGYSKWLINNNYQ
TrGA    (99)  ADGSGLGEPKFELTLKPFTGNWGRPQRDGPALRAIALIGYSKWLINNNYQ
                 *  *  **            * ******** ***  *        *

AaGA    (148) SAATEIVWPLVRNDLSYVAQYWNQTGYDLWEEVNGSSFFTIAVQHRALVE
AnGA    (149) STATDIVWPLVRNDLSYVAQYWNQTGYDLWEEVNGSSFFTIAVQHRALVE
AoGA    (150) SVVKANIWPIYQNDLSYVGQYWNQTGFDLWEEVQGSSFFTVAVQHKALVE
HgGA    (136) STAKSVVWPVVKNDLAYTAQYWNETGFDLWEEVPGSSFFTIASSHRALTE
HvGA    (149) STVSNIIWPIVRNDLNYVAQYWNQTGFDLWEEVNGSSFFTVANQHRALVE
TrGA    (149) STVSNVIWPIVRNDLNYVAQYWNQTGFDLWEEVNGSSFFTVANQHRALVE
              *    **  *** *    * ***** ** ******  ****   *   **   *

AaGA    (198) GSAFATAVGSSCSWCDSQAPQILCYLQSFWTG--EYILANFDSS--RSGK
AnGA    (199) GSAFATAVGSSCSWCDSQAPEILCYLQSFWTG--SFILANFDSS--RSGK
AoGA    (200) GDAFAKALGEECQACS-VAPQILCHLQDFWNG--SAVLSNLPTNG-RSGL
HgGA    (186) GAYLAAQLDTECPPCTTVAPQVLCFQQAFWNSKGNYVVSTSTAGEYRSGK
HvGA    (199) GATLAATLGQSGSTYSSVAPQILCFLQRFWVS-GGYIDSNINTNEGRTGK
TrGA    (199) GATLAATLGQSGSAYSSVAPQVLCFLQRFWVSSGGYVDSNINTNEGRTGK
                *  *           **  ** **   * *                 * *

AaGA    (244) DTNTLLGSIHTFDPEAGCDDSTFQPCSPRALANHKEVVDSFRSIYTLNDG
AnGA    (245) DANTLLGSIHTFDPEAACDDSTFQPCSPRALANHKEVVDSFRSIYTLNDG
AoGA    (246) DTNSLLGSIHTFDPAAACDDTTFQPCSSRALSNHKLVVDSFRSVYGINNG
HgGA    (236) DANSILASIHNFDPEAGCDNLTFQPCSERALANHKAYVDSFRNLYAINKG
HvGA    (248) DANSLLASIHTFDPSLGCDASTFQPCSDKALSNLKVVVDSFRSIYGVNKG
TrGA    (249) DVNSVLTSIHTFDPNLGCDAGTFQPCSDKALSNLKVVVDSFRSIYGVNKG
              * *  * ***  ***  ** * *  *****     *   *   *****   *   *
```

*FIG. 5A*

```
AaGA  (294)  LSDSEAVAVGRYPKDSYYNGNPWFLCTLAAAEQLYDALYQWDKQGSLEIT
AnGA  (295)  LSDSEAVAVGRYPEDTYYNGNPWFLCTLAAAEQLYDALYQWDKQGSLEVT
AoGA  (296)  RGAGKAAAVGPYAEDTYQGGNPWYLTTLVAAELLYDALYQWDKQGQVNVT
HgGA  (286)  IAQGKAVAVGRYSEDVYYNGNPWYLANFAAAEQLYDAIYVWNKQGSITVT
HvGA  (298)  IPAGSAVAIGRYPEDVYFNGNPWYLATFAAAEQLYDSVYVWKKTGSITVT
TrGA  (299)  IPAGAAVAIGRYAEDVYYNGNPWYLATFAAAEQLYDAIYVWKKTGSITVT
             *  *  * *    *  ****  *    *** ***  *  *  *      *

AaGA  (344)  DVSLDFFQALYSDAATGTYSSSSSTYSSIVDAVKTFADGFVSIVETHAAS
AnGA  (345)  DVSLDFFKALYSDAATGTYSSSSSTYSSIVDAVKTFADGFVSIVETHAAS
AoGA  (346)  ETSLPFFKDLSSNVTTGSYAKSSSAYESLTSAVKTYADGFISVVQEYTPD
HgGA  (336)  SVSLPFFRDLVSSVSTGTYSKSSSTFTNIVNAVKAYADGFIEVAAKYTPS
HvGA  (348)  STSSAFFQELVPGVAAGTYSSSQSTFTSIINAISTYADGFLSEAAKYVPA
TrGA  (349)  ATSLAFFQELVPGVTAGTYSSSSSTFTNIINAVSTYADGFLSEAAKYVPA
              *  **   *       *    *  *  *    *     ****

AaGA  (394)  NGSLSEQYDKSDGDELSARDLTWSYAALLTANNRRNSVMPPSWGETSAS-
AnGA  (395)  NGSMSEQYDKSDGEQLSARDLTWSYAALLTANNRRNSVVPASWGETSAS-
AoGA  (396)  GGALAEQYSRDQGTPVSASDLTWSYAAFLSAVGRRNGTVPASWGSSTAN-
HgGA  (386)  NGALAEQYDRNTGKPDSAADLTWSYSAFLSAIDRRAGLVPPSWRASVAKS
HvGA  (398)  DGSLAEQFDRNTGTPLSAVHLTWSYASFLTAAARRAGVVPPSWASSGAN-
TrGA  (399)  DGSLAEQFDRNSGTPLSALHLTWSYASFLTATARRAGIVPPSWANSSAS-
              *   **    *    **   *****  *  *      *  **      *

AaGA  (443)  SVPGTC
AnGA  (444)  SVPGTC
AoGA  (445)  AVPSQC
HgGA  (436)  QLPSTC
HvGA  (447)  TVPSSC
TrGA  (448)  TIPSTC
                *  *
```

*FIG. 5B*

```
gsidsflatetpialqgvlnnigpngadvagasagivvaspsrsdpdyfyswtrdaaltakylvdafiiagnkdle
qtiqeyisaqaqvqtisnpsgdistgglgepkfnvnetaftgpwgrpqrdgpairataliavanylidngqasta
deiiwpivqndlsyvtqywnsstfdlweevegssfftavqhralvegnaiatrinhtcpncvsqapqvlcflqs
ywtgsyvlanfggsgrsgkdvnsilgsihtf

| Trichoderma reesei position | 491 | 492 | 493 | 494 | 495 | 496 | 497 | 498 | 499 | 500 | 501 | 502 | 503 |
|---|---|---|---|---|---|---|---|---|---|---|---|---|---|
| Amino Acid | C | A | T | P | T | S | V | A | V | T | F | H | E |
| Humicola grisea position | 493 | 494 | 495 | 496 | 497 | 498 | 499 | 500 | 501 | 502 | 503 | 504 | 505 |
| Amino Acid | C | A | D | A | S | E | V | Y | V | T | F | N | E |
| Thielavia terrestris position | 489 | 490 | 491 | 492 | 493 | 494 | 495 | 496 | 497 | 498 | 499 | 500 | 501 |
| Amino Acid | C | S | T | P | T | A | V | A | V | T | F | N | E |
| Thermomyces lanuginosus position | 475 | 476 | 477 | 478 | 479 | 480 | 481 | 482 | 483 | 484 | 485 | 486 | 487 |
| Amino Acid | C | T | P | P | S | E | V | T | L | T | F | N | A |
| Talaromyces emersonii position | 482 | 483 | 484 | 485 | 486 | 487 | 488 | 489 | 490 | 491 | 492 | 493 | 494 |
| Amino Acid | C | T | T | P | T | S | V | A | V | T | F | D | E |
| Aspergillus niger position | 509 | 510 | 511 | 512 | 513 | 514 | 515 | 516 | 517 | 518 | 519 | 520 | 521 |
| Amino Acid | C | T | T | P | T | A | V | A | V | T | F | D | L |
| Aspergillus awamori position | 508 | 509 | 510 | 511 | 512 | 513 | 514 | 515 | 516 | 517 | 518 | 519 | 520 |
| Amino Acid | * | T | T | P | T | A | V | A | V | T | F | D | L |

FIG. 5D

| 504 | 505 | 506 | 507 | 508 | 509 | 510 | 511 | 512 | 513 | 514 | 515 | 516 | 517 | 518 | 519 | 520 |
|---|---|---|---|---|---|---|---|---|---|---|---|---|---|---|---|---|
| L | V | S | T | Q | F | G | Q | T | V | K | V | A | G | N | A | A |

| 506 | 507 | 508 | 509 | 510 | 511 | 512 | 513 | 514 | 515 | 516 | 517 | 518 | 519 | 520 | 521 | 522 |
|---|---|---|---|---|---|---|---|---|---|---|---|---|---|---|---|---|
| R | V | S | T | A | W | G | E | T | I | K | V | V | G | N | V | P |

| 502 | 503 | 504 | 505 | 506 | 507 | 508 | 509 | 510 | 511 | 512 | 513 | 514 | 515 | 516 | 517 | 518 |
|---|---|---|---|---|---|---|---|---|---|---|---|---|---|---|---|---|
| R | V | T | Q | W | G | Q | T | I | K | V | V | G | D | A | A |

| 488 | 489 | 490 | 491 | 492 | 493 | 494 | 495 | 496 | 497 | 498 | 499 | 500 | 501 | 502 | 503 | 504 |
|---|---|---|---|---|---|---|---|---|---|---|---|---|---|---|---|---|
| L | V | D | T | A | F | G | Q | N | I | Y | L | V | G | S | I | P |

| 495 | 496 | 497 | 498 | 499 | 500 | 501 | 502 | 503 | 504 | 505 | 506 | 507 | 508 | 509 | 510 | 511 |
|---|---|---|---|---|---|---|---|---|---|---|---|---|---|---|---|---|
| I | V | S | T | S | Y | G | E | T | I | Y | L | A | G | S | I | P |

| 522 | 523 | 524 | 525 | 526 | 527 | 528 | 529 | 530 | 531 | 532 | 533 | 534 | 535 | 536 | 537 | 538 |
|---|---|---|---|---|---|---|---|---|---|---|---|---|---|---|---|---|
| T | A | T | T | Y | G | E | N | I | Y | L | V | G | S | I | S |

| 521 | 522 | 523 | 524 | 525 | 526 | 527 | 528 | 529 | 530 | 531 | 532 | 533 | 534 | 535 | 536 | 537 |
|---|---|---|---|---|---|---|---|---|---|---|---|---|---|---|---|---|
| T | A | T | T | Y | G | E | N | I | Y | L | V | G | S | I | S |

*FIG. 5D Continued*

| Trichoderma reesei position | 521 | 522 | 523 | 524 | 525 | 526 | 527 | 528 | 529 | 530 | 531 | 532 | 533 |
|---|---|---|---|---|---|---|---|---|---|---|---|---|---|
| Amino Acid | A | L | G | N | W | S | T | S | A | A | V | A | L |
| Humicola grisea position | 523 | 524 | 525 | 526 | 527 | 528 | 529 | 530 | 531 | 532 | 533 | 534 | 535 |
| Amino Acid | A | L | G | N | W | D | T | S | K | A | V | T | L |
| Thielavia terrestris position | 519 | 520 | 521 | 522 | 523 | 524 | 525 | 526 | 527 | 528 | 529 | 530 | 531 |
| Amino Acid | A | L | G | G | W | D | T | S | K | A | V | P | L |
| Thermomyces lanuginosus position | 505 | 506 | 507 | 508 | 509 | 510 | 511 | 512 | 513 | 514 | 515 | 516 | 517 |
| Amino Acid | E | L | G | S | W | D | P | A | N | A | L | L | M |
| Talaromyces emersonii position | 512 | 513 | 514 | 515 | 516 | 517 | 518 | 519 | 520 | 521 | 522 | 523 | 524 |
| Amino Acid | E | L | G | N | W | S | T | A | S | A | I | P | L |
| Aspergillus niger position | 539 | 540 | 541 | 542 | 543 | 544 | 545 | 546 | 547 | 548 | 549 | 550 | 551 |
| Amino Acid | Q | L | G | D | W | E | T | S | D | G | I | A | L |
| Aspergillus awamori position | 538 | 539 | 540 | 541 | 542 | 543 | 544 | 545 | 546 | 547 | 548 | 549 | 550 |
| Amino Acid | Q | L | G | D | W | D | T | S | D | G | I | A | L |

*FIG. 5D Continued*

| 534 | 535 | 536 | 537 | 538 | 539 | 540 | 541 | 542 | 543 | 544 | 545 | 546 | 547 | 548 | 549 | 550 |
|---|---|---|---|---|---|---|---|---|---|---|---|---|---|---|---|---|
| D | A | V | N | Y | A | D | N | H | P | L | M | I | G | T | V | N |

| 536 | 537 | 538 | 539 | 540 | 541 | 542 | 543 | 544 | 545 | 546 | 547 | 548 | 549 | 550 | 551 | 552 |
|---|---|---|---|---|---|---|---|---|---|---|---|---|---|---|---|---|
| S | A | S | G | Y | K | S | N | D | P | L | w | S | I | T | V | P |

| 532 | 533 | 534 | 535 | 536 | 537 | 538 | 539 | 540 | 541 | 542 | 543 | 544 | 545 | 546 | 547 | 548 |
|---|---|---|---|---|---|---|---|---|---|---|---|---|---|---|---|---|
| S | A | A | G | Y | T | A | S | D | P | L | W | S | G | T | V | D |

| 518 | 519 | 520 | 521 | 522 | 523 | 524 | 525 | 526 | 527 | 528 | 529 | 530 | 531 | 532 | 533 | 534 |
|---|---|---|---|---|---|---|---|---|---|---|---|---|---|---|---|---|
| S | A | K | S | W | T | S | G | N | P | V | W | T | L | S | I | S |

| 525 | 526 | 527 | 528 | 529 | 530 | 531 | 532 | 533 | 534 | 535 | 536 | 537 | 538 | 539 | 540 | 541 |
|---|---|---|---|---|---|---|---|---|---|---|---|---|---|---|---|---|
| R | A | D | A | Y | T | N | S | N | P | L | W | Y | V | T | V | N |

| 552 | 553 | 554 | 555 | 556 | 557 | 558 | 559 | 560 | 561 | 562 | 563 | 564 | 565 | 566 | 567 | 568 |
|---|---|---|---|---|---|---|---|---|---|---|---|---|---|---|---|---|
| S | A | D | K | Y | T | S | S | D | P | L | W | Y | V | T | V | T |

| 551 | 552 | 553 | 554 | 555 | 556 | 557 | 558 | 559 | 560 | 561 | 562 | 563 | 564 | 565 | 566 | 567 |
|---|---|---|---|---|---|---|---|---|---|---|---|---|---|---|---|---|
| S | A | D | K | Y | T | S | N | P | L | W | • | • | Y | V | T | T |

*FIG. 5D Continued*

| Trichoderma reesei position | 551 | 552 | 553 | 554 | 555 | 556 | 557 | 558 | 559 | 560 | 561 |
|---|---|---|---|---|---|---|---|---|---|---|---|
| AminoAcid | L | E | A | · | G | D | V | V | E | Y | K | Y |

| Humicola grisea position | 553 | 554 | 555 | 556 | 557 | 558 | 559 | 560 | 561 | 562 | 563 | 564 |
|---|---|---|---|---|---|---|---|---|---|---|---|---|
| AminoAcid | I | K | A | T | G | S | A | V | Q | Y | K | Y |

| Thielavia terrestris position | 549 | 550 | 551 | 552 | 553 | 554 | 555 | 556 | 557 | 558 | 559 |
|---|---|---|---|---|---|---|---|---|---|---|---|
| Amino Acid | L | P | A | · | G | L | A | V | Q | Y | K | Y |

| Thermomyces lanuginosus position | 535 | 536 | 537 | 538 | 539 | 540 | 541 | 542 | 543 | 544 | 545 |
|---|---|---|---|---|---|---|---|---|---|---|---|
| Amino Acid | L | P | A | · | G | T | S | F | E | Y | K | F |

| Talaromyces emersonii position | 542 | 543 | 544 | 545 | 546 | 547 | 548 | 549 | 550 | 551 | 552 |
|---|---|---|---|---|---|---|---|---|---|---|---|
| Amino Acid | L | P | P | · | G | T | S | F | E | Y | K | F |

| Aspergillus niger position | 569 | 570 | 571 | 572 | 573 | 574 | 575 | 576 | 577 | 578 | 579 |
|---|---|---|---|---|---|---|---|---|---|---|---|
| Amino Acid | L | P | A | · | G | E | S | F | E | Y | K | F |

| Aspergillus awamori position | 568 | 569 | 570 | 571 | 572 | 573 | 574 | 575 | 576 | 577 | 578 |
|---|---|---|---|---|---|---|---|---|---|---|---|
| Amino Acid | L | P | A | · | G | E | S | F | E | Y | K | F |

FIG. 5E

| 562 | 563 | 564 | 565 | 566 | 567 | 568 | 569 | 570 | 571 | 572 | 573 | 574 | 575 | 576 | 577 | 578 |
|---|---|---|---|---|---|---|---|---|---|---|---|---|---|---|---|---|
| I | N | V | G | Q | D | G | S | V | T | • | W | E | S | D | P | N | H |

| 565 | 566 | 567 | 568 | 569 | 570 | 571 | 572 | 573 | 574 | 575 | 576 | 577 | 578 | 579 | 580 | 581 |
|---|---|---|---|---|---|---|---|---|---|---|---|---|---|---|---|---|
| I | K | V | G | T | N | G | S | K | I | T | • | W | E | S | D | P | N | R |

| 560 | 561 | 562 | 563 | 564 | 565 | 566 | 567 | 568 | 569 | 570 | 571 | 572 | 573 | 574 | 575 | 576 |
|---|---|---|---|---|---|---|---|---|---|---|---|---|---|---|---|---|
| I | N | V | A | A | D | G | G | V | T | • | W | E | A | D | P | N | H |

| 546 | 547 | 548 | 549 | 550 | 551 | 552 | 553 | 554 | 555 | 556 | 557 | 558 | 559 | 560 | 561 | 562 | 563 |
|---|---|---|---|---|---|---|---|---|---|---|---|---|---|---|---|---|---|
| I | R | K | D | D | G | S | S | D | V | V | W | E | S | D | P | N | R |

| 553 | 554 | 555 | 556 | 557 | 558 | 559 | 560 | 561 | 562 | 563 | 564 | 565 | 566 | 567 | 568 | 569 |
|---|---|---|---|---|---|---|---|---|---|---|---|---|---|---|---|---|---|
| F | K | N | Q | T | D | G | T | I | V | • | W | E | D | D | P | N | R |

| 580 | 581 | 582 | 583 | 584 | 585 | 586 | 587 | 588 | 589 | 590 | 591 | 592 | 593 | 594 | 595 | 596 |
|---|---|---|---|---|---|---|---|---|---|---|---|---|---|---|---|---|
| I | R | I | E | S | D | D | S | V | E | • | W | E | S | D | P | N | R |

| 579 | 580 | 581 | 582 | 583 | 584 | 585 | 586 | 587 | 588 | 589 | 590 | 591 | 592 | 593 | 594 | 595 |
|---|---|---|---|---|---|---|---|---|---|---|---|---|---|---|---|---|
| I | R | I | E | S | D | D | S | V | E | • | W | E | S | D | P | N | R | • | • | • | • |

*FIG. 5E Continued*

| Trichoderma reesei position | 579 | 580 | 581 | 582 | 583 | | | | 584 | 585 | 586 |
|---|---|---|---|---|---|---|---|---|---|---|---|
| Amino Acid | T | Y | T | V | P | . | . | . | . | A | V | A |

| Humicola grisea position | 582 | 583 | 584 | 585 | 586 | 587 | 588 | 589 | 590 | 591 | 592 | 593 |
|---|---|---|---|---|---|---|---|---|---|---|---|---|
| Amino Acid | S | I | T | L | Q | T | A | S | S | A | G | K |

| Thielavia terrestris position | 577 | 578 | 579 | 580 | 581 | | | | | 582 | 583 | 584 |
|---|---|---|---|---|---|---|---|---|---|---|---|---|
| Amino Acid | S | F | T | V | P | . | . | . | . | . | A | A |

| Thermomyces lanuginosus position | 564 | 565 | 566 | 567 | 568 | | | | | 569 | 570 | 571 |
|---|---|---|---|---|---|---|---|---|---|---|---|---|
| Amino Acid | S | Y | N | V | P | . | . | . | . | . | K | D |

| Talaromyces emersonii position | 570 | 571 | 572 | 573 | 574 | | | | | 575 | 576 | 577 |
|---|---|---|---|---|---|---|---|---|---|---|---|---|
| Amino Acid | S | Y | T | V | P | . | . | . | . | . | A | Y |

| Aspergillus niger position | 597 | 598 | 599 | 600 | 601 | | | | | 602 | 603 | 604 |
|---|---|---|---|---|---|---|---|---|---|---|---|---|
| Amino Acid | E | Y | T | V | P | . | . | . | . | . | Q | A |

| Aspergillus awamori position | 596 | 597 | 598 | 599 | 600 | | | | | 601 | 602 | 603 |
|---|---|---|---|---|---|---|---|---|---|---|---|---|
| Amino Acid | E | Y | T | V | P | . | . | . | . | . | Q | A |

*FIG. 5E Continued*

| 587 | 588 | 589 | 590 | 591 | 592 | 593 | 594 | 595 | 596 | 597 | 598 | 599 |
|---|---|---|---|---|---|---|---|---|---|---|---|---|
| C | V | T | Q | V | V | K | E | D | T | W | Q | S |

| 594 | 595 | 596 | 597 | 598 | 599 | 600 | | 601 | 602 | 603 | 604 | |
|---|---|---|---|---|---|---|---|---|---|---|---|---|
| C | A | A | Q | T | V | N | . | . | D | S | W | R |

| 585 | 586 | 587 | 588 | 589 | 590 | 591 | 592 | 593 | 594 | 595 | 596 | |
|---|---|---|---|---|---|---|---|---|---|---|---|---|
| C | G | T | A | V | T | R | D | D | T | W | Q | . |

| 572 | 573 | 574 | 575 | 576 | 577 | 578 | 579 | 580 | 581 | 582 | 583 | |
|---|---|---|---|---|---|---|---|---|---|---|---|---|
| C | G | A | N | T | A | T | V | N | S | W | W | R |

| 578 | 579 | 580 | 581 | 582 | 583 | 584 | 585 | 586 | 587 | 588 | 589 | |
|---|---|---|---|---|---|---|---|---|---|---|---|---|
| C | G | Q | T | A | I | L | D | D | S | W | Q | . |

| 605 | 606 | 607 | 608 | 609 | 610 | 611 | 612 | 613 | 614 | 615 | 616 | |
|---|---|---|---|---|---|---|---|---|---|---|---|---|
| C | G | T | S | T | A | T | V | T | D | T | W | R |

| 604 | 605 | 606 | 607 | 608 | 609 | 610 | 611 | 612 | 613 | 614 | 615 | |
|---|---|---|---|---|---|---|---|---|---|---|---|---|
| C | G | E | S | T | A | T | V | T | D | T | W | R |

*FIG. 5E Continued*

VARIANTS OF GLUCOAMYLASE

CROSS-REFERENCE TO RELATED APPLICATIONS

This application is the U.S. National Stage of International Application PCT/EP2011/061082, filed Jun. 30, 2011, which designates the U.S and was published by the International Bureau in English on Jan. 5, 2012, and which claims the benefit of U.S. Provisional Application No. 61/360,891, filed Jul. 1, 2010 and 61/444,481, filed Feb. 18, 2011, Danish Patent Application No. PA 201070337, filed Jul. 15, 2010, and International Application No. PCT/EP2010/062035, filed Aug. 18, 2010, all of which are hereby incorporated by reference in their entirety.

FIELD OF THE INVENTION

Disclosed are combinatorial variants of a parent glucoamylase that have altered properties and are suitable such as for use within brewing and glucose syrup production. Also disclosed are DNA constructs encoding the variants and methods of producing the glucoamylase variants in host cells.

BACKGROUND OF THE INVENTION

Glucoamylase enzymes (glucan 1,4-α-glucohydrolases, EC 3.2.1.3) are starch hydrolyzing exo-acting carbohydrases, which catalyze the removal of successive glucose units from the non-reducing ends of starch or related oligo and polysaccharide molecules. Glucoamylases can hydrolyze both the linear and branched glucosidic linkages of starch (e.g., amylose and amylopectin).

Glucoamylases are produced by numerous strains of bacteria, fungi, yeast and plants. Particularly interesting, and commercially important, glucoamylases are fungal enzymes that are extracellularly produced, for example from strains of *Aspergillus* (Svensson et al., *Carlsberg Res. Commun.* 48: 529-544 (1983); Boel et al., *EMBO J.* 3: 1097-1102 (1984); Hayashida et al., *Agric. Biol. Chem.* 53: 923-929 (1989); U.S. Pat. No. 5,024,941; U.S. Pat. No. 4,794,175 and WO 88/09795); *Talaromyces* (U.S. Pat. No. 4,247,637; U.S. Pat. No. 6,255,084; and U.S. Pat. No. 6,620,924); *Rhizopus* (Ashikari et al., *Agric. Biol. Chem.* 50: 957-964 (1986); Ashikari et al., *App. Microbio. Biotech.* 32: 129-133 (1989) and U.S. Pat. No. 4,863,864); *Humicola* (WO 05/052148 and U.S. Pat. No. 4,618,579); and *Mucor* (Houghton-Larsen et al., *Appl. Microbiol. Biotechnol.* 62: 210-217 (2003)). Many of the genes that code for these enzymes have been cloned and expressed in yeast, fungal and/or bacterial cells.

Commercially, glucoamylases are very important enzymes and have been used in a wide variety of applications that require the hydrolysis of starch (e.g., for producing glucose and other monosaccharides from starch). Glucoamylases are used to produce high fructose corn sweeteners, which comprise over 50% of the sweetener market in the United States.

In general, glucoamylases may be, and commonly are, used with alpha-amylases in starch hydrolyzing processes to hydrolyze starch to dextrins and then glucose. The glucose may then be converted to fructose by other enzymes (e.g., glucose isomerases); crystallized; or used in fermentations to produce numerous end products (e.g., ethanol, citric acid, lactic acid, succinate, ascorbic acid intermediates, glutamic acid, glycerol and 1,3-propanediol). Ethanol produced by using glucoamylases in the fermentation of starch and/or cellulose containing material may be used as a source of fuel or for alcoholic consumption.

At the high solids concentrations used commercially for high glucose corn syrup (HGCS) and high fructose corn syrup (HFCS) production, glucoamylase synthesizes di-, tri-, and tetra-saccharides from glucose by condensation reactions. This occurs because of the slow hydrolysis of alpha-(1-6)-D-glucosidic bonds in starch and the formation of various accumulating condensation products, mainly isomaltose, from D-glucose. Accordingly, the glucose yield in many conventional processes does not exceed 95% of theoretical yield. The amount of syrups produced worldwide by this process is very large and even very small increases in the glucose yield pr ton of starch are commercially important.

Glucoamylase is used in brewing mainly for production of low carb beer. In combination with other amylases (such as from the malt), glucoamylase gives a very extensive hydrolysis of starch, all the way down to glucose units. Glucose is readily converted to alcohol by yeast making it possible for the breweries to obtain a very high alcohol yield from fermentation and at the same time obtain a beer, which is very low in residual carbohydrate. The ferment is diluted down to the desired alcohol % with water, and the final beer is sold as "low carb".

Although glucoamylases have been used successfully in commercial applications for many years, a need still exists for new glucoamylases with altered properties, such as an improved specific activity, a reduced formation of condensation products such as isomaltose and increased thermostability.

Citation or identification of any document in this application is not an admission that such document is available as prior art to the present invention.

SUMMARY OF THE INVENTION

The glucoamylase variants and the use of glucoamylase variants for reducing the synthesis of condensation products during hydrolysis of starch are contemplated herein. These glucoamylase variants contain amino acid substitutions within the catalytic domains and/or the starch binding domain. The variants display altered properties, such as an altered specific activity, a reduced formation of condensation products such as isomaltose and/or altered thermostability.

In one aspect, a glucoamylase variant is described herein comprising the following amino acid substitutions: a) 44R and 539R; or b) 44R, 61I and 539R, the positions corresponding to the respective position in SEQ ID NO:2 or an equivalent position in a parent glucoamylase, wherein the glucoamylase variant has at least 80% sequence identity with SEQ ID NO: 1 or 2, or the parent glucoamylase. In a further aspect, the use is described of a glucoamylase variant for the preparation of an enzymatic composition. In a further aspect, the enzymatic composition comprises at least one additional enzyme selected among amylase, protease, pullulanase, isoamylase, cellulase, glucanase, xylanase, arabinofuranosidase, ferulic acid esterase, xylan acetyl esterase, phytase and a further glucoamylase such as for example an pullulanase and a alpha-amylase.

In a further aspect, the use is described herein of a glucoamylase variant with a starch binding domain and a catalytic domain, said variant comprising two or more amino acid substitutions relative to the amino acid sequence of SEQ ID NO:2 or equivalent parent glucoamylase in interconnecting loop 2', and/or in loop 1, and/or in helix 2, and/or in loop 11, and/or in helix 12 for reducing the synthesis of condensation products during hydrolysis of starch.

In a further aspect, the use is described of a glucoamylase variant comprising two or more amino acid substitutions relative to interconnecting loop 2' with the amino acid sequence from position 518 to position 543 of SEQ ID NO:2 or equivalent sequence of residues in a parent glucoamylase, and/or loop 1 with the amino acid sequence from position 21 to position 51 of SEQ ID NO:2 or equivalent sequence of residues in a parent glucoamylase, and/or helix 2 with the amino acid sequence from position 52 to position 68 of SEQ ID NO:2 or equivalent sequence of residues in a parent glucoamylase, and/or loop 11 with the amino acid sequence from position 396 to position 420 of SEQ ID NO:2 or equivalent sequence of residues in a parent glucoamylase, and/or helix 12 with the amino acid sequence from position 421 to position 434 of SEQ ID NO:2 or equivalent sequence of residues in a parent glucoamylase for reducing the synthesis of condensation products during hydrolysis of starch.

In a further aspect, the use is described of a glucoamylase variant comprising two or more amino acid substitutions relative to the amino acid sequence from position 518 to position 543 of SEQ ID NO:2 or equivalent sequence of residues in a parent glucoamylase, and/or the amino acid sequence from position 21 to position 51 of SEQ ID NO:2 or equivalent sequence of residues in a parent glucoamylase, and/or the amino acid sequence from position 52 to position 68 of SEQ ID NO:2 or equivalent sequence of residues in a parent glucoamylase, and/or the amino acid sequence from position 396 to position 420 of SEQ ID NO:2 or equivalent sequence of residues in a parent glucoamylase, and/or the amino acid sequence from position 421 to position 434 of SEQ ID NO:2 or equivalent sequence of residues in a parent glucoamylase for reducing the synthesis of condensation products during hydrolysis of starch.

In a further aspect, the use is described of a glucoamylase variant wherein said two or more amino acid substitutions are relative to the interconnecting loop 2' with the amino acid sequence from position 518 to position 543 of SEQ ID NO:2, and/or loop 1 with the amino acid sequence from position 21 to position 51 of SEQ ID NO:2, and/or helix 2 with the amino acid sequence from position 52 to position 68 of SEQ ID NO:2, and/or loop 11 with the amino acid sequence from position 396 to position 420 of SEQ ID NO:2, and/or helix 12 with the amino acid sequence from position 421 to position 434 of SEQ ID NO:2.

In a further aspect, the use of a glucoamylase variant which when in its crystal form has a crystal structure for which the atomic coordinates of the main chain atoms have a root-mean-square deviation from the atomic coordinates of the equivalent main chain atoms of TrGA (as defined in Table 20 in WO2009/067218) of less than 0.13 nm following alignment of equivalent main chain atoms, and which have a linker region, a starch binding domain and a catalytic domain, said variant comprising two or more amino acid substitutions relative to the amino acid sequence of the parent glucoamylase in interconnecting loop 2' of the starch binding domain, and/or in loop 1, and/or in helix 2, and/or in loop 11, and/or in helix 12 of the catalytic domain for reducing the synthesis of condensation products during hydrolysis of starch.

In one aspect, the glucoamylase variant comprises two or more amino acid substitutions, wherein an amino acid substitution is in position 539 and an amino acid substitution is in position 44, the positions corresponding to the respective position in SEQ ID NO:2 or an equivalent position in a parent glucoamylase, and which sequence has at least 80% sequence identity to the parent glucoamylase, and wherein the amino acid substitution in position 44 is not 44C.

The present disclosure further relates to a polynucleotide encoding a glucoamylase variant as described herein. One aspect, is a plasmid comprising a nucleic acid. Another aspect, is a vector comprising a polynucleotide as described, or capable of expressing a glucoamylase variant as described. Another aspect, is a host cell comprising, e.g. transformed with, a plasmid or a vector as described. Another aspect, is a host cell, which has stably integrated into the chromosome a nucleic acid sequence encoding the variant glucoamylase. Another aspect is a cell capable of expressing a glucoamylase variant as described. Another aspect is a method of expressing a glucoamylase variant, the method comprising obtaining a host cell or a cell and expressing the glucoamylase variant from the cell or host cell, and optionally purifying the glucoamylase variant.

A further aspect of the disclosure is an enzymatic composition comprising at least one glucoamylase variant as described herein, and the use thereof.

A further aspect of the disclosure is a method for converting starch or partially hydrolyzed starch into a syrup containing glucose, which process includes saccharifying a liquid starch solution in the presence of at least one glucoamylase variant or an enzymatic composition as described herein.

A further aspect of the disclosure is the use of a glucoamylase variant as described herein in a starch conversion process, such as in a continuous starch conversion process, in a process for producing oligosaccharides, maltodextrins or glucose syrups and in a process for producing high fructose corn syrup.

In a further aspect, the use of a glucoamylase variant as described herein in a alcohol fermentation process is provided.

A further aspect of the disclosure is a method for producing a wort for brewing comprising forming a mash from a grist, and contacting the mash with a glucoamylase variant as described or an enzymatic composition as described.

Yet a further aspect of the disclosure is a method for production of a beer which comprises: a) preparing a mash, b) filtering the mash to obtain a wort, and fermenting the wort to obtain a beer, wherein a glucoamylase variant as described is added to: step (a) and/or step (b) and/or step (c).

Yet a further aspect of the disclosure is the use of a glucoamylase variant as described to enhance the production of fermentable sugars in either the mashing step or the fermentation step of a brewing process.

Yet a further aspect of the disclosure is a beer, wherein the beer is produced by the steps of: a) preparing a mash, b) filtering the mash to obtain a wort, c) fermenting the wort to obtain a beer, and d) pasteurizing the beer, wherein a glucoamylase variant as described is added to: step (a) and/or step (b) and/or step (c).

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or embodiments, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1A depicts a *Trichoderma reesei* glucoamylase (TrGA) having 632 amino acids (SEQ ID NO: 1). The signal peptide is underlined, the catalytic region (SEQ ID NO: 3) starting with amino acid residues SVDDFI (SEQ ID NO: 12) and having 453 amino acid residues is in bold; the linker region is in italics and the starch binding domain (SBD) is both italics and underlined. The mature protein of TrGA (SEQ ID NO: 2) includes the catalytic domain (SEQ ID NO: 3), linker region (SEQ ID NO: 10), and starch binding domain (SEQ ID NO: 11). With respect to the SBD numbering of the TrGA glucoamylase molecule, reference is made in the present disclosure to either a) positions 491 to 599 in SEQ ID NO:2 of the mature TrGA, and/or b) positions 1 to 109 in SEQ ID NO:11, which represents the isolated SBD sequence of the mature TrGA. With respect to the catalytic domain numbering of the TrGA molecule, reference is made to SEQ ID NO: 2 and/or SEQ ID NO: 3. FIG. 1B depicts the cDNA (SEQ ID NO:4) that codes for the TrGA.

FIGS. 5A and 5B depict an alignment comparison of the catalytic domains of parent glucoamylases from *Aspergillus awamori* (AaGA) (SEQ ID NO: 5); *Aspergillus niger* (AnGA) (SEQ ID NO: 6); *Aspergillus oryzae* (AoGA) (SEQ ID NO: 7); *Trichoderma reesei* (TrGA) (SEQ ID NO: 3); *Humicola grisea* (HgGA) (SEQ ID NO: 8); and *Hypocrea vinosa* (HvGA) (SEQ ID NO: 9). Identical amino acids are indicated by an asterisk (*). FIG. 5C depicts a *Talaromyces* glucoamylase (TeGA) mature protein sequence (SEQ ID NO: 384). FIGS. 5D and 5E depict an alignment comparing the Starch Binding Domain (SBD) of parent glucoamylases from *Trichoderma reesei* (SEQ ID NO: 11); *Humicola grisea* (HgGA) (SEQ ID NO: 385); *Thermomyces lanuginosus* (ThGA) (SEQ ID NO: 386); *Talaromyces emersonii* (TeGA) (SEQ ID NO: 387); *Aspergillus niger* (AnGA) (SEQ ID NO: 388); *Aspergillus awamori* (AaGA) (SEQ ID NO: 389); and *Thielavia terrestris* (TtGA) (SEQ ID NO: 390).

DETAILED DISCLOSURE OF THE INVENTION

Figure 1C:
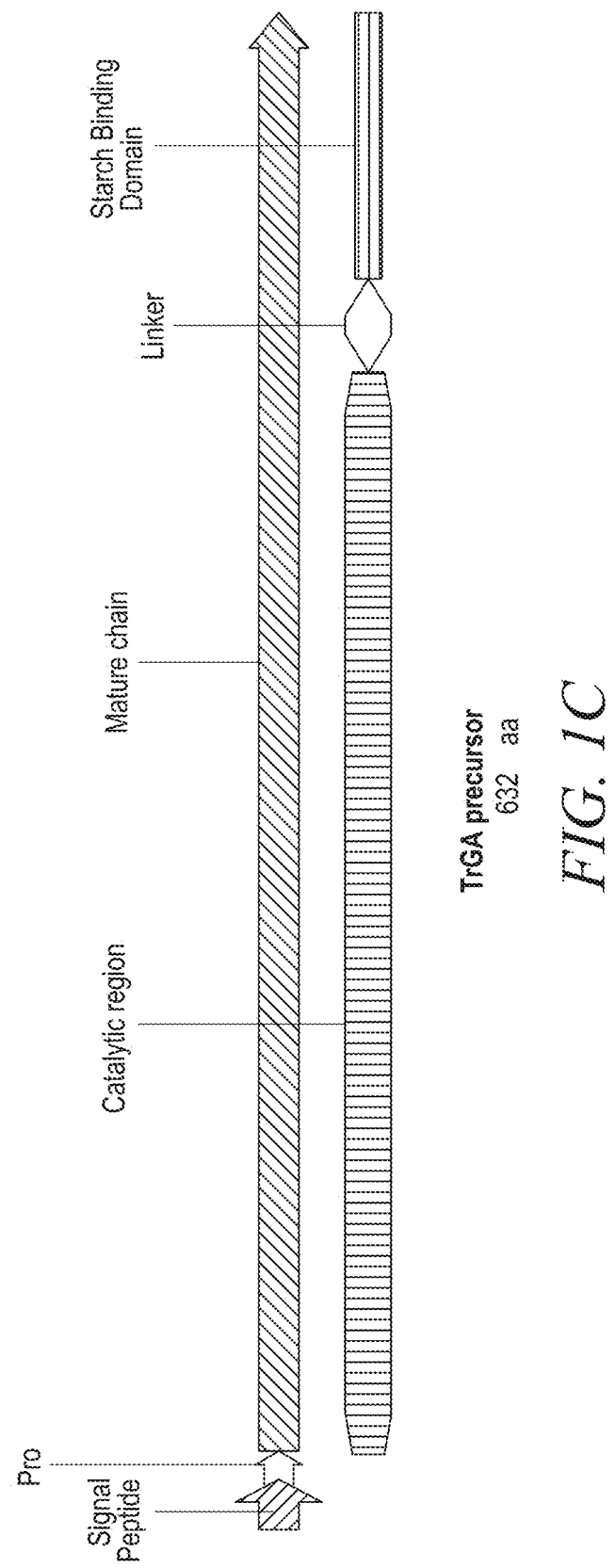
FIG. 1C depicts the precursor and mature protein TrGA domains.

Glucoamylases are commercially important enzymes in a wide variety of applications that require the hydrolysis of starch. The applicants have found that by introducing certain alterations in positions within specific regions of the amino acid sequence of a parent glucoamylase the rate of forming alpha-(1-6) bonds is reduced, and/or the formation of condensation products such as isomaltose is reduced. A reduction of the rate that glucoamylase forms alpha-(1-6) bonds relative to the rate it cleaves alpha-(1-4) bonds has practical implications.

The present inventors have provided a number of variants of a parent glucoamylase, which variants in some embodiments show a reduced condensation and/or a reduced ratio between isomaltose synthesis and starch hydrolysis activity (IS/SH ratio) as compared to the parent glucoamylase. In some embodiments using a glucoamylase variant as described herein in a saccharification process produces a syrup with high glucose percentage. In some embodiments using a glucoamylase variant as described herein results in an enhanced production of fermentable sugars in a mashing and/or fermentation step of a brewing step. In some embodiments using a glucoamylase variant as described herein results in an enhanced real degree of fermentation. These altered properties are obtained by mutating e.g. substituting selected positions in a parent glucoamylase. This will be described in more detail below.

Accordingly, in a further aspect, the use is described of a glucoamylase variant comprising two or more amino acid substitutions relative to interconnecting loop 2' with the amino acid sequence from position 518 to position 543 of SEQ ID NO:2 or equivalent sequence of residues in a parent glucoamylase, and/or loop 1 with the amino acid sequence from position 21 to position 51 of SEQ ID NO:2 or equivalent sequence of residues in a parent glucoamylase, and/or helix 2 with the amino acid sequence from position 52 to position 68 of SEQ ID NO:2 or equivalent sequence of residues in a parent glucoamylase, and/or loop 11 with the amino acid sequence from position 396 to position 420 of SEQ ID NO:2 or equivalent sequence of residues in a parent glucoamylase, and/or helix 12 with the amino acid sequence from position 421 to position 434 of SEQ ID NO:2 or equivalent sequence of residues in a parent glucoamylase for reducing the synthesis of condensation products during hydrolysis of starch.

In a further aspect, the use is described of a glucoamylase variant comprising two or more amino acid substitutions relative to the amino acid sequence from position 518 to position 543 of SEQ ID NO:2 or equivalent sequence of residues in a parent glucoamylase, and/or the amino acid sequence from position 21 to position 51 of SEQ ID NO:2 or equivalent sequence of residues in a parent glucoamylase, and/or the amino acid sequence from position 52 to position 68 of SEQ ID NO:2 or equivalent sequence of residues in a parent glucoamylase, and/or the amino acid sequence from position 396 to position 420 of SEQ ID NO:2 or equivalent sequence of residues in a parent glucoamylase, and/or the amino acid sequence from position 421 to position 434 of SEQ ID NO:2 or equivalent sequence of residues in a parent glucoamylase for reducing the synthesis of condensation products during hydrolysis of starch.

Accordingly, in a further aspect, the use of a glucoamylase variant is described, which glucoamylase variant when in its crystal form has a crystal structure for which the atomic coordinates of the main chain atoms have a root-mean-square deviation from the atomic coordinates of the equivalent main chain atoms of TrGA (as defined in Table 20 in WO2009/067218) of less than 0.13 nm following alignment of equivalent main chain atoms, and which have a linker region, a starch binding domain and a catalytic domain, said variant comprising two or more amino acid substitutions relative to the amino acid sequence of the parent glucoamylase in interconnecting loop 2' of the starch binding domain, and/or in loop 1, and/or in helix 2, and/or in loop 11, and/or in helix 12 of the catalytic domain for reducing the synthesis of condensation products during hydrolysis of starch. In a further aspect, the root-mean-square deviation from the atomic coordinates of the equivalent main chain atoms of TrGA (as defined in Table 20 in WO2009/067218) is less than 0.12 nm, such as less than 0.11 or such as less than 0.10.

In one aspect, the use is described herein of a glucoamylase variant with a starch binding domain and a catalytic domain, said variant comprising two or more amino acid substitutions relative to the amino acid sequence of SEQ ID NO:2 or equivalent parent glucoamylase in interconnecting loop 2', and/or in loop 1, and/or in helix 2, and/or in loop 11, and/or in helix 12 for reducing the synthesis of condensation products during hydrolysis of starch.

In a further aspect, the use is described of a glucoamylase variant wherein said two or more amino acid substitutions are relative to the interconnecting loop 2' with the amino acid sequence from position 518 to position 543 of SEQ ID NO:2 or equivalent sequence of residues in parent glucoamylase, and/or loop 1 with the amino acid sequence from position 21 to position 51 of SEQ ID NO:2 or equivalent sequence of residues in parent glucoamylase, and/or helix 2 with the amino acid sequence from position 52 to position 68 of SEQ ID NO:2 or equivalent sequence of residues in parent glucoamylase, and/or loop 11 with the amino acid sequence from position 396 to position 420 of SEQ ID NO:2 or equivalent sequence of residues in parent glucoamylase, and/or helix 12 with the amino acid sequence from position 421 to position 434 of SEQ ID NO:2 or equivalent sequence of residues in parent glucoamylase.

In a further aspect, the use is described of a glucoamylase variant wherein said two or more amino acid substitutions are relative to the interconnecting loop 2' with the amino acid sequence from position 518 to position 543 of SEQ ID NO:2, and/or loop 1 with the amino acid sequence from position 21 to position 51 of SEQ ID NO:2, and/or helix 2 with the amino acid sequence from position 52 to position 68 of SEQ ID NO:2, and/or loop 11 with the amino acid sequence from position 396 to position 420 of SEQ ID NO:2, and/or helix 12 with the amino acid sequence from position 421 to position 434 of SEQ ID NO:2.

In a further aspect, the two or more amino acid substitutions are at least one such as one, two or three amino acid substitution in the interconnecting loop 2' and at least one such as one, two, three, four, five or six amino acid substitution in loop 1 and/or helix 2 and/or loop 11 and/or helix 12.

In a further aspect, the two or more amino acid substitutions are one, two, three or four amino acid substitutions in the interconnecting loop 2' and one, two, three or four amino acid substitutions in loop 1 and/or helix 2 and/or loop 11 and/or helix 12. In a further aspect, there are one, two, three or four amino acid substitutions in the interconnecting loop 2'. In a further aspect, there are one, two, three or four amino acid substitutions in loop 1. In a further aspect, there are one, two, three or four amino acid substitutions in helix 2. In a further aspect, there are one, two, three or four amino acid substitutions in loop 11. In a further aspect, there are one, two, three or four amino acid substitutions in helix 12.

In a further aspect, the two or more amino acid substitutions are at least one amino acid substitution in interconnecting loop 2' and at least one amino acid substitution in loop 1.

In a further aspect, the two or more amino acid substitutions are at least one amino acid substitution in interconnecting loop 2' and at least one amino acid substitution in helix 2.

In a further aspect, the two or more amino acid substitutions are at least one amino acid substitution in interconnecting loop 2' and at least one amino acid substitution in loop 11.

In a further aspect, the two or more amino acid substitutions are at least one amino acid substitution in interconnecting loop 2' and at least one amino acid substitution in helix 12.

In a further aspect, the two or more amino acid substitutions are at least one amino acid substitution in interconnecting loop 2' and at least one amino acid substitution in loop 1 and at least one amino acid substitution in helix 2.

In a further aspect, the glucoamylase variant has at least one amino acid substitution within position 520-543, 530-543, or 534-543 of interconnecting loop 2', the positions corresponding to the respective position in SEQ ID NO:2 or equivalent positions in a parent glucoamylase.

In a further aspect, the glucoamylase variant has at least one amino acid substitution within the amino acid sequence of position 30-50, 35-48, or 40-46 of loop 1, the positions corresponding to the respective position in SEQ ID NO:2 or equivalent positions in a parent glucoamylase.

In a further aspect, the glucoamylase variant has at least one amino acid substitution within the amino acid sequence of position 50-66, 55-64, or 58-63 of helix 2, the positions corresponding to the respective position in SEQ ID NO:2 or equivalent positions in a parent glucoamylase.

In a further aspect, the glucoamylase variant has at least one amino acid substitution within the amino acid sequence of position 405-420, 410-420, or 415-420 of loop 11, the positions corresponding to the respective position in SEQ ID NO:2 or equivalent positions in a parent glucoamylase.

In a further aspect, the glucoamylase variant has at least one amino acid substitution within the amino acid sequence of position 421-434, 425-434, or 428-434 of helix 12, the positions corresponding to the respective position in SEQ ID NO:2 or equivalent positions in a parent glucoamylase.

In a further aspect, the glucoamylase variant has at least 80%, 85%, 90%, 95%, 98%, or 99.5% sequence identity to the parent glucoamylase, such as at least 80%, 85%, 90%, 95%, 98%, or 99.5% sequence identity to SEQ ID NO: 1, 2, 3, 5, 6, 7, 8, or 9. In one aspect, the glucoamylase variant has at least 80%, 85%, 90%, 95%, 98%, or 99.5% sequence identity to SEQ ID NO:2.

In a further aspect, the parent glucoamylase or the glucoamylase variant has a starch binding domain that has at least 96%, 97%, 98%, 99%, or 99.5% sequence identity with the starch binding domain of SEQ ID NO: 1, 2, 11, 385, 386, 387, 388, 389, or 390. In a further aspect, the parent glucoamylase or the glucoamylase variant has a catalytic domain that has at least 80%, 85%, 90%, 95%, or 99.5% sequence identity with the catalytic domain of SEQ ID NO: 1, 2, 3, 5, 6, 7, 8, or 9.

In one aspect, the glucoamylase variant has an amino acid substitution in position 539 and one or more amino acid substitutions in a position selected from position 44, 61, 417 and 431, the positions corresponding to the respective position in SEQ ID NO:2 or an equivalent position in a parent glucoamylase. In one aspect, the glucoamylase variant has an amino acid substitution in position 539 and a) an amino acid substitution in position 44 and/or b) amino acid substitutions in both positions 417 and 431, the positions corresponding to the respective position in SEQ ID NO:2 or an equivalent position in a parent glucoamylase. In one aspect, the glucoamylase variant has an amino acid substitution in position 539 and an amino acid substitution in position 44, the positions corresponding to the respective position in SEQ ID NO:2 or an equivalent position in a parent glucoamylase. In one aspect, the glucoamylase variant has an amino acid substitution in position 539 and amino acid substitutions in positions 417 and 431, the positions corresponding to the respective position in SEQ ID NO:2 or an equivalent position in a parent glucoamylase. In one aspect, the glucoamylase variant has an amino acid substitution in position 539 and amino acid substitutions in positions 44 and 61, the positions corresponding to the respective position in SEQ ID NO:2 or an equivalent position in a parent glucoamylase. In one aspect, the glucoamylase variant has an amino acid substitution in position 43, the position corresponding to the respective position in SEQ ID NO:2 or an equivalent position in a parent glucoamylase. In one aspect, the glucoamylase variant has an amino acid substitution in position 61, the position corresponding to the respective position in SEQ ID NO:2 or an equivalent position in a parent glucoamylase. In one aspect, the amino acid substitution in position 539 is 539R, the position corresponding to the respective position in SEQ ID NO:2 or an equivalent position in a parent glucoamylase. In one aspect, the amino acid substitution in position 44 is 44R, the position corresponding to the respective position in SEQ ID NO:2 or an equivalent position in a parent glucoamylase. In one aspect, the amino acid substitution in position 417 is 417R/V, the position corresponding to the respective position in SEQ ID NO:2 or an equivalent position in a parent glucoamylase. In one aspect, the amino acid substitution in position 417 is 417R, the position corresponding to the respective position in SEQ ID NO:2 or an equivalent position in a parent glucoamylase. In one aspect, the amino acid substitution in position 417 is 417V, the position corresponding to the respective position in SEQ ID NO:2 or an equivalent position in a parent glucoamylase. In one aspect, the amino acid substitution in position 431 is 431L, the position corresponding to the respective position in SEQ ID NO:2 or an equivalent position in a parent glucoamylase. In one aspect, the amino acid substitution in position 43 is 43R, the position corresponding to the respective position in SEQ ID NO:2 or an equivalent position in a parent glucoamylase. In one aspect, the amino acid substitution in position 61 is 61I, the position corresponding to the respective position in SEQ ID NO:2 or an equivalent position in a parent glucoamylase.

In one aspect, the condensation product is isomaltose. In one aspect, the hydrolysis of starch is in a brewing process. In for example brewing, the formation of isomaltose is undesired because it can not be converted into alcohol during fermentation.

Beer is traditionally referred to as an alcoholic beverage derived from malt, such as malt derived from barley, and optionally adjuncts, such as cereal grains, and flavoured with hops.

Beer can be made from a variety of grains by essentially the same process. All grain starches are glucose homopolymers in which the glucose residues are linked by either alpha-1,4- or alpha-1,6-bonds, with the former predominating.

The process of making fermented malt beverages is commonly referred to as brewing. The principal raw materials used in making these beverages are water, hops and malt. In addition, adjuncts such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, and syrups, such as corn syrup, sugar cane syrup, inverted sugar syrup, barley and/or wheat syrups, and the like may be used as a source of starch. The starch will eventually be converted into dextrins and fermentable sugars.

For a number of reasons, the malt, which is produced principally from selected varieties of barley, is believed to have the greatest effect on the overall character and quality of the beer. First, the malt is the primary flavouring agent in beer. Second, the malt provides the major portion of the fermentable sugar. Third, the malt provides the proteins, which will contribute to the body and foam character of the beer. Fourth, the malt provides the necessary enzymatic activity during mashing.

Hops also contribute significantly to beer quality, including flavouring. In particular, hops (or hops constituents) add desirable bittering substances to the beer. In addition, the hops act as protein precipitants, establish preservative agents and aid in foam formation and stabilization.

The process for making beer is well known in the art, but briefly, it involves five steps: (a) mashing and/or adjunct cooking (b) wort separation and extraction (c) boiling and hopping of wort (d) cooling, fermentation and storage, and (e) maturation, processing and packaging.

Typically, in the first step, milled or crushed malt is mixed with water and held for a period of time under controlled temperatures to permit the enzymes present in the malt to convert the starch present in the malt into fermentable sugars.

In the second step, the mash is transferred to a "lauter tun" or mash filter where the liquid is separated from the grain residue. This sweet liquid is called "wort" and the left over grain residue is called "spent grain". The mash is typically subjected to an extraction, which involves adding water to the mash in order to recover the residual soluble extract from the spent grain.

In the third step, the wort is boiled vigorously. This sterilizes the wort and helps to develop the colour, flavour and odour and inactivates enzyme activities. Hops are added at some point during the boiling.

In the fourth step, the wort is cooled and transferred to a fermentor, which either contains the yeast or to which yeast is added. The yeast converts the sugars by fermentation into alcohol and carbon dioxide gas; at the end of fermentation the fermentor is chilled or the fermentor may be chilled to stop fermentation. The yeast flocculates and is removed.

In the last step, the beer is cooled and stored for a period of time, during which the beer clarifies and its flavour develops, and any material that might impair the appearance, flavour and shelf life of the beer settles out. Prior to packaging, the beer is carbonated and, optionally, filtered and pasteurized.

After fermentation, a beverage is obtained which usually contains from about 2% to about 10% alcohol by weight. The non-fermentable carbohydrates are not converted during fermentation and form the majority of the dissolved solids in the final beer.

This residue remains because of the inability of malt amylases to hydrolyze the alpha-1,6-linkages of the starch. The non-fermentable carbohydrates contribute about 50 calories per 12 ounces of beer.

Further information on conventional brewing processes, as well as definitions for terms used in the field of brewing technology to be applied for the present invention, may be found in "Technology Brewing and Malting" by Wolfgang Kunze of the Research and Teaching Institute of Brewing, Berlin (VLB), 2nd revised Edition 1999, ISBN 3-921690-39-0 or 3rd edition (2004): ISBN 3-921690-49-8.

Recently, there has been a widespread popularization of brewed beverages called light beers, reduced calorie beers or low calorie beers, particularly in the U.S. market. As defined in the U.S., these beers have approximately 30% fewer calories than a manufacturer's "normal" beer.

As used herein, the term "light beers, reduced calorie beers or low calorie beers", refers to the recent, widespread popularization of brewed beverages, particularly in the U.S. market. As defined in the U.S., these highly attenuated beers have approximately 30% fewer calories than a manufacturer's "normal beer". Further information on conventional brewing processes may be found in "Technology Brewing and Malting" by Wolfgang Kunze of the Research and Teaching Institute of Brewing, Berlin (VLB), 3rd completely updated edition, 2004, ISBN 3-921690-49-8."

Disclosed herein is the use of a glucoamylase variant as described herein, wherein the production of fermentable sugar(s) is enhanced as compared to the parent glucoamylase, such as TrGA. Further disclosed herein is the use of a glucoamylase variant as described herein, wherein the production of fermentable sugars is enhanced in a mashing step of the brewing process as compared to the parent glucoamylase, such as TrGA. Disclosed herein is the use of a glucoamylase variant as described herein, wherein the production of fermentable sugars is enhanced in a fermentation step of a brewing process as compared to the parent glucoamylase, such as TrGA. Disclosed herein is the use of a glucoamylase variant as described herein, wherein the fermentable sugar is glucose.

A glucoamylase that can produce glucose with a significantly reduced amount of by-products would be of great commercial interest, e.g. in production of glucose syrup or in brewing. Further disclosed herein is the use of a glucoamylase variant as described herein, wherein the hydrolysis of starch is in a process for producing glucose syrup. In one aspect, the glucoamylase exhibit a reduced ratio between isomaltose synthesis (IS) and starch hydrolysis activity (SH) as compared to the parent glucoamylase, such as TrGA. In one aspect, the glucoamylase exhibit a reduced starch hydrolysis activity, which is not more than 5%, not more than 10% or not more than 15% reduced as compared to the parent glucoamylase, such as TrGA. In one aspect, the glucoamylase exhibit an enhanced real degree of fermentation as compared to the parent glucoamylase such as TrGA. In one aspect, the glucoamylase forms a lower amount of condensation products than the amount of condensation products formed by the glucoamylase Aspergillus niger (AnGA) (SEQ ID NO: 6) under comparable conditions. In one aspect, the glucoamylase forms an amount of condensation products which amount is essentially the same as, not more than 5% higher, not more than 8% higher or not more than 10% higher than the amount of condensation products formed by Aspergillus niger (AnGA) (SEQ ID NO: 6) under comparable conditions. In one aspect, dosing of the glucoamylases are the same based on protein concentration. In one aspect, dosing of the glucoamylases are the same based on measurement of activity in activity assays.

Glucoamylase variants described herein contain amino acid substitutions within the catalytic domain and/or the starch binding domain. The variants may display altered properties such as improved thermostability, altered formation of condensation products such as isomaltose and/or an enhanced real degree of fermentation and/or a reduced ratio between isomaltose synthesis (IS) and starch hydrolysis activity (SH) and/or specific activity. The variants with reduced formation of condensation products such as isomaltose may significantly improve the ability to make desired products in the brewing industry, for example.

1. Definitions and Abbreviations 1.1. Definitions

Unless defined otherwise, all technical and scientific terms used herein have the same meaning as commonly understood by one of ordinary skill in the art to which this disclosure belongs. Singleton et al., Dictionary Of Microbiology And Molecular Biology, 2nd ed., John Wiley and Sons, New York (1994), and Hale & Markham, The Harper Collins Dictionary Of Biology, Harper Perennial, N.Y. (1991) provide one of skill with the general meaning of many of the terms used herein. Certain terms are defined below for the sake of clarity and ease of reference.

As used herein, the term "glucoamylase (EC 3.2.1.3)" refers to an enzyme that catalyzes the release of D-glucose from the non-reducing ends of starch and related oligo- and polysaccharides.

The term "parent" or "parent sequence" refers to a sequence that is native or naturally occurring in a host cell. Parent glucoamylases include, but are not limited to, the glucoamylase sequences set forth in SEQ ID NOs: 1, 2, 3, 5, 6, 7, 8, and 9, and glucoamylases with at least 80% amino acid sequence identity to SEQ ID NO: 2.

As used herein, an "equivalent position" means a position that is common to two parent sequences that is based on an alignment of the amino acid sequence of the parent glucoamylase in question as well as alignment of the three-dimensional structure of the parent glucoamylase in question with the TrGA reference glucoamylase amino acid sequence (SEQ ID NO: 2) and three-dimensional structure. Thus either sequence alignment or structural alignment may be used to determine equivalence.

The term "TrGA" refers to a parent *Trichoderma reesei* glucoamylase sequence having the mature protein sequence illustrated in SEQ ID NO: 2 that includes the catalytic domain having the sequence illustrated in SEQ ID NO: 3. The isolation, cloning and expression of the TrGA are described in WO 2006/060062 and U.S. Pat. No. 7,413,887, both of which are incorporated herein by reference. In some embodiments, the parent sequence refers to a glucoamylase sequence that is the starting point for protein engineering. The numbering of the glucoamylase amino acids herein is based on the sequence alignment of a glucoamylase with TrGA (SEQ ID NO: 2 and/or 3).

The phrase "mature form of a protein or polypeptide" refers to the final functional form of the protein or polypeptide. A mature form of a glucoamylase may lack a signal peptide, for example. To exemplify, a mature form of the TrGA includes the catalytic domain, linker region and starch binding domain having the amino acid sequence of SEQ ID NO: 2.

As used herein, the terms "glucoamylase variant" and "variant" are used in reference to glucoamylases that have some degree of amino acid sequence identity to a parent glucoamylase sequence. A variant is similar to a parent sequence, but has at least one substitution, deletion or insertion in their amino acid sequence that makes them different in sequence from a parent glucoamylase. In some cases, variants have been manipulated and/or engineered to include at least one substitution, deletion, or insertion in their amino acid sequence that makes them different in sequence from a parent. Additionally, a glucoamylase variant may retain the functional characteristics of the parent glucoamylase, e.g., maintaining a glucoamylase activity that is at least about 50%, about 60%, about 70%, about 80%, or about 90% of that of the parent glucoamylase. Can also have higher activity than 100% if that is what one has selected for.

"Variants" may have at least about 45%, about 50%, about 55%, about 60%, about 65%, about 70%, about 75%, about 80%, about 85%, about 88%, about 90%, about 91%, about 92%, about 93%, about 94%, about 95%, about 96%, about 97%, about 98%, about 99%, or about 99.5% sequence identity to a parent polypeptide sequence when optimally aligned for comparison. In some embodiments, the glucoamylase variant may have at least about 45%, about 50%, about 55%, about 60%, about 65%, about 70%, about 75%, about 80%, about 85%, about 88%, about 90%, about 91%, about 92%, about 93%, about 94%, about 95%, about 96%, about 97%, about 98%, about 99%, or about 99.5% sequence identity to the catalytic domain of a parent glucoamylase. In some embodiments, the glucoamylase variant may have at least at least about 45%, about 50%, about 55%, about 60%, about 65%, about 70%, about 75%, about 80%, about 85%, about 88%, about 90%, about 91%, about 92%, about 93%, about 94%, about 95%, about 96%, about 97%, about 98%, about 99%, or about 99.5% sequence identity to the starch binding domain of a parent glucoamylase. The sequence identity can be measured over the entire length of the parent or the variant sequence.

Sequence identity is determined using standard techniques known in the art (see e.g., Smith and Waterman, *Adv. Appl. Math.* 2: 482 (1981); Needleman and Wunsch, *J. Mol. Biol.* 48: 443 (1970); Pearson and Lipman, *Proc. Natl. Acad. Sci. USA* 85: 2444 (1988); programs such as GAP, BESTHT, FASTA, and TFASTA in the Wisconsin Genetics Software Package (Genetics Computer Group, Madison, Wis.); and Devereux et al., *Nucleic Acid Res.*, 12: 387-395 (1984)).

The "percent (%) nucleic acid sequence identity" or "percent (%) amino acid sequence identity" is defined as the percentage of nucleotide residues or amino acid residues in a candidate sequence that are identical with the nucleotide residues or amino acid residues of the starting sequence (e.g., SEQ ID NO 2). The sequence identity can be measured over the entire length of the starting sequence.

"Sequence identity" is determined herein by the method of sequence alignment. For the purpose of the present disclosure, the alignment method is BLAST described by Altschul et al., (Altschul et al., *J. Mol. Biol.* 215: 403-410 (1990); and Karlin et al, *Proc. Natl. Acad. Sci. USA* 90: 5873-5787 (1993)). A particularly useful BLAST program is the WU-BLAST-2 program (see Altschul et al, *Meth. Enzymol.* 266: 460-480 (1996)). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The term "optimal alignment" refers to the alignment giving the highest percent identity score.

As used herein the term "catalytic domain" refers to a structural region of a polypeptide, which contains the active site for substrate hydrolysis.

The term "linker" refers to a short amino acid sequence generally having between 3 and 40 amino acids residues that covalently bind an amino acid sequence comprising a starch binding domain with an amino acid sequence comprising a catalytic domain.

The term "starch binding domain" refers to an amino acid sequence that binds preferentially to a starch substrate.

As used herein, the terms "mutant sequence" and "mutant gene" are used interchangeably and refer to a polynucleotide sequence that has an alteration in at least one codon occurring in a host cell's parent sequence. The expression product of the mutant sequence is a variant protein with an altered amino acid sequence relative to the parent. The expression product may have an altered functional capacity (e.g., enhanced enzymatic activity).

The term "property" or grammatical equivalents thereof in the context of a polypeptide, as used herein, refers to any characteristic or attribute of a polypeptide that can be selected or detected. These properties include, but are not limited to oxidative stability, substrate specificity, catalytic activity, thermal stability, pH activity profile, resistance to proteolytic degradation, $K_M$, $K_{CAT}$, $K_{CAT}/K_M$ ratio, protein folding, ability to bind a substrate and ability to be secreted.

The term "property" or grammatical equivalent thereof in the context of a nucleic acid, as used herein, refers to any characteristic or attribute of a nucleic acid that can be selected or detected. These properties include, but are not limited to, a property affecting gene transcription (e.g., promoter strength or promoter recognition), a property affecting RNA processing (e.g., RNA splicing and RNA stability), a property affecting translation (e.g., regulation, binding of mRNA to ribosomal proteins).

The terms "thermally stable" and "thermostable" refer to glucoamylase variants of the present disclosure that retain a specified amount of enzymatic activity after exposure to a temperature over a given period of time under conditions prevailing during the hydrolysis of starch substrates, for example, while exposed to altered temperatures.

The term "enhanced stability" in the context of a property such as thermostability refers to a higher retained starch hydrolytic activity over time as compared to another reference (i.e., parent) glucoamylase.

The term "diminished stability" in the context of a property such as thermostability refers to a lower retained starch hydrolytic activity over time as compared to another reference glucoamylase.

The term "specific activity" is defined as the activity per mg of glucoamylase protein. In some embodiments, the activity for glucoamylase is determined by the ethanol assay described herein and expressed as the amount of glucose that is produced from the starch substrate. In some embodiments, the protein concentration can be determined using the Caliper assay described herein.

The terms "active" and "biologically active" refer to a biological activity associated with a particular protein. It follows that the biological activity of a given protein refers to any biological activity typically attributed to that protein by those skilled in the art. For example, an enzymatic activity associated with a glucoamylase is hydrolytic and, thus an active glucoamylase has hydrolytic activity.

The terms "polynucleotide" and "nucleic acid", used interchangeably herein, refer to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases.

As used herein, the terms "DNA construct," "transforming DNA" and "expression vector" are used interchangeably to refer to DNA used to introduce sequences into a host cell or organism. The DNA may be generated in vitro by PCR or any other suitable technique(s) known to those in the art. The DNA construct, transforming DNA or recombinant expression cassette can be incorporated into a plasmid, chromosome, mitochondrial DNA, plastid DNA, virus, or nucleic acid fragment. Typically, the recombinant expression cassette portion of an expression vector, DNA construct or transforming DNA includes, among other sequences, a nucleic acid sequence to be transcribed and a promoter. In some embodiments, expression vectors have the ability to incorporate and express heterologous DNA fragments in a host cell.

As used herein, the term "vector" refers to a polynucleotide construct designed to introduce nucleic acids into one or more cell types. Vectors include cloning vectors, expression vectors, shuttle vectors, plasmids, cassettes, and the like.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction.

As used herein, the terms "transformed" and "stably transformed" refers to a cell that has a non-native (heterologous) polynucleotide sequence integrated into its genome or as an episomal plasmid that is maintained for at least two generations.

As used herein, the terms "selectable marker" and "selective marker" refer to a nucleic acid (e.g., a gene) capable of expression in host cells that allows for ease of selection of those hosts containing the vector. Typically, selectable markers are genes that confer antimicrobial resistance or a metabolic advantage on the host cell to allow cells containing the exogenous DNA to be distinguished from cells that have not received any exogenous sequence during the transformation.

As used herein, the term "promoter" refers to a nucleic acid sequence that functions to direct transcription of a downstream gene. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide. Generally, "operably linked" means that the DNA sequences being linked are contiguous, and, in the case of a secretory leader, contiguous and in reading phase.

As used herein the term "gene" refers to a polynucleotide (e.g., a DNA segment), that encodes a polypeptide and includes regions preceding and following the coding regions, as well as intervening sequences (introns) between individual coding segments (exons).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature ($T_m$) of the nucleic acid binding complex or probe. For example, "maximum stringency" typically occurs at about $T_m$–5° C. (5° C. below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denaturated sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous or homologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

In an embodiment of the disclosure, mutated DNA sequences are generated with site saturation mutagenesis in at least one codon. In another embodiment, site saturation mutagenesis is performed for two or more codons. In a further embodiment, mutant DNA sequences have more than about 50%, about 55%, about 60%, about 65%, about 70%, about 75%, about 80%, about 85%, about 90%, about 95%, or about 98% identity with the parent sequence. In alternative embodiments, mutant DNA is generated in vivo using any known mutagenic procedure such as, for example, radiation, nitrosoguanidine, and the like. The desired DNA sequence is then isolated and used in the methods provided herein.

As used herein, "heterologous protein" refers to a protein or polypeptide that does not naturally occur in the host cell.

An enzyme is "over-expressed" in a host cell if the enzyme is expressed in the cell at a higher level than the level at which it is expressed in a corresponding wild-type cell.

The terms "protein" and "polypeptide" are used interchangeability herein. In the present disclosure and claims, the conventional one-letter and three-letter codes for amino acid residues are used. The 3-letter code for amino acids as defined in conformity with the IUPAC-IUB Joint Commission on Biochemical Nomenclature (JCBN). It is also understood that a polypeptide may be coded for by more than one nucleotide sequence due to the degeneracy of the genetic code.

Variants of the disclosure are described by the following nomenclature: [original amino acid residue/position/substituted amino acid residue]. For example, the substitution of leucine for arginine at position 76 is represented as R76L. When more than one amino acid is substituted at a given position, the substitution is represented as 1) Q172C, Q172D or Q172R; 2) Q172C, D, or R, or 3) Q172C/D/R. When a position suitable for substitution is identified herein without a specific amino acid suggested, it is to be understood that any amino acid residue may be substituted for the amino acid residue present in the position. Where a variant glucoamylase contains a deletion in comparison with other glucoamylases the deletion is indicated with "*". For example, a deletion at position R76 is represented as R76*. A deletion of two or more consecutive amino acids is indicated for example as (76-78)*.

A "prosequence" is an amino acid sequence between the signal sequence and mature protein that is necessary for the secretion of the protein. Cleavage of the pro sequence will result in a mature active protein.

The term "signal sequence" or "signal peptide" refers to any sequence of nucleotides and/or amino acids that may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., glucoamylase), or may be from a gene encoding another secreted protein.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Host strain" or "host cell" refers to a suitable host for an expression vector comprising DNA according to the present disclosure.

The terms "derived from" and "obtained from" refer to not only a glucoamylase produced or producible by a strain of the organism in question, but also a glucoamylase encoded by a DNA sequence isolated from such strain and produced in a host organism containing such DNA sequence. Additionally, the term refers to a glucoamylase that is encoded by a DNA sequence of synthetic and/or cDNA origin and that has the identifying characteristics of the glucoamylase in question.

A "derivative" within the scope of this definition generally retains the characteristic hydrolyzing activity observed in the wild-type, native or parent form to the extent that the derivative is useful for similar purposes as the wild-type, native or parent form. Functional derivatives of glucoamylases encompass naturally occurring, synthetically or recombinantly produced peptides or peptide fragments that have the general characteristics of the glucoamylases of the present disclosure.

The term "isolated" refers to a material that is removed from the natural environment if it is naturally occurring. A "purified" protein refers to a protein that is at least partially purified to homogeneity. In some embodiments, a purified protein is more than about 10% pure, about 20% pure, or about 30% pure, as determined by SDS-PAGE. Further aspects of the disclosure encompass the protein in a highly purified form (i.e., more than about 40% pure, about 60% pure, about 80% pure, about 90% pure, about 95% pure, about 97% pure, or about 99% pure), as determined by SDS-PAGE.

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations that were not members of the predefined set of mutations. In some embodiments, the methods include those set forth in U.S. Pat. No. 6,582,914, hereby incorporated by reference. In alternative embodiments, combinatorial mutagenesis methods encompass commercially available kits (e.g., QuikChange® Multisite, Stratagene, San Diego, Calif.).

As used herein, the term "library of mutants" refers to a population of cells that are identical in most of their genome but include different homologues of one or more genes. Such libraries can be used, for example, to identify genes or operons with improved traits.

As used herein the term "dry solids content (DS or ds)" refers to the total solids of a slurry in % on a dry weight basis.

As used herein, the term "initial hit" refers to a variant that was identified by screening a combinatorial consensus mutagenesis library. In some embodiments, initial hits have improved performance characteristics, as compared to the starting gene.

As used herein, the term "improved hit" refers to a variant that was identified by screening an enhanced combinatorial consensus mutagenesis library.

As used herein, the term "target property" refers to the property of the starting gene that is to be altered. It is not intended that the present disclosure be limited to any particular target property. However, in some embodiments, the target property is the stability of a gene product (e.g., resistance to denaturation, proteolysis or other degradative factors), while in other embodiments, the level of production in a production host is altered. Indeed, it is contemplated that any property of a starting gene will find use in the present disclosure. Other definitions of terms may appear throughout the specification.

As used herein, the "process for making beer" may further be applied in the mashing of any grist.

As used herein, the term "grist" refers to any starch and/or sugar containing plant material derivable from any plant and plant part, including tubers (e.g. potatoes), roots (e.g. cassava [Manihot esculenta] roots), stems, leaves and seeds. The grist may comprise grain, such as grain from barley, wheat, rye, oat, corn/maize, rice, milo, millet and sorghum, and e.g. at least 10%, or at least 15%, or at least 25%, or at least 35%, such as at least 50%, at least 75%, at least 90% or even 100% (w/w) of the grist of the wort is derived from grain. In some embodiments the grist may comprise the starch and/or sugar containing plant material obtained from cassava [Manihot esculenta] roots. The grist may comprise malted grain, such as barley malt. Often, at least 10%, or at least 15%, or at least 25%, or at least 35%, such as at least 50%, at least 75%, at least 90% or even 100% (w/w) of the grist of the wort is derived from malted grain. The grist may comprise adjunct, such as up to 10%, or at least 10%, or at least 15%, or at least 25%, or at least 35%, or at least 50%, at least 75%, at least 90%, or even 100% (w/w) of the grist of the wort is adjunct.

The term "adjunct" is understood as the part of the grist which is not barley malt. The adjunct may be any carbohydrate rich material. In term "adjunct" includes starch and/or sugar containing plant material as e.g. defined above under "grist".

The term "fermentation" means, in the context of brewing, the transformation of sugars in the wort, by enzymes in the brewing yeast, into ethanol and carbon dioxide with the formation of other fermentation by-products.

As used herein the term "malt" is understood as any malted cereal grain, such as barley.

As used herein, the term "malt beverage" includes such foam forming fermented malt beverages as full malted beer, ale, dry beer, near beer, light beer, low alcohol beer, low calorie beer, porter, bock beer, stout, malt liquor, non-alcoholic malt liquor and the like. The term "malt beverages" also includes non-foaming beer and alternative malt beverages such as fruit flavoured malt beverages, e.g., citrus flavoured, such as lemon-, orange-, lime-, or berry-flavoured malt beverages, liquor flavoured malt beverages, e.g., vodka-, rum-, or tequila-flavoured malt liquor, or coffee flavoured malt beverages, such as caffeine-flavoured malt liquor, and the like.

The term "mash" is understood as aqueous starch slurry, e.g. comprising crushed barley malt, crushed barley, and/or other adjunct or a combination hereof, mixed with water later to be separated into wort+spent grains.

As used herein, the term "wort" refers to the unfermented liquor run-off following extracting the grist during mashing.

As used herein, the term "spent grains" refers to the drained solids remaining when the grist has been extracted and the wort separated from the mash.

Included within the term "beer" is any fermented wort, produced by the brewing and fermentation of a starch-containing material, mainly derived from cereal grains, such as malted barley. Wheat, maize, and rice may also be used.

As used herein, the term "extract recovery" in the wort is defined as the sum of soluble substances extracted from the grist (malt and adjuncts) expressed in percentage based on dry matter.

As used herein, the term "pasteurization" means heating (e.g. beer) at certain temperatures for certain time intervals. The purpose is normally killing of micro-organisms but pasteurization can also cause inactivation of enzyme activity. Implementation of pasteurisation in the brewing process is typically through the use of a flash pasteuriser or tunnel pasteuriser. As used herein, the term "pasteurisation units or PU" refers to a quantitative measure of pasteurisation. One pasteurisation unit (1 PU) for beer is defined as a heat retention of one minute at 60 degrees Celsius. One calculates that:

$$PU = t \times 1.393^{\wedge}(T-60), \text{ where:}$$

t=time, in minutes, at the pasteurisation temperature in the pasteuriser

T=temperature, in degrees Celsius, in the pasteuriser

[^(T−60) represents the exponent of (T−60)]

Different minimum PU may be used depending on beer type, raw materials and microbial contamination, brewer and perceived effect on beer flavour. Typically, for beer pasteurisation, 14-15 PU are required. Depending on the pasteurising equipment, pasteurisation temperatures are typically in the range of 64-72 degrees Celsius with a pasteurisation time calculated accordingly. Further information may be found in "Technology Brewing and Malting" by Wolfgang Kunze of the Research and Teaching Institute of Brewing, Berlin (VLB), 3rd completely updated edition, 2004, ISBN 3-921690-49-8.

As used herein, the term "non-alcoholic beer" or "low-alcohol beer" refers to a beer containing a maximum of 0.1% to 3.5% or 0.1% to 2.5% such as 0.1% to 0.5% alcohol by volume. Non-alcoholic beer is brewed by traditional methods, but during the finishing stages of the brewing process the alcohol is removed by vacuum evaporation, by taking advantage of the different boiling points of water and alcohol.

As used herein, the term "low-calorie beer" or "beer with a low carbohydrate content" is defined as a beer with a carbohydrate content of 1.5 g/100 g or less and with a real degree of fermentation of at least 80%.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Before the exemplary embodiments are described in more detail, it is to be understood that this disclosure is not limited to particular embodiments described, as such may, of course, vary. Although any methods and materials similar or equivalent to those described herein can be used in the practice or testing of the present disclosure, exemplary methods and materials are now described.

As used herein and in the appended claims, the singular forms "a", "an", and "the" include plural referents unless the context clearly dictates otherwise. Thus, for example, reference to "a gene" includes a plurality of such candidate agents and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present disclosure is not entitled to antedate such publication by virtue of prior invention.

1.2. Abbreviations

GA glucoamylase
GAU glucoamylase unit
wt % weight percent
° C. degrees Centigrade
rpm revolutions per minute
$H_2O$ water
$dH_2O$ deionized water
$dIH_2O$ deionized water, Milli-Q filtration
aa or AA amino acid
bp base pair
kb kilobase pair
kD kilodaltons
g or gm grams
μg micrograms
mg milligrams
μl and μL microliters
ml and mL milliliters
mm millimeters
μmicrometer
M molar
mM millimolar
μM micromolar
U units
V volts
MW molecular weight
MWCO molecular weight cutoff
sec(s) or s(s) second/seconds
min(s) or m(s) minute/minutes
hr(s) or h(s) hour/hours
DO dissolved oxygen
ABS Absorbance
EtOH ethanol
PSS physiological salt solution m/v mass/volume
MTP microtiter plate
N Normal
DP1 monosaccharides
DP2 disaccharides
DP>3 oligosaccharides, sugars having a degree of polymerization greater than 3
ppm parts per million
SBD starch binding domain
CD catalytic domain
PCR polymerase chain reaction
WT wild-type 2. Parent Glucoamylases In some embodiments, the present disclosure provides a glucoamylase variant. The glucoamylase variant is a variant of a parent glucoamylase, which may comprise both a catalytic domain and a starch binding domain. In some embodiments, the parent glucoamylase comprises a catalytic domain having an amino acid sequence as illustrated in SEQ ID NO: 1, 2, 3, 5, 6, 7, 8 or 9 or having an amino acid sequence displaying at least about 80%, about 85%, about 90%, about 95%, about 97%, about 99%, or about 99.5% sequence identity with one or more of the amino acid sequences illustrated in SEQ ID NO: 1, 2, 3, 5, 6, 7, 8, or 9. In yet other embodiments, the parent glucoamylase comprises a catalytic domain encoded by a DNA sequence that hybridizes under medium, high, or stringent conditions with a DNA encoding the catalytic domain of a glucoamylase having one of the amino acid sequences of SEQ ID NO: 1, 2 or 3.

In some embodiments, the parent glucoamylase comprises a starch binding domain having an amino acid sequence as illustrated in SEQ ID NO 1, 2, 11, 385, 386, 387, 388, 389, or 390, or having an amino acid sequence displaying at least about 80%, about 85%, about 90%, about 95%, about 97%, about 99%, or about 99.5% sequence identity with one or more of the amino acid sequence illustrated in SEQ ID NO 1, 2, 11, 385, 386, 387, 388, 389, or 390. In yet other embodiments, the parent glucoamylase comprises a starch binding domain encoded by a DNA sequence that hybridizes under medium, high, or stringent conditions with a DNA encoding the starch binding domain of a glucoamylase having one of the amino acid sequences of SEQ ID NO: 1, 2, or 11.

Predicted structure and known sequences of glucoamylases are conserved among fungal species (Coutinho et al., 1994, *Protein Eng.*, 7:393-400 and Coutinho et al., 1994, *Protein Eng.*, 7: 749-760). In some embodiments, the parent glucoamylase is a filamentous fungal glucoamylase. In some embodiments, the parent glucoamylase is obtained from a *Trichoderma* strain (e.g., *T. reesei, T. longibrachiatum, T. strictipilis, T. asperellum, T. konilangbra* and *T. hazianum*), an *Aspergillus* strain (e.g. *A. niger, A. nidulans, A. kawachi, A. awamori* and *A. orzyae*), a *Talaromyces* strain (e.g. *T. emersonii, T. thermophilus*, and *T. duponti*), a *Hypocrea* strain (e.g. *H. gelatinosa, H. orientalis, H. vinosa*, and *H. citrina*), a *Fusarium* strain (e.g., *F. oxysporum, F. roseum*, and *F. venenatum*), a *Neurospora* strain (e.g., *N. crassa*) and a *Humicola* strain (e.g., *H. grisea, H. insolens* and *H. lanuginose*), a *Penicillium* strain (e.g., *P. notatum* or *P. chrysogenum*), or a *Saccharomycopsis* strain (e.g., *S. fibuligera*).

In some embodiments, the parent glucoamylase may be a bacterial glucoamylase. For example, the polypeptide may be obtained from a gram-positive bacterial strain such as Bacillus (e.g., *B. alkalophilus*, *B. amyloliquefaciens*, *B. lentus*, *B. licheniformis*, *B. stearothermophilus*, *B. subtilis* and *B. thuringiensis*) or a *Streptomyces* strain (e.g., *S. lividans*).

In some embodiments, the parent glucoamylase will comprise a catalytic domain having at least about 80%, about 85%, about 90%, about 93%, about 95%, about 97%, about 98%, or about 99% sequence identity with the catalytic domain of the TrGA amino acid sequence of SEQ ID NO: 3.

In other embodiments, the parent glucoamylase will comprise a catalytic domain having at least about 90%, about 93%, about 95%, about 96%, about 97%, about 98%, or about 99% sequence identity with the catalytic domain of the *Aspergillus* parent glucoamylase of SEQ ID NO: 5 or SEQ ID NO: 6.

In yet other embodiments, the parent glucoamylase will comprise a catalytic domain having at least about 90%, about 95%, about 97%, or about 99% sequence identity with the catalytic domain of the *Humicola grisea* (HgGA) parent glucoamylase of SEQ ID NO: 8.

In some embodiments, the parent glucoamylase will comprise a starch binding domain having at least about 80%, about 85%, about 90%, about 95%, about 97%, or about 98% sequence identity with the starch binding domain of the TrGA amino acid sequence of SEQ ID NO: 1, 2, or 11.

In other embodiments, the parent glucoamylase will comprise a starch binding domain having at least about 90%, about 95%, about 97%, or about 99% sequence identity with the catalytic domain of the *Humicola grisea* (HgGA) glucoamylase of SEQ ID NO: 385.

In other embodiments, the parent glucoamylase will comprise a starch binding domain having at least about 90%, about 95%, about 97%, or about 99% sequence identity with the catalytic domain of the *Thielavia terrestris* (TtGA) glucoamylase of SEQ ID NO: 390.

In other embodiments, the parent glucoamylase will comprise a starch binding domain having at least about 90%, about 95%, about 97%, or about 99% sequence identity with the catalytic domain of the *Thermomyces lanuginosus* (ThGA) glucoamylase of SEQ ID NO: 386.

In other embodiments, the parent glucoamylase will comprise a starch binding domain having at least about 90%, about 95%, about 97%, or about 99% sequence identity with the catalytic domain of the *Talaromyces emersoniit* (TeGA) glucoamylase of SEQ ID NO: 387.

In yet other embodiments, the parent glucoamylase will comprise a starch binding domain having at least about 90%, about 93%, about 95%, about 96%, about 97%, about 98%, or about 99% sequence identity with the starch binding domain of the *Aspergillus* parent glucoamylase of SEQ ID NO: 388 or 389.

In some embodiments, the parent glucoamylase will have at least about 80%, about 85%, about 88%, about 90%, about 93%, about 95%, about 96%, about 97%, about 98%, or about 99% sequence identity with the TrGA amino acid sequence of SEQ ID NO: 1 or 2.

In further embodiments, a *Trichoderma* glucoamylase homologue will be obtained from a *Trichoderma* or *Hypocrea* strain. Some typical *Trichoderma* glucoamylase homologues are described in U.S. Pat. No. 7,413,887 and reference is made specifically to amino acid sequences set forth in SEQ ID NOs: 17-22 and 43-47 of the reference.

In some embodiments, the parent glucoamylase is TrGA comprising the amino acid sequence of SEQ ID NO: 2, or a *Trichoderma* glucoamylase homologue having at least about 80%, about 85%, about 88%, about 90%, about 93%, about 95%, about 96%, about 97%, about 98%, or about 99% sequence identity to the TrGA sequence (SEQ ID NO: 2).

A parent glucoamylase can be isolated and/or identified using standard recombinant DNA techniques. Any standard techniques can be used that are known to the skilled artisan. For example, probes and/or primers specific for conserved regions of the glucoamylase can be used to identify homologs in bacterial or fungal cells (the catalytic domain, the active site, etc.). Alternatively, degenerate PCR can be used to identify homologues in bacterial or fungal cells. In some cases, known sequences, such as in a database, can be analyzed for sequence and/or structural identity to one of the known glucoamylases, including SEQ ID NO: 2, or a known starch binding domains, including SEQ ID NO: 11. Functional assays can also be used to identify glucoamylase activity in a bacterial or fungal cell. Proteins having glucoamylase activity can be isolated and reverse sequenced to isolate the corresponding DNA sequence. Such methods are known to the skilled artisan.

3. Glucoamylase Structural Homology

The central dogma of molecular biology is that the sequence of DNA encoding a gene for a particular enzyme, determines the amino acid sequence of the protein, this sequence in turn determines the three-dimensional folding of the enzyme. This folding brings together disparate residues that create a catalytic center and substrate binding surface and this results in the high specificity and activity of the enzymes in question.

Figure 6:
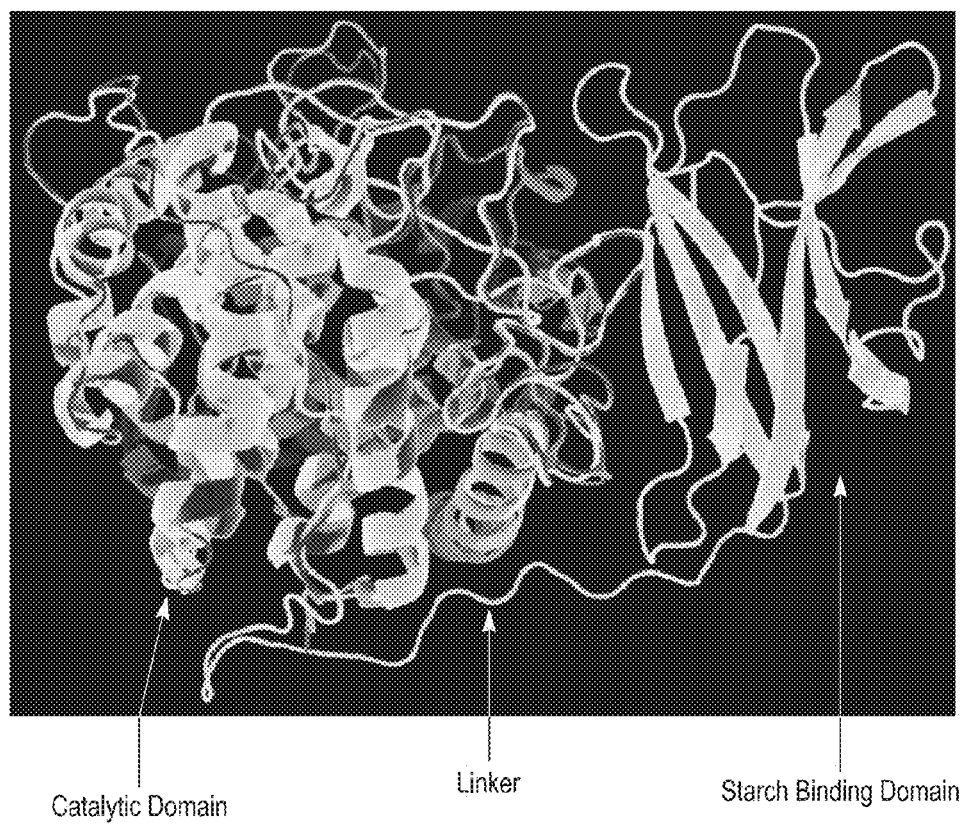
FIG. 6 depicts a comparison of the three dimensional structure of *Trichoderma reesei* glucoamylase (black) (SEQ ID NO: 2) and *Aspergillus awamori* glucoamylase (grey) (SEQ ID NO: 5) viewed from the side. The side is measured in reference to the active site and the active site entrance is at the "top" of the molecule.
Figure 7:
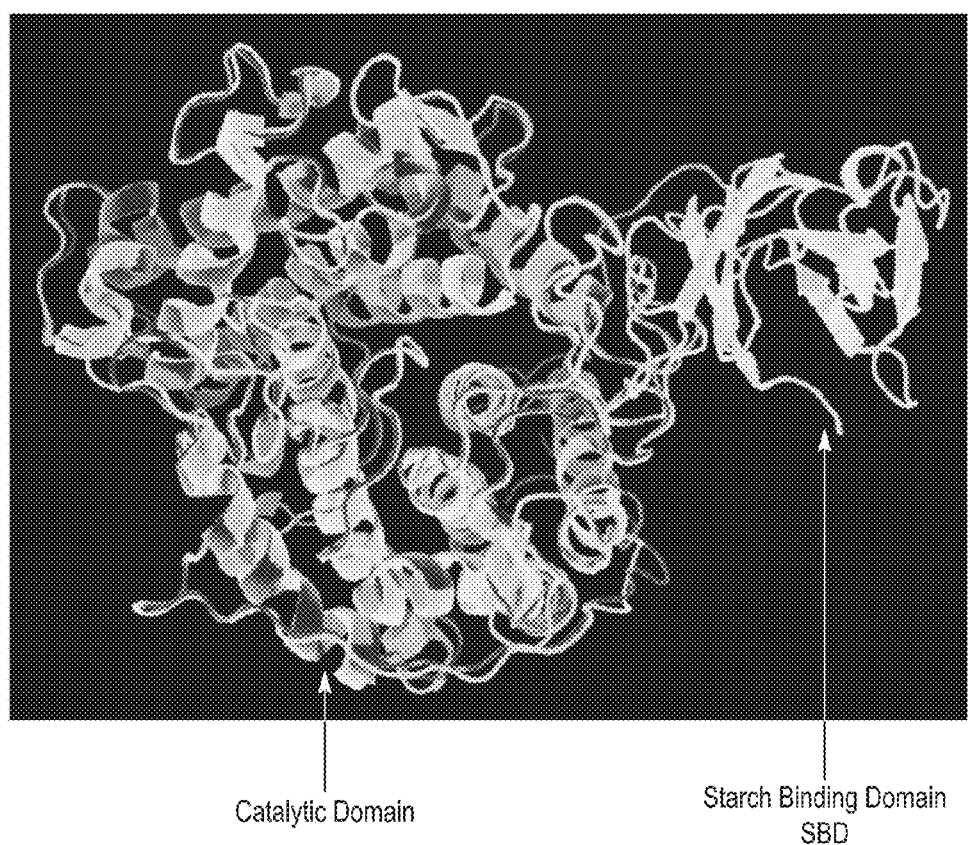
FIG. 7 depicts a comparison of the three dimensional structures of *Trichoderma reesei* glucoamylase (black) (SEQ ID NO: 2) and *Aspergillus awamori* glucoamylase (grey) (SEQ ID NO: 5) viewed from the top.

Glucoamylases consist of as many as three distinct structural domains, a catalytic domain of approximately 450 residues that is structurally conserved in all glucoamylases, generally followed by a linker region consisting of between 30 and 80 residues that are connected to a starch binding domain of approximately 100 residues. The structure of the *Trichoderma reesei* glucoamylase with all three regions intact was determined to 1.8 Angstrom resolution herein (see Table 20 in WO2009/067218 (Danisco US Inc., Genencor Division) page 94-216 incorporated herein by reference and Example 11 in WO2009/067218 (Danisco US Inc., Genencor Division) page 89-93 incorporated herein by reference). Using the coordinates (see Table 20 in WO2009/067218 (Danisco US Inc., Genencor Division) page 94-216 incorporated herein by reference), the structure was aligned with the coordinates of the catalytic domain of the glucoamylase from *Aspergillus awamori* strain X100 that was determined previously (Aleshin, A. E., Hoffman, C., Firsov, L. M., and Honzatko, R. B. Refined crystal structures of glucoamylase from *Aspergillus awamori* var.×100. *J. Mol. Biol.* 238: 575-591 (1994)). The *Aspergillus awamori* crystal structure only included the catalytic domain. As seen in FIGS. 6-7, the structure of the catalytic domains overlap very closely, and it is possible to identify equivalent residues based on this structural superposition. It is believed that all glucoamylases share the basic structure depicted in FIGS. 6-7.

The catalytic domain of TrGA thus has approximately 450 residues such as residues 1-453 of TrGA SEQ ID NO:2 and is a twelve helix double barrel domain. The helices and loops of the catalytic domain can be defined in terms of the residues of TrGA with SEQ ID NO:2 forming them:

| helix 1 | residues 2-20, |
|---|---|
| loop 1 | residues 21-51, |
| helix 2 | residues 52-68, |

| loop 2 | residues 69-71, |
|---|---|
| helix 3 | residues 72-90, |
| loop 3 | residues 91-125, |
| helix 4 | residues 126-145, |
| loop 4 | residues 146, |
| helix 5 | residues 147-169, |
| helix 6 | residues 186-206, |
| loop 6 | residues 207-210, |
| helix 7 | residues 211-227, |
| loop 7 | residues 211-227, |
| helix 8 | residues 250-275, |
| loop 8 | residues 260-275, |
| helix 9 | residues 276-292, |
| loop 9 | residues 293-321, |
| helix 10 | residues 322-342, |
| loop 10 | residues 343-371, |
| helix 11 | residues 372-395, |
| loop 11 | residues 396-420, |
| helix 12 | residues 421-434, |
| loop 12 | residues 435-443, |
| helix 13 | residues 444-447, |
| loop 13 | residues 448-453 |

The linker domain has between 30 and 80 residues such as residues 454-490 of TrGA with SEQ ID NO: 2.

The starch binding domain of TrGA has approximately 100 residues such as residues 496-596 of TrGA with SEQ ID NO:2 consisting of the beta sandwich composed of two twisted three stranded sheets. The sheets, helices and loops of the starch binding domain can be defined in terms of the residues of TrGA with SEQ ID NO:2 forming them:

| sheet 1' | residues 496-504, |
|---|---|
| loop 1' | residues 505-511, |
| sheet 2' | residues 512-517, |
| interconnecting loop 2' | residues 518-543, |
| sheet 3' | residues 544-552, |
| loop 3' | residues 553, |
| sheet 4' | residues 554-565, |
| loop 4' | residues 566-567, |
| sheet 5' | residues 568-572, |
| inter-sheet segment | residues 573-577, |
| sheet 5a' | residues 578-582, |
| loop 5' | residues 583-589, |
| sheet 6' | residues 590-596, |

It is possible to identify equivalent residues based on structural superposition in other glucoamylases as described in further detail below.

FIG. 6 is a comparison of the three dimensional structures of the *Trichoderma reesei* glucoamylase (black) of SEQ ID NO: 2 and of *Aspergillus awamorii* glucoamylase (grey) viewed from the side. In this view, the relationship between the catalytic domain and the linker region and the starch binding domain can be seen.

FIG. 7 is a comparison of the three dimensional structures of the *Trichoderma reesei* glucoamylase (black) of SEQ ID NO: 2 and of *Aspergillus awamorii* glucoamylase (grey) viewed from the top. The glucoamylases shown here and indeed all known glucoamylases to date share this structural homology. The conservation of structure correlates with the conservation of activity and a conserved mechanism of action for all glucoamylases. Given this high homology, changes resulting from site specific variants of the *Trichoderma* glucoamylase resulting in altered functions would also have similar structural and therefore functional consequences in other glucoamylases. Therefore, the teachings of which variants result in desirable benefits can be applied to other glucoamylases.

Figure 8:
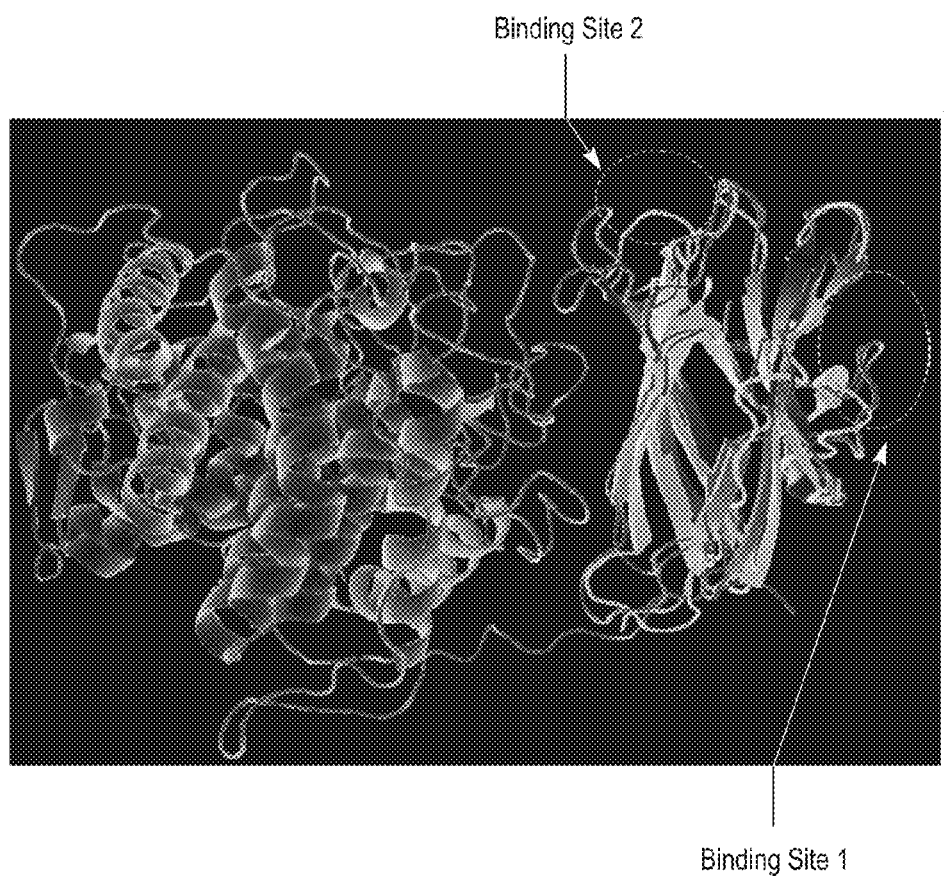
FIG. 8 depicts an alignment of the three dimensional structures of TrGA (SEQ ID NO: 2) and AnGA (SEQ ID NO: 6) viewed from the side showing binding sites 1 and 2.

A further crystal structure was produced using the coordinates in Table 20 in WO2009/067218 (Danisco US Inc., Genencor Division) page 94-216 incorporated herein by reference for the Starch Binding Domain (SBD). The SBD for TrGA was aligned with the SBD for *A. niger*. As shown in FIG. 8, the structure of the *A. niger* and TrGA SBDs overlaps very closely. It is believed that while all starch binding domains share at least some of the basic structure depicted in FIG. 8, some SBDs are more structurally similar than others. For example, the TrGA SBD can be classified as within the carbohydrate binding module 20 family within the CAZY database (cazy.org). The CAZY database describes the families of structurally-related catalytic and carbohydrate-binding modules (or functional domains) of enzymes that degrade, modify, or create glycosidic bonds. Given a high structural homology, site specific variants of the TrGA SBD resulting in altered function would also have similar structural and therefore functional consequences in other glucoamylases having SBDs with similar structure to that of the TrGA SBD, particularly those classified within the carbohydrate binding module 20 family. Thus, the teachings of which variants result in desirable benefits can be applied to other SBDs having structural similarity.

Thus, the amino acid position numbers discussed herein refer to those assigned to the mature *Trichoderma reesei* glucoamylase sequence presented in FIG. 1 (SEQ ID NO: 2). The present disclosure, however, is not limited to the variants of *Trichoderma* glucoamylase, but extends to glucoamylases containing amino acid residues at positions that are "equivalent" to the particular identified residues in *Trichoderma reesei* glucoamylase (SEQ ID NO: 2). In some embodiments of the present disclosure, the parent glucoamylase is a *Talaromyces* GA and the substitutions are made at the equivalent amino acid residue positions in *Talaromyces* glucoamylase (see e.g., SEQ ID NO: 12) as those described herein. In other embodiments, the parent glucoamylase comprises SEQ ID NOs: 5-9 (see FIGS. 5A and 5B). In further embodiments, the parent glucoamylase is a *Penicillium* glucoamylase, such as *Penicillium chrysogenum* (see e.g., SEQ ID NO: 13).

"Structural identity" determines whether the amino acid residues are equivalent. Structural identity is a one-to-one topological equivalent when the two structures (three dimensional and amino acid structures) are aligned. A residue (amino acid) position of a glucoamylase is "equivalent" to a residue of *T. reesei* glucoamylase if it is either homologous (i.e., corresponding in position in either primary or tertiary structure) or analogous to a specific residue or portion of that residue in *T. reesei* glucoamylase (having the same or similar functional capacity to combine, react, or interact chemically).

In order to establish identity to the primary structure, the amino acid sequence of a glucoamylase can be directly compared to *Trichoderma reesei* glucoamylase primary sequence and particularly to a set of residues known to be invariant in glucoamylases for which sequence is known. For example, FIGS. 5A and 5B herein show the conserved residues between glucoamylases. FIGS. 5D and 5E show an alignment of starch binding domains from various glucoamylases. After aligning the conserved residues, allowing for necessary insertions and deletions in order to maintain alignment (i.e. avoiding the elimination of conserved residues through arbitrary deletion and insertion), the residues equivalent to particular amino acids in the primary sequence of *Trichoderma reesei* glucoamylase are defined. Alignment of conserved residues typically should conserve 100% of such residues. However, alignment of greater than about 75% or as little as about 50% of conserved residues is also adequate to define equivalent residues. Further, the structural identity can be used in combination with the sequence identity to identify equivalent residues.

For example, in FIGS. 5A and 5B, the catalytic domains of glucoamylases from six organisms are aligned to provide the maximum amount of homology between amino acid sequences. A comparison of these sequences shows that there are a number of conserved residues contained in each sequence as designated by an asterisk. These conserved residues, thus, may be used to define the corresponding equivalent amino acid residues of *Trichoderma reesei* glucoamylase in other glucoamylases such as glucoamylase from *Aspergillus niger*. Similarly, FIGS. 5D and 5E show the starch binding domains of glucoamylases from seven organisms aligned to identify equivalent residues.

Structural identity involves the identification of equivalent residues between the two structures. "Equivalent residues" can be defined by determining homology at the level of tertiary structure (structural identity) for an enzyme whose tertiary structure has been determined by X-ray crystallography. Equivalent residues are defined as those for which the atomic coordinates of two or more of the main chain atoms of a particular amino acid residue of the *Trichoderma reesei* glucoamylase (N on N, CA on CA, C on C and O on O) are within 0.13 nm and optionally 0.1 nm after alignment. In one aspect, at least 2 or 3 of the four possible main chain atoms are within 0.1 nm after alignment. Alignment is achieved after the best model has been oriented and positioned to give the maximum overlap of atomic coordinates of non-hydrogen protein atoms of the glucoamylase in question to the *Trichoderma reesei* glucoamylase. The best model is the crystallographic model giving the lowest R factor for experimental diffraction data at the highest resolution available.

$$R \text{ factor} = \frac{\sum_h |Fo(h)| - |Fc(h)|}{\sum_h |Fo(h)|}$$

Equivalent residues that are functionally analogous to a specific residue of *Trichoderma reesei* glucoamylase are defined as those amino acids of the enzyme that may adopt a conformation such that they either alter, modify or contribute to protein structure, substrate binding or catalysis in a manner defined and attributed to a specific residue of the *Trichoderma reesei* glucoamylase. Further, they are those residues of the enzyme (for which a tertiary structure has been obtained by X-ray crystallography) that occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Trichoderma reesei* glucoamylase. The coordinates of the three dimensional structure of *Trichoderma reesei* glucoamylase are set forth in Table 20 in WO2009/067218 (Danisco US Inc., Genencor Division) page 94-216 incorporated herein by reference and can be used as outlined above to determine equivalent residues on the level of tertiary structure.

Some of the residues identified for substitution are conserved residues whereas others are not. In the case of residues that are not conserved, the substitution of one or more amino acids is limited to substitutions that produce a variant that has an amino acid sequence that does not correspond to one found in nature. In the case of conserved residues, such substitutions should not result in a naturally-occurring sequence.

4. Glucoamylase Variants

The variants according to the disclosure include at least one substitution, deletion or insertion in the amino acid sequence of a parent glucoamylase that makes the variant different in sequence from a parent glucoamylase. In some embodiments, the variants of the disclosure will have at least about 20%, about 40%, about 50%, about 60%, about 70%, about 80%, about 85%, about 90%, about 95%, about 97%, or about 100% of the glucoamylase activity as that of the TrGA (SEQ ID NO: 2), a parent glucoamylase that has at least 80% sequence identity to TrGA (SEQ ID NO: 2). In some embodiments, the variants according to the disclosure will comprise a substitution, deletion or insertion in at least one amino acid position of the parent TrGA (SEQ ID NO: 2), or in an equivalent position in the sequence of another parent glucoamylase having at least about 80%, about 85%, about 90%, about 95%, about 97%, about 98%, or about 99% sequence identity to the TrGA sequence (SEQ ID NO: 2).

In other embodiments, the variant according to the disclosure will comprise a substitution, deletion or insertion in at least one amino acid position of a fragment of the parent TrGA, wherein the fragment comprises the catalytic domain of the TrGA sequence (SEQ ID NO: 3) or in an equivalent position in a fragment comprising the catalytic domain of a parent glucoamylase having at least about 80%, about 85%, about 90%, about 95%, about 97%, about 98%, or about 99% sequence identity to the catalytic-domain-containing fragment of the SEQ ID NO: 3, 5, 6, 7, 8, or 9. In some embodiments, the fragment will comprise at least about 400, about 425, about 450, or about 500 amino acid residues of TrGA catalytic domain (SEQ ID NO: 3).

In other embodiments, the variant according to the disclosure will comprise a substitution, deletion or insertion in at least one amino acid position of a fragment of the parent TrGA, wherein the fragment comprises the starch binding domain of the TrGA sequence (SEQ ID NO: 11) or in an equivalent position in a fragment comprising the starch binding domain of a parent glucoamylase having at least about 80%, about 85%, about 90%, about 95%, about 97%, about 98%, or about 99% sequence identity to the starch-binding-domain-containing fragment of SEQ ID NO: 11, 385, 386, 387, 388, 389, and 390. In some embodiments, the fragment will comprise at least about 40, about 50, about 60, about 70, about 80, about 90, about 100, or about 109 amino acid residues of TrGA starch binding domain (SEQ ID NO: 11).

In some embodiments, when the parent glucoamylase includes a catalytic domain, a linker region, and a starch binding domain, the variant will comprise a substitution, deletion or insertion in at least one amino acid position of a fragment comprising part of the linker region. In some embodiments, the variant will comprise a substitution deletion, or insertion in the amino acid sequence of a fragment of the TrGA sequence (SEQ ID NO: 2).

Structural identity with reference to an amino acid substitution means that the substitution occurs at the equivalent amino acid position in the homologous glucoamylase or parent glucoamylase. The term equivalent position means a position that is common to two parent sequences that is based on an alignment of the amino acid sequence of the parent glucoamylase in question as well as alignment of the three-dimensional structure of the parent glucoamylase in question with the TrGA reference glucoamylase amino acid sequence and three-dimensional sequence. For example, with reference to FIG. 5A, position 24 in TrGA (SEQ ID NO: 2 or 3) is D24 and the equivalent position for *Aspergillus niger* (SEQ ID NO: 6) is position D25, and the equivalent position for *Aspergillus oryzea* (SEQ ID NO: 7) is position D26. See FIGS. 6 and 7 for an exemplary alignment of the three-dimensional sequence.

Accordingly, in one aspect, a glucoamylase variant is described, which glucoamylase variant when in its crystal form has a crystal structure for which the atomic coordinates of the main chain atoms have a root-mean-square deviation from the atomic coordinates of the equivalent main chain atoms of TrGA (as defined in Table 20 in WO2009/067218) of less than 0.13 nm following alignment of equivalent main chain atoms, and which have a linker region, a starch binding domain and a catalytic domain, said variant comprising two or more amino acid substitutions relative to the amino acid sequence of the parent glucoamylase in interconnecting loop 2' of the starch binding domain, and/or in loop 1, and/or in helix 2, and/or in loop 11, and/or in helix 12 of the catalytic domain. In a further aspect, the root-mean-square deviation from the atomic coordinates of the equivalent main chain atoms of TrGA (as defined in Table 20 in WO2009/067218) is less than 0.12 nm, such as less than 0.11 or such as less than 0.10.

In one aspect, a glucoamylase variant is described, which glucoamylase variant comprises a starch binding domain and a catalytic domain, said variant comprising two or more amino acid substitutions relative to the amino acid sequence of SEQ ID NO:2 or equivalent parent glucoamylase in interconnecting loop 2', and/or in loop 1, and/or in helix 2, and/or in loop 11, and/or in helix 12 for reducing the synthesis of condensation products during hydrolysis of starch.

In a further aspect, a glucoamylase variant is described, which glucoamylase variant comprises two or more amino acid substitutions relative to interconnecting loop 2' with the amino acid sequence from position 518 to position 543 of SEQ ID NO:2 or equivalent sequence of residues in a parent glucoamylase, and/or loop 1 with the amino acid sequence from position 21 to position 51 of SEQ ID NO:2 or equivalent sequence of residues in a parent glucoamylase, and/or helix 2 with the amino acid sequence from position 52 to position 68 of SEQ ID NO:2 or equivalent sequence of residues in a parent glucoamylase, and/or loop 11 with the amino acid sequence from position 396 to position 420 of SEQ ID NO:2 or equivalent sequence of residues in a parent glucoamylase, and/or helix 12 with the amino acid sequence from position 421 to position 434 of SEQ ID NO:2 or equivalent sequence of residues in a parent glucoamylase.

In a further aspect, a glucoamylase variant is described, which glucoamylase variant comprises two or more amino acid substitutions relative to the amino acid sequence from position 518 to position 543 of SEQ ID NO:2 or equivalent sequence of residues in a parent glucoamylase, and/or the amino acid sequence from position 21 to position 51 of SEQ ID NO:2 or equivalent sequence of residues in a parent glucoamylase, and/or the amino acid sequence from position 52 to position 68 of SEQ ID NO:2 or equivalent sequence of residues in a parent glucoamylase, and/or the amino acid sequence from position 396 to position 420 of SEQ ID NO:2 or equivalent sequence of residues in a parent glucoamylase, and/or the amino acid sequence from position 421 to position 434 of SEQ ID NO:2 or equivalent sequence of residues in a parent glucoamylase.

In one aspect, the two or more amino acid substitutions are relative to the interconnecting loop 2' with the amino acid sequence from position 518 to position 543 e.g. in one or more of positions 518, 519, 520, 521, 522, 523, 524, 525, 526, 527, 528, 529, 530, 531, 532, 533, 534, 535, 536, 537, 538, 539, 540, 541, 542 and/or 543 of SEQ ID NO:2, and/or loop 1 with the amino acid sequence from position 21 to position 51 e.g. in one or more of positions 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 and/or 51 of SEQ ID NO:2, and/or helix 2 with the amino acid sequence from position 52 to position 68 e.g. in one or more of positions 52, 53, 54, 55, 56, 57, 58, 59, 60, 61, 62, 63, 64, 65, 66, 67 and/or 68 of SEQ ID NO:2, and/or loop 11 with the amino acid sequence from position 396 to position 420 e.g. in one or more of positions 396, 397, 398, 399, 400, 401, 402, 403, 404, 405, 406, 407, 408, 409, 410, 411, 412, 413, 414, 415, 416, 417, 418, 419 and/or 420 of SEQ ID NO:2, and/or helix 12 with the amino acid sequence from position 421 to position 434 e.g. in one or more of positions 421, 422, 423, 424, 425, 426, 427, 428, 429, 430, 431, 432, 433 and/or 534 of SEQ ID NO:2.

In a further aspect, the two or more amino acid substitutions are at least one amino acid substitution in the interconnecting loop 2' and at least one amino acid substitution in loop 1 and/or helix 2 and/or loop 11 and/or helix 12. In a further aspect, the two or more amino acid substitutions are 1, 2, 3 or 4 amino acid substitutions in the interconnecting loop 2' and 1, 2, 3 or 4 amino acid substitutions in loop 1 and/or helix 2 and/or loop 11 and/or helix 12.

In a further aspect, the two or more amino acid substitutions are at least one amino acid substitution in interconnecting loop 2' and at least one amino acid substitution in loop 1. In a further aspect, the two or more amino acid substitutions are at least one amino acid substitution in interconnecting loop 2' and at least one amino acid substitution in helix 2. In a further aspect, the two or more amino acid substitutions are at least one amino acid substitution in interconnecting loop 2' and at least one amino acid substitution in loop 11. In a further aspect, the two or more amino acid substitutions are at least one amino acid substitution in interconnecting loop 2' and at least one amino acid substitution in helix 12. In a further aspect, the two or more amino acid substitutions are at least one amino acid substitution in interconnecting loop 2' and at least one amino acid substitution in loop 1 and at least one amino acid substitution in helix 2. In a further aspect, the glucoamylase variant has at least one amino acid substitution within position 520-543, 530-543, or 534-543 of interconnecting loop 2', the positions corresponding to the respective position in SEQ ID NO:2 or equivalent positions in a parent glucoamylase. In a further aspect, the glucoamylase variant has at least one amino acid substitution within the amino acid sequence of position 30-50, 35-48, or 40-46 of loop 1, the positions corresponding to the respective position in SEQ ID NO:2 or equivalent positions in a parent glucoamylase. In a further aspect, the glucoamylase variant has at least one amino acid substitution within the amino acid sequence of position 50-66, 55-64, or 58-63 of helix 2, the positions corresponding to the respective position in SEQ ID NO:2 or equivalent positions in a parent glucoamylase. In a further aspect, the glucoamylase variant has at least one amino acid substitution within the amino acid sequence of position 405-420, 410-420, or 415-420 of loop 11, the positions corresponding to the respective position in SEQ ID NO:2 or equivalent positions in a parent glucoamylase. In a further aspect, the glucoamylase variant has at least one amino acid substitution within the amino acid sequence of position 421-434, 425-434, or 428-434 of helix 12, the positions corresponding to the respective position in SEQ ID NO:2 or equivalent positions in a parent glucoamylase.

In one aspect, the glucoamylase variant comprises two or more amino acid substitutions, wherein an amino acid substitution is in position 539 and an amino acid substitution is in position 44, the positions corresponding to the respective position in SEQ ID NO:2 or an equivalent position in a parent glucoamylase, and which sequence has at least 80% sequence identity to the parent glucoamylase, and wherein the amino acid substitution in position 44 is not 44C.

In a further aspect, the glucoamylase variant comprises two or more amino acid substitutions, wherein an amino acid substitution is in position 539 and an amino acid substitution is 44R, the positions corresponding to the respective position in SEQ ID NO:2 or an equivalent position in a parent glucoamylase. In a further aspect, the glucoamylase variant comprises an amino acid substitution in position 61, the position corresponding to the respective position in SEQ ID NO:2 or an equivalent position in a parent glucoamylase. In a further aspect, the amino acid substitution in position 539 is 539R, the position corresponding to the respective position in SEQ ID NO:2 or an equivalent position in a parent glucoamylase. In a further aspect, the amino acid substitution in position 44 is 44R, the position corresponding to the respective position in SEQ ID NO:2 or an equivalent position in a parent glucoamylase. In a further aspect, the amino acid substitution in position 61 is 61I, the position corresponding to the respective position in SEQ ID NO:2 or an equivalent position in a parent glucoamylase.

In a further aspect, the glucoamylase variant comprises the following amino acid substitutions:
a) D44R and A539R; or
b) D44R, N61I and A539R,
the positions corresponding to the respective position in SEQ ID NO:2 or an equivalent position in a parent glucoamylase.

In a further aspect, the glucoamylase variant consist of SEQ ID NO:2 and has the following amino acid substitutions:
a) D44R and A539R; or
b) D44R, N61I and A539R,
the positions corresponding to the respective position in SEQ ID NO:2.

In a further aspect, the glucoamylase variant has a starch binding domain that has at least 96%, 97%, 98%, 99%, or 99.5% sequence identity with the starch binding domain of SEQ ID NO: 1, 2, 11, 385, 386, 387, 388, 389, or 390. In a further aspect, the glucoamylase variant has a catalytic domain that has at least 80%, 85%, 90%, 95%, or 99.5% sequence identity with the catalytic domain of SEQ ID NO: 1, 2, 3, 5, 6, 7, 8, or 9.

In a further aspect, the parent glucoamylase is a fungal glucoamylase.

In a further aspect, the parent glucoamylase is selected from a glucoamylase obtained from a *Trichoderma* spp., an *Aspergillus* spp., a *Humicola* spp., a *Penicillium* spp., a *Talaromycese* spp., or a *Schizosaccharmyces* spp.

In a further aspect, the parent glucoamylase is obtained from a *Trichoderma* spp. or an *Aspergillus* spp.

In a further aspect, the glucoamylase has been purified. The glucoamylases of the present disclosure may be recovered or purified from culture media by a variety of procedures known in the art including centrifugation, filtration, extraction, precipitation and the like.

In some embodiments, the glucoamylase variant will include at least two substitutions in the amino acid sequence of a parent. In further embodiments, the variant may have more than two substitutions. For example, the variant may have 2, 3, 4, 5, 6, 7, 8, 9, 10, 15, 20, or 25 amino acid substitutions, deletions, or insertions as compared to a corresponding parent glucoamylase.

In some embodiments, a glucoamylase variant comprises a substitution, deletion or insertion, and typically a substitution in at least one amino acid position in a position corresponding to the regions of non-conserved amino acids as illustrated in FIGS. 5A, 5B, 5D, and 5E (e.g., amino acid positions corresponding to those positions that are not designated by "*" in FIGS. 5A, 5B, 5D, and 5E).

While the variants may have substitutions in any position of the mature protein sequence (SEQ ID NO: 2), in some embodiments, a glucoamylase variant comprises two or more substitutions in the following positions in the amino acid sequence set forth in SEQ ID NO: 2: 23, 42, 43, 44, 59, 60, 61, 65, 67, 68, 410, 417, 418, 430, 431, 433, 518, 519, 520, 527, 531, 535, 536, 537 or 539, or in an equivalent position in a parent glucoamylase. In a further aspect, the glucoamylase variant comprises one or more further substitutions in the following positions in the amino acid sequence set forth in SEQ ID NO: 2: 10, 14, 15, 72, 73, 97, 98, 99, 102, 110, 113, 114, 133, 140, 144, 145, 147, 152, 153, 164, 182, 204, 205, 214, 216, 219, 228, 229, 230, 231, 236, 239, 241, 242, 263, 264, 265, 268, 269, 276, 284, 291, 294, 300, 301, 303, 311, 338, 342, 344, 346, 349, 359, 361, 364, 375, 379, 382, 390, 391, 393, 394, 436, 442, 444, 448, 451, 493, 494, 495, 502, 503, 508, 511, 563, or 577, or in an equivalent position in a parent glucoamylase. In some embodiments, the parent glucoamylase will have at least about 50%, about 60%, about 70%, about 80%, about 90%, about 95%, about 96%, about 97%, about 98%, or about 99% sequence identity with SEQ ID NO: 2. In other embodiments, the parent glucoamylase will be a *Trichoderma* glucoamylase homologue. In some embodiments, the variant will have altered properties. In some embodiments, the parent glucoamylase will have structural identity with the glucoamylase of SEQ ID NO: 2.

In some embodiments, the glucoamylase variant comprises two or more substitutions in the following positions in the amino acid sequence set forth in SEQ ID NO: 2: P23, T42, I43, D44, P45, D46, F59, K60, N61, T67, E68, R408, S410, S415, L417, H418, T430, A431, R433, N518, A519, A520, T527, V531, A535, V536, N537, and A539 or an equivalent position in parent glucoamylase (e.g., a *Trichoderma* glucoamylase homologue). In a further aspect, the glucoamylase variant comprises one or more substitutions in the following positions in the amino acid sequence set forth in SEQ ID NO: 2: T10, L14, N15, A72, G73, S97, L98, A99, S102, K108, E110, L113, K114, R122, Q124, R125, I133, K140, N144, N145, Y147, S152, N153, N164, F175, N182, A204, T205, S214, V216, Q219, W228, V229, S230, S231, D236, I239, N240, T241, N242, G244, N263, L264, G265, A268, G269, D276, V284, 5291, G294, P300, A301, A303, Y310, A311, D313, Y316, V338, T342, 5344, T346, A349, V359, G361, A364, T375, N379, S382, S390, E391, A393, K394, I436, A442, N443, S444, T448, S451, T493, P494, T495, H502, E503, Q508, Q511, N563, and N577 or in an equivalent position in a parent glucoamylase. In some embodiments, the variant will have altered properties as compared to the parent glucoamylase.

In some embodiments, the glucoamylase variant may differ from the parent glucoamylase only at the specified positions.

In further embodiments, the variant of a glucoamylase parent comprises at least two of the following substitutions in the following positions in an amino acid sequence set forth in SEQ ID NO: 2: T42V, I43Q/R, D44R/C, N61I, T67M, E68C/M, L417K/R/V, T430A/K, A431I/L/Q, R433C/E/G/L/N/S/V/Y, A519I/K/R/Y, A520C/L/P, V531L, A535K/N/P/R, V536M, or A539E/R/S, or a substitution in an equivalent position in a parent glucoamylase. In a further aspect, the glucoamylase variant comprises one or more substitutions in the following positions in the amino acid sequence set forth in SEQ ID NO: 2: T10S, A72Y, G73F/W, S97N, S102A/M/R, K114M/Q, I133T/V, N145I, N153A/D/E/M/S/V, T205Q, Q219S, W228A/F/H/M/V, V229I/L, S230C/F/G/L/N/Q/R, S231L/V, D236R, I239V/Y, N263P, L264D/K, A268C/D/G/K, S291A/F/H/M/T, g294c, A301P/R, V338I/N/Q, T342V, S344M/P/Q/R/V, G361D/E/F/I/L/M/P/S/W/Y, A364D/E/F/G/K/L/M/R/S/T/V/W, T375N, K394S, I436H, T451K, T495K/M/S, E503A/C/V, Q508R, Q511H, N563C/E/I/K/K/Q/T/V, or N577K/P/R, or in an equivalent position in a parent glucoamylase.

In further embodiments, the glucoamylase variant comprises one of the following sets of substitutions, at the relevant positions of SEQ ID NO: 2, or at equivalent positions in a parent glucoamylase:
N61I/L417V/A431L/A539R;
I43Q/N61I/L417V/A431L/A539R;
N61I/L417V/A431L/A535R/A539R
I43Q/L417V/A431L/A535R/A539R;
I43Q/N61I/L417V/A431L/A535R/A539R;
I43Q/N61I/L417V/T430A/A431L/A535R/A539R;
I43Q/L417V/T430A/A431L/Q511H/A535R/A539R/N563I;
N61I/L417V/T430A/A431L/Q511H/A535R/A539R/N563I;
I43Q/N61I/L417V/T430A/A431L/Q511H/A535R/A539R/N563I;
I43R/N61I/L417V/A431L/A539R;
I43R/N61I/L417V/T430A/A431L/A535R/A539R;
G73F/L417R/E503V/A539R/N563K;
I43R/G73F/L417R/E503V/A539R/N563K; and
I43R/G73F/E503V/Q511H/N563K.

In further embodiments, the glucoamylase variant comprises one of the following sets of substitutions, at positions of SEQ ID NO: 2 or equivalent positions in a parent glucoamylase:
L417V/A431L/A539R;
I43Q/L417V/A431L/A539R;
L417V/A431L/A535R/A539R
I43R/L417V/A431L/A539R;
L417R/A431L/A539R; or
L417G/A431L/A539R;
wherein the glucoamylase variant does not have any further substitutions relative to the parent glucoamylase, and wherein the parent glucoamylase has a catalytic domain that has at least 80% sequence identity with SEQ ID NO: 1, 2, 3, 5, 6, 7, 8, or 9. Thus the parent glucoamylase may be any of those described elsewhere.

The parent glucoamylase may comprise a starch binding domain that has at least 95% sequence identity with SEQ ID NO: 1, 2, 11, 385, 386, 387, 388, 389, or 390. The parent glucoamylase may have at least 80% sequence identity with SEQ ID NO: 1 or 2; for example it may comprise SEQ ID NO: 1 or 2. Optionally the parent glucoamylase may consist of SEQ ID NO: 1 or 2.

Glucoamylase variants of the disclosure may also include chimeric or hybrid glucoamylases with, for example a starch binding domain (SBD) from one glucoamylase and a catalytic domain and linker from another. For example, a hybrid glucoamylase can be made by swapping the SBD from AnGA (SEQ ID NO: 6) with the SBD from TrGA (SEQ ID NO: 2), making a hybrid with the AnGA SBD and the TrGA catalytic domain and linker. Alternatively, the SBD and linker from AnGA can be swapped for the SBD and linker of TrGA.

In some aspects, the variant glucoamylase exhibits altered thermostability as compared to the parent glucoamylase. In some aspects, the altered thermostability may be increased thermostability as compared to the parent glucoamylase. In some embodiments, the altered property is altered specific activity compared to the parent glucoamylase. In some embodiments, the altered specific activity may be increased specific activity compared to the parent glucoamylase. In some embodiments, the altered property is increased thermostability at lower temperatures as compared to the parent glucoamylase. In some embodiments, the altered property is both increased specific activity and increased thermostability as compared to the parent glucoamylase.

In one embodiment, some variants may include the substitutions at positions:
D44R/N61I/A539R;
D44R/A539R;
I43Q/D44C/L417V/E503A/Q511H/A539R;
I43Q/L417V/E503A/Q511H/A539R;
I43Q/D44C/N61I/L417V/E503A/Q511H/A539R;
I43Q/N61I/L417V/E503A/Q511H/A539R;
I43R/L417V/E503A/Q511H/A539R;
I43R/N61I/L417V/E503A/Q511H/A539R;
I43R/L417R/E503A/A539R;
I43R/N61I/L417R/E503A/Q511H/A539R;
G73F/T430A/Q511H;
I43R/G73F/T430A;
G73F/T430A/E503V/Q511H;
D44C/G73F/N563K;
D44C/G73F/E503V/Q511H;
D44C/G73F/N563K;
D44C/G73F/L417R/N563K;
D44C/G73F/N563K;
I43R/T43 GA;
I43Q/T430A;
I43Q/T430A/Q511H;
D44C/L417R/N563K;
L417V/T430A/A431L/Q511H/A535R/A539R/N563I;
L417V/T430A/A431Q/Q511H/A535R/A539R/N563I;
L417V/T430A/Q511H/A535R/N563I;
L417V/T430A/Q511H/A539R/N563I;
G294C/L417R/A431L;
G294C/L417V/A431Q;
G294C/L417V/A431L/Q511H;
G294C/L417R/A431Q/Q511H;
L417R/A431L/Q511H;
L417V/A431Q/Q511H;
I43Q/T430A/Q511H/N61I;
I43Q/T430A/Q511H/L417V;
I43Q/T430A/Q511H/A431L;
I43Q/T430A/Q511H/E503A;
I43Q/T430A/Q511H/A539R;
I43Q/T430A/Q511H/N61I/A539R;
I43Q/T430A/Q511H/L417V/A539R;
I43Q/T430A/Q511H/A431L/A539R;
I43Q/T430A/Q511H/A431L/E503A;
I43Q/T430A/Q511H/N61I/A539R/A431L;
I43Q/T430A/Q511H/L417V/A539R/A431L;
I43Q/Q511H/N61I;
I43Q/Q511H/L417V;

I43Q/Q511H/A431L;
I43Q/Q511H/A539R;
I43Q/Q511H/A539R/N61I;
I43Q/Q511H/A539R/E503A;
I43Q/Q511H/A539R/T430M;
I43Q/Q511H/A539R/T430M/N61I;
I43Q/Q511H/A539R/T430M/N61I/L417V;
I43R/T430A/E503V/A535R/N563K;
D44R/E503A/Q511H/N563I;
E503A/N563I;
I43R/T430A/E503A/Q511H/N563K;
D44R/T430A/Q511H/A535R;
L417V/A431L/A539R;
L417V/A431L/A539R/I43Q;
L417V/A431L/A539R/N61I;
L417V/A431L/A539R/A535R;
L417V/A431L/A539R/I43Q/N61I;
L417V/A431L/A539R/N61I/A535R;
L417V/A431L/A539R/A535R/I43Q;
L417V/A431L/A539R/I43Q/N61I/A535R;
L417V/A431L/A539R/I43Q/N61I/A535R/T430A;
L417V/T430A/A431L/Q511H/A535R/A539R/N563I/ I43Q;
L417V/T430A/A431L/Q511H/A535R/A539R/N563I/ N61I;
L417V/T430A/A431L/Q511H/A535R/A539R/N563I/ I43Q/N61I;
L417V/A431L/A539R/I43R;
L417V/A431L/A539R/I43R/N61I;
L417V/A431L/A539R/I43R/N61I/A535R/T430A;
L417R/A431L/A539R;
L417G/A431L/A539R;
G73F/E503V/N563K/L417R/A539R;
G73F/E503V/N563K/I43R/L417R/A539R; and
G73F/E503V/N563K/I43R/Q511H
of SEQ ID NO: 2, or equivalent positions in parent glucoamylases and particularly *Trichoderma* glucoamylase homologues.

In a further embodiment, some variants may include the substitutions at positions:
D44R/N61I/A539R;
D44R/A539R;
I43Q/D44C/L417V/E503A/Q511H/A539R;
I43Q/L417V/E503A/Q511H/A539R;
I43Q/D44C/N61I/L417V/E503A/Q511H/A539R;
I43Q/N61I/L417V/E503A/Q511H/A539R;
I43R/L417V/E503A/Q511H/A539R;
I43R/N61I/L417V/E503A/Q511H/A539R;
I43R/L417R/E503A/A539R;
I43R/N61I/L417R/E503A/Q511H/A539R;
L417V/T430A/A431L/Q511H/A535R/A539R/N563I;
L417V/T430A/A431Q/Q511H/A535R/A539R/N563I;
L417V/T430A/Q511H/A539R/N563I;
I43Q/T430A/Q511H/A539R;
I43Q/T430A/Q511H/N61I/A539R;
I43Q/T430A/Q511H/L417V/A539R;
I43Q/T430A/Q511H/A431L/A539R;
I43Q/T430A/Q511H/N61I/A539R/A431L;
I43Q/T430A/Q511H/L417V/A539R/A431L;
I43Q/Q511H/A539R;
I43Q/Q511H/A539R/N61I;
I43Q/Q511H/A539R/E503A;
I43Q/Q511H/A539R/T430M;
I43Q/Q511H/A539R/T430M/N61I;
I43Q/Q511H/A539R/T430M/N61I/L417V;
L417V/A431L/A539R;
L417V/A431L/A539R/I43Q;
L417V/A431L/A539R/N61I;
L417V/A431L/A539R/A535R;
L417V/A431L/A539R/I43Q/N61I;
L417V/A431L/A539R/N61I/A535R;
L417V/A431L/A539R/A535R/I43Q;
L417V/A431L/A539R/I43Q/N61I/A535R;
L417V/A431L/A539R/I43Q/N61I/A535R/T430A;
L417V/T430A/A431L/Q511H/A535R/A539R/N563I/ I43Q;
L417V/T430A/A431L/Q511H/A535R/A539R/N563I/ N61I;
L417V/T430A/A431L/Q511H/A535R/A539R/N563I/ I43Q/N61I;
L417V/A431L/A539R/I43R;
L417V/A431L/A539R/I43R/N61I;
L417V/A431L/A539R/I43R/N61I/A535R/T430A;
L417R/A431L/A539R;
L417G/A431L/A539R;
G73F/E503V/N563K/L417R/A539R; and
G73F/E503V/N563K/I43R/L417R/A539R
of SEQ ID NO: 2, or equivalent positions in parent glucoamylases and particularly *Trichoderma* glucoamylase homologues.

In a further embodiment, some variants may include the substitutions at positions:
D44R/N61I/A539R;
D44R/A539R;
I43Q/D44C/L417V/E503A/Q511H/A539R;
I43Q/L417V/E503A/Q511H/A539R;
I43Q/D44C/N61I/L417V/E503A/Q511H/A539R;
I43Q/N61I/L417V/E503A/Q511H/A539R;
I43R/L417V/E503A/Q511H/A539R;
I43R/N61I/L417V/E503A/Q511H/A539R;
I43R/L417R/E503A/A539R;
I43R/N61I/L417R/E503A/Q511H/A539R;
L417V/T430A/A431L/Q511H/A535R/A539R/N563I;
L417V/T430A/A431Q/Q511H/A535R/A539R/N563I;
L417V/T430A/Q511H/A539R/N563I;
I43Q/T430A/Q511H/A539R;
I43Q/T430A/Q511H/N61I/A539R;
I43Q/T430A/Q511H/L417V/A539R;
I43Q/T430A/Q511H/A431L/A539R;
I43Q/T430A/Q511H/N61I/A539R/A431L;
I43Q/T430A/Q511H/L417V/A539R/A431L;
I43Q/Q511H/A539R;
I43Q/Q511H/A539R/N61I;
I43Q/Q511H/A539R/E503A;
I43Q/Q511H/A539R/T430M;
I43Q/Q511H/A539R/T430M/N61I;
I43Q/Q511H/A539R/T430M/N61I/L417V;
L417V/A431L/A539R;
L417V/A431L/A539R/I43Q;
L417V/A431L/A539R/N61I;
L417V/A431L/A539R/A535R;
L417V/A431L/A539R/I43Q/N61I;
L417V/A431L/A539R/N61I/A535R;
L417V/A431L/A539R/A535R/I43Q;
L417V/A431L/A539R/I43Q/N61I/A535R;
L417V/A431L/A539R/I43Q/N61I/A535R/T430A;
L417V/T430A/A431L/Q511H/A535R/A539R/N563I/ I43Q;
L417V/T430A/A431L/Q511H/A535R/A539R/N563I/ N61I;
L417V/T430A/A431L/Q511H/A535R/A539R/N563I/ I43Q/N61I;
L417V/A431L/A539R/I43R;
L417V/A431L/A539R/I43R/N61I;

L417V/A431L/A539R/I43R/N61I/A535R/T430A;
L417R/A431L/A539R;
L417G/A431L/A539R;
G73F/E503V/N563K/L417R/A539R; and
G73F/E503V/N563K/I43R/L417R/A539R
of SEQ ID NO: 2, or equivalent positions in parent glucoamylases and particularly *Trichoderma* glucoamylase homologues.

In a further embodiment, some variants may include the substitutions at positions:
D44R/N61I/A539R;
D44R/A539R;
L417V/A431L/A539R;
L417V/A431L/A539R/I43Q;
L417V/A431L/A539R/N61I;
of SEQ ID NO: 2, or equivalent positions in parent glucoamylases and particularly *Trichoderma* glucoamylase homologues.

In a further embodiment, some variants may include the substitutions at positions:
D44R/N61I/A539R;
D44R/A539R;
of SEQ ID NO: 2, or equivalent positions in parent glucoamylases and particularly *Trichoderma* glucoamylase homologues.

In a further embodiment, some variants has the following substitutions: D44R/N61I/A539R or D44R/A539R of SEQ ID NO: 2.

In a further embodiment, the variant comprises SEQ ID NO:1098. In yet a further embodiment, the variant consists of SEQ ID NO:1098. In a further embodiment, the variant comprises SEQ ID NO:1099. In yet a further embodiment, the variant consists of SEQ ID NO:1099.

A number of parent glucoamylases have been aligned with the amino acid sequence of TrGA. FIG. 5 includes the catalytic domain of the following parent glucoamylases *Aspergillus awamori* (AaGA) (SEQ ID NO: 5); *Aspergillus niger* (AnGA) (SEQ ID NO: 6); *Aspergillus orzyae* (AoGA) (SEQ ID NO: 7); *Humicola grisea* (HgGA) (SEQ ID NO: 8); and *Hypocrea vinosa* (HvGA) (SEQ ID NO: 9). The % identity of the catalytic domains is represented in Table 1 below.

TABLE 1

Sequence homology between various fungal glucoamylases

|  | AaGA | AnGA | AoGA | HgGA | HvGA | TrGA |
|---|---|---|---|---|---|---|
| AaGA | 100 | 95 | 58 | 53 | 57 | 56 |
| AnGA |  | 100 | 59 | 53 | 57 | 56 |
| AoGA |  |  | 100 | 55 | 56 | 56 |
| HgGA |  |  |  | 100 | 61 | 63 |
| HvGA |  |  |  |  | 100 | 91 |
| TrGA |  |  |  |  |  | 100 |

In some embodiments, for example, the variant glucoamylase will be derived from a parent glucoamylase that is an *Aspergillus* glucoamylase, a *Humicola* glucoamylase, or a *Hypocrea* glucoamylase.

5. Characterization of Variant Glucoamylases

The present disclosure also provides glucoamylase variants having at least one altered property (e.g., improved property) as compared to a parent glucoamylase and particularly to the TrGA. In some embodiments, at least one altered property (e.g., improved property) is selected from the group consisting of IS/SH-ratio, starch hydrolysis activity, real degree of fermentation, reduced formation of condensation products, acid stability, thermal stability and specific activity. Typically, the altered property is reduced IS/SH-ratio, enhanced real degree of fermentation, reduced formation of condensation products, increased thermal stability and/or increased specific activity. The increased thermal stability typically is at higher temperatures. In one embodiment, the increased pH stability is at high pH. In a further embodiment, the increased pH stability is at low pH.

The glucoamylase variants of the disclosure may also provide higher rates of starch hydrolysis at low substrate concentrations as compared to the parent glucoamylase. The variant may have a higher $V_{max}$ or lower $K_m$ than a parent glucoamylase when tested under the same conditions. For example the variant glucoamylase may have a higher $V_{max}$ at a temperature range of about 25° C. to about 70° C. (e.g., about 25° C. to about 35° C.; about 30° C. to about 35° C.; about 40° C. to about 50° C.; at about 50° C. to about 55° C., or about 55° C. to about 62° C.). The Michaelis-Menten constant, $K_m$ and $V_{max}$ values can be easily determined using standard known procedures. In another aspect, the glucoamylase may also exhibit a reduced starch hydrolysis activity which is not more than 5%, not more than 10% or not more than 15% reduced as compared to the parent glucoamylase such as TrGA.

5.1. Variant Glucoamylases with Altered Thermostability

In some aspects, the disclosure relates to a variant glucoamylase having altered thermal stability as compared to a parent (wild-type). Altered thermostability can be at increased temperatures or at decreased temperatures. Thermostability is measured as the % residual activity after incubation for 1 hour at 64° C. in NaAc buffer pH 4.5. Under these conditions, TrGA has a residual activity of between about 15% and 44% due to day-to-day variation as compared to the initial activity before incubation. Thus, in some embodiments, variants with increased thermostability have a residual activity that is between at least about 1% and at least about 50% more than that of the parent (after incubation for 1 hour at 64° C. in NaAc buffer pH 4.5), including about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, and about 50% as compared to the initial activity before incubation. For example, when the parent residual activity is 15%, a variant with increased thermal stability may have a residual activity of between about 16% and about 75%. In some embodiments, the glucoamylase variant will have improved thermostability such as retaining at least about 50%, about 60%, about 70%, about 75%, about 80%, about 85%, about 90%, about 92%, about 95%, about 96%, about 97%, about 98%, or about 99% enzymatic activity after exposure to altered temperatures over a given time period, for example, at least about 60 minutes, about 120 minutes, about 180 minutes, about 240 minutes, or about 300 minutes. In some embodiments, the variant has increased thermal stability compared to the parent glucoamylase at selected temperatures in the range of about 40°

C. to about 80° C., also in the range of about 50° C. to about 75° C., and in the range of about 60° C. to about 70° C., and at a pH range of about 4.0 to about 6.0. In some embodiments, the thermostability is determined as described in the Assays and Methods. That method may be adapted as appropriate to measure thermostability at other temperatures. Alternatively the thermostability may be determined at 64° C. as described there. In some embodiments, the variant has increased thermal stability at lower temperature compared to the parent glucoamylase at selected temperature in the range of about 20° C. to about 50° C., including about 35° C. to about 45° C. and about 30° C. to about 40° C.

In some embodiments, variants having an improvement in thermostability include one or more deletions, substitutions or insertions and particularly substitutions in the following positions in the amino acid sequence set forth in SEQ ID NO: 2: 10, 42, 43, 44, 59, 61, 68, 72, 73, 97, 98, 99, 102, 114, 133, 140, 144, 152, 153, 182, 204, 205, 214, 216, 228, 229, 230, 231, 236, 241, 242, 263, 264, 265, 268, 269, 276, 284, 291, 294, 300, 301, 303, 311, 338, 342, 344, 346, 349, 359, 361, 364, 375, 379, 382, 390, 391, 393, 394, 410, 417, 430, 431, 433, 436, 442, 444, 448, 451, 493, 495, 503, 508, 511, 518, 519, 520, 527, 531, 535, 536, 537, 539, 563, or 577, or an equivalent position in a parent glucoamylase. In some embodiments, the parent glucoamylase will be a Trichoderma glucoamylase homologue and in further embodiments, the parent glucoamylase will have at least about 50%, about 60%, about 70%, about 80%, about 90%, about 95%, or about 98% sequence identity to SEQ ID NO: 2. In some embodiments, the parent glucoamylase will also have structural identity to SEQ ID NO: 2. In some embodiments, the variant having increased thermostability has a substitution in at least one of the positions: T10S, T42V, I43Q, I43R, D44C, D44R, E68C, E68M, G73F, G73W, K114M, K114R, I133V, N153A, N153E, N153M, N153S, N153V, W228V, V229I, V229L, S230Q, S231V, D236R, L264D, L264K, A268D, S291A, S291F, S291H, S291M, S291T, G294C, A301P, A301R, V338I, V338N, V338Q, S344M, S344P, S344Q, S344R, S344V, G361D, G361E, G361F, G361I, G361L, G361M, G361P, G361S, G361W, G361Y, A364D, A364E, A364F, A364G, A364K, A364L, A364M, A364R, A364S, A364T, A364V, A364W, T375N, L417K, L417R, R433C, R433E, R433G, R433L, R433N, R433S, R433V, I436H, T495K, T495S, E503A, E503C, E503V, Q508R, Q511H, A519K, A519R, A519Y, V531L, A535K, A535N, A535P, A535R, A539E, A539R, A539S, N563C, N563E, N563I, N563K, N563L, N563Q, N563T, N563V, N577K, N577P, or N577R of SEQ ID NO: 2.

5.2. Variant Glucoamylases with Altered Specific Activity

As used herein, specific activity is the activity of the glucoamylase per mg of protein. Activity was determined using the ethanol assay. The screening identified variants having a Performance Index (PI)>1.0 compared to the parent TrGA PI. The PI is calculated from the specific activities (activity/mg enzyme) of the wild-type (WT) and the variant enzymes. It is the quotient "Variant-specific activity/WT-specific activity" and can be a measure of the increase in specific activity of the variant. A PI of about 2 should be about 2 fold better than WT. In some aspects, the disclosure relates to a variant glucoamylase having altered specific activity as compared to a parent or wild-type glucoamylase. In some embodiments, the altered specific activity is increased specific activity. Increased specific activity can be defined as an increased performance index of greater than or equal to about 1, including greater than or equal to about 1.1, about 1.2, about 1.3, about 1.4, about 1.5, about 1.6, about 1.7, about 1.8, about 1.9, and about 2. In some embodiments, the increased specific activity is from about 1.0 to about 5.0, including about 1.1, about 1.2, about 1.3, about 1.4, about 1.5, about 1.6, about 1.7, about 1.8, about 1.9, about 2.0, about 2.1, about 2.2., about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, and about 4.9. In some embodiments, the variant has an at least about 1.0 fold higher specific activity than the parent glucoamylase, including at least about 1.1 fold, about 1.2 fold, about 1.3 fold, about 1.4 fold, about 1.5 fold, about 1.6 fold, about 1.7 fold, about 1.8 fold, about 1.9 fold, about 2.0 fold, about 2.2 fold, about 2.5 fold, about 2.7 fold, about 2.9 fold, about 3.0 fold, about 4.0 fold, and about 5.0 fold.

In some embodiments, variants having an improvement in specific activity include one or more deletions, substitutions or insertions in the following positions in the amino acid sequence set forth in SEQ ID NO: 2: 10, 14, 15, 23, 59, 60, 61, 65, 67, 68, 72, 73, 97, 98, 99, 102, 110, 113, 133, 140, 144, 145, 147, 152, 153, 164, 182, 204, 205, 214, 216, 219, 228, 229, 230, 231, 236, 239, 241, 242, 263, 264, 265, 268, 269, 276, 284, 291, 300, 301, 303, 311, 338, 342, 344, 346, 349, 359, 361, 364, 375, 379, 382, 390, 391, 393, 394, 410, 417, 418, 430, 431, 433, 442, 444, 448, 451, 493, 494, 495, 502, 503, 508, 511, 518, 519, 520, 531, 535, 536, 539, or 563, or an equivalent position in a parent glucoamylase. In some embodiments, the parent glucoamylase will comprise a sequence having at least about 50%, about 60%, about 70%, about 80%, about 90%, or about 95% sequence identity to the sequence of SEQ ID NO: 2. In some embodiments, the parent glucoamylase will also have structural identity to SEQ ID NO: 2. In some embodiments, variants of the disclosure having improved specific activity include a substitution in the following positions in the amino acid sequence set forth in SEQ ID NO: 2: I43Q, I43R, D44C, D44R, N061I, T067M, A072Y, S097N, S102A, S102M, S102R, I133T, N145I, N153D, T205Q, Q219S, W228A, W228F, W228H, W228M, S230C, S230F, S230G, S230L, S230N, S230Q, S230R, S231L, I239V, I239Y, N263P, A268C, A268G, A268K, S291A, G294C, T342V, K394S, L417R, L417V, T430K, A431I, A431L, A431Q, R433Y, T451K, T495M, A519I, A520C, A520L, A520P, A535R, V536M, A539R, N563K, or N563I, or an equivalent position in a parent glucoamylase. In some embodiments, the specific activity of the parent as compared to the variant is determined as described in the Assays and Methods.

5.3. Variant Glucoamylases with Both Altered Thermostability and Altered Specific Activity In some aspects, the disclosure relates to a variant glucoamylase having both altered thermostability and altered specific activity as compared to a parent (e.g., wild-type). In some embodiments, the altered specific activity is an increased specific activity. In some embodiments, the altered thermostability is an increased thermostability at high temperatures (e.g., at temperatures above 80° C.) as compared to the parent glucoamylase.

In some embodiments, variants with an increased thermostability and increased specific activity include one or more deletions, substitutions or insertions and substitutions in the following positions in the amino acid sequence set forth in SEQ ID NO: 2: 10, 15, 43, 44, 59, 61, 68, 72, 73, 97, 99, 102, 140, 153, 182, 204, 205, 214, 228, 229, 230, 231, 236, 241, 242, 264, 265, 268, 276, 284, 291, 294, 300, 301, 303, 311, 338, 344, 346, 349, 359, 361, 364, 375, 379, 382, 391, 393, 394, 410, 430, 433, 444, 448, 451, 495, 503, 511, 520, 531, 535, 536, 539, or 563, or an equivalent position in a parent glucoamylase. In some embodiments, the parent glucoamylase will be a *Trichoderma* glucoamylase homologue and in further embodiments, the parent glucoamylase will have at least about 50%, about 60%, about 70%, about 80%, about 90%, about 95%, or about 98% sequence identity to SEQ ID NO:2. In some embodiments, the parent glucoamylase will also have structural identity to SEQ ID NO: 2. In some embodiments, the variant having increased thermostability and specific activity has a substitution in at least one of the positions: I43Q/R, D44C/R, W228F/H/M, S230C/F/G/N/Q/R, S231L, A268C/D/G/K, S291A, G294C, R433Y, S451K, E503C, Q511H, A520C/L/P, or A535N/P/R of SEQ ID NO: 2.

5.4. Variant Glucoamylases with Production of Fermentable Sugar(s)

In a further aspect, the glucoamylase exhibit an enhanced production of fermentable sugar(s) as compared to the parent glucoamylase such as TrGA. In a further aspect, the glucoamylase exhibit an enhanced production of fermentable sugars in the mashing step of the brewing process as compared to the parent glucoamylase such as TrGA. In a further aspect, the glucoamylase exhibit an enhanced production of fermentable sugars in the fermentation step of the brewing process as compared to the parent glucoamylase such as TrGA. In a further aspect, the fermentable sugar is glucose. A skilled person within the field can determine the production of fermentable sugar(s) by e.g. HPLC techniques.

5.5 Variant Glucoamylases with a Altered Ratio Between Isomaltose Synthesis and Starch Hydrolysis Activity (IS/SH Ratio)

In a further aspect, the glucoamylase exhibit a reduced ratio between isomaltose synthesis and starch hydrolysis activity (IS/SH ratio) as compared to the parent glucoamylase such as TrGA. In a further aspect, the glucoamylase exhibit a starch hydrolysis activity which is not more than 5%, not more than 10% or not more than 15% reduced as compared to the parent glucoamylase such as TrGA.

In one aspect, a screening method for identification of a glucoamylase variant having a reduced synthesis of condensation products during hydrolysis of starch and the glucoamylse variants obtained by the method is provided, the method comprising the steps of measuring the isomaltose synthesis and starch hydrolysis activity of glucoamylase variants and selecting the variants having a reduced starch hydrolysis activity which is not more than 5%, not more than 10% or not more than 15% reduced as compared to the parent glucoamylase and having a reduced ratio between isomaltose synthesis and starch hydrolysis activity (IS/SH ratio) as compared to the parent glucoamylase.

In some embodiments the glucoamylase variants are selecting for having a reduced ratio between isomaltose synthesis and starch hydrolysis activity (IS/SH ratio) as compared to the parent glucoamylase.

In some embodiments the glucoamylase variants are selecting for having the same or increased starch hydrolysis activity and reduced isomaltose synthesis, which is not more than 5%, not more than 10% or not more than 15% reduced as compared to the parent glucoamylase and thereby having a reduced ratio between isomaltose synthesis and starch hydrolysis activity (IS/SH ratio) as compared to the parent glucoamylase.

In a further aspect, the glucoamylase exhibit an enhanced real degree of fermentation as compared to the parent glucoamylase such as TrGA.

5.6 Variant Glucoamylases with an Altered Formation of Condensation Products In one aspect, the glucoamylase forms a lower amount of condensation products than the amount of condensation products formed by *Aspergillus niger* (AnGA) (SEQ ID NO: 6) under the same conditions. In a further aspect, the glucoamylase forms an amount of condensation products which amount is essentially the same as, not more than 5%, not more than 8% or not more than 10% higher than the amount of condensation products formed by *Aspergillus niger* (AnGA) (SEQ ID NO: 6) under the same conditions. In a further aspect, the dosing of the glucoamylases are the same based on protein concentration. In a further aspect, the dosing of the glucoamylases are the same based on measurement of activity in activity assays such as a GAU activity assay as described herein or a starch hydrolysation-activity assay also as described herein.

6. Polynucleotides Encoding Glucoamylases

The present disclosure also relates to isolated polynucleotides encoding the variant glucoamylase. The polynucleotides may be prepared by established techniques known in the art. The polynucleotides may be prepared synthetically, such as by an automatic DNA synthesizer. The DNA sequence may be of mixed genomic (or cDNA) and synthetic origin prepared by ligating fragments together. The polynucleotides may also be prepared by polymerase chain reaction (PCR) using specific primers. In general, reference is made to Minshull J. et al., *Methods* 32(4):416-427 (2004). DNA may also be synthesized by a number of commercial companies such as Geneart AG, Regensburg, Germany.

The present disclosure also provides isolated polynucleotides comprising a nucleotide sequence (i) having at least about 50% identity to SEQ ID NO: 4, including at least about 60%, about 70%, about 80%, about 90%, about 95%, and about 99%, or (ii) being capable of hybridizing to a probe derived from the nucleotide sequence set forth in SEQ ID NO: 4, under conditions of intermediate to high stringency, or (iii) being complementary to a nucleotide sequence having at least 90% sequence identity to the sequence set forth in SEQ ID NO: 4. Probes useful according to the disclosure may include at least about 50, about 100, about 150, about 200, about 250, about 300 or more contiguous nucleotides of SEQ ID NO: 4. In some embodiments, the encoded polypeptide also has structural identity to SEQ ID NO: 2.

The present disclosure further provides isolated polynucleotides that encode variant glucoamylases that comprise an amino acid sequence comprising at least about 50%, about 60%, about 70%, about 80%, about 90%, about 93%, about 95%, about 97%, about 98%, or about 99% amino acid sequence identity to SEQ ID NO: 2. Additionally, the present disclosure provides expression vectors comprising any of the polynucleotides provided above. The present disclosure also provides fragments (i.e., portions) of the DNA encoding the variant glucoamylases provided herein. These fragments find use in obtaining partial length DNA fragments capable of being used to isolate or identify polynucleotides encoding mature glucoamylase enzymes described herein from filamentous fungal cells (e.g., *Trichoderma, Aspergillus, Fusarium, Penicillium*, and *Humicola*), or a segment thereof having glucoamylase activity. In some embodiments, fragments of the DNA may comprise at least about 50, about 100, about 150, about 200, about 250, about 300 or more contiguous nucleotides. In some embodiments, portions of the DNA provided in SEQ ID NO: 4 may be used to obtain parent glucoamylases and particularly *Trichoderma* glucoamylase homologues from other species, such as filamentous fungi that encode a glucoamylase.

7. Production of Glucoamylases

7.1. DNA Constructs and Vectors

According to one embodiment of the disclosure, a DNA construct comprising a polynucleotide as described above encoding a variant glucoamylase encompassed by the disclosure and operably linked to a promoter sequence is assembled to transfer into a host cell. In one aspect, a polynucleotide encoding a glucoamylase variant as disclosed herein is provided.

The DNA construct may be introduced into a host cell using a vector. In one aspect, a vector comprising the polynucleotide, or capable of expressing a glucoamylase variant as disclosed herein is provided. The vector may be any vector that when introduced into a host cell is stably introduced. In some embodiments, the vector is integrated into the host cell genome and is replicated. Vectors include cloning vectors, expression vectors, shuttle vectors, plasmids, phage particles, cassettes and the like. In some embodiments, the vector is an expression vector that comprises regulatory sequences operably linked to the glucoamylase coding sequence.

Examples of suitable expression and/or integration vectors are provided in Sambrook et al. (1989) supra, and Ausubel (1987) supra, and van den Hondel et al. (1991) in Bennett and Lasure (Eds.) More Gene Manipulations In Fungi, Academic Press pp. 396-428 and U.S. Pat. No. 5,874,276. Reference is also made to the Fungal Genetics Stock Center Catalogue of Strains (FGSC, www.fgsc.net) for a list of vectors. Particularly useful vectors include vectors obtained from for example Invitrogen and Promega.

Suitable plasmids for use in bacterial cells include pBR322 and pUC19 permitting replication in *E. coli* and pE194 for example permitting replication in *Bacillus*. Other specific vectors suitable for use in *E. coli* host cells include vectors such as pFB6, pBR322, pUC18, pUC100, pDONR™201, 10 pDONR™221, pENTR™, pGEM® 32 and pGEM®4Z.

Specific vectors suitable for use in fungal cells include pRAX, a general purpose expression vector useful in *Aspergillus*, pRAX with a glaA promoter, and in *Hypocrea/Trichoderma* includes pTrex3g with a cbh1 promoter.

In some embodiments, the promoter that shows transcriptional activity in a bacterial or a fungal host cell may be derived from genes encoding proteins either homologous or heterologous to the host cell. The promoter may be a mutant, a truncated and/or a hybrid promoter. The above-mentioned promoters are known in the art. Examples of suitable promoters useful in fungal cells and particularly filamentous fungal cells such as *Trichoderma* or *Aspergillus* cells include such exemplary promoters as the *T. reesei* promoters cbh1, cbh2, egl1, egl2, eg5, xln1 and xln2. Other examples of useful promoters include promoters from *A. awamori* and *A. niger* glucoamylase genes (glaA) (see Nunberg et al., *Mol. Cell. Biol.* 4: 2306-2315 (1984) and Boel et al., *EMBO J.* 3:1581-1585 (1984)), *A. oryzae* TAKA amylase promoter, the TPI (triose phosphate isomerase) promoter from *S. cerevisiae*, the promoter from *Aspergillus nidulans* acetamidase genes and *Rhizomucor miehei* lipase genes. Examples of suitable promoters useful in bacterial cells include those obtained from the *E. coli* lac operon; *Bacillus licheniformis* alpha-amylase gene (amyL), *B. stearothermophilus* amylase gene (amyS); *Bacillus subtilis* xylA and xylB genes, the beta-lactamase gene, and the tac promoter. In some embodiments, the promoter is one that is native to the host cell. For example, when *T. reesei* is the host, the promoter is a native *T. reesei* promoter. In other embodiments, the promoter is one that is heterologous to the fungal host cell. In some embodiments, the promoter will be the promoter of a parent glucoamylase (e.g., the TrGA promoter).

In some embodiments, the DNA construct includes nucleic acids coding for a signal sequence, that is, an amino acid sequence linked to the amino terminus of the polypeptide that directs the encoded polypeptide into the cell's secretory pathway. The 5' end of the coding sequence of the nucleic acid sequence may naturally include a signal peptide coding region that is naturally linked in translation reading frame with the segment of the glucoamylase coding sequence that encodes the secreted glucoamylase or the 5' end of the coding sequence of the nucleic acid sequence may include a signal peptide that is foreign to the coding sequence. In some embodiments, the DNA construct includes a signal sequence that is naturally associated with a parent glucoamylase gene from which a variant glucoamylase has been obtained. In some embodiments, the signal sequence will be the sequence depicted in SEQ ID NO: 1 or a sequence having at least about 90%, about 94, or about 98% sequence identity thereto. Effective signal sequences may include the signal sequences obtained from other filamentous fungal enzymes, such as from *Trichoderma* (*T. reesei* glucoamylase, cellobiohydrolase I, cellobiohydrolase II, endoglucanase I, endoglucanase II, endoglucanase II, or a secreted proteinase, such as an aspartic proteinase), *Humicola* (*H. insolens* cellobiohydrolase or endoglucanase, or *H. grisea* glucoamylase), or *Aspergillus* (*A. niger* glucoamylase and *A. oryzae* TAKA amylase).

In additional embodiments, a DNA construct or vector comprising a signal sequence and a promoter sequence to be introduced into a host cell are derived from the same source. In some embodiments, the native glucoamylase signal sequence of a *Trichoderma* glucoamylase homologue, such as a signal sequence from a *Hypocrea* strain may be used.

In some embodiments, the expression vector also includes a termination sequence. Any termination sequence functional in the host cell may be used in the present disclosure. In some embodiments, the termination sequence and the promoter sequence are derived from the same source. In another embodiment, the termination sequence is homologous to the host cell. Useful termination sequences include termination sequences obtained from the genes of *Trichoderma reesei* cbl1; *A. niger* or *A. awamori* glucoamylase (Nunberg et al. (1984) supra, and Boel et al., (1984) supra), *Aspergillus nidulans* anthranilate synthase, *Aspergillus oryzae* TAKA amylase, or *A. nidulans* trpC (Punt et al., *Gene* 56:117-124 (1987)).

In some embodiments, an expression vector includes a selectable marker. Examples of selectable markers include ones that confer antimicrobial resistance (e.g., hygromycin and phleomycin). Nutritional selective markers also find use in the present disclosure including those markers known in the art as amdS (acetamidase), argB (ornithine carbamoyl-transferase) and pyrG (orotidine-5' phosphate decarboxylase). Markers useful in vector systems for transformation of *Trichoderma* are known in the art (see, e.g., Finkelstein, Chapter 6 in Biotechnology Of Filamentous Fungi, Finkelstein et al. (1992) Eds. Butterworth-Heinemann, Boston, Mass.; Kinghorn et al. (1992) Applied Molecular Genetics Of Filamentous Fungi, Blackie Academic and Professional, Chapman and Hall, London; Berges and Barreau, *Curr. Genet.* 19:359-365 (1991); and van Hartingsveldt et al., *Mol. Gen. Genet.* 206:71-75 (1987)). In some embodiments, the selective marker is the amdS gene, which encodes the enzyme acetamidase, allowing transformed cells to grow on acetamide as a nitrogen source. The use of *A. nidulans* amdS gene as a selective marker is described in Kelley et al., *EMBO J.* 4:475-479 (1985) and Penttila et al., *Gene* 61:155-164 (1987).

Methods used to ligate the DNA construct comprising a nucleic acid sequence encoding a variant glucoamylase, a promoter, a termination and other sequences and to insert them into a suitable vector are well known in the art. Linking is generally accomplished by ligation at convenient restriction sites. If such sites do not exist, synthetic oligonucleotide linkers are used in accordance with conventional practice (see Sambrook et al. (1989) supra, and Bennett and Lasure, More Gene Manipulations In Fungi, Academic Press, San Diego (1991) pp 70-76). Additionally, vectors can be constructed using known recombination techniques (e.g., Invitrogen Life Technologies, Gateway Technology).

7.2. Host Cells and Transformation of Host Cells

1. The present disclosure also relates to host cells comprising a polynucleotide encoding a variant glucoamylase of the disclosure. In some embodiments, the host cells are chosen from bacterial, fungal, plant and yeast cells. The term host cell includes both the cells, progeny of the cells and protoplasts created from the cells that are used to produce a variant glucoamylase according to the disclosure. In one aspect, a host cell comprising, preferably transformed with a vector is disclosed. In a further aspect, a cell capable of expressing a glucoamylase variant is provided. In a further aspect, the host cell is a protease deficient and/or xylanase deficient and/or glucanase deficient host cell. A protease deficient and/or xylanase deficient and/or native glucanase deficient host cell may be obtained by deleting or silencing the genes coding for the mentioned enzymes. As a consequence the host cell containing the GA-variant is not expressing the mentioned enzymes In some embodiments, the host cells are fungal cells and optionally filamentous fungal host cells. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi of the present disclosure are morphologically, physiologically, and genetically distinct from yeasts. Vegetative growth by filamentous fungi is by hyphal elongation and carbon catabolism is obligatory aerobic. In the present disclosure, the filamentous fungal parent cell may be a cell of a species of, but not limited to, *Trichoderma* (e.g., *Trichoderma reesei*, the asexual morph of *Hypocrea jecorina*, previously classified as *T. longibrachiatum*, *Trichoderma viride*, *Trichoderma koningii*, *Trichoderma harzianum*) (Sheir-Neirs et al., *Appl. Microbiol. Biotechnol.* 20:46-53 (1984); ATCC No. 56765 and ATCC No. 26921), *Penicillium* sp., *Humicola* sp. (e.g., *H. insolens*, *H. lanuginosa* and *H. grisea*), *Chrysosporium* sp. (e.g., *C. lucknowense*), *Gliocladium* sp., *Aspergillus* sp. (e.g., *A. oryzae*, *A. niger, A sojae, A. japonicus, A. nidulans*, and *A. awamori*) (Ward et al., *Appl. Microbiol. Biotechnol.* 39:738-743 (1993) and Goedegebuur et al., *Curr. Genet.* 41:89-98 (2002)), *Fusarium* sp., (e.g., *F. roseum, F. graminum, F. cerealis, F. oxysporum,* and *F. venenatum*), *Neurospora* sp., (*N. crassa*), *Hypocrea* sp., *Mucor* sp. (*M. miehei*), *Rhizopus* sp., and *Emericella* sp. (see also, Innis et al., *Science* 228:21-26 (1985)). The term "*Trichoderma*" or "*Trichoderma* sp." or "*Trichoderma* spp." refer to any fungal genus previously or currently classified as *Trichoderma*.

In some embodiments, the host cells will be gram-positive bacterial cells. Non-limiting examples include strains of *Streptomyces* (e.g., *S. lividans, S. coelicolor,* and *S. griseus*) and *Bacillus*. As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus tearothermophilus.*"

In some embodiments, the host cell is a gram-negative bacterial strain, such as *E. coli* or *Pseudomonas* sp. In other embodiments, the host cells may be yeast cells such as *Saccharomyces* sp., *Schizosaccharomyces* sp., *Pichia* sp., or *Candida* sp. In other embodiments, the host cell will be a genetically engineered host cell wherein native genes have been inactivated, for example by deletion in bacterial or fungal cells. Where it is desired to obtain a fungal host cell having one or more inactivated genes known methods may be used (e.g., methods disclosed in U.S. Pat. No. 5,246,853, U.S. Pat. No. 5,475,101, and WO 92/06209). Gene inactivation may be accomplished by complete or partial deletion, by insertional inactivation or by any other means that renders a gene nonfunctional for its intended purpose (such that the gene is prevented from expression of a functional protein). In some embodiments, when the host cell is a *Trichoderma* cell and particularly a *T. reesei* host cell, the cbh1, cbh2, egl1 and egl2 genes will be inactivated and/or deleted. Exemplary *Trichoderma reesei* host cells having quad-deleted proteins are set forth and described in U.S. Pat. No. 5,847,276 and WO 05/001036. In other embodiments, the host cell is a protease deficient or protease minus strain.

Introduction of a DNA construct or vector into a host cell includes techniques such as transformation; electroporation; nuclear microinjection; transduction; transfection, (e.g., lipofection-mediated and DEAE-Dextrin mediated transfection); incubation with calcium phosphate DNA precipitate; high velocity bombardment with DNA-coated microprojectiles; and protoplast fusion. General transformation techniques are known in the art (see, e.g., Ausubel et al. (1987) supra, chapter 9; and Sambrook et al. (1989) supra, and Campbell et al., *Curr. Genet.* 16:53-56 (1989)).

Transformation methods for *Bacillus* are disclosed in numerous references including Anagnostopoulos C. and J. Spizizen, *J. Bacteriol.* 81:741-746 (1961) and WO 02/14490.

Transformation methods for *Aspergillus* are described in Yelton et al., *Proc. Natl. Acad. Sci. USA* 81:1470-1474

(1984); Berka et al., (1991) in Applications of Enzyme Biotechnology, Eds. Kelly and Baldwin, Plenum Press (NY); Cao et al., *Protein Sci.* 9:991-1001 (2000); Campbell et al., *Curr. Genet.* 16:53-56 (1989), and EP 238 023. The expression of heterologous protein in *Trichoderma* is described in U.S. Pat. No. 6,022,725; U.S. Pat. No. 6,268,328; Harkki et al. *Enzyme Microb. Technol.* 13:227-233 (1991); Harkki et al., *BioTechnol.* 7:596-603 (1989); EP 244,234; EP 215,594; and Nevalainen et al., "The Molecular Biology of *Trichoderma* and its Application to the Expression of Both Homologous and Heterologous Genes", in Molecular Industrial Mycology, Eds. Leong and Berka, Marcel Dekker Inc., NY (1992) pp. 129-148). Reference is also made to WO96/00787 and Bajar et al., *Proc. Natl. Acad. Sci. USA* 88:8202-8212 (1991) for transformation of *Fusarium* strains.

In one specific embodiment, the preparation of *Trichoderma* sp. for transformation involves the preparation of protoplasts from fungal mycelia (see, Campbell et al., *Curr. Genet.* 16:53-56 (1989); Pentilla et al., *Gene* 61:155-164 (1987)). *Agrobacterium tumefaciens*-mediated transformation of filamentous fungi is known (see de Groot et al., *Nat. Biotechnol.* 16:839-842 (1998)). Reference is also made to U.S. Pat. No. 6,022,725 and U.S. Pat. No. 6,268,328 for transformation procedures used with filamentous fungal hosts.

In some embodiments, genetically stable transformants are constructed with vector systems whereby the nucleic acid encoding the variant glucoamylase is stably integrated into a host strain chromosome. Transformants are then purified by known techniques.

In some further embodiments, the host cells are plant cells, such as cells from a monocot plant (e.g., corn, wheat, and sorghum) or cells from a dicot plant (e.g., soybean). Methods for making DNA constructs useful in transformation of plants and methods for plant transformation are known. Some of these methods include *Agrobacterium tumefaciens* mediated gene transfer; microprojectile bombardment, PEG mediated transformation of protoplasts, electroporation and the like. Reference is made to U.S. Pat. No. 6,803,499, U.S. Pat. No. 6,777,589; Fromm et al., *BioTechnol.* 8:833-839 (1990); Potrykus et al., *Mol. Gen. Genet.* 199:169-177 (1985).

7.3. Production of Glucoamylases

The present disclosure further relates to methods of producing the variant glucoamylases, which comprises transforming a host cell with an expression vector comprising a polynucleotide encoding a variant glucoamylase according to the disclosure, culturing the host cell under conditions suitable for expression and production of the variant glucoamylase and optionally recovering the variant glucoamylase. In one aspect, a method of expressing a variant glucoamylase according to the disclosure, the method comprising obtaining a host cell or a cell as disclosed herein and expressing the glucoamylase variant from the cell or host cell, and optionally purifying the glucoamylase variant, is provided. In one aspect, the glucoamylase variant is purified.

In the expression and production methods of the present disclosure the host cells are cultured under suitable conditions in shake flask cultivation, small scale or large scale fermentations (including continuous, batch and fed batch fermentations) in laboratory or industrial fermentors, with suitable medium containing physiological salts and nutrients (see, e.g., Pourquie, J. et al., Biochemistry And Genetics Of Cellulose Degradation, eds. Aubert, J. P. et al., Academic Press, pp. 71-86, 1988 and Ilmen, M. et al., *Appl. Environ. Microbiol.* 63:1298-1306 (1997)). Common commercially prepared media (e.g., Yeast Malt Extract (YM) broth, Luria Bertani (LB) broth and Sabouraud Dextrose (SD) broth) find use in the present disclosure. Culture conditions for bacterial and filamentous fungal cells are known in the art and may be found in the scientific literature and/or from the source of the fungi such as the American Type Culture Collection and Fungal Genetics Stock Center. In cases where a glucoamylase coding sequence is under the control of an inducible promoter, the inducing agent (e.g., a sugar, metal salt or antimicrobial), is added to the medium at a concentration effective to induce glucoamylase expression.

In some embodiments, the present disclosure relates to methods of producing the variant glucoamylase in a plant host comprising transforming a plant cell with a vector comprising a polynucleotide encoding a glucoamylase variant according to the disclosure and growing the plant cell under conditions suitable for the expression and production of the variant.

In some embodiments, assays are carried out to evaluate the expression of a variant glucoamylase by a cell line that has been transformed with a polynucleotide encoding a variant glucoamylase encompassed by the disclosure. The assays can be carried out at the protein level, the RNA level and/or by use of functional bioassays particular to glucoamylase activity and/or production. Some of these assays include Northern blotting, dot blotting (DNA or RNA analysis), RT-PCR (reverse transcriptase polymerase chain reaction), in situ hybridization using an appropriately labeled probe (based on the nucleic acid coding sequence) and conventional Southern blotting and autoradiography.

In addition, the production and/or expression of a variant glucoamylase may be measured in a sample directly, for example, by assays directly measuring reducing sugars such as glucose in the culture medium and by assays for measuring glucoamylase activity, expression and/or production. In particular, glucoamylase activity may be assayed by the 3,5-dinitrosalicylic acid (DNS) method (see Goto et al., *Biosci. Biotechnol. Biochem.* 58:49-54 (1994)). In additional embodiments, protein expression, is evaluated by immunological methods, such as immunohistochemical staining of cells, tissue sections or immunoassay of tissue culture medium, (e.g., by Western blot or ELISA). Such immunoassays can be used to qualitatively and quantitatively evaluate expression of a glucoamylase. The details of such methods are known to those of skill in the art and many reagents for practicing such methods are commercially available.

The glucoamylases of the present disclosure may be recovered or purified from culture media by a variety of procedures known in the art including centrifugation, filtration, extraction, precipitation and the like.

8. Compositions and Uses

In one aspect, the use of a glucoamylase variant as described herein for the preparation of an enzymatic composition, is provided.

The variant glucoamylases of the disclosure may be used in enzyme compositions including but not limited to starch hydrolyzing and saccharifying compositions, cleaning and detergent compositions (e.g., laundry detergents, dish washing detergents, and hard surface cleaning compositions), alcohol fermentation compositions, and in animal feed compositions. Further, the variant glucoamylases may be used in, for example, brewing, healthcare, textile, environmental waste conversion processes, biopulp processing, and biomass conversion applications. The variant glucoamylases of the disclosure may be used in enzyme compositions including a starch hydrolyzing composition, a saccharifying composition, a detergent, an alcohol fermentation enzymatic composition, and an animal feed. In one aspect, the composition is a starch hydrolyzing composition.

In some embodiments, an enzyme composition comprising a variant glucoamylase encompassed by the disclosure will be optionally used in combination with any one or combination of the following enzymes—alpha-amylases, proteases, pullulanases, isoamylases, cellulases, hemicellulases, xylanases, cyclodextrin glycotransferases, lipases, phytases, laccases, oxidases, esterases, cutinases, xylanases, granular starch hydrolyzing enzymes and other glucoamylases.

In some embodiments, an enzyme composition comprising a variant glucoamylase encompassed by the disclosure will be optionally used in combination with any one or combination of the following enzymes—amylase, protease, pullulanase, cellulase, glucanase, xylanase, arabinofuranosidase, ferulic acid esterase, xylan acetyl esterase and a further glucoamylase. In some embodiments, an enzyme composition comprising a variant glucoamylase encompassed by the disclosure will be optionally used in combination with any one or combination of the following enzymes—amylase, pullulanase and a further glucoamylase. In some embodiments, an enzyme composition comprising a variant glucoamylase encompassed by the disclosure will be optionally used in combination with any one or combination of the following enzymes—amylase and pullulanase. In a further aspect, the amylase is alpha-amylase and/or isoamylase. In a further aspect, the glucanase is exoglucanase and/or endoglucanase.

In some embodiments, the enzyme composition will include an alpha-amylase such as fungal alpha-amylases (e.g., *Aspergillus* sp.) or bacterial alpha-amylases (e.g., *Bacillus* sp. such as *B. stearothermophilus*, *B. amyloliquefaciens* and *B. licheniformis*) and variants and hybrids thereof. In the present context, an alpha-amylase (EC 3.2.1.1) catalyses the endohydrolysis of (1->4)-alpha-D-glucosidic linkages in oligosaccharides and polysaccharides. An alpha-amylase acts on starch, glycogen and related polysaccharides and oligosaccharides in a random manner; reducing groups are liberated in the alpha-configuration. In some embodiments, the alpha-amylase is an acid stable alpha-amylase. In some embodiments, the alpha-amylase is *Aspergillus kawachi* alpha-amylase (AkAA), see U.S. Pat. No. 7,037,704. Other alpha-amylases contemplated for use in the compositions of the disclosure include, but are not limited to, bacterial alpha-amylases such as those from *Bacillus subtilis* (AmyE), and *Bacillus licheniformis* (AmyL) and *Geobacillus stearothermophilus* (AmyS) as described by Gray et al. (1986) (Gray G L, Mainzer S E, Rey M W, Lamsa M H, Kindle K L, Carmona C and Requadt C "Structural genes encoding the thermophilic alpha-amylases of *Bacillus stearothermophilus* and *Bacillus licheniformis*" Journal of Bacteriology (1986) 166(2) p 635-643) along with variants and combinations, including combinations of variants of the above. Variants of AmyE, AmyL and AmyS are well known and examples are described in US Patent Application 20100015686 A1 ("Variant Alpha-Amylases from *Bacillus subtilis* and Methods of Uses, Thereof"), US Patent Application 20090314286 A1 ("*Geobacillus stearothermophilus* Alpha-Amylase (AmyS) Variants with Improved Properties"), WO/2006/066594) ("Alpha-Amylase Variants"), US 20090238923 A1 ("Variants Of *Bacillus Licheniformis* Alpha-Amylase With Increased Thermostability And/Or Decreased Calcium Dependence"). Commercially available alpha-amylases contemplated for use in the compositions of the disclosure are known and include GZYME G997, SPEZYME® FRED, SPEZYME® XTRA AMYLEX® 4T, AMYLEX® 3T and AMYLEX® XT (Danisco US, Inc, Genencor Division), TERMAMYL® 120-L and SUPRA® (Novozymes, A/S).

In some embodiments, the enzyme composition will include a pullulanase (EC 3.2.1.41). In one aspect, the pullulanases used herein is pullulanase from e.g. *Pyrococcus* or *Bacillus* sp, such as *Bacillus acidopullulyticus* (e.g., the one described in FEMS Microbiol. Letters 115: 97-106) or *Bacillus deramificans*, or *Bacillus naganoencis*. In one aspect, the pullulanase is the *Bacillus acidopullulyticus* PulB enzyme, described in the paper by Kelly et al. FEMS Microbiology Letters 115 (1994) 97-106. The pullulanase may also be an engineered pullulanases from, e.g., a *Bacillus* strain. Other pullulanases which are preferably used in the processes according to the invention include: *Bacillus deramificans* (U.S. Pat. No. 5,736,375), or the pullulanase may be derived from *Pyrococcus woesei* described in PCT/DK91/00219, or the pullulanase may be derived from *Fervidobacterium* sp. Ven 5 described in PCT/DK92/00079, or the pullulanase may be derived from *Thermococcus celer* described in PCT/DK95/00097, or the pullulanase may be derived from *Pyrodictium abyssei* described in PCT/DK95/00211, or the pullulanase may be derived from *Fervidobacterium pennavorans* described in PCT/DK95/00095, or the pullulanase may be derived from *Desulforococcus mucosus* described in PCT/DK95/00098. The pullulanase (EC 3.2.1.41) may also be derived from, but not limited to, *Klebsiella* (*Aerobacter*) spp. (PulA); for example *Klebsiella planticola*, *Klebsiella* (*Aerobacter*) *aerogenes* and *Klebsiella pneumoniae* (see: Katsuragi et al. Journal of Bacteriology (1987) 169(5) p 2301-2306; Fouts et al. PLoS Genetics (2008) 4(7), E1000141). These pullulanases, along with those from, for example, *Bacillus acidopullulyticus* are members of Glycoside Hydrolase Family 13 In some embodiments, the enzyme composition will include an acid fungal protease. In a further embodiment, the acid fungal protease is derived from a *Trichoderma* sp. and may be any one of the proteases disclosed in U.S. Pat. No. 7,563,607 (published as US 2006/0154353 Jul. 13, 2006), incorporated herein by reference. In a further embodiment, the enzyme composition will include a phytase from *Buttiauxiella* spp. (e.g., BP-17, see also variants disclosed in PCT patent publication WO 2006/043178).

In other embodiments, the variant glucoamylases of the disclosure may be combined with other glucoamylases. In some embodiments, the glucoamylases of the disclosure will be combined with one or more glucoamylases derived from strains of *Aspergillus* or variants thereof, such as *A. oryzae*, *A. niger*, *A. kawachi*, and *A. awamori*; glucoamylases derived from strains of *Humicola* or variants thereof, particularly *H. grisea*, such as the glucoamylase having at least about 90%, about 93%, about 95%, about 96%, about 97%, about 98%, or about 99% sequence identity to SEQ ID NO: 3 disclosed in WO 05/052148; glucoamylases derived from strains of *Talaromyces* or variants thereof, particularly *T. emersonii*; glucoamylases derived from strains of *Athelia* and particularly *A. rolfsii*; glucoamylases derived from strains of *Penicillium*, particularly *P. chrysogenum*.

In particular, the variant glucoamylases may be used for starch conversion processes, and particularly in the production of dextrose for fructose syrups, specialty sugars and in alcohol and other end-product (e.g., organic acid, ascorbic acid, and amino acids) production from fermentation of starch containing substrates (G. M. A. van Beynum et al., Eds. (1985) Starch Conversion Technology, Marcel Dekker Inc. NY). Dextrins produced using variant glucoamylase compositions of the disclosure may result in glucose yields of at least 80%, at least 85%, at least 90% and at least 95%. Production of alcohol from the fermentation of starch substrates using glucoamylases encompassed by the disclosure may include the production of fuel alcohol or portable alcohol. In some embodiments, the production of alcohol will be greater when the variant glucoamylase is used under the same conditions as the parent glucoamylase. In some embodiments, the production of alcohol will be between about 0.5% and 2.5% better, including but not limited to about 0.6%, about 0.7%, about 0.8%, about 0.9%, about 1.0%, about 1.1%, about 1.2%, about 1.3%, about 1.4%, about 1.5%, about 1.6%. about 1.7%, about 1.8%, about 1.9%, about 2.0%, about 2.1%, about 2.2%, about 2.3%, and about 2.4% more alcohol than the parent glucoamylase.

In some embodiments, the variant glucoamylases of the disclosure will find use in the hydrolysis of starch from various plant-based substrates, which are used for alcohol production. In some embodiments, the plant-based substrates will include corn, wheat, barley, rye, milo, rice, sugar cane, potatoes and combinations thereof. In some embodiments, the plant-based substrate will be fractionated plant material, for example a cereal grain such as corn, which is fractionated into components such as fiber, germ, protein and starch (endosperm) (U.S. Pat. No. 6,254,914 and U.S. Pat. No. 6,899,910). Methods of alcohol fermentations are described in The Alcohol Textbook, K. A. Jacques et al., Eds. 2003, Nottingham University Press, UK.

In certain embodiments, the alcohol will be ethanol. In particular, alcohol fermentation production processes are characterized as wet milling or dry milling processes. In some embodiments, the variant glucoamylase will be used in a wet milling fermentation process and in other embodiments the variant glucoamylase will find use in a dry milling process.

Dry grain milling involves a number of basic steps, which generally include: grinding, cooking, liquefaction, saccharification, fermentation and separation of liquid and solids to produce alcohol and other co-products. Plant material and particularly whole cereal grains, such as corn, wheat or rye are ground. In some cases, the grain may be first fractionated into component parts. The ground plant material may be milled to obtain a coarse or fine particle. The ground plant material is mixed with liquid (e.g., water and/or thin stillage) in a slurry tank. The slurry is subjected to high temperatures (e.g., about 90° C. to about 105° C. or higher) in a jet cooker along with liquefying enzymes (e.g., alpha-amylases) to solublize and hydrolyze the starch in the grain to dextrins. The mixture is cooled down and further treated with saccharifying enzymes, such as glucoamylases encompassed by the instant disclosure, to produce glucose. The mash containing glucose may then be fermented for approximately 24 to 120 hours in the presence of fermentation microorganisms, such as ethanol producing microorganism and particularly yeast (*Saccharomyces* spp). The solids in the mash are separated from the liquid phase and alcohol such as ethanol and useful co-products such as distillers' grains are obtained.

In some embodiments, the saccharification step and fermentation step are combined and the process is referred to as simultaneous saccharification and fermentation or simultaneous saccharification, yeast propagation and fermentation.

In other embodiments, the variant glucoamylase is used in a process for starch hydrolysis wherein the temperature of the process is between about 30° C. and about 75° C., in some embodiments, between about 40° C. and about 65° C. In some embodiments, the variant glucoamylase is used in a process for starch hydrolysis at a pH between about 3.0 and about 6.5. The fermentation processes in some embodiments include milling of a cereal grain or fractionated grain and combining the ground cereal grain with liquid to form a slurry that is then mixed in a single vessel with a variant glucoamylase according to the disclosure and optionally other enzymes such as, but not limited to, alpha-amylases, other glucoamylases, phytases, proteases, pullulanases, isoamylases or other enzymes having granular starch hydrolyzing activity and yeast to produce ethanol and other co-products (see e.g., U.S. Pat. No. 4,514,496, WO 04/081193, and WO 04/080923).

In some embodiments, the disclosure pertains to a method of saccharifying a liquid starch solution, which comprises an enzymatic saccharification step using a variant glucoamylase of the disclosure. The liquid starch solution may be produced by solubilising starch in water or an aqueous buffer and optionally heating to gelatinize the starch. Further partial degradation of the starch by amylases may be applied.

The present invention provides a method of using glucoamylase variants of the invention for producing glucose and the like from starch. Generally, the method includes the steps of partially hydrolyzing precursor starch in the presence of alpha-amylase and then further hydrolyzing the release of D-glucose from the non-reducing ends of the starch or related oligo- and polysaccharide molecules in the presence of glucoamylase by cleaving alpha-(1-4) and alpha-(1-6) glucosidic bonds. The partial hydrolysis of the precursor starch utilizing alpha-amylase provides an initial breakdown of the starch molecules by hydrolyzing internal alpha-(1-4)-linkages. In commercial applications, the initial hydrolysis using alpha-amylase is run at a temperature of approximately 105° C. A very high starch concentration is processed, usually 30% to 40% solids. The initial hydrolysis is usually carried out for five minutes at this elevated temperature. The partially hydrolyzed starch can then be transferred to a second tank and incubated for approximately one hour at a temperature of 85° to 90° C. to derive a dextrose equivalent (D.E.) of 10 to 15. The step of further hydrolyzing the release of D-glucose from the non-reducing ends of the starch or related oligo- and polysaccharides molecules in the presence of glucoamylase is normally carried out in a separate tank at a reduced temperature between 30° and 60° C. Often the temperature of the substrate liquid is dropped to between 55° C. and 60° C. The pH of the solution is dropped from 6 to 6.5 to a range between 3 and 5.5. Often, the pH of the solution is 4 to 4.5. The glucoamylase is added to the solution and the reaction is carried out for 24-72 hours, such as 36-48 hours.

Examples of saccharification processes wherein the glucoamylase variants of the invention may be used include the processes described in JP 3-224493; JP 1-191693; JP 62-272987; and EP 452,238. The glucoamylase variant(s) described herein may be used in combination with an enzyme that hydrolyzes only alpha-(1-6)-glucosidic bonds in molecules with at least four glucosyl residues. Preferentially, the glucoamylase variant can be used in combination with pullulanase or alpha-amylase. The use of alpha-amylase and pullulanase for debranching, the molecular properties of the enzymes, and the potential use of the enzymes with glucoamylase is set forth in G. M. A. van Beynum et al., *Starch Conversion Technology*, Marcel Dekker, New York, 1985, 101-142.

In one embodiment, the use of a glucoamylase variant as described herein in a starch conversion process, such as in a continuous saccharification step, is provided. The glucoamylase variants described herein may also be used in immobilised form. This is suitable and often used for producing maltodextrins or glucose syrups or specialty syrups, such as maltose syrups and further for the raffinate stream of oligosaccharides in connection with the production of fructose syrups.

When the desired final sugar product is, e.g., high fructose syrup the dextrose syrup may be converted into fructose. After the saccharification process the pH is increased to a value in the range of 6-8, such as pH 7.5, and the calcium is removed by ion exchange. The dextrose syrup is then converted into high fructose syrup using, e.g., an immobilized glucose isomerase (such as Sweetzyme™ IT).

In other embodiments, the variant glucoamylase is used in a process for beer brewing. Brewing processes are well-known in the art, and generally involve the steps of malting, mashing, and fermentation. Mashing is the process of converting starch from the milled barley malt and solid adjuncts into fermentable and un-fermentable sugars to produce wort. Traditional mashing involves mixing milled barley malt and adjuncts with water at a set temperature and volume to continue the biochemical changes initiated during the malting process. The mashing process is conducted over a period of time at various temperatures in order to activate the endogenous enzymes responsible for the degradation of proteins and carbohydrates. After mashing, the wort is separated from the solids (spent grains). Following wort separation, the wort may be fermented with brewers' yeast to produce a beer. The short-branched glucose oligomers formed during mashing may be further hydrolyzed by addition of exogenous enzymes like glucoamylases and/or alpha-amylases, beta-amylases and pullulanase, among others. The wort may be used as it is or it may be concentrated and/or dried. The concentrated and/or dried wort may be used as brewing extract, as malt extract flavoring, for non-alcoholic malt beverages, malt vinegar, breakfast cereals, for confectionery etc. The wort is fermented to produce an alcoholic beverage, typically a beer, e.g., ale, strong ale, bitter, stout, porter, lager, export beer, malt liquor, barley wine, happoushu, high-alcohol beer, low-alcohol beer, low-calorie beer, or light beer. In another typical embodiment, the wort is fermented to produce portable ethanol.

In some embodiments, the disclosure pertains to a method of hydrolyzing and saccharifying gelatinised and liquefied (typically) grist starch to be used in brewing, whereby an enzymatic composition comprising one or more glucoamylases as contemplated herein, is used to enhance the amount of brewers' yeast fermentable sugars obtained from the starch. A brewing process is used to produce the portable product, beer, where fermentable sugars are converted to ethanol and $CO_2$ by fermentation with brewers' yeast. The fermentable sugars are traditionally derived from starch in cereal grains, optionally supplemented with fermentable sugar sources such as glucose and maltose syrups and cane sugar. Briefly, beer production, well-known in the art, typically includes the steps of malting, mashing, and fermentation.

Historically the first step in beer production is malting—steeping, germination and drying of cereal grain (e.g. barley). During malting enzymes are produced in the germinating cereal (e.g. barley) kernel and there are certain changes in its chemical constituents (known as modification) including some degradation of starch, proteins and beta-glucans.

The malted cereal is milled to give a grist which may be mixed with a milled adjunct (e.g. non-germinated cereal grain) to give a mixed grist. The grist is mixed with water and subjected to mashing; a previously cooked (gelatinised and liquefied) adjunct may be added to the mash. The mashing process is conducted over a period of time at various temperatures in order to hydrolyse cereal proteins, degrade beta-glucans and solubilise and hydrolyse the starch. The hydrolysis of the grist starch in the malt and adjunct in traditional mashing is catalysed by two main enzymes endogenous to malted barley. Alpha-amylase, randomly cleaves alpha-1,4 bonds in the interior of the starch molecule fragmenting them into smaller dextrins. Beta-amylase sequentially cleaves alpha-1,4 bonds from the non-reducing end of the these dextrins producing mainly maltose. Both alpha- and beta-amylase are unable to hydrolyse the alpha-1,6 bonds which forms the branching points of the starch chains in the starch molecule, which results in the accumulation of limit dextrins in the mash. Malt does contain an enzyme, limit dextrinase, which catalyses the hydrolysis of alpha-1,6 bonds but it only shows weak activity at mashing temperatures due to its thermolability. After mashing, the liquid extract (wort) is separated from the spent grain solids (i.e. the insoluble grain and husk material forming part of grist). The objectives of wort separation include: • to obtain good extract recovery, • to obtain good filterability, and • to produce clear wort. Extract recovery and filterability of the wort are important in the economics of the brewing process.

The composition of the wort depends on the raw materials, mashing process and profiles and other variables. A typical wort comprises 65-80% fermentable sugars (glucose, maltose and maltotriose, and 20-35% non-fermentable limit dextrins (sugars with a higher degree of polymerization than maltotriose). An insufficiency of starch hydrolytic enzymes during mashing can arise when brewing with high levels of adjunct unmalted cereal grists. A source of exogenous enzymes, capable of producing fermentable sugars during the mashing process is thus needed. Furthermore, such exogenous enzymes are also needed to reduce the level of non-fermentable sugars in the wort, with a corresponding increase in fermentable sugars, in order to brew highly attenuated beers with a low carbohydrate content. Herein disclosed is a enzyme composition for hydrolysis of starch comprising at least one glucoamylase as contemplated herein, which can be added to the mash or used in the mashing step of a brewing process, in order to cleave alpha-1,4 bonds and/or alpha-1,6 bonds in starch grist and thereby increase the fermentable sugar content of the wort and reduce the residue of non-fermentable sugars in the finished beer. In addition, the wort, so produced may be dried (by for example spray drying) or concentrated (e.g. boiling and evaporation) to provide a syrup or powder.

The grist, as contemplated herein, may comprise any starch and/or sugar containing plant material derivable from any plant and plant part, including tubers, roots, stems, leaves and seeds. Often the grist comprises grain, such as grain from barley, wheat, rye, oat, corn, rice, milo, millet and sorghum, and more preferably, at least 10%, or more preferably at least 15%, even more preferably at least 25%, or most preferably at least 35%, such as at least 50%, at least 75%, at least 90% or even 100% (w/w) of the grist of the wort is derived from grain. Most preferably the grist comprises malted grain, such as barley malt. Preferably, at least 10%, or more preferably at least 15%, even more preferably at least 25%, or most preferably at least 35%, such as at least 50%, at least 75%, at least 90% or even 100% (w/w) of the grist of the wort is derived from malted grain. Preferably the grist comprises adjunct, such as non-malted grain from barley, wheat, rye, oat, corn, rice, milo, millet and sorghum, and more preferably, at least 10%, or more preferably at least 15%, even more preferably at least 25%, or most preferably at least 35%, such as at least 50%, at least 75%, at least 90% or even 100% (w/w) of the grist of the wort is derived from non-malted grain or other adjunct. Adjunct comprising readily fermentable carbohydrates such as sugars or syrups may be added to the malt mash before, during or after the mashing process of the invention but is preferably added after the mashing process. A part of the adjunct may be treated with an alpha-amylase, and/or endopeptidase (protease) and/or a endoglucanase, and/or heat treated before being added to the mash. The enzyme composition, as contemplated herein, may include additional enzyme(s), preferably an enzyme selected from among an alpha-amylase, protease, pullulanase, isoamylase, cellulase, glucanase such as exoglucanase or endoglucanase, xylanase, arabinofuranosidase, feruloyl esterase, xylan acetyl esterase, phytase and glucoamylase. During the mashing process, starch extracted from the grist is gradually hydrolyzed into fermentable sugars and smaller dextrins. Preferably the mash is starch negative to iodine testing, before wort separation.

In one aspect, a pullulanase (E. C. 3.2.1.41) enzyme activity is exogenously supplied and present in the mash. The pullulanase may be added to the mash ingredients, e.g., the water and/or the grist before, during or after forming the mash.

In another aspect, an alpha-amylase enzyme activity is exogenously supplied and present in the mash. The alpha-amylase may be added to the mash ingredients, e.g., the water and/or the grist before, during or after forming the mash.

In a further aspect, both pullulanase and alpha-amylase enzyme activities are exogenously supplied and present in the mash. The alpha-amylase and pullulanase may be added to the mash ingredients, e.g., the water and/or the grist before, during or after forming the mash.

A further enzyme may be added to the mash, said enzyme being selected from the group consisting of among amylase, protease, pullulanase, isoamylase, cellulase, glucanase, xylanase, arabinofuranosidase, ferulic acid esterase, xylan acetyl esterase, phytase and a further glucoamylase.

Prior to the third step of the brewing process, fermentation, the wort is typically transferred to a brew kettle and boiled vigorously for 50-60 minutes. A number of important processes occur during wort boiling (further information may be found in "Technology Brewing and Malting" by Wolfgang Kunze of the Research and Teaching Institute of Brewing, Berlin (VLB), 3rd completely updated edition, 2004, ISBN 3-921690-49-8) including inactivation of the endogenous malt enzymes and any exogenous enzyme added to the mash or adjunct. The boiled wort is then cooled, pitched with brewers' yeast and fermented at temperatures typically ranging from 8-16° C. to convert the fermentable sugars to ethanol. A low-alcohol beer can be produced from the final beer, by a process of vacuum evaporation that serves to selectively remove alcohol.

In an alternative embodiment, the disclosure pertains to a method of enhancing the amount of fermentable sugars in the wort, using an enzymatic composition comprising one or more glucoamylases as contemplated herein (e.g. thermolabile glucoamylase), whereby the enzymatic composition is added to the wort after it has been boiled, such that the one or more glucoamylases are active during the fermentation step. The enzymatic composition can be added to the boiled wort either before, simultaneously, or after the wort is pitched with the brewers' yeast. At the end of the fermentation and maturation step the beer, which may optionally be subjected to vacuum evaporation to produce a low-alcohol beer, is then pasteurized. An inherent advantage of this method lies in the duration of the fermentation process, which is about 6-15 days (depending on pitching rate, fermentation, temperature, etc), which allows more time for the enzymatic cleavage of non-fermentable sugars, as compared to the short mashing step (2-4 h duration). A further advantage of this method lies in the amount of the enzymatic composition needed to achieve the desired decrease in non-fermentable sugars (and increase in fermentable sugars), which corresponds to a significantly lower number of units of enzymatic activity (e.g. units of glucoamylase activity) than would need to be added to the mash to achieve a similar decrease in non-fermentable sugars. In addition, it removes the difficulties often seen during wort separation, especially by lautering, when high dose rates of glucoamylase are added in the mash.

In one aspect, the disclosure pertains to an enzymatic composition comprising at least one additional enzyme selected among amylase, protease, pullulanase, isoamylase, cellulase, glucanase, xylanase, arabinofuranosidase, ferulic acid esterase, xylan acetyl esterase, phytase and a further glucoamylase.

In a further aspect, the disclosure pertains to an enzymatic composition, wherein the composition comprises at least one additional enzyme selected among alpha-amylase and/or pullulanase.

In a further aspect, the disclosure pertains to an enzymatic composition, wherein the composition further comprises alpha-amylase and pullulanase.

In a further aspect, the disclosure pertains to an enzymatic composition, which enzymatic composition comprises less than 1, less than 0.8, less than 0.6, less than 0.5, less than 0.4, less than 0.2, less than 0.125, less than 0.1, less than 0.05, less than 0.01, or less than 0.005 XU of xylanase activity per GAU of a glucoamylase variant as described herein. If desired, xylanase activity may be reduced by different methods known to the skilled person such as e.g. heat treatment, passing through wheat bran, or other materials, which may selectively adsorb xylanase activity.

In a further aspect, the disclosure pertains to an enzymatic composition, which enzymatic composition comprises less than 400, less than 200, less than 50, less than 20, or less than 2 XU of xylanase activity per gram of the composition.

In a further aspect, the disclosure pertains to an enzymatic composition, which enzymatic composition comprises between 0.1-20, 0.1-10, 0.1-5 or 0.2-3 SSU of alpha-amylase activity per GAU of a glucoamylase variant as described herein.

In a further aspect, the disclosure pertains to an enzymatic composition, which enzymatic composition comprises between 0.30-10, 1-8, 3-10 or 5-9 PU of pullulanase activity per GAU of a glucoamylase variant as described herein.

In a further aspect, the disclosure pertains to an enzymatic composition, which enzymatic composition comprises between 0.95-20 SSU of alpha-amylase activity per GAU of a glucoamylase variant as described herein and between 0.30-10 PU of pullulanase activity per GAU of a glucoamylase variant as described herein.

In a further aspect, the disclosure pertains to an enzymatic composition, which enzymatic composition comprises between 0.95-20 SSU of alpha-amylase activity per GAU of a glucoamylase variant as described herein and between 0.30-10 PU of pullulanase activity per GAU of a glucoamylase variant as described herein and less than 1, less than 0.8, less than 0.6, less than 0.5, less than 0.4, less than 0.2, less than 0.125, less than 0.1, less than 0.05, less than 0.01, or less than 0.005 XU of xylanase activity per GAU of a glucoamylase variant as described herein.

In a further aspect, the disclosure pertains to an enzymatic composition, which enzymatic composition comprises between 0.05-10, 0.1-10, 0.1-8, 0.1-5, 0.1-3, 0.2-3, 0.2-2 PU of pullulanase activity per GAU of a glucoamylase variant as described herein.

In a further aspect, the disclosure pertains to an enzymatic composition, which enzymatic composition comprises between 0.1-20, 1-15, 2-10, 3-10 SSU of alpha-amylase activity per GAU of a glucoamylase variant as described herein.

In a further aspect, the disclosure pertains to an enzymatic composition, which enzymatic composition comprises between 0.05-10 PU of pullulanase activity per GAU of a glucoamylase variant as described herein and between 0.1-20 SSU of alpha-amylase activity per GAU of a glucoamylase variant as described herein.

In a further aspect, the disclosure pertains to an enzymatic composition, which enzymatic composition comprises between 0.1-5 PU of pullulanase activity per GAU of a glucoamylase variant as described herein and between 1-15 SSU of alpha-amylase activity per GAU of a glucoamylase variant as described herein.

In a further aspect, the disclosure pertains to an enzymatic composition, which enzymatic composition comprises between 0.2-2 PU of pullulanase activity per GAU of a glucoamylase variant as described herein and between 2-10 SSU of alpha-amylase activity per GAU of a glucoamylase variant as described herein.

In a further aspect, the disclosure pertains to an enzymatic composition, which enzymatic composition comprises between 0.05-10 PU of pullulanase activity per GAU of a glucoamylase variant as described herein and between 0.1-20 SSU of alpha-amylase activity per GAU of a glucoamylase variant as described herein and less than 1, less than 0.8, less than 0.6, less than 0.5, less than 0.4, less than 0.2, less than 0.125, less than 0.1, less than 0.05, less than 0.01, or less than 0.005 XU of xylanase activity per GAU of a glucoamylase variant as described herein.

In a further aspect, the disclosure pertains to an enzymatic composition, which enzymatic composition comprises between 0.1-5 PU of pullulanase activity per GAU of a glucoamylase variant as described herein and between 1-15 SSU of alpha-amylase activity per GAU of a glucoamylase variant as described herein and less than 1, less than 0.8, less than 0.6, less than 0.5, less than 0.4, less than 0.2, less than 0.125, less than 0.1, less than 0.05, less than 0.01, or less than 0.005 XU of xylanase activity per GAU of a glucoamylase variant as described herein.

In a further aspect, the disclosure pertains to an enzymatic composition, which enzymatic composition comprises between 0.2-2 PU of pullulanase activity per GAU of a glucoamylase variant as described herein and between 2-10 SSU of alpha-amylase activity per GAU of a glucoamylase variant as described herein and less than 1, less than 0.8, less than 0.6, less than 0.5, less than 0.4, less than 0.2, less than 0.125, less than 0.1, less than 0.05, less than 0.01, or less than 0.005 XU of xylanase activity per GAU of a glucoamylase variant as described herein.

In one aspect, the glucoamylase variant as described herein is added in an amount of 500-20000 GAU/kg grist. In another aspect, the glucoamylase variant as described herein is added in an amount of 750-10000 GAU/kg grist. In a further aspect, the glucoamylase variant as described herein is added in an amount of 1000-7500 GAU/kg grist.

The present disclosure also provides an animal feed composition or formulation comprising at least one variant glucoamylase encompassed by the disclosure. Methods of using a glucoamylase enzyme in the production of feeds comprising starch are provided in WO 03/049550 (herein incorporated by reference in its entirety). Briefly, the glucoamylase variant is admixed with a feed comprising starch. The glucoamylase is capable of degrading resistant starch for use by the animal. In some embodiments a glucoamylase variant as described herein is used in processes in the generation of fuels based on starch feed stocks. Other objects and advantages of the present disclosure are apparent from the present specification.

Further embodiments according to the invention:

Embodiment 1

Use of a glucoamylase variant comprising two or more amino acid substitutions relative to interconnecting loop 2' with the amino acid sequence from position 518 to position 543 of SEQ ID NO:2 or equivalent sequence of residues in a parent glucoamylase, and/or loop 1 with the amino acid sequence from position 21 to position 51 of SEQ ID NO:2 or equivalent sequence of residues in a parent glucoamylase, and/or helix 2 with the amino acid sequence from position 52 to position 68 of SEQ ID NO:2 or equivalent sequence of residues in a parent glucoamylase, and/or loop 11 with the amino acid sequence from position 396 to position 420 of SEQ ID NO:2 or equivalent sequence of residues in a parent glucoamylase, and/or helix 12 with the amino acid sequence from position 421 to position 434 of SEQ ID NO:2 or equivalent sequence of residues in a parent glucoamylase for reducing the synthesis of condensation products during hydrolysis of starch.

Embodiment 2

Use of a glucoamylase variant, which when in its crystal, form has a crystal structure for which the atomic coordinates of the main chain atoms have a root-mean-square deviation from the atomic coordinates of the equivalent main chain atoms of TrGA (as defined in Table 20 in WO2009/067218) of less than 0.13 nm following alignment of equivalent main chain atoms, and which have a linker region, a starch binding domain and a catalytic domain, said variant comprising two or more amino acid substitutions relative to the amino acid sequence of the parent glucoamylase in interconnecting loop 2' of the starch binding domain, and/or in loop 1, and/or in helix 2, and/or in loop 11, and/or in helix 12 of the catalytic domain for reducing the synthesis of condensation products during hydrolysis of starch.

Embodiment 3

The use of a glucoamylase variant according to any one of the embodiments 1-2, wherein said two or more amino acid substitutions are relative to the interconnecting loop 2' with the amino acid sequence from position 518 to position 543 of SEQ ID NO:2, and/or loop 1 with the amino acid sequence from position 21 to position 51 of SEQ ID NO:2, and/or helix 2 with the amino acid sequence from position 52 to position 68 of SEQ ID NO:2, and/or loop 11 with the amino acid sequence from position 396 to position 420 of SEQ ID NO:2, and/or helix 12 with the amino acid sequence from position 421 to position 434 of SEQ ID NO:2.

Embodiment 4

The use of a glucoamylase variant according to any one of the embodiments 1-3, wherein the two or more amino acid substitutions are at least one amino acid substitution in the interconnecting loop 2' and at least one amino acid substitution in loop 1 and/or helix 2 and/or loop 11 and/or helix 12.

Embodiment 5

The use of a glucoamylase variant according to any one of the embodiments 1-4, wherein the two or more amino acid substitutions are 1, 2, 3 or 4 amino acid substitutions in the interconnecting loop 2' and 1, 2, 3 or 4 amino acid substitutions in loop 1 and/or helix 2 and/or loop 11 and/or helix 12.

Embodiment 6

The use of a glucoamylase variant according to any one of the embodiments 1-5, wherein the two or more amino acid substitutions are at least one amino acid substitution in interconnecting loop 2' and at least one amino acid substitution in loop 1.

Embodiment 7

The use of a glucoamylase variant according to any one of the embodiments 1-6, wherein the two or more amino acid substitutions are at least one amino acid substitution in interconnecting loop 2' and at least one amino acid substitution in helix 2.

Embodiment 8

The use of a glucoamylase variant according to any one of the embodiments 1-7, wherein the two or more amino acid substitutions are at least one amino acid substitution in interconnecting loop 2' and at least one amino acid substitution in loop 11.

Embodiment 9

The use of a glucoamylase variant according to any one of the embodiments 1-8, wherein the two or more amino acid substitutions are at least one amino acid substitution in interconnecting loop 2' and at least one amino acid substitution in helix 12.

Embodiment 10

The use of a glucoamylase variant according to any one of the embodiments 1-9, wherein the two or more amino acid substitutions are at least one amino acid substitution in interconnecting loop 2' and at least one amino acid substitution in loop 1 and at least one amino acid substitution in helix 2.

Embodiment 11

The use of a glucoamylase variant according to any one of embodiments 1-10, wherein the glucoamylase variant has at least one amino acid substitution within position 520-543, 530-543, or 534-543 of interconnecting loop 2', the positions corresponding to the respective position in SEQ ID NO:2 or equivalent positions in a parent glucoamylase.

Embodiment 12

The use of a glucoamylase variant according to any one of embodiments 1-11, wherein the glucoamylase variant has at least one amino acid substitution within the amino acid sequence of position 30-50, 35-48, or 40-46 of loop 1, the positions corresponding to the respective position in SEQ ID NO:2 or equivalent positions in a parent glucoamylase.

Embodiment 13

The use of a glucoamylase variant according to any one of embodiments 1-12, wherein the glucoamylase variant has at least one amino acid substitution within the amino acid sequence of position 50-66, 55-64, or 58-63 of helix 2, the positions corresponding to the respective position in SEQ ID NO:2 or equivalent positions in a parent glucoamylase.

Embodiment 14

The use of a glucoamylase variant according to any one of embodiments 1-13, wherein the glucoamylase variant has at least one amino acid substitution within the amino acid sequence of position 405-420, 410-420, or 415-420 of loop 11, the positions corresponding to the respective position in SEQ ID NO:2 or equivalent positions in a parent glucoamylase.

Embodiment 15

The use of a glucoamylase variant according to any one of embodiments 1-14, wherein the glucoamylase variant has at least one amino acid substitution within the amino acid sequence of position 421-434, 425-434, or 428-434 of helix 12, the positions corresponding to the respective position in SEQ ID NO:2 or equivalent positions in a parent glucoamylase.

Embodiment 16

The use of a glucoamylase variant according to any one of embodiments 1-15, wherein the glucoamylase variant has at least 80%, 85%, 90%, 95%, 98%, or 99.5% sequence identity to the parent glucoamylase.

Embodiment 17

The use of a glucoamylase variant according to any one of embodiments 1-16, wherein the glucoamylase variant has at least 80%, 85%, 90%, 95%, 98%, or 99.5% sequence identity to SEQ ID NO: 1, 2, 3, 5, 6, 7, 8, or 9.

Embodiment 18

The use of a glucoamylase variant to any one of the embodiments 1-17, wherein the glucoamylase variant has a starch binding domain that has at least 96%, 97%, 98%, 99%, or 99.5% sequence identity with the starch binding domain of SEQ ID NO: 1, 2, 11, 385, 386, 387, 388, 389, or 390.

Embodiment 19

The use of a glucoamylase variant according to any one of the embodiments 1-18, wherein the glucoamylase variant has a catalytic domain that has at least 80%, 85%, 90%, 95%, or 99.5% sequence identity with the catalytic domain of SEQ ID NO: 1, 2, 3, 5, 6, 7, 8, or 9.

Embodiment 20

The use of a glucoamylase variant according to any one of embodiments 1-19, wherein the glucoamylase variant has at least 80%, 85%, 90%, 95%, 98%, or 99.5% sequence identity to SEQ ID NO:2.

Embodiment 21

The use of a glucoamylase variant according to any one of embodiments 1-20, wherein the condensation product is isomaltose.

Embodiment 22

The use of a glucoamylase variant according to any one of embodiments 1-21, wherein the hydrolysis of starch is in a brewing process.

Embodiment 23

The use of a glucoamylase variant according to any one of embodiments 1-22, wherein the glucoamylase exhibit an enhanced production of fermentable sugar(s) as compared to the parent glucoamylase, such as TrGA.

Embodiment 24

The use of a glucoamylase variant according to any one of embodiments 1-23, wherein the glucoamylase exhibit an enhanced production of fermentable sugars in a mashing step of the brewing process as compared to the parent glucoamylase, such as TrGA.

Embodiment 25

The use of a glucoamylase variant according to any one of embodiments 1-24, wherein the glucoamylase exhibit an enhanced production of fermentable sugars in a fermentation step of the brewing process as compared to the parent glucoamylase, such as TrGA.

Embodiment 26

The use of a glucoamylase variant according to any one of embodiments 1-25, wherein the fermentable sugar is glucose.

Embodiment 27

The use of a glucoamylase variant according to any one of embodiments 1-26, wherein the hydrolysis of starch is in a process for producing glucose syrup.

Embodiment 28

The use of a glucoamylase variant according to any one of embodiments 1-27, wherein the glucoamylase exhibit a reduced ratio between isomaltose synthesis (IS) and starch hydrolysis activity (SH) as compared to the parent glucoamylase, such as TrGA.

Embodiment 29

The use of a glucoamylase variant according to any one of embodiments 1-28, wherein the glucoamylase exhibit a reduced starch hydrolysis activity, which is not more than 5%, not more than 10% or not more than 15% reduced as compared to the parent glucoamylase, such as TrGA.

Embodiment 30

The use of a glucoamylase variant according to any one of embodiments 1-29, wherein the glucoamylase exhibit an enhanced real degree of fermentation as compared to the parent glucoamylase such as TrGA.

Embodiment 31

The use of a glucoamylase variant according to any one of embodiments 1-30, wherein the glucoamylase forms a lower amount of condensation products than the amount of condensation products formed by the glucoamylase *Aspergillus niger* (AnGA) (SEQ ID NO: 6) under comparable conditions.

Embodiment 32

The use of a glucoamylase variant according to any one of embodiments 1-31, wherein the glucoamylase forms an amount of condensation products which amount is essentially the same as, not more than 5% higher, not more than 8% higher or not more than 10% higher than the amount of condensation products formed by *Aspergillus niger* (AnGA) (SEQ ID NO: 6) under comparable conditions.

Embodiment 33

The use of a glucoamylase variant according to any one of embodiments 31-32, wherein dosing of the glucoamylases are the same based on protein concentration.

Embodiment 34

The use of a glucoamylase variant according to any one of embodiments 31-33, wherein dosing of the glucoamylases are the same based on measurement of activity in activity assays.

Embodiment 35

The use of a glucoamylase variant according to any one of embodiments 1-34, which glucoamylase variant has an amino acid substitution in position 539 and one or more amino acid substitutions in a position selected from position 44, 61, 417 and 431, the positions corresponding to the respective position in SEQ ID NO:2 or an equivalent position in a parent glucoamylase.

Embodiment 36

The use of a glucoamylase variant according to any one of embodiments 1-35, which glucoamylase variant has an amino acid substitution in position 539 and a) an amino acid substitution in position 44 and/or b) amino acid substitutions in both positions 417 and 431, the positions corresponding to the respective position in SEQ ID NO:2 or an equivalent position in a parent glucoamylase.

Embodiment 37

The use of a glucoamylase variant according to any one of embodiments 1-36, which glucoamylase variant has an amino acid substitution in position 539 and an amino acid substitution in position 44, the positions corresponding to the respective position in SEQ ID NO:2 or an equivalent position in a parent glucoamylase.

Embodiment 38

The use of a glucoamylase variant according to any one of embodiments 1-37, which glucoamylase variant has an amino acid substitution in position 539 and amino acid substitutions in positions 417 and 431, the positions corresponding to the respective position in SEQ ID NO:2 or an equivalent position in a parent glucoamylase.

Embodiment 39

The use of a glucoamylase variant according to any one of embodiments 1-38, which glucoamylase variant has an amino acid substitution in position 539 and amino acid substitutions in positions 44 and 61, the positions corresponding to the respective position in SEQ ID NO:2 or an equivalent position in a parent glucoamylase.

Embodiment 40

The use of a glucoamylase variant according to any one of embodiments 1-39, which glucoamylase variant has an amino acid substitution in position 43, the position corresponding to the respective position in SEQ ID NO:2 or an equivalent position in a parent glucoamylase.

Embodiment 41

The use of a glucoamylase variant according to any one of embodiments 1-40, which glucoamylase variant has an amino acid substitution in position 61, the position corresponding to the respective position in SEQ ID NO:2 or an equivalent position in a parent glucoamylase.

Embodiment 42

The use of a glucoamylase variant according to any one of embodiments 1-41, wherein the amino acid substitution in position 539 is 539R, the position corresponding to the respective position in SEQ ID NO:2 or an equivalent position in a parent glucoamylase.

Embodiment 43

The use of a glucoamylase variant according to any one of embodiments 1-42, wherein the amino acid substitution in position 44 is 44R, the position corresponding to the respective position in SEQ ID NO:2 or an equivalent position in a parent glucoamylase.

Embodiment 44

The use of a glucoamylase variant according to any one of embodiments 1-43, wherein the amino acid substitution in position 417 is 417R/V, the position corresponding to the respective position in SEQ ID NO:2 or an equivalent position in a parent glucoamylase.

Embodiment 45

The use of a glucoamylase variant according to any one of embodiments 1-44, wherein the amino acid substitution in position 417 is 417R, the position corresponding to the respective position in SEQ ID NO:2 or an equivalent position in a parent glucoamylase.

Embodiment 46

The use of a glucoamylase variant according to any one of embodiments 1-45, wherein the amino acid substitution in position 417 is 417V, the position corresponding to the respective position in SEQ ID NO:2 or an equivalent position in a parent glucoamylase.

Embodiment 47

The use of a glucoamylase variant according to any one of embodiments 1-46, wherein the amino acid substitution in position 431 is 431L, the position corresponding to the respective position in SEQ ID NO:2 or an equivalent position in a parent glucoamylase.

Embodiment 48

The use of a glucoamylase variant according to any one of embodiments 1-47, wherein the amino acid substitution in position 43 is 43R, the position corresponding to the respective position in SEQ ID NO:2 or an equivalent position in a parent glucoamylase.

Embodiment 49

The use of a glucoamylase variant according to any one of embodiments 1-48, wherein the amino acid substitution in position 61 is 61I, the position corresponding to the respective position in SEQ ID NO:2 or an equivalent position in a parent glucoamylase.

Embodiment 50

A glucoamylase variant as defined in any one of embodiments 1-49.

Embodiment 51

A glucoamylase variant comprising two or more amino acid substitutions, wherein an amino acid substitution is in position 539 and an amino acid substitution is in position 44, the positions corresponding to the respective position in SEQ ID NO:2 or an equivalent position in a parent glucoamylase, and which sequence has at least 80% sequence identity to the parent glucoamylase, and wherein the amino acid substitution in position 44 is not 44C.

Embodiment 52

The glucoamylase variant according to embodiment 51 comprising two or more amino acid substitutions, wherein an amino acid substitution is in position 539 and an amino acid substitution is 44R, the positions corresponding to the

Embodiment 53

The glucoamylase variant according to any one of embodiments 51-52 comprising an amino acid substitution in position 61, the position corresponding to the respective position in SEQ ID NO:2 or an equivalent position in a parent glucoamylase.

Embodiment 54

The glucoamylase variant according to any one of embodiments 51-53, wherein the glucoamylase variant has at least 85%, 90%, 95%, 98%, or 99.5% sequence identity to the parent glucoamylase.

Embodiment 55

The glucoamylase variant according to any one of embodiments 51-54, wherein the glucoamylase variant has at least 85%, 90%, 95%, 98%, or 99.5% sequence identity to SEQ ID NO: 1, 2, 3, 5, 6, 7, 8, or 9.

Embodiment 56

The glucoamylase variant according to any one of embodiments 51-55, wherein the glucoamylase variant has at least 85%, 90%, 95%, 98%, or 99.5% sequence identity to SEQ ID NO:2.

Embodiment 57

The glucoamylase variant according to any one of embodiments 51-56, wherein the amino acid substitution in position 539 is 539R, the position corresponding to the respective position in SEQ ID NO:2 or an equivalent position in a parent glucoamylase.

Embodiment 58

The glucoamylase variant according to any one of embodiments 51-57, wherein the amino acid substitution in position 44 is 44R, the position corresponding to the respective position in SEQ ID NO:2 or an equivalent position in a parent glucoamylase.

Embodiment 59

The glucoamylase variant according to any one of embodiments 51-58, wherein the amino acid substitution in position 61 is 61I, the position corresponding to the respective position in SEQ ID NO:2 or an equivalent position in a parent glucoamylase.

Embodiment 60

The glucoamylase variant according to any one of embodiments 51-59 comprising the following amino acid substitutions:
  a. D44R and A539R; or
  b. D44R, N61I and A539R,
the positions corresponding to the respective position in SEQ ID NO:2 or an equivalent position in a parent glucoamylase.

Embodiment 61

The glucoamylase variant according to any one of embodiments 51-60 consisting of SEQ ID NO:2 and having the following amino acid substitutions:
  a. D44R and A539R; or
  b. D44R, N61I and A539R,
the positions corresponding to the respective position in SEQ ID NO:2.

Embodiment 62

The glucoamylase variant according to any one of embodiments 51-61, wherein the glucoamylase variant has a starch binding domain that has at least 96%, 97%, 98%, 99%, or 99.5% sequence identity with the starch binding domain of SEQ ID NO: 1, 2, 11, 385, 386, 387, 388, 389, or 390.

Embodiment 63

The glucoamylase variant according to any one of embodiments 51-62, wherein the glucoamylase variant has a catalytic domain that has at least 80%, 85%, 90%, 95%, or 99.5% sequence identity with the catalytic domain of SEQ ID NO: 1, 2, 3, 5, 6, 7, 8, or 9.

Embodiment 64

The glucoamylase variant according to any one of embodiments 50-63, wherein the parent glucoamylase is selected from a glucoamylase obtained from a *Trichoderma* spp., an *Aspergillus* spp., a *Humicola* spp., a *Penicillium* spp., a *Talaromyces* spp., or a *Schizosaccharmyces* spp.

Embodiment 65

The glucoamylase variant according to any one of embodiments 50-64, wherein the parent glucoamylase is obtained from a *Trichoderma* spp. or an *Aspergillus* spp.

Embodiment 66

The glucoamylase variant according to any one of embodiments 50-65, which glucoamylase exhibit an enhanced production of fermentable sugar(s) as compared to the parent glucoamylase such as TrGA.

Embodiment 67

The glucoamylase variant according to any one of embodiments 50-66, which glucoamylase exhibit an enhanced production of fermentable sugars in the mashing step of the brewing process as compared to the parent glucoamylase such as TrGA.

Embodiment 68

The glucoamylase variant according to any one of embodiments 50-67, which glucoamylase exhibit an enhanced production of fermentable sugars in the fermentation step of the brewing process as compared to the parent glucoamylase such as TrGA.

Embodiment 69

The glucoamylase variant according to embodiment 68, wherein the fermentable sugar is glucose.

Embodiment 70

The glucoamylase variant according to any one of embodiments 50-69, which glucoamylase exhibit a reduced ratio between isomaltose synthesis and starch hydrolysis activity (IS/SH ratio) as compared to the parent glucoamylase such as TrGA.

Embodiment 71

The glucoamylase variant according to any one of embodiments 50-70, which glucoamylase exhibit a reduced starch hydrolysis activity which is not more than 5%, not more than 10% or not more than 15% reduced as compared to the parent glucoamylase such as TrGA.

Embodiment 72

The glucoamylase variant according to any one of embodiments 50-71, which glucoamylase exhibit an enhanced real degree of fermentation as compared to the parent glucoamylase such as TrGA.

Embodiment 73

The glucoamylase variant according to any one of embodiments 50-72, which glucoamylase forms a lower amount of condensation products than the amount of condensation products formed by *Aspergillus niger* (AnGA) (SEQ ID NO: 6) under the same conditions.

Embodiment 74

The glucoamylase variant according to any one of embodiments 50-73, which glucoamylase forms an amount of condensation products which amount is essentially the same as, not more than 5%, not more than 8%, or not more than 10% higher than the amount of condensation products formed by *Aspergillus niger* (AnGA) (SEQ ID NO: 6) under the same conditions.

Embodiment 75

The glucoamylase variant according to any one of embodiments 73-74, wherein the dosing of the glucoamylases are the same based on protein concentration.

Embodiment 76

The glucoamylase variant according to any one of embodiments 73-74, wherein the dosing of the glucoamylases are the same based on measurement of activity in activity assays.

Embodiment 77

The glucoamylase variant according to any one of embodiments 50-76, which glucoamylase has been purified.

Embodiment 78

A polynucleotide encoding a glucoamylase variant according to any of embodiments 50-77.

Embodiment 79

A vector comprising the polynucleotide according to embodiment 78, or capable of expressing a glucoamylase variant according to any of embodiments 50-77.

Embodiment 80

A host cell comprising a vector according to embodiment 79.

Embodiment 81

A host cell which has stably integrated into the chromosome a nucleic acid encoding the variant glucoamylase according to any of embodiments 50-80.

Embodiment 82

A cell capable of expressing a glucoamylase variant according to any one of embodiments 50-76.

Embodiment 83

The host cell according to any one of embodiments 78-81, or the cell according to embodiment 81, which is a bacterial, fungal or yeast cell.

Embodiment 84

The host cell according to embodiment 83, which is *Trichoderma* spp. such as *Trichoderma reesei*.

Embodiment 85

The host cell according to any one of embodiments 83-84, which is a protease deficient and/or xylanase deficient and/or native glucanase deficient host cell.

Embodiment 86

A method of expressing a glucoamylase variant, the method comprising obtaining a host cell or a cell according to any one of embodiments 80-85 and expressing the glucoamylase variant from the cell or host cell, and optionally purifying the glucoamylase variant.

Embodiment 87

The method according to embodiment 86 comprising purifying the glucoamylase variant.

Embodiment 88

Use of a glucoamylase variant according to any one of embodiments 50-76 for the preparation of an enzymatic composition.

Embodiment 89

An enzymatic composition comprising at least one glucoamylase variant according to any one of embodiments 50-77.

Embodiment 90

The enzymatic composition according to embodiment 89 comprising at least one glucoamylase variant according to any one of embodiments 50-77, wherein the composition is selected from among a starch hydrolyzing composition, a saccharifying composition, a detergent, an alcohol fermentation enzymatic composition, and an animal feed.

Embodiment 91

The enzymatic composition according to embodiment 90, which is a starch hydrolyzing composition.

Embodiment 92

The enzymatic composition according to any one of embodiments 89-91 comprising at least one additional enzyme selected among amylase, protease, pullulanase, cellulase, glucanase, xylanase, arabinofuranosidase, ferulic acid esterase, xylan acetyl esterase, and a further glucoamylase.

Embodiment 93

The enzymatic composition according to embodiment 89-92, wherein the at least one additional enzyme is selected among amylase, pullulanase, and a further glucoamylase.

Embodiment 94

The enzymatic composition according to embodiment 89-93, wherein the at least one additional is selected among amylase and pullulanase.

Embodiment 95

The enzymatic composition according to any one of embodiments 89-94, wherein the amylase is selected among alpha-amylase, and isoamylase.

Embodiment 96

A method for converting starch or partially hydrolyzed starch into a syrup containing glucose, said process including saccharifying a liquid starch solution in the presence of at least one glucoamylase variant according to any one of embodiments 50-77 or an enzymatic composition according to any one of embodiments 89-95.

Embodiment 97

The method according to embodiment 96 of saccharifying a liquid starch solution, which comprises an enzymatic saccharification step using a glucoamylase variant according to embodiment 50-77 or an enzymatic composition according to any one of embodiments 89-95.

Embodiment 98

The method according to any one of embodiments 96-97, further comprising contacting the liquid starch solution with at least one additional enzyme.

Embodiment 99

The method according to embodiment 98, wherein the additional enzyme is selected among amylase, protease, pullulanase, cellulase, glucanase, xylanase, arabinofuranosidase, ferulic acid esterase, xylan acetyl esterase, and glucoamylase.

Embodiment 100

The method according to embodiment 96-99, wherein the additional enzyme is amylase and pullulanase.

Embodiment 101

The method according to embodiment any one of embodiments 96-100, wherein the amylase is selected among alpha-amylase, and isoamylase.

Embodiment 102

Use of a glucoamylase variant according to any one of embodiments 50-77 in a starch conversion process, such as a in a continuous starch conversion process.

Embodiment 103

Use of a glucoamylase variant according to any one of embodiments 50-77 in a process for producing oligosaccharides, maltodextrins, or glucose syrups.

Embodiment 104

Use of a glucoamylase variant according to any one of embodiments 50-77 in a process for producing high fructose corn syrup.

Embodiment 105

A method for producing a wort for brewing comprising forming a mash from a grist, and contacting the mash with a glucoamylase variant according to any one of embodiments 50-77 or an enzymatic composition according to any one of embodiments 89-95.

Embodiment 106

The method of embodiment 105, further comprising contacting the mash with one or more additional enzyme(s)

Embodiment 107

The method according to embodiment 106, wherein the one or more enzyme(s) is selected among amylase, protease, pullulanase, cellulase, endoglucanase, xylanase, arabinofuranosidase, ferulic acid esterase, xylan acetyl esterase, and glucoamylase.

Embodiment 108

The method according to embodiment 107, wherein the one or more enzyme(s) is amylase and/or pullulanase.

Embodiment 109

The method according to embodiment any one of embodiments 107-108, wherein the amylase is alpha-amylase and/or isoamylase.

Embodiment 110

The method according to any one of embodiments 105-109, wherein the grist comprises one or more of malted grain, unmalted grain, adjunct, and any combination thereof.

Embodiment 111

The method of any one of embodiments 105-110, further comprising fermenting the wort to obtain a fermented beverage.

Embodiment 112

The method of any one of embodiments 105-111, further comprising fermenting the wort to obtain a beer.

Embodiment 113

A method for production of a beer which comprises:
a. preparing a mash,
b. filtering the mash to obtain a wort, and
c. fermenting the wort to obtain a beer,
wherein a glucoamylase variant according to any one of embodiments 50-77 is added to: step (a) and/or step (b) and/or step (c).

Embodiment 114

The method of embodiment 113, wherein the beer is subjected to a pasteurization step.

Embodiment 115

Use of a glucoamylase variant according to any one of embodiments 50-77 to enhance the production of fermentable sugars in either the mashing step or the fermentation step of a brewing process.

Embodiment 116

A beer, wherein the beer is produced by the steps of:
a. preparing a mash,
b. filtering the mash to obtain a wort,
c. fermenting the wort to obtain a beer, and
d. pasteurizing the beer,
wherein a glucoamylase variant according to any one of embodiments 50-77 is added to: step (a) and/or step (b) and/or step (c).

Embodiment 117

The beer of embodiment 116, wherein the pasteurized beer is further characterized as being:
a. essentially without glucoamylase activity; and/or
b. a low-calorie beer and/or a low-alcohol beer.

Embodiment 118

Use of a glucoamylase variant according to any one of embodiments 50-77 in an alcohol fermentation process.

Embodiment 119

A screening method for identification of a glucoamylase variant having a reduced ratio between isomaltose synthesis and starch hydrolysis activity (IS/SH ratio) as compared to the parent glucoamylase.

Embodiment 120

A screening method for identification of a glucoamylase variant having the same or increased starch hydrolysis activity and reduced isomaltose synthesis, which is not more than 5%, not more than 10% or not more than 15% reduced as compared to the parent glucoamylase and having a reduced ratio between isomaltose synthesis and starch hydrolysis activity (IS/SH ratio) as compared to the parent glucoamylase.

Embodiment 121

A screening method for identification of a glucoamylase variant having a reduced synthesis of condensation products during hydrolysis of starch, the method comprising the steps of measuring the isomaltose synthesis and starch hydrolysis activity of glucoamylase variants and selecting the variants having a reduced starch hydrolysis activity which is not more than 5%, not more than 10% or not more than 15% reduced as compared to the parent glucoamylase and having a reduced ratio between isomaltose synthesis and starch hydrolysis activity (IS/SH ratio) as compared to the parent glucoamylase.

Embodiment 122

The glucoamylase variant obtained by the method according to any one of embodiments 119-121.

Further embodiments also part of the invention:

Further Embodiment 1

A glucoamylase variant comprising the following amino acid substitutions:
a. D44R and A539R; or
b. D44R, N61I and A539R,
the positions corresponding to the respective position in SEQ ID NO:2 or an equivalent position in a parent glucoamylase, wherein the glucoamylase variant has at least 80% sequence identity with SEQ ID NO: 1 or 2, or the parent glucoamylase.

Further Embodiment 2

The glucoamylase variant according to further embodiment 1 comprising the following amino acid substitutions:
a. D44R and A539R; or
b. D44R, N61I and A539R,
the positions corresponding to the respective position in SEQ ID NO:2 or an equivalent position in a parent glucoamylase, wherein the glucoamylase variant has at least 80% sequence identity with SEQ ID NO: 1 or 2, or the parent glucoamylase.

Further Embodiment 3

The glucoamylase variant according to any one of further embodiments 1-2 comprising the following amino acid substitutions:

a. D44R, N611 and A539R, the positions corresponding to the respective position in SEQ ID NO:2 or an equivalent position in a parent glucoamylase, wherein the glucoamylase variant has at least 80% sequence identity with SEQ ID NO: 1 or 2, or the parent glucoamylase.

Further Embodiment 4

The glucoamylase variant according to any one of further embodiments 1-2 comprising the following amino acid substitutions:
a. D44R and A539R,
the positions corresponding to the respective position in SEQ ID NO:2 or an equivalent position in a parent glucoamylase, wherein the glucoamylase variant has at least 80% sequence identity with SEQ ID NO: 1 or 2, or the parent glucoamylase.

Further Embodiment 5

The glucoamylase variant of any one of further embodiments 1-4, wherein the glucoamylase variant has at least 85% or 90% sequence identity with SEQ ID NO: 1 or 2.

Further Embodiment 6

The glucoamylase variant of further embodiment 5, wherein the glucoamylase variant has at least 95% sequence identity with SEQ ID NO: 1 or 2.

Further Embodiment 7

The glucoamylase variant of further embodiment 6, wherein the glucoamylase variant has at least 99.5% sequence identity with SEQ ID NO: 1 or 2.

Further Embodiment 8

The glucoamylase variant of any one of further embodiments 1-7, wherein the parent glucoamylase comprises SEQ ID NO: 1 or 2.

Further Embodiment 9

The glucoamylase variant of further embodiment 8, wherein the parent glucoamylase consists of SEQ ID NO: 1 or 2.

Further Embodiment 10

The glucoamylase variant according to any one of further embodiments 1-9, wherein the glucoamylase variant has a starch binding domain that has at least 96%, 97%, 98%, 99%, or 99.5% sequence identity with the starch binding domain of SEQ ID NO: 1, 2, 11, 385, 386, 387, 388, 389, or 390.

Further Embodiment 11

The glucoamylase variant according to any one of further embodiments 1-10, wherein the glucoamylase variant has a catalytic domain that has at least 80%, 85%, 90%, 95%, or 99.5% sequence identity with the catalytic domain of SEQ ID NO: 1, 2, 3, 5, 6, 7, 8, or 9.

Further Embodiment 12

The glucoamylase variant according to any one of further embodiments 1-11, wherein the parent glucoamylase is selected from a glucoamylase obtained from a *Trichoderma* spp., an *Aspergillus* spp., a *Humicola* spp., a *Penicillium* spp., a *Talaromyces* spp., or a *Schizosaccharmyces* spp.

Further Embodiment 13

The glucoamylase variant according to any one of further embodiments 1-12, wherein the parent glucoamylase is obtained from a *Trichoderma* spp. or an *Aspergillus* spp.

Further Embodiment 14

The glucoamylase variant according to any one of further embodiments 1-13, which glucoamylase exhibit an enhanced production of fermentable sugar(s) as compared to the parent glucoamylase.

Further Embodiment 15

The glucoamylase variant according to any one of further embodiments 1-14, which glucoamylase exhibit an enhanced production of fermentable sugars in the mashing step of the brewing process as compared to the parent glucoamylase.

Further Embodiment 16

The glucoamylase variant according to any one of further embodiments 1-15, which glucoamylase exhibit an enhanced production of fermentable sugars in the fermentation step of the brewing process as compared to the parent glucoamylase.

Further Embodiment 17

The glucoamylase variant according to further embodiment 16, wherein the fermentable sugar is glucose.

Further Embodiment 18

The glucoamylase variant according to any one of further embodiments 1-17, which glucoamylase exhibit a reduced ratio between isomaltose synthesis and starch hydrolysis activity (IS/SH ratio) as compared to the parent glucoamylase.

Further Embodiment 19

The glucoamylase variant according to any one of further embodiments 1-18, which glucoamylase exhibit a reduced starch hydrolysis activity which is not more than 5%, not more than 10% or not more than 15% reduced as compared to the parent glucoamylase.

Further Embodiment 20

The glucoamylase variant according to any one of further embodiments 1-19, which glucoamylase exhibit an enhanced real degree of fermentation as compared to the parent glucoamylase.

Further Embodiment 21

The glucoamylase variant according to any one of further embodiments 1-20, which glucoamylase forms a lower amount of condensation products than the amount of condensation products formed by *Aspergillus niger* (AnGA) (SEQ ID NO: 6) under the same conditions.

Further Embodiment 22

The glucoamylase variant according to any one of further embodiments 1-21, which glucoamylase forms an amount of condensation products which amount is essentially the same as, not more than 5%, not more than 8%, or not more than 10% higher than the amount of condensation products formed by *Aspergillus niger* (AnGA) (SEQ ID NO: 6) under the same conditions.

Further Embodiment 23

The glucoamylase variant according to any one of further embodiments 18-21, wherein the dosing of the glucoamylases are the same based on protein concentration.

Further Embodiment 24

The glucoamylase variant according to any one of further embodiments 18-23, wherein the dosing of the glucoamylases are the same based on measurement of activity in activity assays.

Further Embodiment 25

The glucoamylase variant according to any one of further embodiments 1-24, which glucoamylase has been purified.

Further Embodiment 26

A polynucleotide encoding a glucoamylase variant according to any of further embodiments 1-25.

Further Embodiment 27

A vector comprising the polynucleotide according to further embodiment 26, or capable of expressing a glucoamylase variant according to any of further embodiments 1-25.

Further Embodiment 28

A host cell comprising a vector according to further embodiment 27.

Further Embodiment 29

A host cell which has stably integrated into the chromosome a nucleic acid encoding the variant glucoamylase according to any of further embodiments 1-25.

Further Embodiment 30

A cell capable of expressing a glucoamylase variant according to any one of further embodiments 1-25.

Further Embodiment 31

The host cell according to any one of further embodiments 28-29, or the cell according to further embodiment 30, which is a bacterial, fungal or yeast cell.

Further Embodiment 32

The host cell according to further embodiment 31, which is *Trichoderma* spp. such as *Trichoderma reesei*.

Further Embodiment 33

The host cell according to any one of further embodiments 28-29 and 31-32, which is a protease deficient and/or xylanase deficient and/or glucanase deficient host cell.

Further Embodiment 34

A method of expressing a glucoamylase variant, the method comprising obtaining a host cell or a cell according to any one of further embodiments 28-33 and expressing the glucoamylase variant from the cell or host cell, and optionally purifying the glucoamylase variant.

Further Embodiment 35

The method according to further embodiment 34 comprising purifying the glucoamylase variant.

Further Embodiment 36

Use of a glucoamylase variant according to any one of further embodiments 1-25 for the preparation of an enzymatic composition.

Further Embodiment 37

An enzymatic composition comprising at least one glucoamylase variant according to any one of further embodiments 1-25.

Further Embodiment 38

An enzymatic composition comprising at least one glucoamylase variant according to any one of embodiments 1-25, said enzyme composition comprising one or more further enzymes.

Further Embodiment 39

The enzymatic composition according to any one of further embodiments 37-38 comprising at least one glucoamylase variant according to any one of further embodiments 1-25, wherein the composition is selected from among a starch hydrolyzing composition, a saccharifying composition, a detergent composition, an alcohol fermentation enzymatic composition, and an animal feed composition.

Further Embodiment 40

An enzymatic composition according to any one of further embodiments 36-39 comprising at least one additional enzyme selected among amylase, protease, pullulanase, isoamylase, cellulase, glucanase, xylanase, arabinofuranosidase, ferulic acid esterase, xylan acetyl esterase, phytase and a further glucoamylase.

Further Embodiment 41

The enzymatic composition according to any one of further embodiments 36-40, wherein the composition comprises at least one additional enzyme selected among alpha-amylase and/or pullulanase.

Further Embodiment 42

The enzymatic composition according to any one of further embodiments 36-41, wherein the composition comprises alpha-amylase and pullulanase.

Further Embodiment 43

The enzymatic composition according to any one of further embodiments 36-42, which enzymatic composition comprises less than 1, less than 0.8, less than 0.6, less than 0.5, less than 0.4, less than 0.2, less than 0.125, less than 0.1, less than 0.05, less than 0.01, or less than 0.005 XU of xylanase activity per GAU of a glucoamylase variant according to any one of further embodiments 1-25.

Further Embodiment 44

The enzymatic composition according to any one of further embodiments 36-43, which enzymatic composition comprises less than 400, less than 200, less than 50, less than 20, or less than 2 XU of xylanase activity per gram of the composition.

Further Embodiment 45

The enzymatic composition according to any one of further embodiments 36-44, which enzymatic composition comprises between 0.1-20, 1-15, 2-10, or 3-10 SSU of alpha-amylase activity per GAU of a glucoamylase variant according to any one of further embodiments 1-25.

Further Embodiment 46

The enzymatic composition according to any one of further embodiments 36-45, which enzymatic composition comprises between 0.05-10, 0.1-10, 0.1-8, 0.1-5, 0.1-3, 0.2-3, or 0.2-2 PU of pullulanase activity per GAU of a glucoamylase variant according to any one of further embodiments 1-25.

Further Embodiment 47

The enzymatic composition according to any one of further embodiments 36-46, which enzymatic composition comprises between 0.05-10 PU of pullulanase activity per GAU of a glucoamylase variant according to any one of further embodiments 1-25 and between 0.1-20 SSU of alpha-amylase activity per GAU of a glucoamylase variant according to any one of further embodiments 1-25.

Further Embodiment 48

The enzymatic composition according to any one of further embodiments 36-47, which enzymatic composition comprises between 0.05-10 PU of pullulanase activity per GAU of a glucoamylase variant according to any one of further embodiments 1-25 and between 0.1-20 SSU of alpha-amylase activity per GAU of a glucoamylase variant according to any one of further embodiments 1-25 and less than 1, less than 0.8, less than 0.6, less than 0.5, less than 0.4, less than 0.2, less than 0.125, less than 0.1, less than 0.05, less than 0.01, or less than 0.005 XU of xylanase activity per GAU of a glucoamylase according to any one of further embodiments 1-25.

Further Embodiment 49

A method for producing a wort for brewing comprising forming a mash from a grist, and contacting the mash with a glucoamylase variant according to any one of further embodiments 1-25 or an enzymatic composition according to any one of further embodiments 36-48.

Further Embodiment 50

The method of further embodiment 49, further comprising contacting the mash with one or more additional enzyme(s)

Further Embodiment 51

The method according to further embodiment 50, wherein the one or more enzyme(s) is selected among amylase, protease, pullulanase, isoamylase, cellulase, endoglucanase, xylanase, arabinofuranosidase, ferulic acid esterase, xylan acetyl esterase, phytase and glucoamylase.

Further Embodiment 52

The method according to further embodiment 51, wherein the one or more enzyme(s) is/are alpha-amylase and/or pullulanase.

Further Embodiment 53

The method according to any one of further embodiments 49-52, wherein the grist comprises one or more of malted grain, unmalted grain, adjunct, and any combination thereof.

Further Embodiment 54

The method of any one of further embodiments 49-53, further comprising fermenting the wort to obtain a fermented beverage.

Further Embodiment 55

The method of any one of further embodiments 49-54, further comprising fermenting the wort to obtain a beer.

Further Embodiment 56

A method for production of a beer which comprises:
a. preparing a mash,
b. filtering the mash to obtain a wort, and
c. fermenting the wort to obtain a beer,
wherein a glucoamylase variant according to any one of further embodiments 1-25 or an enzymatic composition according to any one of further embodiments 36-48 is added to: step (a) and/or step (b) and/or step (c).

Further Embodiment 57

The method of further embodiment 55, wherein the beer is subjected to a pasteurization step.

Further Embodiment 58

Use of a glucoamylase variant according to any one of further embodiments 1-25 or an enzymatic composition according to any one of further embodiments 36-48 to enhance the production of fermentable sugars in either the mashing step or the fermentation step of a brewing process.

Further Embodiment 59

A beer, wherein the beer is produced by the steps of:
a. preparing a mash,
b. filtering the mash to obtain a wort,
c. fermenting the wort to obtain a beer, and
d. pasteurizing the beer,
e. wherein a glucoamylase variant according to any one of further embodiments 1-25 or an enzymatic composition according to any one of further embodiments 36-48 is added to: step (a) and/or step (b) and/or step (c).

Further Embodiment 60

The beer of further embodiment 59, wherein the pasteurized beer is further characterized as being:
a. essentially without glucoamylase activity; and/or
b. a low-calorie beer and/or a low-alcohol beer.

The invention will now be further described by way of the following non-limiting examples.

EXAMPLES

Assays and Methods

The following assays and methods are used in the examples provided below. The methods used to provide variants are described below. However, it should be noted that different methods may be used to provide variants of a parent enzyme and the invention is not limited to the methods used in the examples. It is intended that any suitable means for making variants and selection of variants may be used.

pNPG Glucoamylase Activity Assay for 96-Well Microtiter Plates

The reagent solutions were: NaAc buffer: 200 mM sodium acetate buffer pH 4.5; Substrate: 50 mM p-nitrophenyl-α-D-glucopyranoside (Sigma N-1377) in NaAc buffer (0.3 g/20 ml) and stop solution: 800 mM glycine-NaOH buffer pH 10. 30 µl filtered supernatant was placed in a fresh 96-well flat bottom micro titer plate (MTP). To each well 50 µl NaAc buffer and 120 µl substrate was added and incubated for 30 minutes at 50° C. (Thermolab systems iEMS Incubator/shaker HT). The reaction was terminated by adding 100 µl stop solution. The absorbance was measured at 405 nm in a MTP-reader (Molecular Devices Spectramax 384 plus) and the activity was calculated using a molar extinction coefficient of 0.011 µM/cm.

Thermal Stability Assay 1

With a stock dilution of 150 ppm of purified enzyme (in 50 mM NaAc pH 4.0), a 3 ppm dilution was made by adding 6 µl to 294 µl 50 mM NaAc buffer pH 4.5. The diluted sample was equally divided over 2 MTPs. One MTP (initial plate) was incubated for 1 hr at 4° C. and the other MTP (residual plate) was incubated at 64° C. (Thermolab systems iEMS Incubator/Shaker HT) for 1 hr. The residual plate was chilled for 10 min on ice. 60 µl of both the initial plate and the residual plate was added to 120 µl 4% soluble corn starch pH 3.7 and incubated for 2 hrs at 32° C., 900 rpm in 2 separate MTPs (Thermolabsystems iEMS Incubator/Shaker HT). Activity of both plates was measured in the Hexokinase activity assay, using the ethanol application assay described below.

Thermal stability was calculated as % residual activity as follows:

$$\frac{ABS_{340} \text{ residual} - \text{blank}}{ABS_{340} \text{ initial} - \text{blank}} \times 100\%$$

Hexokinase Activity Assay

Hexokinase cocktail: 10-15 minutes prior to use, 90 ml water was added to a BoatIL container glucose HK R1 (IL test glucose (HK) kit, Instrument Laboratory #182507-40) and gently mixed. 100 µl of Hexokinase cocktail was added to 85 µl of dH$_2$O. 15 µl of sample was added to the mixtures and incubated for 10 minutes in the dark at room temperature. Absorbance was read at 340 nm in a MTP-reader after 10 minutes. Glucose concentrations were calculated according to a glucose (0-1.6 mg/ml) standard curve.

Ethanol Application—Glucose Release from Corn Starch

8% stock solution: 8 g of soluble corn starch (Sigma #S4180) was suspended in 40 ml dH$_2$O at room temperature. The slurry was added in portions to 50 ml of boiling dH$_2$O in a 250 ml flask and cooked for 5 minutes. The starch solution was cooled to 25° C. while stirring and the volume adjusted with remain 10 ml of dH$_2$O.

Stop solution: 800 mM Glycine-NaOH buffer, pH 10.

4% (m/v) soluble starch working solution: stock solution was diluted (1:1) with 100 mM sodium acetate buffer pH 4.0.

6 µl of 150 ppm purified enzyme was diluted with 294 µl 50 mM NaAc buffer pH 4.0 in a flat bottom 96-well MTP. 60 µl of this dilution was added to 120 µl 4% soluble corn starch pH 4.0 and incubated for 2 hrs at 32° C. 900 rpm (Thermolabsystems iEMS Incubator/Shaker HT). The reaction was stopped by adding 90 µl 4° C.—cold Stop Solution. The sample was placed on ice for 20 minutes. Starch was spun down at 1118×g at 10° C. for 5 minutes (SIGMA 6K15) and 15 µl supernatant was used in the Hexokinase activity assay described above to determine the glucose content.

Data Analysis and Calculation of Performance Index of Ethanol Screening Assay

Protein levels were measured using a microfluidic electrophoresis instrument (Caliper Life Sciences, Hopkinton, Mass., USA). The microfluidic chip and protein samples were prepared according to the manufacturer's instructions (LabChip® HT Protein Express, P/N 760301). Culture supernatants were prepared and stored in 96-well microtiter plates at −20° C. until use, when they were thawed by warming in a 37° C. incubator for 30 minutes. After shaking briefly, 2 µl of each culture sample was transferred to a 96-well PCR plate (Bio-Rad, Hercules, Calif., USA) containing 7 µl samples buffer (Caliper) followed by heating the plate to 90° C. for 5 minutes on a thermostatically controlled plate heater. The plate was allowed to cool before adding 40 µl water to each sample. The plate was then placed in the instrument along with a protein standard supplied and calibrated by the manufacturer. As the proteins move past a focal point in the chip, the fluorescence signal is recorded and the protein concentration is determined by quantitating the signal relative to the signal generated by the calibrated set of protein standards.

After the Caliper protein determination the data is processed in the following way.

The calibration ladders are checked for correctness of the peak pattern. If the calibration ladder that is associated with the run does not suffice, it is replaced by a calibration ladder of an adjacent run. For peak detection, the default settings of the global peak find option of the caliper software are used. The peak of interest is selected at 75 kDA+/−10%. The result is exported to a spreadsheet program and the peak area is related to the corresponding activity (ABS340-blank measurement) in the ethanol screening assay.

With the area and activity numbers of 12 Wild Type samples, a calibration line is made using the "Enzyme Kinetics" equation of the program Grafit Version 5 (Erithacus Software, Horley, UK) in combination with a non-linear fit function. The default settings are used to calculate the Km and Vmax parameters. Based on these two parameters, a Michaelis-Menten reference line is made and the specific activity of each variant is calculated.

Based on the specific activity the performance index (PI) is calculated. The PI of a variant is the quotient "Variant-specific activity/WT-specific activity." The PI of WT is 1.0 and a variant with a PI>1.0 has a specific activity that is greater than WT.

Purification of TrGA Variants

Culture supernatants of expressed TrGA variants were purified in one step by affinity chromatography using an AKTA explorer 100 FPLC system (Amersham Biosciences, Piscataway, N.J.). β-cyclodextrin (Sigma-Aldrich, Zwijndrecht, The Netherlands; 85.608-8) was coupled to epoxy activated Sepharose beads (GE Healthcare, Diegem, Belgium; 17-0480-01) and employed for purification. The column was equilibrated with 25 mM sodium acetate buffer pH 4.3 followed by application of concentrated enzyme sample. Bound variants were eluted from the column with 25 mM sodium acetate buffer pH 4.3 containing 10 mM α-cyclodextrin (Sigma, 28705). Purified samples were analyzed using sodium dodecyl sulfate-polyacrylamide gel electrophoresis (SDS-PAGE).

Protein Quantification of Purified TrGA Variants

The protein concentration of purified TrGA variants was determined by anion exchange chromatography using an AKTA explorer 100 FPLC system. Purified sample was injected onto a ResourceQ_1 ml column (GE Healthcare) and a linear gradient of 0 to 500 mM NaCl in 25 mM sodium acetate buffer pH 4.3 was applied to elute bound protein. The peak area was determined and the protein concentration was calculated relative to a TrGA standard with know concentration.

Liquefact Assay

Glucose release of the variants was determined on corn mash liquefact from a local ethanol producer in a 6-well plate. Each well of the plate was filled with 6 g of 26% DS liquefact pH 4.3. Subsequently, 300 ppm enzyme and 400 ppm urea was added and 250 µl sample was collected after 2, 4 and 6 hr incubation at 32° C. The sample was centrifuged for 5 minutes at 14.000×g and 50 µl of the supernatant was transferred to an eppendorf tube containing 50 µl of kill solution (1.1 N sulfuric acid) and allowed to stand for 5 minutes. 250 µl of water was added to the tube and then filtered with a 0.22 µm filter plate and injected onto an HPX-87H column as described below.

Evaluation of Performance of TrGA Variant in Ethanol Fermentations

A sample of corn mash liquefact from a local ethanol producer was obtained and diluted in some cases to 26% DS using thin stillage. The pH of the slurry was adjusted to pH 4.3 using 4 N sulfuric acid. A 100 g or 50 g aliquot of mash was put into a 125 ml shake flask and placed into a 32° C. incubator and allowed to equilibrate. After addition of 100 µl 400 ppm urea, 1 ml purified variant at intended concentration or purified TrGA at 2 different concentrations was added to the shake flasks. Finally, 333 µl of a solution of Red Star Red yeast (15 g hydrated for 30 minutes in 45 ml DI water; Lesaffre yeast Corp. Milwaukee, Wis.) was added to each sample; Samples were collected at 5, 21, 28, 48 and 52 hours and analyzed by HPLC (Agilent 1200 series) using an Aminex HPX-87H column (Bio-Rad).

Ethanol and Carbohydrate Determinations

A 2 ml eppendorf centrifuge tube was filled with fermentor beer and cooled on ice for 10 minutes. The sample was centrifuged for 3 minutes at 14.000×g and 500 µl of the supernatant was transferred to a test tube containing 50 µl of kill solution (1.1 N sulfuric acid) and allowed to stand for 5 minutes. 5.0 ml of water was added to the test tube and then filtered into a 0.22 µm filter plate (multiscreen, Millipore, Amsterdam, the Netherlands) and run on HPLC. Column Temperature: 60° C.; mobile phase: 0.01 N sulfuric acid; flow rate 0.6 ml/min; detector: R1; injection volume: 20 µl. The column separates molecules based on charge and molecular weight; DP1 (monosaccharides); DP2 (disaccharides); DP3 (trisaccharides); DP>3 (oligosaccharides sugars having a degree of polymerization greater than 3); succinic acid; lactic acid; glycerol; methanol; ethanol.

Determination of GAU Activity

Substrate: p-Nitrophenyl-β-maltoside (4 mM), plus thermostable β-glucosidase (5 U/ml) (from assay R-AMGR305/04; Megazyme International Wicklow, Ireland) was freshly prepared Buffer: 200 mM Sodium acetate buffer (pH 4.5).

Enzyme samples were diluted by at least a factor 10 in sodium acetate buffer In a 96 well plate: 20 µl substrate was mixed with 20 µL enzyme solution and incubate at 40° C. with agitation for 10 minutes. 300 µL 2% Trizma base was added to terminate reaction and develop the colour. Absorbance at 400 nm was measured against a reagent blank.

Blanks were prepared by adding 300 µL of Trizma base solution (2%) to 20 µL of substrate with vigorous stirring, followed by the enzyme solution (20 µL). Activity was calculated as follows:

$$\text{Activity } (GAU/\text{ml}) = \frac{\Delta A_{400}}{10} \cdot \frac{340}{20} \cdot \frac{1}{18.1} \cdot \frac{1}{0,88} \cdot \text{Dilution}$$

Where: GAU=International units of enzyme activity. One Unit is the amount of enzyme which release one µmole of p-nitrophenol from the substrate per minute at the defined pH and temperature. $\Delta A_{400}$=absorbance (reaction)−Absorbance (blank). 10=incubation time (min). 340=final reaction volume (µL). 20=volume of enzyme assayed (µL) 18.1=EmM p-nitrophenol in 2% trizma base (pH~8.5) at 400 nm (unit: $\mu M^{-1} \ast cm^{-1}$). 0.88=Light path (cm)

Starch Hydrolysis Activity (SH Activity):

Buffer: 0.1 M Citrate buffer pH 5.4 (made from 0.1 M citric acid and 0.1 M Tri-sodium citrate)

Substrate: 30% soluble starch (Merck, v.nr 1.01257.1000) in buffer (heat slightly until all starch is in solution)

Enzyme: Glucoamylase standardised to 3 GAU/ml on basis of above assay.

60 µL 30% starch was transferred to a 96 well PCR plate. 60 µL enzyme sample or standard was added and mixed by pumping a couple of times with the pipette. Following steps until incubation was carried not as fast as possible.

The PCR plate was covered with sealing tape and following PCR programme was run: 6 min at 63° C., 6 min at 99° C. and 10 min at 4° C. Lid was not heated. After the temperature cycle the PCR plate was centrifuged (app 1 min at 300 rpm) to collect all liquid in the bottom of the wells.

Plates were stored at 4° C. until further analysis. Glucose concentration was measured according to method below and the hydrolysis activity was calculated as follows:

$$\text{Starch hydrolysis activity (M/min)} = \frac{[\text{glucose}]\frac{g}{l}}{180\frac{g}{\text{mol}} \times 6 \text{ min}}$$

Isomaltose Hydrolysis Activity

Same as for starch hydrolysis activity except that substrate is 2% iso-maltose (Sigma 17253) and the first step in the PCR programme is 10 min at 63° C. instead of 6 min.

Determination of Glucose Concentration

Modified from the Megazyme© D-glucose assay (KG-LUC 04/06) and used to determine the amount of glucose released from starch and isomaltose hydrolysis reactions.

The contents of bottle 1 [Reagent Buffer: Potassium phosphate buffer (1.0 M, pH 7.4), p-hydroxybenzoic acid (0.22 M) and sodium azide (0.4% w/v)] was diluted to 1 L with distilled water. The contents of bottle 2 [Reagent Enzymes: Glucose oxidase (>12,000 U) plus peroxidase (>650 U) and 4-aminoantipyrine (80 mg). Freeze-dried powder] was diluted in approx. 20 mL of solution 1 and quantitatively transferred to the bottle containing the remainder of solution 1. This is Glucose Determination Reagent (GOPOD Reagent). It was either used fresh or stored frozen and dark. Before use it was checked that the absorbance ($A_{510}$) of this solution was less than 0.05 when read against distilled water.

In a 96 well plate, add 250 µL of GOPOD reagent to 10 µL of sample solution. Cover the plate with sealing tape and incubate in an Eppendorf thermomixer at 40° C., 700 rpm for 20 min. Read absorbances at 510 nm. A glucose standard curve is made from solutions of 1.4; 1.2; 0.8; 0.4; 0.2 and 0 mg/ml glucose in milli-q water and used for calculation of the sample glucose concentrations.

Determination of Maltose and Isomaltose Synthesis by TLC

Substrate: 30% glucose in 0.1M citric acid buffer, pH 5.4 (heated slightly to bring all glucose into solution).

Enzyme: Glucoamylase standardized to 3 GAU/ml *Aspergillus niger* glucoamylase product (AnGA; Diazyme®X4, Danisco, Denmark) and *Trichoderma reesei* glucoamylase product (TrGA Diazyme TR8 Danisco, Denmark) were always run as references.

Reference: Heat inactivated enzyme sample and/or buffer solution (not used in all cases).

Standards: 1) 0.3% Maltose and 0.1% isomaltose in demineralised water. 2) 0.2% Maltose and 0.05% isomaltose in demineralised water. 3) 0.3% Maltose and 0.1% isomaltose in demineralised water.

Reaction conditions: 60 µl substrate was mixed with 60 µL enzyme solution in wells of a PCR-plate. The plate with was covered with sealing tape and following temperature was run: 120 min at 63° C., 6 min at 99° C., 10 min at 4° C. Lid heated to 70° C. After incubation the plates were given a moderate centrifugation (1 min at 300 rpm), and they were store at 4° C. until further analysis. All samples were run in duplicate.

Quantification of Maltose and Iso-Maltose: Preheat TLC-Plate at 167° C. for 10 min prior to sample application. Dilute all samples and standards 20 times in demineralised water. An automatic TLC sampler (ATS4, CAMAG, Muttenz, Switzerland) was used for accurately transferring 4 µL samples to the TLC plate. Each plate could contain 20 samples, placed in 4 mm wide bands. Plates were heated for 10 min at 40° C. to let bands dry out. The TLC-plates were eluted in AcN, EtAc, 1-propanol, H2O (85:20:50:40), whereafter the plates were heated 5 min at 167° C. to remove excess solvent. The plate was dipped up side down (i.e. by hold the plate on the edge near where the samples were applied) in 5% H2SO4:EtOH (95:5). The dipping solution was made daily. The plates were heated 3 min at 167° C. to visualize spots. Determination of spot intensity was done by scanning in a TLC scanner (CAMAG scanner 3, Muttenz, Switzerland) and quantification was done by drawing a standard-curve based on all maltose and isomaltose concentrations vs. spot intensities. Both maltose and isomaltose concentrations were calculated from this curve, using the fact that the spot intensity vs. concentration is equal for the two compounds.

Figure 10:
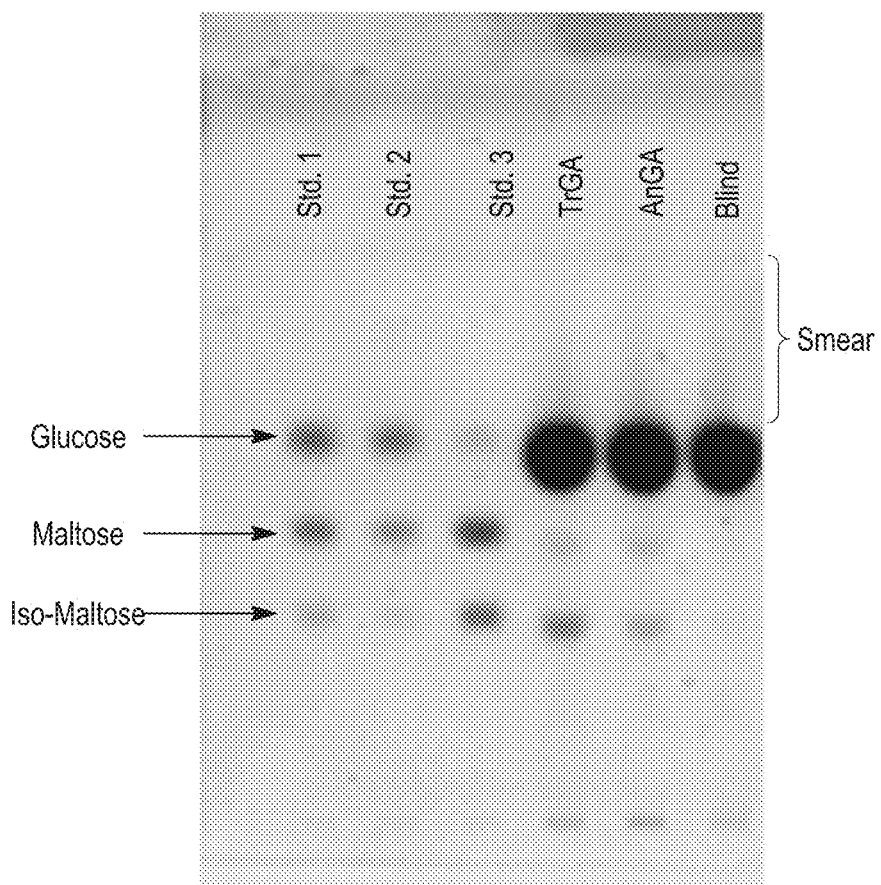
FIG. 10 depicts a TLC plate with standards containing different concentrations of glucose, maltose and isomaltose and samples containing reaction products from glucose incubated with TrGA and AnGA.

FIG. 10 depicts an example of a TLC plate with standards containing different concentrations of glucose, maltose and isomaltose and samples containing reaction products from glucose incubated with *Aspergillus niger* glucoamylase product (AnGA; Diazyme®X4, Danisco, Denmark) and *Trichoderma reesei* glucoamylase product (TrGA Diazyme TR8 Danisco, Denmark). Blind is glucose incubated without enzyme.

The isomaltose synthesis activity (IS activity) is calculated on basis of the isomaltose concentrations determined by TLC according to the following formula:

$$\text{Isomaltose synthesis activity (M/min)} = \frac{[\text{Isomaltose}] \% \times 10\frac{g}{l}}{342\frac{g}{\text{mol}} \times 120 \text{ min}}$$

Thermal Stability Assay 2

As a measure of thermostability of the enzymes under the conditions used in the present experiments, the GAU activity was determined according to the above assay before and after incubation of enzymes in 15% glucose, 0.1M citrate buffer, pH 5.4 at 63° C. for 120 min. Data is presented as % activity lost.

Production of GA by Fermentation

400× Trace element solution: Dilute in 1000 ml of demi water: Anhudrous Citric Acid (175 g), $FeSO_4*7\ H_2O$ (200 g), $ZnSO_4*7\ H_2O$ (16 g), $CuSO_4*5\ H_2O$ (3.2 g), $MnSO_4*H_2O$ (1.4 g), $H_3BO_3$ (0.8 g). It may be helpful to acidify this to get all components into solution. The solution was filtered and sterilized.

LD-medium: Add to ~800 ml of demi water: Casamino acids (9 g), $MgSO_4*7H_2O$ (1 g), $(NH_4)_2SO_4$ (5 g), $KH_2PO_4$ (4.5 g), $CaCl_2*2H_2O$ (1 g), piperazine-1,4-bis(propanesulfonic acid (PIPPS) buffer (33 g), 400× *T. reesei* trace elements (2.5 ml), Adjust pH to 5.5 with NaOH 4N. Adjust final volume to 920 ml.

2×Amd S Base ager (1 liter): Mix $KH_2PO_4$ (30 g), 1M Acetamide (20 ml), 1M CsCl (20 ml), 20% MgSO4.7H2O (6 ml), 20% CaCl2.2H2O (6 ml), *T. reesei* spore elements 400× (2 ml), 50% glucose.H2O (80 ml). Adjust pH to 4.5 with 4N NaOH Make up to 1 L and filter sterilize. Store at 4° C.

Initial Culture: Strains were grown on AmdS-Base agar plates. To produce agar plates minimal media agar was boiled and after cooling down to app. 50° C. it was diluted with 2× AmdS Base 1:1 and poured on petri dishes. After sporulation (app. 6-7 days) the plates were scraped with 2 ml saline 0.015% Tween 80. Approx 1 ml was added to glycerol tubes containing 500-600 µl 35% glycerol and stored at −80° C. The pre-culture fermentations were started directly from this spore suspension.

Pre Culture: The medium is made by adding 2.5% glucose to the LD-medium, which is subsequently made up to 1 L. To produce biomass 50 µl spore suspension is added to 100 ml medium (sterilised in 500 ml shake flask). The flasks are incubated on a rotary shaker at 30° C., 180 rpm for 2 days, then 10 ml suspension is used to inoculate a new shake flask, which is incubated under similar conditions for 1 day. The content of this flask is used to inoculate a fermentor.

Main Culture: To make 1 L of medium, 40 ml glucose/sophorose mix (Danisco, Jamsa, Finland) was added to the LD-medium and made up to 1 L. 6 L fermentors containing 4 L of medium were inoculated with the pre-culture, and grown at pH 3.5 for approximately 16 hours at 34° C., until CER/OUR (Carbondioxide Excretion Rate/Oxygen Uptake Rate) started falling. Then temperature was lowered to 28° C., pH was raised to 4.0 and the fermentation was continued for approximately 80 hours.

Brew Analysis with Determination of Real Degree of Fermentation (RDF)

Pure Malt Brew Analysis

Analysis was carried out at using the following procedure: 70 g milled pilsner malt (Weyermann, Bamberg, Germany) was mashed with 266 ml water. The temperature cycle after mashing in (mixing malt and water) was: 140 minutes at 63.9° C., increasing to 73.9° C. over 10 minutes, 5 minutes at 73.9° C. At the end of mashing, the mashes were cooled, made up to 350 g and filtered. Filtrate volumes were measured after 30 minutes. The filtrated worts were sampled for specific gravity determination, then heated to 99° C. for 10 minutes in a water bath in order to destroy any residual glucoamylase activity. The heat treatment results in a loss of 1.5 g per 200 ml wort. The worts were fermented at 18° C. and 100 rpm in 500 ml conical flasks after yeast addition for at least 88 hours and no more than 120 hours. Specific gravity was determined on the ferments.

Malt-Adjunct Brew Analysis

A modified decoction mashing, using corn grist as adjunct was employed. The brewing protocol was modified from US 2009014247. 40% of the malt was substituted with corn grist with a moisture content of 12.6% (Benntag Nordic; Nordgetreide GmBH Liibec, Germany). All corn grist was heated to 100° C. at 2° C./min, together with 54% of the water and 5% of the malt (well modified Pilsner malt; Fuglsang Denmark). 5 min rests were held at 72° C. and 80° C. and a 10 min rest was held at 100° C. Hereafter the adjunct was cooled to 64° C. and combined with the main mash, also at 64° C. Enzymes were added at this stage, and the 64° C. rest was extended to 250 min. After fermentation the RDF values were determined.

Real degree of fermentation (RDF) value may be calculated according to the equation below:

$$RDF(\%) = \left(1 - \frac{RE}{°P_{initial}}\right) \times 100$$

Where: RE=real extract=$(0.1808 \times °P_{initial}) + (0.8192 \times °P_{final})$, $°P_{initial}$ is the specific gravity of the standardised worts before fermentation and $°P_{final}$ is the specific gravity of the fermented worts expressed in degree plato.

In the present context, Real degree of fermentation (RDF) was determined as follows:

After fermentation samples were filtered and degassed. Specific gravity and alcohol concentration was determined on the ferments using a Beer Alcolyzer Plus and a DMA 5000 Density meter (both from Anton Paar, Graz, Austria). Based on these measurements, the real degree of fermentation (RDF) value is calculated, by the instrument, according to the equation below:

$$RFD(\%) = \frac{OE - E(r)}{OE} \times 100$$

Where: $E(r)$ is the real extract in degree Plato (°P) and OE is the original extract in °P.

Xylanase Assay Method

Samples were diluted in citric acid (0.1 M)—di-sodium-hydrogen phosphate (0.2 M) buffer, pH 5.0, to obtain approx. $OD_{590}$=0.7 in this assay. Three different dilutions of the sample were pre-incubated for 5 minutes at 40° C. At time=5 minutes, 1 Xylazyme tablet (crosslinked, dyed xylan substrate, Megazyme, Bray, Ireland) was added to the enzyme solution in a reaction volume of 1 ml. At time=15 minutes the reaction was terminated by adding 10 ml of 2% TRIS/NaOH, pH 12. Blanks were prepared using 1000 µl buffer instead of enzyme solution. The reaction mixture was centrifuged (1500×g, 10 minutes, 20° C.) and the OD of the supernatant was measured at 590 nm. One xylanase unit (XU) is defined as the xylanase activity increasing $OD_{590}$ with 0.025 per minute.

Pullulanase Assay Method

Principle:

On incubation of Red-Pullulan (partially depolymerised pullulan, which is dyed with Procion Red MX-5B, from assay kit S-RPUL, Megazyme Int., Bray, Ireland) with pullulanase or limit-dextrinase the substrate is depolymerised by an endo-mechanism to produce low molecular-weight dyed fragments which remain in solution on addition of ethanol to the reaction mixture. High-molecular weight material is removed by centrifugation, and the colour of the supernatant is measured at 510 nm. Pullulanase in the assay solution is determined by reference to a standard curve.

Substrate:

0.5 g of powdered substrate was dissolved in to 25 mL of 0.5 M potassium chloride solution.

Buffer: Sodium Acetate, 200 mM, pH 5.0

Enzyme Preparation:

Enzyme is diluted at least 10 times in buffer. If the resulting $A_{510}$ reading was above 1.0 the enzyme was further diluted.

Assay Procedure:

In a test tube 1.0 mL of enzyme solution, pre-equilibrated to 40° C., was mixed with 0.5 mL substrate solution, pre-equilibrated to 40° C. The mix was incubated at 40° C. for 10 min. Reaction was terminated and high-molecular weight substrate was precipitated by the adding 2.5 mL ethanol (95% v/v). The tubes were equilibrate to room temperature for 10 min, then stirred for 10 sec on a vortex mixer and centrifuged at 1,000 g for 10 min. Supernatants were transferred to a 96 well plate and the absorbance of blank and reaction solutions was measured at 510 nm against distilled water. The blank reading was subtracted from the sample reading to obtain the $A_{510}$ used in the formula below.

Activity is determined from the formula: milli-PU/mL=$360*A_{510}+11$.

The blank is prepared by adding ethanol to the Red-Pullulan substrate before addition of the enzyme.

One Unit of activity is defined as the amount of enzyme required to release one mole of D-glucose reducing sugar equivalents per minute from borohydride reduced pullulan, under the defined assay conditions (see Megazyme method S-RPUL 10/08, Megazyme Int., Bray, Ireland).

Alpha-Amylase Assay (SSU) Method

Principle:

Method is based on the release of reducing groups measured, by reference to a standard curve, as glucose from a 20 minute hydrolysis of 4% potato soluble starch at pH 4.5 and 50° C. One Soluble Starch Unit (SSU) is the activity which liberates 1 milligram of glucose equivalents per minute.

Substrate:

4% (w/v) potato soluble starch (Sigma, S 2630) solution in 0.05 M sodium acetate buffer, pH 4.5. The potato soluble starch is slurried in deionised water then added to vigorously boiling water in a flask. The starch solution is boiled, with stirring, for three minutes then cooled to 25° C. and acetic acid and sodium hydroxide solution added to give a 0.05 M sodium acetate buffer, pH 4.5, when made up to the final concentration.

DNS Solution:

1 L of DNS solution is made up by adding to water: 16 g sodium hydroxide followed by 10 g 3-5 dinitro salicylic acid and then 300 g sodium potassium tartrate, each component being dissolved before the next is added. The solution is made up to volume and stored in the dark.

Assay Procedure:

Add 0.4 ml starch substrate and 0.1 ml 0.5M sodium acetate buffer, pH 4.5 to a test tube which is capped and equilibrated to temperature in a water bath set at 50° C. Add 0.1 ml of diluted enzyme solution and after 20 minutes stop the reaction by adding 0.1 ml 2% (w/v) NaOH. Run each enzyme assay in duplicate along with an enzyme blank.

Color Development:

To each tube (assay and blank) add 1.5 ml water and 2.0 ml DNS solution, mix and place in a boiling water bath for 5 minutes then cool the tubes in an ice bath for 10 minutes. Let the tubes stand at room temperature for 20 minutes and read the absorbance at 543 nm.

Standard Curve:

Construct a glucose standard curve corresponding to 0.0-1.0 mg glucose per 2.2 ml water, then adding 2.0 ml of DNS reagent and proceeding as described.

Calculation Of Enzyme Activity (SSU)

Convert absorbance values ($A_{543}$) of samples to mg of glucose using the standard curve, and calculate the $\Delta A_{543}$ mg glucose values [sample−blank] ($\Delta A_{543}$ must be between 0.2-0.4). Activity is determined from the formula:

SSU/ml or g=average($\Delta A_{543}$ mg glucose values [sample−blank])×(1/0.1)×(1/20)×Enzyme Dilution Example 1

Construction of TrGA Site Evaluation Libraries (SELs) in the pTTT Vector for Expression in *Trichoderma reesei*

Figure 2:
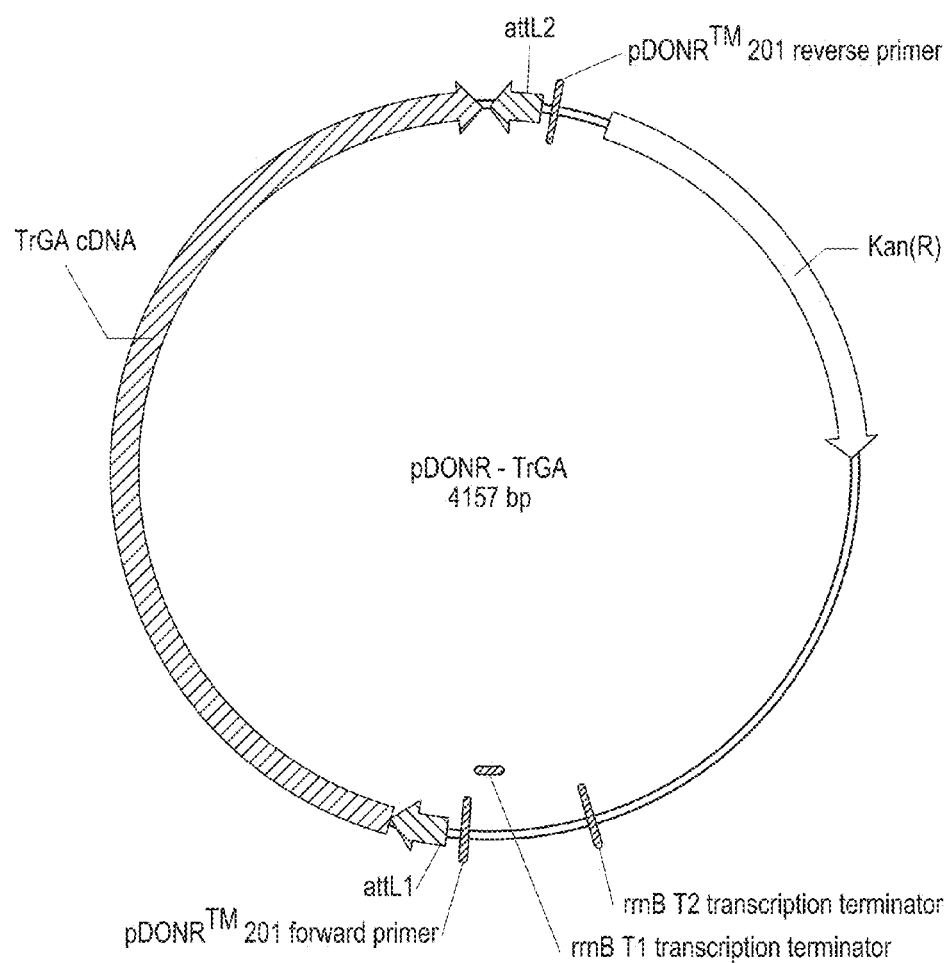
FIG. 2 depicts the destination plasmid pDONR-TrGA which includes the cDNA (SEQ ID NO: 4) of the TrGA.

A *Trichoderma reesei* cDNA sequence (SEQ ID NO: 4) was cloned into pDONR™201 via the Gateway® BP recombination reaction (Invitrogen, Carlsbad, Calif., USA) resulting in the entry vector pDONR-TrGA (FIG. 2). The cDNA sequence (SEQ ID NO: 4) encodes the TrGA signal peptide, the pro-sequence, and the mature protein, including the catalytic domain, linker region and starch binding domain (SEQ ID NO: 1). SEQ ID NO: 4 and SEQ ID NO: 1 are shown in FIGS. 1B and 1B. FIG. 1C illustrates the precursor and mature protein TrGA domains.

Figure 3:
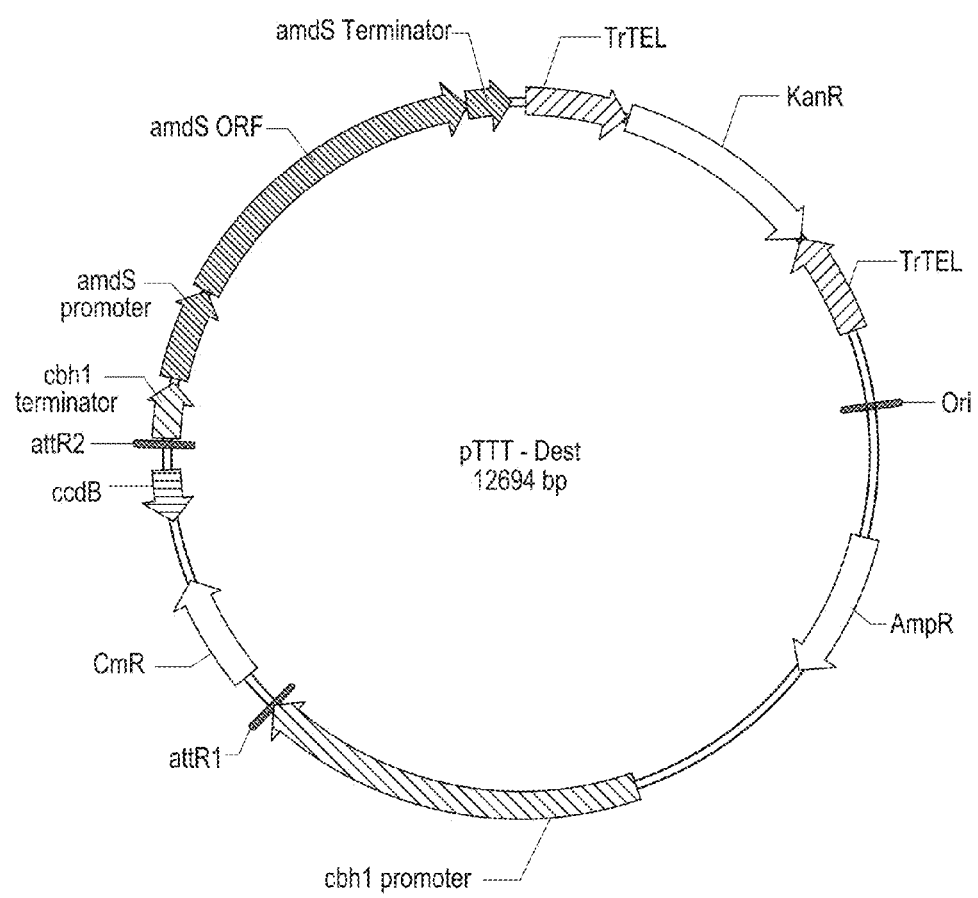
FIG. 3 depicts the plasmid pTTT-Dest.
Figure 4:
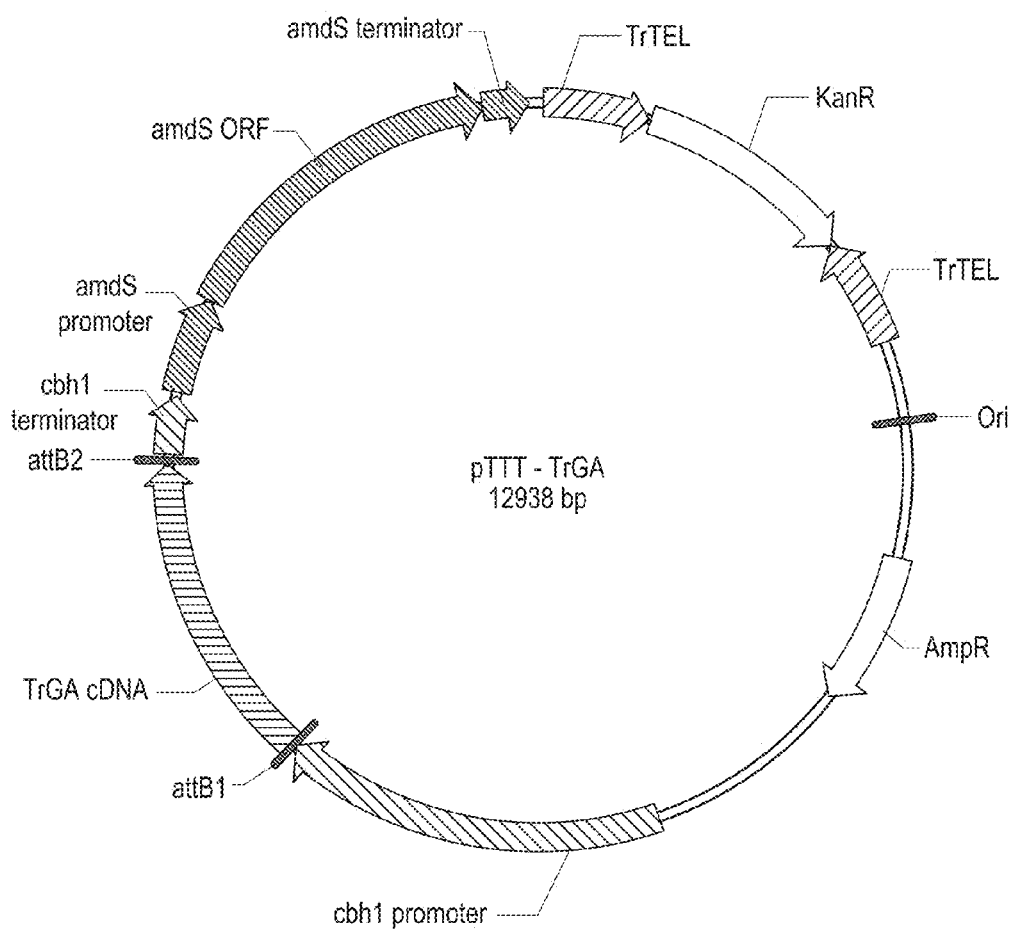
FIG. 4 depicts the final expression vector pTTT-TrGA.

To express the TrGA protein in *Trichoderma reesei*, the TrGA coding sequence (SEQ ID NO: 4) was cloned into the Gateway compatible destination vector pTTT-Dest (FIG. 3) via the GATEWAY® LR recombination reaction. The expression vector contained the *T. reesei* cbhI-derived promoter and terminator regions that allowed for strong inducible expression of a gene of interest. The vector also contained the *Aspergillus nidulans* amdS selective marker that allowed for growth of the transformants on acetamide as a sole nitrogen source. The expression vector also contained *T. reesei* telomere regions that allowed for non-chromosomal plasmid maintenance in a fungal cell. On the destination pTTT-Dest plasmid, the cbhI promoter and terminator regions were separated by the chloramphenicol resistance gene, $Cm^R$, and the lethal *E. coli* gene, ccdB, flanked by the bacteriophage lambda-based specific recombination sites attR1, attR2. This configuration allowed for direct selection of recombinants containing the TrGA gene under control of the cbhI regulatory elements in the right orientation via the GATEWAY® LR recombination reaction. The final expression vector pTTT-TrGA is shown in FIG. 4.

SELs were constructed using the pDONR-TrGA entry vector (FIG. 2) as a template and the primers listed in Table 2. All primers used in the mutagenesis experiments contained the triplet NNS (N=A, C, T, G, and S=C or G) at the position that aligns with the codon of the TrGA sequence designed to be mutated (SEQ ID NO: 1), allowing for a random incorporation of nucleotides at the preselected position. Construction of each SEL library started with two independent PCR amplifications on the pDONR-TrGA entry vector: one using the Gateway F (pDONR201-FW) and a specific mutagenesis primer R (Table 2), and the other—the Gateway primer R (pDONR201-RV) and a specific mutagenesis primer F (Table 2). High fidelity PHUSION DNA polymerase (Finnzymes OY, Espoo, Finland) was used in a PCR amplification reaction including 0.2 µM primers. The reactions were carried out for 25 cycles according to the protocol provided by Finnzymes. 1 µl aliquots of the PCR fragments obtained were used as templates for a subsequent fusion PCR reaction together with the Gateway FW and Gateway RV primers (Invitrogen). This PCR amplification, after 22 cycles, produced a population of the full-length linear TrGA DNA fragments randomly mutated at the specific codon position. The fragments were flanked by the Gateway-specific attL1, attL2 recombination sites on both ends. The DNA fragments were purified with a CHARGESWITCH® PCR clean-up kit (Invitrogen, Carlsbad USA) and then recombined with 100 ng of the pTTT-destination vector (FIG. 3) using the LR CLONASE™ II enzyme mix according to the protocol supplied by Invitrogen. The recombination products that were generated were transformed into *E. coli* Max Efficiency DH5α, as described by the supplier (Invitrogen). The final expression constructs pTTT-TrGA with mutations at the desired position were selected by plating bacteria on 2×YT agar plates (16 g/L Bacto Tryptone (Difco), 10 g/L Bacto Yeast Extract (Difco), 5 g/L NaCl, 16 g/L Bacto Agar (Difco)) with 100 µg/ml ampicillin.

96 single colonies from each library were grown for 24 hrs at 37° C. in MTP containing 200 µL 2×YT medium with 100 µg/ml ampicillin. Cultures were used directly to amplify PCR fragments encompassing the region where a specific mutation was introduced. The specific PCR products obtained were sequenced using an ABI3100 sequence analyzer (Applied Biosystems). Each library contained from 15 to 19 different TrGA variants in the final expression vector. These variants were individually transformed into *T. reesei*, as described below. Libraries are numbered from 1 to 182 referencing the specific amino acid residue in the TrGA sequence that was randomly mutated.

TABLE 2

Primers used to generate TrGA SELs

| AA-position | F/R | DNA Sequence 5' to 3' |
|---|---|---|
| pDONR201- | F | TCGCGTTAACGCTAGCATGGATCTC (SEQ ID NO: 13) |
| pDONR201- | R | TCGCGTTAACGCTAGCATGGATCTC (SEQ ID NO: 14) |
| 4 | F | CGTCACCAAGAGGTCTGTTGACNNSTTCATCAGCACCGAGACGCC (SEQ ID NO: 15) |
| 4 | R | GTCAACAGACCTCTTGGTGACGTCG (SEQ ID NO: 16) |
| 5 | F | CACCAAGAGGTCTGTTGACGACNNSATCAGCACCGAGACGCCTATTGC (SEQ ID NO: 17) |
| 5 | R | GTCGTCAACAGACCTCTTGGTGAC (SEQ ID NO: 18) |
| 10 | F | TGACGACTTCATCAGCACCGAGNNSCCTATTGCACTG (SEQ ID NO: 19) |
| 10 | R | CTCGGTGCTGATGAAGTCGTC (SEQ ID NO: 20) |
| 12 | F | TCATCAGCACCGAGACGCCTNNSGCACTGAACAATCTTCTTTGCA (SEQ ID NO: 21) |
| 12 | R | AGGCGTCTCGGTGCTGATGAAGTCG (SEQ ID NO: 22) |
| 14 | F | CAGCACCGAGACGCCTATTGCANNSAACAATCTTCTT (SEQ ID NO: 23) |
| 14 | R | TGCAATAGGCGTCTCGGTGCT (SEQ ID NO: 24) |
| 15 | F | CACCGAGACGCCTATTGCACTGNNSAATCTTCTTTGC (SEQ ID NO: 25) |
| 15 | R | CAGTGCAATAGGCGTCTCGGT (SEQ ID NO: 26) |
| 23 | F | CAATCTTCTTTGCAATGTTGGTNNSGATGGATGCCGT (SEQ ID NO: 27) |
| 23 | R | ACCAACATTGCAAAGAAGATTG (SEQ ID NO: 28) |
| 24 | F | TTCTTTGCAATGTTGGTCCTNNSGGATGCCGTGCATTCGGCACAT (SEQ ID NO: 29) |
| 24 | R | AGGACCAACATTGCAAAGAAGATTG (SEQ ID NO: 30) |
| 29 | F | GTCCTGATGGATGCCGTGCANNSGGCACATCAGCTGGTGCGGTGA (SEQ ID NO: 31) |
| 29 | R | TGCACGGCATCCATCAGGACCAACA (SEQ ID NO: 32) |
| 42 | F | TGCGGTGATTGCATCTCCCAGCNNSATTGACCCGGAC (SEQ ID NO: 33) |
| 42 | R | GCTGGGAGATGCAATCACCGCA (SEQ ID NO: 34) |
| 43 | F | TGATTGCATCTCCCAGCACANNSGACCCGGACTACTATTACATGT (SEQ ID NO: 35) |
| 43 | R | TGTGCTGGGAGATGCAATCACCGCA (SEQ ID NO: 36) |
| 44 | F | TTGCATCTCCCAGCACAATTNNSCCGGACTACTATTACATGTGGA (SEQ ID NO: 37) |
| 44 | R | AATTGTGCTGGGAGATGCAATCACC (SEQ ID NO: 38) |
| 45 | F | CATCTCCCAGCACAATTGACNNSGACTACTATTACATGTGGACGC (SEQ ID NO: 39) |
| 45 | R | GTCAATTGTGCTGGGAGATGCAATC (SEQ ID NO: 40) |
| 46 | F | CTCCCAGCACAATTGACCCGNNSTACTATTACATGTGGACGCGAGA (SEQ ID NO: 41) |
| 46 | R | CGGGTCAATTGTGCTGGGAGATGCA (SEQ ID NO: 42) |
| 47 | F | CCAGCACAATTGACCCGGACNNSTATTACATGTGGACGCGAGATA (SEQ ID NO: 43) |
| 47 | R | GTCCGGGTCAATTGTGCTGGGAGAT (SEQ ID NO: 44) |
| 49 | F | CAATTGACCCGGACTACTATNNSATGTGGACGCGAGATAGCGCTC (SEQ ID NO: 45) |
| 49 | R | ATAGTAGTCCGGGTCAATTGTGCTG (SEQ ID NO: 46) |
| 51 | F | ACCCGGACTACTATTACATGNNSACGCGAGATAGCGCTCTTGTCT (SEQ ID NO: 47) |
| 51 | R | CATGTAATAGTAGTCCGGGTCAATT (SEQ ID NO: 48) |
| 59 | F | GACGCGAGATAGCGCTCTTGTCNNSAAGAACCTCATC (SEQ ID NO: 49) |
| 59 | R | GACAAGAGCGCTATCTCGCGT (SEQ ID NO: 50) |
| 60 | F | GCGAGATAGCGCTCTTGTCTTCNNSAACCTCATCGAC (SEQ ID NO: 51) |
| 60 | R | GAAGACAAGAGCGCTATCTCG (SEQ ID NO: 52) |
| 61 | F | AGATAGCGCTCTTGTCTTCAAGNNSCTCATCGACCGC (SEQ ID NO: 53) |
| 61 | R | CTTGAAGACAAGAGCGCTATC (SEQ ID NO: 54) |
| 65 | F | TGTCTTCAAGAACCTCATCGACNNSTTCACCGAAACG (SEQ ID NO: 55) |
| 65 | R | GTCGATGAGGTTCTTGAAGAC (SEQ ID NO: 56) |
| 67 | F | CAAGAACCTCATCGACCGCTTCNNSGAAACGTACGAT (SEQ ID NO: 57) |
| 67 | R | GAAGCGGTCGATGAGGTTCTT (SEQ ID NO: 58) |
| 68 | F | GAACCTCATCGACCGCTTCACCNNSACGTACGATGCG (SEQ ID NO: 59) |
| 68 | R | GGTGAAGCGGTCGATGAGGTT (SEQ ID NO: 60) |
| 70 | F | TCGACCGCTTCACCGAAACGNNSGATGCGGGCCTGCAGCGCCGCA (SEQ ID NO: 61) |
| 70 | R | CGTTTCGGTGAAGCGGTCGATGAGG (SEQ ID NO: 62) |
| 72 | F | CCGCTTCACCGAAACGTACGATNNSGGCCTGCAGCGC (SEQ ID NO: 63) |
| 72 | R | ATCGTACGTTTCGGTGAAGCGG (SEQ ID NO: 64) |

TABLE 2-continued

Primers used to generate TrGA SELs

| AA-position | F/R | DNA Sequence 5' to 3' |
|---|---|---|
| 73 | F | CTTCACCGAAACGTACGATGCGNNSCTGCAGCGCCGC (SEQ ID NO: 65) |
| 73 | R | CGCATCGTACGTTTCGGTGAA (SEQ ID NO: 66) |
| 75 | F | AAACGTACGATGCGGGCCTGNNSCGCCGCATCGAGCAGTACATTA (SEQ ID NO: 67) |
| 75 | R | CAGGCCCGCATCGTACGTTTCGGTG (SEQ ID NO: 68) |
| 76 | F | CGTACGATGCGGGCCTGCAGNNSCGCATCGAGCAGTACATTACTG (SEQ ID NO: 69) |
| 76 | R | CTGCAGGCCCGCATCGTACGTTTCG (SEQ ID NO: 70) |
| 94 | F | CTCTCCAGGGCCTCTCTAACNNSCGGGCTCCCTCGCGGACGGCT (SEQ ID NO: 71) |
| 94 | R | GTTAGAGAGGCCCTGGAGAGTGACC (SEQ ID NO: 72) |
| 97 | F | GGGCCTCTCTAACCCCTCGGGCNNSCTCGCGGACGGC (SEQ ID NO: 73) |
| 97 | R | GCCCGAGGGGTTAGAGAGGCC (SEQ ID NO: 74) |
| 98 | F | CCTCTCTAACCCCTCGGGCTCCNNSGCGGACGGCTCT (SEQ ID NO: 75) |
| 98 | R | GGAGCCCGAGGGGTTAGAGAG (SEQ ID NO: 76) |
| 99 | F | CTCTAACCCCTCGGGCTCCCTCNNSGACGGCTCTGGT (SEQ ID NO: 77) |
| 99 | R | GAGGGAGCCCGAGGGGTTAGA (SEQ ID NO: 78) |
| 100 | F | ACCCCTCGGGCTCCCTCGCGNNSGGCTCTGGTCTCGGCGAGCCA (SEQ ID NO: 79) |
| 100 | R | CGCGAGGGAGCCCGAGGGGTTAGAG (SEQ ID NO: 80) |
| 102 | F | CTCGGGCTCCCTCGCGGACGGCNNSGGTCTCGGCGAG (SEQ ID NO: 81) |
| 102 | R | GCCGTCCGCGAGGGAGCCCGA (SEQ ID NO: 82) |
| 110 | F | TGGTCTCGGCGAGCCCAAGTTTNNSTTGACCCTGAAG (SEQ ID NO: 83) |
| 110 | R | AAACTTGGGCTCGCCGAGACCA (SEQ ID NO: 84) |
| 111 | F | TCTCGGCGAGCCCAAGTTTGAGNNSACCCTGAAGCCT (SEQ ID NO: 85) |
| 111 | R | CTCAAACTTGGGCTCGCCGAG (SEQ ID NO: 86) |
| 113 | F | CGAGCCCAAGTTTGAGTTGACCNNSAAGCCTTTCACC (SEQ ID NO: 87) |
| 113 | R | GGTCAACTCAAACTTGGGCTC (SEQ ID NO: 88) |
| 114 | F | CCAAGTTTGAGTTGACCCTGNNSCCTTTCACCGGCAACTGGGGTC (SEQ ID NO: 89) |
| 114 | R | CAGGGTCAACTCAAACTTGGGCTCG (SEQ ID NO: 90) |
| 116 | F | TTGAGTTGACCCTGAAGCCTNNSACCGGCAACTGGGGTCGACCGCA (SEQ ID NO: 91) |
| 116 | R | AGGCTTCAGGGTCAACTCAAACTTG (SEQ ID NO: 92) |
| 119 | F | CCCTGAAGCCTTTCACCGGCNNSTGGGGTCGACCGCAGCGGGATG (SEQ ID NO: 93) |
| 119 | R | GCCGGTGAAAGGCTTCAGGGTCAAC (SEQ ID NO: 94) |
| 122 | F | CTTTCACCGGCAACTGGGGTNNSCCGCAGCGGGATGGCCCAGCTC (SEQ ID NO: 95) |
| 122 | R | ACCCCAGTTGCCGGTGAAAGGCTTC (SEQ ID NO: 96) |
| 125 | F | GCAACTGGGGTCGACCGCAGNNSGATGGCCCAGCTCTGCGAGCCA (SEQ ID NO: 97) |
| 125 | R | CTGCGGTCGACCCCAGTTGCCGGTG (SEQ ID NO: 98) |
| 133 | F | GGATGGCCCAGCTCTGCGAGCCNNSGCCTTGATTGGA (SEQ ID NO: 99) |
| 133 | R | GGCTCGCAGAGCTGGGCCATCC (SEQ ID NO: 100) |
| 137 | F | TGCGAGCCATTGCCTTGATTNNSTACTCAAAGTGGCTCATCAACA (SEQ ID NO: 101) |
| 137 | R | AATCAAGGCAATGGCTCGCAGAGCT (SEQ ID NO: 102) |
| 140 | F | CATTGCCTTGATTGGATACTCANNSTGGCTCATCAAC (SEQ ID NO: 103) |
| 140 | R | TGAGTATCCAATCAAGGCAATG (SEQ ID NO: 104) |
| 144 | F | TGGATACTCAAAGTGGCTCATCNNSAACAACTATCAG (SEQ ID NO: 105) |
| 144 | R | GATGAGCCACTTTGAGTATCC (SEQ ID NO: 106) |
| 145 | F | ATACTCAAAGTGGCTCATCAACNNSAACTATCAGTCG (SEQ ID NO: 107) |
| 145 | R | GTTGATGAGCCACTTTGAGTA (SEQ ID NO: 108) |
| 146 | F | CAAAGTGGCTCATCAACAACNNSTATCAGTCGACTGTGTCCAACG (SEQ ID NO: 109) |
| 146 | R | GTTGTTGATGAGCCACTTTGAGTAT (SEQ ID NO: 110) |
| 147 | F | AAAGTGGCTCATCAACAACAACNNSCAGTCGACTGTG (SEQ ID NO: 111) |
| 147 | R | GTTGTTGTTGATGAGCCACTT (SEQ ID NO: 112) |
| 148 | F | GGCTCATCAACAACAACTATNNSTCGACTGTGTCCAACGTCATCT (SEQ ID NO: 113) |
| 148 | R | ATAGTTGTTGTTGATGAGCCACTTT (SEQ ID NO: 114) |
| 152 | F | CAACAACTATCAGTCGACTGTGNNSAACGTCATCTGG (SEQ ID NO: 115) |
| 152 | R | CACAGTCGACTGATAGTTGTT (SEQ ID NO: 116) |
| 153 | F | CAACTATCAGTCGACTGTGTCCNNSGTCATCTGGCCT (SEQ ID NO: 117) |

TABLE 2-continued

Primers used to generate TrGA SELs

| AA-position | F/R | DNA Sequence 5' to 3' |
|---|---|---|
| 153 | R | GGACACAGTCGACTGATAGTT (SEQ ID NO: 118) |
| 164 | F | GCCTATTGTGCGCAACGACCTCNNSTATGTTGCCCAGT (SEQ ID NO: 119) |
| 164 | R | GAGGTCGTTGCGCACAATAGG (SEQ ID NO: 120) |
| 169 | F | ACCTCAACTATGTTGCCCAGNNSTGGAACCAAACCGGCTTTGACC (SEQ ID NO: 121) |
| 169 | R | CTGGGCAACATAGTTGAGGTCGTTG (SEQ ID NO: 122) |
| 172 | F | ATGTTGCCCAGTACTGGAACNNSACCGGCTTTGACCTCTGGGAAG (SEQ ID NO: 123) |
| 172 | R | GTTCCAGTACTGGGCAACATAGTTG (SEQ ID NO: 124) |
| 175 | F | AGTACTGGAACCAAACCGGCNNSGACCTCTGGGAAGAAGTCAATG (SEQ ID NO: 125) |
| 175 | R | GCCGGTTTGGTTCCAGTACTGGGCA (SEQ ID NO: 126) |
| 178 | F | ACCAAACCGGCTTTGACCTCNNSGAAGAAGTCAATGGGAGCTCAT (SEQ ID NO: 127) |
| 178 | R | GAGGTCAAAGCCGGTTTGGTTCCAG (SEQ ID NO: 128) |
| 180 | F | CCGGCTTTGACCTCTGGGAANNSGTCAATGGGAGCTCATTCTTTA (SEQ ID NO: 129) |
| 180 | R | TTCCCAGAGGTCAAAGCCGGTTTGG (SEQ ID NO: 130) |
| 181 | F | GCTTTGACCTCTGGGAAGAANNSAATGGGAGCTCATTCTTTACTG (SEQ ID NO: 131) |
| 181 | R | TTCTTCCCAGAGGTCAAAGCCGGTT (SEQ ID NO: 132) |
| 182 | F | CTTTGACCTCTGGGAAGAAGTCNNSGGGAGCTCATTC (SEQ ID NO: 133) |
| 182 | R | GACTTCTTCCCAGAGGTCAAAG (SEQ ID NO: 134) |
| 204 | F | TGTCGAGGGCGCCACTCTTGCTNNSACTCTTGGCCAG (SEQ ID NO: 135) |
| 204 | R | AGCAAGAGTGGCGCCCTCGAC (SEQ ID NO: 136) |
| 205 | F | CGAGGGCGCCACTCTTGCTGCCNNSCTTGGCCAGTCG (SEQ ID NO: 137) |
| 205 | R | GGCAGCAAGAGTGGCGCCCTC (SEQ ID NO: 138) |
| 208 | F | CTCTTGCTGCCACTCTTGGCNNSTCGGGAAGCGCTTATTCATCTG (SEQ ID NO: 139) |
| 208 | R | GCCAAGAGTGGCAGCAAGAGTGGCG (SEQ ID NO: 140) |
| 211 | F | CCACTCTTGGCCAGTCGGGANNSGCTTATTCATCTGTTGCTCCCC (SEQ ID NO: 141) |
| 211 | R | TCCCGACTGGCCAAGAGTGGCAGCA (SEQ ID NO: 142) |
| 214 | F | TGGCCAGTCGGGAAGCGCTTATNNSTCTGTTGCTCCC (SEQ ID NO: 143) |
| 214 | R | ATAAGCGCTTCCCGACTGGCC (SEQ ID NO: 144) |
| 216 | F | GTCGGGAAGCGCTTATTCATCTNNSGCTCCCCAGGT (SEQ ID NO: 145) |
| 216 | R | AGATGAATAAGCGCTTCCCGA (SEQ ID NO: 146) |
| 219 | F | CGCTTATTCATCTGTTGCTCCCNNSGTTTTGTGCTTT (SEQ ID NO: 147) |
| 219 | R | GGGAGCAACAGATGAATAAGC (SEQ ID NO: 148) |
| 228 | F | TGTGCTTTCTCCAACGATTCNNSGTGTCGTCTGGTGGATACGTCG (SEQ ID NO: 149) |
| 228 | R | GAATCGTTGGAGAAAGCACAAAACCT (SEQ ID NO: 150) |
| 229 | F | GTGCTTTCTCCAACGATTCTGGNNSTCGTCTGGTGGA (SEQ ID NO: 151) |
| 229 | R | CCAGAATCGTTGGAGAAAGCA (SEQ ID NO: 152) |
| 230 | F | CTTTCTCCAACGATTCTGGGTGNNSTCTGGTGGATACG (SEQ ID NO: 153) |
| 230 | R | CACCCAGAATCGTTGGAGAAA (SEQ ID NO: 154) |
| 231 | F | TCTCCAACGATTCTGGGTGTCGNNSGGTGGATACGTC (SEQ ID NO: 155) |
| 231 | R | CGACACCCAGAATCGTTGGAGA (SEQ ID NO: 156) |
| 236 | F | GGTGTCGTCTGGTGGATACGTCNNSTCCAACATCAACAC (SEQ ID NO: 157) |
| 236 | R | GACGTATCCACCAGACGACAC (SEQ ID NO: 158) |
| 239 | F | TGGTGGATACGTCGACTCCAACNNSAACACCAACGAG (SEQ ID NO: 159) |
| 239 | R | GTTGGAGTCGACGTATCCACC (SEQ ID NO: 160) |
| 240 | F | TGGATACGTCGACTCCAACATCNNSACCAACGAGGGCA (SEQ ID NO: 161) |
| 240 | R | GATGTTGGAGTCGACGTATCCA (SEQ ID NO: 162) |
| 241 | F | ATACGTCGACTCCAACATCAACNNSAACGAGGGCAGGAC (SEQ ID NO: 163) |
| 241 | R | GTTGATGTTGGAGTCGACGTA (SEQ ID NO: 164) |
| 242 | F | TCGACTCCAACATCAACACCNNSGAGGGCAGGACTGGCAAGGATG (SEQ ID NO: 165) |
| 242 | R | GGTGTTGATGTTGGAGTCGACGTAT (SEQ ID NO: 166) |
| 243 | F | ACTCCAACATCAACACCAACNNSGGCAGGACTGGCAAGGATGTCA (SEQ ID NO: 167) |

TABLE 2-continued
Primers used to generate TrGA SELs

| AA-position | F/R | DNA Sequence 5' to 3' |
|---|---|---|
| 243 | R | GTTGGTGTTGATGTTGGAGTCGACG (SEQ ID NO: 168) |
| 244 | F | CTCCAACATCAACACCAACGAGNNSAGGACTGGCAAG (SEQ ID NO: 169) |
| 244 | R | CTCGTTGGTGTTGATGTTGGAGT (SEQ ID NO: 170) |
| 245 | F | ACATCAACACCAACGAGGGCNNSACTGGCAAGGATGTCAACTCCG (SEQ ID NO: 171) |
| 245 | R | GCCCTCGTTGGTGTTGATGTTGGAGT (SEQ ID NO: 172) |
| 263 | F | TTCCATCCACACCTTCGATCCCNNSCTTGGCTGTGAC (SEQ ID NO: 173) |
| 263 | R | GGGATCGAAGGTGTGGATGGA (SEQ ID NO: 174) |
| 264 | F | CATCCACACCTTCGATCCCAACNNSGGCTGTGACGCA (SEQ ID NO: 175) |
| 264 | R | GTTGGGATCGAAGGTGTGGAT (SEQ ID NO: 176) |
| 265 | F | CCACACCTTCGATCCCAACCTTNNSTGTGACGCAGGC (SEQ ID NO: 177) |
| 265 | R | AAGGTTGGGATCGAAGGTGTG (SEQ ID NO: 178) |
| 268 | F | CGATCCCAACCTTGGCTGTGACNNSGGCACCTTCCAGC (SEQ ID NO: 179) |
| 268 | R | GTCACAGCCAAGGTTGGGATC (SEQ ID NO: 180) |
| 269 | F | TCCCAACCTTGGCTGTGACGCANNSACCTTCCAGCCA (SEQ ID NO: 181) |
| 269 | R | TGCGTCACAGCCAAGGTTGGG (SEQ ID NO: 182) |
| 276 | F | AGGCACCTTCCAGCCATGCAGTNNSAAAGCGCTCTCC (SEQ ID NO: 183) |
| 276 | R | ACTGCATGGCTGGAAGGTGCC (SEQ ID NO: 184) |
| 284 | F | CAAAGCGCTCTCCAACCTCAAGNNSGTTGTCGACTCCT (SEQ ID NO: 185) |
| 284 | R | CTTGAGGTTGGAGAGCGCTTT (SEQ ID NO: 186) |
| 291 | F | GGTTGTTGTCGACTCCTTCCGCNNSATCTACGGCGTG (SEQ ID NO: 187) |
| 291 | R | GCGGAAGGAGTCGACAACAAC (SEQ ID NO: 188) |
| 292 | F | TTGTCGACTCCTTCCGCTCCNNSTACGGCGTGAACAAGGGCATTC (SEQ ID NO: 189) |
| 292 | R | GGAGCGGAAGGAGTCGACAACAACC (SEQ ID NO: 190) |
| 294 | F | ACTCCTTCCGCTCCATCTACNNSGTGAACAAGGGCATTCCTGCCG (SEQ ID NO: 191) |
| 294 | R | GTAGATGGAGCGGAAGGAGTCGACA (SEQ ID NO: 192) |
| 297 | F | GCTCCATCTACGGCGTGAACNNSGGCATTCCTGCCGGTGCTGCCG (SEQ ID NO: 193) |
| 297 | R | GTTCACGCCGTAGATGGAGCGGAAG (SEQ ID NO: 194) |
| 300 | F | CTACGGCGTGAACAAGGGCATTNNSGCCGGTGCTGCCG (SEQ ID NO: 195) |
| 300 | R | AATGCCCTTGTTCACGCCGTA (SEQ ID NO: 196) |
| 301 | F | CGGCGTGAACAAGGGCATTCCTNNSGGTGCTGCCGTC (SEQ ID NO: 197) |
| 301 | R | AGGAATGCCCTTGTTCACGCC (SEQ ID NO: 198) |
| 303 | F | GAACAAGGGCATTCCTGCCGGTNNSGCCGTCGCCATT (SEQ ID NO: 199) |
| 303 | R | ACCGGCAGGAATGCCCTTGTT (SEQ ID NO: 200) |
| 309 | F | GTGCTGCCGTCGCCATTGGCNNSTATGCAGAGGATGTGTACTACA (SEQ ID NO: 201) |
| 309 | R | GCCAATGGCGACGGCAGCACCGGCA (SEQ ID NO: 202) |
| 310 | F | CTGCCGTCGCCATTGGCCGGNNSGCAGAGGATGTGTACTACAACG (SEQ ID NO: 203) |
| 310 | R | CCGGCCAATGGCGACGGCAGCACCG (SEQ ID NO: 204) |
| 311 | F | TGCCGTCGCCATTGGCCGGTATNNSGAGGATGTGTAC (SEQ ID NO: 205) |
| 311 | R | ATACCGGCCAATGGCGACGGC (SEQ ID NO: 206) |
| 313 | F | CCATTGGCCGGTATGCAGAGNNSGTGTACTACAACGGCAACCCTT (SEQ ID NO: 207) |
| 313 | F | CCATTGGCCGGTATGCAGAGNNSGTGTACTACAACGGCAACCCTT (SEQ ID NO: 208) |
| 313 | R | CTCTGCATACCGGCCAATGGCGACG (SEQ ID NO: 209) |
| 313 | R | CTCTGCATACCGGCCAATGGCGACG (SEQ ID NO: 210) |
| 314 | F | TTGGCCGGTATGCAGAGGATNNSTACTACAACGGCAACCCTTGGT (SEQ ID NO: 211) |
| 314 | R | ATCCTCTGCATACCGGCCAATGGCG (SEQ ID NO: 212) |
| 315 | F | GCCGGTATGCAGAGGATGTGNNSTACAACGGCAACCCTTGGTATC (SEQ ID NO: 213) |
| 315 | R | CACATCCTCTGCATACCGGCCAATG (SEQ ID NO: 214) |
| 316 | F | GGTATGCAGAGGATGTGTACNNSAACGGCAACCCTTGGTATCTTG (SEQ ID NO: 215) |
| 316 | R | GTACACATCCTCTGCATACCGGCCAAT (SEQ ID NO: 216) |
| 317 | F | ATGCAGAGGATGTGTACTACNNSGGCAACCCTTGGTATCTTGCTA (SEQ ID NO: 217) |

TABLE 2-continued

Primers used to generate TrGA SELs

| AA-position | F/R | DNA Sequence 5' to 3' |
|---|---|---|
| 317 | F | ATGCAGAGGATGTGTACTACNNSGGCAACCCTTGGTATCTTGCTA (SEQ ID NO: 218) |
| 317 | R | GTAGTACACATCCTCTGCATACCGGC (SEQ ID NO: 219) |
| 317 | R | GTAGTACACATCCTCTGCATACCGGC (SEQ ID NO: 220) |
| 321 | F | TGTACTACAACGGCAACCCTNNSTATCTTGCTACATTTGCTGCTG (SEQ ID NO: 221) |
| 321 | F | TGTACTACAACGGCAACCCTNNSTATCTTGCTACATTTGCTGCTG (SEQ ID NO: 222) |
| 321 | R | AGGGTTGCCGTTGTAGTACACATCC (SEQ ID NO: 223) |
| 321 | R | AGGGTTGCCGTTGTAGTACACATCC (SEQ ID NO: 224) |
| 338 | F | GCAGCTGTACGATGCCATCTACNNSTGGAAGAAGACG (SEQ ID NO: 225) |
| 338 | R | GTAGATGGCATCGTACAGCTG (SEQ ID NO: 226) |
| 340 | F | ACGATGCCATCTACGTCTGGNNSAAGACGGGCTCCATCACGGTGA (SEQ ID NO: 227) |
| 340 | R | CCAGACGTAGATGGCATCGTACAGC (SEQ ID NO: 228) |
| 341 | F | ATGCCATCTACGTCTGGAAGNNSACGGGCTCCATCACGGTGACCG (SEQ ID NO: 229) |
| 341 | R | CTTCCAGACGTAGATGGCATCGTACAGC (SEQ ID NO: 230) |
| 342 | F | ATGCCATCTACGTCTGGAAGAAGNNSGGCTCCATCACG (SEQ ID NO: 231) |
| 342 | R | CTTCTTCCAGACGTAGATGGC (SEQ ID NO: 232) |
| 344 | F | CTACGTCTGGAAGAAGACGGGCNNSATCACGGTGACC (SEQ ID NO: 233) |
| 344 | R | GCCCGTCTTCTTCCAGACGTAG (SEQ ID NO: 234) |
| 346 | F | CTGGAAGAAGACGGGCTCCATCNNSGTGACCGCCACCTC (SEQ ID NO: 235) |
| 346 | R | GATGGAGCCCGTCTTCTTCCA (SEQ ID NO: 236) |
| 349 | F | GACGGGCTCCATCACGGTGACCNNSACCTCCCTGGCC (SEQ ID NO: 237) |
| 349 | R | GGTCACCGTGATGGAGCCCGT (SEQ ID NO: 238) |
| 350 | F | GCTCCATCACGGTGACCGCCNNSTCCCTGGCCTTCTTCCAGGAGC (SEQ ID NO: 239) |
| 350 | R | GGCGGTCACCGTGATGGAGCCCGTC (SEQ ID NO: 240) |
| 356 | F | CCACCTCCCTGGCCTTCTTCNNSGAGCTTGTTCCTGGCGTGACGG (SEQ ID NO: 241) |
| 356 | R | GAAGAAGGCCAGGGAGGTGGCGGTC (SEQ ID NO: 242) |
| 359 | F | CCTGGCCTTCTTCCAGGAGCTTNNSCCTGGCGTGACG (SEQ ID NO: 243) |
| 359 | R | AAGCTCCTGGAAGAAGGCCAG (SEQ ID NO: 244) |
| 361 | F | CTTCTTCCAGGAGCTTGTTCCTNNSGTGACGGCCGGG (SEQ ID NO: 245) |
| 361 | R | AGGAACAAGCTCCTGGAAGAA (SEQ ID NO: 246) |
| 363 | F | AGGAGCTTGTTCCTGGCGTGNNSGCCGGGACCTACTCCAGCAGCT (SEQ ID NO: 247) |
| 363 | R | CACGCCAGGAACAAGCTCCTGGAAG (SEQ ID NO: 248) |
| 364 | F | GGAGCTTGTTCCTGGCGTGACGNNSGGGACCTACTCC (SEQ ID NO: 249) |
| 364 | R | CGTCACGCCAGGAACAAGCTC (SEQ ID NO: 250) |
| 368 | F | GCGTGACGGCCGGGACCTACNNSAGCAGCTCTTCGACCTTTACCA (SEQ ID NO: 251) |
| 368 | R | GTAGGTCCCGGCCGTCACGCCAGGA (SEQ ID NO: 252) |
| 369 | F | TGACGGCCGGGACCTACTCCNNSAGCTCTTCGACCTTTACCAACA (SEQ ID NO: 253) |
| 369 | R | GGAGTAGGTCCCGGCCGTCACGCCA (SEQ ID NO: 254) |
| 375 | F | CTCCAGCAGCTCTTCGACCTTTNNSAACATCATCAACG (SEQ ID NO: 255) |
| 375 | R | AAAGGTCGAAGAGCTGCTGGA (SEQ ID NO: 256) |
| 376 | F | GCAGCTCTTCGACCTTTACCNNSATCATCAACGCCGTCTCGACAT (SEQ ID NO: 257) |
| 376 | R | GGTAAAGGTCGAAGAGCTGCTGGAG (SEQ ID NO: 258) |
| 379 | F | TTCGACCTTTACCAACATCATCNNSGCCGTCTCGACA (SEQ ID NO: 259) |
| 379 | R | GATGATGTTGGTAAAGGTCGA (SEQ ID NO: 260) |
| 382 | F | TACCAACATCATCAACGCCGTCNNSACATACGCCGAT (SEQ ID NO: 261) |
| 382 | R | GACGGCGTTGATGATGTTGGT (SEQ ID NO: 262) |
| 390 | F | GACATACGCCGATGGCTTCCTCNNSGAGGCTGCCAAG (SEQ ID NO: 263) |
| 390 | R | GAGGAAGCCATCGGCGTATGT (SEQ ID NO: 264) |
| 391 | F | ATACGCCGATGGCTTCCTCAGCNNSGCTGCCAAGTAC (SEQ ID NO: 265) |
| 391 | R | GCTGAGGAAGCCATCGGCGTA (SEQ ID NO: 266) |
| 393 | F | CGATGGCTTCCTCAGCGAGGCTNNSAAGTACGTCCCC (SEQ ID NO: 267) |

TABLE 2-continued

Primers used to generate TrGA SELs

| AA-position | F/R | DNA Sequence 5' to 3' |
|---|---|---|
| 393 | R | AGCCTCGCTGAGGAAGCCATC (SEQ ID NO: 268) |
| 394 | F | TGGCTTCCTCAGCGAGGCTGCCNNSTACGTCCCCGCC (SEQ ID NO: 269) |
| 394 | R | GGCAGCCTCGCTGAGGAAGCC (SEQ ID NO: 270) |
| 395 | F | TCCTCAGCGAGGCTGCCAAGNNSGTCCCCGCCGACGGTTCGCTGG (SEQ ID NO: 271) |
| 395 | R | CTTGGCAGCCTCGCTGAGGAAGCCA (SEQ ID NO: 272) |
| 398 | F | AGGCTGCCAAGTACGTCCCCNNSGACGGTTCGCTGGCCGAGCAGTT (SEQ ID NO: 273) |
| 398 | R | GGGGACGTACTTGGCAGCCTCGCTG (SEQ ID NO: 274) |
| 401 | F | AGTACGTCCCCGCCGACGGTNNSCTGGCCGAGCAGTTTGACCGCA (SEQ ID NO: 275) |
| 401 | R | ACCGTCGGCGGGACGTACTTGGCAG (SEQ ID NO: 276) |
| 408 | F | CGCTGGCCGAGCAGTTTGACNNSAACAGCGGCACTCCGCTGTCTG (SEQ ID NO: 277) |
| 408 | R | GTCAAACTGCTCGGCCAGCGAACCG (SEQ ID NO: 278) |
| 409 | F | TGGCCGAGCAGTTTGACCGCNNSAGCGGCACTCCGCTGTCTGCGC (SEQ ID NO: 279) |
| 409 | R | GCGGTCAAACTGCTCGGCCAGCGAA (SEQ ID NO: 280) |
| 410 | F | GGCCGAGCAGTTTGACCGCAACNNSGGCACTCCGCTG (SEQ ID NO: 281) |
| 410 | R | GTTGCGGTCAAACTGCTCGGC (SEQ ID NO: 282) |
| 412 | F | AGTTTGACCGCAACAGCGGCNNSCCGCTGTCTGCGCTTCACCTGA (SEQ ID NO: 283) |
| 412 | R | GCCGCTGTTGCGGTCAAACTGCTCG (SEQ ID NO: 284) |
| 415 | F | GCAACAGCGGCACTCCGCTGNNSGCGCTTCACCTGACGTGGTCGT (SEQ ID NO: 285) |
| 415 | R | CAGCGGAGTGCCGCTGTTGCGGTCA (SEQ ID NO: 286) |
| 417 | F | CAGCGGCACTCCGCTGTCTGCGNNSCACCTGACGTGGT (SEQ ID NO: 287) |
| 417 | R | CGCAGACAGCGGAGTGCCGCT (SEQ ID NO: 288) |
| 418 | F | GCACTCCGCTGTCTGCGCTTNNSCTGACGTGGTCGTACGCCTCGT (SEQ ID NO: 289) |
| 418 | R | AAGCGCAGACAGCGGAGTGCCGCTG (SEQ ID NO: 290) |
| 421 | F | TGTCTGCGCTTCACCTGACGNNSTCGTACGCCTCGTTCTTGACAG (SEQ ID NO: 291) |
| 421 | R | CGTCAGGTGAAGCGCAGACAGCGGA (SEQ ID NO: 292) |
| 430 | F | GTACGCCTCGTTCTTGACAGCCNNSGCCCGTCGGGCT (SEQ ID NO: 293) |
| 430 | R | GGCTGTCAAGAACGAGGCGTA (SEQ ID NO: 294) |
| 431 | F | CGCCTCGTTCTTGACAGCCACGNNSCGTCGGGCTGGC (SEQ ID NO: 295) |
| 431 | R | CGTGGCTGTCAAGAACGAGGC (SEQ ID NO: 296) |
| 433 | F | TCTTGACAGCCACGGCCCGTNNSGCTGGCATCGTGCCCCCCTCGT (SEQ ID NO: 297) |
| 433 | R | ACGGGCCGTGGCTGTCAAGAACGAG (SEQ ID NO: 298) |
| 436 | F | CCACGGCCCGTCGGGCTGGCNNSGTGCCCCCCTCGTGGGCCAACA (SEQ ID NO: 299) |
| 436 | R | GCCAGCCCGACGGGCCGTGGCTGTC (SEQ ID NO: 300) |
| 442 | F | TGGCATCGTGCCCCCCTCGTGGNNSAACAGCAGCGCT (SEQ ID NO: 301) |
| 442 | R | CCACGAGGGGGGCACGATGCC (SEQ ID NO: 302) |
| 443 | F | CATCGTGCCCCCCTCGTGGGCCNNSAGCAGCGCTAGC (SEQ ID NO: 303) |
| 443 | R | GGCCCACGAGGGGGGCACGAT (SEQ ID NO: 304) |
| 444 | F | CGTGCCCCCCTCGTGGGCCAACNNSAGCGCTAGCACG (SEQ ID NO: 305) |
| 444 | R | GTTGGCCCACGAGGGGGGCAC (SEQ ID NO: 306) |
| 448 | F | GTGGGCCAACAGCAGCGCTAGCNNSATCCCCTCGACG (SEQ ID NO: 307) |
| 451 | F | GCAGCGCTAGCACGATCCCCNNSACGTGCTCCGGCGCGTCCGTGG (SEQ ID NO: 308) |
| 451 | R | GGGGATCGTGCTAGCGCTGCTGTTG (SEQ ID NO: 309) |
| 493 | F | CTACACGCCCCTGCCCTGCGCGNNSCCAACCTCCGTG (SEQ ID NO: 310) |
| 493 | R | CGCGCAGGGCAGGGGCGTGTA (SEQ ID NO: 311) |
| 494 | F | CACGCCCCTGCCCTGCGCGACCNNSACCTCCGTGGCC (SEQ ID NO: 312) |
| 494 | R | GGTCGCGCAGGGCAGGGGCGT (SEQ ID NO: 313) |
| 495 | F | GCCCCTGCCCTGCGCGACCCCANNSTCCGTGGCCGTC (SEQ ID NO: 314) |
| 495 | R | TGGGGTCGCGCAGGGCAGGGG (SEQ ID NO: 315) |
| 501 | F | CCCAACCTCCGTGGCCGTCACCNNSACGAGCTCGTGT (SEQ ID NO: 316) |
| 501 | R | GGTGACGGCCACGGAGGTTGG (SEQ ID NO: 317) |

TABLE 2-continued

Primers used to generate TrGA SELs

| AA-position | F/R | DNA Sequence 5' to 3' |
|---|---|---|
| 502 | F | AACCTCCGTGGCCGTCACCTTCNNSGAGCTCGTGTCG (SEQ ID NO: 318) |
| 502 | R | GAAGGTGACGGCCACGGAGGT (SEQ ID NO: 319) |
| 503 | F | CTCCGTGGCCGTCACCTTCCACNNSCTCGTGTCGACACA (SEQ ID NO: 320) |
| 503 | R | GTGGAAGGTGACGGCCACGGA (SEQ ID NO: 321) |
| 508 | F | CTTCCACGAGCTCGTGTCGACANNSTTTGGCCAGACG (SEQ ID NO: 322) |
| 508 | R | TGTCGACACGAGCTCGTGGAA (SEQ ID NO: 323) |
| 511 | F | GCTCGTGTCGACACAGTTTGGCNNSACGGTCAAGGTG (SEQ ID NO: 324) |
| 511 | R | GCCAAACTGTGTCGACACGAG (SEQ ID NO: 325) |
| 514 | F | CACAGTTTGGCCAGACGGTCNNSGTGGCGGGCAACGCCGCGGCCC (SEQ ID NO: 326) |
| 514 | R | GACCGTCTGGCCAAACTGTGTCGAC (SEQ ID NO: 327) |
| 517 | F | TGGCCAGACGGTCAAGGTGGCGNNSAACGCCGCGGCCCTGGG (SEQ ID NO: 328) |
| 517 | R | CGCCACCTTGACCGTCTGGCCAAACTG (SEQ ID NO: 329) |
| 518 | F | CCAGACGGTCAAGGTGGCGGGCNNSGCCGCGGCCCTGGGCAACT (SEQ ID NO: 330) |
| 518 | R | GCCCGCCACCTTGACCGTCTGGCCAAA (SEQ ID NO: 331) |
| 519 | F | GACGGTCAAGGTGGCGGGCAACNNSGCGGCCCTGGGCAACT (SEQ ID NO: 332) |
| 519 | R | GTTGCCCGCCACCTTGACCGTCTGGCC (SEQ ID NO: 333) |
| 520 | F | GGTCAAGGTGGCGGGCAACGCCNNSGCCCTGGGCAACTGGA (SEQ ID NO: 334) |
| 520 | R | GGCGTTGCCCGCCACCTTGACCGTCTG (SEQ ID NO: 335) |
| 525 | F | CAACGCCGCGGCCCTGGGCAACNNSAGCACGAGCGCCGCCG (SEQ ID NO: 336) |
| 525 | R | GTTGCCCAGGGCCGCGGCGTTGCCCGC (SEQ ID NO: 337) |
| 527 | F | CGCGGCCCTGGGCAACTGGAGCNNSAGCGCCGCCGTGGCTC (SEQ ID NO: 338) |
| 527 | R | GCTCCAGTTGCCCAGGGCCGCGGCGTT (SEQ ID NO: 339) |
| 531 | F | CAACTGGAGCACGAGCGCCGCCNNSGCTCTGGACGCCGTCA (SEQ ID NO: 340) |
| 531 | R | GGCGGCGCTCGTGCTCCAGTTGCCCAG (SEQ ID NO: 341) |
| 533 | F | GAGCACGAGCGCCGCCGTGGCTNNSGACGCCGTCAACTATGC (SEQ ID NO: 342) |
| 533 | R | AGCCACGGCGGCGCTCGTGCTCCAGTT (SEQ ID NO: 343) |
| 535 | F | GAGCGCCGCCGTGGCTCTGGACNNSGTCAACTATGCCGATA (SEQ ID NO: 344) |
| 535 | R | GTCCAGAGCCACGGCGGCGCTCGTGCT (SEQ ID NO: 345) |
| 536 | F | CGCCGCCGTGGCTCTGGACGCCNNSAACTATGCCGATAACC (SEQ ID NO: 346) |
| 536 | R | GGCGTCCAGAGCCACGGCGGCGCTCGT (SEQ ID NO: 347) |
| 537 | F | CGCCGTGGCTCTGGACGCCGTCNNSTATGCCGATAAC (SEQ ID NO: 348) |
| 537 | F | CGCCGTGGCTCTGGACGCCGTCNNSTATGCCGATAACCACCCC (SEQ ID NO: 349) |
| 537 | R | GACGGCGTCCAGAGCCACGGCGGCGCT (SEQ ID NO: 350) |
| 537 | R | GACGGCGTCCAGAGCCACGGCGGCGCT (SEQ ID NO: 351) |
| 538 | F | CGTGGCTCTGGACGCCGTCAACNNSGCCGATAACCACCCCC (SEQ ID NO: 352) |
| 538 | R | GTTGACGGCGTCCAGAGCCACGGCGGCG (SEQ ID NO: 353) |
| 539 | F | GGCTCTGGACGCCGTCAACTATNNSGATAACCACCCCCTGT (SEQ ID NO: 354) |
| 539 | R | ATAGTTGACGGCGTCCAGAGCCACGGC (SEQ ID NO: 355) |
| 540 | F | TCTGGACGCCGTCAACTATGCCNNSAACCACCCCCTGTGGATT (SEQ ID NO: 356) |
| 540 | R | GGCATAGTTGACGGCGTCCAGAGCCAC (SEQ ID NO: 357) |
| 541 | F | GGACGCCGTCAACTATGCCGATNNSCACCCCCTGTGGATTGGG (SEQ ID NO: 358) |
| 541 | R | ATCGGCATAGTTGACGGCGTCCAGAGC (SEQ ID NO: 359) |
| 545 | F | CTATGCCGATAACCACCCCCTGNNSATTGGGACGGTCAACCTC (SEQ ID NO: 360) |
| 545 | R | CAGGGGGTGGTTATCGGCATAGTTGAC (SEQ ID NO: 361) |
| 546 | F | TGCCGATAACCACCCCCTGTGGNNSGGGACGGTCAACCTCGAG (SEQ ID NO: 362) |
| 546 | R | CCACAGGGGGTGGTTATCGGCATAGTT (SEQ ID NO: 363) |
| 547 | F | CGATAACCACCCCCTGTGGATTNNSACGGTCAACCTCGAGGCT (SEQ ID NO: 364) |
| 547 | R | AATCCACAGGGGGTGGTTATCGGCATA (SEQ ID NO: 365) |
| 549 | F | CCACCCCCTGTGGATTGGGACGNNSAACCTCGAGGCTGGAGAC (SEQ ID NO: 366) |
| 549 | R | CGTCCCAATCCACAGGGGGTGGTTATC (SEQ ID NO: 367) |

TABLE 2-continued

Primers used to generate TrGA SELs

| AA-position | F/R | DNA Sequence 5' to 3' |
|---|---|---|
| 551 | F | CCTGTGGATTGGGACGGTCAACNNSGAGGCTGGAGA CGTCGTG (SEQ ID NO: 368) |
| 551 | R | GTTGACCGTCCCAATCCACAGGGGGTG (SEQ ID NO: 369) |
| 561 | F | TGGAGACGTCGTGGAGTACAAGNNSATCAATGTGGG CCAAGAT (SEQ ID NO: 370) |
| 561 | R | CTTGTACTCCACGACGTCTCCAGCCTC (SEQ ID NO: 371) |
| 563 | F | CGTCGTGGAGTACAAGTACATCNNSGTGGGCCAAG ATGGCTCC (SEQ ID NO: 372) |
| 563 | R | GATGTACTTGTACTCCACGACGTCTCC (SEQ ID NO: 373) |
| 567 | F | CAAGTACATCAATGTGGGCCAANNSGGCTCCGTGAC CTGGGAG (SEQ ID NO: 374) |
| 567 | R | TTGGCCCACATTGATGTACTTGTACTC (SEQ ID NO: 375) |
| 569 | F | CATCAATGTGGGCCAAGATGGCNNSGTGACCTGGGA GAGTGAT (SEQ ID NO: 376) |
| 569 | R | GCCATCTTGGCCCACATTGATGTACTTG (SEQ ID NO: 377) |
| 577 | F | CGTGACCTGGGAGAGTGATCCCNNSCACACTTACAC GGTTCCT (SEQ ID NO: 378) |
| 577 | R | GGGATCACTCTCCCAGGTCACGGAGCC (SEQ ID NO: 379) |
| 579 | F | CTGGGAGAGTGATCCCAACCACNNSTACACGGTTCC TGCGGTG (SEQ ID NO: 380) |
| 579 | R | GTGGTTGGGATCACTCTCCCAGGTCAC (SEQ ID NO: 381) |
| 583 | F | TCCCAACCACACTTACACGGTTNNSGCGGTGGCTTG TGTGACG (SEQ ID NO: 382) |
| 583 | R | AACCGTGTAAGTGTGGTTGGGATCACT (SEQ ID NO: 383) |

Example 2

Transformation of TrGA SELs into *Trichoderma reesei*

The SELs were transformed into *T. reesei* using the PEG protoplast method. The *E. coli* clones of the SELs confirmed by sequence analysis were grown overnight at 37° C. in deep well microtiter plates (Greiner Art. No. 780271) containing 1200 µl of 2xYT medium with ampicillin (100 µg/ml) and kanamycin (50 µg/ml). Plasmid DNAs were isolated from the cultures using CHEMAGIC® Plasmid Mini Kit (Chemagen—Biopolymer Technologie AG, Baesweiler, Germany) and were transformed individually into a *T. reesei* host strain derived from RL-P37 bearing four gene deletions (Δcbh1, Δcbh2, Δegl1, Δegl2, i.e., "quad-deleted;" see U.S. Pat. No. 5,847,276, WO 92/06184, and WO 05/001036) using the PEG-Protoplast method (Penttilä et al. (1987) *Gene* 61:155-164) with the following modifications.

For protoplast preparation, spores were grown for 16-24 hours at 24° C. in *Trichoderma* Minimal Medium (MM) (20 g/L glucose, 15 g/L $KH_2PO_4$, pH 4.5, 5 g/L $(NH_4)_2SO_4$, 0.6 g/L $MgSO_4.7H_2O$, 0.6 g/L $CaCl_2.2H_2O$, 1 ml of 1000× *T. reesei* Trace elements solution {5 g/L $FeSO_4.7H_2O$, 1.4 g/L $ZnSO_4.7H_2O$, 1.6 g/L $MnSO_4.H_2O$, 3.7 g/L $CoCl_2.6H_2O$}) with shaking at 150 rpm. Germinating spores were harvested by centrifugation and treated with 15 mg/ml of β-D-glucanase-G (Interspex—Art. No. 0439-1) solution to lyse the fungal cell walls. Further preparation of protoplasts was performed by a standard method, as described by Penttila et al. (1987 supra).

The transformation method was scaled down 10 fold. In general, transformation mixtures containing up to 600 ng of DNA and $1-5\times10^5$ protoplasts in a total volume of 25 µl were treated with 200 ml of 25% PEG solution, diluted with 2 volumes of 1.2 M sorbitol solution, mixed with 3% selective top agarose MM with acetamide (the same Minimal Medium as mentioned above but $(NH_4)_2SO_4$ was substituted with 20 mM acetamide) and poured onto 2% selective agarose with acetamide either in 24 well microtiter plates or in a 20×20 cm Q-tray divided in 48 wells. The plates were incubated at 28° C. for 5 to 8 days. Spores from the total population of transformants regenerated on each individual well were harvested from the plates using a solution of 0.85% NaCl, 0.015% Tween 80. Spore suspensions were used to inoculate fermentations in 96 wells MTPs. In the case of 24 well MTPs, an additional plating step on a fresh 24 well MTP with selective acetamide MM was introduced in order to enrich the spore numbers.

Example 3

Fermentation of *T. reesei* Transformants Expressing TrGA Variants in a MTP Format The transformants were fermented and the supernatants containing the expressed variant TrGA proteins were tested for various properties. In brief, 96-well filter plates (Corning Art. No. 3505) containing in each well 200 µl of LD-GSM medium (5.0 g/L $(NH_4)_2SO_4$, 33 g/L 1,4-Piperazinebis(propanesulfonic acid), pH 5.5, 9.0 g/L Casamino acids, 1.0 g/L $KH_2PO_4$, 1.0 g/L $CaCl_2.2H_2O$, 1.0 g/L $MgSO_4.7H_2O$, 2.5 ml/L of 1000× *T. reesei* trace elements, 20 g/L Glucose, 10 g/L Sophorose) were inoculated in quadruplicate with spore suspensions of *T. reesei* transformants expressing TrGA variants (more than $10^4$ sporesper well). The plates were incubated at 28° C. with 230 rpm shaking and 80% humidity for 6 days. Culture supernatants were harvested by vacuum filtration. The supernatants were used in different assays for screening of variants with improved properties.

Example 4

Preparation of the Whole Broth Samples from GA-Producing Transformants

TrGA producing transformants were initially pre-grown in 250 ml shake flasks containing 30 ml of ProFlo medium. Proflo medium contained: 30 g/L α-lactose, 6.5 g/L $(NH_4)_2SO_4$, 2 g/L $KH_2PO_4$, 0.3 g/L $MgSO_4.7H_2O$, 0.2 g/L $CaCl_2.2H_2O$, 1 ml/L 1000× trace element salt solution as mentioned above, 2 ml/L 10% Tween 80, 22.5 g/L ProFlo cottonseed flour (Traders protein, Memphis, Tenn.), 0.72 g/L $CaCO_3$. After two days of growth at 28° C. and 140 rpm, 10% of the Proflo culture was transferred into a 250 ml shake flask containing 30 ml of Lactose Defined Medium. The composition of the Lactose Defined Medium was as follows: 5 g/L $(NH_4)_2SO_4$, 33 g/L 1,4-Piperazinebis (propanesulfonic acid) buffer, pH 5.5, 9 g/L casamino acids, 4.5 g/L $KH_2PO_4$, 1.0 g/L $MgSO_4.7H_2O$, 5 ml/L Mazu DF60-P antifoam (Mazur Chemicals, IL), 1 ml/L of 1000× trace element solution. 40 ml/L of 40% (w/v) lactose solution was added to the medium after sterilization. Shake flasks with the Lactose Defined Medium were incubated at 28° C., 140 rpm for 4-5 days.

Mycelium was removed from the culture samples by centrifugation and the supernatant was analyzed for total protein content (BCA Protein Assay Kit, Pierce Cat. No. 23225) and GA activity, as described above in the Assays and Methods section.

The protein profile of the whole broth samples was determined by SDS-PAGE electrophoresis. Samples of the culture supernatant were mixed with an equal volume of 2× sample loading buffer with reducing agent and separated on NUPAGE® Novex 10% Bis-Tris Gel with MES SDS Running Buffer (Invitrogen, Carlsbad, Calif., USA). Polypeptide bands were visualized in the SDS gel with SIMPLYBLUE SafeStain (Invitrogen, Carlsbad, Calif., USA).

Example 5

Thermal Stability of the Variants

The thermal stability was measured according to above assay "Thermal stability assay 2".

The parent molecule under the conditions described had a residual activity of 87.2%, Table 3 shows the residual activity for the variants, which were selected from an initial screen for fermentation in large scale and further analysis. The material used was crude fermentation broth from shake flasks. Residual activity was calculated on basis of GAU activity before and after 120 min incubation at 63° C. in 0.1M citrate buffer pH 5.4, containing 15% glucose.

TABLE 3

Thermostability for selected TrGA variants, shown as residual activity after incubation for 120 min at 63° C. in 0.1M citrate buffer pH 5.4, containing 15% glucose.

| Variant | Residual activity |
|---|---|
| D44R/N61I/A539R (BRW 11) | 84.2 |
| L417R/A431L/A539R (VAR16) | 88.5 |
| D44R/A539R (BRW 1) | 99.0 |
| N61I/L417V/A431L/A539R (VAR3) | 86.2 |
| I43R/L417V/A431L/A539R (VAR13) | 89.8 |
| BRW 2 | 92.4 |
| I43Q/D44C/N61I/L417V/E503A/Q511H/A539R (ALL3) | 86.6 |
| I43Q/D44C/L417V/E503A/Q511H (ALL1) | 90.1 |
| I43R/N61I/L417R/E503A/Q511H/A539R (ALL8) | 84.6 |
| I43Q/N61I/T430M/Q511H/A539R (RB19) | 83.0 |
| I43Q/N61I/T430A/A431L/Q511H/A539R (RB10) | 82.3 |
| Diazyme X4 (AnGA reference product) | 72.3 |
| Diazyme TR8 (TrGA reference product) | 87.2 |
| I43R/G73F/T430A (C2 Negative Control) | 88.3 |
| I43Q/L417V/Q511H (RB13 Negative Control) | 74.1 |

Example 6

Determination of Isomaltose Synthesis and Starch Hydrolysis and Ratio Thereof

Variants were tested according to above assays: "Starch hydrolysis activity" and "Determination of maltose and isomaltose synthesis by TLC". The IS/SH ratio was calculated from the results of these analysis as described. Table 4 summarises the data for the variants selected for fermentation in large scale and further analysis. The material used was crude fermentation broth from shake flasks.

TABLE 4

Isomaltose synthesis activity (IS), starch hydrolysis activity (SH) and IS/SH ratio of selected TrGA variants

| Variant (Parent glucaoamylase TrGA, SEQ ID No: 2) | Iso-maltose synthesis M/min *10E−05 | Starch hydro-lysis M/min | Iso-maltose synthesis Relative to DiazymeX4 | (IS/SH) *10E−04 |
|---|---|---|---|---|
| D44R/N61I/A539R (BRW 11) | 2.7 | 0.078 | 1.1 | 3.4 |
| L417R/A431L/A539R (VAR16) | 3.4 | 0.078 | 1.4 | 4.4 |
| D44R/A539R (BRW 1) | 3.2 | 0.071 | 1.4 | 4.5 |
| N61I/L417V/A431L/A539R (VAR3) | 4.3 | 0.089 | 1.5 | 4.8 |
| I43R/L417V/A431L/A539R (VAR13) | 4.1 | 0.082 | 1.6 | 5.0 |
| BRW 2 | 3.9 | 0.079 | 1.6 | 5.0 |
| I43Q/D44C/N61I/L417V/E503A/Q511H/A539R (ALL3) | 3.8 | 0.074 | 1.6 | 5.1 |
| I43Q/D44C/L417V/E503A/Q511H (ALL1) | 3.7 | 0.072 | 1.6 | 5.2 |
| I43R/N61I/L417R/E503A/Q511H/A539R (ALL8) | 4.3 | 0.079 | 1.7 | 5.4 |
| I43Q/N61I/T430M/Q511H/A539R (RB19) | 4.7 | 0.085 | 1.8 | 5.6 |
| I43Q/N61I/T430A/A431L/Q511H/A539R (RB10) | 5.3 | 0.089 | 1.8 | 5.9 |
| Diazyme X4 (AnGA reference product) | | | 1.0 | 3.2 |
| Diazyme TR8 (TrGA reference product) | | | 2.5 | 7.9 |
| I43R/G73F/T430A (C2 Negative Control) | 8.7 | 0.0789 | 5.0 | 16 |
| I43Q/L417V/Q511H (RB13 Negative Control) | 8.1 | 0.0508 | 3.4 | 11 |

Example 7

Brew Analysis with Determination of Real Degree of Fermentation (RDF)

All the variants shown in table 3 and 4 were grown in fermentors and GA enzyme was collected and purified (as described above under "Purification of TrGA variants"). The purified enzymes were reanalysed for IS/SH ratio as described above in Example 6 and thermostability was measured as described in Example 5. Brew analysis with determination of RDF value was carried out on the four variants which showed the best combination of IS/SH ratio and thermostability (Brew11, Brew1, Var16 and Var13) as described above under "Brew analysis with determination of real degree of fermentation (RDF)". RDF values are listed in Table 5.

TABLE 5

RDF values of selected purified TrGA-variants, purified wild type TrGA and purified AnGA. Below values were obtained using the above described "Pure malt brew analysis"-method.

| Purified GA | RDF | STDEV |
|---|---|---|
| AnGA (purified from DIAZYME ® X4) | 82.5 | 0.064 |
| TrGA (purified from DIAZYME ® TR8) | 82.0 | 0.028 |
| D44R/N61I/A539R (BRW 11) | 82.50 | 0.005 |
| D44R/A539R (BRW 1) | 82.33 | 0.050 |
| L417R/A431L/A539R (VAR16) | 81.93 | 0.113 |
| I43R/L417V/A431L/A539R (VAR13) | 81.86 | 0.085 |

Example 8

Construction and Characterization of Combinatorial Variants

Based on data a selected set of variants with single substitutions were further characterized. These variants have single substitution at positions: 43, 44, 61, 73, 294, 417, 430, 431, 503, 511, 535, 539, and 563. Among these sites, 43, 44, and 294 were identified in a previous screening experiment in *Schizosaccharomyces pombe*. See WO 08/045,489, which is incorporated herein by reference. Variants were purified from large-scale fermentation, and PIs of thermal stability and specific activities were determined. Specifically, specific activities were determined using various substrates, including DP7, cornstarch, and liquefact. The results are shown in Table 6.

TABLE 6

PIs of a selected set of single site variants, each of which is obtained from a 500 ml fermentation.

| Variants | P.I. DP7-FPLC | P.I. CornStarch-FPLC | P.I. Thermal Stability | P.I. Liquefact-FPLC |
|---|---|---|---|---|
| N61I | 1.16 | 1.35 | 1.00 | 1.66 |
| A431L | 1.15 | 1.38 | 1.18 | 1.51 |
| L417V | 1.18 | 1.32 | 1.02 | 1.40 |
| A431Q | 1.06 | 1.20 | 0.92 | 1.24 |
| G294C | 1.01 | 0.84 | 0.94 | 1.23 |
| N563K | 1.07 | 1.12 | 1.97 | 1.15 |
| Q511H | 1.05 | 1.09 | 1.52 | 1.13 |
| T430M | 1.05 | 1.15 | 0.89 | 1.09 |
| E503A | 1.08 | 1.16 | 1.40 | 1.09 |
| I43Q | 1.11 | 1.24 | 0.94 | 1.08 |
| A539R | 1.15 | 1.37 | 1.43 | 1.08 |
| I43R | 1.03 | 1.07 | 1.41 | 1.07 |
| L417R | 1.23 | 1.27 | 1.51 | 1.04 |
| T430A | 1.13 | 1.35 | 1.23 | 1.04 |
| G73F | 1.06 | 1.06 | 1.45 | 1.03 |
| D44R | 0.97 | 1.06 | 1.46 | 0.98 |
| N563I | 1.09 | 1.22 | 2.06 | 0.92 |
| D44C | 0.80 | 0.82 | 0.96 | 0.91 |
| E503V | 1.17 | 1.07 | 1.66 | 0.88 |
| A535R | 1.09 | 1.44 | 1.47 | 0.85 |

Additionally, combinatorial variants were constructed using the PCR method with substitutions among: 43, 44, 61, 73, 294, 417, 430, 431, 503, 511, 535, 539, and 563. Briefly, the combinatorial variants were constructed by using plasmid pDONR-TrGA (FIG. 2) as the backbone. The methodology to construct combinatorial variants is based on the Gateway technology (Invitrogen, Carlsbad, Calif.). The primers used to create the combinatorial variants are shown in Tables 2 and 7. The following synthetic construct approach was chosen for the construction of all combinatorial variants.

CTCTCT [XbaI site] [MF] GAGAGGGG [attB1] [GAP combinatorial variant][attB2 sites] CCCCAGAG [MR] [HindIII] AGAGAG This construct was treated with restriction enzymes Xba-I and HindIII. The digested fragments were ligated into Xba-I/HindIII treated pBC (a pUC19 derived vector). The ligation mixture was transformed to *E. coli* DH10B (Invitrogen, Carlsbad, Calif.) and plated onto selective agar supplemented with 100 µg/ml ampicillin. The plates were incubated for 16 h at 37° C. Colonies from the selective plates were isolated and inoculated into selective liquid medium. After 16 h incubation at 37° C. and 250 rpm the plasmids were isolated using a standard plasmid isolation kit and combined with pDONR 2.21 (Invitrogen, Carlsbad, Calif.) to create a Gateway entry vector with the specific combinatorial variants. The reaction mixture was transformed into *E. coli* Max efficiency DH5α (Invitrogen, Carlsbad, Calif.) and plated on selective agar (2×TY supplemented with 50 µg kanamycin/ml). After overnight incubation at 37° C., single colonies were picked for sequence analysis (BaseClear B.V., Leiden, Netherlands). The combinatorial variants were subcloned in pTrexTrTel and expressed in a *T. reesei* host strain as described in WO 06/060062.

TABLE 7

Primers used to construct combinatorial variants

| Primer | DNA sequence | SEQ ID NO: |
|---|---|---|
| Var1 Basic-1 | GAGAGAGTGCGGGCCTCTTCGCTATTTCTAGA | 391 |
| Var1 Basic-2 | CAAAATAAAATCATTATTTGTCTAGAAATAGCGAAGAGGC | 392 |
| Var1 Basic-3 | CAAATAATGATTTTATTTTGACTGATAGTGACCTGTTCGT | 393 |
| Var1 Basic-4 | TTGCTCATCAATGTGTTGCAACGAACAGGTCACTATCAGT | 394 |
| Var1 Basic-5 | TGCAACACATTGATGAGCAATGCTTTTTTATAATGCCAAC | 395 |
| Var1 Basic-6 | AGCCTGCTTTTTTGTACAAAGTTGGCATTATAAAAAAGCA | 396 |

TABLE 7-continued

Primers used to construct combinatorial variants

| Primer | DNA sequence | SEQ ID NO: |
|---|---|---|
| Var1 Basic-7 | TTTGTACAAAAAAGCAGGCTATGCACGTCCTGTCGACTGC | 397 |
| Var1 Basic-8 | CAACGGAGCCGAGCAGCACCGCAGTCGACAGGACGTGCAT | 398 |
| Var1 Basic-9 | GGTGCTGCTCGGCTCCGTTGCCGTTCAAAAGGTCCTGGGA | 399 |
| Var1 Basic-10 | AGACCGCTTGATCCTGGTCTTCCCAGGACCTTTTGAACGG | 400 |
| Var1 Basic-11 | AGACCAGGATCAAGCGGTCTGTCCGACGTCACCAAGAGGT | 401 |
| Var1 Basic-12 | GCTGATGAAGTCGTCAACAGACCTCTTGGTGACGTCGGAC | 402 |
| Var1 Basic-13 | CTGTTGACGACTTCATCAGCACCGAGACGCCTATTGCACT | 403 |
| Var1 Basic-14 | CATTGCAAAGAAGATTGTTCAGTGCAATAGGCGTCTCGGT | 404 |
| Var1 Basic-15 | GAACAATCTTCTTTGCAATGTTGGTCCTGATGGATGCCGT | 405 |
| Var1 Basic-16 | CCAGCTGATGTGCCGAATGCACGGCATCCATCAGGACCAA | 406 |
| Var1 Basic-17 | GCATTCGGCACATCAGCTGGTGCGGTGATTGCATCTCCCA | 407 |
| Var1 Basic-18 | GTAGTCCGGGTCAATTGTGCTGGGAGATGCAATCACCGCA | 408 |
| Var1 Basic-19 | GCACAATTGACCCGGACTACTATTACATGTGGACGCGAGA | 409 |
| Var1 Basic-20 | TCTTGAAGACAAGAGCGCTATCTCGCGTCCACATGTAATA | 410 |
| Var1 Basic-21 | TAGCGCTCTTGTCTTCAAGAACCTCATCGACCGCTTCACC | 411 |
| Var1 Basic-22 | AGGCCCGCATCGTACGTTTCGGTGAAGCGGTCGATGAGGT | 412 |
| Var1 Basic-23 | GAAACGTACGATGCGGGCCTGCAGCGCCGCATCGAGCAGT | 413 |
| Var1 Basic-24 | AGTGACCTGGGCAGTAATGTACTGCTCGATGCGGCGCTGC | 414 |
| Var1 Basic-25 | ACATTACTGCCCAGGTCACTCTCCAGGGCCTCTCTAACCC | 415 |
| Var1 Basic-26 | CGTCCGCGAGGGAGCCCGAGGGGTTAGAGAGGCCCTGGAG | 416 |
| Var1 Basic-27 | CTCGGGCTCCCTCGCGGACGGCTCTGGTCTCGGCGAGCCC | 417 |
| Var1 Basic-28 | TTCAGGGTCAACTCAAACTTGGGCTCGCCGAGACCAGAGC | 418 |
| Var1 Basic-29 | AAGTTTGAGTTGACCCTGAAGCCTTTCACCGGCAACTGGG | 419 |
| Var1 Basic-30 | GCCATCCCGCTGCGGTCGACCCCAGTTGCCGGTGAAAGGC | 420 |
| Var1 Basic-31 | GTCGACCGCAGCGGGATGGCCCAGCTCTGCGAGCCATTGC | 421 |
| Var1 Basic-32 | ACTTTGAGTATCCAATCAAGGCAATGGCTCGCAGAGCTGG | 422 |
| Var1 Basic-33 | CTTGATTGGATACTCAAAGTGGCTCATCAACAACAACTAT | 423 |
| Var1 Basic-34 | ACGTTGGACACAGTCGACTGATAGTTGTTGTTGATGAGCC | 424 |
| Var1 Basic-35 | CAGTCGACTGTGTCCAACGTCATCTGGCCTATTGTGCGCA | 425 |
| Var1 Basic-36 | GGCAACATAGTTGAGGTCGTTGCGCACAATAGGCCAGATG | 426 |
| Var1 Basic-37 | ACGACCTCAACTATGTTGCCCAGTACTGGAACCAAACCGG | 427 |
| Var1 Basic-38 | CTTCTTCCCAGAGGTCAAAGCCGGTTTGGTTCCAGTACTG | 428 |
| Var1 Basic-39 | CTTTGACCTCTGGGAAGAAGTCAATGGGAGCTCATTCTTT | 429 |
| Var1 Basic-40 | CGGTGCTGGTTGGCAACAGTAAAGAATGAGCTCCCATTGA | 430 |
| Var1 Basic-41 | ACTGTTGCCAACCAGCACCGAGCACTTGTCGAGGGCGCCA | 431 |
| Var1 Basic-42 | GCCAAGAGTGGCAGCAAGAGTGGCGCCCTCGACAAGTGCT | 432 |
| Var1 Basic-43 | CTCTTGCTGCCACTCTTGGCCAGTCGGGAAGCGCTTATTC | 433 |

TABLE 7-continued

Primers used to construct combinatorial variants

| Primer | DNA sequence | SEQ ID NO: |
|---|---|---|
| Var1 Basic-44 | AAACCTGGGGAGCAACAGATGAATAAGCGCTTCCCGACTG | 434 |
| Var1 Basic-45 | ATCTGTTGCTCCCCAGGTTTTGTGCTTTCTCCAACGATTC | 435 |
| Var1 Basic-46 | TATCCACCAGACGACACCCAGAATCGTTGGAGAAAGCACA | 436 |
| Var1 Basic-47 | TGGGTGTCGTCTGGTGGATACGTCGACTCCAACATCAACA | 437 |
| Var1 Basic-48 | GCCAGTCCTGCCCTCGTTGGTGTTGATGTTGGAGTCGACG | 438 |
| Var1 Basic-49 | CCAACGAGGGCAGGACTGGCAAGGATGTCAACTCCGTCCT | 439 |
| Var1 Basic-50 | CGAAGGTGTGGATGGAAGTCAGGACGGAGTTGACATCCTT | 440 |
| Var1 Basic-51 | GACTTCCATCCACACCTTCGATCCCAACCTTGGCTGTGAC | 441 |
| Var1 Basic-52 | CATGGCTGGAAGGTGCCTGCGTCACAGCCAAGGTTGGGAT | 442 |
| Var1 Basic-53 | GCAGGCACCTTCCAGCCATGCAGTGACAAAGCGCTCTCCA | 443 |
| Var1 Basic-54 | GTCGACAACAACCTTGAGGTTGGAGAGCGCTTTGTCACTG | 444 |
| Var1 Basic-55 | ACCTCAAGGTTGTTGTCGACTCCTTCCGCTCCATCTACGG | 445 |
| Var1 Basic-56 | CAGGAATGCCCTTGTTCACGCCGTAGATGGAGCGGAAGGA | 446 |
| Var1 Basic-57 | CGTGAACAAGGGCATTCCTGCCGGTGCTGCCGTCGCCATT | 447 |
| Var1 Basic-58 | ACATCCTCTGCATACCGGCCAATGGCGACGGCAGCACCGG | 448 |
| Var1 Basic-59 | GGCCGGTATGCAGAGGATGTGTACTACAACGGCAACCCTT | 449 |
| Var1 Basic-60 | AGCAAATGTAGCAAGATACCAAGGGTTGCCGTTGTAGTAC | 450 |
| Var1 Basic-61 | GGTATCTTGCTACATTTGCTGCTGCCGAGCAGCTGTACGA | 451 |
| Var1 Basic-62 | TCTTCCAGACGTAGATGGCATCGTACAGCTGCTCGGCAGC | 452 |
| Var1 Basic-63 | TGCCATCTACGTCTGGAAGAAGACGGGCTCCATCACGGTG | 453 |
| Var1 Basic-64 | AAGGCCAGGGAGGTGGCGGTCACCGTGATGGAGCCCGTCT | 454 |
| Var1 Basic-65 | ACCGCCACCTCCCTGGCCTTCTTCCAGGAGCTTGTTCCTG | 455 |
| Var1 Basic-66 | GTAGGTCCCGGCCGTCACGCCAGGAACAAGCTCCTGGAAG | 456 |
| Var1 Basic-67 | GCGTGACGGCCGGGACCTACTCCAGCAGCTCTTCGACCTT | 457 |
| Var1 Basic-68 | CGGCGTTGATGATGTTGGTAAAGGTCGAAGAGCTGCTGGA | 458 |
| Var1 Basic-69 | TACCAACATCATCAACGCCGTCTCGACATACGCCGATGGC | 459 |
| Var1 Basic-70 | TTGGCAGCCTCGCTGAGGAAGCCATCGGCGTATGTCGAGA | 460 |
| Var1 Basic-71 | TTCCTCAGCGAGGCTGCCAAGTACGTCCCCGCCGACGGTT | 461 |
| Var1 Basic-72 | GTCAAACTGCTCGGCCAGCGAACCGTCGGCGGGGACGTAC | 462 |
| Var1 Basic-73 | CGCTGGCCGAGCAGTTTGACCGCAACAGCGGCACTCCGCT | 463 |
| Var1 Basic-74 | ACGTCAGGTGAACCGCAGACAGCGGAGTGCCGCTGTTGCG | 464 |
| Var1 Basic-75 | GTCTGCGGTTCACCTGACGTGGTCGTACGCCTCGTTCTTG | 465 |
| Var1 Basic-76 | GCCCGACGAAGCGTGGCTGTCAAGAACGAGGCGTACGACC | 466 |
| Var1 Basic-77 | ACAGCCACGCTTCGTCGGGCTGGCATCGTGCCCCCCTCGT | 467 |
| Var1 Basic-78 | GCTAGCGCTGCTGTTGGCCCACGAGGGGGGCACGATGCCA | 468 |
| Var1 Basic-79 | GGGCCAACAGCAGCGCTAGCACGATCCCCTCGACGTGCTC | 469 |
| Var1 Basic-80 | ATCCGACCACGGACGCGCCGGAGCACGTCGAGGGGATCGT | 470 |
| Var1 Basic-81 | CGGCGCGTCCGTGGTCGGATCCTACTCGCGTCCCACCGCC | 471 |

TABLE 7-continued

Primers used to construct combinatorial variants

| Primer | DNA sequence | SEQ ID NO: |
|---|---|---|
| Var1 Basic-82 | TGCGACGGAGGGAATGACGTGGCGGTGGGACGCGAGTAGG | 472 |
| Var1 Basic-83 | ACGTCATTCCCTCCGTCGCAGACGCCCAAGCCTGGCGTGC | 473 |
| Var1 Basic-84 | CGTGTAGGGAGTACCGGAAGGCACGCCAGGCTTGGGCGTC | 474 |
| Var1 Basic-85 | CTTCCGGTACTCCCTACACGCCCTGCCCTGCGCGACCCC | 475 |
| Var1 Basic-86 | AGGTGACGGCCACGGAGGTTGGGGTCGCGCAGGGCAGGGG | 476 |
| Var1 Basic-87 | AACCTCCGTGGCCGTCACCTTCCACGAGCTCGTGTCGACA | 477 |
| Var1 Basic-88 | TTGACCGTCTGGCCAAACTGTGTCGACACGAGCTCGTGGA | 478 |
| Var1 Basic-89 | CAGTTTGGCCAGACGGTCAAGGTGGCGGGCAACGCCGCGG | 479 |
| Var1 Basic-90 | CGTGCTCCAGTTGCCCAGGGCGCGGCGTTGCCCGCCACC | 480 |
| Var1 Basic-91 | CCCTGGGCAACTGGAGCACGAGCGCCGCCGTGGCTCTGGA | 481 |
| Var1 Basic-92 | TATCACGATAGTTGACGGCGTCCAGAGCCACGGCGGCGCT | 482 |
| Var1 Basic-93 | CGCCGTCAACTATCGTGATAACCACCCCCTGTGGATTGGG | 483 |
| Var1 Basic-94 | CCAGCCTCGAGGTTGACCGTCCCAATCCACAGGGGGTGGT | 484 |
| Var1 Basic-95 | ACGGTCAACCTCGAGGCTGGAGACGTCGTGGAGTACAAGT | 485 |
| Var1 Basic-96 | ATCTTGGCCCACATTGATGTACTTGTACTCCACGACGTCT | 486 |
| Var1 Basic-97 | ACATCAATGTGGGCCAAGATGGCTCCGTGACCTGGGAGAG | 487 |
| Var1 Basic-98 | TGTAAGTGTGGTTGGGATCACTCTCCCAGGTCACGGAGCC | 488 |
| Var1 Basic-99 | TGATCCCAACCACACTTACACGGTTCCTGCGGTGGCTTGT | 489 |
| Var1 Basic-100 | TCCTTGACAACCTGCGTCACACAAGCCACCGCAGGAACCG | 490 |
| Var1 Basic-101 | GTGACGCAGGTTGTCAAGGAGGACACCTGGCAGTCGTAAA | 491 |
| Var1 Basic-102 | CTTTGTACAAGAAAGCTGGGTTTACGACTGCCAGGTGTCC | 492 |
| Var1 Basic-103 | CCCAGCTTTCTTGTACAAAGTTGGCATTATAAGAAAGCAT | 493 |
| Var1 Basic-104 | TTGCAACAAATTGATAAGCAATGCTTTCTTATAATGCCAA | 494 |
| Var1 Basic-105 | TGCTTATCAATTTGTTGCAACGAACAGGTCACTATCAGTC | 495 |
| Var1 Basic-106 | TCAAATAATGATTTTATTTTGACTGATAGTGACCTGTTCG | 496 |
| Var1 Basic-107 | AAAATAAAATCATTATTTGAAGCTTAAGCCTGGGGTGCCT | 497 |
| Var1 Basic-108 | AGAGAGTCATTAGGCACCCCAGGCTTAAGCT | 498 |
| Var2-18 | GTAGTCCGGGTCTTGTGTGCTGGGAGATGCAATCACCGCA | 499 |
| Var2-19 | GCACACAAGACCCGGACTACTATTACATGTGGACGCGAGA | 500 |
| Var3-21 | TAGCGCTCTTGTCTTCAAGATTCTCATCGACCGCTTCACC | 501 |
| Var3-22 | AGGCCCGCATCGTACGTTTCGGTGAAGCGGTCGATGAGAA | 502 |
| Var4-92 | TATCACGATAGTTGACACGGTCCAGAGCCACGGCGGCGCT | 503 |
| Var4-93 | CCGTGTCAACTATCGTGATAACCACCCCCTGTGGATTGGG | 504 |
| Var5-18 | GTAGTCCGGGTCTTGTGTGCTGGGAGATGCAATCACCGCA | 505 |
| Var5-19 | GCACACAAGACCCGGACTACTATTACATGTGGACGCGAGA | 506 |
| Var5-21 | TAGCGCTCTTGTCTTCAAGATTCTCATCGACCGCTTCACC | 507 |
| Var5-22 | AGGCCCGCATCGTACGTTTCGGTGAAGCGGTCGATGAGAA | 508 |

TABLE 7-continued

Primers used to construct combinatorial variants

| Primer | DNA sequence | SEQ ID NO: |
|---|---|---|
| Var6-21 | TAGCGCTCTTGTCTTCAAGATTCTCATCGACCGCTTCACC | 509 |
| Var6-22 | AGGCCCGCATCGTACGTTTCGGTGAAGCGGTCGATGAGAA | 510 |
| Var6-92 | TATCACGATAGTTGACACGGTCCAGAGCCACGGCGGCGCT | 511 |
| Var6-93 | CCGTGTCAACTATCGTGATAACCACCCCCTGTGGATTGGG | 512 |
| Var7-92 | TATCACGATAGTTGACACGGTCCAGAGCCACGGCGGCGCT | 513 |
| Var7-93 | CCGTGTCAACTATCGTGATAACCACCCCCTGTGGATTGGG | 514 |
| Var7-18 | GTAGTCCGGGTCTTGTGTGCTGGGAGATGCAATCACCGCA | 515 |
| Var7-19 | GCACACAAGACCCGGACTACTATTACATGTGGACGCGAGA | 516 |
| Var8-18 | GTAGTCCGGGTCTTGTGTGCTGGGAGATGCAATCACCGCA | 517 |
| Var8-19 | GCACACAAGACCCGGACTACTATTACATGTGGACGCGAGA | 518 |
| Var8-21 | TAGCGCTCTTGTCTTCAAGATTCTCATCGACCGCTTCACC | 519 |
| Var8-22 | AGGCCCGCATCGTACGTTTCGGTGAAGCGGTCGATGAGAA | 520 |
| Var8-92 | TATCACGATAGTTGACACGGTCCAGAGCCACGGCGGCGCT | 521 |
| Var8-93 | CCGTGTCAACTATCGTGATAACCACCCCCTGTGGATTGGG | 522 |
| Var9-18 | GTAGTCCGGGTCTTGTGTGCTGGGAGATGCAATCACCGCA | 523 |
| Var9-19 | GCACACAAGACCCGGACTACTATTACATGTGGACGCGAGA | 524 |
| Var9-21 | TAGCGCTCTTGTCTTCAAGATTCTCATCGACCGCTTCACC | 525 |
| Var9-22 | AGGCCCGCATCGTACGTTTCGGTGAAGCGGTCGATGAGAA | 526 |
| Var9-92 | TATCACGATAGTTGACACGGTCCAGAGCCACGGCGGCGCT | 527 |
| Var9-93 | CCGTGTCAACTATCGTGATAACCACCCCCTGTGGATTGGG | 528 |
| Var9-76 | GCCCGACGAAGAGCGGCTGTCAAGAACGAGGCGTACGACC | 529 |
| Var9-77 | ACAGCCGCTCTTCGTCGGGCTGGCATCGTGCCCCCCTCGT | 530 |
| Var10-76 | GCCCGACGAAGAGCGGCTGTCAAGAACGAGGCGTACGACC | 531 |
| Var10-77 | ACAGCCGCTCTTCGTCGGGCTGGCATCGTGCCCCCCTCGT | 532 |
| Var10-88 | TTGACCGTATGGCCAAACTGTGTCGACACGAGCTCGTGGA | 533 |
| Var10-89 | CAGTTTGGCCATACGGTCAAGGTGGCGGGCAACGCCGCGG | 534 |
| Var10-92 | TATCACGATAGTTGACACGGTCCAGAGCCACGGCGGCGCT | 535 |
| Var10-93 | CCGTGTCAACTATCGTGATAACCACCCCCTGTGGATTGGG | 536 |
| Var10-96 | ATCTTGGCCCACAATGATGTACTTGTACTCCACGACGTCT | 537 |
| Var10-97 | ACATCATTGTGGGCCAAGATGGCTCCGTGACCTGGGAGAG | 538 |
| Var10-18 | GTAGTCCGGGTCTTGTGTGCTGGGAGATGCAATCACCGCA | 539 |
| Var10-19 | GCACACAAGACCCGGACTACTATTACATGTGGACGCGAGA | 540 |
| Var11-76 | GCCCGACGAAGAGCGGCTGTCAAGAACGAGGCGTACGACC | 541 |
| Var11-77 | ACAGCCGCTCTTCGTCGGGCTGGCATCGTGCCCCCCTCGT | 542 |
| Var11-88 | TTGACCGTATGGCCAAACTGTGTCGACACGAGCTCGTGGA | 543 |
| Var11-89 | CAGTTTGGCCATACGGTCAAGGTGGCGGGCAACGCCGCGG | 544 |
| Var11-92 | TATCACGATAGTTGACACGGTCCAGAGCCACGGCGGCGCT | 545 |
| Var11-93 | CCGTGTCAACTATCGTGATAACCACCCCCTGTGGATTGGG | 546 |

TABLE 7-continued

Primers used to construct combinatorial variants

| Primer | DNA sequence | SEQ ID NO: |
|---|---|---|
| Var11-96 | ATCTTGGCCCACAATGATGTACTTGTACTCCACGACGTCT | 547 |
| Var11-97 | ACATCATTGTGGGCCAAGATGGCTCCGTGACCTGGGAGAG | 548 |
| Var11-21 | TAGCGCTCTTGTCTTCAAGATTCTCATCGACCGCTTCACC | 549 |
| Var11-22 | AGGCCCGCATCGTACGTTTCGGTGAAGCGGTCGATGAGAA | 550 |
| Var12-76 | GCCCGACGAAGAGCGGCTGTCAAGAACGAGGCGTACGACC | 551 |
| Var12-77 | ACAGCCGCTCTTCGTCGGGCTGGCATCGTGCCCCCCTCGT | 552 |
| Var12-88 | TTGACCGTATGGCCAAACTGTGTCGACACGAGCTCGTGGA | 553 |
| Var12-89 | CAGTTTGGCCATACGGTCAAGGTGGCGGGCAACGCCGCGG | 554 |
| Var12-92 | TATCACGATAGTTGACACGGTCCAGAGCCACGGCGGCGCT | 555 |
| Var12-93 | CCGTGTCAACTATCGTGATAACCACCCCCTGTGGATTGGG | 556 |
| Var12-96 | ATCTTGGCCCACAATGATGTACTTGTACTCCACGACGTCT | 557 |
| Var12-97 | ACATCATTGTGGGCCAAGATGGCTCCGTGACCTGGGAGAG | 558 |
| Var12-18 | GTAGTCCGGGTCTTGTGTGCTGGGAGATGCAATCACCGCA | 559 |
| Var12-19 | GCACACAAGACCCGGACTACTATTACATGTGGACGCGAGA | 560 |
| Var12-21 | TAGCGCTCTTGTCTTCAAGATTCTCATCGACCGCTTCACC | 561 |
| Var12-22 | AGGCCCGCATCGTACGTTTCGGTGAAGCGGTCGATGAGAA | 562 |
| Var13-18 | GTAGTCCGGGTCACGTGTGCTGGGAGATGCAATCACCGCA | 563 |
| Var13-19 | GCACACGTGACCCGGACTACTATTACATGTGGACGCGAGA | 564 |
| Var14-18 | GTAGTCCGGGTCACGTGTGCTGGGAGATGCAATCACCGCA | 565 |
| Var14-19 | GCACACGTGACCCGGACTACTATTACATGTGGACGCGAGA | 566 |
| Var14-21 | TAGCGCTCTTGTCTTCAAGATTCTCATCGACCGCTTCACC | 567 |
| Var14-22 | AGGCCCGCATCGTACGTTTCGGTGAAGCGGTCGATGAGAA | 568 |
| Var15-18 | GTAGTCCGGGTCACGTGTGCTGGGAGATGCAATCACCGCA | 569 |
| Var15-19 | GCACACGTGACCCGGACTACTATTACATGTGGACGCGAGA | 570 |
| Var15-21 | TAGCGCTCTTGTCTTCAAGATTCTCATCGACCGCTTCACC | 571 |
| Var15-22 | AGGCCCGCATCGTACGTTTCGGTGAAGCGGTCGATGAGAA | 572 |
| Var15-92 | TATCACGATAGTTGACACGGTCCAGAGCCACGGCGGCGCT | 573 |
| Var15-93 | CCGTGTCAACTATCGTGATAACCACCCCCTGTGGATTGGG | 574 |
| Var15-76 | GCCCGACGAAGAGCGGCTGTCAAGAACGAGGCGTACGACC | 575 |
| Var15-77 | ACAGCCGCTCTTCGTCGGGCTGGCATCGTGCCCCCCTCGT | 576 |
| Var16-74 | ACGTCAGGTGACGCGCAGACAGCGGAGTGCCGCTGTTGCG | 577 |
| Var16-75 | GTCTGCGCGTCACCTGACGTGGTCGTACGCCTCGTTCTTG | 578 |
| Var17-74 | ACGTCAGGTGACCCGCAGACAGCGGAGTGCCGCTG1TGCG | 579 |
| Var17-75 | GTCTGCGGGTCACCTGACGTGGTCGTACGCCTCGTTCTTG | 580 |
| Var18-22 | AGAAACGCATCGTACGTTTCGGTGAAGCGGTCGATGAGGT | 581 |
| Var18-23 | GAAACGTACGATGCGTTTCTGCAGCGCCGCATCGAGCAGT | 582 |
| Var18-74 | ACGTCAGGTGACGCGCAGACAGCGGAGTGCCGCTGTTGCG | 583 |

TABLE 7-continued

Primers used to construct combinatorial variants

| Primer | DNA sequence | SEQ ID NO: |
|---|---|---|
| Var18-75 | GTCTGCGCGTCACCTGACGTGGTCGTACGCCTCGTTCTTG | 584 |
| Var18-76 | GCCCGACGGGCCGTGGCTGTCAAGAACGAGGCGTACGACC | 585 |
| Var18-77 | ACAGCCACGGCCCGTCGGGCTGGCATCGTGCCCCCCTCGT | 586 |
| Var18-87 | AACCTCCGTGGCCGTCACCTTCCACGTTCTCGTGTCGACA | 587 |
| Var18-88 | TTGACCGTCTGGCCAAACTGTGTCGACACGAGAACGTGGA | 588 |
| Var18-96 | ATCTTGGCCCACTTTGATGTACTTGTACTCCACGACGTCT | 589 |
| Var18-97 | ACATCAAAGTGGGCCAAGATGGCTCCGTGACCTGGGAGAG | 590 |
| Var19-18 | GTAGTCCGGGTCACGTGTGCTGGGAGATGCAATCACCGCA | 591 |
| Var19-19 | GCACACGTGACCCGGACTACTATTACATGTGGACGCGAGA | 592 |
| Var19-22 | AGAAACGCATCGTACGTTTCGGTGAAGCGGTCGATGAGGT | 593 |
| Var19-23 | GAAACGTACGATGCGTTTCTGCAGCGCCGCATCGAGCAGT | 594 |
| Var19-74 | ACGTCAGGTGACGCGCAGACAGCGGAGTGCCGCTGTTGCG | 595 |
| Var19-75 | GTCTGCGCGTCACCTGACGTGGTCGTACGCCTCGTTCTTG | 596 |
| Var19-76 | GCCCGACGGGCCGTGGCTGTCAAGAACGAGGCGTACGACC | 597 |
| Var19-77 | ACAGCCACGGCCCGTCGGGCTGGCATCGTGCCCCCCTCGT | 598 |
| Var19-87 | AACCTCCGTGGCCGTCACCTTCCACGTTCTCGTGTCGACA | 599 |
| Var19-88 | TTGACCGTCTGGCCAAACTGTGTCGACACGAGAACGTGGA | 600 |
| Var19-96 | ATCTTGGCCCACTTTGATGTACTTGTACTCCACGACGTCT | 601 |
| Var19-97 | ACATCAAAGTGGGCCAAGATGGCTCCGTGACCTGGGAGAG | 602 |
| Var20-18 | GTAGTCCGGGTCACGTGTGCTGGGAGATGCAATCACCGCA | 603 |
| Var20-19 | GCACACGTGACCCGGACTACTATTACATGTGGACGCGAGA | 604 |
| Var20-22 | AGAAACGCATCGTACGTTTCGGTGAAGCGGTCGATGAGGT | 605 |
| Var20-23 | GAAACGTACGATGCGTTTCTGCAGCGCCGCATCGAGCAGT | 606 |
| Var20-74 | ACGTCAGGTGAAGCGCAGACAGCGGAGTGCCGCTGTTGCG | 607 |
| Var20-75 | GTCTGCGCTTCACCTGACGTGGTCGTACGCCTCGTTCTTG | 608 |
| Var20-76 | GCCCGACGGGCCGTGGCTGTCAAGAACGAGGCGTACGACC | 609 |
| Var20-77 | ACAGCCACGGCCCGTCGGGCTGGCATCGTGCCCCCCTCGT | 610 |
| Var20-87 | AACCTCCGTGGCCGTCACCTTCCACGTTCTCGTGTCGACA | 611 |
| Var20-88 | TTGACCGTATGGCCAAACTGTGTCGACACGAGAACGTGGA | 612 |
| Var20-89 | CAGTTTGGCCATACGGTCAAGGTGGCGGGCAACGCCGCGG | 613 |
| Var20-93 | TATCGGCATAGTTGACGGCGTCCAGAGCCACGGCGGCGCT | 614 |
| Var20-94 | CGCCGTCAACTATGCCGATAACCACCCCCTGTGGATTGGG | 615 |
| Var20-96 | ATCTTGGCCCACTTTGATGTACTTGTACTCCACGACGTCT | 616 |
| Var20-97 | ACATCAAAGTGGGCCAAGATGGCTCCGTGACCTGGGAGAG | 617 |
| GAV Basic-1 | ACAAGTTTGTACAAAAAAGCAGGCT | 618 |
| GAV Basic-2 | GCAGTCGACAGGACGTGCATAGCCTGCTTTTTTGTACAAA | 619 |
| GAV Basic-3 | ATGCACGTCCTGTCGACTGCGGTGCTGCTCGGCTCCGTTG | 620 |
| GAV Basic-4 | TCCCAGGACCTTTTGAACGGCAACGGAGCCGAGCAGCACC | 621 |

TABLE 7-continued

Primers used to construct combinatorial variants

| Primer | DNA sequence | SEQ ID NO: |
|---|---|---|
| GAV Basic-5 | CCGTTCAAAAGGTCCTGGGAAGACCAGGATCAAGCGGTCT | 622 |
| GAV Basic-6 | ACCTCTTGGTGACGTCGGACAGACCGCTTGATCCTGGTCT | 623 |
| GAV Basic-7 | GTCCGACGTCACCAAGAGGTCTGTTGACGACTTCATCAGC | 624 |
| GAV Basic-8 | AGTGCAATAGGCGTCTCGGTGCTGATGAAGTCGTCAACAG | 625 |
| GAV Basic-9 | ACCGAGACGCCTATTGCACTGAACAATCTTCTTTGCAATG | 626 |
| GAV Basic-10 | ACGGCATCCATCAGGACCAACATTGCAAGAAGATTGTTC | 627 |
| GAV Basic-11 | TTGGTCCTGATGGATGCCGTGCATTCGGCACATCAGCTGG | 628 |
| GAV Basic-12 | TGGGAGATGCAATCACCGCACCAGCTGATGTGCCGAATGC | 629 |
| GAV Basic-13 | TGCGGTGATTGCATCTCCCAGCACAATTGACCCGGACTAC | 630 |
| GAV Basic-14 | TCTCGCGTCCACATGTAATAGTAGTCCGGGTCAATTGTGC | 631 |
| GAV Basic-15 | TATTACATGTGGACGCGAGATAGCGCTCTTGTCTTCAAGA | 632 |
| GAV Basic-16 | GGTGAAGCGGTCGATGAGGTTCTTGAAGACAAGAGCGCTA | 633 |
| GAV Basic-17 | ACCTCATCGACCGCTTCACCGAAACGTACGATGCGGGCCT | 634 |
| GAV Basic-18 | ACTGCTCGATGCGGCGCTGCAGGCCCGCATCGTACGTTTC | 635 |
| GAV Basic-19 | GCAGCGCCGCATCGAGCAGTACATTACTGCCCAGGTCACT | 636 |
| GAV Basic-20 | GGGTTAGAGAGGCCCTGGAGAGTGACCTGGGCAGTAATGT | 637 |
| GAV Basic-21 | CTCCAGGGCCTCTCTAACCCCTCGGGCTCCCTCGCGGACG | 638 |
| GAV Basic-22 | GGGCTCGCCGAGACCAGAGCCGTCCGCGAGGGAGCCCGAG | 639 |
| GAV Basic-23 | GCTCTGGTCTCGGCGAGCCCAAGTTTGAGTTGACCCTGAA | 640 |
| GAV Basic-24 | CCCAGTTGCCGGTGAAAGGCTTCAGGGTCAACTCAAACTT | 641 |
| GAV Basic-25 | GCCTTTCACCGGCAACTGGGGTCGACCGCAGCGGGATGGC | 642 |
| GAV Basic-26 | GCAATGGCTCGCAGAGCTGGGCCATCCCGCTGCGGTCGAC | 643 |
| GAV Basic-27 | CCAGCTCTGCGAGCCATTGCCTTGATTGGATACTCAAAGT | 644 |
| GAV Basic-28 | ATAGTTGTTGTTGATGAGCCACTTTGAGTATCCAATCAAG | 645 |
| GAV Basic-29 | GGCTCATCAACAACAACTATCAGTCGACTGTGTCCAACGT | 646 |
| GAV Basic-30 | TGCGCACAATAGGCCAGATGACGTTGGACACAGTCGACTG | 647 |
| GAV Basic-31 | CATCTGGCCTATTGTGCGCAACGACCTCAACTATGTTGCC | 648 |
| GAV Basic-32 | CCGGTTTGGTTCCAGTACTGGGCAACATAGTTGAGGTCGT | 649 |
| GAV Basic-33 | CAGTACTGGAACCAAACCGGCTTTGACCTCTGGGAAGAAG | 650 |
| GAV Basic-34 | AAAGAATGAGCTCCCATTGACTTCTTCCCAGAGGTCAAAG | 651 |
| GAV Basic-35 | TCAATGGGAGCTCATTCTTTACTGTTGCCAACCAGCACCG | 652 |
| GAV Basic-36 | TGGCGCCCTCGACAAGTGCTCGGTGCTGGTTGGCAACAGT | 653 |
| GAV Basic-37 | AGCACTTGTCGAGGGCGCCACTCTTGCTGCCACTCTTGGC | 654 |
| GAV Basic-38 | GAATAAGCGCTTCCCGACTGGCCAAGAGTGGCAGCAAGAG | 655 |
| GAV Basic-39 | CAGTCGGGAAGCGCTTATTCATCTGTTGCTCCCCAGGTTT | 656 |
| GAV Basic-40 | GAATCGTTGGAGAAAGCACAAAACCTGGGGAGCAACAGAT | 657 |
| GAV Basic-41 | TGTGCTTTCTCCAACGATTCTGGGTGTCGTCTGGTGGATA | 658 |

TABLE 7-continued

Primers used to construct combinatorial variants

| Primer | DNA sequence | SEQ ID NO: |
|---|---|---|
| GAV Basic-42 | TGTTGATGTTGGAGTCGACGTATCCACCAGACGACACCCA | 659 |
| GAV Basic-43 | CGTCGACTCCAACATCAACACCAACGAGGGCAGGACTGGC | 660 |
| GAV Basic-44 | AGGACGGAGTTGACATCCTTGCCAGTCCTGCCCTCGTTGG | 661 |
| GAV Basic-45 | AAGGATGTCAACTCCGTCCTGACTTCCATCCACACCTTCG | 662 |
| GAV Basic-46 | GTCACAGCCAAGGTTGGGATCGAAGGTGTGGATGGAAGTC | 663 |
| GAV Basic-47 | ATCCCAACCTTGGCTGTGACGCAGGCACCTTCCAGCCATG | 664 |
| GAV Basic-48 | TGGAGAGCGCTTTGTCACTGCATGGCTGGAAGGTGCCTGC | 665 |
| GAV Basic-49 | CAGTGACAAAGCGCTCTCCAACCTCAAGGTTGTTGTCGAC | 666 |
| GAV Basic-50 | CCGTAGATGGAGCGGAAGGAGTCGACAACAACCTTGAGGT | 667 |
| GAV Basic-51 | TCCTTCCGCTCCATCTACGGCGTGAACAAGGGCATTCCTG | 668 |
| GAV Basic-52 | AATGGCGACGGCAGCACCGGCAGGAATGCCCTTGTTCACG | 669 |
| GAV Basic-53 | CCGGTGCTGCCGTCGCCATTGGCCGGTATGCAGAGGATGT | 670 |
| GAV Basic-54 | AAGGGTTGCCGTTGTAGTACACATCCTCTGCATACCGGCC | 671 |
| GAV Basic-55 | GTACTACAACGGCAACCCTTGGTATCTTGCTACATTTGCT | 672 |
| GAV Basic-56 | TCGTACAGCTGCTCGGCAGCAGCAAATGTAGCAAGATACC | 673 |
| GAV Basic-57 | GCTGCCGAGCAGCTGTACGATGCCATCTACGTCTGGAAGA | 674 |
| GAV Basic-58 | CACCGTGATGGAGCCCGTCTTCTTCCAGACGTAGATGGCA | 675 |
| GAV Basic-59 | AGACGGGCTCCATCACGGTGACCGCCACCTCCCTGGCCTT | 676 |
| GAV Basic-60 | CAGGAACAAGCTCCTGGAAGAAGGCCAGGGAGGTGGCGGT | 677 |
| GAV Basic-61 | CTTCCAGGAGCTTGTTCCTGGCGTGACGGCCGGGACCTAC | 678 |
| GAV Basic-62 | AAGGTCGAAGAGCTGCTGGAGTAGGTCCCGGCCGTCACGC | 679 |
| GAV Basic-63 | TCCAGCAGCTCTTCGACCTTTACCAACATCATCAACGCCG | 680 |
| GAV Basic-64 | GCCATCGGCGTATGTCGAGACGGCGTTGATGATGTTGGTA | 681 |
| GAV Basic-65 | TCTCGACATACGCCGATGGCTTCCTCAGCGAGGCTGCCAA | 682 |
| GAV Basic-66 | AACCGTCGGCGGGACGTACTTGGCAGCCTCGCTGAGGAA | 683 |
| GAV Basic-67 | GTACGTCCCCGCCGACGGTTCGCTGGCCGAGCAGTTTGAC | 684 |
| GAV Basic-68 | AGCGGAGTGCCGCTGTTGCGGTCAAACTGCTCGGCCAGCG | 685 |
| GAV Basic-69 | CGCAACAGCGGCACTCCGCTGTCTGCGCTTCACCTGACGT | 686 |
| GAV Basic-70 | CAAGAACGAGGCGTACGACCACGTCAGGTGAAGCGCAGAC | 687 |
| GAV Basic-71 | GGTCGTACGCCTCGTTCTTGACAGCCACGGCCCGTCGGGC | 688 |
| GAV Basic-72 | ACGAGGGGGCACGATGCCAGCCCGACGGGCCGTGGCTGT | 689 |
| GAV Basic-73 | TGGCATCGTGCCCCCCTCGTGGGCCAACAGCAGCGCTAGC | 690 |
| GAV Basic-74 | GAGCACGTCGAGGGGATCGTGCTAGCGCTGCTGTTGGCCC | 691 |
| GAV Basic-75 | ACGATCCCCTCGACGTGCTCCGGCGCGTCCGTGGTCGGAT | 692 |
| GAV Basic-76 | GGCGGTGGGACGCGAGTAGGATCCGACCACGGACGCGCCG | 693 |
| GAV Basic-77 | CCTACTCGCGTCCCACCGCCACGTCATTCCCTCCGTCGCA | 694 |
| GAV Basic-78 | GCACGCCAGGCTTGGGCGTCTGCGACGGAGGGAATGACGT | 695 |
| GAV Basic-79 | GACGCCCAAGCCTGGCGTGCCTTCCGGTACTCCCTACACG | 696 |

TABLE 7-continued

Primers used to construct combinatorial variants

| Primer | DNA sequence | SEQ ID NO: |
|---|---|---|
| GAV Basic-80 | GGGGTCGCGCAGGGCAGGGGCGTGTAGGGAGTACCGGAAG | 697 |
| GAV Basic-81 | CCCCTGCCCTGCGCGACCCCAACCTCCGTGGCCGTCACCT | 698 |
| GAV Basic-82 | TGTCGACACGAGCTCGTGGAAGGTGACGGCCACGGAGGTT | 699 |
| GAV Basic-83 | TCCACGAGCTCGTGTCGACACAGTTTGGCCAGACGGTCAA | 700 |
| GAV Basic-84 | CCGCGGCGTTGCCCGCCACCTTGACCGTCTGGCCAAACTG | 701 |
| GAV Basic-85 | GGTGGCGGGCAACGCCGCGGCCCTGGGCAACTGGAGCACG | 702 |
| GAV Basic-86 | TCCAGAGCCACGGCGGCGCTCGTGCTCCAGTTGCCCAGGG | 703 |
| GAV Basic-87 | AGCGCCGCCGTGGCTCTGGACGCCGTCAACTATGCCGATA | 704 |
| GAV Basic-88 | CCCAATCCACAGGGGGTGGTTATCGGCATAGTTGACGGCG | 705 |
| GAV Basic-89 | ACCACCCCTGTGGATTGGGACGGTCAACCTCGAGGCTGG | 706 |
| GAV Basic-90 | ACTTGTACTCCACGACGTCTCCAGCCTCGAGGTTGACCGT | 707 |
| GAV Basic-91 | AGACGTCGTGGAGTACAAGTACATCAATGTGGGCCAAGAT | 708 |
| GAV Basic-92 | CTCTCCCAGGTCACGGAGCCATCTTGGCCCACATTGATGT | 709 |
| GAV Basic-93 | GGCTCCGTGACCTGGGAGAGTGATCCCAACCACACTTACA | 710 |
| GAV Basic-94 | ACAAGCCACCGCAGGAACCGTGTAAGTGTGGTTGGGATCA | 711 |
| GAV Basic-95 | CGGTTCCTGCGGTGGCTTGTGTGACGCAGGTTGTCAAGGA | 712 |
| GAV Basic-96 | TTTACGACTGCCAGGTGTCCTCCTTGACAACCTGCGTCAC | 713 |
| GAV Basic-97 | GGACACCTGGCAGTCGTAAACCCAGCTTTCTTGTACAAAG | 714 |
| GAV Basic-98 | ACCACTTTGTACAAGAAAGCTGGG | 715 |
| A111-13 | TGCGGTGATTGCATCTCCCAGCACACTTTGCCCGGACTAC | 716 |
| A111-14 | TCTCGCGTCCACATGTAATAGTAGTCCGGGCAAAGTGTGC | 717 |
| A111-69 | CGCAACAGCGGCACTCCGCTGTCTGCGGTTCACCTGACGT | 718 |
| A111-70 | CAAGAACGAGGCGTACGACCACGTCAGGTGAACCGCAGAC | 719 |
| A111-82 | TGTCGACACGAGCGCGTGGAAGGTGACGGCCACGGAGGTT | 720 |
| A111-83 | TCCACGCGCTCGTGTCGACACAGTTTGGCCACACGGTCAA | 721 |
| A111-84 | CCGCGGCGTTGCCCGCCACCTTGACCGTGTGGCCAAACTG | 722 |
| A111-87 | AGCGCCGCCGTGGCTCTGGACGCCGTCAACTATAGAGATA | 723 |
| A111-88 | CCCAATCCACAGGGGGTGGTTATCTCTATAGTTGACGGCG | 724 |
| A112-13 | TGCGGTGATTGCATCTCCCAGCACACTTGACCCGGACTAC | 725 |
| A112-14 | TCTCGCGTCCACATGTAATAGTAGTCCGGGTCAAGTGTGC | 726 |
| A112-69 | CGCAACAGCGGCACTCCGCTGTCTGCGGTTCACCTGACGT | 727 |
| A112-70 | CAAGAACGAGGCGTACGACCACGTCAGGTGAACCGCAGAC | 728 |
| A112-82 | TGTCGACACGAGCGCGTGGAAGGTGACGGCCACGGAGGTT | 729 |
| A112-83 | TCCACGCGCTCGTGTCGACACAGTTTGGCCACACGGTCAA | 730 |
| A112-84 | CCGCGGCGTTGCCCGCCACCTTGACCGTGTGGCCAAACTG | 731 |
| A112-87 | AGCGCCGCCGTGGCTCTGGACGCCGTCAACTATAGAGATA | 732 |
| A112-88 | CCCAATCCACAGGGGGTGGTTATCTCTATAGTTGACGGCG | 733 |

TABLE 7-continued

Primers used to construct combinatorial variants

| Primer | DNA sequence | SEQ ID NO: |
|---|---|---|
| A113-13 | TGCGGTGATTGCATCTCCCAGCACACTTTGCCCGGACTAC | 734 |
| A113-14 | TCTCGCGTCCACATGTAATAGTAGTCCGGGCAAAGTGTGC | 735 |
| A113-16 | GGTGAAGCGGTCGATGAGGATCTTGAAGACAAGAGCGCTA | 736 |
| A113-17 | TCCTCATCGACCGCTTCACCGAAACGTACGATGCGGGCCT | 737 |
| A113-69 | CGCAACAGCGGCACTCCGCTGTCTGCGGTTCACCTGACGT | 738 |
| A113-70 | CAAGAACGAGGCGTACGACCACGTCAGGTGAACCGCAGAC | 739 |
| A113-82 | TGTCGACACGAGCGCGTGGAAGGTGACGGCCACGGAGGTT | 740 |
| A113-83 | TCCACGCGCTCGTGTCGACACAGTTTGGCCACACGGTCAA | 741 |
| A113-84 | CCGCGGCGTTGCCCGCCACCTTGACCGTGTGGCCAAACTG | 742 |
| A113-87 | AGCGCCGCCGTGGCTCTGGACGCCGTCAACTATAGAGATA | 743 |
| A113-88 | CCCAATCCACAGGGGGTGGTTATCTCTATAGTTGACGGCG | 744 |
| A114-13 | TGCGGTGATTGCATCTCCCAGCACACTTGACCCGGACTAC | 745 |
| A114-14 | TCTCGCGTCCACATGTAATAGTAGTCCGGGTCAAGTGTGC | 746 |
| A114-16 | GGTGAAGCGGTCGATGAGGATCTTGAAGACAAGAGCGCTA | 747 |
| A114-17 | TCCTCATCGACCGCTTCACCGAAACGTACGATGCGGGCCT | 748 |
| A114-69 | CGCAACAGCGGCACTCCGCTGTCTGCGGTTCACCTGACGT | 749 |
| A114-70 | CAAGAACGAGGCGTACGACCACGTCAGGTGAACCGCAGAC | 750 |
| A114-82 | TGTCGACACGAGCGCGTGGAAGGTGACGGCCACGGAGGTT | 751 |
| A114-83 | TCCACGCGCTCGTGTCGACACAGTTTGGCCACACGGTCAA | 752 |
| A114-84 | CCGCGGCGTTGCCCGCCACCTTGACCGTGTGGCCAAACTG | 753 |
| A114-87 | AGCGCCGCCGTGGCTCTGGACGCCGTCAACTATAGAGATA | 754 |
| A114-88 | CCCAATCCACAGGGGGTGGTTATCTCTATAGTTGACGGCG | 755 |
| A115-13 | TGCGGTGATTGCATCTCCCAGCACAAGAGACCCGGACTAC | 756 |
| A115-14 | TCTCGCGTCCACATGTAATAGTAGTCCGGGTCTCTTGTGC | 757 |
| A115-69 | CGCAACAGCGGCACTCCGCTGTCTGCGGTTCACCTGACGT | 758 |
| A115-70 | CAAGAACGAGGCGTACGACCACGTCAGGTGAACCGCAGAC | 759 |
| A115-82 | TGTCGACACGAGCGCGTGGAAGGTGACGGCCACGGAGGTT | 760 |
| A115-83 | TCCACGCGCTCGTGTCGACACAGTTTGGCCACACGGTCAA | 761 |
| A115-84 | CCGCGGCGTTGCCCGCCACCTTGACCGTGTGGCCAAACTG | 762 |
| A115-87 | AGCGCCGCCGTGGCTCTGGACGCCGTCAACTATAGAGATA | 763 |
| A115-88 | CCCAATCCACAGGGGGTGGTTATCTCTATAGTTGACGGCG | 764 |
| A116-13 | TGCGGTGATTGCATCTCCCAGCACAAGAGACCCGGACTAC | 765 |
| A116-14 | TCTCGCGTCCACATGTAATAGTAGTCCGGGTCTCTTGTGC | 766 |
| A116-16 | GGTGAAGCGGTCGATGAGGATCTTGAAGACAAGAGCGCTA | 767 |
| A116-17 | TCCTCATCGACCGCTTCACCGAAACGTACGATGCGGGCCT | 768 |
| A116-69 | CGCAACAGCGGCACTCCGCTGTCTGCGGTTCACCTGACGT | 769 |
| A116-70 | CAAGAACGAGGCGTACGACCACGTCAGGTGAACCGCAGAC | 770 |
| A116-82 | TGTCGACACGAGCGCGTGGAAGGTGACGGCCACGGAGGTT | 771 |

TABLE 7-continued

Primers used to construct combinatorial variants

| Primer | DNA sequence | SEQ ID NO: |
|---|---|---|
| A116-83 | TCCACGCGCTCGTGTCGACACAGTTTGGCCACACGGTCAA | 772 |
| A116-84 | CCGCGGCGTTGCCCGCCACCTTGACCGTGTGGCCAAACTG | 773 |
| A116-87 | AGCGCCGCCGTGGCTCTGGACGCCGTCAACTATAGAGATA | 774 |
| A116-88 | CCCAATCCACAGGGGTGGTTATCTCTATAGTTGACGGCG | 775 |
| A117-13 | TGCGGTGATTGCATCTCCCAGCACAAGAGACCCGGACTAC | 776 |
| A117-14 | TCTCGCGTCCACATGTAATAGTAGTCCGGGTCTCTTGTGC | 777 |
| A117-69 | CGCAACAGCGGCACTCCGCTGTCTGCGAGACACCTGACGT | 778 |
| A117-70 | CAAGAACGAGGCGTACGACCACGTCAGGTGTCTCGCAGAC | 779 |
| A117-82 | TGTCGACACGAGCGCGTGGAAGGTGACGGCCACGGAGGTT | 780 |
| A117-83 | TCCACGCGCTCGTGTCGACACAGTTTGGCCACACGGTCAA | 781 |
| A117-84 | CCGCGGCGTTGCCCGCCACCTTGACCGTGTGGCCAAACTG | 782 |
| A117-87 | AGCGCCGCCGTGGCTCTGGACGCCGTCAACTATAGAGATA | 783 |
| A117-88 | CCCAATCCACAGGGGTGGTTATCTCTATAGTTGACGGCG | 784 |
| A118-13 | TGCGGTGATTGCATCTCCCAGCACAAGAGACCCGGACTAC | 785 |
| A118-14 | TCTCGCGTCCACATGTAATAGTAGTCCGGGTCTCTTGTGC | 786 |
| A118-16 | GGTGAAGCGGTCGATGAGGATCTTGAAGACAAGAGCGCTA | 787 |
| A118-17 | TCCTCATCGACCGCTTCACCGAAACGTACGATGCGGGCCT | 788 |
| A118-69 | CGCAACAGCGGCACTCCGCTGTCTGCGAGACACCTGACGT | 789 |
| A118-70 | CAAGAACGAGGCGTACGACCACGTCAGGTGTCTCGCAGAC | 790 |
| A118-82 | TGTCGACACGAGCGCGTGGAAGGTGACGGCCACGGAGGTT | 791 |
| A118-83 | TCCACGCGCTCGTGTCGACACAGTTTGGCCACACGGTCAA | 792 |
| A118-84 | CCGCGGCGTTGCCCGCCACCTTGACCGTGTGGCCAAACTG | 793 |
| A118-87 | AGCGCCGCCGTGGCTCTGGACGCCGTCAACTATAGAGATA | 794 |
| A118-88 | CCCAATCCACAGGGGTGGTTATCTCTATAGTTGACGGCG | 795 |
| CS1-69 | CGCAACAGCGGCACTCCGCTGTCTGCGGTTCACCTGACGT | 796 |
| CS1-70 | CAAGAACGAGGCGTACGACCACGTCAGGTGAACCGCAGAC | 797 |
| CS1-71 | GGTCGTACGCCTCGTTCTTGACAGCCGCGCTCCGTCGGGC | 798 |
| CS1-72 | ACGAGGGGGCACGATGCCAGCCCGACGGAGCGCGGCTGT | 799 |
| CS1-83 | TCCACGAGCTCGTGTCGACACAGTTTGGCCACACGGTCAA | 800 |
| CS1-84 | CCGCGGCGTTGCCCGCCACCTTGACCGTGTGGCCAAACTG | 801 |
| CS1-87 | AGCGCCGCCGTGGCTCTGGACCGCGTCAACTATCGCGATA | 802 |
| CS1-88 | CCCAATCCACAGGGGTGGTTATCGCGATAGTTGACGCGG | 803 |
| CS1-91 | AGACGTCGTGGAGTACAAGTACATCATTGTGGGCCAAGAT | 804 |
| CS1-92 | CTCTCCCAGGTCACGGAGCCATCTTGGCCCACAATGATGT | 805 |
| CS2-69 | CGCAACAGCGGCACTCCGCTGTCTGCGGTTCACCTGACGT | 806 |
| CS2-70 | CAAGAACGAGGCGTACGACCACGTCAGGTGAACCGCAGAC | 807 |
| CS2-71 | GGTCGTACGCCTCGTTCTTGACAGCCGCGCAACGTCGGGC | 808 |

TABLE 7-continued

Primers used to construct combinatorial variants

| Primer | DNA sequence | SEQ ID NO: |
|---|---|---|
| CS2-72 | ACGAGGGGGCACGATGCCAGCCCGACGTTGCGCGGCTGT | 809 |
| CS2-83 | TCCACGAGCTCGTGTCGACACAGTTTGGCCACACGGTCAA | 810 |
| CS2-84 | CCGCGGCGTTGCCCGCCACCTTGACCGTGTGGCCAAACTG | 811 |
| CS2-87 | AGCGCCGCCGTGGCTCTGGACCGCGTCAACTATCGCGATA | 812 |
| CS2-88 | CCCAATCCACAGGGGTGGTTATCGCGATAGTTGACGCGG | 813 |
| CS2-91 | AGACGTCGTGGAGTACAAGTACATCATTGTGGGCCAAGAT | 814 |
| CS2-92 | CTCTCCCAGGTCACGGAGCCATCTTGGCCCACAATGATGT | 815 |
| CS3-69 | CGCAACAGCGGCACTCCGCTGTCTGCGGTTCACCTGACGT | 816 |
| CS3-70 | CAAGAACGAGGCGTACGACCACGTCAGGTGAACCGCAGAC | 817 |
| CS3-71 | GGTCGTACGCCTCGTTCTTGACAGCCGCGGCCCGTCGGGC | 818 |
| CS3-72 | ACGAGGGGGCACGATGCCAGCCCGACGGCCGCGGCTGT | 819 |
| CS3-83 | TCCACGAGCTCGTGTCGACACAGTTTGGCCACACGGTCAA | 820 |
| CS3-84 | CCGCGGCGTTGCCCGCCACCTTGACCGTGTGGCCAAACTG | 821 |
| CS3-87 | AGCGCCGCCGTGGCTCTGGACCGCGTCAACTATGCCGATA | 822 |
| CS3-88 | CCCAATCCACAGGGGTGGTTATCGGCATAGTTGACGCGG | 823 |
| CS3-91 | AGACGTCGTGGAGTACAAGTACATCATTGTGGGCCAAGAT | 824 |
| CS3-92 | CTCTCCCAGGTCACGGAGCCATCTTGGCCCACAATGATGT | 825 |
| CS4-69 | CGCAACAGCGGCACTCCGCTGTCTGCGGTTCACCTGACGT | 826 |
| CS4-70 | CAAGAACGAGGCGTACGACCACGTCAGGTGAACCGCAGAC | 827 |
| CS4-71 | GGTCGTACGCCTCGTTCTTGACAGCCGCGGCCCGTCGGGC | 828 |
| CS4-72 | ACGAGGGGGCACGATGCCAGCCCGACGGGCCGCGGCTGT | 829 |
| CS4-83 | TCCACGAGCTCGTGTCGACACAGTTTGGCCACACGGTCAA | 830 |
| CS4-84 | CCGCGGCGTTGCCCGCCACCTTGACCGTGTGGCCAAACTG | 831 |
| CS4-87 | AGCGCCGCCGTGGCTCTGGACGCCGTCAACTATCGCGATA | 832 |
| CS4-88 | CCCAATCCACAGGGGTGGTTATCGCGATAGTTGACGGCG | 833 |
| CS4-91 | AGACGTCGTGGAGTACAAGTACATCATTGTGGGCCAAGAT | 834 |
| CS4-92 | CTCTCCCAGGTCACGGAGCCATCTTGGCCCACAATGATGT | 835 |
| LQ1-50 | CAGTAGATGGAGCGGAAGGAGTCGACAACAACCTTGAGGT | 836 |
| LQ1-51 | TCCTTCCGCTCCATCTACTGCGTGAACAAGGGCATTCCTG | 837 |
| LQ1-69 | CGCAACAGCGGCACTCCGCTGTCTGCGAGACACCTGACGT | 838 |
| LQ1-70 | CAAGAACGAGGCGTACGACCACGTCAGGTGTCTCGCAGAC | 839 |
| LQ1-71 | GGTCGTACGCCTCGTTCTTGACAGCCACGCTCCGTCGGGC | 840 |
| LQ1-72 | ACGAGGGGGCACGATGCCAGCCCGACGGAGCGTGGCTGT | 841 |
| LQ2-50 | CAGTAGATGGAGCGGAAGGAGTCGACAACAACCTTGAGGT | 842 |
| LQ2-51 | TCCTTCCGCTCCATCTACTGCGTGAACAAGGGCATTCCTG | 843 |
| LQ2-69 | CGCAACAGCGGCACTCCGCTGTCTGCGGTACACCTGACGT | 844 |
| LQ2-70 | CAAGAACGAGGCGTACGACCACGTCAGGTGTACCGCAGAC | 845 |
| LQ2-71 | GGTCGTACGCCTCGTTCTTGACAGCCACGCAGCGTCGGGC | 846 |

TABLE 7-continued

Primers used to construct combinatorial variants

| Primer | DNA sequence | SEQ ID NO: |
|---|---|---|
| LQ2-72 | ACGAGGGGGCACGATGCCAGCCCGACGCTGCGTGGCTGT | 847 |
| LQ3-50 | CAGTAGATGGAGCGGAAGGAGTCGACAACAACCTTGAGGT | 848 |
| LQ3-51 | TCCTTCCGCTCCATCTACTGCGTGAACAAGGGCATTCCTG | 849 |
| LQ3-69 | CGCAACAGCGGCACTCCGCTGTCTGCGGTACACCTGACGT | 850 |
| LQ3-70 | CAAGAACGAGGCGTACGACCACGTCAGGTGTACCGCAGAC | 851 |
| LQ3-71 | GGTCGTACGCCTCGTTCTTGACAGCCACGTTACGTCGGGC | 852 |
| LQ3-72 | ACGAGGGGGCACGATGCCAGCCCGACGTAACGTGGCTGT | 853 |
| LQ3-83 | TCCACGAGCTCGTGTCGACACAGTTTGGCCACACGGTCAA | 854 |
| LQ3-84 | CCGCGGCGTTGCCCGCCACCTTGACCGTGTGGCCAAACTG | 855 |
| LQ4-50 | CAGTAGATGGAGCGGAAGGAGTCGACAACAACCTTGAGGT | 856 |
| LQ4-51 | TCCTTCCGCTCCATCTACTGCGTGAACAAGGGCATTCCTG | 857 |
| LQ4-69 | CGCAACAGCGGCACTCCGCTGTCTGCGAGACACCTGACGT | 858 |
| LQ4-70 | CAAGAACGAGGCGTACGACCACGTCAGGTGTCTCGCAGAC | 859 |
| LQ4-71 | GGTCGTACGCCTCGTTCTTGACAGCCACGCAGCGTCGGGC | 860 |
| LQ4-72 | ACGAGGGGGCACGATGCCAGCCCGACGCTGCGTGGCTGT | 861 |
| LQ4-83 | TCCACGAGCTCGTGTCGACACAGTTTGGCCACACGGTCAA | 862 |
| LQ4-84 | CCGCGGCGTTGCCCGCCACCTTGACCGTGTGGCCAAACTG | 863 |
| LQ5-69 | CGCAACAGCGGCACTCCGCTGTCTGCGCGTCACCTGACGT | 864 |
| LQ5-70 | CAAGAACGAGGCGTACGACCACGTCAGGTGACGCGCAGAC | 865 |
| LQ5-71 | GGTCGTACGCCTCGTTCTTGACAGCCACGCTCCGTCGGGC | 866 |
| LQ5-72 | ACGAGGGGGCACGATGCCAGCCCGACGGAGCGTGGCTGT | 867 |
| LQ5-83 | TCCACGAGCTCGTGTCGACACAGTTTGGCCACACGGTCAA | 868 |
| LQ5-84 | CCGCGGCGTTGCCCGCCACCTTGACCGTGTGGCCAAACTG | 869 |
| LQ6-69 | CGCAACAGCGGCACTCCGCTGTCTGCGGTTCACCTGACGT | 870 |
| LQ6-70 | CAAGAACGAGGCGTACGACCACGTCAGGTGAACCGCAGAC | 871 |
| LQ6-71 | GGTCGTACGCCTCGTTCTTGACAGCCACGCTTCGTCGGGC | 872 |
| LQ6-72 | ACGAGGGGGCACGATGCCAGCCCGACGAAGCGTGGCTGT | 873 |
| LQ6-83 | TCCACGAGCTCGTGTCGACACAGTTTGGCCATACGGTCAA | 874 |
| LQ6-84 | CCGCGGCGTTGCCCGCCACCTTGACCGTATGGCCAAACTG | 875 |
| TS1-13 | TGCGGTGATTGCATCTCCCAGCACAAGAGACCCGGACTAC | 876 |
| TS1-14 | TCTCGCGTCCACATGTAATAGTAGTCCGGGTCTCTTGTGC | 877 |
| TS1-71 | GGTCGTACGCCTCGTTCTTGACAGCCGCAGCCCGTCGGGC | 878 |
| TS1-72 | ACGAGGGGGCACGATGCCAGCCCGACGGGCTGCGGCTGT | 879 |
| TS1-82 | TGTCGACACGAGCACGTGGAAGGTGACGGCCACGGAGGTT | 880 |
| TS1-83 | TCCACGTGCTCGTGTCGACACAGTTTGGCCAGACGGTCAA | 881 |
| TS1-87 | AGCGCCGCCGTGGCTCTGGACCGCGTCAACTATGCCGATA | 882 |
| TS1-88 | CCCAATCCACAGGGGGTGGTTATCGGCATAGTTGACGCGG | 883 |

TABLE 7-continued

Primers used to construct combinatorial variants

| Primer | DNA sequence | SEQ ID NO: |
|---|---|---|
| TS1-91 | AGACGTCGTGGAGTACAAGTACATCAAAGTGGGCCAAGAT | 884 |
| TS1-92 | CTCTCCCAGGTCACGGAGCCATCTTGGCCCACTTTGATGT | 885 |
| TS2-13 | TGCGGTGATTGCATCTCCCAGCACAATTAGACCGGACTAC | 886 |
| TS2-14 | TCTCGCGTCCACATGTAATAGTAGTCCGGTCTAATTGTGC | 887 |
| TS2-82 | TGTCGACACGAGCGCGTGGAAGGTGACGGCCACGGAGGTT | 888 |
| TS2-83 | TCCACGCGCTCGTGTCGACACAGTTTGGCCACACGGTCAA | 889 |
| TS2-84 | CCGCGGCGTTGCCCGCCACCTTGACCGTGTGGCCAAACTG | 890 |
| TS2-91 | AGACGTCGTGGAGTACAAGTACATCATTGTGGGCCAAGAT | 891 |
| TS2-92 | CTCTCCCAGGTCACGGAGCCATCTTGGCCCACAATGATGT | 892 |
| TS3-82 | TGTCGACACGAGCGCGTGGAAGGTGACGGCCACGGAGGTT | 893 |
| TS3-83 | TCCACGCGCTCGTGTCGACACAGTTTGGCCAGACGGTCAA | 894 |
| TS3-91 | AGACGTCGTGGAGTACAAGTACATCATTGTGGGCCAAGAT | 895 |
| TS3-92 | CTCTCCCAGGTCACGGAGCCATCTTGGCCCACAATGATGT | 896 |
| TS4-13 | TGCGGTGATTGCATCTCCCAGCACAAGAGACCCGGACTAC | 897 |
| TS4-14 | TCTCGCGTCCACATGTAATAGTAGTCCGGGTCTCTTGTGC | 898 |
| TS4-71 | GGTCGTACGCCTCGTTCTTGACAGCCGCGGCCCGTCGGGC | 899 |
| TS4-72 | ACGAGGGGGCACGATGCCAGCCCGACGGGCCGCGGCTGT | 900 |
| TS4-82 | TGTCGACACGAGCGCGTGGAAGGTGACGGCCACGGAGGTT | 901 |
| TS4-83 | TCCACGCGCTCGTGTCGACACAGTTTGGCCACACGGTCAA | 902 |
| TS4-84 | CCGCGGCGTTGCCCGCCACCTTGACCGTGTGGCCAAACTG | 903 |
| TS4-91 | AGACGTCGTGGAGTACAAGTACATCATTGTGGGCCAAGAT | 904 |
| TS4-92 | CTCTCCCAGGTCACGGAGCCATCTTGGCCCACAATGATGT | 905 |
| TS5-13 | TGCGGTGATTGCATCTCCCAGCACAATTCGCCCGGACTAC | 906 |
| TS5-14 | TCTCGCGTCCACATGTAATAGTAGTCCGGGCGAATTGTGC | 907 |
| TS5-71 | GGTCGTACGCCTCGTTCTTGACAGCCGCGGCCCGTCGGGC | 908 |
| TS5-72 | ACGAGGGGGCACGATGCCAGCCCGACGGGCCGCGGCTGT | 909 |
| TS5-83 | TCCACGAGCTCGTGTCGACACAGTTTGGCCACACGGTCAA | 910 |
| TS5-84 | CCGCGGCGTTGCCCGCCACCTTGACCGTGTGGCCAAACTG | 911 |
| TS5-87 | AGCGCCGCCGTGGCTCTGGACGCGGTCAACTATGCCGATA | 912 |
| TS5-88 | CCCAATCCACAGGGGGTGGTTATCGGCATAGTTGACCGCG | 913 |
| GAV st-1 | GAGAGGGGACAAGTTTGTACAAAAAAGCAGGCT | 914 |
| GAV st-2 | GCAGTCGACAGGACGTGCATAGCCTGLTTTTTTGTACAAA | 915 |
| GAV st-3 | ATGCACGTCCTGTCGACTGCGGTGCTGCTCGGCTCCGTTG | 916 |
| GAV st-4 | TCCCAGGACCTTTTGAACGGCAACGGAGCCGAGCAGCACC | 917 |
| GAV st-5 | CCGTTCAAAAGGTCCTGGGAAGACCAGGATCAAGCGGTCT | 918 |
| GAV st-6 | ACCTCTTGGTGACGTCGGACAGACCGCTTGATCCTGGTCT | 919 |
| GAV st-7 | GTCCGACGTCACCAAGAGGTCTGTTGACGACTTCATCAGC | 920 |
| GAV st-8 | AGTGCAATAGGCGTCTCGGTGCTGATGAAGTCGTCAACAG | 921 |

TABLE 7-continued

Primers used to construct combinatorial variants

| Primer | DNA sequence | SEQ ID NO: |
|---|---|---|
| GAV st-9 | ACCGAGACGCCTATTGCACTGAACAATCTTCTTTGCAATG | 922 |
| GAV st-10 | ACGGCATCCATCAGGACCAACATTGCAAAGAAGATTGTTC | 923 |
| GAV st-11 | TTGGTCCTGATGGATGCCGTGCATTCGGCACATCAGCTGG | 924 |
| GAV st-12 | TGGGAGATGCAATCACCGCACCAGCTGATGTGCCGAATGC | 925 |
| GAV st-13 | TGCGGTGATTGCATCTCCCAGCACACAAGACCCGGACTAC | 926 |
| GAV st-14 | TCTCGCGTCCACATGTAATAGTAGTCCGGGTCTTGTGTGC | 927 |
| GAV st-15 | TATTACATGTGGACGCGAGATAGCGCTCTTGTCTTCAAGA | 928 |
| GAV st-16 | GGTGAAGCGGTCGATGAGGTTCTTGAAGACAAGAGCGCTA | 929 |
| GAV st-17 | ACCTCATCGACCGCTTCACCGAAACGTACGATGCGGGCCT | 930 |
| GAV st-18 | ACTGCTCGATGCGGCGCTGCAGGCCCGCATCGTACGTTTC | 931 |
| GAV st-19 | GCAGCGCCGCATCGAGCAGTACATTACTGCCCAGGTCACT | 932 |
| GAV st-20 | GGGTTAGAGAGGCCCTGGAGAGTGACCTGGGCAGTAATGT | 933 |
| GAV st-21 | CTCCAGGGCCTCTCTAACCCCTCGGGCTCCCTCGCGGACG | 934 |
| GAV st-22 | GGGCTCGCCGAGACCAGAGCCGTCCGCGAGGGAGCCCGAG | 935 |
| GAV st-23 | GCTCTGGTCTCGGCGAGCCAAGTTTGAGTTGACCCTGAA | 936 |
| GAV st-24 | CCCAGTTGCCGGTGAAAGGCTTCAGGGTCAACTCAAACTT | 937 |
| GAV st-25 | GCCTTTCACCGGCAACTGGGGTCGACCGCAGCGGGATGGC | 938 |
| GAV st-26 | GCAATGGCTCGCAGAGCTGGGCCATCCCGCTGCGGTCGAC | 939 |
| GAV st-27 | CCAGCTCTGCGAGCCATTGCCTTGATTGGATACTCAAAGT | 940 |
| GAV st-28 | ATAGTTGTTGTTGATGAGCCACTTTGAGTATCCAATCAAG | 941 |
| GAV st-29 | GGCTCATCAACAACAACTATCAGTCGACTGTGTCCAACGT | 942 |
| GAV st-30 | TGCGCACAATAGGCCAGATGACGTTGGACACAGTCGACTG | 943 |
| GAV st-31 | CATCTGGCCTATTGTGCGCAACGACCTCAACTATGTTGCC | 944 |
| GAV st-32 | CCGGTTTGGTTCCAGTACTGGGCAACATAGTTGAGGTCGT | 945 |
| GAV st-33 | CAGTACTGGAACCAAACCGGCTTTGACCTCTGGGAAGAAG | 946 |
| GAV st-34 | AAAGAATGAGCTCCCATTGACTTCTTCCCAGAGGTCAAAG | 947 |
| GAV st-35 | TCAATGGGAGCTCATTCTTTACTGTTGCCAACCAGCACCG | 948 |
| GAV st-36 | TGGCGCCCTCGACAAGTGCTCGGTGCTGGTTGGCAACAGT | 949 |
| GAV st-37 | AGCACTTGTCGAGGGCGCCACTCTTGCTGCCACTCTTGGC | 950 |
| GAV st-38 | GAATAAGCGCTTCCCGACTGGCCAAGAGTGGCAGCAAGAG | 951 |
| GAV st-39 | CAGTCGGGAAGCGCTTATTCATCTGTTGCTCCCCAGGTTT | 952 |
| GAV st-40 | GAATCGTTGGAGAAAGCACAAAACCTGGGGAGCAACAGAT | 953 |
| GAV st-41 | TGTGCTTTCTCCAACGATTCTGGGTGTCGTCTGGTGGATA | 954 |
| GAV st-42 | TGTTGATGTGGAGTCGACGTATCCACCAGACGACACCCA | 955 |
| GAV st-43 | CGTCGACTCCAACATCAACACCAACGAGGGCAGGACTGGC | 956 |
| GAV st-44 | AGGACGGAGTTGACATCCTTGCCAGTCCTGCCCTCGTTGG | 957 |
| GAV st-45 | AAGGATGTCAACTCCGTCCTGACTTCCATCCACACCTTCG | 958 |

TABLE 7-continued

Primers used to construct combinatorial variants

| Primer | DNA sequence | SEQ ID NO: |
|---|---|---|
| GAV st-46 | GTCACAGCCAAGGTTGGGATCGAAGGTGTGGATGGAAGTC | 959 |
| GAV st-47 | ATCCCAACCTTGGCTGTGACGCAGGCACCTTCCAGCCATG | 960 |
| GAV st-48 | TGGAGAGCGCTTTGTCACTGCATGGCTGGAAGGTGCCTGC | 961 |
| GAV st-49 | CAGTGACAAAGCGCTCTCCAACCTCAAGGTTGTTGTCGAC | 962 |
| GAV st-50 | CCGTAGATGGAGCGGAAGGAGTCGACAACAACCTTGAGGT | 963 |
| GAV st-51 | TCCTTCCGCTCCATCTACGGCGTGAACAAGGGCATTCCTG | 964 |
| GAV st-52 | AATGGCGACGGCAGCACCGGCAGGAATGCCCTTGTTCACG | 965 |
| GAV st-53 | CCGGTGCTGCCGTCGCCATTGGCCGGTATGCAGAGGATGT | 966 |
| GAV st-54 | AAGGGTTGCCGTTGTAGTACACATCCTCTGCATACCGGCC | 967 |
| GAV st-55 | GTACTACAACGGCAACCCTTGGTATCTTGCTACATTTGCT | 968 |
| GAV st-56 | TCGTACAGCTGCTCGGCAGCAGCAAATGTAGCAAGATACC | 969 |
| GAV st-57 | GCTGCCGAGCAGCTGTACGATGCCATCTACGTCTGGAAGA | 970 |
| GAV st-58 | CACCGTGATGGAGCCCGTCTTCTTCCAGACGTAGATGGCA | 971 |
| GAV st-59 | AGACGGGCTCCATCACGGTGACCGCCACCTCCCTGGCCTT | 972 |
| GAV st-60 | CAGGAACAAGCTCCTGGAAGAAGGCCAGGGAGGTGGCGGT | 973 |
| GAV st-61 | CTTCCAGGAGCTTGTTCCTGGCGTGACGGCCGGGACCTAC | 974 |
| GAV st-62 | AAGGTCGAAGAGCTGCTGGAGTAGGTCCCGGCCGTCACGC | 975 |
| GAV st-63 | TCCAGCAGCTCTTCGACCTTTACCAACATCATCAACGCCG | 976 |
| GAV st-64 | GCCATCGGCGTATGTCGAGACGGCGTTGATGATGTTGGTA | 977 |
| GAV st-65 | TCTCGACATACGCCGATGGCTTCCTCAGCGAGGCTGCCAA | 978 |
| GAV st-66 | AACCGTCGGCGGGACGTACTTGGCAGCCTCGCTGAGGAA | 979 |
| GAV st-67 | GTACGTCCCCGCCGACGGTTCGCTGGCCGAGCAGTTTGAC | 980 |
| GAV st-68 | AGCGGAGTGCCGCTGTTGCGGTCAAACTGCTCGGCCAGCG | 981 |
| GAV st-69 | CGCAACAGCGGCACTCCGCTGTCTGCGCTTCACCTGACGT | 982 |
| GAV st-70 | CAAGAACGAGGCGTACGACCACGTCAGGTGAAGCGCAGAC | 983 |
| GAV st-71 | GGTCGTACGCCTCGTTCTTGACAGCCACGGCCCGTCGGGC | 984 |
| GAV st-72 | ACGAGGGGGCACGATGCCAGCCCGACGGGCCGTGGCTGT | 985 |
| GAV st-73 | TGGCATCGTGCCCCCCTCGTGGGCCAACAGCAGCGCTAGC | 986 |
| GAV st-74 | GAGCACGTCGAGGGGATCGTGCTAGCGCTGCTGTTGGCCC | 987 |
| GAV st-75 | ACGATCCCCTCGACGTGCTCCGGCGCGTCCGTGGTCGGAT | 988 |
| GAV st-76 | GGCGGTGGGACGCGAGTAGGATCCGACCACGGACGCGCCG | 989 |
| GAV st-77 | CCTACTCGCGTCCCACCGCCACGTCATTCCCTCCGTCGCA | 990 |
| GAV st-78 | GCACGCCAGGCTTGGGCGTCTGCGACGGAGGGAATGACGT | 991 |
| GAV st-79 | GACGCCCAAGCCTGGCGTGCCTTCCGGTACTCCCTACACG | 992 |
| GAV st-80 | GGGGTCGCGCAGGGCAGGGGCGTGTAGGGAGTACCGGAAG | 993 |
| GAV st-81 | CCCCTGCCCTGCGCGACCCCAACCTCCGTGGCCGTCACCT | 994 |
| GAV st-82 | TGTCGACACGAGCTCGTGGAAGGTGACGGCCACGGAGGTT | 995 |
| GAV st-83 | TCCACGAGCTCGTGTCGACACAGTTTGGCCACACGGTCAA | 996 |

TABLE 7-continued

Primers used to construct combinatorial variants

| Primer | DNA sequence | SEQ ID NO: |
|---|---|---|
| GAV st-84 | CCGCGGCGTTGCCCGCCACCTTGACCGTGTGGCCAAACTG | 997 |
| GAV st-85 | GGTGGCGGGCAACGCCGCGGCCCTGGGCAACTGGAGCACG | 998 |
| GAV st-86 | TCCAGAGCCACGGCGGCGCTCGTGCTCCAGTTGCCCAGGG | 999 |
| GAV st-87 | AGCGCCGCCGTGGCTCTGGACGCCGTCAACTATGCCGATA | 1000 |
| GAV st-88 | CCCAATCCACAGGGGGTGGTTATCGGCATAGTTGACGGCG | 1001 |
| GAV st-89 | ACCACCCCTGTGGATTGGGACGGTCAACCTCGAGGCTGG | 1002 |
| GAV st-90 | ACTTGTACTCCACGACGTCTCCAGCCTCGAGGTTGACCGT | 1003 |
| GAV st-91 | AGACGTCGTGGAGTACAAGTACATCAATGTGGGCCAAGAT | 1004 |
| GAV st-92 | CTCTCCCAGGTCACGGAGCCATCTTGGCCCACATTGATGT | 1005 |
| GAV st-93 | GGCTCCGTGACCTGGGAGAGTGATCCCAACCACACTTACA | 1006 |
| GAV st-94 | ACAAGCCACCGCAGGAACCGTGTAAGTGTGGTTGGGATCA | 1007 |
| GAV st-95 | CGGTTCCTGCGGTGGCTTGTGTGACGCAGGTTGTCAAGGA | 1008 |
| GAV st-96 | TTTACGACTGCCAGGTGTCCTCCTTGACAACCTGCGTCAC | 1009 |
| GAV st-97 | GGACACCTGGCAGTCGTAAACCCAGCTTTCTTGTACAAAG | 1010 |
| GAV st-98 | CTCTGGGGACCACTTTGTACAAGAAAGCTGGG | 1011 |
| RB1-16 | GGTGAAGCGGTCGATGAGGATCTTGAAGACAAGAGCGCTA | 1012 |
| RB1-17 | TCCTCATCGACCGCTTCACCGAAACGTACGATGCGGGCCT | 1013 |
| RB1-71 | GGTCGTACGCCTCGTTCTTGACAGCCGCGGCCCGTCGGGC | 1014 |
| RB1-72 | ACGAGGGGGCACGATGCCAGCCCGACGGCCGCGGCTGT | 1015 |
| RB2-69 | CGCAACAGCGGCACTCCGCTGTCTGCGGTTCACCTGACGT | 1016 |
| RB2-70 | CAAGAACGAGGCGTACGACCACGTCAGGTGAACCGCAGAC | 1017 |
| RB2-71 | GGTCGTACGCCTCGTTCTTGACAGCCGCGGCCCGTCGGGC | 1018 |
| RB2-72 | ACGAGGGGGCACGATGCCAGCCCGACGGCCGCGGCTGT | 1019 |
| RB3-71 | GGTCGTACGCCTCGTTCTTGACAGCCGCGCTCCGTCGGGC | 1020 |
| RB3-72 | ACGAGGGGGCACGATGCCAGCCCGACGGAGCGCGGCTGT | 1021 |
| RB1-71 | GGTCGTACGCCTCGTTCTTGACAGCCGCGGCCCGTCGGGC | 1022 |
| RB1-72 | ACGAGGGGGCACGATGCCAGCCCGACGGCCGCGGCTGT | 1023 |
| RB4-82 | TGTCGACACGAGCGCGTGGAAGGTGACGGCCACGGAGGTT | 1024 |
| RB4-83 | TCCACGCGCTCGTGTCGACACAGTTTGGCCACACGGTCAA | 1025 |
| RB4-71 | GGTCGTACGCCTCGTTCTTGACAGCCGCGGCCCGTCGGGC | 1026 |
| RB4-72 | ACGAGGGGGCACGATGCCAGCCCGACGGGCCGCGGCTGT | 1027 |
| RB5-71 | GGTCGTACGCCTCGTTCTTGACAGCCGCGGCCCGTCGGGC | 1028 |
| RB5-72 | ACGAGGGGGCACGATGCCAGCCCGACGGGCCGCGGCTGT | 1029 |
| RB5-87 | AGCGCCGCCGTGGCTCTGGACGCCGTCAACTATCGCGATA | 1030 |
| RB5-88 | CCCAATCCACAGGGGGTGGTTATCGCGATAGTTGACGGCG | 1031 |
| RB6-16 | GGTGAAGCGGTCGATGAGGATCTTGAAGACAAGAGCGCTA | 1032 |
| RB6-17 | TCCTCATCGACCGCTTCACCGAAACGTACGATGCGGGCCT | 1033 |

TABLE 7-continued

Primers used to construct combinatorial variants

| Primer | DNA sequence | SEQ ID NO: |
|---|---|---|
| RB6-71 | GGTCGTACGCCTCGTTCTTGACAGCCGCGGCCCGTCGGGC | 1034 |
| RB6-72 | ACGAGGGGGCACGATGCCAGCCCGACGGGCCGCGGCTGT | 1035 |
| RB6-87 | AGCGCCGCCGTGGCTCTGGACGCCGTCAACTATCGCGATA | 1036 |
| RB6-88 | CCCAATCCACAGGGGGTGGTTATCGCGATAGTTGACGGCG | 1037 |
| RB7-69 | CGCAACAGCGGCACTCCGCTGTCTGCGGTTCACCTGACGT | 1038 |
| RB7-70 | CAAGAACGAGGCGTACGACCACGTCAGGTGAACCGCAGAC | 1039 |
| RB7-71 | GGTCGTACGCCTCGTTCTTGACAGCCGCGGCCCGTCGGGC | 1040 |
| RB7-72 | ACGAGGGGGCACGATGCCAGCCCGACGGGCCGCGGCTGT | 1041 |
| RB7-87 | AGCGCCGCCGTGGCTCTGGACGCCGTCAACTATCGCGATA | 1042 |
| RB7-88 | CCCAATCCACAGGGGGTGGTTATCGCGATAGTTGACGGCG | 1043 |
| RB8-71 | GGTCGTACGCCTCGTTCTTGACAGCCGCGCTCCGTCGGGC | 1044 |
| RB8-72 | ACGAGGGGGCACGATGCCAGCCCGACGGAGCGCGGCTGT | 1045 |
| RB8-87 | AGCGCCGCCGTGGCTCTGGACGCCGTCAACTATCGCGATA | 1046 |
| RB8-88 | CCCAATCCACAGGGGGTGGTTATCGCGATAGTTGACGGCG | 1047 |
| RB9-71 | GGTCGTACGCCTCGTTCTTGACAGCCGCGCTCCGTCGGGC | 1048 |
| RB9-72 | ACGAGGGGGCACGATGCCAGCCCGACGGAGCGCGGCTGT | 1049 |
| RB9-82 | TGTCGACACGAGCGCGTGGAAGGTGACGGCCACGGAGGTT | 1050 |
| RB9-83 | TCCACGCGCTCGTGTCGACACAGTTTGGCCACACGGTCAA | 1051 |
| RB10-16 | GGTGAAGCGGTCGATGAGGATCTTGAAGACAAGAGCGCTA | 1052 |
| RB10-17 | TCCTCATCGACCGCTTCACCGAAACGTACGATGCGGGCCT | 1053 |
| RB10-71 | GGTCGTACGCCTCGTTCTTGACAGCCGCGCTCCGTCGGGC | 1054 |
| RB10-72 | ACGAGGGGGCACGATGCCAGCCCGACGGAGCGCGGCTGT | 1055 |
| RB10-87 | AGCGCCGCCGTGGCTCTGGACGCCGTCAACTATCGCGATA | 1056 |
| RB10-88 | CCCAATCCACAGGGGGTGGTTATCGCGATAGTTGACGGCG | 1057 |
| RB11-69 | CGCAACAGCGGCACTCCGCTGTCTGCGGTTCACCTGACGT | 1058 |
| RB11-70 | CAAGAACGAGGCGTACGACCACGTCAGGTGAACCGCAGAC | 1059 |
| RB11-71 | GGTCGTACGCCTCGTTCTTGACAGCCGCGCTCCGTCGGGC | 1060 |
| RB11-72 | ACGAGGGGGCACGATGCCAGCCCGACGGAGCGCGGCTGT | 1061 |
| RB11-87 | AGCGCCGCCGTGGCTCTGGACGCCGTCAACTATCGCGATA | 1062 |
| RB11-88 | CCCAATCCACAGGGGGTGGTTATCGCGATAGTTGACGGCG | 1063 |
| RB12-16 | GGTGAAGCGGTCGATGAGGATCTTGAAGACAAGAGCGCTA | 1064 |
| RB12-17 | TCCTCATCGACCGCTTCACCGAAACGTACGATGCGGGCCT | 1065 |
| RB13-69 | CGCAACAGCGGCACTCCGCTGTCTGCGGTTCACCTGACGT | 1066 |
| RB13-70 | CAAGAACGAGGCGTACGACCACGTCAGGTGAACCGCAGAC | 1067 |
| RB14-71 | GGTCGTACGCCTCGTTCTTGACAGCCACGCTCCGTCGGGC | 1068 |
| RB14-72 | ACGAGGGGGCACGATGCCAGCCCGACGGAGCGTGGCTGT | 1069 |
| RB15-87 | AGCGCCGCCGTGGCTCTGGACGCCGTCAACTATCGCGATA | 1070 |
| RB15-88 | CCCAATCCACAGGGGGTGGTTATCGCGATAGTTGACGGCG | 1071 |

TABLE 7-continued

Primers used to construct combinatorial variants

| Primer | DNA sequence | SEQ ID NO: |
|---|---|---|
| RB16-16 | GGTGAAGCGGTCGATGAGGATCTTGAAGACAAGAGCGCTA | 1072 |
| RB16-17 | TCCTCATCGACCGCTTCACCGAAACGTACGATGCGGGCCT | 1073 |
| RB16-87 | AGCGCCGCCGTGGCTCTGGACGCCGTCAACTATCGCGATA | 1074 |
| RB16-88 | CCCAATCCACAGGGGGTGGTTATCGCGATAGTTGACGGCG | 1075 |
| RB17-82 | TGTCGACACGAGCGCGTGGAAGGTGACGGCCACGGAGGTT | 1076 |
| RB17-83 | TCCACGCGCTCGTGTCGACACAGTTTGGCCACACGGTCAA | 1077 |
| RB17-87 | AGCGCCGCCGTGGCTCTGGACGCCGTCAACTATCGCGATA | 1078 |
| RB17-88 | CCCAATCCACAGGGGGTGGTTATCGCGATAGTTGACGGCG | 1079 |
| RB18-71 | GGTCGTACGCCTCGTTCTTGACAGCCATGGCCCGTCGGGC | 1080 |
| RB18-72 | ACGAGGGGGCACGATGCCAGCCCGACGGGCCATGGCTGT | 1081 |
| RB18-87 | AGCGCCGCCGTGGCTCTGGACGCCGTCAACTATCGCGATA | 1082 |
| RB18-88 | CCCAATCCACAGGGGGTGGTTATCGCGATAGTTGACGGCG | 1083 |
| RB19-16 | GGTGAAGCGGTCGATGAGGATCTTGAAGACAAGAGCGCTA | 1084 |
| RB19-17 | TCCTCATCGACCGCTTCACCGAAACGTACGATGCGGGCCT | 1085 |
| RB19-71 | GGTCGTACGCCTCGTTCTTGACAGCCATGGCCCGTCGGGC | 1086 |
| RB19-72 | ACGAGGGGGCACGATGCCAGCCCGACGGGCCATGGCTGT | 1087 |
| RB19-87 | AGCGCCGCCGTGGCTCTGGACGCCGTCAACTATCGCGATA | 1088 |
| RB19-88 | CCCAATCCACAGGGGGTGGTTATCGCGATAGTTGACGGCG | 1089 |
| RB20-16 | GGTGAAGCGGTCGATGAGGATCTTGAAGACAAGAGCGCTA | 1090 |
| RB20-17 | TCCTCATCGACCGCTTCACCGAAACGTACGATGCGGGCCT | 1091 |
| RB20-69 | CGCAACAGCGGCACTCCGCTGTCTGCGGTTCACCTGACGT | 1092 |
| RB20-70 | CAAGAACGAGGCGTACGACCACGTCAGGTGAACCGCAGAC | 1093 |
| RB20-71 | GGTCGTACGCCTCGTTCTTGACAGCCATGGCCCGTCGGGC | 1094 |
| RB20-72 | ACGAGGGGGCACGATGCCAGCCCGACGGGCCATGGCTGT | 1095 |
| RB20-87 | AGCGCCGCCGTGGCTCTGGACGCCGTCAACTATCGCGATA | 1096 |
| RB20-88 | CCCAATCCACAGGGGGTGGTTATCGCGATAGTTGACGGCG | 1097 |

Variants were purified from large-scale fermentation, i.e., 100 ml or 500 ml fermentation, and PIs of thermal stability (Ts) and specific activities were determined. Specifically, specific activities were determined using different substrates, including DP2, DP3, DP4, DP5, DP6, DP7, cornstarch (CS), and liquefact (Liq). PIs are presented in Table 8. "N/D" in Table 8 stands for "not done."

TABLE 8

PIs of representative combinatorial variants

| Variant | Mutations | DP2 | DP3 | DP4 | DP5 | DP6 | DP7 | CS | Ts | Liq. |
|---|---|---|---|---|---|---|---|---|---|---|
| ALL1 | I43Q/D44C/L417V/E503A/Q511H/A539R | 0.89 | 1.22 | 1.08 | 1.10 | 1.17 | 1.02 | 1.27 | 1.95 | 1.59 |
| ALL2 | I43Q/L417V/E503A/Q511H/A539R | 1.13 | 1.50 | 1.24 | 1.19 | 1.32 | 1.24 | 1.52 | 1.84 | 1.96 |
| ALL3 | I43Q/D44C/N61I/L417V/E503A/Q511H/A539R | 0.69 | 1.09 | 0.91 | 0.89 | 0.96 | 0.99 | 1.30 | 1.43 | 1.64 |
| ALL4 | I43Q/N61I/L417V/E503A/Q511H/A539R | 0.89 | 1.40 | 1.15 | 1.15 | 1.25 | 1.12 | 1.52 | 1.79 | 1.73 |
| ALL5 | I43R/L417V/E503A/Q511H/A539R | 1.10 | 1.50 | N/D | N/D | N/D | 1.04 | 1.17 | 2.37 | 1.87 |
| ALL6 | I43R/N61I/L417V/E503A/Q511H/A539R | 0.93 | 1.52 | N/D | N/D | N/D | 1.37 | 1.53 | 1.84 | 2.24 |
| ALL7 | I43R/L417R/E503A/A539R | 1.19 | 1.38 | 1.29 | 1.23 | 1.33 | 1.20 | 1.54 | 1.67 | 1.62 |

TABLE 8-continued

PIs of representative combinatorial variants

| Variant | Mutations | DP2 | DP3 | DP4 | DP5 | DP6 | DP7 | CS | Ts | Liq. |
|---|---|---|---|---|---|---|---|---|---|---|
| ALL8 | I43R/N61I/L417R/E503A/Q511H/A539R | 1.07 | 1.56 | N/D | N/D | N/D | 1.08 | 1.14 | 1.84 | 2.11 |
| C1 | G73F/T430A/Q511H | 0.82 | 0.80 | 0.95 | 0.95 | 1.06 | 0.94 | 1.07 | 1.84 | 0.96 |
| C2 | I43R/G73F/T430A | 0.96 | 0.97 | 1.14 | 1.17 | 1.28 | 1.07 | 1.25 | 1.91 | 1.18 |
| C4 | G73F/T430A/E503V/Q511H | 0.97 | 0.80 | 1.10 | 1.08 | 1.17 | 1.04 | 1.06 | 2.57 | 1.01 |
| C5 | D44C/G73F/N563K | 0.77 | 0.77 | 0.86 | 0.87 | 0.95 | 0.77 | 0.71 | 2.16 | 0.97 |
| C7 | D44C/G73F/E503V/Q511H | 0.74 | 0.71 | 0.82 | 0.84 | 0.93 | 0.78 | 0.79 | 2.10 | 0.89 |
| C8 | D44C/G73F/N563K | 0.78 | 0.76 | 0.81 | 0.91 | 0.94 | 0.79 | 1.05 | 2.28 | N/D |
| C9 | D44C/G73F/L417R/N563K | 0.82 | 0.86 | 0.96 | 1.07 | 1.08 | 0.96 | 1.00 | 2.57 | 1.22 |
| C11 | D44C/G73F/N563K | 0.74 | 0.68 | 0.81 | 0.92 | 0.90 | 0.76 | 1.04 | 2.42 | N/D |
| C12 | I43R/T430A | 1.02 | 1.06 | 1.21 | 1.21 | 1.32 | 1.03 | 1.35 | 1.60 | 1.26 |
| C13 | I43Q/T430A | 0.96 | 0.94 | 1.13 | 1.14 | 1.24 | 1.04 | 1.29 | 1.10 | 1.45 |
| C14 | I43Q/T430A/Q511H | 1.08 | 1.11 | 1.13 | 1.14 | 1.23 | 1.13 | 1.34 | 1.33 | 1.46 |
| C15 | D44C/L417R/N563K | 0.84 | 0.88 | 0.95 | 1.07 | 1.08 | 0.85 | 1.09 | 2.30 | 0.99 |
| CS1 | L417V/T430A/A431L/Q511H/A535R/A539R/N563I | 0.78 | 1.19 | 1.35 | 1.29 | 1.42 | 1.28 | 1.44 | 1.56 | 2.35 |
| CS2 | L417V/T430A/A431Q/Q511H/A535R/A539R/N563I | 0.96 | 1.39 | 1.46 | 1.42 | 1.52 | 1.60 | 1.77 | 1.56 | 2.32 |
| CS3 | L417V/T430A/Q511H/A535R/N563I | 1.00 | 1.17 | N/D | N/D | N/D | 0.98 | 1.40 | 1.69 | 1.78 |
| CS4 | L417V/T430A/Q511H/A539R/N563I | 1.11 | 1.36 | N/D | N/D | N/D | 1.21 | 1.53 | 1.95 | 1.73 |
| LQ1 | G294C/L417R/A431L | 1.10 | 1.47 | 1.18 | 1.18 | 1.35 | 1.10 | 0.98 | 1.04 | 1.77 |
| LQ2 | G294C/L417V/A431Q | 1.15 | 1.56 | 1.32 | 1.30 | 1.46 | 1.22 | 1.08 | 1.02 | 2.08 |
| LQ3 | G294C/L417V/A431L/Q511H | 0.99 | 1.41 | N/D | N/D | N/D | 1.21 | 1.29 | 2.07 | |
| LQ4 | G294C/L417R/A431Q/Q511H | 1.20 | 1.49 | 1.11 | 1.13 | 1.27 | 1.08 | 1.19 | 1.43 | 1.65 |
| LQ5 | L417R/A431L/Q511H | N/D | N/D | N/D | N/D | N/D | 1.02 | 1.21 | 1.56 | 1.88 |
| LQ6 | L417V/A431Q/Q511H | 0.94 | 1.30 | 1.20 | 1.18 | 1.28 | 1.25 | 1.33 | 1.35 | 2.05 |
| RB1 | I43Q/T430A/Q511H/N61I | 0.90 | 1.13 | 1.00 | 1.03 | 1.13 | 1.08 | 1.15 | 1.27 | 1.47 |
| RB2 | I43Q/T430A/Q511H/L417V | 1.12 | 1.34 | N/D | N/D | N/D | 1.09 | 1.38 | 1.42 | 1.87 |
| RB3 | I43Q/T430A/Q511H/A431L | 0.87 | 1.05 | 1.03 | 1.05 | 1.15 | 1.10 | 1.25 | 1.29 | 1.70 |
| RB4 | I43Q/T430A/Q511H/E503A | 0.99 | 1.00 | 1.05 | 1.04 | 1.13 | 1.09 | 1.29 | 1.47 | 1.50 |
| RB5 | I43Q/T430A/Q511H/A539R | 0.98 | 1.22 | 1.06 | 1.02 | 1.11 | 1.10 | 1.45 | 1.47 | 1.59 |
| RB6 | I43Q/T430A/Q511H/N61I/A539R | 0.75 | 1.09 | 1.09 | 1.05 | 1.14 | 1.23 | N/D | 0.94 | N/D |
| RB7 | I43Q/T430A/Q511H/L417V/A539R | 1.20 | 1.62 | N/D | N/D | N/D | 1.29 | 1.44 | 1.85 | 2.17 |
| RB8 | I43Q/T430A/Q511H/A431L/A539R | 0.90 | 1.38 | N/D | N/D | N/D | 1.25 | 1.38 | 1.59 | 2.18 |
| RB9 | I43Q/T430A/Q511H/A431L/E503A | 0.79 | 0.82 | 0.95 | 0.92 | 1.02 | 1.03 | 1.39 | 1.69 | 1.55 |
| RB10 | I43Q/T430A/Q511H/N61I/A539R/A431L | 0.68 | 1.27 | N/D | N/D | N/D | 0.87 | 1.47 | 1.29 | 1.73 |
| RB11 | I43Q/T430A/Q511H/L417V/A539R/A431L | 0.89 | 1.50 | N/D | N/D | N/D | 1.05 | 1.36 | 1.58 | 2.03 |
| RB12 | I43Q/Q511H/N61I | 0.75 | 0.80 | 0.91 | 0.91 | 1.00 | 0.82 | 1.25 | 1.37 | 1.56 |
| RB13 | I43Q/Q511H/L417V | 0.97 | 0.94 | 0.96 | 0.93 | 1.05 | 0.94 | 1.38 | 1.50 | 1.50 |
| RB14 | I43Q/Q511H/A431L | 0.73 | 0.75 | 0.89 | 0.88 | 0.94 | 0.89 | 1.31 | 1.37 | 1.55 |
| RB15 | I43Q/Q511H/A539R | 0.90 | 0.88 | 1.03 | 0.99 | 1.07 | 1.05 | 1.42 | 1.52 | 1.69 |
| RB16 | I43Q/Q511H/A539R/N61I | 0.78 | 0.96 | 1.22 | 1.18 | 1.26 | 0.94 | 1.43 | 1.60 | 1.34 |
| RB17 | I43Q/Q511H/E503A | 1.02 | 1.15 | 1.16 | 1.12 | 1.21 | 1.20 | 1.38 | 1.68 | 1.40 |
| RB18 | I43Q/Q511H/A539R/T430M | 0.81 | 0.84 | 1.03 | 0.99 | 1.08 | 0.54 | 1.44 | 1.64 | 1.40 |
| RB19 | I43Q/Q511H/A539R/T430M/N61I | 0.77 | 1.21 | N/D | N/D | N/D | 1.07 | 1.50 | 1.47 | 1.88 |
| RB20 | I43Q/Q511H/A539R/T430M/N61I/L417V | 0.73 | 1.35 | N/D | N/D | N/D | 0.96 | 1.55 | 1.79 | 1.95 |
| TS1 | I43R/T430A/E503V/A535R/N563K | 1.09 | 0.95 | 1.13 | 1.09 | 1.17 | 1.19 | N/D | 2.13 | N/D |
| TS2 | D44R/E503A/Q511H/N563I | 0.80 | 0.70 | 0.88 | 0.89 | 0.96 | 0.85 | 1.14 | 1.53 | 1.23 |
| TS3 | E503A/N563I | 0.93 | 0.73 | 0.91 | 0.88 | 0.96 | 0.92 | 1.17 | 1.39 | 1.04 |
| TS4 | I43R/T430A/E503A/Q511H/N563K | 0.92 | 0.77 | 0.95 | 0.89 | 1.02 | 1.06 | 1.33 | 1.66 | 1.33 |
| TS5 | D44R/T430A/Q511H/A535R | 0.74 | 0.68 | 0.83 | 0.83 | 0.91 | 0.91 | 0.95 | 1.59 | 1.21 |
| Var1 | L417V/A431L/A539R | 0.69 | 1.06 | N/D | 1.12 | N/D | 1.16 | 1.26 | 1.18 | 1.40 |
| Var2 | L417V/A431L/A539R/I43Q | 0.69 | 1.13 | N/D | 1.15 | N/D | 1.18 | 1.40 | 1.12 | 1.53 |
| Var3 | L417V/A431L/A539R/N61I | 0.43 | 0.91 | N/D | 0.99 | N/D | 1.06 | 1.29 | 1.14 | 1.38 |
| Var4 | L417V/A431L/A539R/A535R | 0.64 | 0.97 | N/D | 1.03 | N/D | 1.07 | 1.22 | 1.49 | 1.22 |
| Var5 | L417V/A431L/A539R/I43Q/N61I | 0.38 | 0.86 | N/D | 0.94 | N/D | 1.04 | 1.25 | 1.07 | 1.24 |
| Var6 | L417V/A431L/A539R/N61I/A535R | 0.32 | 0.72 | N/D | 0.82 | N/D | 0.90 | 1.16 | 1.86 | 1.15 |
| Var7 | L417V/A431L/A539R/A535R/I43Q | 0.65 | 0.99 | N/D | 1.03 | N/D | 1.10 | 1.22 | 1.29 | 1.26 |
| Var8 | L417V/A431L/A539R/I43Q/N61I/A535R | 0.32 | 0.73 | N/D | 0.80 | N/D | 0.94 | 1.11 | 1.08 | 1.12 |
| Var9 | L417V/A431L/A539R/I43Q/N61I/A535R/T430A | 0.25 | 0.70 | N/D | 0.71 | N/D | 0.84 | 0.99 | 1.13 | 1.14 |
| Var10 | L417V/T430A/A431L/Q511H/A535R/A539R/N563I/I43Q | 0.53 | 0.98 | N/D | 0.97 | N/D | 1.06 | 1.08 | 1.86 | 1.63 |
| Var11 | L417V/T430A/A431L/Q511H/A535R/A539R/N563I/N61I | 0.38 | 0.80 | N/D | 0.86 | N/D | 0.95 | 1.16 | 1.51 | 1.15 |
| Var12 | L417V/T430A/A431L/Q511H/A535R/A539R/N563I/I43Q/N61I | 0.31 | 0.78 | N/D | 0.84 | N/D | 0.94 | 1.17 | 1.81 | 1.30 |
| Var13 | L417V/A431L/A539R/I43R | 0.67 | 1.08 | N/D | 1.12 | N/D | 1.18 | 1.32 | 1.83 | 1.55 |
| Var14 | L417V/A431L/A539R/I43R/N61I | 0.43 | 0.99 | N/D | 1.01 | N/D | 1.09 | 1.24 | 1.70 | 1.48 |
| Var15 | L417V/A431L/A539R/I43R/N61I/A535R/T430A | 0.39 | 0.94 | N/D | 0.96 | N/D | 1.09 | 1.34 | 1.96 | 1.59 |
| Var16 | L417R/A431L/A539R | 0.70 | 1.01 | N/D | 1.03 | N/D | 1.11 | 1.23 | 1.33 | 1.31 |
| Var17 | L417G/A431L/A539R | 0.70 | 1.15 | N/D | 1.14 | N/D | 1.19 | 1.20 | 1.23 | 1.42 |
| Var18 | G73F/E503V/N563K/L417R/A539R | 0.93 | 1.14 | N/D | 1.12 | N/D | 1.11 | 1.08 | 2.71 | 0.98 |
| Var19 | G73F/E503V/N563K/I43R/L417R/A539R | 1.24 | 1.47 | N/D | 1.43 | N/D | 1.33 | 1.38 | 2.58 | 1.21 |
| Var20 | G73F/E503V/N563K/I43R/Q511H | 0.94 | 0.95 | N/D | 0.95 | N/D | 0.97 | 1.02 | 2.47 | 0.84 |

Example 9

Homology Between TrGA and AaGA

The crystal structure of the TrGA identified in Example 11 in WO2009/067218 (Danisco US Inc., Genencor Division) page 89-93 incorporated herein by reference was superposed on the previously identified crystal structure of the *Aspergillus awamori* GA (AaGA). The AaGA crystal structure was obtained from the protein database (PDB) and the form of AaGA that was crystallized was the form containing only a catalytic domain (PDB entry number: 1GLM). The structure of the TrGA with all three regions intact was determined to 1.8 Angstrom resolution herein (see Table 20 in WO2009/067218 (Danisco US Inc., Genencor Division) page 94-216 incorporated herein by reference and Example 11 in WO2009/067218 (Danisco US Inc., Genencor Division) page 89-93 incorporated herein by reference). Using the coordinates (see Table 20 in WO2009/067218 (Danisco US Inc., Genencor Division) page 94-216 incorporated herein by reference), the structure was aligned with the coordinates of the catalytic domain from *Aspergillus awamori* strain X100 that was determined previously (Aleshin et al., J. Mol. Biol. 238: 575-591 (1994)). As seen in FIGS. 6-7, the structure of the catalytic domain overlapped very closely and allowed the identification of equivalent residues based on the structural superposition.

Based on this analysis, sites were identified that could be mutated in TrGA and result in increased thermostability and/or specific activity. There sites include 108, 124, 175, and 316 at the active site. Also identified were specific pairwise variants Y47W/Y315F and Y47F/Y315W. Other sites identified were 143, D44, P45, D46, R122, R125, V181, E242, Y310, D313, V314, N317, R408, and N409. Because of the high structural homology, it is expected that beneficial variants found at sites in the TrGA would have similar consequence in *Aspergillus awamori* and other homologous glucoamylases.

The TrGA linker, residues 454-490 is defined as the segment spanning the region between two disulfide bridges, one between residues 222 and 453 and one between residues 491 and 587. Nine of the residues in the linker are prolines. From the crystal structure, the linker extends from the back of the molecule in a wide arc followed by an abrupt turn after the lysine 477 residue on the surface near the substrate binding surface. The linker extends as a random coil that is anchored by interactions of the side chains of Tyr 452, Pro 465, Phe 470, Gln 474, Pro 475, Lys 477, Val 480 and Tyr 486 to regions on the surface of the catalytic domain.

Figure 9:
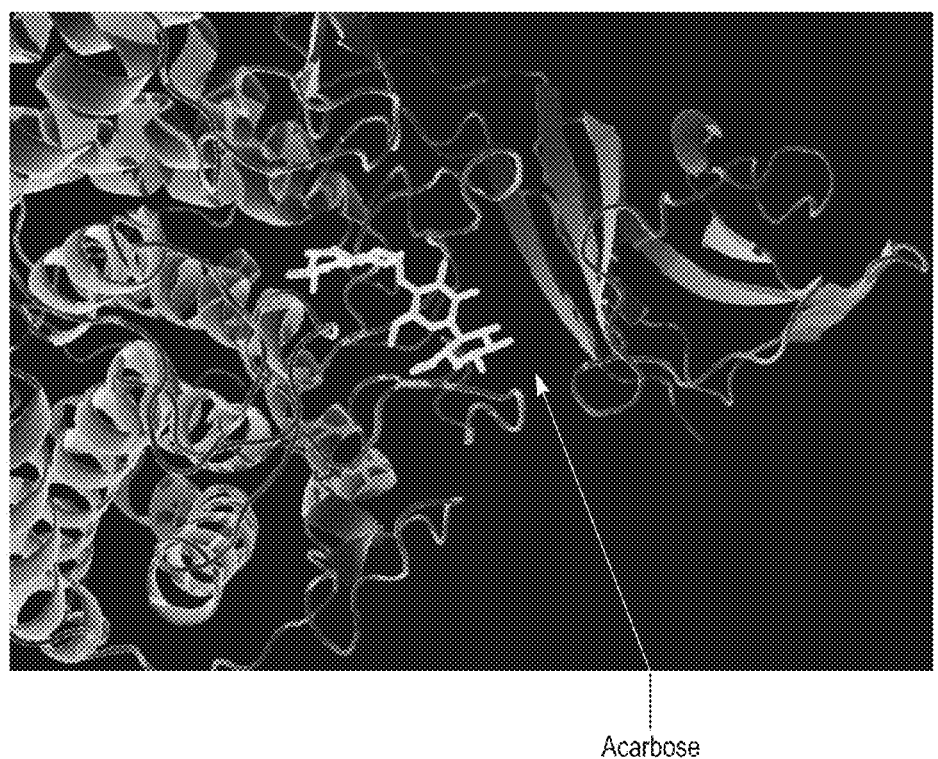
FIG. 9 depicts a model of the binding of acarbose to the TrGA crystal structure.

The starch binding domain is composed of a beta-sandwich of two twisted beta sheets, tethered at one end by a disulfide bridge between Cys 491 and Cys 587 and at the other end, having a series of loops that comprise a binding site for starch connected by long loops. The structure of the TrGA SBD is quite similar to the averaged structure of the AnGA SBD determined by NMR (Sorimachi et al., Structure 5: 647-661 (1997)) and the SBD of beta amylase from *Bacillus cereus* (Mikami, B. et al., Biochemistry 38: 7050-61 (1999)). FIG. 9 shows an alignment of the AnGA and TrGA crystal structures including the SBD. When aligned with one or both of these SBD's, one loop stands out as being highly variable, corresponding to residues 537-543 (in *A. niger* the loop is 554-560 and in *B. cereus* the loop is 462-465). In the NMR structure of beta-cyclodextrin, a starch analog complexed to the SBD of AnGA (Sorimachi et al. (1997) supra), the loop shifts substantially upon binding to cyclodextrin. Thus, this loop is designated the "flexible loop." This flexible loop forms part of the "binding site 2" (see FIG. 9 for this binding site in TrGA). A second binding site was also identified in AnGA (binding site 1), a primary site that shares similarities with other carbohydrate binding proteins. Overall, conservation of residues and even side conformations in the binding site 1 of these SBDs is very high. The figures demonstrate the interactions in these binding sites between the SBD and the catalytic domain that serve to bind to the starch.

Taken together, there appears to be a common pattern for the interactions between the linker and SBD with the catalytic domain. The interaction is in the form of an anchoring side chain that interacts with the surface area of the neighboring domain. In general, the anchor residue is found on the linker segment. In the case of interactions between the CD and SBD, the anchor residues can be contributed from either domain as in the case of residues Ile 43 and Phe 29 that come from the CD or residue 592, which comes from the SBD.

Example 10

Model of Acarbose Binding to TrGA

The crystal structure of the TrGA complexed with the inhibitor acarbose has been determined. Crystals of the complex were obtained by soaking pre-grown native TrGA crystals in acarbose. After soaking for 3 days the crystals were mounted in a seal glass capillary tube and x-ray diffraction was collected with a Rigaku Raxis IV++ image plate detector to a resolution of 2.0 Å. The coordinates were fitted to a difference electron density map. The model was refined to an R-factor of 0.154 with an R-free of 0.201 for a total of 41276 reflection representing all data collected between 27 and 2.0 Å resolution. The model of the resulting refined structure is shown in FIG. 9.

Based on the knowledge that the presence of the SBD has an impact on hydrolysis of insoluble starch, it followed that there should be an interaction of the SBD with larger starch molecules. Thus, the structure of the TrGA was compared with known structures of (1) an acarbose bound CD of AaGA and (2) an SBD from *A. niger* complexed with beta-cyclodextrin. This showed that the beta-cyclodextrin bound at binding site 2 was close to the substrate location as indicated by the location of acarbose bound to the *A. awamori* CD. Thus, the coordinates of acarbose from the structure model of the AaGA (pdb enty1GAI, Aleshin, et al. 1994 supra) were aligned into the TrGA active site. Further, the AnGA SBD structure bound to cyclodextrin (pdb entry 1AC0: Sorimachi, et al 1997 supra) was aligned. From this, a model was made for acarbose binding to TrGA (see FIG. 9). The model showed that the SBD would localize the TrGA CD near disrupted starch, and also prevent the enzyme from diffusing away from the substrate while releasing the product from the active site after hydrolysis. The SBD of TrGA would bind to starch along site 1, and favor localization where a disrupted fragment could bind to site 2 within a loose end that points into the catalytic site (the active side for the catalytic domain). This model shows how the proposed function of the enzyme is contributed by the structure of the SBD and linker. The amino acid side chains involved in the specific interaction between the CD, the linker and the SBD are specific for *Trichoderma reesei* GA, however, in other glucoamylases, complementary sequence changes would enable similar overall interactions and domain juxtaposition.

Based on this model, sites were identified for which substitutions could be made in the TrGA SBD to result in increased stability and/or specific activity. Thus, two loops that are part of binding site 1 are likely candidates for alterations to increase or decrease binding to the larger starch molecule. These are loop 1 (aa 560-570) and loop 2 (aa 523-527). Because the two Trp (tryptophan) residues at amino acids 525 and 572 are likely involved directly in starch binding, they would not be as conducive to change. However, the underlying residues, including 516-518 would be conducive, as would the underlying residues 558-562. The loop from residues 570-578 is also a good candidate for alterations. Residues 534-541 are part of the binding site 2 that interacts with the catalytic site on the CD. Thus, these might be a good candidate for alterations that may increase or decrease specific activity.

Because of the high structural homology of the TrGA SBD, it is expected that beneficial variants found at sites in *Trichoderma reesei* GA would have similar consequences in *Aspergillus awamori* and other homologous glucoamylases. Thus, the structure of the TrGA SBD provides a basis for engineering this and related enzymes for altered properties as compared to a parent glucoamylase. These altered properties may be advantageous for processes in the generation of fuels based on starch feed stocks.

Example 11

Enzymes Used

Purified variant of the *Trichoderma reesei* glucoamulase (TrGA) with mutations D44R and A539R. The variant is expressed in *Trichoderma reesei* and is hereafter called BRW 1. Glucoamylase product from fermentation of *Aspergillus niger*, sold under the name DIAZYME® X4. Pullulanase product from *Bacillus deramnificans* expressed in *Bacillus licheniformis*, sold under the name DIAZYME® P10. Acid α-amylase product from *Aspergillus kawachi* expressed in *Trichoderma reesei*, sold under the name GC626.

Results:

Table 9 below shows the RDF values obtained with different combinations of glucoamylase, pullulanase and alpha-amylase using the above described "Malt-adjunct brew analysis"-method. The glucoamylase, pullulanase and alpha-amylase activity were measured as described above. Three replicates were made for each dose. The average RDF and standard deviation are listed. For glucoamylases the amount of glucoamylase protein added/kg of grist is listed. Additionally the corresponding activity in GAU/kg of grist is listed. For alpha-amylase and pullulanase the number of enzyme units added/kg of grist is listed together with the corresponding amount of enzyme product (GC626 and DIAZYME® P10 respectively) added/kg of grist. *DIAZYME® X4 also contains some alpha-amylase activity. The number of units of alpha-amylase added when dosing this product is also listed in the table.

It is seen from Table 9, dose 2 and 3 that BRW1 performs better in terms of RDF obtained than TrGA. This correlates well with the fact that the BRW1 variant has a lower level of reversion activity. When dosed at 1022 mg glucoamylase protein/kg of grist BRW1 performs on level with DIAZYME® X4 (compare dose 1 and 3). Note that the glucoamylase in DIAZYME® X4 (*Aspergillus niger* glucoamylase) and the BRW1 glucoamylase have similar levels of reversion activity. The alpha-amylase activity present in DIAZYME® X4 probably means that the RDF value obtained is slightly higher than what pure *Aspergillus niger* glucoamylase would give. This only emphasizes that the BRW1 molecule performs as well if not better than *Aspergillus niger* glucoamylase.

When the dose of BRW1 is doubled from 1022 to 2044 mg/kg of grist, the RDF value increases from 83.2 to 84.8 (compare doses 3 and 4). RDF values can also be increased by adding auxiliary enzymes. When BRW1 is combined with alpha-amylase at 28172 SSU/kg of grist and pullulanase at 1961 PU/kg of grist the RDF value increases from 83.2 to 84.1 (compare doses 3 and 5). At high dose of BRW1 (2044 mg/kg of grist) there is also a benefit of adding auxiliary enzymes, but not as pronounced as with the low dose of BRW1 (compare differences in RDF between dose 3 and 5 and dose 4 and 6).

Sequences

Following are sequences, which are herein incorporated by reference in their entirety.

| Dose | Enzyme composition | Glucoamylase added | | α-Amylase added | | Pullulanase added | | RDF | |
|---|---|---|---|---|---|---|---|---|---|
| | | mg Protein /kg grist | GAU/ kg grist | SSU/ kg grist | g prod./ kg grist | PU/ kg grist | g. prod./ kg grist | Average (n = 3) | StDev |
| 1 | DiazymeX4 | 1022 | 2871 | 1768* | — | | | 83.3 | 0.047 |
| 2 | TrGA | 1022 | 4088 | | | | | 82.3 | 0.054 |
| 3 | BRW1 | 1022 | 3781 | | | | | 83.2 | 0.050 |
| 4 | BRW1 | 2044 | 7563 | | | | | 84.8 | 0.001 |
| 5 | BRW1 + GC626 + Diazyme P10 | 1022 | 3781 | 28172 | 2.46 | 1961 | 2.06 | 84.1 | 0.098 |
| 6 | BRW1 + GC626 + Diazyme P10 | 2044 | 7563 | 56344 | 4.93 | 3907 | 4.11 | 85.1 | 0.169 |

SEQ ID NO: 1: *Trichoderma reesei* glucoamylase, full length; with signal peptide
<210> 1
<211> 632
<212> PRT
<213> *Trichoderma reesei*

<400> 1

| | | | | | | | | | | | | | | | |
|---|---|---|---|---|---|---|---|---|---|---|---|---|---|---|---|
| Met | His | Val | Leu | Ser | Thr | Ala | Val | Leu | Leu | Gly | Ser | Val | Ala | Val | Gln |
| 1 | | | | 5 | | | | | 10 | | | | | 15 | |

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
            35                  40                  45

Asn Leu Leu Cys Asn Val Gly Pro Asp Gly Cys Arg Ala Phe Gly Thr
 50                      55                  60

Ser Ala Gly Ala Val Ile Ala Ser Pro Ser Thr Ile Asp Pro Asp Tyr
 65                      70                  75                      80

Tyr Tyr Met Trp Thr Arg Asp Ser Ala Leu Val Phe Lys Asn Leu Ile
             85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
            115                 120                 125

Gly Ser Leu Ala Asp Gly Ser Gly Leu Gly Glu Pro Lys Phe Glu Leu
 130                     135                 140

Thr Leu Lys Pro Phe Thr Gly Asn Trp Gly Arg Pro Gln Arg Asp Gly
 145                     150                 155                     160

Pro Ala Leu Arg Ala Ile Ala Leu Ile Gly Tyr Ser Lys Trp Leu Ile
            165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
            195                 200                 205

Asp Leu Trp Glu Glu Val Asn Gly Ser Ser Phe Phe Thr Val Ala Asn
            210                 215                 220

Gln His Arg Ala Leu Val Glu Gly Ala Thr Leu Ala Ala Thr Leu Gly
 225                     230                 235                     240

Gln Ser Gly Ser Ala Tyr Ser Ser Val Ala Pro Gln Val Leu Cys Phe
            245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Val Leu Thr
            275                 280                 285

Ser Ile His Thr Phe Asp Pro Asn Leu Gly Cys Asp Ala Gly Thr Phe
 290                     295                 300

Gln Pro Cys Ser Asp Lys Ala Leu Ser Asn Leu Lys Val Val Val Asp
 305                     310                 315                     320

Ser Phe Arg Ser Ile Tyr Gly Val Asn Lys Gly Ile Pro Ala Gly Ala
            325                 330                 335

Ala Val Ala Ile Gly Arg Tyr Ala Glu Asp Val Tyr Tyr Asn Gly Asn
            340                 345                 350

Pro Trp Tyr Leu Ala Thr Phe Ala Ala Ala Glu Gln Leu Tyr Asp Ala
            355                 360                 365

Ile Tyr Val Trp Lys Lys Thr Gly Ser Ile Thr Val Thr Ala Thr Ser
            370                 375                 380

Leu Ala Phe Phe Gln Glu Leu Val Pro Gly Val Thr Ala Gly Thr Tyr
 385                     390                 395                     400

```
Ser Ser Ser Ser Ser Thr Phe Thr Asn Ile Ile Asn Ala Val Ser Thr
                405                 410                 415

Tyr Ala Asp Gly Phe Leu Ser Glu Ala Ala Lys Tyr Val Pro Ala Asp
            420                 425                 430

Gly Ser Leu Ala Glu Gln Phe Asp Arg Asn Ser Gly Thr Pro Leu Ser
            435                 440                 445

Ala Leu His Leu Thr Trp Ser Tyr Ala Ser Phe Leu Thr Ala Thr Ala
        450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
                485                 490                 495

Arg Pro Thr Ala Thr Ser Phe Pro Pro Ser Gln Thr Pro Lys Pro Gly
            500                 505                 510

Val Pro Ser Gly Thr Pro Tyr Thr Pro Leu Pro Cys Ala Thr Pro Thr
        515                 520                 525

Ser Val Ala Val Thr Phe His Glu Leu Val Ser Thr Gln Phe Gly Gln
        530                 535                 540

Thr Val Lys Val Ala Gly Asn Ala Ala Ala Leu Gly Asn Trp Ser Thr
545                 550                 555                 560

Ser Ala Ala Val Ala Leu Asp Ala Val Asn Tyr Ala Asp Asn His Pro
                565                 570                 575

Leu Trp Ile Gly Thr Val Asn Leu Glu Ala Gly Asp Val Val Glu Tyr
            580                 585                 590

Lys Tyr Ile Asn Val Gly Gln Asp Gly Ser Val Thr Trp Glu Ser Asp
            595                 600                 605

Pro Asn His Thr Tyr Thr Val Pro Ala Val Ala Cys Val Thr Gln Val
        610                 615                 620

Val Lys Glu Asp Thr Trp Gln Ser
625                 630

SEQ ID NO: 2: Trichoderma reesei glucoamylase, mature protein; without signal
peptide
<210>   2
<211>   599
<212>   PRT
<213>   Trichoderma reesei <400>   2
Ser Val Asp Asp Phe Ile Ser Thr Glu Thr Pro Ile Ala Leu Asn Asn
1                 5                  10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Ile Asp Pro Asp Tyr Tyr
            35                  40                  45

Tyr Met Trp Thr Arg Asp Ser Ala Leu Val Phe Lys Asn Leu Ile Asp
        50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140
```

```
Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
            165                 170                 175

Leu Trp Glu Glu Val Asn Gly Ser Ser Phe Phe Thr Val Ala Asn Gln
        180                 185                 190

His Arg Ala Leu Val Glu Gly Ala Thr Leu Ala Ala Thr Leu Gly Gln
    195                 200                 205

Ser Gly Ser Ala Tyr Ser Val Ala Pro Gln Val Leu Cys Phe Leu
210                 215                 220

Gln Arg Phe Trp Val Ser Ser Gly Tyr Val Asp Ser Asn Ile Asn
225                 230                 235                 240

Thr Asn Glu Gly Arg Thr Gly Lys Asp Val Asn Ser Val Leu Thr Ser
            245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Asp Ser
    275                 280                 285

Phe Arg Ser Ile Tyr Gly Val Asn Lys Gly Ile Pro Ala Gly Ala Ala
290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
        355                 360                 365

Ser Ser Ser Ser Thr Phe Thr Asn Ile Ile Asn Ala Val Ser Thr Tyr
370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
            435                 440                 445

Ile Pro Ser Thr Cys Ser Gly Ala Ser Val Val Gly Ser Tyr Ser Arg
450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
            485                 490                 495

Val Ala Val Thr Phe His Glu Leu Val Ser Thr Gln Phe Gly Gln Thr
                500                 505                 510

Val Lys Val Ala Gly Asn Ala Ala Ala Leu Gly Asn Trp Ser Thr Ser
            515                 520                 525

Ala Ala Val Ala Leu Asp Ala Val Asn Tyr Ala Asp Asn His Pro Leu
530                 535                 540

Trp Ile Gly Thr Val Asn Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575
```

```
Asn His Thr Tyr Thr Val Pro Ala Val Ala Cys Val Thr Gln Val Val
            580                 585                 590

Lys Glu Asp Thr Trp Gln Ser
        595

SEQ ID NO: 3: Trichoderma reesei glucoamylase catalytic domain, 1-453 of mature
TrGA, CD
<210>    3
<211>    453
<212>    PRT
<213>    Trichoderma reesei <400>    3
Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
        130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
        210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Val Asp Ser
        275                 280                 285

Phe Arg Ser Ile Tyr Gly Val Asn Lys Gly Ile Pro Ala Gly Ala Ala
        290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
```

```
                355                 360                 365
Ser Ser Ser Ser Thr Phe Thr Asn Ile Ile Asn Ala Val Ser Thr Tyr
    370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
        435                 440                 445

Ile Pro Ser Thr Cys
    450

SEQ ID NO: 4: Trichoderma reesei glucoamylase cDNA
<210>   4
<211>   1899
<212>   DNA
<213>   Trichoderma reesei

<400>   4
```

| | | | | | |
|---|---|---|---|---|---|
| atgcacgtcc | tgtcgactgc | ggtgctgctc | ggctccgttg | ccgttcaaaa | ggtcctggga | 60 |
| agaccaggat | caagcggtct | gtccgacgtc | accaagaggt | ctgttgacga | cttcatcagc | 120 |
| accgagacgc | ctattgcact | gaacaatctt | ctttgcaatg | ttggtcctga | tggatgccgt | 180 |
| gcattcggca | catcagctgg | tgcggtgatt | gcatctccca | gcacaattga | cccggactac | 240 |
| tattacatgt | ggacgcgaga | tagcgctctt | gtcttcaaga | acctcatcga | ccgcttcacc | 300 |
| gaaacgtacg | atgcgggcct | gcagcgccgc | atcgagcagt | acattactgc | ccaggtcact | 360 |
| ctccagggcc | tctctaaccc | ctcgggctcc | ctcgcggacg | gctctggtct | cggcgagccc | 420 |
| aagtttgagt | tgaccctgaa | gcctttcacc | ggcaactggg | gtcgaccgca | gcgggatggc | 480 |
| ccagctctgc | gagccattgc | cttgattgga | tactcaaagt | ggctcatcaa | caacaactat | 540 |
| cagtcgactg | tgtccaacgt | catctggcct | attgtgcgca | acgacctcaa | ctatgttgcc | 600 |
| cagtactgga | accaaaccgg | ctttgacctc | tgggaagaag | tcaatgggag | ctcattcttt | 660 |
| actgttgcca | accagcaccg | agcacttgtc | gagggcgcca | ctcttgctgc | cactcttggc | 720 |
| cagtcgggaa | gcgcttattc | atctgttgct | ccccaggttt | tgtgctttct | ccaacgattc | 780 |
| tgggtgtcgt | ctggtggata | cgtcgactcc | aacatcaaca | ccaacgaggg | caggactggc | 840 |
| aaggatgtca | actccgtcct | gacttccatc | cacaccttcg | atcccaacct | tggctgtgac | 900 |
| gcaggcacct | tccagccatg | cagtgacaaa | gcgctctcca | acctcaaggt | tgttgtcgac | 960 |
| tccttccgct | ccatctacgg | cgtgaacaag | ggcattcctg | ccggtgctgc | cgtcgccatt | 1020 |
| ggccggtatg | cagaggatgt | gtactacaac | ggcaaccctt | ggtatcttgc | tcatttgct | 1080 |
| gctgccgagc | agctgtacga | tgccatctac | gtctggaaga | agacgggctc | catcacggtg | 1140 |
| accgccacct | ccctggcctt | cttccaggag | cttgttcctg | gcgtgacggc | cgggacctac | 1200 |
| tccagcagct | cttcgacctt | taccaacatc | atcaacgccg | tctcgacata | cgccgatggc | 1260 |
| ttcctcagcg | aggctgccaa | gtacgtcccc | gccgacggtt | cgctggccga | gcagtttgac | 1320 |
| cgcaacagcg | gcactccgct | gtctgcgctt | cacctgacgt | ggtcgtacgc | ctcgttcttg | 1380 |
| acagccacgg | cccgtcgggc | tggcatcgtg | ccccctcgt | gggccaacag | cagcgctagc | 1440 |
| acgatcccct | cgacgtgctc | cggcgcgtcc | gtggtcggat | cctactcgcg | tcccaccgcc | 1500 |
| acgtcattcc | ctccgtcgca | gacgcccaag | cctggcgtgc | cttccggtac | tcctacacg | 1560 |
| cccctgccct | gcgcgacccc | aacctccgtg | gccgtcacct | tccacgagct | cgtgtcgaca | 1620 |

```
cagtttggcc agacggtcaa ggtggcgggc aacgccgcgg ccctgggcaa ctggagcacg    1680
agcgccgccg tggctctgga cgccgtcaac tatgccgata accaccccct gtggattggg    1740
acggtcaacc tcgaggctgg agacgtcgtg gagtacaagt acatcaatgt gggccaagat    1800
ggctccgtga cctgggagag tgatcccaac cacacttaca cggttcctgc ggtggcttgt    1860
gtgacgcagg ttgtcaagga ggacacctgg cagtcgtaa                          1899
```

SEQ ID NO: 5: *Aspergillus awamori* GA (AaGA); CD
<210>    5
<211>    448
<212>    PRT
<213>    *Aspergillus awamori*

<400>    5

```
Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
            20                  25                  30

Asp Ser Gly Ile Val Val Ala Ser Pro Ser Thr Asp Asn Pro Asp Tyr
        35                  40                  45

Phe Tyr Thr Trp Thr Arg Asp Ser Gly Leu Val Ile Lys Thr Leu Val
    50                  55                  60

Asp Leu Phe Arg Asn Gly Asp Thr Asp Leu Leu Ser Thr Ile Glu Asn
65                  70                  75                  80

Tyr Ile Ser Ser Gln Ala Ile Val Gln Gly Ile Ser Asn Pro Ser Gly
                85                  90                  95

Asp Leu Ser Ser Gly Gly Leu Gly Glu Pro Lys Phe Asn Val Asp Glu
            100                 105                 110

Thr Ala Tyr Thr Gly Ser Trp Gly Arg Pro Gln Arg Asp Gly Pro Ala
        115                 120                 125

Leu Arg Ala Thr Ala Met Ile Gly Phe Arg Gln Trp Leu Leu Asp Asn
    130                 135                 140

Gly Tyr Thr Ser Ala Ala Thr Glu Ile Val Trp Pro Leu Val Arg Asn
145                 150                 155                 160

Asp Leu Ser Tyr Val Ala Gln Tyr Trp Asn Gln Thr Gly Tyr Asp Leu
                165                 170                 175

Trp Glu Glu Val Asn Gly Ser Ser Phe Phe Thr Ile Ala Val Gln His
            180                 185                 190

Arg Ala Leu Val Glu Gly Ser Ala Phe Ala Thr Ala Val Gly Ser Ser
        195                 200                 205

Cys Ser Trp Cys Asp Ser Gln Ala Pro Gln Ile Leu Cys Tyr Leu Gln
    210                 215                 220

Ser Phe Trp Thr Gly Glu Tyr Ile Leu Ala Asn Phe Asp Ser Ser Arg
225                 230                 235                 240

Ser Gly Lys Asp Thr Asn Thr Leu Leu Gly Ser Ile His Thr Phe Asp
                245                 250                 255

Pro Glu Ala Gly Cys Asp Asp Ser Thr Phe Gln Pro Cys Ser Pro Arg
            260                 265                 270

Ala Leu Ala Asn His Lys Glu Val Val Asp Ser Phe Arg Ser Ile Tyr
        275                 280                 285

Thr Leu Asn Asp Gly Leu Ser Asp Ser Glu Ala Val Ala Val Gly Arg
    290                 295                 300

Tyr Pro Lys Asp Ser Tyr Tyr Asn Gly Asn Pro Trp Phe Leu Cys Thr
305                 310                 315                 320

Leu Ala Ala Ala Glu Gln Leu Tyr Asp Ala Leu Tyr Gln Trp Asp Lys
                325                 330                 335

Gln Gly Ser Leu Glu Ile Thr Asp Val Ser Leu Asp Phe Phe Gln Ala
```

-continued

```
                       340                 345                 350
Leu Tyr Ser Asp Ala Ala Thr Gly Thr Tyr Ser Ser Ser Ser Thr
                355                 360                 365

Tyr Ser Ser Ile Val Asp Ala Val Lys Thr Phe Ala Asp Gly Phe Val
            370                 375                 380

Ser Ile Val Glu Thr His Ala Ala Ser Asn Gly Ser Leu Ser Glu Gln
385                 390                 395                 400

Tyr Asp Lys Ser Asp Gly Asp Glu Leu Ser Ala Arg Asp Leu Thr Trp
                405                 410                 415

Ser Tyr Ala Ala Leu Leu Thr Ala Asn Asn Arg Arg Asn Ser Val Met
            420                 425                 430

Pro Pro Ser Trp Gly Glu Thr Ser Ala Ser Ser Val Pro Gly Thr Cys
        435                 440                 445

SEQ ID NO: 6: Aspergillus niger (AnGA), CD
<210>   6
<211>   449
<212> PRT
<213> Aspergillus niger <400>   6
Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
            20                  25                  30

Asp Ser Gly Ile Val Val Ala Ser Pro Ser Thr Asp Asn Pro Asp Tyr
        35                  40                  45

Phe Tyr Thr Trp Thr Arg Asp Ser Gly Leu Val Leu Lys Thr Leu Val
    50                  55                  60

Asp Leu Phe Arg Asn Gly Asp Thr Ser Leu Leu Ser Thr Ile Glu Asn
65                  70                  75                  80

Tyr Ile Ser Ala Gln Ala Ile Val Gln Gly Ile Ser Asn Pro Ser Gly
                85                  90                  95

Asp Leu Ser Ser Gly Ala Gly Leu Gly Glu Pro Lys Phe Asn Val Asp
            100                 105                 110

Glu Thr Ala Tyr Thr Gly Ser Trp Gly Arg Pro Gln Arg Asp Gly Pro
        115                 120                 125

Ala Leu Arg Ala Thr Ala Met Ile Gly Phe Gly Gln Trp Leu Leu Asp
    130                 135                 140

Asn Gly Tyr Thr Ser Thr Ala Thr Asp Ile Val Trp Pro Leu Val Arg
145                 150                 155                 160

Asn Asp Leu Ser Tyr Val Ala Gln Tyr Trp Asn Gln Thr Gly Tyr Asp
                165                 170                 175

Leu Trp Glu Glu Val Asn Gly Ser Ser Phe Phe Thr Ile Ala Val Gln
            180                 185                 190

His Arg Ala Leu Val Glu Gly Ser Ala Phe Ala Thr Ala Val Gly Ser
        195                 200                 205

Ser Cys Ser Trp Cys Asp Ser Gln Ala Pro Glu Ile Leu Cys Tyr Leu
    210                 215                 220

Gln Ser Phe Trp Thr Gly Ser Phe Ile Leu Ala Asn Phe Asp Ser Ser
225                 230                 235                 240

Arg Ser Gly Lys Asp Ala Asn Thr Leu Leu Gly Ser Ile His Thr Phe
                245                 250                 255

Asp Pro Glu Ala Ala Cys Asp Asp Ser Thr Phe Gln Pro Cys Ser Pro
            260                 265                 270

Arg Ala Leu Ala Asn His Lys Glu Val Val Asp Ser Phe Arg Ser Ile
        275                 280                 285
```

-continued

```
Tyr Thr Leu Asn Asp Gly Leu Ser Asp Ser Glu Val Ala Val Gly
290                 295                 300

Arg Tyr Pro Glu Asp Thr Tyr Asn Gly Asn Pro Trp Phe Leu Cys
305                 310                 315                 320

Thr Leu Ala Ala Ala Glu Gln Leu Tyr Asp Ala Leu Tyr Gln Trp Asp
                325                 330                 335

Lys Gln Gly Ser Leu Glu Val Thr Asp Val Ser Leu Asp Phe Phe Lys
                340                 345                 350

Ala Leu Tyr Ser Asp Ala Ala Thr Gly Thr Tyr Ser Ser Ser Ser Ser
                355                 360                 365

Thr Tyr Ser Ser Ile Val Asp Ala Val Lys Thr Phe Ala Asp Gly Phe
370                 375                 380

Val Ser Ile Val Glu Thr His Ala Ala Ser Asn Gly Ser Met Ser Glu
385                 390                 395                 400

Gln Tyr Asp Lys Ser Asp Gly Glu Gln Leu Ser Ala Arg Asp Leu Thr
                405                 410                 415

Trp Ser Tyr Ala Ala Leu Leu Thr Ala Asn Asn Arg Arg Asn Ser Val
                420                 425                 430

Val Pro Ala Ser Trp Gly Glu Thr Ser Ala Ser Ser Val Pro Gly Thr
                435                 440                 445

Cys
```

SEQ ID NO: 7: *Aspergillus oryzae* (AoGA), CD
<210> 7
<211> 450
<212> PRT
<213> *Aspergillus oryzae*

<400> 7
```
Gln Ser Asp Leu Asn Ala Phe Ile Glu Ala Gln Thr Pro Ile Ala Lys
1               5                   10                  15

Gln Gly Tyr Leu Asn Asn Ile Gly Ala Asp Gly Lys Leu Val Glu Gly
                20                  25                  30

Ala Ala Ala Gly Ile Val Tyr Ala Ser Pro Ser Lys Ser Asn Pro Asp
                35                  40                  45

Tyr Phe Tyr Thr Trp Thr Arg Asp Ala Gly Leu Thr Met Glu Glu Tyr
50                  55                  60

Ile Glu Gln Phe Ile Gly Gly Asp Ala Thr Leu Glu Ser Thr Ile Gln
65                  70                  75                  80

Asn Tyr Val Asp Ser Gln Ala Asn Glu Gln Ala Val Ser Asn Pro Ser
                85                  90                  95

Gly Gly Leu Ser Asp Gly Ser Gly Leu Ala Glu Pro Lys Phe Tyr Tyr
                100                 105                 110

Asn Ile Ser Gln Phe Thr Asp Ser Trp Gly Arg Pro Gln Arg Asp Gly
                115                 120                 125

Pro Ala Leu Arg Ala Ser Ala Leu Ile Ala Tyr Gly Asn Ser Leu Ile
                130                 135                 140

Ser Ser Asp Lys Gln Ser Val Val Lys Ala Asn Ile Trp Pro Ile Tyr
145                 150                 155                 160

Gln Asn Asp Leu Ser Tyr Val Gly Gln Tyr Trp Asn Gln Thr Gly Phe
                165                 170                 175

Asp Leu Trp Glu Glu Val Gln Gly Ser Ser Phe Phe Thr Val Ala Val
                180                 185                 190

Gln His Lys Ala Leu Val Glu Gly Asp Ala Phe Ala Lys Ala Leu Gly
                195                 200                 205

Glu Glu Cys Gln Ala Cys Ser Val Ala Pro Gln Ile Leu Cys His Leu
                210                 215                 220
```

```
Gln Asp Phe Trp Asn Gly Ser Ala Val Leu Ser Asn Leu Pro Thr Asn
225                 230                 235                 240

Gly Arg Ser Gly Leu Asp Thr Asn Ser Leu Leu Gly Ser Ile His Thr
            245                 250                 255

Phe Asp Pro Ala Ala Ala Cys Asp Asp Thr Thr Phe Gln Pro Cys Ser
        260                 265                 270

Ser Arg Ala Leu Ser Asn His Lys Leu Val Val Asp Ser Phe Arg Ser
    275                 280                 285

Val Tyr Gly Ile Asn Asn Gly Arg Gly Ala Gly Lys Ala Ala Ala Val
290                 295                 300

Gly Pro Tyr Ala Glu Asp Thr Tyr Gln Gly Gly Asn Pro Trp Tyr Leu
305                 310                 315                 320

Thr Thr Leu Val Ala Ala Glu Leu Leu Tyr Asp Ala Leu Tyr Gln Trp
            325                 330                 335

Asp Lys Gln Gly Gln Val Asn Val Thr Glu Thr Ser Leu Pro Phe Phe
        340                 345                 350

Lys Asp Leu Ser Ser Asn Val Thr Thr Gly Ser Tyr Ala Lys Ser Ser
    355                 360                 365

Ser Ala Tyr Glu Ser Leu Thr Ser Ala Val Lys Thr Tyr Ala Asp Gly
370                 375                 380

Phe Ile Ser Val Val Gln Glu Tyr Thr Pro Asp Gly Ala Leu Ala
385                 390                 395                 400

Glu Gln Tyr Ser Arg Asp Gln Gly Thr Pro Val Ser Ala Ser Asp Leu
            405                 410                 415

Thr Trp Ser Tyr Ala Ala Phe Leu Ser Ala Val Gly Arg Arg Asn Gly
        420                 425                 430

Thr Val Pro Ala Ser Trp Gly Ser Ser Thr Ala Asn Ala Val Pro Ser
    435                 440                 445

Gln Cys
    450

SEQ ID NO: 8: Humicola grisea glucoamylase (HgGA); CD
<210>   8
<211>   441
<212> PRT
<213> Humicola grisea <400>   8
Ala Ala Val Asp Thr Phe Ile Asn Thr Glu Lys Pro Ile Ala Trp Asn
1               5                   10                  15

Lys Leu Leu Ala Asn Ile Gly Pro Asn Gly Lys Ala Ala Pro Gly Ala
            20                  25                  30

Ala Ala Gly Val Val Ile Ala Ser Pro Ser Arg Thr Asp Pro Pro Tyr
        35                  40                  45

Phe Phe Thr Trp Thr Pro Asp Ala Ala Leu Val Leu Thr Gly Ile Ile
    50                  55                  60

Glu Ser Leu Gly His Asn Tyr Asn Thr Thr Leu Gln Gln Val Ser Asn
65                  70                  75                  80

Pro Ser Gly Thr Phe Ala Asp Gly Ser Gly Leu Gly Glu Ala Lys Phe
            85                  90                  95

Asn Val Asp Leu Thr Ala Phe Thr Gly Glu Trp Gly Arg Pro Gln Arg
            100                 105                 110

Asp Gly Pro Pro Leu Arg Ala Ile Ala Leu Ile Gln Tyr Ala Lys Trp
        115                 120                 125

Leu Ile Ala Asn Gly Tyr Lys Ser Thr Ala Lys Ser Val Val Trp Pro
    130                 135                 140

Val Val Lys Asn Asp Leu Ala Tyr Thr Ala Gln Tyr Trp Asn Glu Thr
145                 150                 155                 160
```

```
Gly Phe Asp Leu Trp Glu Val Pro Gly Ser Ser Phe Thr Ile
            165                 170                 175

Ala Ser Ser His Arg Ala Leu Thr Glu Gly Ala Tyr Leu Ala Ala Gln
            180                 185                 190

Leu Asp Thr Glu Cys Pro Pro Cys Thr Thr Val Ala Pro Gln Val Leu
            195                 200                 205

Cys Phe Gln Gln Ala Phe Trp Asn Ser Lys Gly Asn Tyr Val Val Ser
            210                 215                 220

Thr Ser Thr Ala Gly Glu Tyr Arg Ser Gly Lys Asp Ala Asn Ser Ile
225                 230                 235                 240

Leu Ala Ser Ile His Asn Phe Asp Pro Glu Ala Gly Cys Asp Asn Leu
            245                 250                 255

Thr Phe Gln Pro Cys Ser Glu Arg Ala Leu Ala Asn His Lys Ala Tyr
            260                 265                 270

Val Asp Ser Phe Arg Asn Leu Tyr Ala Ile Asn Lys Gly Ile Ala Gln
            275                 280                 285

Gly Lys Ala Val Ala Val Gly Arg Tyr Ser Glu Asp Val Tyr Tyr Asn
            290                 295                 300

Gly Asn Pro Trp Tyr Leu Ala Asn Phe Ala Ala Ala Glu Gln Leu Tyr
305                 310                 315                 320

Asp Ala Ile Tyr Val Trp Asn Lys Gln Gly Ser Ile Thr Val Thr Ser
            325                 330                 335

Val Ser Leu Pro Phe Phe Arg Asp Leu Val Ser Ser Val Ser Thr Gly
            340                 345                 350

Thr Tyr Ser Lys Ser Ser Ser Thr Phe Thr Asn Ile Val Asn Ala Val
            355                 360                 365

Lys Ala Tyr Ala Asp Gly Phe Ile Glu Val Ala Ala Lys Tyr Thr Pro
            370                 375                 380

Ser Asn Gly Ala Leu Ala Glu Gln Tyr Asp Arg Asn Thr Gly Lys Pro
385                 390                 395                 400

Asp Ser Ala Ala Asp Leu Thr Trp Ser Tyr Ser Ala Phe Leu Ser Ala
            405                 410                 415

Ile Asp Arg Arg Ala Gly Leu Val Pro Pro Ser Trp Arg Ala Ser Val
            420                 425                 430

Ala Lys Ser Gln Leu Pro Ser Thr Cys
            435                 440

SEQ ID NO: 9: Hypocrea vinosa glucoamylase (HvGA); CD
<210>   9
<211>   452
<212> PRT
<213> Hypocrea vinosa <400>   9
Ser Val Asp Asp Phe Ile Asn Thr Gln Thr Pro Ile Ala Leu Asn Asn
1                5                  10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Thr Asp Pro Asp Tyr Tyr
            35                  40                  45

Tyr Met Trp Thr Arg Asp Ser Ala Leu Val Phe Lys Asn Ile Val Asp
        50                  55                  60

Arg Phe Thr Gln Gln Tyr Asp Ala Gly Leu Gln Arg Arg Ile Glu Gln
65                  70                  75                  80

Tyr Ile Ser Ala Gln Val Thr Leu Gln Gly Ile Ser Asn Pro Ser Gly
            85                  90                  95

Ser Leu Ser Asp Gly Ser Gly Leu Gly Glu Pro Lys Phe Glu Leu Thr
```

```
                       100                 105                 110
Leu Ser Gln Phe Thr Gly Asn Trp Gly Arg Pro Gln Arg Asp Gly Pro
            115                 120                 125

Ala Leu Arg Ala Ile Ala Leu Ile Gly Tyr Ser Lys Trp Leu Ile Asn
        130                 135                 140

Asn Asn Tyr Gln Ser Thr Val Ser Asn Ile Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Thr Tyr Ser Ser Val Ala Pro Gln Ile Leu Cys Phe Leu
    210                 215                 220

Gln Arg Phe Trp Val Ser Gly Gly Tyr Ile Asp Ser Asn Ile Asn Thr
225                 230                 235                 240

Asn Glu Gly Arg Thr Gly Lys Asp Ala Asn Ser Leu Leu Ala Ser Ile
                245                 250                 255

His Thr Phe Asp Pro Ser Leu Gly Cys Asp Ala Ser Thr Phe Gln Pro
            260                 265                 270

Cys Ser Asp Lys Ala Leu Ser Asn Leu Lys Val Val Asp Her Phe
        275                 280                 285

Arg Ser Ile Tyr Gly Val Asn Lys Gly Ile Pro Ala Gly Ser Ala Val
    290                 295                 300

Ala Ile Gly Arg Tyr Pro Glu Asp Val Tyr Phe Asn Gly Asn Pro Trp
305                 310                 315                 320

Tyr Leu Ala Thr Phe Ala Ala Ala Glu Gln Leu Tyr Asp Ser Val Tyr
                325                 330                 335

Val Trp Lys Lys Thr Gly Ser Ile Thr Val Thr Ser Thr Ser Ser Ala
            340                 345                 350

Phe Phe Gln Glu Leu Val Pro Gly Val Ala Ala Gly Thr Tyr Ser Ser
        355                 360                 365

Ser Gln Ser Thr Phe Thr Ser Ile Ile Asn Ala Ile Ser Thr Tyr Ala
    370                 375                 380

Asp Gly Phe Leu Ser Glu Ala Ala Lys Tyr Val Pro Ala Asp Gly Ser
385                 390                 395                 400

Leu Ala Glu Gln Phe Asp Arg Asn Thr Gly Thr Pro Leu Ser Ala Val
                405                 410                 415

His Leu Thr Trp Ser Tyr Ala Ser Phe Leu Thr Ala Ala Ala Arg Arg
            420                 425                 430

Ala Gly Val Val Pro Pro Ser Trp Ala Ser Ser Gly Ala Asn Thr Val
        435                 440                 445

Pro Ser Ser Cys
    450

SEQ ID NO: 10: TrGA, linker region
<210>   10
<211>   37
<212> PRT
<213> Trichoderma reesei <400>   10
Ser Gly Ala Ser Val Gly Ser Tyr Ser Arg Pro Thr Ala Thr Ser
1                5                 10                  15

Phe Pro Pro Ser Gln Thr Pro Lys Pro Gly Val Pro Ser Gly Thr Pro
            20                  25                  30
```

Tyr Thr Pro Leu Pro
                35

SEQ ID NO: 11: TrGA, SBD
<210>  11
<211>  109
<212>  PRT

<213> *Trichoderma reesei*
<400>  11
Cys Ala Thr Pro Thr Ser Val Ala Val Thr Phe His Glu Leu Val Ser
1               5                   10                  15

Thr Gln Phe Gly Gln Thr Val Lys Val Ala Gly Asn Ala Ala Ala Leu
            20                  25                  30

Gly Asn Trp Ser Thr Ser Ala Ala Val Ala Leu Asp Ala Val Asn Tyr
        35                  40                  45

Ala Asp Asn His Pro Leu Trp Ile Gly Thr Val Asn Leu Glu Ala Gly
65                  70                  75                  80

Asp Val Val Glu Tyr Lys Tyr Ile Asn Val Gly Gln Asp Gly Ser Val
65                  70                  75                  80

Thr Trp Glu Ser Asp Pro Asn His Thr Tyr Thr Val Pro Ala Val Ala
            85                  90                  95

Cys Val Thr Gln Val Val Lys Glu Asp Thr Trp Gln Ser
            100                 105

SEQ ID NO: 12 SVDDFI: start of the TrGA mature protein
<210>  12
<211>  6
<212>  PRT
<213> *Trichoderma reesei*

<400>  12
Ser Val Asp Asp Phe Ile
1               5

SEQ ID NO: 384 *Talaromyces* GA mature protein
<210>  384
<211>  588
<212>  PRT
<213> *Talaromyces* sp.

<400>  384
Gly Ser Leu Asp Ser Phe Leu Ala Thr Glu Thr Pro Ile Ala Leu Gln
1               5                   10                  15

Gly Val Leu Asn Asn Ile Gly Pro Asn Gly Ala Asp Val Ala Gly Ala
            20                  25                  30

Ser Ala Gly Ile Val Val Ala Ser Pro Ser Arg Ser Asp Pro Asp Tyr
        35                  40                  45

Phe Tyr Ser Trp Thr Arg Asp Ala Ala Leu Thr Ala Lys Tyr Leu Val
    50                  55                  60

Asp Ala Phe Ile Ala Gly Asn Lys Asp Leu Glu Gln Thr Ile Gln Glu
65                  70                  75                  80

Tyr Ile Ser Ala Gln Ala Gln Val Gln Thr Ile Ser Asn Pro Ser Gly
            85                  90                  95

Asp Leu Ser Thr Gly Gly Leu Gly Glu Pro Lys Phe Asn Val Asn Glu
            100                 105                 110

Thr Ala Phe Thr Gly Pro Trp Gly Arg Pro Gln Arg Asp Gly Pro Ala
            115                 120                 125

Leu Arg Ala Thr Ala Leu Ile Ala Tyr Ala Asn Tyr Leu Ile Asp Asn
        130                 135                 140

Gly Gln Ala Ser Thr Ala Asp Glu Ile Ile Trp Pro Ile Val Gln Asn
145                 150                 155                 160

Asp Leu Ser Tyr Val Thr Gln Tyr Trp Asn Ser Ser Thr Phe Asp Leu
            165                 170                 175

```
Trp Glu Glu Val Glu Gly Ser Ser Phe Phe Thr Thr Ala Val Gln His
            180                 185                 190
Arg Ala Leu Val Glu Gly Asn Ala Leu Ala Thr Arg Leu Asn His Thr
            195                 200                 205
Cys Pro Asn Cys Val Ser Gln Ala Pro Gln Val Leu Cys Phe Leu Gln
210                 215                 220
Ser Tyr Trp Thr Gly Ser Tyr Val Leu Ala Asn Phe Gly Ser Gly
225                 230                 235                 240
Arg Ser Gly Lys Asp Val Asn Ser Ile Leu Gly Ser Ile His Thr Phe
                245                 250                 255
Asp Pro Ala Gly Gly Cys Asp Asp Ser Thr Phe Gln Pro Cys Ser Ala
                260                 265                 270
Arg Ala Leu Ala Asn His Lys Val Val Thr Asp Ser Phe Arg Ser Val
            275                 280                 285
Tyr Ala Val Asn Ser Gly Ile Ala Glu Gly Ser Ala Val Ala Val Gly
            290                 295                 300
Arg Tyr Pro Glu Asp Val Tyr Gln Gly Gly Asn Pro Trp Tyr Leu Ala
305                 310                 315                 320
Thr Ala Ala Ala Glu Gln Leu Tyr Asp Ala Ile Tyr Gln Trp Asn
                325                 330                 335
Lys Ile Gly Ser Ile Ser Ile Thr Asp Val Ser Leu Ala Phe Phe Gln
                340                 345                 350
Asp Ile Tyr Pro Ser Ala Ala Val Gly Thr Tyr Asn Ser Gly Ser Ser
                355                 360                 365
Thr Phe Asn Asp Ile Ile Ser Ala Val Gln Thr Tyr Ala Asp Gly Tyr
            370                 375                 380
Leu Ser Ile Ile Glu Lys Tyr Thr Pro Ser Asp Gly Ser Leu Thr Glu
385                 390                 395                 400
Gln Phe Ser Arg Ser Asp Gly Thr Pro Leu Ser Ala Ser Gly Leu Thr
                405                 410                 415
Trp Ser Tyr Ala Ser Leu Leu Thr Ala Ala Arg Arg Gln Ser Ile
                420                 425                 430
Val Pro Ala Ser Trp Gly Glu Ser Ser Ala Ser Ser Val Pro Ala Val
            435                 440                 445
Cys Ser Ala Thr Ser Ala Thr Gly Pro Tyr Ser Thr Ala Thr Asn Thr
450                 455                 460
Ala Trp Pro Ser Ser Gly Ser Gly Pro Ser Thr Thr Thr Ser Val Pro
465                 470                 475                 480
Cys Thr Thr Pro Thr Ser Val Ala Val Thr Phe Asp Glu Ile Val Ser
                485                 490                 495
Thr Thr Tyr Gly Glu Thr Ile Tyr Leu Ala Gly Ser Ile Pro Glu Leu
                500                 505                 510
Gly Asn Trp Ser Pro Ser Ser Ala Ile Pro Leu Arg Ala Asp Ala Tyr
            515                 520                 525
Thr Ser Ser Asn Pro Leu Trp Tyr Val Thr Leu Asn Leu Pro Ala Gly
            530                 535                 540
Thr Ser Phe Glu Tyr Lys Phe Phe Lys Lys Glu Thr Asp Gly Thr Ile
545                 550                 555                 560
Val Trp Glu Asp Asp Pro Asn Arg Ser Tyr Thr Val Pro Ala Tyr Cys
                565                 570                 575
Gly Gln Thr Thr Ala Ile Leu Asp Asp Ser Trp Gln
                580                 585

SEQ ID NO: 385 Humicola grisea GA SBD
<210>  385
<211>  112
```

```
<212> PRT
<213> Humicola grisea

<400> 385
Cys Ala Asp Ala Ser Glu Val Tyr Val Thr Phe Asn Glu Arg Val Ser
1               5                   10                  15

Thr Ala Trp Gly Glu Thr Ile Lys Val Val Gly Asn Val Pro Ala Leu
            20                  25                  30

Gly Asn Trp Asp Thr Ser Lys Ala Val Thr Leu Ser Ala Ser Gly Tyr
        35                  40                  45

Lys Ser Asn Asp Pro Leu Trp Ser Ile Thr Val Pro Ile Lys Ala Thr
    50                  55                  60

Gly Ser Ala Val Gln Tyr Lys Tyr Ile Lys Val Gly Thr Asn Gly Lys
65                  70                  75                  80

Ile Thr Trp Glu Ser Asp Pro Asn Arg Ser Ile Thr Leu Gln Thr Ala
                85                  90                  95

Ser Ser Ala Gly Lys Cys Ala Ala Gln Thr Val Asn Asp Ser Trp Arg
            100                 105                 110

SEQ ID NO: 386 Thermomyces lanuginosus GA SBD
<210> 386
<211> 109
<212> PRT
<213> Thermomyces lanuginosus
<400> 386
Cys Thr Pro Pro Ser Glu Val Thr Leu Thr Phe Asn Ala Leu Val Asp
1               5                   10                  15

Thr Ala Phe Gly Gln Asn Ile Tyr Leu Val Gly Ser Ile Pro Glu Leu
            20                  25                  30

Gly Ser Trp Asp Pro Ala Asn Ala Leu Leu Met Ser Ala Lys Ser Trp
        35                  40                  45

Thr Ser Gly Asn Pro Val Trp Thr Leu Ser Ile Ser Leu Pro Ala Gly
    50                  55                  60

Thr Ser Phe Glu Tyr Lys Phe Ile Arg Lys Asp Asp Gly Ser Ser Asp
65                  70                  75                  80

Val Val Trp Glu Ser Asp Pro Asn Arg Ser Tyr Asn Val Pro Lys Asp
                85                  90                  95

Cys Gly Ala Asn Thr Ala Thr Val Asn Ser Trp Trp Arg
            100                 105

SEQ ID NO: 387 Talaromyces emersonii GA SBD
<210> 387
<211> 108
<212> PRT
<213> Talaromyces emersonii
<400> 387
Cys Thr Thr Pro Thr Ser Val Ala Val Thr Phe Asp Glu Ile Val Ser
1               5                   10                  15

Thr Ser Tyr Gly Glu Thr Ile Tyr Leu Ala Gly Ser Ile Pro Glu Leu
            20                  25                  30

Gly Asn Trp Ser Thr Ala Ser Ala Ile Pro Leu Arg Ala Asp Ala Tyr
        35                  40                  45

Thr Asn Ser Asn Pro Leu Trp Tyr Val Thr Val Asn Leu Pro Pro Gly
    50                  55                  60

Thr Ser Phe Glu Tyr Lys Phe Phe Lys Asn Gln Thr Asp Gly Thr Ile
65                  70                  75                  80

Val Trp Glu Asp Asp Pro Asn Arg Ser Tyr Thr Val Pro Ala Tyr Cys
                85                  90                  95

Gly Gln Thr Thr Ala Ile Leu Asp Asp Ser Trp Gln
            100                 105
```

```
SEQ ID NO: 388 Aspergillus niger GA SBD
<210> 388
<211> 108
<212> PRT
<213> Aspergillus niger
<400> 388
Cys Thr Thr Pro Thr Ala Val Ala Val Thr Phe Asp Leu Thr Ala Thr
1               5                   10                  15

Thr Thr Tyr Gly Glu Asn Ile Tyr Leu Val Gly Ser Ile Ser Gln Leu
            20                  25                  30

Gly Asp Trp Glu Thr Ser Asp Gly Ile Ala Leu Ser Ala Asp Lys Tyr
        35                  40                  45

Thr Ser Ser Asp Pro Leu Trp Tyr Val Thr Val Thr Leu Pro Ala Gly
    50                  55                  60

Glu Ser Phe Glu Tyr Lys Phe Ile Arg Ile Glu Ser Asp Asp Ser Val
65                  70                  75                  80

Glu Trp Glu Ser Asp Pro Asn Arg Glu Tyr Thr Val Pro Gln Ala Cys
                85                  90                  95

Gly Thr Ser Thr Ala Thr Val Thr Asp Thr Trp Arg
            100                 105

SEQ ID NO: 389 Aspergillus awamori GA SBD
<210> 389
<211> 108
<212> PRT
<213> Aspergillus awamori
<400> 389
Cys Thr Thr Pro Thr Ala Val Ala Val Thr Phe Asp Leu Thr Ala Thr
1               5                   10                  15

Thr Thr Tyr Gly Glu Asn Ile Tyr Leu Val Gly Ser Ile Ser Gln Leu
            20                  25                  30

Gly Asp Trp Asp Thr Ser Asp Gly Ile Ala Leu Ser Ala Asp Lys Tyr
        35                  40                  45

Thr Ser Ser Asn Pro Leu Trp Tyr Val Thr Val Thr Leu Pro Ala Gly
    50                  55                  60

Glu Ser Phe Glu Tyr Lys Phe Ile Arg Ile Glu Ser Asp Asp Ser Val
65                  70                  75                  80

Glu Trp Glu Ser Asp Pro Asn Arg Glu Tyr Thr Val Pro Gln Ala Cys
                85                  90                  95

Gly Glu Ser Thr Ala Thr Val Thr Asp Thr Trp Arg
            100                 105

SEQ ID NO: 390 Thielavia terrestris GA SBD
<210> 390
<211> 108
<212> PRT
<213> Thielavia terrestris
<400> 390
Cys Ser Thr Pro Thr Ala Val Ala Val Thr Phe Asn Glu Arg Val Thr
1               5                   10                  15

Thr Gln Trp Gly Gln Thr Ile Lys Val Val Gly Asp Ala Ala Ala Leu
            20                  25                  30

Gly Gly Trp Asp Thr Ser Lys Ala Val Pro Leu Ser Ala Ala Gly Tyr
        35                  40                  45

Thr Ala Ser Asp Pro Leu Trp Ser Gly Thr Val Asp Leu Pro Ala Gly
    50                  55                  60

Leu Ala Val Gln Tyr Lys Tyr Ile Asn Val Ala Ala Asp Gly Gly Val
65                  70                  75                  80

Thr Trp Glu Ala Asp Pro Asn His Ser Phe Thr Val Pro Ala Ala Cys
                85                  90                  95
```

-continued

```
Gly Thr Thr Ala Val Thr Arg Asp Asp Thr Trp Gln
            100                 105

SEQ ID NO: 1098 Trichoderma reesei glucoamylase variant
SVDDFISTETPIALNNLLCNVGPDGCRAFGTSAGAVIASPSTIRPDYYYMWTRDSALVFKNLIDRFTETYDAGLQRRIE

QYITAQVTLQGLSNPSGSLADGSGLGEPKFELTLKPFTGNWGRPQRDGPALRAIALIGYSKWLINNNYQSTVSNVIWPI

VRNDLNYVAQYWNQTGFDLWEEVNGSSFFTVANQHRALVEGATLAATLGQSGSAYSSVAPQVLCFLQRFWVSSGGYVDS

NINTNEGRTGKDVNSVLTSIHTFDPNLGCDAGTFQPCSDKALSNLKVVVDSFRSIYGVNKGIPAGAAVAIGRYAEDVYY

NGNPWYLATFAAAEQLYDAIYVWKKTGSITVTATSLAFFQELVPGVTAGTYSSSSSTFTNIINAVSTYADGFLSEAAKY

VPADGSLAEQFDRNSGTPLSALHLTWSYASFLTATARRAGIVPPSWANSSASTIPSTCSGASVVGSYSRPTATSFPPSQ

TPKPGVPSGTPYTPLPCATPTSVAVTFHELVSTQFGQTVKVAGNAAALGNWSTSAAVALDAVNYRDNHPLWIGTVNLEA

GDVVEYKYINVGQDGSVTWESDPNHTYTVPAVACVTQVVKEDTWQS

SEQ ID NO: 1099 Trichoderma reesei glucoamylase variant
SVDDFISTETPIALNNLLCNVGPDGCRAFGTSAGAVIASPSTIRPDYYYMWTRDSALVFKILIDRFTETYDAGLQRRIE

QYITAQVTLQGLSNPSGSLADGSGLGEPKFELTLKPFTGNWGRPQRDGPALRAIALIGYSKWLINNNYQSTVSNVIWPI

VRNDLNYVAQYWNQTGFDLWEEVNGSSFFTVANQHRALVEGATLAATLGQSGSAYSSVAPQVLCFLQRFWVSSGGYVDS

NINTNEGRTGKDVNSVLTSIHTFDPNLGCDAGTFQPCSDKALSNLKVVVDSFRSIYGVNKGIPAGAAVAIGRYAEDVYY

NGNPWYLATFAAAEQLYDAIYVWKKTGSITVTATSLAFFQELVPGVTAGTYSSSSSTFTNIINAVSTYADGFLSEAAKY

VPADGSLAEQFDRNSGTPLSALHLTWSYASFLTATARRAGIVPPSWANSSASTIPSTCSGASVVGSYSRPTATSFPPSQ

TPKPGVPSGTPYTPLPCATPTSVAVTFHELVSTQFGQTVKVAGNAAALGNWSTSAAVALDAVNYRDNHPLWIGTVNLEA

GDVVEYKYINVGQDGSVTWESDPNHTYTVPAVACVTQVVKEDTWQS
```

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Various modifications and variations of the described methods and system of the disclosure will be apparent to those skilled in the art without departing from the scope and spirit of the disclosure. Although the disclosure has been described in connection with specific representative embodiments, it should be understood that the subject matters as claimed should not be unduly limited to such specific embodiments. Indeed, various modifications of the described modes for carrying out the disclosure that are obvious to those skilled in the art are intended to be within the scope of the following claims.

SEQUENCE LISTING

```
<160> NUMBER OF SEQ ID NOS: 1099

<210> SEQ ID NO 1
<211> LENGTH: 632
<212> TYPE: PRT
<213> ORGANISM: Trichoderma reesei

<400> SEQUENCE: 1

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Ile Asp Pro Asp Tyr
65                  70                  75                  80
```

-continued

Tyr Tyr Met Trp Thr Arg Asp Ser Ala Leu Val Phe Lys Asn Leu Ile
            85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
            115                 120                 125

Gly Ser Leu Ala Asp Gly Ser Gly Leu Gly Glu Pro Lys Phe Glu Leu
            130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
            165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
            195                 200                 205

Asp Leu Trp Glu Glu Val Asn Gly Ser Ser Phe Phe Thr Val Ala Asn
            210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
            245                 250                 255

Leu Gln Arg Phe Trp Val Ser Ser Gly Tyr Val Asp Ser Asn Ile
            260                 265                 270

Asn Thr Asn Glu Gly Arg Thr Gly Lys Asp Val Asn Ser Val Leu Thr
            275                 280                 285

Ser Ile His Thr Phe Asp Pro Asn Leu Gly Cys Asp Ala Gly Thr Phe
290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
            325                 330                 335

Ala Val Ala Ile Gly Arg Tyr Ala Glu Asp Val Tyr Tyr Asn Gly Asn
            340                 345                 350

Pro Trp Tyr Leu Ala Thr Phe Ala Ala Ala Glu Gln Leu Tyr Asp Ala
            355                 360                 365

Ile Tyr Val Trp Lys Lys Thr Gly Ser Ile Thr Val Thr Ala Thr Ser
            370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
            405                 410                 415

Tyr Ala Asp Gly Phe Leu Ser Glu Ala Ala Lys Tyr Val Pro Ala Asp
            420                 425                 430

Gly Ser Leu Ala Glu Gln Phe Asp Arg Asn Ser Gly Thr Pro Leu Ser
            435                 440                 445

Ala Leu His Leu Thr Trp Ser Tyr Ala Ser Phe Leu Thr Ala Thr Ala
            450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
            485                 490                 495

Arg Pro Thr Ala Thr Ser Phe Pro Pro Ser Gln Thr Pro Lys Pro Gly

```
                500             505             510
Val Pro Ser Gly Thr Pro Tyr Thr Pro Leu Pro Cys Ala Thr Pro Thr
            515                 520             525

Ser Val Ala Val Thr Phe His Glu Leu Val Ser Thr Gln Phe Gly Gln
        530                 535             540

Thr Val Lys Val Ala Gly Asn Ala Ala Leu Gly Asn Trp Ser Thr
545                 550                 555                 560

Ser Ala Ala Val Ala Leu Asp Ala Val Asn Tyr Ala Asp Asn His Pro
                565                 570                 575

Leu Trp Ile Gly Thr Val Asn Leu Glu Ala Gly Asp Val Val Glu Tyr
            580                 585                 590

Lys Tyr Ile Asn Val Gly Gln Asp Gly Ser Val Thr Trp Glu Ser Asp
        595                 600                 605

Pro Asn His Thr Tyr Thr Val Pro Ala Val Ala Cys Val Thr Gln Val
    610                 615                 620

Val Lys Glu Asp Thr Trp Gln Ser
625                 630

<210> SEQ ID NO 2
<211> LENGTH: 599
<212> TYPE: PRT
<213> ORGANISM: Trichoderma reesei

<400> SEQUENCE: 2

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240
```

Thr Asn Glu Gly Arg Thr Gly Lys Asp Val Asn Ser Val Leu Thr Ser
            245                 250                 255

Ile His Thr Phe Asp Pro Asn Leu Gly Cys Asp Ala Gly Thr Phe Gln
        260                 265                 270

Pro Cys Ser Asp Lys Ala Leu Ser Asn Leu Lys Val Val Asp Ser
    275                 280                 285

Phe Arg Ser Ile Tyr Gly Val Asn Lys Gly Ile Pro Ala Gly Ala Ala
290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Glu Gln Leu Tyr Asp Ala Ile
            325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
            355                 360                 365

Ser Ser Ser Ser Thr Phe Thr Asn Ile Ile Asn Ala Val Ser Thr Tyr
        370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
            405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
        435                 440                 445

Ile Pro Ser Thr Cys Ser Gly Ala Ser Val Val Gly Ser Tyr Ser Arg
450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
            485                 490                 495

Val Ala Val Thr Phe His Glu Leu Val Ser Thr Gln Phe Gly Gln Thr
            500                 505                 510

Val Lys Val Ala Gly Asn Ala Ala Leu Gly Asn Trp Ser Thr Ser
            515                 520                 525

Ala Ala Val Ala Leu Asp Ala Val Asn Tyr Ala Asp Asn His Pro Leu
            530                 535                 540

Trp Ile Gly Thr Val Asn Leu Glu Ala Gly Asp Val Val Glu Tyr Lys
545                 550                 555                 560

Tyr Ile Asn Val Gly Gln Asp Gly Ser Val Thr Trp Glu Ser Asp Pro
            565                 570                 575

Asn His Thr Tyr Thr Val Pro Ala Val Ala Cys Val Thr Gln Val Val
            580                 585                 590

Lys Glu Asp Thr Trp Gln Ser
            595

<210> SEQ ID NO 3
<211> LENGTH: 453
<212> TYPE: PRT
<213> ORGANISM: Trichoderma reesei

<400> SEQUENCE: 3

Ser Val Asp Asp Phe Ile Ser Thr Glu Thr Pro Ile Ala Leu Asn Asn
1               5                   10                  15

-continued

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
 50                  55                  60

Arg Phe Thr Glu Thr Tyr Asp Ala Gly Leu Gln Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Val Asp Ser
        275                 280                 285

Phe Arg Ser Ile Tyr Gly Val Asn Lys Gly Ile Pro Ala Gly Ala Ala
    290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
        355                 360                 365

Ser Ser Ser Ser Thr Phe Thr Asn Ile Ile Asn Ala Val Ser Thr Tyr
    370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
          435                 440                 445

Ile Pro Ser Thr Cys
    450

<210> SEQ ID NO 4
<211> LENGTH: 1899
<212> TYPE: DNA
<213> ORGANISM: Trichoderma reesei

<400> SEQUENCE: 4

| | | | | | |
|---|---|---|---|---|---|
| atgcacgtcc | tgtcgactgc | ggtgctgctc | ggctccgttg | ccgttcaaaa | ggtcctggga | 60 |
| agaccaggat | caagcggtct | gtccgacgtc | accaagaggt | ctgttgacga | cttcatcagc | 120 |
| accgagacgc | ctattgcact | gaacaatctt | ctttgcaatg | ttggtcctga | tggatgccgt | 180 |
| gcattcggca | catcagctgg | tgcggtgatt | gcatctccca | gcacaattga | cccggactac | 240 |
| tattacatgt | ggacgcgaga | tagcgctctt | gtcttcaaga | acctcatcga | ccgcttcacc | 300 |
| gaaacgtacg | atgcgggcct | gcagcgccgc | atcgagcagt | acattactgc | caggtcact | 360 |
| ctccagggcc | tctctaaccc | ctcgggctcc | ctcgcggacg | gctctggtct | cggcgagccc | 420 |
| aagtttgagt | tgaccctgaa | gcctttcacc | ggcaactggg | gtcgaccgca | gcgggatggc | 480 |
| ccagctctgc | gagccattgc | cttgattgga | tactcaaagt | ggctcatcaa | caacaactat | 540 |
| cagtcgactg | tgtccaacgt | catctggcct | attgtgcgca | acgacctcaa | ctatgttgcc | 600 |
| cagtactgga | accaaaccgg | ctttgacctc | tgggaagaag | tcaatgggag | ctcattcttt | 660 |
| actgttgcca | accagcaccg | agcacttgtc | gagggcgcca | ctcttgctgc | cactcttggc | 720 |
| cagtcgggaa | gcgcttattc | atctgttgct | ccccaggttt | tgtgctttct | ccaacgattc | 780 |
| tgggtgtcgt | ctggtggata | cgtcgactcc | aacatcaaca | ccaacgaggg | caggactggc | 840 |
| aaggatgtca | actccgtcct | gacttccatc | cacaccttcg | atcccaacct | tgctgtgac | 900 |
| gcaggcacct | tccagccatg | cagtgacaaa | gcgctctcca | acctcaaggt | tgttgtcgac | 960 |
| tccttccgct | ccatctacgg | cgtgaacaag | ggcattcctg | ccggtgctgc | cgtcgccatt | 1020 |
| ggccggtatg | cagaggatgt | gtactacaac | ggcaaccctt | ggtatcttgc | tacatttgct | 1080 |
| gctgccgagc | agctgtacga | tgccatctac | gtctggaaga | agacgggctc | catcacggtg | 1140 |
| accgccacct | ccctggcctt | cttccaggag | cttgttcctg | gcgtgacggc | cgggacctac | 1200 |
| tccagcagct | cttcgacctt | taccaacatc | atcaacgccg | tctcgacata | cgccgatggc | 1260 |
| ttcctcagcg | aggctgccaa | gtacgtcccc | gccgacggtt | cgctggccga | gcagtttgac | 1320 |
| cgcaacagcg | gcactccgct | gtctgcgctt | cacctgacgt | ggtcgtacgc | ctcgttcttg | 1380 |
| acagccacgg | cccgtcgggc | tggcatcgtg | cccccctcgt | gggccaacag | cagcgctagc | 1440 |
| acgatcccct | cgacgtgctc | cggcgcgtcc | gtggtcggat | cctactcgcg | tcccaccgcc | 1500 |
| acgtcattcc | ctccgtcgca | gacgcccaag | cctggcgtgc | cttccggtac | tccctacacg | 1560 |
| cccctgccct | gcgcgacccc | aacctccgtg | gccgtcacct | tccacgagct | cgtgtcgaca | 1620 |
| cagtttggcc | agacggtcaa | ggtggcgggc | aacgccgcgg | ccctgggcaa | ctggagcacg | 1680 |
| agcgccgccg | tggctctgga | cgccgtcaac | tatgccgata | ccaccccct | gtggattggg | 1740 |
| acggtcaacc | tcgaggctgg | agacgtcgtg | gagtacaagt | acatcaatgt | gggccaagat | 1800 |
| ggctccgtga | cctgggagag | tgatcccaac | cacacttaca | cggttcctgc | ggtggcttgt | 1860 |
| gtgacgcagg | ttgtcaagga | ggacacctgg | cagtcgtaa | | | 1899 |

```
<210> SEQ ID NO 5
<211> LENGTH: 448
<212> TYPE: PRT
<213> ORGANISM: Aspergillus awamori

<400> SEQUENCE: 5

Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
            20                  25                  30

Asp Ser Gly Ile Val Val Ala Ser Pro Ser Thr Asp Asn Pro Asp Tyr
        35                  40                  45

Phe Tyr Thr Trp Thr Arg Asp Ser Gly Leu Val Ile Lys Thr Leu Val
50                  55                  60

Asp Leu Phe Arg Asn Gly Asp Thr Asp Leu Leu Ser Thr Ile Glu Asn
65                  70                  75                  80

Tyr Ile Ser Ser Gln Ala Ile Val Gln Gly Ile Ser Asn Pro Ser Gly
                85                  90                  95

Asp Leu Ser Ser Gly Gly Leu Gly Glu Pro Lys Phe Asn Val Asp Glu
            100                 105                 110

Thr Ala Tyr Thr Gly Ser Trp Gly Arg Pro Gln Arg Asp Gly Pro Ala
        115                 120                 125

Leu Arg Ala Thr Ala Met Ile Gly Phe Arg Gln Trp Leu Leu Asp Asn
130                 135                 140

Gly Tyr Thr Ser Ala Ala Thr Glu Ile Val Trp Pro Leu Val Arg Asn
145                 150                 155                 160

Asp Leu Ser Tyr Val Ala Gln Tyr Trp Asn Gln Thr Gly Tyr Asp Leu
                165                 170                 175

Trp Glu Glu Val Asn Gly Ser Ser Phe Phe Thr Ile Ala Val Gln His
            180                 185                 190

Arg Ala Leu Val Glu Gly Ser Ala Phe Ala Thr Ala Val Gly Ser Ser
        195                 200                 205

Cys Ser Trp Cys Asp Ser Gln Ala Pro Gln Ile Leu Cys Tyr Leu Gln
210                 215                 220

Ser Phe Trp Thr Gly Glu Tyr Ile Leu Ala Asn Phe Asp Ser Ser Arg
225                 230                 235                 240

Ser Gly Lys Asp Thr Asn Thr Leu Leu Gly Ser Ile His Thr Phe Asp
                245                 250                 255

Pro Glu Ala Gly Cys Asp Asp Ser Thr Phe Gln Pro Cys Ser Pro Arg
            260                 265                 270

Ala Leu Ala Asn His Lys Glu Val Val Asp Ser Phe Arg Ser Ile Tyr
        275                 280                 285

Thr Leu Asn Asp Gly Leu Ser Asp Ser Glu Ala Val Ala Val Gly Arg
290                 295                 300

Tyr Pro Lys Asp Ser Tyr Tyr Asn Gly Asn Pro Trp Phe Leu Cys Thr
305                 310                 315                 320

Leu Ala Ala Ala Glu Gln Leu Tyr Asp Ala Leu Tyr Gln Trp Asp Lys
                325                 330                 335

Gln Gly Ser Leu Glu Ile Thr Asp Val Ser Leu Asp Phe Phe Gln Ala
            340                 345                 350

Leu Tyr Ser Asp Ala Ala Thr Gly Thr Tyr Ser Ser Ser Ser Ser Thr
        355                 360                 365

Tyr Ser Ser Ile Val Asp Ala Val Lys Thr Phe Ala Asp Gly Phe Val
370                 375                 380
```

```
Ser Ile Val Glu Thr His Ala Ala Ser Asn Gly Ser Leu Ser Glu Gln
385                 390                 395                 400

Tyr Asp Lys Ser Asp Gly Asp Glu Leu Ser Ala Arg Asp Leu Thr Trp
                405                 410                 415

Ser Tyr Ala Ala Leu Leu Thr Ala Asn Asn Arg Arg Asn Ser Val Met
                420                 425                 430

Pro Pro Ser Trp Gly Glu Thr Ser Ala Ser Val Pro Gly Thr Cys
                435                 440                 445

<210> SEQ ID NO 6
<211> LENGTH: 449
<212> TYPE: PRT
<213> ORGANISM: Aspergillus niger

<400> SEQUENCE: 6

Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
                20                  25                  30

Asp Ser Gly Ile Val Val Ala Ser Pro Ser Thr Asp Asn Pro Asp Tyr
            35                  40                  45

Phe Tyr Thr Trp Thr Arg Asp Ser Gly Leu Val Leu Lys Thr Leu Val
50                  55                  60

Asp Leu Phe Arg Asn Gly Asp Thr Ser Leu Leu Ser Thr Ile Glu Asn
65                  70                  75                  80

Tyr Ile Ser Ala Gln Ala Ile Val Gln Gly Ile Ser Asn Pro Ser Gly
                85                  90                  95

Asp Leu Ser Ser Gly Ala Gly Leu Gly Glu Pro Lys Phe Asn Val Asp
                100                 105                 110

Glu Thr Ala Tyr Thr Gly Ser Trp Gly Arg Pro Gln Arg Asp Gly Pro
            115                 120                 125

Ala Leu Arg Ala Thr Ala Met Ile Gly Phe Gly Gln Trp Leu Leu Asp
        130                 135                 140

Asn Gly Tyr Thr Ser Thr Ala Thr Asp Ile Val Trp Pro Leu Val Arg
145                 150                 155                 160

Asn Asp Leu Ser Tyr Val Ala Gln Tyr Trp Asn Gln Thr Gly Tyr Asp
                165                 170                 175

Leu Trp Glu Glu Val Asn Gly Ser Ser Phe Phe Thr Ile Ala Val Gln
            180                 185                 190

His Arg Ala Leu Val Glu Gly Ser Ala Phe Ala Thr Ala Val Gly Ser
        195                 200                 205

Ser Cys Ser Trp Cys Asp Ser Gln Ala Pro Glu Ile Leu Cys Tyr Leu
    210                 215                 220

Gln Ser Phe Trp Thr Gly Ser Phe Ile Leu Ala Asn Phe Asp Ser Ser
225                 230                 235                 240

Arg Ser Gly Lys Asp Ala Asn Thr Leu Leu Gly Ser Ile His Thr Phe
                245                 250                 255

Asp Pro Glu Ala Ala Cys Asp Asp Ser Thr Phe Gln Pro Cys Ser Pro
            260                 265                 270

Arg Ala Leu Ala Asn His Lys Glu Val Val Asp Ser Phe Arg Ser Ile
        275                 280                 285

Tyr Thr Leu Asn Asp Gly Leu Ser Asp Ser Glu Ala Val Ala Val Gly
    290                 295                 300

Arg Tyr Pro Glu Asp Thr Tyr Tyr Asn Gly Asn Pro Trp Phe Leu Cys
305                 310                 315                 320
```

```
Thr Leu Ala Ala Ala Glu Gln Leu Tyr Asp Ala Leu Tyr Gln Trp Asp
                325                 330                 335

Lys Gln Gly Ser Leu Glu Val Thr Asp Val Ser Leu Asp Phe Phe Lys
            340                 345                 350

Ala Leu Tyr Ser Asp Ala Ala Thr Gly Thr Tyr Ser Ser Ser Ser Ser
            355                 360                 365

Thr Tyr Ser Ser Ile Val Asp Ala Val Lys Thr Phe Ala Asp Gly Phe
    370                 375                 380

Val Ser Ile Val Glu Thr His Ala Ala Ser Asn Gly Ser Met Ser Glu
385                 390                 395                 400

Gln Tyr Asp Lys Ser Asp Gly Glu Gln Leu Ser Ala Arg Asp Leu Thr
                405                 410                 415

Trp Ser Tyr Ala Ala Leu Leu Thr Ala Asn Asn Arg Arg Asn Ser Val
            420                 425                 430

Val Pro Ala Ser Trp Gly Glu Thr Ser Ala Ser Ser Val Pro Gly Thr
            435                 440                 445

Cys

<210> SEQ ID NO 7
<211> LENGTH: 450
<212> TYPE: PRT
<213> ORGANISM: Aspergillus oryzae

<400> SEQUENCE: 7

Gln Ser Asp Leu Asn Ala Phe Ile Glu Ala Gln Thr Pro Ile Ala Lys
1               5                   10                  15

Gln Gly Tyr Leu Asn Asn Ile Gly Ala Asp Gly Lys Leu Val Glu Gly
            20                  25                  30

Ala Ala Ala Gly Ile Val Tyr Ala Ser Pro Ser Lys Ser Asn Pro Asp
        35                  40                  45

Tyr Phe Tyr Thr Trp Thr Arg Asp Ala Gly Leu Thr Met Glu Glu Tyr
    50                  55                  60

Ile Glu Gln Phe Ile Gly Gly Asp Ala Thr Leu Glu Ser Thr Ile Gln
65                  70                  75                  80

Asn Tyr Val Asp Ser Gln Ala Asn Glu Gln Ala Val Ser Asn Pro Ser
                85                  90                  95

Gly Gly Leu Ser Asp Gly Ser Gly Leu Ala Glu Pro Lys Phe Tyr Tyr
            100                 105                 110

Asn Ile Ser Gln Phe Thr Asp Ser Trp Gly Arg Pro Gln Arg Asp Gly
        115                 120                 125

Pro Ala Leu Arg Ala Ser Ala Leu Ile Ala Tyr Gly Asn Ser Leu Ile
    130                 135                 140

Ser Ser Asp Lys Gln Ser Val Val Lys Ala Asn Ile Trp Pro Ile Tyr
145                 150                 155                 160

Gln Asn Asp Leu Ser Tyr Val Gly Gln Tyr Trp Asn Gln Thr Gly Phe
                165                 170                 175

Asp Leu Trp Glu Glu Val Gln Gly Ser Ser Phe Phe Thr Val Ala Val
            180                 185                 190

Gln His Lys Ala Leu Val Glu Gly Asp Ala Phe Ala Lys Ala Leu Gly
        195                 200                 205

Glu Glu Cys Gln Ala Cys Ser Val Ala Pro Gln Ile Leu Cys His Leu
    210                 215                 220

Gln Asp Phe Trp Asn Gly Ser Ala Val Leu Ser Asn Leu Pro Thr Asn
225                 230                 235                 240
```

```
Gly Arg Ser Gly Leu Asp Thr Asn Ser Leu Leu Gly Ser Ile His Thr
                245                 250                 255

Phe Asp Pro Ala Ala Cys Asp Asp Thr Thr Phe Gln Pro Cys Ser
            260                 265                 270

Ser Arg Ala Leu Ser Asn His Lys Leu Val Val Asp Ser Phe Arg Ser
                275                 280                 285

Val Tyr Gly Ile Asn Asn Gly Arg Gly Ala Gly Lys Ala Ala Ala Val
            290                 295                 300

Gly Pro Tyr Ala Glu Asp Thr Tyr Gln Gly Gly Asn Pro Trp Tyr Leu
305                 310                 315                 320

Thr Thr Leu Val Ala Ala Glu Leu Leu Tyr Asp Ala Leu Tyr Gln Trp
                325                 330                 335

Asp Lys Gln Gly Gln Val Asn Val Thr Glu Thr Ser Leu Pro Phe Phe
            340                 345                 350

Lys Asp Leu Ser Ser Asn Val Thr Thr Gly Ser Tyr Ala Lys Ser Ser
            355                 360                 365

Ser Ala Tyr Glu Ser Leu Thr Ser Ala Val Lys Thr Tyr Ala Asp Gly
            370                 375                 380

Phe Ile Ser Val Val Gln Glu Tyr Thr Pro Asp Gly Gly Ala Leu Ala
385                 390                 395                 400

Glu Gln Tyr Ser Arg Asp Gln Gly Thr Pro Val Ser Ala Ser Asp Leu
                405                 410                 415

Thr Trp Ser Tyr Ala Ala Phe Leu Ser Ala Val Gly Arg Arg Asn Gly
            420                 425                 430

Thr Val Pro Ala Ser Trp Gly Ser Ser Thr Ala Asn Ala Val Pro Ser
            435                 440                 445

Gln Cys
    450

<210> SEQ ID NO 8
<211> LENGTH: 441
<212> TYPE: PRT
<213> ORGANISM: Humicola grisea

<400> SEQUENCE: 8

Ala Ala Val Asp Thr Phe Ile Asn Thr Glu Lys Pro Ile Ala Trp Asn
1               5                   10                  15

Lys Leu Leu Ala Asn Ile Gly Pro Asn Gly Lys Ala Ala Pro Gly Ala
                20                  25                  30

Ala Ala Gly Val Val Ile Ala Ser Pro Ser Arg Thr Asp Pro Pro Tyr
            35                  40                  45

Phe Phe Thr Trp Thr Pro Asp Ala Ala Leu Val Leu Thr Gly Ile Ile
        50                  55                  60

Glu Ser Leu Gly His Asn Tyr Asn Thr Thr Leu Gln Gln Val Ser Asn
65                  70                  75                  80

Pro Ser Gly Thr Phe Ala Asp Gly Ser Gly Leu Gly Glu Ala Lys Phe
                85                  90                  95

Asn Val Asp Leu Thr Ala Phe Thr Gly Glu Trp Gly Arg Pro Gln Arg
            100                 105                 110

Asp Gly Pro Pro Leu Arg Ala Ile Ala Leu Ile Gln Tyr Ala Lys Trp
        115                 120                 125

Leu Ile Ala Asn Gly Tyr Lys Ser Thr Ala Lys Ser Val Val Trp Pro
    130                 135                 140

Val Val Lys Asn Asp Leu Ala Tyr Thr Ala Gln Tyr Trp Asn Glu Thr
```

```
                145                 150                 155                 160
Gly Phe Asp Leu Trp Glu Glu Val Pro Gly Ser Ser Phe Phe Thr Ile
                165                 170                 175

Ala Ser Ser His Arg Ala Leu Thr Glu Gly Ala Tyr Leu Ala Ala Gln
                180                 185                 190

Leu Asp Thr Glu Cys Pro Pro Cys Thr Val Ala Pro Gln Val Leu
                195                 200                 205

Cys Phe Gln Gln Ala Phe Trp Asn Ser Lys Gly Asn Tyr Val Val Ser
210                 215                 220

Thr Ser Thr Ala Gly Glu Tyr Arg Ser Gly Lys Asp Ala Asn Ser Ile
225                 230                 235                 240

Leu Ala Ser Ile His Asn Phe Asp Pro Glu Ala Gly Cys Asp Asn Leu
                245                 250                 255

Thr Phe Gln Pro Cys Ser Glu Arg Ala Leu Ala Asn His Lys Ala Tyr
                260                 265                 270

Val Asp Ser Phe Arg Asn Leu Tyr Ala Ile Asn Lys Gly Ile Ala Gln
                275                 280                 285

Gly Lys Ala Val Ala Val Gly Arg Tyr Ser Glu Asp Val Tyr Tyr Asn
                290                 295                 300

Gly Asn Pro Trp Tyr Leu Ala Asn Phe Ala Ala Glu Gln Leu Tyr
305                 310                 315                 320

Asp Ala Ile Tyr Val Trp Asn Lys Gln Gly Ser Ile Thr Val Thr Ser
                325                 330                 335

Val Ser Leu Pro Phe Phe Arg Asp Leu Val Ser Ser Val Ser Thr Gly
                340                 345                 350

Thr Tyr Ser Lys Ser Ser Ser Thr Phe Thr Asn Ile Val Asn Ala Val
                355                 360                 365

Lys Ala Tyr Ala Asp Gly Phe Ile Glu Val Ala Ala Lys Tyr Thr Pro
                370                 375                 380

Ser Asn Gly Ala Leu Ala Glu Gln Tyr Asp Arg Asn Thr Gly Lys Pro
385                 390                 395                 400

Asp Ser Ala Ala Asp Leu Thr Trp Ser Tyr Ser Ala Phe Leu Ser Ala
                405                 410                 415

Ile Asp Arg Arg Ala Gly Leu Val Pro Pro Ser Trp Arg Ala Ser Val
                420                 425                 430

Ala Lys Ser Gln Leu Pro Ser Thr Cys
                435                 440

<210> SEQ ID NO 9
<211> LENGTH: 452
<212> TYPE: PRT
<213> ORGANISM: Hypocrea vinosa

<400> SEQUENCE: 9

Ser Val Asp Asp Phe Ile Asn Thr Gln Thr Pro Ile Ala Leu Asn Asn
1                   5                   10                  15

Leu Leu Cys Asn Val Gly Pro Asp Gly Cys Arg Ala Phe Gly Thr Ser
                    20                  25                  30

Ala Gly Ala Val Ile Ala Ser Pro Ser Thr Thr Asp Pro Asp Tyr Tyr
                    35                  40                  45

Tyr Met Trp Thr Arg Asp Ser Ala Leu Val Phe Lys Asn Ile Val Asp
                50                  55                  60

Arg Phe Thr Gln Gln Tyr Asp Ala Gly Leu Gln Arg Arg Ile Glu Gln
65                  70                  75                  80
```

```
Tyr Ile Ser Ala Gln Val Thr Leu Gln Gly Ile Ser Asn Pro Ser Gly
                 85                  90                  95

Ser Leu Ser Asp Gly Ser Gly Leu Gly Glu Pro Lys Phe Glu Leu Thr
            100                 105                 110

Leu Ser Gln Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Ile Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Thr Tyr Ser Ser Val Ala Pro Gln Ile Leu Cys Phe Leu
    210                 215                 220

Gln Arg Phe Trp Val Ser Gly Tyr Ile Asp Ser Asn Ile Asn Thr
225                 230                 235                 240

Asn Glu Gly Arg Thr Gly Lys Asp Ala Asn Ser Leu Leu Ala Ser Ile
                245                 250                 255

His Thr Phe Asp Pro Ser Leu Gly Cys Asp Ala Ser Thr Phe Gln Pro
            260                 265                 270

Cys Ser Asp Lys Ala Leu Ser Asn Leu Lys Val Val Asp Ser Phe
        275                 280                 285

Arg Ser Ile Tyr Gly Val Asn Lys Gly Ile Pro Ala Gly Ser Ala Val
    290                 295                 300

Ala Ile Gly Arg Tyr Pro Glu Asp Val Tyr Phe Asn Gly Asn Pro Trp
305                 310                 315                 320

Tyr Leu Ala Thr Phe Ala Ala Ala Glu Gln Leu Tyr Asp Ser Val Tyr
                325                 330                 335

Val Trp Lys Lys Thr Gly Ser Ile Thr Val Thr Ser Thr Ser Ser Ala
            340                 345                 350

Phe Phe Gln Glu Leu Val Pro Gly Val Ala Ala Gly Thr Tyr Ser Ser
        355                 360                 365

Ser Gln Ser Thr Phe Thr Ser Ile Ile Asn Ala Ile Ser Thr Tyr Ala
    370                 375                 380

Asp Gly Phe Leu Ser Glu Ala Lys Tyr Val Pro Ala Asp Gly Ser
385                 390                 395                 400

Leu Ala Glu Gln Phe Asp Arg Asn Thr Gly Thr Pro Leu Ser Ala Val
                405                 410                 415

His Leu Thr Trp Ser Tyr Ala Ser Phe Leu Thr Ala Ala Arg Arg
            420                 425                 430

Ala Gly Val Val Pro Pro Ser Trp Ala Ser Ser Gly Ala Asn Thr Val
    435                 440                 445

Pro Ser Ser Cys
    450

<210> SEQ ID NO 10
<211> LENGTH: 37
<212> TYPE: PRT
<213> ORGANISM: Trichoderma reesei

<400> SEQUENCE: 10
```

```
Ser Gly Ala Ser Val Gly Ser Tyr Ser Arg Pro Thr Ala Thr Ser
1               5                   10                  15

Phe Pro Pro Ser Gln Thr Pro Lys Pro Gly Val Pro Ser Gly Thr Pro
                20                  25                  30

Tyr Thr Pro Leu Pro
            35
```

<210> SEQ ID NO 11
<211> LENGTH: 109
<212> TYPE: PRT
<213> ORGANISM: Trichoderma reesei

<400> SEQUENCE: 11

```
Cys Ala Thr Pro Thr Ser Val Ala Val Thr Phe His Glu Leu Val Ser
1               5                   10                  15

Thr Gln Phe Gly Gln Thr Val Lys Val Ala Gly Asn Ala Ala Ala Leu
                20                  25                  30

Gly Asn Trp Ser Thr Ser Ala Ala Val Ala Leu Asp Ala Val Asn Tyr
            35                  40                  45

Ala Asp Asn His Pro Leu Trp Ile Gly Thr Val Asn Leu Glu Ala Gly
50                  55                  60

Asp Val Val Glu Tyr Lys Tyr Ile Asn Val Gly Gln Asp Gly Ser Val
65                  70                  75                  80

Thr Trp Glu Ser Asp Pro Asn His Thr Tyr Thr Val Pro Ala Val Ala
                85                  90                  95

Cys Val Thr Gln Val Val Lys Glu Asp Thr Trp Gln Ser
            100                 105
```

<210> SEQ ID NO 12
<211> LENGTH: 6
<212> TYPE: PRT
<213> ORGANISM: Trichoderma reesei

<400> SEQUENCE: 12

```
Ser Val Asp Asp Phe Ile
1               5
```

<210> SEQ ID NO 13
<211> LENGTH: 25
<212> TYPE: DNA
<213> ORGANISM: Artificial
<220> FEATURE:
<223> OTHER INFORMATION: DNA primer

<400> SEQUENCE: 13
tcgcgttaac gctagcatgg atctc                                    25

<210> SEQ ID NO 14
<211> LENGTH: 25
<212> TYPE: DNA
<213> ORGANISM: Artificial
<220> FEATURE:
<223> OTHER INFORMATION: DNA primer

<400> SEQUENCE: 14
tcgcgttaac gctagcatgg atctc                                    25

<210> SEQ ID NO 15
<211> LENGTH: 45
<212> TYPE: DNA
<213> ORGANISM: Artificial

```
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 15
cgtcaccaag aggtctgttg acnnsttcat cagcaccgag acgcc                45

<210> SEQ ID NO 16
<211> LENGTH: 25
<212> TYPE: DNA
<213> ORGANISM: Artificial
<220> FEATURE:
<223> OTHER INFORMATION: DNA primer

<400> SEQUENCE: 16
gtcaacagac ctcttggtga cgtcg                                      25

<210> SEQ ID NO 17
<211> LENGTH: 48
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 17
caccaagagg tctgttgacg acnnsatcag caccgagacg cctattgc             48

<210> SEQ ID NO 18
<211> LENGTH: 24
<212> TYPE: DNA
<213> ORGANISM: Artificial
<220> FEATURE:
<223> OTHER INFORMATION: DNA primer

<400> SEQUENCE: 18
gtcgtcaaca gacctcttgg tgac                                       24

<210> SEQ ID NO 19
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 19
tgacgacttc atcagcaccg agnnscctat tgcactg                         37

<210> SEQ ID NO 20
<211> LENGTH: 21
<212> TYPE: DNA
<213> ORGANISM: Artificial
<220> FEATURE:
<223> OTHER INFORMATION: DNA primer

<400> SEQUENCE: 20
ctcggtgctg atgaagtcgt c                                          21
```

<210> SEQ ID NO 21
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 21
tcatcagcac cgagacgcct nnsgcactga acaatcttct ttgca            45

<210> SEQ ID NO 22
<211> LENGTH: 25
<212> TYPE: DNA
<213> ORGANISM: Artificial
<220> FEATURE:
<223> OTHER INFORMATION: DNA primer

<400> SEQUENCE: 22
aggcgtctcg gtgctgatga agtcg            25

<210> SEQ ID NO 23
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 23
cagcaccgag acgcctattg cannsaacaa tcttctt            37

<210> SEQ ID NO 24
<211> LENGTH: 21
<212> TYPE: DNA
<213> ORGANISM: Artificial
<220> FEATURE:
<223> OTHER INFORMATION: DNA primer

<400> SEQUENCE: 24
tgcaataggc gtctcggtgc t            21

<210> SEQ ID NO 25
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 25
caccgagacg cctattgcac tgnnsaatct tctttgc            37

<210> SEQ ID NO 26
<211> LENGTH: 21
<212> TYPE: DNA
<213> ORGANISM: Artificial
<220> FEATURE:
<223> OTHER INFORMATION: DNA primer

```
<400> SEQUENCE: 26
cagtgcaata ggcgtctcgg t                                      21

<210> SEQ ID NO 27
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 27
caatcttctt tgcaatgttg gtnnsgatgg atgccgt                     37

<210> SEQ ID NO 28
<211> LENGTH: 22
<212> TYPE: DNA
<213> ORGANISM: Artificial
<220> FEATURE:
<223> OTHER INFORMATION: DNA primer

<400> SEQUENCE: 28
accaacattg caaagaagat tg                                     22

<210> SEQ ID NO 29
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 29
ttctttgcaa tgttggtcct nnsggatgcc gtgcattcgg cacat            45

<210> SEQ ID NO 30
<211> LENGTH: 25
<212> TYPE: DNA
<213> ORGANISM: Artificial
<220> FEATURE:
<223> OTHER INFORMATION: DNA primer

<400> SEQUENCE: 30
aggaccaaca ttgcaaagaa gattg                                  25

<210> SEQ ID NO 31
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 31
gtcctgatgg atgccgtgca nnsggcacat cagctggtgc ggtga            45

<210> SEQ ID NO 32
```

```
<211> LENGTH: 25
<212> TYPE: DNA
<213> ORGANISM: Artificial
<220> FEATURE:
<223> OTHER INFORMATION: DNA primer

<400> SEQUENCE: 32
tgcacggcat ccatcaggac caaca                                              25

<210> SEQ ID NO 33
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 33
tgcggtgatt gcatctccca gcnnsattga cccggac                                 37

<210> SEQ ID NO 34
<211> LENGTH: 22
<212> TYPE: DNA
<213> ORGANISM: Artificial
<220> FEATURE:
<223> OTHER INFORMATION: DNA primer

<400> SEQUENCE: 34
gctgggagat gcaatcaccg ca                                                 22

<210> SEQ ID NO 35
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 35
tgattgcatc tcccagcaca nnsgacccgg actactatta catgt                        45

<210> SEQ ID NO 36
<211> LENGTH: 25
<212> TYPE: DNA
<213> ORGANISM: Artificial
<220> FEATURE:
<223> OTHER INFORMATION: DNA primer

<400> SEQUENCE: 36
tgtgctggga gatgcaatca ccgca                                              25

<210> SEQ ID NO 37
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 37
```

```
ttgcatctcc cagcacaatt nnsccggact actattacat gtgga          45
```

<210> SEQ ID NO 38
<211> LENGTH: 25
<212> TYPE: DNA
<213> ORGANISM: Artificial
<220> FEATURE:
<223> OTHER INFORMATION: DNA primer

<400> SEQUENCE: 38

```
aattgtgctg ggagatgcaa tcacc                                25
```

<210> SEQ ID NO 39
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 39

```
catctcccag cacaattgac nnsgactact attacatgtg gacgc          45
```

<210> SEQ ID NO 40
<211> LENGTH: 25
<212> TYPE: DNA
<213> ORGANISM: Artificial
<220> FEATURE:
<223> OTHER INFORMATION: DNA primer

<400> SEQUENCE: 40

```
gtcaattgtg ctgggagatg caatc                                25
```

<210> SEQ ID NO 41
<211> LENGTH: 46
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 41

```
ctcccagcac aattgacccg nnstactatt acatgtggac gcgaga         46
```

<210> SEQ ID NO 42
<211> LENGTH: 25
<212> TYPE: DNA
<213> ORGANISM: Artificial
<220> FEATURE:
<223> OTHER INFORMATION: DNA primer

<400> SEQUENCE: 42

```
cgggtcaatt gtgctgggag atgca                                25
```

<210> SEQ ID NO 43
<211> LENGTH: 45
<212> TYPE: DNA
<213> ORGANISM: Artificial
<220> FEATURE:
<223> OTHER INFORMATION: DNA primer
<220> FEATURE:

```
<221> NAME/KEY: misc_feature
<222> LOCATION: (21)..(22)
<223> OTHER INFORMATION: n is a, c, g, or t

<400> SEQUENCE: 43
ccagcacaat tgacccggac nnstattaca tgtggacgcg agata                45

<210> SEQ ID NO 44
<211> LENGTH: 25
<212> TYPE: DNA
<213> ORGANISM: Artificial
<220> FEATURE:
<223> OTHER INFORMATION: DNA primer

<400> SEQUENCE: 44
gtccgggtca attgtgctgg gagat                                      25

<210> SEQ ID NO 45
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 45
caattgaccc ggactactat nnsatgtgga cgcgagatag cgctc                45

<210> SEQ ID NO 46
<211> LENGTH: 25
<212> TYPE: DNA
<213> ORGANISM: Artificial
<220> FEATURE:
<223> OTHER INFORMATION: DNA primer

<400> SEQUENCE: 46
atagtagtcc gggtcaattg tgctg                                      25

<210> SEQ ID NO 47
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 47
acccggacta ctattacatg nnsacgcgag atagcgctct tgtct                45

<210> SEQ ID NO 48
<211> LENGTH: 25
<212> TYPE: DNA
<213> ORGANISM: Artificial
<220> FEATURE:
<223> OTHER INFORMATION: DNA primer

<400> SEQUENCE: 48
catgtaatag tagtccgggt caatt                                      25

<210> SEQ ID NO 49
<211> LENGTH: 37
```

```
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 49
gacgcgagat agcgctcttg tcnnsaagaa cctcatc                              37

<210> SEQ ID NO 50
<211> LENGTH: 21
<212> TYPE: DNA
<213> ORGANISM: Artificial
<220> FEATURE:
<223> OTHER INFORMATION: DNA primer

<400> SEQUENCE: 50
gacaagagcg ctatctcgcg t                                               21

<210> SEQ ID NO 51
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 51
gcgagatagc gctcttgtct tcnnsaacct catcgac                              37

<210> SEQ ID NO 52
<211> LENGTH: 21
<212> TYPE: DNA
<213> ORGANISM: Artificial
<220> FEATURE:
<223> OTHER INFORMATION: DNA primer

<400> SEQUENCE: 52
gaagacaaga gcgctatctc g                                               21

<210> SEQ ID NO 53
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 53
agatagcgct cttgtcttca agnnsctcat cgaccgc                              37

<210> SEQ ID NO 54
<211> LENGTH: 21
<212> TYPE: DNA
<213> ORGANISM: Artificial
<220> FEATURE:
<223> OTHER INFORMATION: DNA primer

<400> SEQUENCE: 54
```

```
cttgaagaca agagcgctat c                                              21

<210> SEQ ID NO 55
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 55
tgtcttcaag aacctcatcg acnnsttcac cgaaacg                             37

<210> SEQ ID NO 56
<211> LENGTH: 21
<212> TYPE: DNA
<213> ORGANISM: Artificial
<220> FEATURE:
<223> OTHER INFORMATION: DNA primer

<400> SEQUENCE: 56
gtcgatgagg ttcttgaaga c                                              21

<210> SEQ ID NO 57
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 57
caagaacctc atcgaccgct tcnnsgaaac gtacgat                             37

<210> SEQ ID NO 58
<211> LENGTH: 21
<212> TYPE: DNA
<213> ORGANISM: Artificial
<220> FEATURE:
<223> OTHER INFORMATION: DNA primer

<400> SEQUENCE: 58
gaagcggtcg atgaggttct t                                              21

<210> SEQ ID NO 59
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 59
gaacctcatc gaccgcttca ccnnsacgta cgatgcg                             37

<210> SEQ ID NO 60
<211> LENGTH: 21
<212> TYPE: DNA
<213> ORGANISM: Artificial
```

```
<220> FEATURE:
<223> OTHER INFORMATION: DNA primer

<400> SEQUENCE: 60
ggtgaagcgg tcgatgaggt t                                              21

<210> SEQ ID NO 61
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 61
tcgaccgctt caccgaaacg nnsgatgcgg gcctgcagcg ccgca                    45

<210> SEQ ID NO 62
<211> LENGTH: 25
<212> TYPE: DNA
<213> ORGANISM: Artificial
<220> FEATURE:
<223> OTHER INFORMATION: DNA primer

<400> SEQUENCE: 62
cgtttcggtg aagcggtcga tgagg                                          25

<210> SEQ ID NO 63
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 63
ccgcttcacc gaaacgtacg atnnsggcct gcagcgc                             37

<210> SEQ ID NO 64
<211> LENGTH: 22
<212> TYPE: DNA
<213> ORGANISM: Artificial
<220> FEATURE:
<223> OTHER INFORMATION: DNA primer

<400> SEQUENCE: 64
atcgtacgtt tcggtgaagc gg                                             22

<210> SEQ ID NO 65
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 65
cttcaccgaa acgtacgatg cgnnsctgca gcgccgc                             37
```

<210> SEQ ID NO 66
<211> LENGTH: 21
<212> TYPE: DNA
<213> ORGANISM: Artificial
<220> FEATURE:
<223> OTHER INFORMATION: DNA primer

<400> SEQUENCE: 66
cgcatcgtac gtttcggtga a                                      21

<210> SEQ ID NO 67
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 67
aaacgtacga tgcgggcctg nnscgccgca tcgagcagta catta            45

<210> SEQ ID NO 68
<211> LENGTH: 25
<212> TYPE: DNA
<213> ORGANISM: Artificial
<220> FEATURE:
<223> OTHER INFORMATION: DNA primer

<400> SEQUENCE: 68
caggcccgca tcgtacgttt cggtg                                  25

<210> SEQ ID NO 69
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 69
cgtacgatgc gggcctgcag nnscgcatcg agcagtacat tactg            45

<210> SEQ ID NO 70
<211> LENGTH: 25
<212> TYPE: DNA
<213> ORGANISM: Artificial
<220> FEATURE:
<223> OTHER INFORMATION: DNA primer

<400> SEQUENCE: 70
ctgcaggccc gcatcgtacg tttcg                                  25

<210> SEQ ID NO 71
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 71
ctctccaggg cctctctaac nnstcgggct ccctcgcgga cggct    45

<210> SEQ ID NO 72
<211> LENGTH: 25
<212> TYPE: DNA
<213> ORGANISM: Artificial
<220> FEATURE:
<223> OTHER INFORMATION: DNA primer

<400> SEQUENCE: 72
gttagagagg ccctggagag tgacc    25

<210> SEQ ID NO 73
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 73
gggcctctct aacccctcgg gcnnsctcgc ggacggc    37

<210> SEQ ID NO 74
<211> LENGTH: 21
<212> TYPE: DNA
<213> ORGANISM: Artificial
<220> FEATURE:
<223> OTHER INFORMATION: DNA primer

<400> SEQUENCE: 74
gcccgagggg ttagagaggc c    21

<210> SEQ ID NO 75
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 75
cctctctaac ccctcgggct ccnnsgcgga cggctct    37

<210> SEQ ID NO 76
<211> LENGTH: 21
<212> TYPE: DNA
<213> ORGANISM: Artificial
<220> FEATURE:
<223> OTHER INFORMATION: DNA primer

<400> SEQUENCE: 76
ggagcccgag gggttagaga g    21

<210> SEQ ID NO 77
<211> LENGTH: 37
<212> TYPE: DNA
<213> ORGANISM: Artificial
<220> FEATURE:

```
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 77
ctctaacccc tcgggctccc tcnnsgacgg ctctggt                              37

<210> SEQ ID NO 78
<211> LENGTH: 21
<212> TYPE: DNA
<213> ORGANISM: Artificial
<220> FEATURE:
<223> OTHER INFORMATION: DNA primer

<400> SEQUENCE: 78
gagggagccc gagggggttag a                                              21

<210> SEQ ID NO 79
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 79 accccctcggg ctccctcgcg nnsggctctg gtctcggcga gccca                    45

<210> SEQ ID NO 80
<211> LENGTH: 25
<212> TYPE: DNA
<213> ORGANISM: Artificial
<220> FEATURE:
<223> OTHER INFORMATION: DNA primer

<400> SEQUENCE: 80
cgcgagggag cccgaggggt tagag                                           25

<210> SEQ ID NO 81
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 81
ctcgggctcc ctcgcggacg gcnnsggtct cggcgag                              37

<210> SEQ ID NO 82
<211> LENGTH: 21
<212> TYPE: DNA
<213> ORGANISM: Artificial
<220> FEATURE:
<223> OTHER INFORMATION: DNA primer

<400> SEQUENCE: 82
gccgtccgcg agggagcccg a                                               21
```

```
<210> SEQ ID NO 83
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 83
tggtctcggc gagcccaagt ttnnsttgac cctgaag                37

<210> SEQ ID NO 84
<211> LENGTH: 22
<212> TYPE: DNA
<213> ORGANISM: Artificial
<220> FEATURE:
<223> OTHER INFORMATION: DNA primer

<400> SEQUENCE: 84
aaacttgggc tcgccgagac ca                22

<210> SEQ ID NO 85
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 85
tctcggcgag cccaagtttg agnnsaccct gaagcct                37

<210> SEQ ID NO 86
<211> LENGTH: 21
<212> TYPE: DNA
<213> ORGANISM: Artificial
<220> FEATURE:
<223> OTHER INFORMATION: DNA primer

<400> SEQUENCE: 86
ctcaaacttg ggctcgccga g                21

<210> SEQ ID NO 87
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 87
cgagcccaag tttgagttga ccnnsaagcc tttcacc                37

<210> SEQ ID NO 88
<211> LENGTH: 21
<212> TYPE: DNA
<213> ORGANISM: Artificial
<220> FEATURE:
<223> OTHER INFORMATION: DNA primer
```

```
<400> SEQUENCE: 88
ggtcaactca aacttgggct c                                              21

<210> SEQ ID NO 89
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 89
ccaagtttga gttgaccctg nnsccttca ccggcaactg gggtc                     45

<210> SEQ ID NO 90
<211> LENGTH: 25
<212> TYPE: DNA
<213> ORGANISM: Artificial
<220> FEATURE:
<223> OTHER INFORMATION: DNA primer

<400> SEQUENCE: 90
cagggtcaac tcaaacttgg gctcg                                          25

<210> SEQ ID NO 91
<211> LENGTH: 46
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 91
ttgagttgac cctgaagcct nnsaccggca actggggtcg accgca                   46

<210> SEQ ID NO 92
<211> LENGTH: 25
<212> TYPE: DNA
<213> ORGANISM: Artificial
<220> FEATURE:
<223> OTHER INFORMATION: DNA primer

<400> SEQUENCE: 92
aggcttcagg gtcaactcaa acttg                                          25

<210> SEQ ID NO 93
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 93
ccctgaagcc tttcaccggc nnstggggtc gaccgcagcg ggatg                    45

<210> SEQ ID NO 94
<211> LENGTH: 25
```

<210> SEQ ID NO 94
<211> LENGTH: 25
<212> TYPE: DNA
<213> ORGANISM: Artificial
<220> FEATURE:
<223> OTHER INFORMATION: DNA primer

<400> SEQUENCE: 94
gccggtgaaa ggcttcaggg tcaac                                           25

<210> SEQ ID NO 95
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 95
ctttcaccgg caactggggt nnsccgcagc gggatggccc agctc                     45

<210> SEQ ID NO 96
<211> LENGTH: 25
<212> TYPE: DNA
<213> ORGANISM: Artificial
<220> FEATURE:
<223> OTHER INFORMATION: DNA primer

<400> SEQUENCE: 96
accccagttg ccggtgaaag gcttc                                           25

<210> SEQ ID NO 97
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 97
gcaactgggg tcgaccgcag nnsgatggcc cagctctgcg agcca                     45

<210> SEQ ID NO 98
<211> LENGTH: 25
<212> TYPE: DNA
<213> ORGANISM: Artificial
<220> FEATURE:
<223> OTHER INFORMATION: DNA primer

<400> SEQUENCE: 98
ctgcggtcga ccccagttgc cggtg                                           25

<210> SEQ ID NO 99
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 99
ggatggccca gctctgcgag ccnnsgcctt gattgga    37

<210> SEQ ID NO 100
<211> LENGTH: 22
<212> TYPE: DNA
<213> ORGANISM: Artificial
<220> FEATURE:
<223> OTHER INFORMATION: DNA primer

<400> SEQUENCE: 100
ggctcgcaga gctgggccat cc    22

<210> SEQ ID NO 101
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 101
tgcgagccat tgccttgatt nnstactcaa agtggctcat caaca    45

<210> SEQ ID NO 102
<211> LENGTH: 25
<212> TYPE: DNA
<213> ORGANISM: Artificial
<220> FEATURE:
<223> OTHER INFORMATION: DNA primer

<400> SEQUENCE: 102
aatcaaggca atggctcgca gagct    25

<210> SEQ ID NO 103
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 103
cattgccttg attggatact cannstggct catcaac    37

<210> SEQ ID NO 104
<211> LENGTH: 22
<212> TYPE: DNA
<213> ORGANISM: Artificial
<220> FEATURE:
<223> OTHER INFORMATION: DNA primer

<400> SEQUENCE: 104
tgagtatcca atcaaggcaa tg    22

<210> SEQ ID NO 105
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature

```
<222> LOCATION: (23)..(24)
<223> OTHER INFORMATION: n is a, c, g, or t

<400> SEQUENCE: 105
tggatactca aagtggctca tcnnsaacaa ctatcag                              37

<210> SEQ ID NO 106
<211> LENGTH: 21
<212> TYPE: DNA
<213> ORGANISM: Artificial
<220> FEATURE:
<223> OTHER INFORMATION: DNA primer

<400> SEQUENCE: 106
gatgagccac tttgagtatc c                                              21

<210> SEQ ID NO 107
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 107
atactcaaag tggctcatca acnnsaacta tcagtcg                              37

<210> SEQ ID NO 108
<211> LENGTH: 21
<212> TYPE: DNA
<213> ORGANISM: Artificial
<220> FEATURE:
<223> OTHER INFORMATION: DNA primer

<400> SEQUENCE: 108
gttgatgagc cactttgagt a                                              21

<210> SEQ ID NO 109
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 109
caaagtggct catcaacaac nnstatcagt cgactgtgtc caacg                     45

<210> SEQ ID NO 110
<211> LENGTH: 25
<212> TYPE: DNA
<213> ORGANISM: Artificial
<220> FEATURE:
<223> OTHER INFORMATION: DNA primer

<400> SEQUENCE: 110
gttgttgatg agccactttg agtat                                          25

<210> SEQ ID NO 111
<211> LENGTH: 37
<212> TYPE: DNA
```

```
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 111
aaagtggctc atcaacaaca acnnscagtc gactgtg                              37

<210> SEQ ID NO 112
<211> LENGTH: 21
<212> TYPE: DNA
<213> ORGANISM: Artificial
<220> FEATURE:
<223> OTHER INFORMATION: DNA primer

<400> SEQUENCE: 112
gttgttgttg atgagccact t                                               21

<210> SEQ ID NO 113
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 113
ggctcatcaa caacaactat nnstcgactg tgtccaacgt catct                     45

<210> SEQ ID NO 114
<211> LENGTH: 25
<212> TYPE: DNA
<213> ORGANISM: Artificial
<220> FEATURE:
<223> OTHER INFORMATION: DNA primer

<400> SEQUENCE: 114
atagttgttg ttgatgagcc acttt                                           25

<210> SEQ ID NO 115
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 115
caacaactat cagtcgactg tgnnsaacgt catctgg                              37

<210> SEQ ID NO 116
<211> LENGTH: 21
<212> TYPE: DNA
<213> ORGANISM: Artificial
<220> FEATURE:
<223> OTHER INFORMATION: DNA primer

<400> SEQUENCE: 116
cacagtcgac tgatagttgt t                                               21
```

<210> SEQ ID NO 117
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 117
caactatcag tcgactgtgt ccnnsgtcat ctggcct        37

<210> SEQ ID NO 118
<211> LENGTH: 21
<212> TYPE: DNA
<213> ORGANISM: Artificial
<220> FEATURE:
<223> OTHER INFORMATION: DNA primer

<400> SEQUENCE: 118
ggacacagtc gactgatagt t        21

<210> SEQ ID NO 119
<211> LENGTH: 38
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 119
gcctattgtg cgcaacgacc tcnnstatgt tgcccagt        38

<210> SEQ ID NO 120
<211> LENGTH: 21
<212> TYPE: DNA
<213> ORGANISM: Artificial
<220> FEATURE:
<223> OTHER INFORMATION: DNA primer

<400> SEQUENCE: 120
gaggtcgttg cgcacaatag g        21

<210> SEQ ID NO 121
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 121
acctcaacta tgttgcccag nnstggaacc aaaccggctt tgacc        45

<210> SEQ ID NO 122
<211> LENGTH: 25
<212> TYPE: DNA
<213> ORGANISM: Artificial
<220> FEATURE:

```
<223> OTHER INFORMATION: DNA primer

<400> SEQUENCE: 122
ctgggcaaca tagttgaggt cgttg                                   25

<210> SEQ ID NO 123
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 123
atgttgccca gtactggaac nnsaccggct tgacctctg ggaag              45

<210> SEQ ID NO 124
<211> LENGTH: 25
<212> TYPE: DNA
<213> ORGANISM: Artificial
<220> FEATURE:
<223> OTHER INFORMATION: DNA primer

<400> SEQUENCE: 124
gttccagtac tgggcaacat agttg                                   25

<210> SEQ ID NO 125
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 125
agtactggaa ccaaaccggc nnsgacctct gggaagaagt caatg              45

<210> SEQ ID NO 126
<211> LENGTH: 25
<212> TYPE: DNA
<213> ORGANISM: Artificial
<220> FEATURE:
<223> OTHER INFORMATION: DNA primer

<400> SEQUENCE: 126
gccggtttgg ttccagtact gggca                                   25

<210> SEQ ID NO 127
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 127
accaaaccgg ctttgacctc nnsgaagaag tcaatgggag ctcat              45
```

```
<210> SEQ ID NO 128
<211> LENGTH: 25
<212> TYPE: DNA
<213> ORGANISM: Artificial
<220> FEATURE:
<223> OTHER INFORMATION: DNA primer

<400> SEQUENCE: 128
gaggtcaaag ccggtttggt tccag                                          25

<210> SEQ ID NO 129
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 129
ccggctttga cctctgggaa nnsgtcaatg ggagctcatt cttta                    45

<210> SEQ ID NO 130
<211> LENGTH: 25
<212> TYPE: DNA
<213> ORGANISM: Artificial
<220> FEATURE:
<223> OTHER INFORMATION: DNA primer

<400> SEQUENCE: 130
ttcccagagg tcaaagccgg tttgg                                          25

<210> SEQ ID NO 131
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 131
gctttgacct ctgggaagaa nnsaatggga gctcattctt tactg                    45

<210> SEQ ID NO 132
<211> LENGTH: 25
<212> TYPE: DNA
<213> ORGANISM: Artificial
<220> FEATURE:
<223> OTHER INFORMATION: DNA primer

<400> SEQUENCE: 132
ttcttcccag aggtcaaagc cggtt                                          25

<210> SEQ ID NO 133
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t
```

```
<400> SEQUENCE: 133
ctttgacctc tgggaagaag tcnnsgggag ctcattc                              37

<210> SEQ ID NO 134
<211> LENGTH: 22
<212> TYPE: DNA
<213> ORGANISM: Artificial
<220> FEATURE:
<223> OTHER INFORMATION: DNA primer

<400> SEQUENCE: 134
gacttcttcc cagaggtcaa ag                                             22

<210> SEQ ID NO 135
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 135
tgtcgagggc gccactcttg ctnnsactct tggccag                             37

<210> SEQ ID NO 136
<211> LENGTH: 21
<212> TYPE: DNA
<213> ORGANISM: Artificial
<220> FEATURE:
<223> OTHER INFORMATION: DNA primer

<400> SEQUENCE: 136
agcaagagtg gcgccctcga c                                              21

<210> SEQ ID NO 137
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 137
cgagggcgcc actcttgctg ccnnscttgg ccagtcg                             37

<210> SEQ ID NO 138
<211> LENGTH: 21
<212> TYPE: DNA
<213> ORGANISM: Artificial
<220> FEATURE:
<223> OTHER INFORMATION: DNA primer

<400> SEQUENCE: 138
ggcagcaaga gtggcgccct c                                              21

<210> SEQ ID NO 139
<211> LENGTH: 45
<212> TYPE: DNA
<213> ORGANISM: Artificial
<220> FEATURE:
<223> OTHER INFORMATION: DNA primer
```

```
<220> FEATURE:
<221> NAME/KEY: misc_feature
<222> LOCATION: (21)..(22)
<223> OTHER INFORMATION: n is a, c, g, or t

<400> SEQUENCE: 139
ctcttgctgc cactcttggc nnstcgggaa gcgcttattc atctg            45

<210> SEQ ID NO 140
<211> LENGTH: 25
<212> TYPE: DNA
<213> ORGANISM: Artificial
<220> FEATURE:
<223> OTHER INFORMATION: DNA primer

<400> SEQUENCE: 140
gccaagagtg gcagcaagag tggcg                                   25

<210> SEQ ID NO 141
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 141
ccactcttgg ccagtcggga nnsgcttatt catctgttgc tcccc            45

<210> SEQ ID NO 142
<211> LENGTH: 25
<212> TYPE: DNA
<213> ORGANISM: Artificial
<220> FEATURE:
<223> OTHER INFORMATION: DNA primer

<400> SEQUENCE: 142
tcccgactgg ccaagagtgg cagca                                   25

<210> SEQ ID NO 143
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 143
tggccagtcg ggaagcgctt atnnstctgt tgctccc                     37

<210> SEQ ID NO 144
<211> LENGTH: 21
<212> TYPE: DNA
<213> ORGANISM: Artificial
<220> FEATURE:
<223> OTHER INFORMATION: DNA primer

<400> SEQUENCE: 144
ataagcgctt cccgactggc c                                       21

<210> SEQ ID NO 145
```

```
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 145
gtcgggaagc gcttattcat ctnnsgctcc ccaggtt                              37

<210> SEQ ID NO 146
<211> LENGTH: 21
<212> TYPE: DNA
<213> ORGANISM: Artificial
<220> FEATURE:
<223> OTHER INFORMATION: DNA primer

<400> SEQUENCE: 146
agatgaataa gcgcttcccg a                                              21

<210> SEQ ID NO 147
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 147
cgcttattca tctgttgctc ccnnsgtttt gtgcttt                              37

<210> SEQ ID NO 148
<211> LENGTH: 21
<212> TYPE: DNA
<213> ORGANISM: Artificial
<220> FEATURE:
<223> OTHER INFORMATION: DNA primer

<400> SEQUENCE: 148
gggagcaaca gatgaataag c                                              21

<210> SEQ ID NO 149
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 149
tgtgctttct ccaacgattc nnsgtgtcgt ctggtggata cgtcg                     45

<210> SEQ ID NO 150
<211> LENGTH: 26
<212> TYPE: DNA
<213> ORGANISM: Artificial
<220> FEATURE:
<223> OTHER INFORMATION: DNA primer

<400> SEQUENCE: 150
```

```
gaatcgttgg agaaagcaca aaacct                                          26
```

```
<210> SEQ ID NO 151
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 151
gtgctttctc caacgattct ggnnstcgtc tggtgga                              37
```

```
<210> SEQ ID NO 152
<211> LENGTH: 21
<212> TYPE: DNA
<213> ORGANISM: Artificial
<220> FEATURE:
<223> OTHER INFORMATION: DNA primer

<400> SEQUENCE: 152
ccagaatcgt tggagaaagc a                                               21
```

```
<210> SEQ ID NO 153
<211> LENGTH: 38
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 153
ctttctccaa cgattctggg tgnnstctgg tggatacg                             38
```

```
<210> SEQ ID NO 154
<211> LENGTH: 21
<212> TYPE: DNA
<213> ORGANISM: Artificial
<220> FEATURE:
<223> OTHER INFORMATION: DNA primer

<400> SEQUENCE: 154
cacccagaat cgttggagaa a                                               21
```

```
<210> SEQ ID NO 155
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 155
tctccaacga ttctgggtgt cgnnsggtgg atacgtc                              37
```

```
<210> SEQ ID NO 156
<211> LENGTH: 22
<212> TYPE: DNA
```

```
<213> ORGANISM: Artificial
<220> FEATURE:
<223> OTHER INFORMATION: DNA primer

<400> SEQUENCE: 156
cgacacccag aatcgttgga ga                                              22

<210> SEQ ID NO 157
<211> LENGTH: 39
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 157
ggtgtcgtct ggtggatacg tcnnstccaa catcaacac                            39

<210> SEQ ID NO 158
<211> LENGTH: 21
<212> TYPE: DNA
<213> ORGANISM: Artificial
<220> FEATURE:
<223> OTHER INFORMATION: DNA primer

<400> SEQUENCE: 158
gacgtatcca ccagacgaca c                                               21

<210> SEQ ID NO 159
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 159
tggtggatac gtcgactcca acnnsaacac caacgag                              37

<210> SEQ ID NO 160
<211> LENGTH: 21
<212> TYPE: DNA
<213> ORGANISM: Artificial
<220> FEATURE:
<223> OTHER INFORMATION: DNA primer

<400> SEQUENCE: 160
gttggagtcg acgtatccac c                                               21

<210> SEQ ID NO 161
<211> LENGTH: 38
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 161
tggatacgtc gactccaaca tcnnsaccaa cgagggca                             38
```

<210> SEQ ID NO 162
<211> LENGTH: 22
<212> TYPE: DNA
<213> ORGANISM: Artificial
<220> FEATURE:
<223> OTHER INFORMATION: DNA primer

<400> SEQUENCE: 162
gatgttggag tcgacgtatc ca                                        22

<210> SEQ ID NO 163
<211> LENGTH: 39
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 163
atacgtcgac tccaacatca acnnsaacga gggcaggac                      39

<210> SEQ ID NO 164
<211> LENGTH: 21
<212> TYPE: DNA
<213> ORGANISM: Artificial
<220> FEATURE:
<223> OTHER INFORMATION: DNA primer

<400> SEQUENCE: 164
gttgatgttg gagtcgacgt a                                         21

<210> SEQ ID NO 165
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 165
tcgactccaa catcaacacc nnsgagggca ggactggcaa ggatg               45

<210> SEQ ID NO 166
<211> LENGTH: 25
<212> TYPE: DNA
<213> ORGANISM: Artificial
<220> FEATURE:
<223> OTHER INFORMATION: DNA primer

<400> SEQUENCE: 166
ggtgttgatg ttggagtcga cgtat                                     25

<210> SEQ ID NO 167
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)

<223> OTHER INFORMATION: n is a, c, g, or t

<400> SEQUENCE: 167
actccaacat caacaccaac nnsggcagga ctggcaagga tgtca    45

<210> SEQ ID NO 168
<211> LENGTH: 25
<212> TYPE: DNA
<213> ORGANISM: Artificial
<220> FEATURE:
<223> OTHER INFORMATION: DNA primer

<400> SEQUENCE: 168
gttggtgttg atgttggagt cgacg    25

<210> SEQ ID NO 169
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 169
ctccaacatc aacaccaacg agnnsaggac tggcaag    37

<210> SEQ ID NO 170
<211> LENGTH: 23
<212> TYPE: DNA
<213> ORGANISM: Artificial
<220> FEATURE:
<223> OTHER INFORMATION: DNA primer

<400> SEQUENCE: 170
ctcgttggtg ttgatgttgg agt    23

<210> SEQ ID NO 171
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 171
acatcaacac caacgagggc nnsactggca aggatgtcaa ctccg    45

<210> SEQ ID NO 172
<211> LENGTH: 26
<212> TYPE: DNA
<213> ORGANISM: Artificial
<220> FEATURE:
<223> OTHER INFORMATION: DNA primer

<400> SEQUENCE: 172
gccctcgttg gtgttgatgt tggagt    26

<210> SEQ ID NO 173
<211> LENGTH: 37
<212> TYPE: DNA
<213> ORGANISM: Artificial

```
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 173
ttccatccac accttcgatc ccnnscttgg ctgtgac                              37

<210> SEQ ID NO 174
<211> LENGTH: 21
<212> TYPE: DNA
<213> ORGANISM: Artificial
<220> FEATURE:
<223> OTHER INFORMATION: DNA primer

<400> SEQUENCE: 174
gggatcgaag gtgtggatgg a                                              21

<210> SEQ ID NO 175
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 175
catccacacc ttcgatccca acnnsggctg tgacgca                              37

<210> SEQ ID NO 176
<211> LENGTH: 21
<212> TYPE: DNA
<213> ORGANISM: Artificial
<220> FEATURE:
<223> OTHER INFORMATION: DNA primer

<400> SEQUENCE: 176
gttgggatcg aaggtgtgga t                                              21

<210> SEQ ID NO 177
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 177
ccacaccttc gatcccaacc ttnnstgtga cgcaggc                              37

<210> SEQ ID NO 178
<211> LENGTH: 21
<212> TYPE: DNA
<213> ORGANISM: Artificial
<220> FEATURE:
<223> OTHER INFORMATION: DNA primer

<400> SEQUENCE: 178
aaggttggga tcgaaggtgt g                                              21
```

<210> SEQ ID NO 179
<211> LENGTH: 38
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 179
cgatcccaac cttggctgtg acnnsggcac cttccagc                         38

<210> SEQ ID NO 180
<211> LENGTH: 21
<212> TYPE: DNA
<213> ORGANISM: Artificial
<220> FEATURE:
<223> OTHER INFORMATION: DNA primer

<400> SEQUENCE: 180
gtcacagcca aggttgggat c                                           21

<210> SEQ ID NO 181
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 181
tcccaacctt ggctgtgacg cannsacctt ccagcca                          37

<210> SEQ ID NO 182
<211> LENGTH: 21
<212> TYPE: DNA
<213> ORGANISM: Artificial
<220> FEATURE:
<223> OTHER INFORMATION: DNA primer

<400> SEQUENCE: 182
tgcgtcacag ccaaggttgg g                                           21

<210> SEQ ID NO 183
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 183
aggcaccttc cagccatgca gtnnsaaagc gctctcc                          37

<210> SEQ ID NO 184
<211> LENGTH: 21
<212> TYPE: DNA
<213> ORGANISM: Artificial
<220> FEATURE:
<223> OTHER INFORMATION: DNA primer

<400> SEQUENCE: 184
actgcatggc tggaaggtgc c                                                 21

<210> SEQ ID NO 185
<211> LENGTH: 38
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 185
caaagcgctc tccaacctca agnnsgttgt cgactcct                               38

<210> SEQ ID NO 186
<211> LENGTH: 21
<212> TYPE: DNA
<213> ORGANISM: Artificial
<220> FEATURE:
<223> OTHER INFORMATION: DNA primer

<400> SEQUENCE: 186
cttgaggttg gagagcgctt t                                                 21

<210> SEQ ID NO 187
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 187
ggttgttgtc gactccttcc gcnnsatcta cggcgtg                                37

<210> SEQ ID NO 188
<211> LENGTH: 21
<212> TYPE: DNA
<213> ORGANISM: Artificial
<220> FEATURE:
<223> OTHER INFORMATION: DNA primer

<400> SEQUENCE: 188
gcggaaggag tcgacaacaa c                                                 21

<210> SEQ ID NO 189
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 189
ttgtcgactc cttccgctcc nnstacggcg tgaacaaggg cattc                       45

<210> SEQ ID NO 190

```
<211> LENGTH: 25
<212> TYPE: DNA
<213> ORGANISM: Artificial
<220> FEATURE:
<223> OTHER INFORMATION: DNA primer

<400> SEQUENCE: 190
ggagcggaag gagtcgacaa caacc                                          25

<210> SEQ ID NO 191
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 191
actccttccg ctccatctac nnsgtgaaca agggcattcc tgccg                    45

<210> SEQ ID NO 192
<211> LENGTH: 25
<212> TYPE: DNA
<213> ORGANISM: Artificial
<220> FEATURE:
<223> OTHER INFORMATION: DNA primer

<400> SEQUENCE: 192
gtagatggag cggaaggagt cgaca                                          25

<210> SEQ ID NO 193
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 193
gctccatcta cggcgtgaac nnsggcattc ctgccggtgc tgccg                    45

<210> SEQ ID NO 194
<211> LENGTH: 25
<212> TYPE: DNA
<213> ORGANISM: Artificial
<220> FEATURE:
<223> OTHER INFORMATION: DNA primer

<400> SEQUENCE: 194
gttcacgccg tagatggagc ggaag                                          25

<210> SEQ ID NO 195
<211> LENGTH: 38
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 195
```

```
ctacggcgtg aacaagggca ttnnsgccgg tgctgccg                              38
```

<210> SEQ ID NO 196
<211> LENGTH: 21
<212> TYPE: DNA
<213> ORGANISM: Artificial
<220> FEATURE:
<223> OTHER INFORMATION: DNA primer

<400> SEQUENCE: 196

```
aatgcccttg ttcacgccgt a                                               21
```

<210> SEQ ID NO 197
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 197

```
cggcgtgaac aagggcattc ctnnsggtgc tgccgtc                              37
```

<210> SEQ ID NO 198
<211> LENGTH: 21
<212> TYPE: DNA
<213> ORGANISM: Artificial
<220> FEATURE:
<223> OTHER INFORMATION: DNA primer

<400> SEQUENCE: 198

```
aggaatgccc ttgttcacgc c                                               21
```

<210> SEQ ID NO 199
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 199

```
gaacaagggc attcctgccg gtnnsgccgt cgccatt                              37
```

<210> SEQ ID NO 200
<211> LENGTH: 21
<212> TYPE: DNA
<213> ORGANISM: Artificial
<220> FEATURE:
<223> OTHER INFORMATION: DNA primer

<400> SEQUENCE: 200

```
accggcagga atgcccttgt t                                               21
```

<210> SEQ ID NO 201
<211> LENGTH: 45
<212> TYPE: DNA
<213> ORGANISM: Artificial
<220> FEATURE:
<223> OTHER INFORMATION: DNA primer
<220> FEATURE:

<221> NAME/KEY: misc_feature
<222> LOCATION: (21)..(22)
<223> OTHER INFORMATION: n is a, c, g, or t

<400> SEQUENCE: 201
gtgctgccgt cgccattggc nnstatgcag aggatgtgta ctaca            45

<210> SEQ ID NO 202
<211> LENGTH: 25
<212> TYPE: DNA
<213> ORGANISM: Artificial
<220> FEATURE:
<223> OTHER INFORMATION: DNA primer

<400> SEQUENCE: 202
gccaatggcg acggcagcac cggca            25

<210> SEQ ID NO 203
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 203
ctgccgtcgc cattggccgg nnsgcagagg atgtgtacta caacg            45

<210> SEQ ID NO 204
<211> LENGTH: 25
<212> TYPE: DNA
<213> ORGANISM: Artificial
<220> FEATURE:
<223> OTHER INFORMATION: DNA primer

<400> SEQUENCE: 204
ccggccaatg gcgacggcag caccg            25

<210> SEQ ID NO 205
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 205
tgccgtcgcc attggccggt atnnsgagga tgtgtac            37

<210> SEQ ID NO 206
<211> LENGTH: 21
<212> TYPE: DNA
<213> ORGANISM: Artificial
<220> FEATURE:
<223> OTHER INFORMATION: DNA primer

<400> SEQUENCE: 206
ataccggcca atggcgacgg c            21

<210> SEQ ID NO 207
<211> LENGTH: 45

```
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 207
ccattggccg gtatgcagag nnsgtgtact acaacggcaa ccctt            45

<210> SEQ ID NO 208
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 208
ccattggccg gtatgcagag nnsgtgtact acaacggcaa ccctt            45

<210> SEQ ID NO 209
<211> LENGTH: 25
<212> TYPE: DNA
<213> ORGANISM: Artificial
<220> FEATURE:
<223> OTHER INFORMATION: DNA primer

<400> SEQUENCE: 209
ctctgcatac cggccaatgg cgacg                                  25

<210> SEQ ID NO 210
<211> LENGTH: 25
<212> TYPE: DNA
<213> ORGANISM: Artificial
<220> FEATURE:
<223> OTHER INFORMATION: DNA primer

<400> SEQUENCE: 210
ctctgcatac cggccaatgg cgacg                                  25

<210> SEQ ID NO 211
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 211
ttggccggta tgcagaggat nnstactaca acggcaaccc ttggt            45

<210> SEQ ID NO 212
<211> LENGTH: 25
<212> TYPE: DNA
<213> ORGANISM: Artificial
<220> FEATURE:
<223> OTHER INFORMATION: DNA primer

<400> SEQUENCE: 212
```
atcctctgca taccggccaa tggcg                                    25

<210> SEQ ID NO 213
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 213
gccggtatgc agaggatgtg nnstacaacg gcaacccttg gtatc              45

<210> SEQ ID NO 214
<211> LENGTH: 25
<212> TYPE: DNA
<213> ORGANISM: Artificial
<220> FEATURE:
<223> OTHER INFORMATION: DNA primer

<400> SEQUENCE: 214
cacatcctct gcataccggc caatg                                    25

<210> SEQ ID NO 215
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 215
ggtatgcaga ggatgtgtac nnsaacggca accttggta tcttg               45

<210> SEQ ID NO 216
<211> LENGTH: 27
<212> TYPE: DNA
<213> ORGANISM: Artificial
<220> FEATURE:
<223> OTHER INFORMATION: DNA primer

<400> SEQUENCE: 216
gtacacatcc tctgcatacc ggccaat                                  27

<210> SEQ ID NO 217
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 217
atgcagagga tgtgtactac nnsggcaacc cttggtatct tgcta              45

<210> SEQ ID NO 218
<211> LENGTH: 45
<212> TYPE: DNA
<213> ORGANISM: Artificial

```
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 218
atgcagagga tgtgtactac nnsggcaacc cttggtatct tgcta          45

<210> SEQ ID NO 219
<211> LENGTH: 26
<212> TYPE: DNA
<213> ORGANISM: Artificial
<220> FEATURE:
<223> OTHER INFORMATION: DNA primer

<400> SEQUENCE: 219
gtagtacaca tcctctgcat accggc                                26

<210> SEQ ID NO 220
<211> LENGTH: 26
<212> TYPE: DNA
<213> ORGANISM: Artificial
<220> FEATURE:
<223> OTHER INFORMATION: DNA primer

<400> SEQUENCE: 220
gtagtacaca tcctctgcat accggc                                26

<210> SEQ ID NO 221
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 221
tgtactacaa cggcaaccct nnstatcttg ctacatttgc tgctg           45

<210> SEQ ID NO 222
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 222
tgtactacaa cggcaaccct nnstatcttg ctacatttgc tgctg           45

<210> SEQ ID NO 223
<211> LENGTH: 25
<212> TYPE: DNA
<213> ORGANISM: Artificial
<220> FEATURE:
<223> OTHER INFORMATION: DNA primer

<400> SEQUENCE: 223
agggttgccg ttgtagtaca catcc                                 25
```

<210> SEQ ID NO 224
<211> LENGTH: 25
<212> TYPE: DNA
<213> ORGANISM: Artificial
<220> FEATURE:
<223> OTHER INFORMATION: DNA primer

<400> SEQUENCE: 224
agggttgccg ttgtagtaca catcc                                                25

<210> SEQ ID NO 225
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 225
gcagctgtac gatgccatct acnnstggaa gaagacg                                   37

<210> SEQ ID NO 226
<211> LENGTH: 21
<212> TYPE: DNA
<213> ORGANISM: Artificial
<220> FEATURE:
<223> OTHER INFORMATION: DNA primer

<400> SEQUENCE: 226
gtagatggca tcgtacagct g                                                    21

<210> SEQ ID NO 227
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 227
acgatgccat ctacgtctgg nnsaagacgg gctccatcac ggtga                          45

<210> SEQ ID NO 228
<211> LENGTH: 25
<212> TYPE: DNA
<213> ORGANISM: Artificial
<220> FEATURE:
<223> OTHER INFORMATION: DNA primer

<400> SEQUENCE: 228
ccagacgtag atggcatcgt acagc                                                25

<210> SEQ ID NO 229
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

```
<400> SEQUENCE: 229
atgccatcta cgtctggaag nnsacgggct ccatcacggt gaccg        45

<210> SEQ ID NO 230
<211> LENGTH: 28
<212> TYPE: DNA
<213> ORGANISM: Artificial
<220> FEATURE:
<223> OTHER INFORMATION: DNA primer

<400> SEQUENCE: 230
cttccagacg tagatggcat cgtacagc                            28

<210> SEQ ID NO 231
<211> LENGTH: 38
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (24)..(25)
<223> OTHER INFORMATION: n is a, c, g, or t

<400> SEQUENCE: 231
atgccatcta cgtctggaag aagnnsggct ccatcacg                 38

<210> SEQ ID NO 232
<211> LENGTH: 21
<212> TYPE: DNA
<213> ORGANISM: Artificial
<220> FEATURE:
<223> OTHER INFORMATION: DNA primer

<400> SEQUENCE: 232
cttcttccag acgtagatgg c                                   21

<210> SEQ ID NO 233
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 233
ctacgtctgg aagaagacgg gcnnsatcac ggtgacc                  37

<210> SEQ ID NO 234
<211> LENGTH: 22
<212> TYPE: DNA
<213> ORGANISM: Artificial
<220> FEATURE:
<223> OTHER INFORMATION: DNA primer

<400> SEQUENCE: 234
gcccgtcttc ttccagacgt ag                                  22

<210> SEQ ID NO 235
<211> LENGTH: 39
<212> TYPE: DNA
<213> ORGANISM: Artificial
<220> FEATURE:
```

```
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 235
ctggaagaag acgggctcca tcnnsgtgac cgccacctc                               39

<210> SEQ ID NO 236
<211> LENGTH: 21
<212> TYPE: DNA
<213> ORGANISM: Artificial
<220> FEATURE:
<223> OTHER INFORMATION: DNA primer

<400> SEQUENCE: 236
gatggagccc gtcttcttcc a                                                 21

<210> SEQ ID NO 237
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 237
gacgggctcc atcacggtga ccnnsacctc cctggcc                                37

<210> SEQ ID NO 238
<211> LENGTH: 21
<212> TYPE: DNA
<213> ORGANISM: Artificial
<220> FEATURE:
<223> OTHER INFORMATION: DNA primer

<400> SEQUENCE: 238
ggtcaccgtg atggagcccg t                                                 21

<210> SEQ ID NO 239
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 239
gctccatcac ggtgaccgcc nnstccctgg ccttcttcca ggagc                       45

<210> SEQ ID NO 240
<211> LENGTH: 25
<212> TYPE: DNA
<213> ORGANISM: Artificial
<220> FEATURE:
<223> OTHER INFORMATION: DNA primer

<400> SEQUENCE: 240
ggcggtcacc gtgatggagc ccgtc                                             25
```

```
<210> SEQ ID NO 241
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 241
ccacctccct ggccttcttc nnsgagcttg ttcctggcgt gacgg          45

<210> SEQ ID NO 242
<211> LENGTH: 25
<212> TYPE: DNA
<213> ORGANISM: Artificial
<220> FEATURE:
<223> OTHER INFORMATION: DNA primer

<400> SEQUENCE: 242
gaagaaggcc agggaggtgg cggtc                                25

<210> SEQ ID NO 243
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 243
cctggccttc ttccaggagc ttnnscctgg cgtgacg                   37

<210> SEQ ID NO 244
<211> LENGTH: 21
<212> TYPE: DNA
<213> ORGANISM: Artificial
<220> FEATURE:
<223> OTHER INFORMATION: DNA primer

<400> SEQUENCE: 244
aagctcctgg aagaaggcca g                                    21

<210> SEQ ID NO 245
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 245
cttcttccag gagcttgttc ctnnsgtgac ggccggg                   37

<210> SEQ ID NO 246
<211> LENGTH: 21
<212> TYPE: DNA
<213> ORGANISM: Artificial
<220> FEATURE:
<223> OTHER INFORMATION: DNA primer
```

```
<400> SEQUENCE: 246
aggaacaagc tcctggaaga a                                              21

<210> SEQ ID NO 247
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 247
aggagcttgt tcctggcgtg nnsgccggga cctactccag cagct                    45

<210> SEQ ID NO 248
<211> LENGTH: 25
<212> TYPE: DNA
<213> ORGANISM: Artificial
<220> FEATURE:
<223> OTHER INFORMATION: DNA primer

<400> SEQUENCE: 248
cacgccagga acaagctcct ggaag                                          25

<210> SEQ ID NO 249
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 249
ggagcttgtt cctggcgtga cgnnsgggac ctactcc                             37

<210> SEQ ID NO 250
<211> LENGTH: 21
<212> TYPE: DNA
<213> ORGANISM: Artificial
<220> FEATURE:
<223> OTHER INFORMATION: DNA primer

<400> SEQUENCE: 250
cgtcacgcca ggaacaagct c                                              21

<210> SEQ ID NO 251
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 251
gcgtgacggc cgggacctac nnsagcagct cttcgacctt tacca                    45

<210> SEQ ID NO 252
<211> LENGTH: 25
```

```
<212> TYPE: DNA
<213> ORGANISM: Artificial
<220> FEATURE:
<223> OTHER INFORMATION: DNA primer

<400> SEQUENCE: 252
gtaggtcccg gccgtcacgc cagga                                              25

<210> SEQ ID NO 253
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 253
tgacggccgg gacctactcc nnsagctctt cgacctttac caaca                        45

<210> SEQ ID NO 254
<211> LENGTH: 25
<212> TYPE: DNA
<213> ORGANISM: Artificial
<220> FEATURE:
<223> OTHER INFORMATION: DNA primer

<400> SEQUENCE: 254
ggagtaggtc ccggccgtca cgcca                                              25

<210> SEQ ID NO 255
<211> LENGTH: 38
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 255
ctccagcagc tcttcgacct ttnnsaacat catcaacg                                38

<210> SEQ ID NO 256
<211> LENGTH: 21
<212> TYPE: DNA
<213> ORGANISM: Artificial
<220> FEATURE:
<223> OTHER INFORMATION: DNA primer

<400> SEQUENCE: 256
aaaggtcgaa gagctgctgg a                                                  21

<210> SEQ ID NO 257
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 257
```
gcagctcttc gacctttacc nnsatcatca acgccgtctc gacat            45

<210> SEQ ID NO 258
<211> LENGTH: 25
<212> TYPE: DNA
<213> ORGANISM: Artificial
<220> FEATURE:
<223> OTHER INFORMATION: DNA primer

<400> SEQUENCE: 258
ggtaaaggtc gaagagctgc tggag                                  25

<210> SEQ ID NO 259
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 259
ttcgaccttt accaacatca tcnnsgccgt ctcgaca                     37

<210> SEQ ID NO 260
<211> LENGTH: 21
<212> TYPE: DNA
<213> ORGANISM: Artificial
<220> FEATURE:
<223> OTHER INFORMATION: DNA primer

<400> SEQUENCE: 260
gatgatgttg gtaaaggtcg a                                      21

<210> SEQ ID NO 261
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 261
taccaacatc atcaacgccg tcnnsacata cgccgat                     37

<210> SEQ ID NO 262
<211> LENGTH: 21
<212> TYPE: DNA
<213> ORGANISM: Artificial
<220> FEATURE:
<223> OTHER INFORMATION: DNA primer

<400> SEQUENCE: 262
gacggcgttg atgatgttgg t                                      21

<210> SEQ ID NO 263
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature

```
<222> LOCATION: (23)..(24)
<223> OTHER INFORMATION: n is a, c, g, or t

<400> SEQUENCE: 263
gacatacgcc gatggcttcc tcnnsgaggc tgccaag                             37

<210> SEQ ID NO 264
<211> LENGTH: 21
<212> TYPE: DNA
<213> ORGANISM: Artificial
<220> FEATURE:
<223> OTHER INFORMATION: DNA primer

<400> SEQUENCE: 264
gaggaagcca tcggcgtatg t                                             21

<210> SEQ ID NO 265
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 265
atacgccgat ggcttcctca gcnnsgctgc caagtac                            37

<210> SEQ ID NO 266
<211> LENGTH: 21
<212> TYPE: DNA
<213> ORGANISM: Artificial
<220> FEATURE:
<223> OTHER INFORMATION: DNA primer

<400> SEQUENCE: 266
gctgaggaag ccatcggcgt a                                             21

<210> SEQ ID NO 267
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 267
cgatggcttc ctcagcgagg ctnnsaagta cgtcccc                            37

<210> SEQ ID NO 268
<211> LENGTH: 21
<212> TYPE: DNA
<213> ORGANISM: Artificial
<220> FEATURE:
<223> OTHER INFORMATION: DNA primer

<400> SEQUENCE: 268
agcctcgctg aggaagccat c                                             21

<210> SEQ ID NO 269
<211> LENGTH: 37
<212> TYPE: DNA
```

```
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 269
tggcttcctc agcgaggctg ccnnstacgt ccccgcc                        37

<210> SEQ ID NO 270
<211> LENGTH: 21
<212> TYPE: DNA
<213> ORGANISM: Artificial
<220> FEATURE:
<223> OTHER INFORMATION: DNA primer

<400> SEQUENCE: 270
ggcagcctcg ctgaggaagc c                                         21

<210> SEQ ID NO 271
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 271
tcctcagcga ggctgccaag nnsgtccccg ccgacggttc gctgg               45

<210> SEQ ID NO 272
<211> LENGTH: 25
<212> TYPE: DNA
<213> ORGANISM: Artificial
<220> FEATURE:
<223> OTHER INFORMATION: DNA primer

<400> SEQUENCE: 272
cttggcagcc tcgctgagga agcca                                     25

<210> SEQ ID NO 273
<211> LENGTH: 46
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 273
aggctgccaa gtacgtcccc nnsgacggtt cgctggccga gcagtt              46

<210> SEQ ID NO 274
<211> LENGTH: 25
<212> TYPE: DNA
<213> ORGANISM: Artificial
<220> FEATURE:
<223> OTHER INFORMATION: DNA primer

<400> SEQUENCE: 274
ggggacgtac ttggcagcct cgctg                                     25
```

<210> SEQ ID NO 275
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 275
agtacgtccc cgccgacggt nnsctggccg agcagtttga ccgca    45

<210> SEQ ID NO 276
<211> LENGTH: 26
<212> TYPE: DNA
<213> ORGANISM: Artificial
<220> FEATURE:
<223> OTHER INFORMATION: DNA primer

<400> SEQUENCE: 276
accgtcggcg gggacgtact tggcag    26

<210> SEQ ID NO 277
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 277
cgctggccga gcagtttgac nnsaacagcg gcactccgct gtctg    45

<210> SEQ ID NO 278
<211> LENGTH: 25
<212> TYPE: DNA
<213> ORGANISM: Artificial
<220> FEATURE:
<223> OTHER INFORMATION: DNA primer

<400> SEQUENCE: 278
gtcaaactgc tcggccagcg aaccg    25

<210> SEQ ID NO 279
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 279
tggccgagca gtttgaccgc nnsagcggca ctccgctgtc tgcgc    45

<210> SEQ ID NO 280
<211> LENGTH: 25
<212> TYPE: DNA
<213> ORGANISM: Artificial
<220> FEATURE:

```
<223> OTHER INFORMATION: DNA primer

<400> SEQUENCE: 280
gcggtcaaac tgctcggcca gcgaa                                              25

<210> SEQ ID NO 281
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 281
ggccgagcag tttgaccgca acnnsggcac tccgctg                                 37

<210> SEQ ID NO 282
<211> LENGTH: 21
<212> TYPE: DNA
<213> ORGANISM: Artificial
<220> FEATURE:
<223> OTHER INFORMATION: DNA primer

<400> SEQUENCE: 282
gttgcggtca aactgctcgg c                                                  21

<210> SEQ ID NO 283
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 283
agtttgaccg caacagcggc nnsccgctgt ctgcgcttca cctga                        45

<210> SEQ ID NO 284
<211> LENGTH: 25
<212> TYPE: DNA
<213> ORGANISM: Artificial
<220> FEATURE:
<223> OTHER INFORMATION: DNA primer

<400> SEQUENCE: 284
gccgctgttg cggtcaaact gctcg                                              25

<210> SEQ ID NO 285
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 285
gcaacagcgg cactccgctg nnsgcgcttc acctgacgtg gtcgt                        45
```

-continued

```
<210> SEQ ID NO 286
<211> LENGTH: 25
<212> TYPE: DNA
<213> ORGANISM: Artificial
<220> FEATURE:
<223> OTHER INFORMATION: DNA primer

<400> SEQUENCE: 286
cagcggagtg ccgctgttgc ggtca                                              25

<210> SEQ ID NO 287
<211> LENGTH: 38
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 287
cagcggcact ccgctgtctg cgnnscacct gacgtggt                                38

<210> SEQ ID NO 288
<211> LENGTH: 21
<212> TYPE: DNA
<213> ORGANISM: Artificial
<220> FEATURE:
<223> OTHER INFORMATION: DNA primer

<400> SEQUENCE: 288
cgcagacagc ggagtgccgc t                                                  21

<210> SEQ ID NO 289
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 289
gcactccgct gtctgcgctt nnsctgacgt ggtcgtacgc ctcgt                        45

<210> SEQ ID NO 290
<211> LENGTH: 25
<212> TYPE: DNA
<213> ORGANISM: Artificial
<220> FEATURE:
<223> OTHER INFORMATION: DNA primer

<400> SEQUENCE: 290
aagcgcagac agcggagtgc cgctg                                              25

<210> SEQ ID NO 291
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t
```

<400> SEQUENCE: 291
tgtctgcgct tcacctgacg nnstcgtacg cctcgttctt gacag         45

<210> SEQ ID NO 292
<211> LENGTH: 25
<212> TYPE: DNA
<213> ORGANISM: Artificial
<220> FEATURE:
<223> OTHER INFORMATION: DNA primer

<400> SEQUENCE: 292
cgtcaggtga agcgcagaca gcgga         25

<210> SEQ ID NO 293
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 293
gtacgcctcg ttcttgacag ccnnsgcccg tcgggct         37

<210> SEQ ID NO 294
<211> LENGTH: 21
<212> TYPE: DNA
<213> ORGANISM: Artificial
<220> FEATURE:
<223> OTHER INFORMATION: DNA primer

<400> SEQUENCE: 294
ggctgtcaag aacgaggcgt a         21

<210> SEQ ID NO 295
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 295
cgcctcgttc ttgacagcca cgnnscgtcg ggctggc         37

<210> SEQ ID NO 296
<211> LENGTH: 21
<212> TYPE: DNA
<213> ORGANISM: Artificial
<220> FEATURE:
<223> OTHER INFORMATION: DNA primer

<400> SEQUENCE: 296
cgtggctgtc aagaacgagg c         21

<210> SEQ ID NO 297
<211> LENGTH: 45
<212> TYPE: DNA
<213> ORGANISM: Artificial
<220> FEATURE:
<223> OTHER INFORMATION: DNA primer

```
<220> FEATURE:
<221> NAME/KEY: misc_feature
<222> LOCATION: (21)..(22)
<223> OTHER INFORMATION: n is a, c, g, or t

<400> SEQUENCE: 297
tcttgacagc cacggcccgt nnsgctggca tcgtgccccc ctcgt        45

<210> SEQ ID NO 298
<211> LENGTH: 25
<212> TYPE: DNA
<213> ORGANISM: Artificial
<220> FEATURE:
<223> OTHER INFORMATION: DNA primer

<400> SEQUENCE: 298
acgggccgtg gctgtcaaga acgag                              25

<210> SEQ ID NO 299
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 299
ccacggcccg tcgggctggc nnsgtgcccc cctcgtgggc aaca         45

<210> SEQ ID NO 300
<211> LENGTH: 25
<212> TYPE: DNA
<213> ORGANISM: Artificial
<220> FEATURE:
<223> OTHER INFORMATION: DNA primer

<400> SEQUENCE: 300
gccagcccga cgggccgtgg ctgtc                              25

<210> SEQ ID NO 301
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 301
tggcatcgtg ccccctcgt ggnnsaacag cagcgct                  37

<210> SEQ ID NO 302
<211> LENGTH: 21
<212> TYPE: DNA
<213> ORGANISM: Artificial
<220> FEATURE:
<223> OTHER INFORMATION: DNA primer

<400> SEQUENCE: 302
ccacgagggg ggcacgatgc c                                  21

<210> SEQ ID NO 303
```

```
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 303
catcgtgccc ccctcgtggg ccnnsagcag cgctagc                              37

<210> SEQ ID NO 304
<211> LENGTH: 21
<212> TYPE: DNA
<213> ORGANISM: Artificial
<220> FEATURE:
<223> OTHER INFORMATION: DNA primer

<400> SEQUENCE: 304
ggcccacgag gggggcacga t                                               21

<210> SEQ ID NO 305
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 305 cgtgccccc tcgtgggcca acnnsagcgc tagcacg                               37

<210> SEQ ID NO 306
<211> LENGTH: 21
<212> TYPE: DNA
<213> ORGANISM: Artificial
<220> FEATURE:
<223> OTHER INFORMATION: DNA primer

<400> SEQUENCE: 306
gttggcccac gagggggggca c                                              21

<210> SEQ ID NO 307
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 307
gtgggccaac agcagcgcta gcnnsatccc ctcgacg                              37

<210> SEQ ID NO 308
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
```

```
<222> LOCATION: (21)..(22)
<223> OTHER INFORMATION: n is a, c, g, or t

<400> SEQUENCE: 308
gcagcgctag cacgatcccc nnsacgtgct ccggcgcgtc cgtgg            45

<210> SEQ ID NO 309
<211> LENGTH: 25
<212> TYPE: DNA
<213> ORGANISM: Artificial
<220> FEATURE:
<223> OTHER INFORMATION: DNA primer

<400> SEQUENCE: 309
ggggatcgtg ctagcgctgc tgttg                                  25

<210> SEQ ID NO 310
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 310
ctacacgccc ctgccctgcg cgnnsccaac ctccgtg                     37

<210> SEQ ID NO 311
<211> LENGTH: 21
<212> TYPE: DNA
<213> ORGANISM: Artificial
<220> FEATURE:
<223> OTHER INFORMATION: DNA primer

<400> SEQUENCE: 311
cgcgcagggc aggggcgtgt a                                      21

<210> SEQ ID NO 312
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 312
cacgcccctg ccctgcgcga ccnnsacctc cgtggcc                     37

<210> SEQ ID NO 313
<211> LENGTH: 21
<212> TYPE: DNA
<213> ORGANISM: Artificial
<220> FEATURE:
<223> OTHER INFORMATION: DNA primer

<400> SEQUENCE: 313
ggtcgcgcag ggcagggggcg t                                     21

<210> SEQ ID NO 314
<211> LENGTH: 37
<212> TYPE: DNA
```

<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 314
gcccctgccc tgcgcgaccc cannstccgt ggccgtc                     37

<210> SEQ ID NO 315
<211> LENGTH: 21
<212> TYPE: DNA
<213> ORGANISM: Artificial
<220> FEATURE:
<223> OTHER INFORMATION: DNA primer

<400> SEQUENCE: 315
tggggtcgcg cagggcaggg g                                      21

<210> SEQ ID NO 316
<211> LENGTH: 38
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 316
cccaacctcc gtggccgtca ccnnscacga gctcgtgt                    38

<210> SEQ ID NO 317
<211> LENGTH: 21
<212> TYPE: DNA
<213> ORGANISM: Artificial
<220> FEATURE:
<223> OTHER INFORMATION: DNA primer

<400> SEQUENCE: 317
ggtgacggcc acggaggttg g                                      21

<210> SEQ ID NO 318
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 318
aacctccgtg gccgtcacct tcnnsgagct cgtgtcg                     37

<210> SEQ ID NO 319
<211> LENGTH: 21
<212> TYPE: DNA
<213> ORGANISM: Artificial
<220> FEATURE:
<223> OTHER INFORMATION: DNA primer

<400> SEQUENCE: 319
gaaggtgacg gccacggagg t                                      21

<210> SEQ ID NO 320
<211> LENGTH: 39
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 320
ctccgtggcc gtcaccttcc acnnsctcgt gtcgacaca                39

<210> SEQ ID NO 321
<211> LENGTH: 21
<212> TYPE: DNA
<213> ORGANISM: Artificial
<220> FEATURE:
<223> OTHER INFORMATION: DNA primer

<400> SEQUENCE: 321
gtggaaggtg acggccacgg a                                  21

<210> SEQ ID NO 322
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 322
cttccacgag ctcgtgtcga cannstttgg ccagacg                 37

<210> SEQ ID NO 323
<211> LENGTH: 21
<212> TYPE: DNA
<213> ORGANISM: Artificial
<220> FEATURE:
<223> OTHER INFORMATION: DNA primer

<400> SEQUENCE: 323
tgtcgacacg agctcgtgga a                                  21

<210> SEQ ID NO 324
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 324
gctcgtgtcg acacagtttg gcnnsacggt caaggtg                 37

<210> SEQ ID NO 325
<211> LENGTH: 21
<212> TYPE: DNA
<213> ORGANISM: Artificial
<220> FEATURE:

```
<223> OTHER INFORMATION: DNA primer

<400> SEQUENCE: 325
gccaaactgt gtcgacacga g                                              21

<210> SEQ ID NO 326
<211> LENGTH: 45
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (21)..(22)
<223> OTHER INFORMATION: n is a, c, g, or t

<400> SEQUENCE: 326
cacagtttgg ccagacggtc nnsgtggcgg gcaacgccgc ggccc                    45

<210> SEQ ID NO 327
<211> LENGTH: 25
<212> TYPE: DNA
<213> ORGANISM: Artificial
<220> FEATURE:
<223> OTHER INFORMATION: DNA primer

<400> SEQUENCE: 327
gaccgtctgg ccaaactgtg tcgac                                          25

<210> SEQ ID NO 328
<211> LENGTH: 42
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 328
tggccagacg gtcaaggtgg cgnnsaacgc cgcggccctg gg                       42

<210> SEQ ID NO 329
<211> LENGTH: 27
<212> TYPE: DNA
<213> ORGANISM: Artificial
<220> FEATURE:
<223> OTHER INFORMATION: DNA primer

<400> SEQUENCE: 329
cgccaccttg accgtctggc caaactg                                        27

<210> SEQ ID NO 330
<211> LENGTH: 44
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 330
ccagacggtc aaggtggcgg gcnnsgccgc ggccctgggc aact                     44
```

<210> SEQ ID NO 331
<211> LENGTH: 27
<212> TYPE: DNA
<213> ORGANISM: Artificial
<220> FEATURE:
<223> OTHER INFORMATION: DNA primer

<400> SEQUENCE: 331
gcccgccacc ttgaccgtct ggccaaa                                            27

<210> SEQ ID NO 332
<211> LENGTH: 41
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 332
gacggtcaag gtggcgggca acnnsgcggc cctgggcaac t                            41

<210> SEQ ID NO 333
<211> LENGTH: 27
<212> TYPE: DNA
<213> ORGANISM: Artificial
<220> FEATURE:
<223> OTHER INFORMATION: DNA primer

<400> SEQUENCE: 333
gttgcccgcc accttgaccg tctggcc                                            27

<210> SEQ ID NO 334
<211> LENGTH: 41
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 334
ggtcaaggtg gcgggcaacg ccnnsgccct gggcaactgg a                            41

<210> SEQ ID NO 335
<211> LENGTH: 27
<212> TYPE: DNA
<213> ORGANISM: Artificial
<220> FEATURE:
<223> OTHER INFORMATION: DNA primer

<400> SEQUENCE: 335
ggcgttgccc gccaccttga ccgtctg                                            27

<210> SEQ ID NO 336
<211> LENGTH: 41
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

```
<400> SEQUENCE: 336
caacgccgcg gccctgggca acnnsagcac gagcgccgcc g                              41

<210> SEQ ID NO 337
<211> LENGTH: 27
<212> TYPE: DNA
<213> ORGANISM: Artificial
<220> FEATURE:
<223> OTHER INFORMATION: DNA primer

<400> SEQUENCE: 337
gttgcccagg gccgcggcgt tgcccgc                                              27

<210> SEQ ID NO 338
<211> LENGTH: 41
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 338
cgcggccctg ggcaactgga gcnnsagcgc cgccgtggct c                              41

<210> SEQ ID NO 339
<211> LENGTH: 27
<212> TYPE: DNA
<213> ORGANISM: Artificial
<220> FEATURE:
<223> OTHER INFORMATION: DNA primer

<400> SEQUENCE: 339
gctccagttg cccagggccg cggcgtt                                              27

<210> SEQ ID NO 340
<211> LENGTH: 41
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 340
caactggagc acgagcgccg ccnnsgctct ggacgccgtc a                              41

<210> SEQ ID NO 341
<211> LENGTH: 27
<212> TYPE: DNA
<213> ORGANISM: Artificial
<220> FEATURE:
<223> OTHER INFORMATION: DNA primer

<400> SEQUENCE: 341
ggcggcgctc gtgctccagt tgcccag                                              27

<210> SEQ ID NO 342
<211> LENGTH: 42
<212> TYPE: DNA
<213> ORGANISM: Artificial
<220> FEATURE:
<223> OTHER INFORMATION: DNA primer
```

```
<220> FEATURE:
<221> NAME/KEY: misc_feature
<222> LOCATION: (23)..(24)
<223> OTHER INFORMATION: n is a, c, g, or t

<400> SEQUENCE: 342
gagcacgagc gccgccgtgg ctnnsgacgc cgtcaactat gc                           42

<210> SEQ ID NO 343
<211> LENGTH: 27
<212> TYPE: DNA
<213> ORGANISM: Artificial
<220> FEATURE:
<223> OTHER INFORMATION: DNA primer

<400> SEQUENCE: 343
agccacggcg gcgctcgtgc tccagtt                                            27

<210> SEQ ID NO 344
<211> LENGTH: 41
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 344
gagcgccgcc gtggctctgg acnnsgtcaa ctatgccgat a                            41

<210> SEQ ID NO 345
<211> LENGTH: 27
<212> TYPE: DNA
<213> ORGANISM: Artificial
<220> FEATURE:
<223> OTHER INFORMATION: DNA primer

<400> SEQUENCE: 345
gtccagagcc acggcggcgc tcgtgct                                            27

<210> SEQ ID NO 346
<211> LENGTH: 41
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 346
cgccgccgtg gctctggacg ccnnsaacta tgccgataac c                            41

<210> SEQ ID NO 347
<211> LENGTH: 27
<212> TYPE: DNA
<213> ORGANISM: Artificial
<220> FEATURE:
<223> OTHER INFORMATION: DNA primer

<400> SEQUENCE: 347
ggcgtccaga gccacggcgg cgctcgt                                            27

<210> SEQ ID NO 348
```

```
<211> LENGTH: 37
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 348
cgccgtggct ctggacgccg tcnnstatgc cgataac                              37

<210> SEQ ID NO 349
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 349
cgccgtggct ctggacgccg tcnnstatgc cgataaccac ccc                       43

<210> SEQ ID NO 350
<211> LENGTH: 27
<212> TYPE: DNA
<213> ORGANISM: Artificial
<220> FEATURE:
<223> OTHER INFORMATION: DNA primer

<400> SEQUENCE: 350
gacggcgtcc agagccacgg cggcgct                                         27

<210> SEQ ID NO 351
<211> LENGTH: 27
<212> TYPE: DNA
<213> ORGANISM: Artificial
<220> FEATURE:
<223> OTHER INFORMATION: DNA primer

<400> SEQUENCE: 351
gacggcgtcc agagccacgg cggcgct                                         27

<210> SEQ ID NO 352
<211> LENGTH: 41
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 352
cgtggctctg gacgccgtca acnnsgccga taaccacccc c                         41

<210> SEQ ID NO 353
<211> LENGTH: 28
<212> TYPE: DNA
<213> ORGANISM: Artificial
<220> FEATURE:
<223> OTHER INFORMATION: DNA primer

<400> SEQUENCE: 353
```
gttgacggcg tccagagcca cggcggcg                                          28

<210> SEQ ID NO 354
<211> LENGTH: 41
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 354
ggctctggac gccgtcaact atnnsgataa ccaccccctg t                           41

<210> SEQ ID NO 355
<211> LENGTH: 27
<212> TYPE: DNA
<213> ORGANISM: Artificial
<220> FEATURE:
<223> OTHER INFORMATION: DNA primer

<400> SEQUENCE: 355
atagttgacg gcgtccagag ccacggc                                           27

<210> SEQ ID NO 356
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 356
tctggacgcc gtcaactatg ccnnsaacca ccccctgtgg att                         43

<210> SEQ ID NO 357
<211> LENGTH: 27
<212> TYPE: DNA
<213> ORGANISM: Artificial
<220> FEATURE:
<223> OTHER INFORMATION: DNA primer

<400> SEQUENCE: 357
ggcatagttg acggcgtcca gagccac                                           27

<210> SEQ ID NO 358
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 358
ggacgccgtc aactatgccg atnnscaccc cctgtggatt ggg                         43

<210> SEQ ID NO 359
<211> LENGTH: 27
<212> TYPE: DNA

```
<213> ORGANISM: Artificial
<220> FEATURE:
<223> OTHER INFORMATION: DNA primer

<400> SEQUENCE: 359
atcggcatag ttgacggcgt ccagagc                                              27

<210> SEQ ID NO 360
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 360
ctatgccgat aaccacccccc tgnnsattgg gacggtcaac ctc                           43

<210> SEQ ID NO 361
<211> LENGTH: 27
<212> TYPE: DNA
<213> ORGANISM: Artificial
<220> FEATURE:
<223> OTHER INFORMATION: DNA primer

<400> SEQUENCE: 361 caggggtgg ttatcggcat agttgac                                              27

<210> SEQ ID NO 362
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 362
tgccgataac caccccctgt ggnnsgggac ggtcaacctc gag                           43

<210> SEQ ID NO 363
<211> LENGTH: 27
<212> TYPE: DNA
<213> ORGANISM: Artificial
<220> FEATURE:
<223> OTHER INFORMATION: DNA primer

<400> SEQUENCE: 363
ccacaggggg tggttatcgg catagtt                                             27

<210> SEQ ID NO 364
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 364
cgataaccac cccctgtgga ttnnsacggt caacctcgag gct                           43
```

<210> SEQ ID NO 365
<211> LENGTH: 27
<212> TYPE: DNA
<213> ORGANISM: Artificial
<220> FEATURE:
<223> OTHER INFORMATION: DNA primer

<400> SEQUENCE: 365
aatccacagg gggtggttat cggcata                                        27

<210> SEQ ID NO 366
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 366
ccaccccctg tggattggga cgnnsaacct cgaggctgga gac                      43

<210> SEQ ID NO 367
<211> LENGTH: 27
<212> TYPE: DNA
<213> ORGANISM: Artificial
<220> FEATURE:
<223> OTHER INFORMATION: DNA primer

<400> SEQUENCE: 367
cgtcccaatc cacaggggt ggttatc                                         27

<210> SEQ ID NO 368
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 368
cctgtggatt gggacggtca acnnsgaggc tggagacgtc gtg                      43

<210> SEQ ID NO 369
<211> LENGTH: 27
<212> TYPE: DNA
<213> ORGANISM: Artificial
<220> FEATURE:
<223> OTHER INFORMATION: DNA primer

<400> SEQUENCE: 369
gttgaccgtc ccaatccaca gggggtg                                        27

<210> SEQ ID NO 370
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)

<223> OTHER INFORMATION: n is a, c, g, or t

<400> SEQUENCE: 370
tggagacgtc gtggagtaca agnnsatcaa tgtgggccaa gat             43

<210> SEQ ID NO 371
<211> LENGTH: 27
<212> TYPE: DNA
<213> ORGANISM: Artificial
<220> FEATURE:
<223> OTHER INFORMATION: DNA primer

<400> SEQUENCE: 371
cttgtactcc acgacgtctc cagcctc             27

<210> SEQ ID NO 372
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 372
cgtcgtggag tacaagtaca tcnnsgtggg ccaagatggc tcc             43

<210> SEQ ID NO 373
<211> LENGTH: 27
<212> TYPE: DNA
<213> ORGANISM: Artificial
<220> FEATURE:
<223> OTHER INFORMATION: DNA primer

<400> SEQUENCE: 373
gatgtacttg tactccacga cgtctcc             27

<210> SEQ ID NO 374
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 374
caagtacatc aatgtgggcc aannsggctc cgtgacctgg gag             43

<210> SEQ ID NO 375
<211> LENGTH: 27
<212> TYPE: DNA
<213> ORGANISM: Artificial
<220> FEATURE:
<223> OTHER INFORMATION: DNA primer

<400> SEQUENCE: 375
ttggcccaca ttgatgtact tgtactc             27

<210> SEQ ID NO 376
<211> LENGTH: 43
<212> TYPE: DNA
<213> ORGANISM: Artificial

```
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 376
catcaatgtg ggccaagatg gcnnsgtgac ctgggagagt gat              43

<210> SEQ ID NO 377
<211> LENGTH: 28
<212> TYPE: DNA
<213> ORGANISM: Artificial
<220> FEATURE:
<223> OTHER INFORMATION: DNA primer

<400> SEQUENCE: 377
gccatcttgg cccacattga tgtacttg                                28

<210> SEQ ID NO 378
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 378
cgtgacctgg gagagtgatc ccnnscacac ttacacggtt cct              43

<210> SEQ ID NO 379
<211> LENGTH: 27
<212> TYPE: DNA
<213> ORGANISM: Artificial
<220> FEATURE:
<223> OTHER INFORMATION: DNA primer

<400> SEQUENCE: 379
gggatcactc tcccaggtca cggagcc                                 27

<210> SEQ ID NO 380
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 380
ctgggagagt gatcccaacc acnnstacac ggttcctgcg gtg              43

<210> SEQ ID NO 381
<211> LENGTH: 27
<212> TYPE: DNA
<213> ORGANISM: Artificial
<220> FEATURE:
<223> OTHER INFORMATION: DNA primer

<400> SEQUENCE: 381
gtggttggga tcactctccc aggtcac                                 27
```

<210> SEQ ID NO 382
<211> LENGTH: 43
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (23)..(24)
<223> OTHER INFORMATION: n is a, c, g, or t

<400> SEQUENCE: 382
tcccaaccac acttacacgg ttnnsgcggt ggcttgtgtg acg        43

<210> SEQ ID NO 383
<211> LENGTH: 27
<212> TYPE: DNA
<213> ORGANISM: Artificial
<220> FEATURE:
<223> OTHER INFORMATION: DNA primer

<400> SEQUENCE: 383
aaccgtgtaa gtgtggttgg gatcact        27

<210> SEQ ID NO 384
<211> LENGTH: 588
<212> TYPE: PRT
<213> ORGANISM: Talaromyces sp.

<400> SEQUENCE: 384

Gly Ser Leu Asp Ser Phe Leu Ala Thr Glu Thr Pro Ile Ala Leu Gln
1               5                   10                  15

Gly Val Leu Asn Asn Ile Gly Pro Asn Gly Ala Asp Val Ala Gly Ala
            20                  25                  30

Ser Ala Gly Ile Val Val Ala Ser Pro Ser Arg Ser Asp Pro Asp Tyr
        35                  40                  45

Phe Tyr Ser Trp Thr Arg Asp Ala Ala Leu Thr Ala Lys Tyr Leu Val
    50                  55                  60

Asp Ala Phe Ile Ala Gly Asn Lys Asp Leu Glu Gln Thr Ile Gln Glu
65                  70                  75                  80

Tyr Ile Ser Ala Gln Ala Gln Val Gln Thr Ile Ser Asn Pro Ser Gly
                85                  90                  95

Asp Leu Ser Thr Gly Gly Leu Gly Glu Pro Lys Phe Asn Val Asn Glu
            100                 105                 110

Thr Ala Phe Thr Gly Pro Trp Gly Arg Pro Gln Arg Asp Gly Pro Ala
        115                 120                 125

Leu Arg Ala Thr Ala Leu Ile Ala Tyr Ala Asn Tyr Leu Ile Asp Asn
    130                 135                 140

Gly Gln Ala Ser Thr Ala Asp Glu Ile Ile Trp Pro Ile Val Gln Asn
145                 150                 155                 160

Asp Leu Ser Tyr Val Thr Gln Tyr Trp Asn Ser Ser Thr Phe Asp Leu
                165                 170                 175

Trp Glu Glu Val Glu Gly Ser Ser Phe Phe Thr Thr Ala Val Gln His
            180                 185                 190

Arg Ala Leu Val Glu Gly Asn Ala Leu Ala Thr Arg Leu Asn His Thr
        195                 200                 205

Cys Pro Asn Cys Val Ser Gln Ala Pro Gln Val Leu Cys Phe Leu Gln
    210                 215                 220

Ser Tyr Trp Thr Gly Ser Tyr Val Leu Ala Asn Phe Gly Gly Ser Gly

```
            225                 230                 235                 240
Arg Ser Gly Lys Asp Val Asn Ser Ile Leu Gly Ser Ile His Thr Phe
                245                 250                 255

Asp Pro Ala Gly Gly Cys Asp Ser Thr Phe Gln Pro Cys Ser Ala
            260                 265                 270

Arg Ala Leu Ala Asn His Lys Val Val Thr Asp Ser Phe Arg Ser Val
                275                 280                 285

Tyr Ala Val Asn Ser Gly Ile Ala Glu Gly Ser Ala Val Ala Val Gly
                290                 295                 300

Arg Tyr Pro Glu Asp Val Tyr Gln Gly Gly Asn Pro Trp Tyr Leu Ala
305                 310                 315                 320

Thr Ala Ala Ala Glu Gln Leu Tyr Asp Ala Ile Tyr Gln Trp Asn
                325                 330                 335

Lys Ile Gly Ser Ile Ser Ile Thr Asp Val Ser Leu Ala Phe Phe Gln
                340                 345                 350

Asp Ile Tyr Pro Ser Ala Ala Val Gly Thr Tyr Asn Ser Gly Ser Ser
                355                 360                 365

Thr Phe Asn Asp Ile Ile Ser Ala Val Gln Thr Tyr Ala Asp Gly Tyr
                370                 375                 380

Leu Ser Ile Ile Glu Lys Tyr Thr Pro Ser Asp Gly Ser Leu Thr Glu
385                 390                 395                 400

Gln Phe Ser Arg Ser Asp Gly Thr Pro Leu Ser Ala Ser Gly Leu Thr
                405                 410                 415

Trp Ser Tyr Ala Ser Leu Leu Thr Ala Ala Ala Arg Arg Gln Ser Ile
                420                 425                 430

Val Pro Ala Ser Trp Gly Glu Ser Ser Ala Ser Ser Val Pro Ala Val
                435                 440                 445

Cys Ser Ala Thr Ser Ala Thr Gly Pro Tyr Ser Thr Ala Thr Asn Thr
                450                 455                 460

Ala Trp Pro Ser Ser Gly Ser Gly Pro Ser Thr Thr Thr Ser Val Pro
465                 470                 475                 480

Cys Thr Thr Pro Thr Ser Val Ala Val Thr Phe Asp Glu Ile Val Ser
                485                 490                 495

Thr Thr Tyr Gly Glu Thr Ile Tyr Leu Ala Gly Ser Ile Pro Glu Leu
                500                 505                 510

Gly Asn Trp Ser Pro Ser Ser Ala Ile Pro Leu Arg Ala Asp Ala Tyr
                515                 520                 525

Thr Ser Ser Asn Pro Leu Trp Tyr Val Thr Leu Asn Leu Pro Ala Gly
                530                 535                 540

Thr Ser Phe Glu Tyr Lys Phe Phe Lys Lys Glu Thr Asp Gly Thr Ile
545                 550                 555                 560

Val Trp Glu Asp Asp Pro Asn Arg Ser Tyr Thr Val Pro Ala Tyr Cys
                565                 570                 575

Gly Gln Thr Thr Ala Ile Leu Asp Asp Ser Trp Gln
                580                 585

<210> SEQ ID NO 385
<211> LENGTH: 112
<212> TYPE: PRT
<213> ORGANISM: Humicola grisea

<400> SEQUENCE: 385

Cys Ala Asp Ala Ser Glu Val Tyr Val Thr Phe Asn Glu Arg Val Ser
1               5                   10                  15
```

```
Thr Ala Trp Gly Glu Thr Ile Lys Val Val Gly Asn Val Pro Ala Leu
            20                  25                  30

Gly Asn Trp Asp Thr Ser Lys Ala Val Thr Leu Ser Ala Ser Gly Tyr
        35                  40                  45

Lys Ser Asn Asp Pro Leu Trp Ser Ile Thr Val Pro Ile Lys Ala Thr
 50                  55                  60

Gly Ser Ala Val Gln Tyr Lys Tyr Ile Lys Val Gly Thr Asn Gly Lys
 65                  70                  75                  80

Ile Thr Trp Glu Ser Asp Pro Asn Arg Ser Ile Thr Leu Gln Thr Ala
                85                  90                  95

Ser Ser Ala Gly Lys Cys Ala Ala Gln Thr Val Asn Asp Ser Trp Arg
            100                 105                 110

<210> SEQ ID NO 386
<211> LENGTH: 109
<212> TYPE: PRT
<213> ORGANISM: Thermomyces lanuginosus

<400> SEQUENCE: 386

Cys Thr Pro Pro Ser Glu Val Thr Leu Thr Phe Asn Ala Leu Val Asp
1               5                   10                  15

Thr Ala Phe Gly Gln Asn Ile Tyr Leu Val Gly Ser Ile Pro Glu Leu
            20                  25                  30

Gly Ser Trp Asp Pro Ala Asn Ala Leu Leu Met Ser Ala Lys Ser Trp
        35                  40                  45

Thr Ser Gly Asn Pro Val Trp Thr Leu Ser Ile Ser Leu Pro Ala Gly
 50                  55                  60

Thr Ser Phe Glu Tyr Lys Phe Ile Arg Lys Asp Asp Gly Ser Ser Asp
 65                  70                  75                  80

Val Val Trp Glu Ser Asp Pro Asn Arg Ser Tyr Asn Val Pro Lys Asp
                85                  90                  95

Cys Gly Ala Asn Thr Ala Thr Val Asn Ser Trp Trp Arg
            100                 105

<210> SEQ ID NO 387
<211> LENGTH: 108
<212> TYPE: PRT
<213> ORGANISM: Talaromyces emersonii

<400> SEQUENCE: 387

Cys Thr Thr Pro Thr Ser Val Ala Val Thr Phe Asp Glu Ile Val Ser
1               5                   10                  15

Thr Ser Tyr Gly Glu Thr Ile Tyr Leu Ala Gly Ser Ile Pro Glu Leu
            20                  25                  30

Gly Asn Trp Ser Thr Ala Ser Ala Ile Pro Leu Arg Ala Asp Ala Tyr
        35                  40                  45

Thr Asn Ser Asn Pro Leu Trp Tyr Val Thr Val Asn Leu Pro Pro Gly
 50                  55                  60

Thr Ser Phe Glu Tyr Lys Phe Phe Lys Asn Gln Thr Asp Gly Thr Ile
 65                  70                  75                  80

Val Trp Glu Asp Pro Asn Arg Ser Tyr Thr Val Pro Ala Tyr Cys
                85                  90                  95

Gly Gln Thr Thr Ala Ile Leu Asp Asp Ser Trp Gln
            100                 105

<210> SEQ ID NO 388
<211> LENGTH: 108
```

```
<212> TYPE: PRT
<213> ORGANISM: Aspergillus niger

<400> SEQUENCE: 388

Cys Thr Thr Pro Thr Ala Val Ala Val Thr Phe Asp Leu Thr Ala Thr
1               5                   10                  15

Thr Thr Tyr Gly Glu Asn Ile Tyr Leu Val Gly Ser Ile Ser Gln Leu
            20                  25                  30

Gly Asp Trp Glu Thr Ser Asp Gly Ile Ala Leu Ser Ala Asp Lys Tyr
        35                  40                  45

Thr Ser Ser Asp Pro Leu Trp Tyr Val Thr Val Thr Leu Pro Ala Gly
    50                  55                  60

Glu Ser Phe Glu Tyr Lys Phe Ile Arg Ile Glu Ser Asp Asp Ser Val
65                  70                  75                  80

Glu Trp Glu Ser Asp Pro Asn Arg Glu Tyr Thr Val Pro Gln Ala Cys
                85                  90                  95

Gly Thr Ser Thr Ala Thr Val Thr Asp Thr Trp Arg
            100                 105

<210> SEQ ID NO 389
<211> LENGTH: 108
<212> TYPE: PRT
<213> ORGANISM: Aspergillus awamori

<400> SEQUENCE: 389

Cys Thr Thr Pro Thr Ala Val Ala Val Thr Phe Asp Leu Thr Ala Thr
1               5                   10                  15

Thr Thr Tyr Gly Glu Asn Ile Tyr Leu Val Gly Ser Ile Ser Gln Leu
            20                  25                  30

Gly Asp Trp Asp Thr Ser Asp Gly Ile Ala Leu Ser Ala Asp Lys Tyr
        35                  40                  45

Thr Ser Ser Asn Pro Leu Trp Tyr Val Thr Val Thr Leu Pro Ala Gly
    50                  55                  60

Glu Ser Phe Glu Tyr Lys Phe Ile Arg Ile Glu Ser Asp Asp Ser Val
65                  70                  75                  80

Glu Trp Glu Ser Asp Pro Asn Arg Glu Tyr Thr Val Pro Gln Ala Cys
                85                  90                  95

Gly Glu Ser Thr Ala Thr Val Thr Asp Thr Trp Arg
            100                 105

<210> SEQ ID NO 390
<211> LENGTH: 108
<212> TYPE: PRT
<213> ORGANISM: Thielavia terrestris

<400> SEQUENCE: 390

Cys Ser Thr Pro Thr Ala Val Ala Val Thr Phe Asn Glu Arg Val Thr
1               5                   10                  15

Thr Gln Trp Gly Gln Thr Ile Lys Val Val Gly Asp Ala Ala Ala Leu
            20                  25                  30

Gly Gly Trp Asp Thr Ser Lys Ala Val Pro Leu Ser Ala Ala Gly Tyr
        35                  40                  45

Thr Ala Ser Asp Pro Leu Trp Ser Gly Thr Val Asp Leu Pro Ala Gly
    50                  55                  60

Leu Ala Val Gln Tyr Lys Tyr Ile Asn Val Ala Ala Asp Gly Gly Val
65                  70                  75                  80

Thr Trp Glu Ala Asp Pro Asn His Ser Phe Thr Val Pro Ala Ala Cys
```

```
                85                  90                  95
Gly Thr Thr Ala Val Thr Arg Asp Asp Thr Trp Gln
            100                 105
```

<210> SEQ ID NO 391
<211> LENGTH: 32
<212> TYPE: DNA
<213> ORGANISM: Artificial
<220> FEATURE:
<223> OTHER INFORMATION: DNA Primer

<400> SEQUENCE: 391
gagagagtgc gggcctcttc gctatttcta ga                          32

<210> SEQ ID NO 392
<211> LENGTH: 40
<212> TYPE: DNA
<213> ORGANISM: Artificial
<220> FEATURE:
<223> OTHER INFORMATION: DNA Primer

<400> SEQUENCE: 392
caaaataaaa tcattatttg tctagaaata gcgaagaggc                  40

<210> SEQ ID NO 393
<211> LENGTH: 40
<212> TYPE: DNA
<213> ORGANISM: Artificial
<220> FEATURE:
<223> OTHER INFORMATION: DNA Primer

<400> SEQUENCE: 393
caaataatga ttttatttg actgatagtg acctgttcgt                   40

<210> SEQ ID NO 394
<211> LENGTH: 40
<212> TYPE: DNA
<213> ORGANISM: Artificial
<220> FEATURE:
<223> OTHER INFORMATION: DNA Primer

<400> SEQUENCE: 394
ttgctcatca atgtgttgca acgaacaggt cactatcagt                  40

<210> SEQ ID NO 395
<211> LENGTH: 40
<212> TYPE: DNA
<213> ORGANISM: Artificial
<220> FEATURE:
<223> OTHER INFORMATION: DNA Primer

<400> SEQUENCE: 395
tgcaacacat tgatgagcaa tgcttttta taatgccaac                   40

<210> SEQ ID NO 396
<211> LENGTH: 40
<212> TYPE: DNA
<213> ORGANISM: Artificial
<220> FEATURE:
<223> OTHER INFORMATION: DNA Primer

<400> SEQUENCE: 396
agcctgcttt tttgtacaaa gttggcatta taaaaaagca                  40

<210> SEQ ID NO 397

```
<211> LENGTH: 40
<212> TYPE: DNA
<213> ORGANISM: Artificial
<220> FEATURE:
<223> OTHER INFORMATION: DNA Primer

<400> SEQUENCE: 397
tttgtacaaa aaagcaggct atgcacgtcc tgtcgactgc                              40

<210> SEQ ID NO 398
<211> LENGTH: 40
<212> TYPE: DNA
<213> ORGANISM: Artificial
<220> FEATURE:
<223> OTHER INFORMATION: DNA Primer

<400> SEQUENCE: 398
caacggagcc gagcagcacc gcagtcgaca ggacgtgcat                              40

<210> SEQ ID NO 399
<211> LENGTH: 40
<212> TYPE: DNA
<213> ORGANISM: Artificial
<220> FEATURE:
<223> OTHER INFORMATION: DNA Primer

<400> SEQUENCE: 399
ggtgctgctc ggctccgttg ccgttcaaaa ggtcctggga                              40

<210> SEQ ID NO 400
<211> LENGTH: 40
<212> TYPE: DNA
<213> ORGANISM: Artificial
<220> FEATURE:
<223> OTHER INFORMATION: DNA Primer

<400> SEQUENCE: 400
agaccgcttg atcctggtct tcccaggacc ttttgaacgg                              40

<210> SEQ ID NO 401
<211> LENGTH: 40
<212> TYPE: DNA
<213> ORGANISM: Artificial
<220> FEATURE:
<223> OTHER INFORMATION: DNA Primer

<400> SEQUENCE: 401
agaccaggat caagcggtct gtccgacgtc accaagaggt                              40

<210> SEQ ID NO 402
<211> LENGTH: 40
<212> TYPE: DNA
<213> ORGANISM: Artificial
<220> FEATURE:
<223> OTHER INFORMATION: DNA Primer

<400> SEQUENCE: 402
gctgatgaag tcgtcaacag acctcttggt gacgtcggac                              40

<210> SEQ ID NO 403
<211> LENGTH: 40
<212> TYPE: DNA
<213> ORGANISM: Artificial
<220> FEATURE:
<223> OTHER INFORMATION: DNA Primer

<400> SEQUENCE: 403
```

```
ctgttgacga cttcatcagc accgagacgc ctattgcact                               40

<210> SEQ ID NO 404
<211> LENGTH: 40
<212> TYPE: DNA
<213> ORGANISM: Artificial
<220> FEATURE:
<223> OTHER INFORMATION: DNA Primer

<400> SEQUENCE: 404
cattgcaaag aagattgttc agtgcaatag gcgtctcggt                               40

<210> SEQ ID NO 405
<211> LENGTH: 40
<212> TYPE: DNA
<213> ORGANISM: Artificial
<220> FEATURE:
<223> OTHER INFORMATION: DNA Primer

<400> SEQUENCE: 405
gaacaatctt ctttgcaatg ttggtcctga tggatgccgt                               40

<210> SEQ ID NO 406
<211> LENGTH: 40
<212> TYPE: DNA
<213> ORGANISM: Artificial
<220> FEATURE:
<223> OTHER INFORMATION: DNA Primer

<400> SEQUENCE: 406
ccagctgatg tgccgaatgc acggcatcca tcaggaccaa                               40

<210> SEQ ID NO 407
<211> LENGTH: 40
<212> TYPE: DNA
<213> ORGANISM: Artificial
<220> FEATURE:
<223> OTHER INFORMATION: DNA Primer

<400> SEQUENCE: 407
gcattcggca catcagctgg tgcggtgatt gcatctccca                               40

<210> SEQ ID NO 408
<211> LENGTH: 40
<212> TYPE: DNA
<213> ORGANISM: Artificial
<220> FEATURE:
<223> OTHER INFORMATION: DNA Primer

<400> SEQUENCE: 408
gtagtccggg tcaattgtgc tgggagatgc aatcaccgca                               40

<210> SEQ ID NO 409
<211> LENGTH: 40
<212> TYPE: DNA
<213> ORGANISM: Artificial
<220> FEATURE:
<223> OTHER INFORMATION: DNA Primer

<400> SEQUENCE: 409
gcacaattga cccggactac tattacatgt ggacgcgaga                               40

<210> SEQ ID NO 410
<211> LENGTH: 40
<212> TYPE: DNA
```

```
<213> ORGANISM: Artificial
<220> FEATURE:
<223> OTHER INFORMATION: DNA Primer

<400> SEQUENCE: 410
tcttgaagac aagagcgcta tctcgcgtcc acatgtaata                            40

<210> SEQ ID NO 411
<211> LENGTH: 40
<212> TYPE: DNA
<213> ORGANISM: Artificial
<220> FEATURE:
<223> OTHER INFORMATION: DNA Primer

<400> SEQUENCE: 411
tagcgctctt gtcttcaaga acctcatcga ccgcttcacc                            40

<210> SEQ ID NO 412
<211> LENGTH: 40
<212> TYPE: DNA
<213> ORGANISM: Artificial
<220> FEATURE:
<223> OTHER INFORMATION: DNA Primer

<400> SEQUENCE: 412
aggcccgcat cgtacgtttc ggtgaagcgg tcgatgaggt                            40

<210> SEQ ID NO 413
<211> LENGTH: 40
<212> TYPE: DNA
<213> ORGANISM: Artificial
<220> FEATURE:
<223> OTHER INFORMATION: DNA Primer

<400> SEQUENCE: 413
gaaacgtacg atgcgggcct gcagcgccgc atcgagcagt                            40

<210> SEQ ID NO 414
<211> LENGTH: 40
<212> TYPE: DNA
<213> ORGANISM: Artificial
<220> FEATURE:
<223> OTHER INFORMATION: DNA Primer

<400> SEQUENCE: 414
agtgacctgg gcagtaatgt actgctcgat gcggcgctgc                            40

<210> SEQ ID NO 415
<211> LENGTH: 40
<212> TYPE: DNA
<213> ORGANISM: Artificial
<220> FEATURE:
<223> OTHER INFORMATION: DNA Primer

<400> SEQUENCE: 415
acattactgc ccaggtcact ctccagggcc tctctaaccc                            40

<210> SEQ ID NO 416
<211> LENGTH: 40
<212> TYPE: DNA
<213> ORGANISM: Artificial
<220> FEATURE:
<223> OTHER INFORMATION: DNA Primer

<400> SEQUENCE: 416
cgtccgcgag ggagcccgag gggttagaga ggccctggag                            40
```

<210> SEQ ID NO 417
<211> LENGTH: 40
<212> TYPE: DNA
<213> ORGANISM: Artificial
<220> FEATURE:
<223> OTHER INFORMATION: DNA Primer

<400> SEQUENCE: 417
ctcgggctcc ctcgcggacg gctctggtct cggcgagccc                            40

<210> SEQ ID NO 418
<211> LENGTH: 40
<212> TYPE: DNA
<213> ORGANISM: Artificial
<220> FEATURE:
<223> OTHER INFORMATION: DNA Primer

<400> SEQUENCE: 418
ttcagggtca actcaaactt gggctcgccg agaccagagc                            40

<210> SEQ ID NO 419
<211> LENGTH: 40
<212> TYPE: DNA
<213> ORGANISM: Artificial
<220> FEATURE:
<223> OTHER INFORMATION: DNA Primer

<400> SEQUENCE: 419
aagtttgagt tgaccctgaa gcctttcacc ggcaactggg                            40

<210> SEQ ID NO 420
<211> LENGTH: 40
<212> TYPE: DNA
<213> ORGANISM: Artificial
<220> FEATURE:
<223> OTHER INFORMATION: DNA Primer

<400> SEQUENCE: 420
gccatcccgc tgcggtcgac cccagttgcc ggtgaaaggc                            40

<210> SEQ ID NO 421
<211> LENGTH: 40
<212> TYPE: DNA
<213> ORGANISM: Artificial
<220> FEATURE:
<223> OTHER INFORMATION: DNA Primer

<400> SEQUENCE: 421
gtcgaccgca gcgggatggc ccagctctgc gagccattgc                            40

<210> SEQ ID NO 422
<211> LENGTH: 40
<212> TYPE: DNA
<213> ORGANISM: Artificial
<220> FEATURE:
<223> OTHER INFORMATION: DNA Primer

<400> SEQUENCE: 422
actttgagta tccaatcaag gcaatggctc gcagagctgg                            40

<210> SEQ ID NO 423
<211> LENGTH: 40
<212> TYPE: DNA
<213> ORGANISM: Artificial
<220> FEATURE:

<223> OTHER INFORMATION: DNA Primer

<400> SEQUENCE: 423
cttgattgga tactcaaagt ggctcatcaa caacaactat                                40

<210> SEQ ID NO 424
<211> LENGTH: 40
<212> TYPE: DNA
<213> ORGANISM: Artificial
<220> FEATURE:
<223> OTHER INFORMATION: DNA Primer

<400> SEQUENCE: 424
acgttggaca cagtcgactg atagttgttg ttgatgagcc                                40

<210> SEQ ID NO 425
<211> LENGTH: 40
<212> TYPE: DNA
<213> ORGANISM: Artificial
<220> FEATURE:
<223> OTHER INFORMATION: DNA Primer

<400> SEQUENCE: 425
cagtcgactg tgtccaacgt catctggcct attgtgcgca                                40

<210> SEQ ID NO 426
<211> LENGTH: 40
<212> TYPE: DNA
<213> ORGANISM: Artificial
<220> FEATURE:
<223> OTHER INFORMATION: DNA Primer

<400> SEQUENCE: 426
ggcaacatag ttgaggtcgt tgcgcacaat aggccagatg                                40

<210> SEQ ID NO 427
<211> LENGTH: 40
<212> TYPE: DNA
<213> ORGANISM: Artificial
<220> FEATURE:
<223> OTHER INFORMATION: DNA Primer

<400> SEQUENCE: 427
acgacctcaa ctatgttgcc cagtactgga accaaaccgg                                40

<210> SEQ ID NO 428
<211> LENGTH: 40
<212> TYPE: DNA
<213> ORGANISM: Artificial
<220> FEATURE:
<223> OTHER INFORMATION: DNA Primer

<400> SEQUENCE: 428
cttcttccca gaggtcaaag ccggtttggt tccagtactg                                40

<210> SEQ ID NO 429
<211> LENGTH: 40
<212> TYPE: DNA
<213> ORGANISM: Artificial
<220> FEATURE:
<223> OTHER INFORMATION: DNA Primer

<400> SEQUENCE: 429
ctttgacctc tgggaagaag tcaatgggag ctcattcttt                                40

<210> SEQ ID NO 430
<211> LENGTH: 40
<212> TYPE: DNA
<213> ORGANISM: Artificial
<220> FEATURE:
<223> OTHER INFORMATION: DNA Primer

<400> SEQUENCE: 430
cggtgctggt tggcaacagt aaagaatgag ctcccattga        40

<210> SEQ ID NO 431
<211> LENGTH: 40
<212> TYPE: DNA
<213> ORGANISM: Artificial
<220> FEATURE:
<223> OTHER INFORMATION: DNA Primer

<400> SEQUENCE: 431
actgttgcca accagcaccg agcacttgtc gagggcgcca        40

<210> SEQ ID NO 432
<211> LENGTH: 40
<212> TYPE: DNA
<213> ORGANISM: Artificial
<220> FEATURE:
<223> OTHER INFORMATION: DNA Primer

<400> SEQUENCE: 432
gccaagagtg gcagcaagag tggcgccctc gacaagtgct        40

<210> SEQ ID NO 433
<211> LENGTH: 40
<212> TYPE: DNA
<213> ORGANISM: Artificial
<220> FEATURE:
<223> OTHER INFORMATION: DNA Primer

<400> SEQUENCE: 433
ctcttgctgc cactcttggc cagtcgggaa gcgcttattc        40

<210> SEQ ID NO 434
<211> LENGTH: 40
<212> TYPE: DNA
<213> ORGANISM: Artificial
<220> FEATURE:
<223> OTHER INFORMATION: DNA Primer

<400> SEQUENCE: 434
aaacctgggg agcaacagat gaataagcgc ttcccgactg        40

<210> SEQ ID NO 435
<211> LENGTH: 40
<212> TYPE: DNA
<213> ORGANISM: Artificial
<220> FEATURE:
<223> OTHER INFORMATION: DNA Primer

<400> SEQUENCE: 435
atctgttgct ccccaggttt tgtgctttct ccaacgattc        40

<210> SEQ ID NO 436
<211> LENGTH: 40
<212> TYPE: DNA
<213> ORGANISM: Artificial
<220> FEATURE:
<223> OTHER INFORMATION: DNA Primer

<400> SEQUENCE: 436
tatccaccag acgacaccca gaatcgttgg agaaagcaca                40

<210> SEQ ID NO 437
<211> LENGTH: 40
<212> TYPE: DNA
<213> ORGANISM: Artificial
<220> FEATURE:
<223> OTHER INFORMATION: DNA Primer

<400> SEQUENCE: 437
tgggtgtcgt ctggtggata cgtcgactcc aacatcaaca                40

<210> SEQ ID NO 438
<211> LENGTH: 40
<212> TYPE: DNA
<213> ORGANISM: Artificial
<220> FEATURE:
<223> OTHER INFORMATION: DNA Primer

<400> SEQUENCE: 438
gccagtcctg ccctcgttgg tgttgatgtt ggagtcgacg                40

<210> SEQ ID NO 439
<211> LENGTH: 40
<212> TYPE: DNA
<213> ORGANISM: Artificial
<220> FEATURE:
<223> OTHER INFORMATION: DNA Primer

<400> SEQUENCE: 439
ccaacgaggg caggactggc aaggatgtca actccgtcct                40

<210> SEQ ID NO 440
<211> LENGTH: 40
<212> TYPE: DNA
<213> ORGANISM: Artificial
<220> FEATURE:
<223> OTHER INFORMATION: DNA Primer

<400> SEQUENCE: 440
cgaaggtgtg gatggaagtc aggacggagt tgacatcctt                40

<210> SEQ ID NO 441
<211> LENGTH: 40
<212> TYPE: DNA
<213> ORGANISM: Artificial
<220> FEATURE:
<223> OTHER INFORMATION: DNA Primer

<400> SEQUENCE: 441
gacttccatc cacaccttcg atcccaacct tggctgtgac                40

<210> SEQ ID NO 442
<211> LENGTH: 40
<212> TYPE: DNA
<213> ORGANISM: Artificial
<220> FEATURE:
<223> OTHER INFORMATION: DNA Primer

<400> SEQUENCE: 442
catggctgga aggtgcctgc gtcacagcca aggttgggat                40

<210> SEQ ID NO 443
<211> LENGTH: 40

```
<212> TYPE: DNA
<213> ORGANISM: Artificial
<220> FEATURE:
<223> OTHER INFORMATION: DNA Primer

<400> SEQUENCE: 443
gcaggcacct tccagccatg cagtgacaaa gcgctctcca                              40

<210> SEQ ID NO 444
<211> LENGTH: 40
<212> TYPE: DNA
<213> ORGANISM: Artificial
<220> FEATURE:
<223> OTHER INFORMATION: DNA Primer

<400> SEQUENCE: 444
gtcgacaaca accttgaggt tggagagcgc tttgtcactg                              40

<210> SEQ ID NO 445
<211> LENGTH: 40
<212> TYPE: DNA
<213> ORGANISM: Artificial
<220> FEATURE:
<223> OTHER INFORMATION: DNA Primer

<400> SEQUENCE: 445
acctcaaggt tgttgtcgac tccttccgct ccatctacgg                              40

<210> SEQ ID NO 446
<211> LENGTH: 40
<212> TYPE: DNA
<213> ORGANISM: Artificial
<220> FEATURE:
<223> OTHER INFORMATION: DNA Primer

<400> SEQUENCE: 446
caggaatgcc cttgttcacg ccgtagatgg agcggaagga                              40

<210> SEQ ID NO 447
<211> LENGTH: 40
<212> TYPE: DNA
<213> ORGANISM: Artificial
<220> FEATURE:
<223> OTHER INFORMATION: DNA Primer

<400> SEQUENCE: 447
cgtgaacaag ggcattcctg ccggtgctgc cgtcgccatt                              40

<210> SEQ ID NO 448
<211> LENGTH: 40
<212> TYPE: DNA
<213> ORGANISM: Artificial
<220> FEATURE:
<223> OTHER INFORMATION: DNA Primer

<400> SEQUENCE: 448
acatcctctg cataccggcc aatggcgacg gcagcaccgg                              40

<210> SEQ ID NO 449
<211> LENGTH: 40
<212> TYPE: DNA
<213> ORGANISM: Artificial
<220> FEATURE:
<223> OTHER INFORMATION: DNA Primer

<400> SEQUENCE: 449
```
ggccggtatg cagaggatgt gtactacaac ggcaaccctt                            40

<210> SEQ ID NO 450
<211> LENGTH: 40
<212> TYPE: DNA
<213> ORGANISM: Artificial
<220> FEATURE:
<223> OTHER INFORMATION: DNA Primer

<400> SEQUENCE: 450
agcaaatgta gcaagatacc aagggttgcc gttgtagtac                            40

<210> SEQ ID NO 451
<211> LENGTH: 40
<212> TYPE: DNA
<213> ORGANISM: Artificial
<220> FEATURE:
<223> OTHER INFORMATION: DNA Primer

<400> SEQUENCE: 451
ggtatcttgc tacatttgct gctgccgagc agctgtacga                            40

<210> SEQ ID NO 452
<211> LENGTH: 40
<212> TYPE: DNA
<213> ORGANISM: Artificial
<220> FEATURE:
<223> OTHER INFORMATION: DNA Primer

<400> SEQUENCE: 452
tcttccagac gtagatggca tcgtacagct gctcggcagc                            40

<210> SEQ ID NO 453
<211> LENGTH: 40
<212> TYPE: DNA
<213> ORGANISM: Artificial
<220> FEATURE:
<223> OTHER INFORMATION: DNA Primer

<400> SEQUENCE: 453
tgccatctac gtctggaaga agacgggctc catcacggtg                            40

<210> SEQ ID NO 454
<211> LENGTH: 40
<212> TYPE: DNA
<213> ORGANISM: Artificial
<220> FEATURE:
<223> OTHER INFORMATION: DNA Primer

<400> SEQUENCE: 454
aaggccaggg aggtggcggt caccgtgatg gagcccgtct                            40

<210> SEQ ID NO 455
<211> LENGTH: 40
<212> TYPE: DNA
<213> ORGANISM: Artificial
<220> FEATURE:
<223> OTHER INFORMATION: DNA Primer

<400> SEQUENCE: 455
accgccacct ccctggcctt cttccaggag cttgttcctg                            40

<210> SEQ ID NO 456
<211> LENGTH: 40
<212> TYPE: DNA
<213> ORGANISM: Artificial

```
<220> FEATURE:
<223> OTHER INFORMATION: DNA Primer

<400> SEQUENCE: 456
gtaggtcccg gccgtcacgc caggaacaag ctcctggaag                              40

<210> SEQ ID NO 457
<211> LENGTH: 40
<212> TYPE: DNA
<213> ORGANISM: Artificial
<220> FEATURE:
<223> OTHER INFORMATION: DNA Primer

<400> SEQUENCE: 457
gcgtgacggc cgggacctac tccagcagct cttcgacctt                              40

<210> SEQ ID NO 458
<211> LENGTH: 40
<212> TYPE: DNA
<213> ORGANISM: Artificial
<220> FEATURE:
<223> OTHER INFORMATION: DNA Primer

<400> SEQUENCE: 458
cggcgttgat gatgttggta aaggtcgaag agctgctgga                              40

<210> SEQ ID NO 459
<211> LENGTH: 40
<212> TYPE: DNA
<213> ORGANISM: Artificial
<220> FEATURE:
<223> OTHER INFORMATION: DNA Primer

<400> SEQUENCE: 459
taccaacatc atcaacgccg tctcgacata cgccgatggc                              40

<210> SEQ ID NO 460
<211> LENGTH: 40
<212> TYPE: DNA
<213> ORGANISM: Artificial
<220> FEATURE:
<223> OTHER INFORMATION: DNA Primer

<400> SEQUENCE: 460
ttggcagcct cgctgaggaa gccatcggcg tatgtcgaga                              40

<210> SEQ ID NO 461
<211> LENGTH: 40
<212> TYPE: DNA
<213> ORGANISM: Artificial
<220> FEATURE:
<223> OTHER INFORMATION: DNA Primer

<400> SEQUENCE: 461
ttcctcagcg aggctgccaa gtacgtcccc gccgacggtt                              40

<210> SEQ ID NO 462
<211> LENGTH: 40
<212> TYPE: DNA
<213> ORGANISM: Artificial
<220> FEATURE:
<223> OTHER INFORMATION: DNA Primer

<400> SEQUENCE: 462
gtcaaactgc tcggccagcg aaccgtcggc ggggacgtac                              40
```

<210> SEQ ID NO 463
<211> LENGTH: 40
<212> TYPE: DNA
<213> ORGANISM: Artificial
<220> FEATURE:
<223> OTHER INFORMATION: DNA Primer

<400> SEQUENCE: 463
cgctggccga gcagtttgac cgcaacagcg gcactccgct                                 40

<210> SEQ ID NO 464
<211> LENGTH: 40
<212> TYPE: DNA
<213> ORGANISM: Artificial
<220> FEATURE:
<223> OTHER INFORMATION: DNA Primer

<400> SEQUENCE: 464
acgtcaggtg aaccgcagac agcggagtgc cgctgttgcg                                 40

<210> SEQ ID NO 465
<211> LENGTH: 40
<212> TYPE: DNA
<213> ORGANISM: Artificial
<220> FEATURE:
<223> OTHER INFORMATION: DNA Primer

<400> SEQUENCE: 465
gtctgcggtt cacctgacgt ggtcgtacgc ctcgttcttg                                 40

<210> SEQ ID NO 466
<211> LENGTH: 40
<212> TYPE: DNA
<213> ORGANISM: Artificial
<220> FEATURE:
<223> OTHER INFORMATION: DNA Primer

<400> SEQUENCE: 466
gcccgacgaa gcgtggctgt caagaacgag gcgtacgacc                                 40

<210> SEQ ID NO 467
<211> LENGTH: 40
<212> TYPE: DNA
<213> ORGANISM: Artificial
<220> FEATURE:
<223> OTHER INFORMATION: DNA Primer

<400> SEQUENCE: 467
acagccacgc ttcgtcgggc tggcatcgtg ccccccctcgt                                40

<210> SEQ ID NO 468
<211> LENGTH: 40
<212> TYPE: DNA
<213> ORGANISM: Artificial
<220> FEATURE:
<223> OTHER INFORMATION: DNA Primer

<400> SEQUENCE: 468
gctagcgctg ctgttggccc acgagggggg cacgatgcca                                 40

<210> SEQ ID NO 469
<211> LENGTH: 40
<212> TYPE: DNA
<213> ORGANISM: Artificial
<220> FEATURE:
<223> OTHER INFORMATION: DNA Primer

<400> SEQUENCE: 469
gggccaacag cagcgctagc acgatcccct cgacgtgctc                    40

<210> SEQ ID NO 470
<211> LENGTH: 40
<212> TYPE: DNA
<213> ORGANISM: Artificial
<220> FEATURE:
<223> OTHER INFORMATION: DNA Primer

<400> SEQUENCE: 470
atccgaccac ggacgcgccg gagcacgtcg aggggatcgt                    40

<210> SEQ ID NO 471
<211> LENGTH: 40
<212> TYPE: DNA
<213> ORGANISM: Artificial
<220> FEATURE:
<223> OTHER INFORMATION: DNA Primer

<400> SEQUENCE: 471
cggcgcgtcc gtggtcggat cctactcgcg tcccaccgcc                    40

<210> SEQ ID NO 472
<211> LENGTH: 40
<212> TYPE: DNA
<213> ORGANISM: Artificial
<220> FEATURE:
<223> OTHER INFORMATION: DNA Primer

<400> SEQUENCE: 472
tgcgacggag ggaatgacgt ggcggtggga cgcgagtagg                    40

<210> SEQ ID NO 473
<211> LENGTH: 40
<212> TYPE: DNA
<213> ORGANISM: Artificial
<220> FEATURE:
<223> OTHER INFORMATION: DNA Primer

<400> SEQUENCE: 473
acgtcattcc ctccgtcgca gacgcccaag cctggcgtgc                    40

<210> SEQ ID NO 474
<211> LENGTH: 40
<212> TYPE: DNA
<213> ORGANISM: Artificial
<220> FEATURE:
<223> OTHER INFORMATION: DNA Primer

<400> SEQUENCE: 474
cgtgtaggga gtaccggaag gcacgccagg cttgggcgtc                    40

<210> SEQ ID NO 475
<211> LENGTH: 40
<212> TYPE: DNA
<213> ORGANISM: Artificial
<220> FEATURE:
<223> OTHER INFORMATION: DNA Primer

<400> SEQUENCE: 475
cttccggtac tccctacacg cccctgccct gcgcgacccc                    40

<210> SEQ ID NO 476

<210> SEQ ID NO 476
<211> LENGTH: 40
<212> TYPE: DNA
<213> ORGANISM: Artificial
<220> FEATURE:
<223> OTHER INFORMATION: DNA Primer

<400> SEQUENCE: 476
aggtgacggc cacggaggtt ggggtcgcgc agggcagggg          40

<210> SEQ ID NO 477
<211> LENGTH: 40
<212> TYPE: DNA
<213> ORGANISM: Artificial
<220> FEATURE:
<223> OTHER INFORMATION: DNA Primer

<400> SEQUENCE: 477
aacctccgtg gccgtcacct tccacgagct cgtgtcgaca          40

<210> SEQ ID NO 478
<211> LENGTH: 40
<212> TYPE: DNA
<213> ORGANISM: Artificial
<220> FEATURE:
<223> OTHER INFORMATION: DNA Primer

<400> SEQUENCE: 478
ttgaccgtct ggccaaactg tgtcgacacg agctcgtgga          40

<210> SEQ ID NO 479
<211> LENGTH: 40
<212> TYPE: DNA
<213> ORGANISM: Artificial
<220> FEATURE:
<223> OTHER INFORMATION: DNA Primer

<400> SEQUENCE: 479
cagtttggcc agacggtcaa ggtggcgggc aacgccgcgg          40

<210> SEQ ID NO 480
<211> LENGTH: 40
<212> TYPE: DNA
<213> ORGANISM: Artificial
<220> FEATURE:
<223> OTHER INFORMATION: DNA Primer

<400> SEQUENCE: 480
cgtgctccag ttgcccaggg ccgcggcgtt gcccgccacc          40

<210> SEQ ID NO 481
<211> LENGTH: 40
<212> TYPE: DNA
<213> ORGANISM: Artificial
<220> FEATURE:
<223> OTHER INFORMATION: DNA Primer

<400> SEQUENCE: 481
ccctgggcaa ctggagcacg agcgccgccg tggctctgga          40

<210> SEQ ID NO 482
<211> LENGTH: 40
<212> TYPE: DNA
<213> ORGANISM: Artificial
<220> FEATURE:
<223> OTHER INFORMATION: DNA Primer

<400> SEQUENCE: 482

-continued tatcacgata gttgacggcg tccagagcca cggcggcgct 40

<210> SEQ ID NO 483
<211> LENGTH: 40
<212> TYPE: DNA
<213> ORGANISM: Artificial
<220> FEATURE:
<223> OTHER INFORMATION: DNA Primer

<400> SEQUENCE: 483
cgccgtcaac tatcgtgata accaccccct gtggattggg 40

<210> SEQ ID NO 484
<211> LENGTH: 40
<212> TYPE: DNA
<213> ORGANISM: Artificial
<220> FEATURE:
<223> OTHER INFORMATION: DNA Primer

<400> SEQUENCE: 484
ccagcctcga ggttgaccgt cccaatccac aggggtggt 40

<210> SEQ ID NO 485
<211> LENGTH: 40
<212> TYPE: DNA
<213> ORGANISM: Artificial
<220> FEATURE:
<223> OTHER INFORMATION: DNA Primer

<400> SEQUENCE: 485
acggtcaacc tcgaggctgg agacgtcgtg gagtacaagt 40

<210> SEQ ID NO 486
<211> LENGTH: 40
<212> TYPE: DNA
<213> ORGANISM: Artificial
<220> FEATURE:
<223> OTHER INFORMATION: DNA Primer

<400> SEQUENCE: 486
atcttggccc acattgatgt acttgtactc cacgacgtct 40

<210> SEQ ID NO 487
<211> LENGTH: 40
<212> TYPE: DNA
<213> ORGANISM: Artificial
<220> FEATURE:
<223> OTHER INFORMATION: DNA Primer

<400> SEQUENCE: 487
acatcaatgt gggccaagat ggctccgtga cctgggagag 40

<210> SEQ ID NO 488
<211> LENGTH: 40
<212> TYPE: DNA
<213> ORGANISM: Artificial
<220> FEATURE:
<223> OTHER INFORMATION: DNA Primer

<400> SEQUENCE: 488
tgtaagtgtg gttgggatca ctctcccagg tcacggagcc 40

<210> SEQ ID NO 489
<211> LENGTH: 40
<212> TYPE: DNA

```
<213> ORGANISM: Artificial
<220> FEATURE:
<223> OTHER INFORMATION: DNA Primer

<400> SEQUENCE: 489
tgatcccaac cacacttaca cggttcctgc ggtggcttgt                          40

<210> SEQ ID NO 490
<211> LENGTH: 40
<212> TYPE: DNA
<213> ORGANISM: Artificial
<220> FEATURE:
<223> OTHER INFORMATION: DNA Primer

<400> SEQUENCE: 490
tccttgacaa cctgcgtcac acaagccacc gcaggaaccg                          40

<210> SEQ ID NO 491
<211> LENGTH: 40
<212> TYPE: DNA
<213> ORGANISM: Artificial
<220> FEATURE:
<223> OTHER INFORMATION: DNA Primer

<400> SEQUENCE: 491
gtgacgcagg ttgtcaagga ggacacctgg cagtcgtaaa                          40

<210> SEQ ID NO 492
<211> LENGTH: 40
<212> TYPE: DNA
<213> ORGANISM: Artificial
<220> FEATURE:
<223> OTHER INFORMATION: DNA Primer

<400> SEQUENCE: 492
ctttgtacaa gaaagctggg tttacgactg ccaggtgtcc                          40

<210> SEQ ID NO 493
<211> LENGTH: 40
<212> TYPE: DNA
<213> ORGANISM: Artificial
<220> FEATURE:
<223> OTHER INFORMATION: DNA Primer

<400> SEQUENCE: 493
cccagctttc ttgtacaaag ttggcattat aagaaagcat                          40

<210> SEQ ID NO 494
<211> LENGTH: 40
<212> TYPE: DNA
<213> ORGANISM: Artificial
<220> FEATURE:
<223> OTHER INFORMATION: DNA Primer

<400> SEQUENCE: 494
ttgcaacaaa ttgataagca atgctttctt ataatgccaa                          40

<210> SEQ ID NO 495
<211> LENGTH: 40
<212> TYPE: DNA
<213> ORGANISM: Artificial
<220> FEATURE:
<223> OTHER INFORMATION: DNA Primer

<400> SEQUENCE: 495
tgcttatcaa tttgttgcaa cgaacaggtc actatcagtc                          40
```

<210> SEQ ID NO 496
<211> LENGTH: 40
<212> TYPE: DNA
<213> ORGANISM: Artificial
<220> FEATURE:
<223> OTHER INFORMATION: DNA Primer

<400> SEQUENCE: 496
tcaaataatg attttatttt gactgatagt gacctgttcg					40

<210> SEQ ID NO 497
<211> LENGTH: 40
<212> TYPE: DNA
<213> ORGANISM: Artificial
<220> FEATURE:
<223> OTHER INFORMATION: DNA Primer

<400> SEQUENCE: 497
aaaataaaat cattatttga agcttaagcc tggggtgcct					40

<210> SEQ ID NO 498
<211> LENGTH: 31
<212> TYPE: DNA
<213> ORGANISM: Artificial
<220> FEATURE:
<223> OTHER INFORMATION: DNA Primer

<400> SEQUENCE: 498
agagagtcat taggcacccc aggcttaagc t					31

<210> SEQ ID NO 499
<211> LENGTH: 40
<212> TYPE: DNA
<213> ORGANISM: Artificial
<220> FEATURE:
<223> OTHER INFORMATION: DNA Primer

<400> SEQUENCE: 499
gtagtccggg tcttgtgtgc tgggagatgc aatcaccgca					40

<210> SEQ ID NO 500
<211> LENGTH: 40
<212> TYPE: DNA
<213> ORGANISM: Artificial
<220> FEATURE:
<223> OTHER INFORMATION: DNA Primer

<400> SEQUENCE: 500
gcacacaaga cccggactac tattacatgt ggacgcgaga					40

<210> SEQ ID NO 501
<211> LENGTH: 40
<212> TYPE: DNA
<213> ORGANISM: Artificial
<220> FEATURE:
<223> OTHER INFORMATION: DNA Primer

<400> SEQUENCE: 501
tagcgctctt gtcttcaaga ttctcatcga ccgcttcacc					40

<210> SEQ ID NO 502
<211> LENGTH: 40
<212> TYPE: DNA
<213> ORGANISM: Artificial
<220> FEATURE:

<223> OTHER INFORMATION: DNA Primer

<400> SEQUENCE: 502
aggcccgcat cgtacgtttc ggtgaagcgg tcgatgagaa                              40

<210> SEQ ID NO 503
<211> LENGTH: 40
<212> TYPE: DNA
<213> ORGANISM: Artificial
<220> FEATURE:
<223> OTHER INFORMATION: DNA Primer

<400> SEQUENCE: 503
tatcacgata gttgacacgg tccagagcca cggcggcgct                              40

<210> SEQ ID NO 504
<211> LENGTH: 40
<212> TYPE: DNA
<213> ORGANISM: Artificial
<220> FEATURE:
<223> OTHER INFORMATION: DNA Primer

<400> SEQUENCE: 504
ccgtgtcaac tatcgtgata accacccccT gtggattggg                              40

<210> SEQ ID NO 505
<211> LENGTH: 40
<212> TYPE: DNA
<213> ORGANISM: Artificial
<220> FEATURE:
<223> OTHER INFORMATION: DNA Primer

<400> SEQUENCE: 505
gtagtccggg tcttgtgtgc tgggagatgc aatcaccgca                              40

<210> SEQ ID NO 506
<211> LENGTH: 40
<212> TYPE: DNA
<213> ORGANISM: Artificial
<220> FEATURE:
<223> OTHER INFORMATION: DNA Primer

<400> SEQUENCE: 506
gcacacaaga cccggactac tattacatgt ggacgcgaga                              40

<210> SEQ ID NO 507
<211> LENGTH: 40
<212> TYPE: DNA
<213> ORGANISM: Artificial
<220> FEATURE:
<223> OTHER INFORMATION: DNA Primer

<400> SEQUENCE: 507
tagcgctctt gtcttcaaga ttctcatcga ccgcttcacc                              40

<210> SEQ ID NO 508
<211> LENGTH: 40
<212> TYPE: DNA
<213> ORGANISM: Artificial
<220> FEATURE:
<223> OTHER INFORMATION: DNA Primer

<400> SEQUENCE: 508
aggcccgcat cgtacgtttc ggtgaagcgg tcgatgagaa                              40

```
<210> SEQ ID NO 509
<211> LENGTH: 40
<212> TYPE: DNA
<213> ORGANISM: Artificial
<220> FEATURE:
<223> OTHER INFORMATION: DNA Primer

<400> SEQUENCE: 509
tagcgctctt gtcttcaaga ttctcatcga ccgcttcacc                40

<210> SEQ ID NO 510
<211> LENGTH: 40
<212> TYPE: DNA
<213> ORGANISM: Artificial
<220> FEATURE:
<223> OTHER INFORMATION: DNA Primer

<400> SEQUENCE: 510
aggcccgcat cgtacgtttc ggtgaagcgg tcgatgagaa                40

<210> SEQ ID NO 511
<211> LENGTH: 40
<212> TYPE: DNA
<213> ORGANISM: Artificial
<220> FEATURE:
<223> OTHER INFORMATION: DNA Primer

<400> SEQUENCE: 511
tatcacgata gttgacacgg tccagagcca cggcggcgct                40

<210> SEQ ID NO 512
<211> LENGTH: 40
<212> TYPE: DNA
<213> ORGANISM: Artificial
<220> FEATURE:
<223> OTHER INFORMATION: DNA Primer

<400> SEQUENCE: 512
ccgtgtcaac tatcgtgata accaccccct gtggattggg                40

<210> SEQ ID NO 513
<211> LENGTH: 40
<212> TYPE: DNA
<213> ORGANISM: Artificial
<220> FEATURE:
<223> OTHER INFORMATION: DNA Primer

<400> SEQUENCE: 513
tatcacgata gttgacacgg tccagagcca cggcggcgct                40

<210> SEQ ID NO 514
<211> LENGTH: 40
<212> TYPE: DNA
<213> ORGANISM: Artificial
<220> FEATURE:
<223> OTHER INFORMATION: DNA Primer

<400> SEQUENCE: 514
ccgtgtcaac tatcgtgata accaccccct gtggattggg                40

<210> SEQ ID NO 515
<211> LENGTH: 40
<212> TYPE: DNA
<213> ORGANISM: Artificial
<220> FEATURE:
<223> OTHER INFORMATION: DNA Primer
```

<400> SEQUENCE: 515
gtagtccggg tcttgtgtgc tgggagatgc aatcaccgca                40

<210> SEQ ID NO 516
<211> LENGTH: 40
<212> TYPE: DNA
<213> ORGANISM: Artificial
<220> FEATURE:
<223> OTHER INFORMATION: DNA Primer

<400> SEQUENCE: 516
gcacacaaga cccggactac tattacatgt ggacgcgaga                40

<210> SEQ ID NO 517
<211> LENGTH: 40
<212> TYPE: DNA
<213> ORGANISM: Artificial
<220> FEATURE:
<223> OTHER INFORMATION: DNA Primer

<400> SEQUENCE: 517
gtagtccggg tcttgtgtgc tgggagatgc aatcaccgca                40

<210> SEQ ID NO 518
<211> LENGTH: 40
<212> TYPE: DNA
<213> ORGANISM: Artificial
<220> FEATURE:
<223> OTHER INFORMATION: DNA Primer

<400> SEQUENCE: 518
gcacacaaga cccggactac tattacatgt ggacgcgaga                40

<210> SEQ ID NO 519
<211> LENGTH: 40
<212> TYPE: DNA
<213> ORGANISM: Artificial
<220> FEATURE:
<223> OTHER INFORMATION: DNA Primer

<400> SEQUENCE: 519
tagcgctctt gtcttcaaga ttctcatcga ccgcttcacc                40

<210> SEQ ID NO 520
<211> LENGTH: 40
<212> TYPE: DNA
<213> ORGANISM: Artificial
<220> FEATURE:
<223> OTHER INFORMATION: DNA Primer

<400> SEQUENCE: 520
aggcccgcat cgtacgtttc ggtgaagcgg tcgatgagaa                40

<210> SEQ ID NO 521
<211> LENGTH: 40
<212> TYPE: DNA
<213> ORGANISM: Artificial
<220> FEATURE:
<223> OTHER INFORMATION: DNA Primer

<400> SEQUENCE: 521
tatcacgata gttgacacgg tccagagcca cggcggcgct                40

<210> SEQ ID NO 522
<211> LENGTH: 40

```
<212> TYPE: DNA
<213> ORGANISM: Artificial
<220> FEATURE:
<223> OTHER INFORMATION: DNA Primer

<400> SEQUENCE: 522
ccgtgtcaac tatcgtgata accaccccct gtggattggg                           40

<210> SEQ ID NO 523
<211> LENGTH: 40
<212> TYPE: DNA
<213> ORGANISM: Artificial
<220> FEATURE:
<223> OTHER INFORMATION: DNA Primer

<400> SEQUENCE: 523
gtagtccggg tcttgtgtgc tgggagatgc aatcaccgca                           40

<210> SEQ ID NO 524
<211> LENGTH: 40
<212> TYPE: DNA
<213> ORGANISM: Artificial
<220> FEATURE:
<223> OTHER INFORMATION: DNA Primer

<400> SEQUENCE: 524
gcacacaaga cccggactac tattacatgt ggacgcgaga                           40

<210> SEQ ID NO 525
<211> LENGTH: 40
<212> TYPE: DNA
<213> ORGANISM: Artificial
<220> FEATURE:
<223> OTHER INFORMATION: DNA Primer

<400> SEQUENCE: 525
tagcgctctt gtcttcaaga ttctcatcga ccgcttcacc                           40

<210> SEQ ID NO 526
<211> LENGTH: 40
<212> TYPE: DNA
<213> ORGANISM: Artificial
<220> FEATURE:
<223> OTHER INFORMATION: DNA Primer

<400> SEQUENCE: 526
aggcccgcat cgtacgtttc ggtgaagcgg tcgatgagaa                           40

<210> SEQ ID NO 527
<211> LENGTH: 40
<212> TYPE: DNA
<213> ORGANISM: Artificial
<220> FEATURE:
<223> OTHER INFORMATION: DNA Primer

<400> SEQUENCE: 527
tatcacgata gttgacacgg tccagagcca cggcggcgct                           40

<210> SEQ ID NO 528
<211> LENGTH: 40
<212> TYPE: DNA
<213> ORGANISM: Artificial
<220> FEATURE:
<223> OTHER INFORMATION: DNA Primer

<400> SEQUENCE: 528
```
ccgtgtcaac tatcgtgata accaccccct gtggattggg           40

<210> SEQ ID NO 529
<211> LENGTH: 40
<212> TYPE: DNA
<213> ORGANISM: Artificial
<220> FEATURE:
<223> OTHER INFORMATION: DNA Primer

<400> SEQUENCE: 529
gcccgacgaa gagcggctgt caagaacgag gcgtacgacc           40

<210> SEQ ID NO 530
<211> LENGTH: 40
<212> TYPE: DNA
<213> ORGANISM: Artificial
<220> FEATURE:
<223> OTHER INFORMATION: DNA Primer

<400> SEQUENCE: 530
acagccgctc ttcgtcgggc tggcatcgtg cccccctcgt           40

<210> SEQ ID NO 531
<211> LENGTH: 40
<212> TYPE: DNA
<213> ORGANISM: Artificial
<220> FEATURE:
<223> OTHER INFORMATION: DNA Primer

<400> SEQUENCE: 531
gcccgacgaa gagcggctgt caagaacgag gcgtacgacc           40

<210> SEQ ID NO 532
<211> LENGTH: 40
<212> TYPE: DNA
<213> ORGANISM: Artificial
<220> FEATURE:
<223> OTHER INFORMATION: DNA Primer

<400> SEQUENCE: 532
acagccgctc ttcgtcgggc tggcatcgtg cccccctcgt           40

<210> SEQ ID NO 533
<211> LENGTH: 40
<212> TYPE: DNA
<213> ORGANISM: Artificial
<220> FEATURE:
<223> OTHER INFORMATION: DNA Primer

<400> SEQUENCE: 533
ttgaccgtat ggccaaactg tgtcgacacg agctcgtgga           40

<210> SEQ ID NO 534
<211> LENGTH: 40
<212> TYPE: DNA
<213> ORGANISM: Artificial
<220> FEATURE:
<223> OTHER INFORMATION: DNA Primer

<400> SEQUENCE: 534
cagtttggcc atacggtcaa ggtggcgggc aacgccgcgg           40

<210> SEQ ID NO 535
<211> LENGTH: 40
<212> TYPE: DNA
<213> ORGANISM: Artificial

<220> FEATURE:
<223> OTHER INFORMATION: DNA Primer

<400> SEQUENCE: 535
tatcacgata gttgacacgg tccagagcca cggcggcgct           40

<210> SEQ ID NO 536
<211> LENGTH: 40
<212> TYPE: DNA
<213> ORGANISM: Artificial
<220> FEATURE:
<223> OTHER INFORMATION: DNA Primer

<400> SEQUENCE: 536
ccgtgtcaac tatcgtgata accacccccct gtggattggg          40

<210> SEQ ID NO 537
<211> LENGTH: 40
<212> TYPE: DNA
<213> ORGANISM: Artificial
<220> FEATURE:
<223> OTHER INFORMATION: DNA Primer

<400> SEQUENCE: 537
atcttggccc acaatgatgt acttgtactc cacgacgtct          40

<210> SEQ ID NO 538
<211> LENGTH: 40
<212> TYPE: DNA
<213> ORGANISM: Artificial
<220> FEATURE:
<223> OTHER INFORMATION: DNA Primer

<400> SEQUENCE: 538
acatcattgt gggccaagat ggctccgtga cctgggagag          40

<210> SEQ ID NO 539
<211> LENGTH: 40
<212> TYPE: DNA
<213> ORGANISM: Artificial
<220> FEATURE:
<223> OTHER INFORMATION: DNA Primer

<400> SEQUENCE: 539
gtagtccggg tcttgtgtgc tgggagatgc aatcaccgca          40

<210> SEQ ID NO 540
<211> LENGTH: 40
<212> TYPE: DNA
<213> ORGANISM: Artificial
<220> FEATURE:
<223> OTHER INFORMATION: DNA Primer

<400> SEQUENCE: 540
gcacacaaga cccggactac tattacatgt ggacgcgaga          40

<210> SEQ ID NO 541
<211> LENGTH: 40
<212> TYPE: DNA
<213> ORGANISM: Artificial
<220> FEATURE:
<223> OTHER INFORMATION: DNA Primer

<400> SEQUENCE: 541
gcccgacgaa gagcggctgt caagaacgag gcgtacgacc          40

<210> SEQ ID NO 542
<211> LENGTH: 40
<212> TYPE: DNA
<213> ORGANISM: Artificial
<220> FEATURE:
<223> OTHER INFORMATION: DNA Primer

<400> SEQUENCE: 542
acagccgctc ttcgtcgggc tggcatcgtg cccccctcgt                40

<210> SEQ ID NO 543
<211> LENGTH: 40
<212> TYPE: DNA
<213> ORGANISM: Artificial
<220> FEATURE:
<223> OTHER INFORMATION: DNA Primer

<400> SEQUENCE: 543
ttgaccgtat ggccaaactg tgtcgacacg agctcgtgga                40

<210> SEQ ID NO 544
<211> LENGTH: 40
<212> TYPE: DNA
<213> ORGANISM: Artificial
<220> FEATURE:
<223> OTHER INFORMATION: DNA Primer

<400> SEQUENCE: 544
cagtttggcc atacggtcaa ggtggcgggc aacgccgcgg                40

<210> SEQ ID NO 545
<211> LENGTH: 40
<212> TYPE: DNA
<213> ORGANISM: Artificial
<220> FEATURE:
<223> OTHER INFORMATION: DNA Primer

<400> SEQUENCE: 545
tatcacgata gttgacacgg tccagagcca cggcggcgct                40

<210> SEQ ID NO 546
<211> LENGTH: 40
<212> TYPE: DNA
<213> ORGANISM: Artificial
<220> FEATURE:
<223> OTHER INFORMATION: DNA Primer

<400> SEQUENCE: 546
ccgtgtcaac tatcgtgata accacccccct gtggattggg                40

<210> SEQ ID NO 547
<211> LENGTH: 40
<212> TYPE: DNA
<213> ORGANISM: Artificial
<220> FEATURE:
<223> OTHER INFORMATION: DNA Primer

<400> SEQUENCE: 547
atcttggccc acaatgatgt acttgtactc cacgacgtct                40

<210> SEQ ID NO 548
<211> LENGTH: 40
<212> TYPE: DNA
<213> ORGANISM: Artificial
<220> FEATURE:
<223> OTHER INFORMATION: DNA Primer

<400> SEQUENCE: 548
acatcattgt gggccaagat ggctccgtga cctgggagag                40

<210> SEQ ID NO 549
<211> LENGTH: 40
<212> TYPE: DNA
<213> ORGANISM: Artificial
<220> FEATURE:
<223> OTHER INFORMATION: DNA Primer

<400> SEQUENCE: 549
tagcgctctt gtcttcaaga ttctcatcga ccgcttcacc                40

<210> SEQ ID NO 550
<211> LENGTH: 40
<212> TYPE: DNA
<213> ORGANISM: Artificial
<220> FEATURE:
<223> OTHER INFORMATION: DNA Primer

<400> SEQUENCE: 550
aggcccgcat cgtacgtttc ggtgaagcgg tcgatgagaa                40

<210> SEQ ID NO 551
<211> LENGTH: 40
<212> TYPE: DNA
<213> ORGANISM: Artificial
<220> FEATURE:
<223> OTHER INFORMATION: DNA Primer

<400> SEQUENCE: 551
gcccgacgaa gagcggctgt caagaacgag gcgtacgacc                40

<210> SEQ ID NO 552
<211> LENGTH: 40
<212> TYPE: DNA
<213> ORGANISM: Artificial
<220> FEATURE:
<223> OTHER INFORMATION: DNA Primer

<400> SEQUENCE: 552
acagccgctc ttcgtcgggc tggcatcgtg ccccnctcgt                40

<210> SEQ ID NO 553
<211> LENGTH: 40
<212> TYPE: DNA
<213> ORGANISM: Artificial
<220> FEATURE:
<223> OTHER INFORMATION: DNA Primer

<400> SEQUENCE: 553
ttgaccgtat ggccaaactg tgtcgacacg agctcgtgga                40

<210> SEQ ID NO 554
<211> LENGTH: 40
<212> TYPE: DNA
<213> ORGANISM: Artificial
<220> FEATURE:
<223> OTHER INFORMATION: DNA Primer

<400> SEQUENCE: 554
cagtttggcc atacggtcaa ggtggcgggc aacgccgcgg                40

<210> SEQ ID NO 555

```
<211> LENGTH: 40
<212> TYPE: DNA
<213> ORGANISM: Artificial
<220> FEATURE:
<223> OTHER INFORMATION: DNA Primer

<400> SEQUENCE: 555
tatcacgata gttgacacgg tccagagcca cggcggcgct                    40

<210> SEQ ID NO 556
<211> LENGTH: 40
<212> TYPE: DNA
<213> ORGANISM: Artificial
<220> FEATURE:
<223> OTHER INFORMATION: DNA Primer

<400> SEQUENCE: 556
ccgtgtcaac tatcgtgata accacccct gtggattggg                     40

<210> SEQ ID NO 557
<211> LENGTH: 40
<212> TYPE: DNA
<213> ORGANISM: Artificial
<220> FEATURE:
<223> OTHER INFORMATION: DNA Primer

<400> SEQUENCE: 557
atcttggccc acaatgatgt acttgtactc cacgacgtct                    40

<210> SEQ ID NO 558
<211> LENGTH: 40
<212> TYPE: DNA
<213> ORGANISM: Artificial
<220> FEATURE:
<223> OTHER INFORMATION: DNA Primer

<400> SEQUENCE: 558
acatcattgt gggccaagat ggctccgtga cctgggagag                    40

<210> SEQ ID NO 559
<211> LENGTH: 40
<212> TYPE: DNA
<213> ORGANISM: Artificial
<220> FEATURE:
<223> OTHER INFORMATION: DNA Primer

<400> SEQUENCE: 559
gtagtccggg tcttgtgtgc tgggagatgc aatcaccgca                    40

<210> SEQ ID NO 560
<211> LENGTH: 40
<212> TYPE: DNA
<213> ORGANISM: Artificial
<220> FEATURE:
<223> OTHER INFORMATION: DNA Primer

<400> SEQUENCE: 560
gcacacaaga cccggactac tattacatgt ggacgcgaga                    40

<210> SEQ ID NO 561
<211> LENGTH: 40
<212> TYPE: DNA
<213> ORGANISM: Artificial
<220> FEATURE:
<223> OTHER INFORMATION: DNA Primer

<400> SEQUENCE: 561
```
tagcgctctt gtcttcaaga ttctcatcga ccgcttcacc                    40

<210> SEQ ID NO 562
<211> LENGTH: 40
<212> TYPE: DNA
<213> ORGANISM: Artificial
<220> FEATURE:
<223> OTHER INFORMATION: DNA Primer

<400> SEQUENCE: 562
aggcccgcat cgtacgtttc ggtgaagcgg tcgatgagaa                    40

<210> SEQ ID NO 563
<211> LENGTH: 40
<212> TYPE: DNA
<213> ORGANISM: Artificial
<220> FEATURE:
<223> OTHER INFORMATION: DNA Primer

<400> SEQUENCE: 563
gtagtccggg tcacgtgtgc tgggagatgc aatcaccgca                    40

<210> SEQ ID NO 564
<211> LENGTH: 40
<212> TYPE: DNA
<213> ORGANISM: Artificial
<220> FEATURE:
<223> OTHER INFORMATION: DNA Primer

<400> SEQUENCE: 564
gcacacgtga cccggactac tattacatgt ggacgcgaga                    40

<210> SEQ ID NO 565
<211> LENGTH: 40
<212> TYPE: DNA
<213> ORGANISM: Artificial
<220> FEATURE:
<223> OTHER INFORMATION: DNA Primer

<400> SEQUENCE: 565
gtagtccggg tcacgtgtgc tgggagatgc aatcaccgca                    40

<210> SEQ ID NO 566
<211> LENGTH: 40
<212> TYPE: DNA
<213> ORGANISM: Artificial
<220> FEATURE:
<223> OTHER INFORMATION: DNA Primer

<400> SEQUENCE: 566
gcacacgtga cccggactac tattacatgt ggacgcgaga                    40

<210> SEQ ID NO 567
<211> LENGTH: 40
<212> TYPE: DNA
<213> ORGANISM: Artificial
<220> FEATURE:
<223> OTHER INFORMATION: DNA Primer

<400> SEQUENCE: 567
tagcgctctt gtcttcaaga ttctcatcga ccgcttcacc                    40

<210> SEQ ID NO 568
<211> LENGTH: 40
<212> TYPE: DNA

```
<213> ORGANISM: Artificial
<220> FEATURE:
<223> OTHER INFORMATION: DNA Primer

<400> SEQUENCE: 568
aggcccgcat cgtacgtttc ggtgaagcgg tcgatgagaa                    40

<210> SEQ ID NO 569
<211> LENGTH: 40
<212> TYPE: DNA
<213> ORGANISM: Artificial
<220> FEATURE:
<223> OTHER INFORMATION: DNA Primer

<400> SEQUENCE: 569
gtagtccggg tcacgtgtgc tgggagatgc aatcaccgca                    40

<210> SEQ ID NO 570
<211> LENGTH: 40
<212> TYPE: DNA
<213> ORGANISM: Artificial
<220> FEATURE:
<223> OTHER INFORMATION: DNA Primer

<400> SEQUENCE: 570
gcacacgtga cccggactac tattacatgt ggacgcgaga                    40

<210> SEQ ID NO 571
<211> LENGTH: 40
<212> TYPE: DNA
<213> ORGANISM: Artificial
<220> FEATURE:
<223> OTHER INFORMATION: DNA Primer

<400> SEQUENCE: 571
tagcgctctt gtcttcaaga ttctcatcga ccgcttcacc                    40

<210> SEQ ID NO 572
<211> LENGTH: 40
<212> TYPE: DNA
<213> ORGANISM: Artificial
<220> FEATURE:
<223> OTHER INFORMATION: DNA Primer

<400> SEQUENCE: 572
aggcccgcat cgtacgtttc ggtgaagcgg tcgatgagaa                    40

<210> SEQ ID NO 573
<211> LENGTH: 40
<212> TYPE: DNA
<213> ORGANISM: Artificial
<220> FEATURE:
<223> OTHER INFORMATION: DNA Primer

<400> SEQUENCE: 573
tatcacgata gttgacacgg tccagagcca cggcggcgct                    40

<210> SEQ ID NO 574
<211> LENGTH: 40
<212> TYPE: DNA
<213> ORGANISM: Artificial
<220> FEATURE:
<223> OTHER INFORMATION: DNA Primer

<400> SEQUENCE: 574
ccgtgtcaac tatcgtgata accaccccct gtggattggg                    40
```

<210> SEQ ID NO 575
<211> LENGTH: 40
<212> TYPE: DNA
<213> ORGANISM: Artificial
<220> FEATURE:
<223> OTHER INFORMATION: DNA Primer

<400> SEQUENCE: 575
gcccgacgaa gagcggctgt caagaacgag gcgtacgacc          40

<210> SEQ ID NO 576
<211> LENGTH: 40
<212> TYPE: DNA
<213> ORGANISM: Artificial
<220> FEATURE:
<223> OTHER INFORMATION: DNA Primer

<400> SEQUENCE: 576
acagccgctc ttcgtcgggc tggcatcgtg ccccctcgt          40

<210> SEQ ID NO 577
<211> LENGTH: 40
<212> TYPE: DNA
<213> ORGANISM: Artificial
<220> FEATURE:
<223> OTHER INFORMATION: DNA Primer

<400> SEQUENCE: 577
acgtcaggtg acgcgcagac agcggagtgc cgctgttgcg          40

<210> SEQ ID NO 578
<211> LENGTH: 40
<212> TYPE: DNA
<213> ORGANISM: Artificial
<220> FEATURE:
<223> OTHER INFORMATION: DNA Primer

<400> SEQUENCE: 578
gtctgcgcgt cacctgacgt ggtcgtacgc ctcgttcttg          40

<210> SEQ ID NO 579
<211> LENGTH: 40
<212> TYPE: DNA
<213> ORGANISM: Artificial
<220> FEATURE:
<223> OTHER INFORMATION: DNA Primer

<400> SEQUENCE: 579
acgtcaggtg acccgcagac agcggagtgc cgctgttgcg          40

<210> SEQ ID NO 580
<211> LENGTH: 40
<212> TYPE: DNA
<213> ORGANISM: Artificial
<220> FEATURE:
<223> OTHER INFORMATION: DNA Primer

<400> SEQUENCE: 580
gtctgcgggt cacctgacgt ggtcgtacgc ctcgttcttg          40

<210> SEQ ID NO 581
<211> LENGTH: 40
<212> TYPE: DNA
<213> ORGANISM: Artificial
<220> FEATURE:

<223> OTHER INFORMATION: DNA Primer

<400> SEQUENCE: 581
agaaacgcat cgtacgtttc ggtgaagcgg tcgatgaggt                              40

<210> SEQ ID NO 582
<211> LENGTH: 40
<212> TYPE: DNA
<213> ORGANISM: Artificial
<220> FEATURE:
<223> OTHER INFORMATION: DNA Primer

<400> SEQUENCE: 582
gaaacgtacg atgcgtttct gcagcgccgc atcgagcagt                              40

<210> SEQ ID NO 583
<211> LENGTH: 40
<212> TYPE: DNA
<213> ORGANISM: Artificial
<220> FEATURE:
<223> OTHER INFORMATION: DNA Primer

<400> SEQUENCE: 583
acgtcaggtg acgcgcagac agcggagtgc cgctgttgcg                              40

<210> SEQ ID NO 584
<211> LENGTH: 40
<212> TYPE: DNA
<213> ORGANISM: Artificial
<220> FEATURE:
<223> OTHER INFORMATION: DNA Primer

<400> SEQUENCE: 584
gtctgcgcgt cacctgacgt ggtcgtacgc ctcgttcttg                              40

<210> SEQ ID NO 585
<211> LENGTH: 40
<212> TYPE: DNA
<213> ORGANISM: Artificial
<220> FEATURE:
<223> OTHER INFORMATION: DNA Primer

<400> SEQUENCE: 585
gcccgacggg ccgtggctgt caagaacgag gcgtacgacc                              40

<210> SEQ ID NO 586
<211> LENGTH: 40
<212> TYPE: DNA
<213> ORGANISM: Artificial
<220> FEATURE:
<223> OTHER INFORMATION: DNA Primer

<400> SEQUENCE: 586
acagccacgg cccgtcgggc tggcatcgtg ccccctcgt                               40

<210> SEQ ID NO 587
<211> LENGTH: 40
<212> TYPE: DNA
<213> ORGANISM: Artificial
<220> FEATURE:
<223> OTHER INFORMATION: DNA Primer

<400> SEQUENCE: 587
aacctccgtg gccgtcacct tccacgttct cgtgtcgaca                              40

<210> SEQ ID NO 588
<211> LENGTH: 40
<212> TYPE: DNA
<213> ORGANISM: Artificial
<220> FEATURE:
<223> OTHER INFORMATION: DNA Primer

<400> SEQUENCE: 588
ttgaccgtct ggccaaactg tgtcgacacg agaacgtgga        40

<210> SEQ ID NO 589
<211> LENGTH: 40
<212> TYPE: DNA
<213> ORGANISM: Artificial
<220> FEATURE:
<223> OTHER INFORMATION: DNA Primer

<400> SEQUENCE: 589
atcttggccc actttgatgt acttgtactc cacgacgtct        40

<210> SEQ ID NO 590
<211> LENGTH: 40
<212> TYPE: DNA
<213> ORGANISM: Artificial
<220> FEATURE:
<223> OTHER INFORMATION: DNA Primer

<400> SEQUENCE: 590
acatcaaagt gggccaagat ggctccgtga cctgggagag        40

<210> SEQ ID NO 591
<211> LENGTH: 40
<212> TYPE: DNA
<213> ORGANISM: Artificial
<220> FEATURE:
<223> OTHER INFORMATION: DNA Primer

<400> SEQUENCE: 591
gtagtccggg tcacgtgtgc tgggagatgc aatcaccgca        40

<210> SEQ ID NO 592
<211> LENGTH: 40
<212> TYPE: DNA
<213> ORGANISM: Artificial
<220> FEATURE:
<223> OTHER INFORMATION: DNA Primer

<400> SEQUENCE: 592
gcacacgtga cccggactac tattacatgt ggacgcgaga        40

<210> SEQ ID NO 593
<211> LENGTH: 40
<212> TYPE: DNA
<213> ORGANISM: Artificial
<220> FEATURE:
<223> OTHER INFORMATION: DNA Primer

<400> SEQUENCE: 593
agaaacgcat cgtacgtttc ggtgaagcgg tcgatgaggt        40

<210> SEQ ID NO 594
<211> LENGTH: 40
<212> TYPE: DNA
<213> ORGANISM: Artificial
<220> FEATURE:
<223> OTHER INFORMATION: DNA Primer

```
<400> SEQUENCE: 594
gaaacgtacg atgcgtttct gcagcgccgc atcgagcagt                              40

<210> SEQ ID NO 595
<211> LENGTH: 40
<212> TYPE: DNA
<213> ORGANISM: Artificial
<220> FEATURE:
<223> OTHER INFORMATION: DNA Primer

<400> SEQUENCE: 595
acgtcaggtg acgcgcagac agcggagtgc cgctgttgcg                              40

<210> SEQ ID NO 596
<211> LENGTH: 40
<212> TYPE: DNA
<213> ORGANISM: Artificial
<220> FEATURE:
<223> OTHER INFORMATION: DNA Primer

<400> SEQUENCE: 596
gtctgcgcgt cacctgacgt ggtcgtacgc ctcgttcttg                              40

<210> SEQ ID NO 597
<211> LENGTH: 40
<212> TYPE: DNA
<213> ORGANISM: Artificial
<220> FEATURE:
<223> OTHER INFORMATION: DNA Primer

<400> SEQUENCE: 597
gcccgacggg ccgtggctgt caagaacgag gcgtacgacc                              40

<210> SEQ ID NO 598
<211> LENGTH: 40
<212> TYPE: DNA
<213> ORGANISM: Artificial
<220> FEATURE:
<223> OTHER INFORMATION: DNA Primer

<400> SEQUENCE: 598
acagccacgg cccgtcgggc tggcatcgtg cccccctcgt                              40

<210> SEQ ID NO 599
<211> LENGTH: 40
<212> TYPE: DNA
<213> ORGANISM: Artificial
<220> FEATURE:
<223> OTHER INFORMATION: DNA Primer

<400> SEQUENCE: 599
aacctccgtg gccgtcacct tccacgttct cgtgtcgaca                              40

<210> SEQ ID NO 600
<211> LENGTH: 40
<212> TYPE: DNA
<213> ORGANISM: Artificial
<220> FEATURE:
<223> OTHER INFORMATION: DNA Primer

<400> SEQUENCE: 600
ttgaccgtct ggccaaactg tgtcgacacg agaacgtgga                              40

<210> SEQ ID NO 601
<211> LENGTH: 40
```

```
<212> TYPE: DNA
<213> ORGANISM: Artificial
<220> FEATURE:
<223> OTHER INFORMATION: DNA Primer

<400> SEQUENCE: 601
atcttggccc actttgatgt acttgtactc cacgacgtct                40

<210> SEQ ID NO 602
<211> LENGTH: 40
<212> TYPE: DNA
<213> ORGANISM: Artificial
<220> FEATURE:
<223> OTHER INFORMATION: DNA Primer

<400> SEQUENCE: 602
acatcaaagt gggccaagat ggctccgtga cctgggagag                40

<210> SEQ ID NO 603
<211> LENGTH: 40
<212> TYPE: DNA
<213> ORGANISM: Artificial
<220> FEATURE:
<223> OTHER INFORMATION: DNA Primer

<400> SEQUENCE: 603
gtagtccggg tcacgtgtgc tgggagatgc aatcaccgca                40

<210> SEQ ID NO 604
<211> LENGTH: 40
<212> TYPE: DNA
<213> ORGANISM: Artificial
<220> FEATURE:
<223> OTHER INFORMATION: DNA Primer

<400> SEQUENCE: 604
gcacacgtga cccggactac tattacatgt ggacgcgaga                40

<210> SEQ ID NO 605
<211> LENGTH: 40
<212> TYPE: DNA
<213> ORGANISM: Artificial
<220> FEATURE:
<223> OTHER INFORMATION: DNA Primer

<400> SEQUENCE: 605
agaaacgcat cgtacgtttc ggtgaagcgg tcgatgaggt                40

<210> SEQ ID NO 606
<211> LENGTH: 40
<212> TYPE: DNA
<213> ORGANISM: Artificial
<220> FEATURE:
<223> OTHER INFORMATION: DNA Primer

<400> SEQUENCE: 606
gaaacgtacg atgcgtttct gcagcgccgc atcgagcagt                40

<210> SEQ ID NO 607
<211> LENGTH: 40
<212> TYPE: DNA
<213> ORGANISM: Artificial
<220> FEATURE:
<223> OTHER INFORMATION: DNA Primer

<400> SEQUENCE: 607
```
acgtcaggtg aagcgcagac agcggagtgc cgctgttgcg                    40

<210> SEQ ID NO 608
<211> LENGTH: 40
<212> TYPE: DNA
<213> ORGANISM: Artificial
<220> FEATURE:
<223> OTHER INFORMATION: DNA Primer

<400> SEQUENCE: 608
gtctgcgctt cacctgacgt ggtcgtacgc ctcgttcttg                    40

<210> SEQ ID NO 609
<211> LENGTH: 40
<212> TYPE: DNA
<213> ORGANISM: Artificial
<220> FEATURE:
<223> OTHER INFORMATION: DNA Primer

<400> SEQUENCE: 609
gcccgacggg ccgtggctgt caagaacgag gcgtacgacc                    40

<210> SEQ ID NO 610
<211> LENGTH: 40
<212> TYPE: DNA
<213> ORGANISM: Artificial
<220> FEATURE:
<223> OTHER INFORMATION: DNA Primer

<400> SEQUENCE: 610
acagccacgg cccgtcgggc tggcatcgtg ccccccctcgt                   40

<210> SEQ ID NO 611
<211> LENGTH: 40
<212> TYPE: DNA
<213> ORGANISM: Artificial
<220> FEATURE:
<223> OTHER INFORMATION: DNA Primer

<400> SEQUENCE: 611
aacctccgtg gccgtcacct tccacgttct cgtgtcgaca                    40

<210> SEQ ID NO 612
<211> LENGTH: 40
<212> TYPE: DNA
<213> ORGANISM: Artificial
<220> FEATURE:
<223> OTHER INFORMATION: DNA Primer

<400> SEQUENCE: 612
ttgaccgtat ggccaaactg tgtcgacacg agaacgtgga                    40

<210> SEQ ID NO 613
<211> LENGTH: 40
<212> TYPE: DNA
<213> ORGANISM: Artificial
<220> FEATURE:
<223> OTHER INFORMATION: DNA Primer

<400> SEQUENCE: 613
cagtttggcc atacggtcaa ggtggcgggc aacgccgcgg                    40

<210> SEQ ID NO 614
<211> LENGTH: 40
<212> TYPE: DNA
<213> ORGANISM: Artificial

```
<220> FEATURE:
<223> OTHER INFORMATION: DNA Primer

<400> SEQUENCE: 614
tatcggcata gttgacggcg tccagagcca cggcggcgct                              40

<210> SEQ ID NO 615
<211> LENGTH: 40
<212> TYPE: DNA
<213> ORGANISM: Artificial
<220> FEATURE:
<223> OTHER INFORMATION: DNA Primer

<400> SEQUENCE: 615
cgccgtcaac tatgccgata accacccect gtggattggg                              40

<210> SEQ ID NO 616
<211> LENGTH: 40
<212> TYPE: DNA
<213> ORGANISM: Artificial
<220> FEATURE:
<223> OTHER INFORMATION: DNA Primer

<400> SEQUENCE: 616
atcttggccc actttgatgt acttgtactc cacgacgtct                              40

<210> SEQ ID NO 617
<211> LENGTH: 40
<212> TYPE: DNA
<213> ORGANISM: Artificial
<220> FEATURE:
<223> OTHER INFORMATION: DNA Primer

<400> SEQUENCE: 617
acatcaaagt gggccaagat ggctccgtga cctgggagag                              40

<210> SEQ ID NO 618
<211> LENGTH: 25
<212> TYPE: DNA
<213> ORGANISM: Artificial
<220> FEATURE:
<223> OTHER INFORMATION: DNA Primer

<400> SEQUENCE: 618
acaagtttgt acaaaaaagc aggct                                              25

<210> SEQ ID NO 619
<211> LENGTH: 40
<212> TYPE: DNA
<213> ORGANISM: Artificial
<220> FEATURE:
<223> OTHER INFORMATION: DNA Primer

<400> SEQUENCE: 619
gcagtcgaca ggacgtgcat agcctgcttt tttgtacaaa                              40

<210> SEQ ID NO 620
<211> LENGTH: 40
<212> TYPE: DNA
<213> ORGANISM: Artificial
<220> FEATURE:
<223> OTHER INFORMATION: DNA Primer

<400> SEQUENCE: 620
atgcacgtcc tgtcgactgc ggtgctgctc ggctccgttg                              40
```

<210> SEQ ID NO 621
<211> LENGTH: 40
<212> TYPE: DNA
<213> ORGANISM: Artificial
<220> FEATURE:
<223> OTHER INFORMATION: DNA Primer

<400> SEQUENCE: 621
tcccaggacc ttttgaacgg caacggagcc gagcagcacc                                 40

<210> SEQ ID NO 622
<211> LENGTH: 40
<212> TYPE: DNA
<213> ORGANISM: Artificial
<220> FEATURE:
<223> OTHER INFORMATION: DNA Primer

<400> SEQUENCE: 622
ccgttcaaaa ggtcctggga agaccaggat caagcggtct                                 40

<210> SEQ ID NO 623
<211> LENGTH: 40
<212> TYPE: DNA
<213> ORGANISM: Artificial
<220> FEATURE:
<223> OTHER INFORMATION: DNA Primer

<400> SEQUENCE: 623
acctcttggt gacgtcggac agaccgcttg atcctggtct                                 40

<210> SEQ ID NO 624
<211> LENGTH: 40
<212> TYPE: DNA
<213> ORGANISM: Artificial
<220> FEATURE:
<223> OTHER INFORMATION: DNA Primer

<400> SEQUENCE: 624
gtccgacgtc accaagaggt ctgttgacga cttcatcagc                                 40

<210> SEQ ID NO 625
<211> LENGTH: 40
<212> TYPE: DNA
<213> ORGANISM: Artificial
<220> FEATURE:
<223> OTHER INFORMATION: DNA Primer

<400> SEQUENCE: 625
agtgcaatag gcgtctcggt gctgatgaag tcgtcaacag                                 40

<210> SEQ ID NO 626
<211> LENGTH: 40
<212> TYPE: DNA
<213> ORGANISM: Artificial
<220> FEATURE:
<223> OTHER INFORMATION: DNA Primer

<400> SEQUENCE: 626
accgagacgc ctattgcact gaacaatctt ctttgcaatg                                 40

<210> SEQ ID NO 627
<211> LENGTH: 40
<212> TYPE: DNA
<213> ORGANISM: Artificial
<220> FEATURE:
<223> OTHER INFORMATION: DNA Primer -continued

<400> SEQUENCE: 627
acggcatcca tcaggaccaa cattgcaaag aagattgttc                    40

<210> SEQ ID NO 628
<211> LENGTH: 40
<212> TYPE: DNA
<213> ORGANISM: Artificial
<220> FEATURE:
<223> OTHER INFORMATION: DNA Primer

<400> SEQUENCE: 628
ttggtcctga tggatgccgt gcattcggca catcagctgg                    40

<210> SEQ ID NO 629
<211> LENGTH: 40
<212> TYPE: DNA
<213> ORGANISM: Artificial
<220> FEATURE:
<223> OTHER INFORMATION: DNA Primer

<400> SEQUENCE: 629
tgggagatgc aatcaccgca ccagctgatg tgccgaatgc                    40

<210> SEQ ID NO 630
<211> LENGTH: 40
<212> TYPE: DNA
<213> ORGANISM: Artificial
<220> FEATURE:
<223> OTHER INFORMATION: DNA Primer

<400> SEQUENCE: 630
tgcggtgatt gcatctccca gcacaattga cccggactac                    40

<210> SEQ ID NO 631
<211> LENGTH: 40
<212> TYPE: DNA
<213> ORGANISM: Artificial
<220> FEATURE:
<223> OTHER INFORMATION: DNA Primer

<400> SEQUENCE: 631
tctcgcgtcc acatgtaata gtagtccggg tcaattgtgc                    40

<210> SEQ ID NO 632
<211> LENGTH: 40
<212> TYPE: DNA
<213> ORGANISM: Artificial
<220> FEATURE:
<223> OTHER INFORMATION: DNA Primer

<400> SEQUENCE: 632
tattacatgt ggacgcgaga tagcgctctt gtcttcaaga                    40

<210> SEQ ID NO 633
<211> LENGTH: 40
<212> TYPE: DNA
<213> ORGANISM: Artificial
<220> FEATURE:
<223> OTHER INFORMATION: DNA Primer

<400> SEQUENCE: 633
ggtgaagcgg tcgatgaggt tcttgaagac aagagcgcta                    40

<210> SEQ ID NO 634

-continued

```
<211> LENGTH: 40
<212> TYPE: DNA
<213> ORGANISM: Artificial
<220> FEATURE:
<223> OTHER INFORMATION: DNA Primer

<400> SEQUENCE: 634
acctcatcga ccgcttcacc gaaacgtacg atgcgggcct                              40

<210> SEQ ID NO 635
<211> LENGTH: 40
<212> TYPE: DNA
<213> ORGANISM: Artificial
<220> FEATURE:
<223> OTHER INFORMATION: DNA Primer

<400> SEQUENCE: 635
actgctcgat gcggcgctgc aggcccgcat cgtacgtttc                              40

<210> SEQ ID NO 636
<211> LENGTH: 40
<212> TYPE: DNA
<213> ORGANISM: Artificial
<220> FEATURE:
<223> OTHER INFORMATION: DNA Primer

<400> SEQUENCE: 636
gcagcgccgc atcgagcagt acattactgc ccaggtcact                              40

<210> SEQ ID NO 637
<211> LENGTH: 40
<212> TYPE: DNA
<213> ORGANISM: Artificial
<220> FEATURE:
<223> OTHER INFORMATION: DNA Primer

<400> SEQUENCE: 637
gggttagaga ggccctggag agtgacctgg gcagtaatgt                              40

<210> SEQ ID NO 638
<211> LENGTH: 40
<212> TYPE: DNA
<213> ORGANISM: Artificial
<220> FEATURE:
<223> OTHER INFORMATION: DNA Primer

<400> SEQUENCE: 638
ctccagggcc tctctaaccc ctcgggctcc ctcgcggacg                              40

<210> SEQ ID NO 639
<211> LENGTH: 40
<212> TYPE: DNA
<213> ORGANISM: Artificial
<220> FEATURE:
<223> OTHER INFORMATION: DNA Primer

<400> SEQUENCE: 639
gggctcgccg agaccagagc cgtccgcgag ggagcccgag                              40

<210> SEQ ID NO 640
<211> LENGTH: 40
<212> TYPE: DNA
<213> ORGANISM: Artificial
<220> FEATURE:
<223> OTHER INFORMATION: DNA Primer

<400> SEQUENCE: 640
```

```
gctctggtct cggcgagccc aagtttgagt tgaccctgaa                    40
```

<210> SEQ ID NO 641
<211> LENGTH: 40
<212> TYPE: DNA
<213> ORGANISM: Artificial
<220> FEATURE:
<223> OTHER INFORMATION: DNA Primer

<400> SEQUENCE: 641

```
cccagttgcc ggtgaaaggc ttcagggtca actcaaactt                    40
```

<210> SEQ ID NO 642
<211> LENGTH: 40
<212> TYPE: DNA
<213> ORGANISM: Artificial
<220> FEATURE:
<223> OTHER INFORMATION: DNA Primer

<400> SEQUENCE: 642

```
gcctttcacc ggcaactggg gtcgaccgca gcgggatggc                    40
```

<210> SEQ ID NO 643
<211> LENGTH: 40
<212> TYPE: DNA
<213> ORGANISM: Artificial
<220> FEATURE:
<223> OTHER INFORMATION: DNA Primer

<400> SEQUENCE: 643

```
gcaatggctc gcagagctgg gccatcccgc tgcggtcgac                    40
```

<210> SEQ ID NO 644
<211> LENGTH: 40
<212> TYPE: DNA
<213> ORGANISM: Artificial
<220> FEATURE:
<223> OTHER INFORMATION: DNA Primer

<400> SEQUENCE: 644

```
ccagctctgc gagccattgc cttgattgga tactcaaagt                    40
```

<210> SEQ ID NO 645
<211> LENGTH: 40
<212> TYPE: DNA
<213> ORGANISM: Artificial
<220> FEATURE:
<223> OTHER INFORMATION: DNA Primer

<400> SEQUENCE: 645

```
atagttgttg ttgatgagcc actttgagta tccaatcaag                    40
```

<210> SEQ ID NO 646
<211> LENGTH: 40
<212> TYPE: DNA
<213> ORGANISM: Artificial
<220> FEATURE:
<223> OTHER INFORMATION: DNA Primer

<400> SEQUENCE: 646

```
ggctcatcaa caacaactat cagtcgactg tgtccaacgt                    40
```

<210> SEQ ID NO 647
<211> LENGTH: 40
<212> TYPE: DNA

```
<213> ORGANISM: Artificial
<220> FEATURE:
<223> OTHER INFORMATION: DNA Primer

<400> SEQUENCE: 647
tgcgcacaat aggccagatg acgttggaca cagtcgactg                              40

<210> SEQ ID NO 648
<211> LENGTH: 40
<212> TYPE: DNA
<213> ORGANISM: Artificial
<220> FEATURE:
<223> OTHER INFORMATION: DNA Primer

<400> SEQUENCE: 648
catctggcct attgtgcgca acgacctcaa ctatgttgcc                              40

<210> SEQ ID NO 649
<211> LENGTH: 40
<212> TYPE: DNA
<213> ORGANISM: Artificial
<220> FEATURE:
<223> OTHER INFORMATION: DNA Primer

<400> SEQUENCE: 649
ccggtttggt tccagtactg ggcaacatag ttgaggtcgt                              40

<210> SEQ ID NO 650
<211> LENGTH: 40
<212> TYPE: DNA
<213> ORGANISM: Artificial
<220> FEATURE:
<223> OTHER INFORMATION: DNA Primer

<400> SEQUENCE: 650
cagtactgga accaaaccgg ctttgacctc tgggaagaag                              40

<210> SEQ ID NO 651
<211> LENGTH: 40
<212> TYPE: DNA
<213> ORGANISM: Artificial
<220> FEATURE:
<223> OTHER INFORMATION: DNA Primer

<400> SEQUENCE: 651
aaagaatgag ctcccattga cttcttccca gaggtcaaag                              40

<210> SEQ ID NO 652
<211> LENGTH: 40
<212> TYPE: DNA
<213> ORGANISM: Artificial
<220> FEATURE:
<223> OTHER INFORMATION: DNA Primer

<400> SEQUENCE: 652
tcaatgggag ctcattcttt actgttgcca accagcaccg                              40

<210> SEQ ID NO 653
<211> LENGTH: 40
<212> TYPE: DNA
<213> ORGANISM: Artificial
<220> FEATURE:
<223> OTHER INFORMATION: DNA Primer

<400> SEQUENCE: 653
tggcgccctc gacaagtgct cggtgctggt tggcaacagt                              40
```

<210> SEQ ID NO 654
<211> LENGTH: 40
<212> TYPE: DNA
<213> ORGANISM: Artificial
<220> FEATURE:
<223> OTHER INFORMATION: DNA Primer

<400> SEQUENCE: 654
agcacttgtc gagggcgcca ctcttgctgc cactcttggc				40

<210> SEQ ID NO 655
<211> LENGTH: 40
<212> TYPE: DNA
<213> ORGANISM: Artificial
<220> FEATURE:
<223> OTHER INFORMATION: DNA Primer

<400> SEQUENCE: 655
gaataagcgc ttcccgactg gccaagagtg gcagcaagag				40

<210> SEQ ID NO 656
<211> LENGTH: 40
<212> TYPE: DNA
<213> ORGANISM: Artificial
<220> FEATURE:
<223> OTHER INFORMATION: DNA Primer

<400> SEQUENCE: 656
cagtcgggaa gcgcttattc atctgttgct ccccaggttt				40

<210> SEQ ID NO 657
<211> LENGTH: 40
<212> TYPE: DNA
<213> ORGANISM: Artificial
<220> FEATURE:
<223> OTHER INFORMATION: DNA Primer

<400> SEQUENCE: 657
gaatcgttgg agaaagcaca aaacctgggg agcaacagat				40

<210> SEQ ID NO 658
<211> LENGTH: 40
<212> TYPE: DNA
<213> ORGANISM: Artificial
<220> FEATURE:
<223> OTHER INFORMATION: DNA Primer

<400> SEQUENCE: 658
tgtgctttct ccaacgattc tgggtgtcgt ctggtggata				40

<210> SEQ ID NO 659
<211> LENGTH: 40
<212> TYPE: DNA
<213> ORGANISM: Artificial
<220> FEATURE:
<223> OTHER INFORMATION: DNA Primer

<400> SEQUENCE: 659
tgttgatgtt ggagtcgacg tatccaccag acgacaccca				40

<210> SEQ ID NO 660
<211> LENGTH: 40
<212> TYPE: DNA
<213> ORGANISM: Artificial
<220> FEATURE:

<223> OTHER INFORMATION: DNA Primer

<400> SEQUENCE: 660
cgtcgactcc aacatcaaca ccaacgaggg caggactggc                    40

<210> SEQ ID NO 661
<211> LENGTH: 40
<212> TYPE: DNA
<213> ORGANISM: Artificial
<220> FEATURE:
<223> OTHER INFORMATION: DNA Primer

<400> SEQUENCE: 661
aggacggagt tgacatcctt gccagtcctg ccctcgttgg                    40

<210> SEQ ID NO 662
<211> LENGTH: 40
<212> TYPE: DNA
<213> ORGANISM: Artificial
<220> FEATURE:
<223> OTHER INFORMATION: DNA Primer

<400> SEQUENCE: 662
aaggatgtca actccgtcct gacttccatc cacaccttcg                    40

<210> SEQ ID NO 663
<211> LENGTH: 40
<212> TYPE: DNA
<213> ORGANISM: Artificial
<220> FEATURE:
<223> OTHER INFORMATION: DNA Primer

<400> SEQUENCE: 663
gtcacagcca aggttgggat cgaaggtgtg gatggaagtc                    40

<210> SEQ ID NO 664
<211> LENGTH: 40
<212> TYPE: DNA
<213> ORGANISM: Artificial
<220> FEATURE:
<223> OTHER INFORMATION: DNA Primer

<400> SEQUENCE: 664
atcccaacct tggctgtgac gcaggcacct tccagccatg                    40

<210> SEQ ID NO 665
<211> LENGTH: 40
<212> TYPE: DNA
<213> ORGANISM: Artificial
<220> FEATURE:
<223> OTHER INFORMATION: DNA Primer

<400> SEQUENCE: 665
tggagagcgc tttgtcactg catggctgga aggtgcctgc                    40

<210> SEQ ID NO 666
<211> LENGTH: 40
<212> TYPE: DNA
<213> ORGANISM: Artificial
<220> FEATURE:
<223> OTHER INFORMATION: DNA Primer

<400> SEQUENCE: 666
cagtgacaaa gcgctctcca acctcaaggt tgttgtcgac                    40

```
<210> SEQ ID NO 667
<211> LENGTH: 40
<212> TYPE: DNA
<213> ORGANISM: Artificial
<220> FEATURE:
<223> OTHER INFORMATION: DNA Primer

<400> SEQUENCE: 667
ccgtagatgg agcggaagga gtcgacaaca accttgaggt                    40

<210> SEQ ID NO 668
<211> LENGTH: 40
<212> TYPE: DNA
<213> ORGANISM: Artificial
<220> FEATURE:
<223> OTHER INFORMATION: DNA Primer

<400> SEQUENCE: 668
tccttccgct ccatctacgg cgtgaacaag ggcattcctg                    40

<210> SEQ ID NO 669
<211> LENGTH: 40
<212> TYPE: DNA
<213> ORGANISM: Artificial
<220> FEATURE:
<223> OTHER INFORMATION: DNA Primer

<400> SEQUENCE: 669
aatggcgacg gcagcaccgg caggaatgcc cttgttcacg                    40

<210> SEQ ID NO 670
<211> LENGTH: 40
<212> TYPE: DNA
<213> ORGANISM: Artificial
<220> FEATURE:
<223> OTHER INFORMATION: DNA Primer

<400> SEQUENCE: 670
ccggtgctgc cgtcgccatt ggccggtatg cagaggatgt                    40

<210> SEQ ID NO 671
<211> LENGTH: 40
<212> TYPE: DNA
<213> ORGANISM: Artificial
<220> FEATURE:
<223> OTHER INFORMATION: DNA Primer

<400> SEQUENCE: 671
aagggttgcc gttgtagtac acatcctctg cataccggcc                    40

<210> SEQ ID NO 672
<211> LENGTH: 40
<212> TYPE: DNA
<213> ORGANISM: Artificial
<220> FEATURE:
<223> OTHER INFORMATION: DNA Primer

<400> SEQUENCE: 672
gtactacaac ggcaaccctt ggtatcttgc tacatttgct                    40

<210> SEQ ID NO 673
<211> LENGTH: 40
<212> TYPE: DNA
<213> ORGANISM: Artificial
<220> FEATURE:
<223> OTHER INFORMATION: DNA Primer
```

-continued

<400> SEQUENCE: 673
tcgtacagct gctcggcagc agcaaatgta gcaagatacc                                40

<210> SEQ ID NO 674
<211> LENGTH: 40
<212> TYPE: DNA
<213> ORGANISM: Artificial
<220> FEATURE:
<223> OTHER INFORMATION: DNA Primer

<400> SEQUENCE: 674
gctgccgagc agctgtacga tgccatctac gtctggaaga                                40

<210> SEQ ID NO 675
<211> LENGTH: 40
<212> TYPE: DNA
<213> ORGANISM: Artificial
<220> FEATURE:
<223> OTHER INFORMATION: DNA Primer

<400> SEQUENCE: 675
caccgtgatg gagcccgtct tcttccagac gtagatggca                                40

<210> SEQ ID NO 676
<211> LENGTH: 40
<212> TYPE: DNA
<213> ORGANISM: Artificial
<220> FEATURE:
<223> OTHER INFORMATION: DNA Primer

<400> SEQUENCE: 676
agacgggctc catcacggtg accgccacct ccctggcctt                                40

<210> SEQ ID NO 677
<211> LENGTH: 40
<212> TYPE: DNA
<213> ORGANISM: Artificial
<220> FEATURE:
<223> OTHER INFORMATION: DNA Primer

<400> SEQUENCE: 677
caggaacaag ctcctggaag aaggccaggg aggtggcggt                                40

<210> SEQ ID NO 678
<211> LENGTH: 40
<212> TYPE: DNA
<213> ORGANISM: Artificial
<220> FEATURE:
<223> OTHER INFORMATION: DNA Primer

<400> SEQUENCE: 678
cttccaggag cttgttcctg gcgtgacggc cgggacctac                                40

<210> SEQ ID NO 679
<211> LENGTH: 40
<212> TYPE: DNA
<213> ORGANISM: Artificial
<220> FEATURE:
<223> OTHER INFORMATION: DNA Primer

<400> SEQUENCE: 679
aaggtcgaag agctgctgga gtaggtcccg gccgtcacgc                                40

<210> SEQ ID NO 680
<211> LENGTH: 40

-continued

<212> TYPE: DNA
<213> ORGANISM: Artificial
<220> FEATURE:
<223> OTHER INFORMATION: DNA Primer

<400> SEQUENCE: 680
tccagcagct cttcgacctt taccaacatc atcaacgccg    40

<210> SEQ ID NO 681
<211> LENGTH: 40
<212> TYPE: DNA
<213> ORGANISM: Artificial
<220> FEATURE:
<223> OTHER INFORMATION: DNA Primer

<400> SEQUENCE: 681
gccatcggcg tatgtcgaga cggcgttgat gatgttggta    40

<210> SEQ ID NO 682
<211> LENGTH: 40
<212> TYPE: DNA
<213> ORGANISM: Artificial
<220> FEATURE:
<223> OTHER INFORMATION: DNA Primer

<400> SEQUENCE: 682
tctcgacata cgccgatggc ttcctcagcg aggctgccaa    40

<210> SEQ ID NO 683
<211> LENGTH: 40
<212> TYPE: DNA
<213> ORGANISM: Artificial
<220> FEATURE:
<223> OTHER INFORMATION: DNA Primer

<400> SEQUENCE: 683
aaccgtcggc ggggacgtac ttggcagcct cgctgaggaa    40

<210> SEQ ID NO 684
<211> LENGTH: 40
<212> TYPE: DNA
<213> ORGANISM: Artificial
<220> FEATURE:
<223> OTHER INFORMATION: DNA Primer

<400> SEQUENCE: 684
gtacgtcccc gccgacggtt cgctggccga gcagtttgac    40

<210> SEQ ID NO 685
<211> LENGTH: 40
<212> TYPE: DNA
<213> ORGANISM: Artificial
<220> FEATURE:
<223> OTHER INFORMATION: DNA Primer

<400> SEQUENCE: 685
agcggagtgc cgctgttgcg gtcaaactgc tcggccagcg    40

<210> SEQ ID NO 686
<211> LENGTH: 40
<212> TYPE: DNA
<213> ORGANISM: Artificial
<220> FEATURE:
<223> OTHER INFORMATION: DNA Primer

<400> SEQUENCE: 686
cgcaacagcg gcactccgct gtctgcgctt cacctgacgt                40

<210> SEQ ID NO 687
<211> LENGTH: 40
<212> TYPE: DNA
<213> ORGANISM: Artificial
<220> FEATURE:
<223> OTHER INFORMATION: DNA Primer

<400> SEQUENCE: 687
caagaacgag gcgtacgacc acgtcaggtg aagcgcagac                40

<210> SEQ ID NO 688
<211> LENGTH: 40
<212> TYPE: DNA
<213> ORGANISM: Artificial
<220> FEATURE:
<223> OTHER INFORMATION: DNA Primer

<400> SEQUENCE: 688
ggtcgtacgc ctcgttcttg acagccacgg cccgtcgggc                40

<210> SEQ ID NO 689
<211> LENGTH: 40
<212> TYPE: DNA
<213> ORGANISM: Artificial
<220> FEATURE:
<223> OTHER INFORMATION: DNA Primer

<400> SEQUENCE: 689 acgaggggggg cacgatgcca gcccgacggg ccgtggctgt                40

<210> SEQ ID NO 690
<211> LENGTH: 40
<212> TYPE: DNA
<213> ORGANISM: Artificial
<220> FEATURE:
<223> OTHER INFORMATION: DNA Primer

<400> SEQUENCE: 690
tggcatcgtg ccccccctcgt gggccaacag cagcgctagc                40

<210> SEQ ID NO 691
<211> LENGTH: 40
<212> TYPE: DNA
<213> ORGANISM: Artificial
<220> FEATURE:
<223> OTHER INFORMATION: DNA Primer

<400> SEQUENCE: 691
gagcacgtcg aggggatcgt gctagcgctg ctgttggccc                40

<210> SEQ ID NO 692
<211> LENGTH: 40
<212> TYPE: DNA
<213> ORGANISM: Artificial
<220> FEATURE:
<223> OTHER INFORMATION: DNA Primer

<400> SEQUENCE: 692
acgatcccct cgacgtgctc cggcgcgtcc gtggtcggat                40

<210> SEQ ID NO 693
<211> LENGTH: 40
<212> TYPE: DNA
<213> ORGANISM: Artificial

```
<220> FEATURE:
<223> OTHER INFORMATION: DNA Primer

<400> SEQUENCE: 693
ggcggtggga cgcgagtagg atccgaccac ggacgcgccg                              40

<210> SEQ ID NO 694
<211> LENGTH: 40
<212> TYPE: DNA
<213> ORGANISM: Artificial
<220> FEATURE:
<223> OTHER INFORMATION: DNA Primer

<400> SEQUENCE: 694
cctactcgcg tcccaccgcc acgtcattcc ctccgtcgca                              40

<210> SEQ ID NO 695
<211> LENGTH: 40
<212> TYPE: DNA
<213> ORGANISM: Artificial
<220> FEATURE:
<223> OTHER INFORMATION: DNA Primer

<400> SEQUENCE: 695
gcacgccagg cttgggcgtc tgcgacggag ggaatgacgt                              40

<210> SEQ ID NO 696
<211> LENGTH: 40
<212> TYPE: DNA
<213> ORGANISM: Artificial
<220> FEATURE:
<223> OTHER INFORMATION: DNA Primer

<400> SEQUENCE: 696
gacgcccaag cctggcgtgc cttccggtac tccctacacg                              40

<210> SEQ ID NO 697
<211> LENGTH: 40
<212> TYPE: DNA
<213> ORGANISM: Artificial
<220> FEATURE:
<223> OTHER INFORMATION: DNA Primer

<400> SEQUENCE: 697
ggggtcgcgc agggcagggg cgtgtaggga gtaccggaag                              40

<210> SEQ ID NO 698
<211> LENGTH: 40
<212> TYPE: DNA
<213> ORGANISM: Artificial
<220> FEATURE:
<223> OTHER INFORMATION: DNA Primer

<400> SEQUENCE: 698
cccctgccct gcgcgacccc aacctccgtg gccgtcacct                              40

<210> SEQ ID NO 699
<211> LENGTH: 40
<212> TYPE: DNA
<213> ORGANISM: Artificial
<220> FEATURE:
<223> OTHER INFORMATION: DNA Primer

<400> SEQUENCE: 699
tgtcgacacg agctcgtgga aggtgacggc cacggaggtt                              40
```

<210> SEQ ID NO 700
<211> LENGTH: 40
<212> TYPE: DNA
<213> ORGANISM: Artificial
<220> FEATURE:
<223> OTHER INFORMATION: DNA Primer

<400> SEQUENCE: 700
tccacgagct cgtgtcgaca cagtttggcc agacggtcaa                                40

<210> SEQ ID NO 701
<211> LENGTH: 40
<212> TYPE: DNA
<213> ORGANISM: Artificial
<220> FEATURE:
<223> OTHER INFORMATION: DNA Primer

<400> SEQUENCE: 701
ccgcggcgtt gcccgccacc ttgaccgtct ggccaaactg                                40

<210> SEQ ID NO 702
<211> LENGTH: 40
<212> TYPE: DNA
<213> ORGANISM: Artificial
<220> FEATURE:
<223> OTHER INFORMATION: DNA Primer

<400> SEQUENCE: 702
ggtggcgggc aacgccgcgg ccctgggcaa ctggagcacg                                40

<210> SEQ ID NO 703
<211> LENGTH: 40
<212> TYPE: DNA
<213> ORGANISM: Artificial
<220> FEATURE:
<223> OTHER INFORMATION: DNA Primer

<400> SEQUENCE: 703
tccagagcca cggcggcgct cgtgctccag ttgcccaggg                                40

<210> SEQ ID NO 704
<211> LENGTH: 40
<212> TYPE: DNA
<213> ORGANISM: Artificial
<220> FEATURE:
<223> OTHER INFORMATION: DNA Primer

<400> SEQUENCE: 704
agcgccgccg tggctctgga cgccgtcaac tatgccgata                                40

<210> SEQ ID NO 705
<211> LENGTH: 40
<212> TYPE: DNA
<213> ORGANISM: Artificial
<220> FEATURE:
<223> OTHER INFORMATION: DNA Primer

<400> SEQUENCE: 705
cccaatccac aggggggtggt tatcggcata gttgacggcg                               40

<210> SEQ ID NO 706
<211> LENGTH: 40
<212> TYPE: DNA
<213> ORGANISM: Artificial
<220> FEATURE:
<223> OTHER INFORMATION: DNA Primer

```
<400> SEQUENCE: 706
accaccccct gtggattggg acggtcaacc tcgaggctgg                                40

<210> SEQ ID NO 707
<211> LENGTH: 40
<212> TYPE: DNA
<213> ORGANISM: Artificial
<220> FEATURE:
<223> OTHER INFORMATION: DNA Primer

<400> SEQUENCE: 707
acttgtactc cacgacgtct ccagcctcga ggttgaccgt                                40

<210> SEQ ID NO 708
<211> LENGTH: 40
<212> TYPE: DNA
<213> ORGANISM: Artificial
<220> FEATURE:
<223> OTHER INFORMATION: DNA Primer

<400> SEQUENCE: 708
agacgtcgtg gagtacaagt acatcaatgt gggccaagat                                40

<210> SEQ ID NO 709
<211> LENGTH: 40
<212> TYPE: DNA
<213> ORGANISM: Artificial
<220> FEATURE:
<223> OTHER INFORMATION: DNA Primer

<400> SEQUENCE: 709
ctctcccagg tcacggagcc atcttggccc acattgatgt                                40

<210> SEQ ID NO 710
<211> LENGTH: 40
<212> TYPE: DNA
<213> ORGANISM: Artificial
<220> FEATURE:
<223> OTHER INFORMATION: DNA Primer

<400> SEQUENCE: 710
ggctccgtga cctgggagag tgatcccaac cacacttaca                                40

<210> SEQ ID NO 711
<211> LENGTH: 40
<212> TYPE: DNA
<213> ORGANISM: Artificial
<220> FEATURE:
<223> OTHER INFORMATION: DNA Primer

<400> SEQUENCE: 711
acaagccacc gcaggaaccg tgtaagtgtg gttgggatca                                40

<210> SEQ ID NO 712
<211> LENGTH: 40
<212> TYPE: DNA
<213> ORGANISM: Artificial
<220> FEATURE:
<223> OTHER INFORMATION: DNA Primer

<400> SEQUENCE: 712
cggttcctgc ggtggcttgt gtgacgcagg ttgtcaagga                                40

<210> SEQ ID NO 713
```

```
<211> LENGTH: 40
<212> TYPE: DNA
<213> ORGANISM: Artificial
<220> FEATURE:
<223> OTHER INFORMATION: DNA Primer

<400> SEQUENCE: 713
tttacgactg ccaggtgtcc tccttgacaa cctgcgtcac                           40

<210> SEQ ID NO 714
<211> LENGTH: 40
<212> TYPE: DNA
<213> ORGANISM: Artificial
<220> FEATURE:
<223> OTHER INFORMATION: DNA Primer

<400> SEQUENCE: 714
ggacacctgg cagtcgtaaa cccagctttc ttgtacaaag                           40

<210> SEQ ID NO 715
<211> LENGTH: 24
<212> TYPE: DNA
<213> ORGANISM: Artificial
<220> FEATURE:
<223> OTHER INFORMATION: DNA Primer

<400> SEQUENCE: 715
accactttgt acaagaaagc tggg                                            24

<210> SEQ ID NO 716
<211> LENGTH: 40
<212> TYPE: DNA
<213> ORGANISM: Artificial
<220> FEATURE:
<223> OTHER INFORMATION: DNA Primer

<400> SEQUENCE: 716
tgcggtgatt gcatctccca gcacactttg cccggactac                           40

<210> SEQ ID NO 717
<211> LENGTH: 40
<212> TYPE: DNA
<213> ORGANISM: Artificial
<220> FEATURE:
<223> OTHER INFORMATION: DNA Primer

<400> SEQUENCE: 717
tctcgcgtcc acatgtaata gtagtccggg caaagtgtgc                           40

<210> SEQ ID NO 718
<211> LENGTH: 40
<212> TYPE: DNA
<213> ORGANISM: Artificial
<220> FEATURE:
<223> OTHER INFORMATION: DNA Primer

<400> SEQUENCE: 718
cgcaacagcg gcactccgct gtctgcggtt cacctgacgt                           40

<210> SEQ ID NO 719
<211> LENGTH: 40
<212> TYPE: DNA
<213> ORGANISM: Artificial
<220> FEATURE:
<223> OTHER INFORMATION: DNA Primer

<400> SEQUENCE: 719
```
caagaacgag gcgtacgacc acgtcaggtg aaccgcagac     40

<210> SEQ ID NO 720
<211> LENGTH: 40
<212> TYPE: DNA
<213> ORGANISM: Artificial
<220> FEATURE:
<223> OTHER INFORMATION: DNA Primer

<400> SEQUENCE: 720
tgtcgacacg agcgcgtgga aggtgacggc cacggaggtt     40

<210> SEQ ID NO 721
<211> LENGTH: 40
<212> TYPE: DNA
<213> ORGANISM: Artificial
<220> FEATURE:
<223> OTHER INFORMATION: DNA Primer

<400> SEQUENCE: 721
tccacgcgct cgtgtcgaca cagtttggcc acacggtcaa     40

<210> SEQ ID NO 722
<211> LENGTH: 40
<212> TYPE: DNA
<213> ORGANISM: Artificial
<220> FEATURE:
<223> OTHER INFORMATION: DNA Primer

<400> SEQUENCE: 722
ccgcggcgtt gcccgccacc ttgaccgtgt ggccaaactg     40

<210> SEQ ID NO 723
<211> LENGTH: 40
<212> TYPE: DNA
<213> ORGANISM: Artificial
<220> FEATURE:
<223> OTHER INFORMATION: DNA Primer

<400> SEQUENCE: 723
agcgccgccg tggctctgga cgccgtcaac tatagagata     40

<210> SEQ ID NO 724
<211> LENGTH: 40
<212> TYPE: DNA
<213> ORGANISM: Artificial
<220> FEATURE:
<223> OTHER INFORMATION: DNA Primer

<400> SEQUENCE: 724
cccaatccac aggggtggt tatctctata gttgacggcg     40

<210> SEQ ID NO 725
<211> LENGTH: 40
<212> TYPE: DNA
<213> ORGANISM: Artificial
<220> FEATURE:
<223> OTHER INFORMATION: DNA Primer

<400> SEQUENCE: 725
tgcggtgatt gcatctccca gcacacttga cccggactac     40

<210> SEQ ID NO 726
<211> LENGTH: 40
<212> TYPE: DNA

```
<213> ORGANISM: Artificial
<220> FEATURE:
<223> OTHER INFORMATION: DNA Primer

<400> SEQUENCE: 726
tctcgcgtcc acatgtaata gtagtccggg tcaagtgtgc                             40

<210> SEQ ID NO 727
<211> LENGTH: 40
<212> TYPE: DNA
<213> ORGANISM: Artificial
<220> FEATURE:
<223> OTHER INFORMATION: DNA Primer

<400> SEQUENCE: 727
cgcaacagcg gcactccgct gtctgcggtt cacctgacgt                             40

<210> SEQ ID NO 728
<211> LENGTH: 40
<212> TYPE: DNA
<213> ORGANISM: Artificial
<220> FEATURE:
<223> OTHER INFORMATION: DNA Primer

<400> SEQUENCE: 728
caagaacgag gcgtacgacc acgtcaggtg aaccgcagac                             40

<210> SEQ ID NO 729
<211> LENGTH: 40
<212> TYPE: DNA
<213> ORGANISM: Artificial
<220> FEATURE:
<223> OTHER INFORMATION: DNA Primer

<400> SEQUENCE: 729
tgtcgacacg agcgcgtgga aggtgacggc cacggaggtt                             40

<210> SEQ ID NO 730
<211> LENGTH: 40
<212> TYPE: DNA
<213> ORGANISM: Artificial
<220> FEATURE:
<223> OTHER INFORMATION: DNA Primer

<400> SEQUENCE: 730
tccacgcgct cgtgtcgaca cagtttggcc acacggtcaa                             40

<210> SEQ ID NO 731
<211> LENGTH: 40
<212> TYPE: DNA
<213> ORGANISM: Artificial
<220> FEATURE:
<223> OTHER INFORMATION: DNA Primer

<400> SEQUENCE: 731
ccgcggcgtt gcccgccacc ttgaccgtgt ggccaaactg                             40

<210> SEQ ID NO 732
<211> LENGTH: 40
<212> TYPE: DNA
<213> ORGANISM: Artificial
<220> FEATURE:
<223> OTHER INFORMATION: DNA Primer

<400> SEQUENCE: 732
agcgccgccg tggctctgga cgccgtcaac tatagagata                             40
```

<210> SEQ ID NO 733
<211> LENGTH: 40
<212> TYPE: DNA
<213> ORGANISM: Artificial
<220> FEATURE:
<223> OTHER INFORMATION: DNA Primer

<400> SEQUENCE: 733
cccaatccac aggggtggt tatctctata gttgacggcg                40

<210> SEQ ID NO 734
<211> LENGTH: 40
<212> TYPE: DNA
<213> ORGANISM: Artificial
<220> FEATURE:
<223> OTHER INFORMATION: DNA Primer

<400> SEQUENCE: 734
tgcggtgatt gcatctccca gcacactttg cccggactac                40

<210> SEQ ID NO 735
<211> LENGTH: 40
<212> TYPE: DNA
<213> ORGANISM: Artificial
<220> FEATURE:
<223> OTHER INFORMATION: DNA Primer

<400> SEQUENCE: 735
tctcgcgtcc acatgtaata gtagtccggg caaagtgtgc                40

<210> SEQ ID NO 736
<211> LENGTH: 40
<212> TYPE: DNA
<213> ORGANISM: Artificial
<220> FEATURE:
<223> OTHER INFORMATION: DNA Primer

<400> SEQUENCE: 736
ggtgaagcgg tcgatgagga tcttgaagac aagagcgcta                40

<210> SEQ ID NO 737
<211> LENGTH: 40
<212> TYPE: DNA
<213> ORGANISM: Artificial
<220> FEATURE:
<223> OTHER INFORMATION: DNA Primer

<400> SEQUENCE: 737
tcctcatcga ccgcttcacc gaaacgtacg atgcgggcct                40

<210> SEQ ID NO 738
<211> LENGTH: 40
<212> TYPE: DNA
<213> ORGANISM: Artificial
<220> FEATURE:
<223> OTHER INFORMATION: DNA Primer

<400> SEQUENCE: 738
cgcaacagcg gcactccgct gtctgcggtt cacctgacgt                40

<210> SEQ ID NO 739
<211> LENGTH: 40
<212> TYPE: DNA
<213> ORGANISM: Artificial
<220> FEATURE:

<223> OTHER INFORMATION: DNA Primer

<400> SEQUENCE: 739
caagaacgag gcgtacgacc acgtcaggtg aaccgcagac        40

<210> SEQ ID NO 740
<211> LENGTH: 40
<212> TYPE: DNA
<213> ORGANISM: Artificial
<220> FEATURE:
<223> OTHER INFORMATION: DNA Primer

<400> SEQUENCE: 740
tgtcgacacg agcgcgtgga aggtgacggc cacggaggtt        40

<210> SEQ ID NO 741
<211> LENGTH: 40
<212> TYPE: DNA
<213> ORGANISM: Artificial
<220> FEATURE:
<223> OTHER INFORMATION: DNA Primer

<400> SEQUENCE: 741
tccacgcgct cgtgtcgaca cagtttggcc acacggtcaa        40

<210> SEQ ID NO 742
<211> LENGTH: 40
<212> TYPE: DNA
<213> ORGANISM: Artificial
<220> FEATURE:
<223> OTHER INFORMATION: DNA Primer

<400> SEQUENCE: 742
ccgcggcgtt gcccgccacc ttgaccgtgt ggccaaactg        40

<210> SEQ ID NO 743
<211> LENGTH: 40
<212> TYPE: DNA
<213> ORGANISM: Artificial
<220> FEATURE:
<223> OTHER INFORMATION: DNA Primer

<400> SEQUENCE: 743
agcgccgccg tggctctgga cgccgtcaac tatagagata        40

<210> SEQ ID NO 744
<211> LENGTH: 40
<212> TYPE: DNA
<213> ORGANISM: Artificial
<220> FEATURE:
<223> OTHER INFORMATION: DNA Primer

<400> SEQUENCE: 744
cccaatccac aggggtggt tatctctata gttgacggcg        40

<210> SEQ ID NO 745
<211> LENGTH: 40
<212> TYPE: DNA
<213> ORGANISM: Artificial
<220> FEATURE:
<223> OTHER INFORMATION: DNA Primer

<400> SEQUENCE: 745
tgcggtgatt gcatctccca gcacacttga cccggactac        40

```
<210> SEQ ID NO 746
<211> LENGTH: 40
<212> TYPE: DNA
<213> ORGANISM: Artificial
<220> FEATURE:
<223> OTHER INFORMATION: DNA Primer

<400> SEQUENCE: 746
tctcgcgtcc acatgtaata gtagtccggg tcaagtgtgc                 40

<210> SEQ ID NO 747
<211> LENGTH: 40
<212> TYPE: DNA
<213> ORGANISM: Artificial
<220> FEATURE:
<223> OTHER INFORMATION: DNA Primer

<400> SEQUENCE: 747
ggtgaagcgg tcgatgagga tcttgaagac aagagcgcta                 40

<210> SEQ ID NO 748
<211> LENGTH: 40
<212> TYPE: DNA
<213> ORGANISM: Artificial
<220> FEATURE:
<223> OTHER INFORMATION: DNA Primer

<400> SEQUENCE: 748
tcctcatcga ccgcttcacc gaaacgtacg atgcgggcct                 40

<210> SEQ ID NO 749
<211> LENGTH: 40
<212> TYPE: DNA
<213> ORGANISM: Artificial
<220> FEATURE:
<223> OTHER INFORMATION: DNA Primer

<400> SEQUENCE: 749
cgcaacagcg gcactccgct gtctgcggtt cacctgacgt                 40

<210> SEQ ID NO 750
<211> LENGTH: 40
<212> TYPE: DNA
<213> ORGANISM: Artificial
<220> FEATURE:
<223> OTHER INFORMATION: DNA Primer

<400> SEQUENCE: 750
caagaacgag gcgtacgacc acgtcaggtg aaccgcagac                 40

<210> SEQ ID NO 751
<211> LENGTH: 40
<212> TYPE: DNA
<213> ORGANISM: Artificial
<220> FEATURE:
<223> OTHER INFORMATION: DNA Primer

<400> SEQUENCE: 751
tgtcgacacg agcgcgtgga aggtgacggc cacggaggtt                 40

<210> SEQ ID NO 752
<211> LENGTH: 40
<212> TYPE: DNA
<213> ORGANISM: Artificial
<220> FEATURE:
<223> OTHER INFORMATION: DNA Primer
```

```
<400> SEQUENCE: 752
tccacgcgct cgtgtcgaca cagtttggcc acacggtcaa                    40

<210> SEQ ID NO 753
<211> LENGTH: 40
<212> TYPE: DNA
<213> ORGANISM: Artificial
<220> FEATURE:
<223> OTHER INFORMATION: DNA Primer

<400> SEQUENCE: 753
ccgcggcgtt gcccgccacc ttgaccgtgt ggccaaactg                    40

<210> SEQ ID NO 754
<211> LENGTH: 40
<212> TYPE: DNA
<213> ORGANISM: Artificial
<220> FEATURE:
<223> OTHER INFORMATION: DNA Primer

<400> SEQUENCE: 754
agcgccgccg tggctctgga cgccgtcaac tatagagata                    40

<210> SEQ ID NO 755
<211> LENGTH: 40
<212> TYPE: DNA
<213> ORGANISM: Artificial
<220> FEATURE:
<223> OTHER INFORMATION: DNA Primer

<400> SEQUENCE: 755
cccaatccac aggggtggt tatctctata gttgacggcg                     40

<210> SEQ ID NO 756
<211> LENGTH: 40
<212> TYPE: DNA
<213> ORGANISM: Artificial
<220> FEATURE:
<223> OTHER INFORMATION: DNA Primer

<400> SEQUENCE: 756
tgcggtgatt gcatctccca gcacaagaga cccggactac                    40

<210> SEQ ID NO 757
<211> LENGTH: 40
<212> TYPE: DNA
<213> ORGANISM: Artificial
<220> FEATURE:
<223> OTHER INFORMATION: DNA Primer

<400> SEQUENCE: 757
tctcgcgtcc acatgtaata gtagtccggg tctcttgtgc                    40

<210> SEQ ID NO 758
<211> LENGTH: 40
<212> TYPE: DNA
<213> ORGANISM: Artificial
<220> FEATURE:
<223> OTHER INFORMATION: DNA Primer

<400> SEQUENCE: 758
cgcaacagcg gcactccgct gtctgcggtt cacctgacgt                    40

<210> SEQ ID NO 759
<211> LENGTH: 40
```

```
<212> TYPE: DNA
<213> ORGANISM: Artificial
<220> FEATURE:
<223> OTHER INFORMATION: DNA Primer

<400> SEQUENCE: 759
caagaacgag gcgtacgacc acgtcaggtg aaccgcagac                            40

<210> SEQ ID NO 760
<211> LENGTH: 40
<212> TYPE: DNA
<213> ORGANISM: Artificial
<220> FEATURE:
<223> OTHER INFORMATION: DNA Primer

<400> SEQUENCE: 760
tgtcgacacg agcgcgtgga aggtgacggc cacggaggtt                            40

<210> SEQ ID NO 761
<211> LENGTH: 40
<212> TYPE: DNA
<213> ORGANISM: Artificial
<220> FEATURE:
<223> OTHER INFORMATION: DNA Primer

<400> SEQUENCE: 761
tccacgcgct cgtgtcgaca cagtttggcc acacggtcaa                            40

<210> SEQ ID NO 762
<211> LENGTH: 40
<212> TYPE: DNA
<213> ORGANISM: Artificial
<220> FEATURE:
<223> OTHER INFORMATION: DNA Primer

<400> SEQUENCE: 762
ccgcggcgtt gcccgccacc ttgaccgtgt ggccaaactg                            40

<210> SEQ ID NO 763
<211> LENGTH: 40
<212> TYPE: DNA
<213> ORGANISM: Artificial
<220> FEATURE:
<223> OTHER INFORMATION: DNA Primer

<400> SEQUENCE: 763
agcgccgccg tggctctgga cgccgtcaac tatagagata                            40

<210> SEQ ID NO 764
<211> LENGTH: 40
<212> TYPE: DNA
<213> ORGANISM: Artificial
<220> FEATURE:
<223> OTHER INFORMATION: DNA Primer

<400> SEQUENCE: 764
cccaatccac aggggtggt tatctctata gttgacggcg                             40

<210> SEQ ID NO 765
<211> LENGTH: 40
<212> TYPE: DNA
<213> ORGANISM: Artificial
<220> FEATURE:
<223> OTHER INFORMATION: DNA Primer

<400> SEQUENCE: 765
```

```
tgcggtgatt gcatctccca gcacaagaga cccggactac                             40

<210> SEQ ID NO 766
<211> LENGTH: 40
<212> TYPE: DNA
<213> ORGANISM: Artificial
<220> FEATURE:
<223> OTHER INFORMATION: DNA Primer

<400> SEQUENCE: 766
tctcgcgtcc acatgtaata gtagtccggg tctcttgtgc                             40

<210> SEQ ID NO 767
<211> LENGTH: 40
<212> TYPE: DNA
<213> ORGANISM: Artificial
<220> FEATURE:
<223> OTHER INFORMATION: DNA Primer

<400> SEQUENCE: 767
ggtgaagcgg tcgatgagga tcttgaagac aagagcgcta                             40

<210> SEQ ID NO 768
<211> LENGTH: 40
<212> TYPE: DNA
<213> ORGANISM: Artificial
<220> FEATURE:
<223> OTHER INFORMATION: DNA Primer

<400> SEQUENCE: 768
tcctcatcga ccgcttcacc gaaacgtacg atgcgggcct                             40

<210> SEQ ID NO 769
<211> LENGTH: 40
<212> TYPE: DNA
<213> ORGANISM: Artificial
<220> FEATURE:
<223> OTHER INFORMATION: DNA Primer

<400> SEQUENCE: 769
cgcaacagcg gcactccgct gtctgcggtt cacctgacgt                             40

<210> SEQ ID NO 770
<211> LENGTH: 40
<212> TYPE: DNA
<213> ORGANISM: Artificial
<220> FEATURE:
<223> OTHER INFORMATION: DNA Primer

<400> SEQUENCE: 770
caagaacgag gcgtacgacc acgtcaggtg aaccgcagac                             40

<210> SEQ ID NO 771
<211> LENGTH: 40
<212> TYPE: DNA
<213> ORGANISM: Artificial
<220> FEATURE:
<223> OTHER INFORMATION: DNA Primer

<400> SEQUENCE: 771
tgtcgacacg agcgcgtgga aggtgacggc cacggaggtt                             40

<210> SEQ ID NO 772
<211> LENGTH: 40
<212> TYPE: DNA
<213> ORGANISM: Artificial
```

```
<220> FEATURE:
<223> OTHER INFORMATION: DNA Primer

<400> SEQUENCE: 772
tccacgcgct cgtgtcgaca cagtttggcc acacggtcaa                              40

<210> SEQ ID NO 773
<211> LENGTH: 40
<212> TYPE: DNA
<213> ORGANISM: Artificial
<220> FEATURE:
<223> OTHER INFORMATION: DNA Primer

<400> SEQUENCE: 773
ccgcggcgtt gcccgccacc ttgaccgtgt ggccaaactg                              40

<210> SEQ ID NO 774
<211> LENGTH: 40
<212> TYPE: DNA
<213> ORGANISM: Artificial
<220> FEATURE:
<223> OTHER INFORMATION: DNA Primer

<400> SEQUENCE: 774
agcgccgccg tggctctgga cgccgtcaac tatagagata                              40

<210> SEQ ID NO 775
<211> LENGTH: 40
<212> TYPE: DNA
<213> ORGANISM: Artificial
<220> FEATURE:
<223> OTHER INFORMATION: DNA Primer

<400> SEQUENCE: 775
cccaatccac aggggtggt tatctctata gttgacggcg                               40

<210> SEQ ID NO 776
<211> LENGTH: 40
<212> TYPE: DNA
<213> ORGANISM: Artificial
<220> FEATURE:
<223> OTHER INFORMATION: DNA Primer

<400> SEQUENCE: 776
tgcggtgatt gcatctccca gcacaagaga cccggactac                              40

<210> SEQ ID NO 777
<211> LENGTH: 40
<212> TYPE: DNA
<213> ORGANISM: Artificial
<220> FEATURE:
<223> OTHER INFORMATION: DNA Primer

<400> SEQUENCE: 777
tctcgcgtcc acatgtaata gtagtccggg tctcttgtgc                              40

<210> SEQ ID NO 778
<211> LENGTH: 40
<212> TYPE: DNA
<213> ORGANISM: Artificial
<220> FEATURE:
<223> OTHER INFORMATION: DNA Primer

<400> SEQUENCE: 778
cgcaacagcg gcactccgct gtctgcgaga cacctgacgt                              40
```

<210> SEQ ID NO 779
<211> LENGTH: 40
<212> TYPE: DNA
<213> ORGANISM: Artificial
<220> FEATURE:
<223> OTHER INFORMATION: DNA Primer

<400> SEQUENCE: 779
caagaacgag gcgtacgacc acgtcaggtg tctcgcagac        40

<210> SEQ ID NO 780
<211> LENGTH: 40
<212> TYPE: DNA
<213> ORGANISM: Artificial
<220> FEATURE:
<223> OTHER INFORMATION: DNA Primer

<400> SEQUENCE: 780
tgtcgacacg agcgcgtgga aggtgacggc cacggaggtt        40

<210> SEQ ID NO 781
<211> LENGTH: 40
<212> TYPE: DNA
<213> ORGANISM: Artificial
<220> FEATURE:
<223> OTHER INFORMATION: DNA Primer

<400> SEQUENCE: 781
tccacgcgct cgtgtcgaca cagtttggcc acacggtcaa        40

<210> SEQ ID NO 782
<211> LENGTH: 40
<212> TYPE: DNA
<213> ORGANISM: Artificial
<220> FEATURE:
<223> OTHER INFORMATION: DNA Primer

<400> SEQUENCE: 782
ccgcggcgtt gcccgccacc ttgaccgtgt ggccaaactg        40

<210> SEQ ID NO 783
<211> LENGTH: 40
<212> TYPE: DNA
<213> ORGANISM: Artificial
<220> FEATURE:
<223> OTHER INFORMATION: DNA Primer

<400> SEQUENCE: 783
agcgccgccg tggctctgga cgccgtcaac tatagagata        40

<210> SEQ ID NO 784
<211> LENGTH: 40
<212> TYPE: DNA
<213> ORGANISM: Artificial
<220> FEATURE:
<223> OTHER INFORMATION: DNA Primer

<400> SEQUENCE: 784
cccaatccac aggggtggt tatctctata gttgacggcg        40

<210> SEQ ID NO 785
<211> LENGTH: 40
<212> TYPE: DNA
<213> ORGANISM: Artificial
<220> FEATURE:
<223> OTHER INFORMATION: DNA Primer

<400> SEQUENCE: 785
tgcggtgatt gcatctccca gcacaagaga cccggactac                                    40

<210> SEQ ID NO 786
<211> LENGTH: 40
<212> TYPE: DNA
<213> ORGANISM: Artificial
<220> FEATURE:
<223> OTHER INFORMATION: DNA Primer

<400> SEQUENCE: 786
tctcgcgtcc acatgtaata gtagtccggg tctcttgtgc                                    40

<210> SEQ ID NO 787
<211> LENGTH: 40
<212> TYPE: DNA
<213> ORGANISM: Artificial
<220> FEATURE:
<223> OTHER INFORMATION: DNA Primer

<400> SEQUENCE: 787
ggtgaagcgg tcgatgagga tcttgaagac aagagcgcta                                    40

<210> SEQ ID NO 788
<211> LENGTH: 40
<212> TYPE: DNA
<213> ORGANISM: Artificial
<220> FEATURE:
<223> OTHER INFORMATION: DNA Primer

<400> SEQUENCE: 788
tcctcatcga ccgcttcacc gaaacgtacg atgcgggcct                                    40

<210> SEQ ID NO 789
<211> LENGTH: 40
<212> TYPE: DNA
<213> ORGANISM: Artificial
<220> FEATURE:
<223> OTHER INFORMATION: DNA Primer

<400> SEQUENCE: 789
cgcaacagcg gcactccgct gtctgcgaga cacctgacgt                                    40

<210> SEQ ID NO 790
<211> LENGTH: 40
<212> TYPE: DNA
<213> ORGANISM: Artificial
<220> FEATURE:
<223> OTHER INFORMATION: DNA Primer

<400> SEQUENCE: 790
caagaacgag gcgtacgacc acgtcaggtg tctcgcagac                                    40

<210> SEQ ID NO 791
<211> LENGTH: 40
<212> TYPE: DNA
<213> ORGANISM: Artificial
<220> FEATURE:
<223> OTHER INFORMATION: DNA Primer

<400> SEQUENCE: 791
tgtcgacacg agcgcgtgga aggtgacggc cacggaggtt                                    40

<210> SEQ ID NO 792

```
<211> LENGTH: 40
<212> TYPE: DNA
<213> ORGANISM: Artificial
<220> FEATURE:
<223> OTHER INFORMATION: DNA Primer

<400> SEQUENCE: 792
tccacgcgct cgtgtcgaca cagtttggcc acacggtcaa                               40

<210> SEQ ID NO 793
<211> LENGTH: 40
<212> TYPE: DNA
<213> ORGANISM: Artificial
<220> FEATURE:
<223> OTHER INFORMATION: DNA Primer

<400> SEQUENCE: 793
ccgcggcgtt gcccgccacc ttgaccgtgt ggccaaactg                               40

<210> SEQ ID NO 794
<211> LENGTH: 40
<212> TYPE: DNA
<213> ORGANISM: Artificial
<220> FEATURE:
<223> OTHER INFORMATION: DNA Primer

<400> SEQUENCE: 794
agcgccgccg tggctctgga cgccgtcaac tatagagata                               40

<210> SEQ ID NO 795
<211> LENGTH: 40
<212> TYPE: DNA
<213> ORGANISM: Artificial
<220> FEATURE:
<223> OTHER INFORMATION: DNA Primer

<400> SEQUENCE: 795
cccaatccac aggggtggt tatctctata gttgacggcg                                40

<210> SEQ ID NO 796
<211> LENGTH: 40
<212> TYPE: DNA
<213> ORGANISM: Artificial
<220> FEATURE:
<223> OTHER INFORMATION: DNA Primer

<400> SEQUENCE: 796
cgcaacagcg gcactccgct gtctgcggtt cacctgacgt                               40

<210> SEQ ID NO 797
<211> LENGTH: 40
<212> TYPE: DNA
<213> ORGANISM: Artificial
<220> FEATURE:
<223> OTHER INFORMATION: DNA Primer

<400> SEQUENCE: 797
caagaacgag gcgtacgacc acgtcaggtg aaccgcagac                               40

<210> SEQ ID NO 798
<211> LENGTH: 40
<212> TYPE: DNA
<213> ORGANISM: Artificial
<220> FEATURE:
<223> OTHER INFORMATION: DNA Primer

<400> SEQUENCE: 798
```

-continued ggtcgtacgc ctcgttcttg acagccgcgc tccgtcgggc    40

<210> SEQ ID NO 799
<211> LENGTH: 40
<212> TYPE: DNA
<213> ORGANISM: Artificial
<220> FEATURE:
<223> OTHER INFORMATION: DNA Primer

<400> SEQUENCE: 799 acgaggggg cacgatgcca gcccgacgga gcgcggctgt    40

<210> SEQ ID NO 800
<211> LENGTH: 40
<212> TYPE: DNA
<213> ORGANISM: Artificial
<220> FEATURE:
<223> OTHER INFORMATION: DNA Primer

<400> SEQUENCE: 800
tccacgagct cgtgtcgaca cagtttggcc acacggtcaa    40

<210> SEQ ID NO 801
<211> LENGTH: 40
<212> TYPE: DNA
<213> ORGANISM: Artificial
<220> FEATURE:
<223> OTHER INFORMATION: DNA Primer

<400> SEQUENCE: 801
ccgcggcgtt gcccgccacc ttgaccgtgt ggccaaactg    40

<210> SEQ ID NO 802
<211> LENGTH: 40
<212> TYPE: DNA
<213> ORGANISM: Artificial
<220> FEATURE:
<223> OTHER INFORMATION: DNA Primer

<400> SEQUENCE: 802
agcgccgccg tggctctgga ccgcgtcaac tatcgcgata    40

<210> SEQ ID NO 803
<211> LENGTH: 40
<212> TYPE: DNA
<213> ORGANISM: Artificial
<220> FEATURE:
<223> OTHER INFORMATION: DNA Primer

<400> SEQUENCE: 803
cccaatccac aggggtggt tatcgcgata gttgacgcgg    40

<210> SEQ ID NO 804
<211> LENGTH: 40
<212> TYPE: DNA
<213> ORGANISM: Artificial
<220> FEATURE:
<223> OTHER INFORMATION: DNA Primer

<400> SEQUENCE: 804
agacgtcgtg gagtacaagt acatcattgt gggccaagat    40

<210> SEQ ID NO 805
<211> LENGTH: 40
<212> TYPE: DNA

```
<213> ORGANISM: Artificial
<220> FEATURE:
<223> OTHER INFORMATION: DNA Primer

<400> SEQUENCE: 805
ctctcccagg tcacggagcc atcttggccc acaatgatgt                    40

<210> SEQ ID NO 806
<211> LENGTH: 40
<212> TYPE: DNA
<213> ORGANISM: Artificial
<220> FEATURE:
<223> OTHER INFORMATION: DNA Primer

<400> SEQUENCE: 806
cgcaacagcg gcactccgct gtctgcggtt cacctgacgt                    40

<210> SEQ ID NO 807
<211> LENGTH: 40
<212> TYPE: DNA
<213> ORGANISM: Artificial
<220> FEATURE:
<223> OTHER INFORMATION: DNA Primer

<400> SEQUENCE: 807
caagaacgag gcgtacgacc acgtcaggtg aaccgcagac                    40

<210> SEQ ID NO 808
<211> LENGTH: 40
<212> TYPE: DNA
<213> ORGANISM: Artificial
<220> FEATURE:
<223> OTHER INFORMATION: DNA Primer

<400> SEQUENCE: 808
ggtcgtacgc ctcgttcttg acagccgcgc aacgtcgggc                    40

<210> SEQ ID NO 809
<211> LENGTH: 40
<212> TYPE: DNA
<213> ORGANISM: Artificial
<220> FEATURE:
<223> OTHER INFORMATION: DNA Primer

<400> SEQUENCE: 809 acgaggggg cacgatgcca gcccgacgtt gcgcggctgt                     40

<210> SEQ ID NO 810
<211> LENGTH: 40
<212> TYPE: DNA
<213> ORGANISM: Artificial
<220> FEATURE:
<223> OTHER INFORMATION: DNA Primer

<400> SEQUENCE: 810
tccacgagct cgtgtcgaca cagtttggcc acacggtcaa                    40

<210> SEQ ID NO 811
<211> LENGTH: 40
<212> TYPE: DNA
<213> ORGANISM: Artificial
<220> FEATURE:
<223> OTHER INFORMATION: DNA Primer

<400> SEQUENCE: 811
ccgcggcgtt gcccgccacc ttgaccgtgt ggccaaactg                    40
```

<210> SEQ ID NO 812
<211> LENGTH: 40
<212> TYPE: DNA
<213> ORGANISM: Artificial
<220> FEATURE:
<223> OTHER INFORMATION: DNA Primer

<400> SEQUENCE: 812
agcgccgccg tggctctgga ccgcgtcaac tatcgcgata			40

<210> SEQ ID NO 813
<211> LENGTH: 40
<212> TYPE: DNA
<213> ORGANISM: Artificial
<220> FEATURE:
<223> OTHER INFORMATION: DNA Primer

<400> SEQUENCE: 813
cccaatccac aggggtggt tatcgcgata gttgacgcgg			40

<210> SEQ ID NO 814
<211> LENGTH: 40
<212> TYPE: DNA
<213> ORGANISM: Artificial
<220> FEATURE:
<223> OTHER INFORMATION: DNA Primer

<400> SEQUENCE: 814
agacgtcgtg gagtacaagt acatcattgt gggccaagat			40

<210> SEQ ID NO 815
<211> LENGTH: 40
<212> TYPE: DNA
<213> ORGANISM: Artificial
<220> FEATURE:
<223> OTHER INFORMATION: DNA Primer

<400> SEQUENCE: 815
ctctcccagg tcacggagcc atcttggccc acaatgatgt			40

<210> SEQ ID NO 816
<211> LENGTH: 40
<212> TYPE: DNA
<213> ORGANISM: Artificial
<220> FEATURE:
<223> OTHER INFORMATION: DNA Primer

<400> SEQUENCE: 816
cgcaacagcg gcactccgct gtctgcggtt cacctgacgt			40

<210> SEQ ID NO 817
<211> LENGTH: 40
<212> TYPE: DNA
<213> ORGANISM: Artificial
<220> FEATURE:
<223> OTHER INFORMATION: DNA Primer

<400> SEQUENCE: 817
caagaacgag gcgtacgacc acgtcaggtg aaccgcagac			40

<210> SEQ ID NO 818
<211> LENGTH: 40
<212> TYPE: DNA
<213> ORGANISM: Artificial
<220> FEATURE:

```
<223> OTHER INFORMATION: DNA Primer

<400> SEQUENCE: 818
ggtcgtacgc ctcgttcttg acagccgcgg cccgtcgggc                              40

<210> SEQ ID NO 819
<211> LENGTH: 40
<212> TYPE: DNA
<213> ORGANISM: Artificial
<220> FEATURE:
<223> OTHER INFORMATION: DNA Primer

<400> SEQUENCE: 819 acgaggggggg cacgatgcca gcccgacggg ccgcggctgt                             40

<210> SEQ ID NO 820
<211> LENGTH: 40
<212> TYPE: DNA
<213> ORGANISM: Artificial
<220> FEATURE:
<223> OTHER INFORMATION: DNA Primer

<400> SEQUENCE: 820
tccacgagct cgtgtcgaca cagtttggcc acacggtcaa                              40

<210> SEQ ID NO 821
<211> LENGTH: 40
<212> TYPE: DNA
<213> ORGANISM: Artificial
<220> FEATURE:
<223> OTHER INFORMATION: DNA Primer

<400> SEQUENCE: 821
ccgcggcgtt gcccgccacc ttgaccgtgt ggccaaactg                              40

<210> SEQ ID NO 822
<211> LENGTH: 40
<212> TYPE: DNA
<213> ORGANISM: Artificial
<220> FEATURE:
<223> OTHER INFORMATION: DNA Primer

<400> SEQUENCE: 822
agcgccgccg tggctctgga ccgcgtcaac tatgccgata                              40

<210> SEQ ID NO 823
<211> LENGTH: 40
<212> TYPE: DNA
<213> ORGANISM: Artificial
<220> FEATURE:
<223> OTHER INFORMATION: DNA Primer

<400> SEQUENCE: 823
cccaatccac aggggtggt tatcggcata gttgacgcgg                               40

<210> SEQ ID NO 824
<211> LENGTH: 40
<212> TYPE: DNA
<213> ORGANISM: Artificial
<220> FEATURE:
<223> OTHER INFORMATION: DNA Primer

<400> SEQUENCE: 824
agacgtcgtg gagtacaagt acatcattgt gggccaagat                              40
```

<210> SEQ ID NO 825
<211> LENGTH: 40
<212> TYPE: DNA
<213> ORGANISM: Artificial
<220> FEATURE:
<223> OTHER INFORMATION: DNA Primer

<400> SEQUENCE: 825
ctctcccagg tcacggagcc atcttggccc acaatgatgt         40

<210> SEQ ID NO 826
<211> LENGTH: 40
<212> TYPE: DNA
<213> ORGANISM: Artificial
<220> FEATURE:
<223> OTHER INFORMATION: DNA Primer

<400> SEQUENCE: 826
cgcaacagcg gcactccgct gtctgcggtt cacctgacgt         40

<210> SEQ ID NO 827
<211> LENGTH: 40
<212> TYPE: DNA
<213> ORGANISM: Artificial
<220> FEATURE:
<223> OTHER INFORMATION: DNA Primer

<400> SEQUENCE: 827
caagaacgag gcgtacgacc acgtcaggtg aaccgcagac         40

<210> SEQ ID NO 828
<211> LENGTH: 40
<212> TYPE: DNA
<213> ORGANISM: Artificial
<220> FEATURE:
<223> OTHER INFORMATION: DNA Primer

<400> SEQUENCE: 828
ggtcgtacgc ctcgttcttg acagccgcgg cccgtcgggc         40

<210> SEQ ID NO 829
<211> LENGTH: 40
<212> TYPE: DNA
<213> ORGANISM: Artificial
<220> FEATURE:
<223> OTHER INFORMATION: DNA Primer

<400> SEQUENCE: 829 acgaggggggg cacgatgcca gcccgacggg ccgcggctgt        40

<210> SEQ ID NO 830
<211> LENGTH: 40
<212> TYPE: DNA
<213> ORGANISM: Artificial
<220> FEATURE:
<223> OTHER INFORMATION: DNA Primer

<400> SEQUENCE: 830
tccacgagct cgtgtcgaca cagtttggcc acacggtcaa         40

<210> SEQ ID NO 831
<211> LENGTH: 40
<212> TYPE: DNA
<213> ORGANISM: Artificial
<220> FEATURE:
<223> OTHER INFORMATION: DNA Primer

```
<400> SEQUENCE: 831
ccgcggcgtt gcccgccacc ttgaccgtgt ggccaaactg                                40

<210> SEQ ID NO 832
<211> LENGTH: 40
<212> TYPE: DNA
<213> ORGANISM: Artificial
<220> FEATURE:
<223> OTHER INFORMATION: DNA Primer

<400> SEQUENCE: 832
agcgccgccg tggctctgga cgccgtcaac tatcgcgata                                40

<210> SEQ ID NO 833
<211> LENGTH: 40
<212> TYPE: DNA
<213> ORGANISM: Artificial
<220> FEATURE:
<223> OTHER INFORMATION: DNA Primer

<400> SEQUENCE: 833
cccaatccac aggggtggt tatcgcgata gttgacggcg                                 40

<210> SEQ ID NO 834
<211> LENGTH: 40
<212> TYPE: DNA
<213> ORGANISM: Artificial
<220> FEATURE:
<223> OTHER INFORMATION: DNA Primer

<400> SEQUENCE: 834
agacgtcgtg gagtacaagt acatcattgt gggccaagat                                40

<210> SEQ ID NO 835
<211> LENGTH: 40
<212> TYPE: DNA
<213> ORGANISM: Artificial
<220> FEATURE:
<223> OTHER INFORMATION: DNA Primer

<400> SEQUENCE: 835
ctctcccagg tcacggagcc atcttggccc acaatgatgt                                40

<210> SEQ ID NO 836
<211> LENGTH: 40
<212> TYPE: DNA
<213> ORGANISM: Artificial
<220> FEATURE:
<223> OTHER INFORMATION: DNA Primer

<400> SEQUENCE: 836
cagtagatgg agcggaagga gtcgacaaca accttgaggt                                40

<210> SEQ ID NO 837
<211> LENGTH: 40
<212> TYPE: DNA
<213> ORGANISM: Artificial
<220> FEATURE:
<223> OTHER INFORMATION: DNA Primer

<400> SEQUENCE: 837
tccttccgct ccatctactg cgtgaacaag ggcattcctg                                40

<210> SEQ ID NO 838
<211> LENGTH: 40
```

```
<212> TYPE: DNA
<213> ORGANISM: Artificial
<220> FEATURE:
<223> OTHER INFORMATION: DNA Primer

<400> SEQUENCE: 838
cgcaacagcg gcactccgct gtctgcgaga cacctgacgt         40

<210> SEQ ID NO 839
<211> LENGTH: 40
<212> TYPE: DNA
<213> ORGANISM: Artificial
<220> FEATURE:
<223> OTHER INFORMATION: DNA Primer

<400> SEQUENCE: 839
caagaacgag gcgtacgacc acgtcaggtg tctcgcagac         40

<210> SEQ ID NO 840
<211> LENGTH: 40
<212> TYPE: DNA
<213> ORGANISM: Artificial
<220> FEATURE:
<223> OTHER INFORMATION: DNA Primer

<400> SEQUENCE: 840
ggtcgtacgc ctcgttcttg acagccacgc tccgtcgggc         40

<210> SEQ ID NO 841
<211> LENGTH: 40
<212> TYPE: DNA
<213> ORGANISM: Artificial
<220> FEATURE:
<223> OTHER INFORMATION: DNA Primer

<400> SEQUENCE: 841 acgaggggg cacgatgcca gcccgacgga gcgtggctgt         40

<210> SEQ ID NO 842
<211> LENGTH: 40
<212> TYPE: DNA
<213> ORGANISM: Artificial
<220> FEATURE:
<223> OTHER INFORMATION: DNA Primer

<400> SEQUENCE: 842
cagtagatgg agcggaagga gtcgacaaca accttgaggt         40

<210> SEQ ID NO 843
<211> LENGTH: 40
<212> TYPE: DNA
<213> ORGANISM: Artificial
<220> FEATURE:
<223> OTHER INFORMATION: DNA Primer

<400> SEQUENCE: 843
tccttccgct ccatctactg cgtgaacaag ggcattcctg         40

<210> SEQ ID NO 844
<211> LENGTH: 40
<212> TYPE: DNA
<213> ORGANISM: Artificial
<220> FEATURE:
<223> OTHER INFORMATION: DNA Primer

<400> SEQUENCE: 844
```
cgcaacagcg gcactccgct gtctgcggta cacctgacgt                                40

<210> SEQ ID NO 845
<211> LENGTH: 40
<212> TYPE: DNA
<213> ORGANISM: Artificial
<220> FEATURE:
<223> OTHER INFORMATION: DNA Primer

<400> SEQUENCE: 845
caagaacgag gcgtacgacc acgtcaggtg taccgcagac                                40

<210> SEQ ID NO 846
<211> LENGTH: 40
<212> TYPE: DNA
<213> ORGANISM: Artificial
<220> FEATURE:
<223> OTHER INFORMATION: DNA Primer

<400> SEQUENCE: 846
ggtcgtacgc ctcgttcttg acagccacgc agcgtcgggc                                40

<210> SEQ ID NO 847
<211> LENGTH: 40
<212> TYPE: DNA
<213> ORGANISM: Artificial
<220> FEATURE:
<223> OTHER INFORMATION: DNA Primer

<400> SEQUENCE: 847 acgaggggg cacgatgcca gcccgacgct gcgtggctgt                                 40

<210> SEQ ID NO 848
<211> LENGTH: 40
<212> TYPE: DNA
<213> ORGANISM: Artificial
<220> FEATURE:
<223> OTHER INFORMATION: DNA Primer

<400> SEQUENCE: 848
cagtagatgg agcggaagga gtcgacaaca accttgaggt                                40

<210> SEQ ID NO 849
<211> LENGTH: 40
<212> TYPE: DNA
<213> ORGANISM: Artificial
<220> FEATURE:
<223> OTHER INFORMATION: DNA Primer

<400> SEQUENCE: 849
tccttccgct ccatctactg cgtgaacaag ggcattcctg                                40

<210> SEQ ID NO 850
<211> LENGTH: 40
<212> TYPE: DNA
<213> ORGANISM: Artificial
<220> FEATURE:
<223> OTHER INFORMATION: DNA Primer

<400> SEQUENCE: 850
cgcaacagcg gcactccgct gtctgcggta cacctgacgt                                40

<210> SEQ ID NO 851
<211> LENGTH: 40
<212> TYPE: DNA
<213> ORGANISM: Artificial

```
<220> FEATURE:
<223> OTHER INFORMATION: DNA Primer

<400> SEQUENCE: 851
caagaacgag gcgtacgacc acgtcaggtg taccgcagac              40

<210> SEQ ID NO 852
<211> LENGTH: 40
<212> TYPE: DNA
<213> ORGANISM: Artificial
<220> FEATURE:
<223> OTHER INFORMATION: DNA Primer

<400> SEQUENCE: 852
ggtcgtacgc ctcgttcttg acagccacgt tacgtcgggc              40

<210> SEQ ID NO 853
<211> LENGTH: 40
<212> TYPE: DNA
<213> ORGANISM: Artificial
<220> FEATURE:
<223> OTHER INFORMATION: DNA Primer

<400> SEQUENCE: 853 acgaggggg cacgatgcca gcccgacgta acgtggctgt               40

<210> SEQ ID NO 854
<211> LENGTH: 40
<212> TYPE: DNA
<213> ORGANISM: Artificial
<220> FEATURE:
<223> OTHER INFORMATION: DNA Primer

<400> SEQUENCE: 854
tccacgagct cgtgtcgaca cagtttggcc acacggtcaa              40

<210> SEQ ID NO 855
<211> LENGTH: 40
<212> TYPE: DNA
<213> ORGANISM: Artificial
<220> FEATURE:
<223> OTHER INFORMATION: DNA Primer

<400> SEQUENCE: 855
ccgcggcgtt gcccgccacc ttgaccgtgt ggccaaactg              40

<210> SEQ ID NO 856
<211> LENGTH: 40
<212> TYPE: DNA
<213> ORGANISM: Artificial
<220> FEATURE:
<223> OTHER INFORMATION: DNA Primer

<400> SEQUENCE: 856
cagtagatgg agcggaagga gtcgacaaca accttgaggt              40

<210> SEQ ID NO 857
<211> LENGTH: 40
<212> TYPE: DNA
<213> ORGANISM: Artificial
<220> FEATURE:
<223> OTHER INFORMATION: DNA Primer

<400> SEQUENCE: 857
tccttccgct ccatctactg cgtgaacaag ggcattcctg              40
```

<210> SEQ ID NO 858
<211> LENGTH: 40
<212> TYPE: DNA
<213> ORGANISM: Artificial
<220> FEATURE:
<223> OTHER INFORMATION: DNA Primer

<400> SEQUENCE: 858
cgcaacagcg gcactccgct gtctgcgaga cacctgacgt          40

<210> SEQ ID NO 859
<211> LENGTH: 40
<212> TYPE: DNA
<213> ORGANISM: Artificial
<220> FEATURE:
<223> OTHER INFORMATION: DNA Primer

<400> SEQUENCE: 859
caagaacgag gcgtacgacc acgtcaggtg tctcgcagac          40

<210> SEQ ID NO 860
<211> LENGTH: 40
<212> TYPE: DNA
<213> ORGANISM: Artificial
<220> FEATURE:
<223> OTHER INFORMATION: DNA Primer

<400> SEQUENCE: 860
ggtcgtacgc ctcgttcttg acagccacgc agcgtcgggc          40

<210> SEQ ID NO 861
<211> LENGTH: 40
<212> TYPE: DNA
<213> ORGANISM: Artificial
<220> FEATURE:
<223> OTHER INFORMATION: DNA Primer

<400> SEQUENCE: 861 acgaggggg cacgatgcca gcccgacgct gcgtggctgt          40

<210> SEQ ID NO 862
<211> LENGTH: 40
<212> TYPE: DNA
<213> ORGANISM: Artificial
<220> FEATURE:
<223> OTHER INFORMATION: DNA Primer

<400> SEQUENCE: 862
tccacgagct cgtgtcgaca cagtttggcc acacggtcaa          40

<210> SEQ ID NO 863
<211> LENGTH: 40
<212> TYPE: DNA
<213> ORGANISM: Artificial
<220> FEATURE:
<223> OTHER INFORMATION: DNA Primer

<400> SEQUENCE: 863
ccgcggcgtt gcccgccacc ttgaccgtgt ggccaaactg          40

<210> SEQ ID NO 864
<211> LENGTH: 40
<212> TYPE: DNA
<213> ORGANISM: Artificial
<220> FEATURE:
<223> OTHER INFORMATION: DNA Primer

<400> SEQUENCE: 864
cgcaacagcg gcactccgct gtctgcgcgt cacctgacgt    40

<210> SEQ ID NO 865
<211> LENGTH: 40
<212> TYPE: DNA
<213> ORGANISM: Artificial
<220> FEATURE:
<223> OTHER INFORMATION: DNA Primer

<400> SEQUENCE: 865
caagaacgag gcgtacgacc acgtcaggtg acgcgcagac    40

<210> SEQ ID NO 866
<211> LENGTH: 40
<212> TYPE: DNA
<213> ORGANISM: Artificial
<220> FEATURE:
<223> OTHER INFORMATION: DNA Primer

<400> SEQUENCE: 866
ggtcgtacgc ctcgttcttg acagccacgc tccgtcgggc    40

<210> SEQ ID NO 867
<211> LENGTH: 40
<212> TYPE: DNA
<213> ORGANISM: Artificial
<220> FEATURE:
<223> OTHER INFORMATION: DNA Primer

<400> SEQUENCE: 867 acgaggggg cacgatgcca gcccgacgga gcgtggctgt    40

<210> SEQ ID NO 868
<211> LENGTH: 40
<212> TYPE: DNA
<213> ORGANISM: Artificial
<220> FEATURE:
<223> OTHER INFORMATION: DNA Primer

<400> SEQUENCE: 868
tccacgagct cgtgtcgaca cagtttggcc acacggtcaa    40

<210> SEQ ID NO 869
<211> LENGTH: 40
<212> TYPE: DNA
<213> ORGANISM: Artificial
<220> FEATURE:
<223> OTHER INFORMATION: DNA Primer

<400> SEQUENCE: 869
ccgcggcgtt gcccgccacc ttgaccgtgt ggccaaactg    40

<210> SEQ ID NO 870
<211> LENGTH: 40
<212> TYPE: DNA
<213> ORGANISM: Artificial
<220> FEATURE:
<223> OTHER INFORMATION: DNA Primer

<400> SEQUENCE: 870
cgcaacagcg gcactccgct gtctgcggtt cacctgacgt    40

<210> SEQ ID NO 871

```
<211> LENGTH: 40
<212> TYPE: DNA
<213> ORGANISM: Artificial
<220> FEATURE:
<223> OTHER INFORMATION: DNA Primer

<400> SEQUENCE: 871
caagaacgag gcgtacgacc acgtcaggtg aaccgcagac                              40

<210> SEQ ID NO 872
<211> LENGTH: 40
<212> TYPE: DNA
<213> ORGANISM: Artificial
<220> FEATURE:
<223> OTHER INFORMATION: DNA Primer

<400> SEQUENCE: 872
ggtcgtacgc ctcgttcttg acagccacgc ttcgtcgggc                              40

<210> SEQ ID NO 873
<211> LENGTH: 40
<212> TYPE: DNA
<213> ORGANISM: Artificial
<220> FEATURE:
<223> OTHER INFORMATION: DNA Primer

<400> SEQUENCE: 873 acgaggggg cacgatgcca gcccgacgaa gcgtggctgt                               40

<210> SEQ ID NO 874
<211> LENGTH: 40
<212> TYPE: DNA
<213> ORGANISM: Artificial
<220> FEATURE:
<223> OTHER INFORMATION: DNA Primer

<400> SEQUENCE: 874
tccacgagct cgtgtcgaca cagtttggcc atacggtcaa                              40

<210> SEQ ID NO 875
<211> LENGTH: 40
<212> TYPE: DNA
<213> ORGANISM: Artificial
<220> FEATURE:
<223> OTHER INFORMATION: DNA Primer

<400> SEQUENCE: 875
ccgcggcgtt gcccgccacc ttgaccgtat ggccaaactg                              40

<210> SEQ ID NO 876
<211> LENGTH: 40
<212> TYPE: DNA
<213> ORGANISM: Artificial
<220> FEATURE:
<223> OTHER INFORMATION: DNA Primer

<400> SEQUENCE: 876
tgcggtgatt gcatctccca gcacaagaga cccggactac                              40

<210> SEQ ID NO 877
<211> LENGTH: 40
<212> TYPE: DNA
<213> ORGANISM: Artificial
<220> FEATURE:
<223> OTHER INFORMATION: DNA Primer

<400> SEQUENCE: 877
```
tctcgcgtcc acatgtaata gtagtccggg tctcttgtgc                                    40

<210> SEQ ID NO 878
<211> LENGTH: 40
<212> TYPE: DNA
<213> ORGANISM: Artificial
<220> FEATURE:
<223> OTHER INFORMATION: DNA Primer

<400> SEQUENCE: 878
ggtcgtacgc ctcgttcttg acagccgcag cccgtcgggc                                    40

<210> SEQ ID NO 879
<211> LENGTH: 40
<212> TYPE: DNA
<213> ORGANISM: Artificial
<220> FEATURE:
<223> OTHER INFORMATION: DNA Primer

<400> SEQUENCE: 879 acgaggggg cacgatgcca gcccgacggg ctgcggctgt                                     40

<210> SEQ ID NO 880
<211> LENGTH: 40
<212> TYPE: DNA
<213> ORGANISM: Artificial
<220> FEATURE:
<223> OTHER INFORMATION: DNA Primer

<400> SEQUENCE: 880
tgtcgacacg agcacgtgga aggtgacggc cacggaggtt                                    40

<210> SEQ ID NO 881
<211> LENGTH: 40
<212> TYPE: DNA
<213> ORGANISM: Artificial
<220> FEATURE:
<223> OTHER INFORMATION: DNA Primer

<400> SEQUENCE: 881
tccacgtgct cgtgtcgaca cagtttggcc agacggtcaa                                    40

<210> SEQ ID NO 882
<211> LENGTH: 40
<212> TYPE: DNA
<213> ORGANISM: Artificial
<220> FEATURE:
<223> OTHER INFORMATION: DNA Primer

<400> SEQUENCE: 882
agcgccgccg tggctctgga ccgcgtcaac tatgccgata                                    40

<210> SEQ ID NO 883
<211> LENGTH: 40
<212> TYPE: DNA
<213> ORGANISM: Artificial
<220> FEATURE:
<223> OTHER INFORMATION: DNA Primer

<400> SEQUENCE: 883
cccaatccac aggggtggt tatcggcata gttgacgcgg                                     40

<210> SEQ ID NO 884
<211> LENGTH: 40
<212> TYPE: DNA

```
<213> ORGANISM: Artificial
<220> FEATURE:
<223> OTHER INFORMATION: DNA Primer

<400> SEQUENCE: 884
agacgtcgtg gagtacaagt acatcaaagt gggccaagat                    40

<210> SEQ ID NO 885
<211> LENGTH: 40
<212> TYPE: DNA
<213> ORGANISM: Artificial
<220> FEATURE:
<223> OTHER INFORMATION: DNA Primer

<400> SEQUENCE: 885
ctctcccagg tcacggagcc atcttggccc actttgatgt                    40

<210> SEQ ID NO 886
<211> LENGTH: 40
<212> TYPE: DNA
<213> ORGANISM: Artificial
<220> FEATURE:
<223> OTHER INFORMATION: DNA Primer

<400> SEQUENCE: 886
tgcggtgatt gcatctccca gcacaattag accggactac                    40

<210> SEQ ID NO 887
<211> LENGTH: 40
<212> TYPE: DNA
<213> ORGANISM: Artificial
<220> FEATURE:
<223> OTHER INFORMATION: DNA Primer

<400> SEQUENCE: 887
tctcgcgtcc acatgtaata gtagtccggt ctaattgtgc                    40

<210> SEQ ID NO 888
<211> LENGTH: 40
<212> TYPE: DNA
<213> ORGANISM: Artificial
<220> FEATURE:
<223> OTHER INFORMATION: DNA Primer

<400> SEQUENCE: 888
tgtcgacacg agcgcgtgga aggtgacggc cacggaggtt                    40

<210> SEQ ID NO 889
<211> LENGTH: 40
<212> TYPE: DNA
<213> ORGANISM: Artificial
<220> FEATURE:
<223> OTHER INFORMATION: DNA Primer

<400> SEQUENCE: 889
tccacgcgct cgtgtcgaca cagtttggcc acacggtcaa                    40

<210> SEQ ID NO 890
<211> LENGTH: 40
<212> TYPE: DNA
<213> ORGANISM: Artificial
<220> FEATURE:
<223> OTHER INFORMATION: DNA Primer

<400> SEQUENCE: 890
ccgcggcgtt gcccgccacc ttgaccgtgt ggccaaactg                    40
```

```
<210> SEQ ID NO 891
<211> LENGTH: 40
<212> TYPE: DNA
<213> ORGANISM: Artificial
<220> FEATURE:
<223> OTHER INFORMATION: DNA Primer

<400> SEQUENCE: 891
agacgtcgtg gagtacaagt acatcattgt gggccaagat            40

<210> SEQ ID NO 892
<211> LENGTH: 40
<212> TYPE: DNA
<213> ORGANISM: Artificial
<220> FEATURE:
<223> OTHER INFORMATION: DNA Primer

<400> SEQUENCE: 892
ctctcccagg tcacggagcc atcttggccc acaatgatgt            40

<210> SEQ ID NO 893
<211> LENGTH: 40
<212> TYPE: DNA
<213> ORGANISM: Artificial
<220> FEATURE:
<223> OTHER INFORMATION: DNA Primer

<400> SEQUENCE: 893
tgtcgacacg agcgcgtgga aggtgacggc cacggaggtt            40

<210> SEQ ID NO 894
<211> LENGTH: 40
<212> TYPE: DNA
<213> ORGANISM: Artificial
<220> FEATURE:
<223> OTHER INFORMATION: DNA Primer

<400> SEQUENCE: 894
tccacgcgct cgtgtcgaca cagtttggcc agacggtcaa            40

<210> SEQ ID NO 895
<211> LENGTH: 40
<212> TYPE: DNA
<213> ORGANISM: Artificial
<220> FEATURE:
<223> OTHER INFORMATION: DNA Primer

<400> SEQUENCE: 895
agacgtcgtg gagtacaagt acatcattgt gggccaagat            40

<210> SEQ ID NO 896
<211> LENGTH: 40
<212> TYPE: DNA
<213> ORGANISM: Artificial
<220> FEATURE:
<223> OTHER INFORMATION: DNA Primer

<400> SEQUENCE: 896
ctctcccagg tcacggagcc atcttggccc acaatgatgt            40

<210> SEQ ID NO 897
<211> LENGTH: 40
<212> TYPE: DNA
<213> ORGANISM: Artificial
<220> FEATURE:
```

<223> OTHER INFORMATION: DNA Primer

<400> SEQUENCE: 897
tgcggtgatt gcatctccca gcacaagaga cccggactac                            40

<210> SEQ ID NO 898
<211> LENGTH: 40
<212> TYPE: DNA
<213> ORGANISM: Artificial
<220> FEATURE:
<223> OTHER INFORMATION: DNA Primer

<400> SEQUENCE: 898
tctcgcgtcc acatgtaata gtagtccggg tctcttgtgc                            40

<210> SEQ ID NO 899
<211> LENGTH: 40
<212> TYPE: DNA
<213> ORGANISM: Artificial
<220> FEATURE:
<223> OTHER INFORMATION: DNA Primer

<400> SEQUENCE: 899
ggtcgtacgc ctcgttcttg acagccgcgg cccgtcgggc                            40

<210> SEQ ID NO 900
<211> LENGTH: 40
<212> TYPE: DNA
<213> ORGANISM: Artificial
<220> FEATURE:
<223> OTHER INFORMATION: DNA Primer

<400> SEQUENCE: 900 acgaggggggg cacgatgcca gcccgacggg ccgcggctgt                            40

<210> SEQ ID NO 901
<211> LENGTH: 40
<212> TYPE: DNA
<213> ORGANISM: Artificial
<220> FEATURE:
<223> OTHER INFORMATION: DNA Primer

<400> SEQUENCE: 901
tgtcgacacg agcgcgtgga aggtgacggc cacggaggtt                            40

<210> SEQ ID NO 902
<211> LENGTH: 40
<212> TYPE: DNA
<213> ORGANISM: Artificial
<220> FEATURE:
<223> OTHER INFORMATION: DNA Primer

<400> SEQUENCE: 902
tccacgcgct cgtgtcgaca cagtttggcc acacggtcaa                            40

<210> SEQ ID NO 903
<211> LENGTH: 40
<212> TYPE: DNA
<213> ORGANISM: Artificial
<220> FEATURE:
<223> OTHER INFORMATION: DNA Primer

<400> SEQUENCE: 903
ccgcggcgtt gcccgccacc ttgaccgtgt ggccaaactg                            40

<210> SEQ ID NO 904
<211> LENGTH: 40
<212> TYPE: DNA
<213> ORGANISM: Artificial
<220> FEATURE:
<223> OTHER INFORMATION: DNA Primer

<400> SEQUENCE: 904
agacgtcgtg gagtacaagt acatcattgt gggccaagat  40

<210> SEQ ID NO 905
<211> LENGTH: 40
<212> TYPE: DNA
<213> ORGANISM: Artificial
<220> FEATURE:
<223> OTHER INFORMATION: DNA Primer

<400> SEQUENCE: 905
ctctcccagg tcacggagcc atcttggccc acaatgatgt  40

<210> SEQ ID NO 906
<211> LENGTH: 40
<212> TYPE: DNA
<213> ORGANISM: Artificial
<220> FEATURE:
<223> OTHER INFORMATION: DNA Primer

<400> SEQUENCE: 906
tgcggtgatt gcatctccca gcacaattcg cccggactac  40

<210> SEQ ID NO 907
<211> LENGTH: 40
<212> TYPE: DNA
<213> ORGANISM: Artificial
<220> FEATURE:
<223> OTHER INFORMATION: DNA Primer

<400> SEQUENCE: 907
tctcgcgtcc acatgtaata gtagtccggg cgaattgtgc  40

<210> SEQ ID NO 908
<211> LENGTH: 40
<212> TYPE: DNA
<213> ORGANISM: Artificial
<220> FEATURE:
<223> OTHER INFORMATION: DNA Primer

<400> SEQUENCE: 908
ggtcgtacgc ctcgttcttg acagccgcgg cccgtcgggc  40

<210> SEQ ID NO 909
<211> LENGTH: 40
<212> TYPE: DNA
<213> ORGANISM: Artificial
<220> FEATURE:
<223> OTHER INFORMATION: DNA Primer

<400> SEQUENCE: 909 acgaggggggg cacgatgcca gcccgacggg ccgcggctgt  40

<210> SEQ ID NO 910
<211> LENGTH: 40
<212> TYPE: DNA
<213> ORGANISM: Artificial
<220> FEATURE:
<223> OTHER INFORMATION: DNA Primer -continued

```
<400> SEQUENCE: 910
tccacgagct cgtgtcgaca cagtttggcc acacggtcaa                              40

<210> SEQ ID NO 911
<211> LENGTH: 40
<212> TYPE: DNA
<213> ORGANISM: Artificial
<220> FEATURE:
<223> OTHER INFORMATION: DNA Primer

<400> SEQUENCE: 911
ccgcggcgtt gcccgccacc ttgaccgtgt ggccaaactg                              40

<210> SEQ ID NO 912
<211> LENGTH: 40
<212> TYPE: DNA
<213> ORGANISM: Artificial
<220> FEATURE:
<223> OTHER INFORMATION: DNA Primer

<400> SEQUENCE: 912
agcgccgccg tggctctgga cgcggtcaac tatgccgata                              40

<210> SEQ ID NO 913
<211> LENGTH: 40
<212> TYPE: DNA
<213> ORGANISM: Artificial
<220> FEATURE:
<223> OTHER INFORMATION: DNA Primer

<400> SEQUENCE: 913
cccaatccac aggggtggt tatcggcata gttgaccgcg                               40

<210> SEQ ID NO 914
<211> LENGTH: 33
<212> TYPE: DNA
<213> ORGANISM: Artificial
<220> FEATURE:
<223> OTHER INFORMATION: DNA Primer

<400> SEQUENCE: 914 gagagggac aagtttgtac aaaaaagcag gct                                      33

<210> SEQ ID NO 915
<211> LENGTH: 40
<212> TYPE: DNA
<213> ORGANISM: Artificial
<220> FEATURE:
<223> OTHER INFORMATION: DNA Primer

<400> SEQUENCE: 915
gcagtcgaca ggacgtgcat agcctgcttt tttgtacaaa                              40

<210> SEQ ID NO 916
<211> LENGTH: 40
<212> TYPE: DNA
<213> ORGANISM: Artificial
<220> FEATURE:
<223> OTHER INFORMATION: DNA Primer

<400> SEQUENCE: 916
atgcacgtcc tgtcgactgc ggtgctgctc ggctccgttg                              40

<210> SEQ ID NO 917
<211> LENGTH: 40
```

```
<212> TYPE: DNA
<213> ORGANISM: Artificial
<220> FEATURE:
<223> OTHER INFORMATION: DNA Primer

<400> SEQUENCE: 917
tcccaggacc ttttgaacgg caacggagcc gagcagcacc                                40

<210> SEQ ID NO 918
<211> LENGTH: 40
<212> TYPE: DNA
<213> ORGANISM: Artificial
<220> FEATURE:
<223> OTHER INFORMATION: DNA Primer

<400> SEQUENCE: 918
ccgttcaaaa ggtcctggga agaccaggat caagcggtct                                40

<210> SEQ ID NO 919
<211> LENGTH: 40
<212> TYPE: DNA
<213> ORGANISM: Artificial
<220> FEATURE:
<223> OTHER INFORMATION: DNA Primer

<400> SEQUENCE: 919
acctcttggt gacgtcggac agaccgcttg atcctggtct                                40

<210> SEQ ID NO 920
<211> LENGTH: 40
<212> TYPE: DNA
<213> ORGANISM: Artificial
<220> FEATURE:
<223> OTHER INFORMATION: DNA Primer

<400> SEQUENCE: 920
gtccgacgtc accaagaggt ctgttgacga cttcatcagc                                40

<210> SEQ ID NO 921
<211> LENGTH: 40
<212> TYPE: DNA
<213> ORGANISM: Artificial
<220> FEATURE:
<223> OTHER INFORMATION: DNA Primer

<400> SEQUENCE: 921
agtgcaatag gcgtctcggt gctgatgaag tcgtcaacag                                40

<210> SEQ ID NO 922
<211> LENGTH: 40
<212> TYPE: DNA
<213> ORGANISM: Artificial
<220> FEATURE:
<223> OTHER INFORMATION: DNA Primer

<400> SEQUENCE: 922
accgagacgc ctattgcact gaacaatctt ctttgcaatg                                40

<210> SEQ ID NO 923
<211> LENGTH: 40
<212> TYPE: DNA
<213> ORGANISM: Artificial
<220> FEATURE:
<223> OTHER INFORMATION: DNA Primer

<400> SEQUENCE: 923
```
acggcatcca tcaggaccaa cattgcaaag aagattgttc         40

<210> SEQ ID NO 924
<211> LENGTH: 40
<212> TYPE: DNA
<213> ORGANISM: Artificial
<220> FEATURE:
<223> OTHER INFORMATION: DNA Primer

<400> SEQUENCE: 924
ttggtcctga tggatgccgt gcattcggca catcagctgg         40

<210> SEQ ID NO 925
<211> LENGTH: 40
<212> TYPE: DNA
<213> ORGANISM: Artificial
<220> FEATURE:
<223> OTHER INFORMATION: DNA Primer

<400> SEQUENCE: 925
tgggagatgc aatcaccgca ccagctgatg tgccgaatgc         40

<210> SEQ ID NO 926
<211> LENGTH: 40
<212> TYPE: DNA
<213> ORGANISM: Artificial
<220> FEATURE:
<223> OTHER INFORMATION: DNA Primer

<400> SEQUENCE: 926
tgcggtgatt gcatctccca gcacacaaga cccggactac         40

<210> SEQ ID NO 927
<211> LENGTH: 40
<212> TYPE: DNA
<213> ORGANISM: Artificial
<220> FEATURE:
<223> OTHER INFORMATION: DNA Primer

<400> SEQUENCE: 927
tctcgcgtcc acatgtaata gtagtccggg tcttgtgtgc         40

<210> SEQ ID NO 928
<211> LENGTH: 40
<212> TYPE: DNA
<213> ORGANISM: Artificial
<220> FEATURE:
<223> OTHER INFORMATION: DNA Primer

<400> SEQUENCE: 928
tattacatgt ggacgcgaga tagcgctctt gtcttcaaga         40

<210> SEQ ID NO 929
<211> LENGTH: 40
<212> TYPE: DNA
<213> ORGANISM: Artificial
<220> FEATURE:
<223> OTHER INFORMATION: DNA Primer

<400> SEQUENCE: 929
ggtgaagcgg tcgatgaggt tcttgaagac aagagcgcta         40

<210> SEQ ID NO 930
<211> LENGTH: 40
<212> TYPE: DNA
<213> ORGANISM: Artificial

```
<220> FEATURE:
<223> OTHER INFORMATION: DNA Primer

<400> SEQUENCE: 930
acctcatcga ccgcttcacc gaaacgtacg atgcgggcct                              40

<210> SEQ ID NO 931
<211> LENGTH: 40
<212> TYPE: DNA
<213> ORGANISM: Artificial
<220> FEATURE:
<223> OTHER INFORMATION: DNA Primer

<400> SEQUENCE: 931
actgctcgat gcggcgctgc aggcccgcat cgtacgtttc                              40

<210> SEQ ID NO 932
<211> LENGTH: 40
<212> TYPE: DNA
<213> ORGANISM: Artificial
<220> FEATURE:
<223> OTHER INFORMATION: DNA Primer

<400> SEQUENCE: 932
gcagcgccgc atcgagcagt acattactgc ccaggtcact                              40

<210> SEQ ID NO 933
<211> LENGTH: 40
<212> TYPE: DNA
<213> ORGANISM: Artificial
<220> FEATURE:
<223> OTHER INFORMATION: DNA Primer

<400> SEQUENCE: 933
gggttagaga ggccctggag agtgacctgg gcagtaatgt                              40

<210> SEQ ID NO 934
<211> LENGTH: 40
<212> TYPE: DNA
<213> ORGANISM: Artificial
<220> FEATURE:
<223> OTHER INFORMATION: DNA Primer

<400> SEQUENCE: 934
ctccagggcc tctctaaccc ctcgggctcc ctcgcggacg                              40

<210> SEQ ID NO 935
<211> LENGTH: 40
<212> TYPE: DNA
<213> ORGANISM: Artificial
<220> FEATURE:
<223> OTHER INFORMATION: DNA Primer

<400> SEQUENCE: 935
gggctcgccg agaccagagc cgtccgcgag ggagcccgag                              40

<210> SEQ ID NO 936
<211> LENGTH: 40
<212> TYPE: DNA
<213> ORGANISM: Artificial
<220> FEATURE:
<223> OTHER INFORMATION: DNA Primer

<400> SEQUENCE: 936
gctctggtct cggcgagccc aagtttgagt tgaccctgaa                              40
```

<210> SEQ ID NO 937
<211> LENGTH: 40
<212> TYPE: DNA
<213> ORGANISM: Artificial
<220> FEATURE:
<223> OTHER INFORMATION: DNA Primer

<400> SEQUENCE: 937
cccagttgcc ggtgaaaggc ttcagggtca actcaaactt                              40

<210> SEQ ID NO 938
<211> LENGTH: 40
<212> TYPE: DNA
<213> ORGANISM: Artificial
<220> FEATURE:
<223> OTHER INFORMATION: DNA Primer

<400> SEQUENCE: 938
gcctttcacc ggcaactggg gtcgaccgca gcgggatggc                              40

<210> SEQ ID NO 939
<211> LENGTH: 40
<212> TYPE: DNA
<213> ORGANISM: Artificial
<220> FEATURE:
<223> OTHER INFORMATION: DNA Primer

<400> SEQUENCE: 939
gcaatggctc gcagagctgg gccatcccgc tgcggtcgac                              40

<210> SEQ ID NO 940
<211> LENGTH: 40
<212> TYPE: DNA
<213> ORGANISM: Artificial
<220> FEATURE:
<223> OTHER INFORMATION: DNA Primer

<400> SEQUENCE: 940
ccagctctgc gagccattgc cttgattgga tactcaaagt                              40

<210> SEQ ID NO 941
<211> LENGTH: 40
<212> TYPE: DNA
<213> ORGANISM: Artificial
<220> FEATURE:
<223> OTHER INFORMATION: DNA Primer

<400> SEQUENCE: 941
atagttgttg ttgatgagcc actttgagta tccaatcaag                              40

<210> SEQ ID NO 942
<211> LENGTH: 40
<212> TYPE: DNA
<213> ORGANISM: Artificial
<220> FEATURE:
<223> OTHER INFORMATION: DNA Primer

<400> SEQUENCE: 942
ggctcatcaa caacaactat cagtcgactg tgtccaacgt                              40

<210> SEQ ID NO 943
<211> LENGTH: 40
<212> TYPE: DNA
<213> ORGANISM: Artificial
<220> FEATURE:
<223> OTHER INFORMATION: DNA Primer

<400> SEQUENCE: 943
tgcgcacaat aggccagatg acgttggaca cagtcgactg                                40

<210> SEQ ID NO 944
<211> LENGTH: 40
<212> TYPE: DNA
<213> ORGANISM: Artificial
<220> FEATURE:
<223> OTHER INFORMATION: DNA Primer

<400> SEQUENCE: 944
catctggcct attgtgcgca acgacctcaa ctatgttgcc                                40

<210> SEQ ID NO 945
<211> LENGTH: 40
<212> TYPE: DNA
<213> ORGANISM: Artificial
<220> FEATURE:
<223> OTHER INFORMATION: DNA Primer

<400> SEQUENCE: 945
ccggtttggt tccagtactg ggcaacatag ttgaggtcgt                                40

<210> SEQ ID NO 946
<211> LENGTH: 40
<212> TYPE: DNA
<213> ORGANISM: Artificial
<220> FEATURE:
<223> OTHER INFORMATION: DNA Primer

<400> SEQUENCE: 946
cagtactgga accaaaccgg ctttgacctc tgggaagaag                                40

<210> SEQ ID NO 947
<211> LENGTH: 40
<212> TYPE: DNA
<213> ORGANISM: Artificial
<220> FEATURE:
<223> OTHER INFORMATION: DNA Primer

<400> SEQUENCE: 947
aaagaatgag ctcccattga cttcttccca gaggtcaaag                                40

<210> SEQ ID NO 948
<211> LENGTH: 40
<212> TYPE: DNA
<213> ORGANISM: Artificial
<220> FEATURE:
<223> OTHER INFORMATION: DNA Primer

<400> SEQUENCE: 948
tcaatgggag ctcattcttt actgttgcca accagcaccg                                40

<210> SEQ ID NO 949
<211> LENGTH: 40
<212> TYPE: DNA
<213> ORGANISM: Artificial
<220> FEATURE:
<223> OTHER INFORMATION: DNA Primer

<400> SEQUENCE: 949
tggcgccctc gacaagtgct cggtgctggt tggcaacagt                                40

<210> SEQ ID NO 950

-continued

<210> SEQ ID NO 950
<211> LENGTH: 40
<212> TYPE: DNA
<213> ORGANISM: Artificial
<220> FEATURE:
<223> OTHER INFORMATION: DNA Primer

<400> SEQUENCE: 950
agcacttgtc gagggcgcca ctcttgctgc cactcttggc        40

<210> SEQ ID NO 951
<211> LENGTH: 40
<212> TYPE: DNA
<213> ORGANISM: Artificial
<220> FEATURE:
<223> OTHER INFORMATION: DNA Primer

<400> SEQUENCE: 951
gaataagcgc ttcccgactg gccaagagtg gcagcaagag        40

<210> SEQ ID NO 952
<211> LENGTH: 40
<212> TYPE: DNA
<213> ORGANISM: Artificial
<220> FEATURE:
<223> OTHER INFORMATION: DNA Primer

<400> SEQUENCE: 952
cagtcgggaa gcgcttattc atctgttgct ccccaggttt        40

<210> SEQ ID NO 953
<211> LENGTH: 40
<212> TYPE: DNA
<213> ORGANISM: Artificial
<220> FEATURE:
<223> OTHER INFORMATION: DNA Primer

<400> SEQUENCE: 953
gaatcgttgg agaaagcaca aaacctgggg agcaacagat        40

<210> SEQ ID NO 954
<211> LENGTH: 40
<212> TYPE: DNA
<213> ORGANISM: Artificial
<220> FEATURE:
<223> OTHER INFORMATION: DNA Primer

<400> SEQUENCE: 954
tgtgctttct ccaacgattc tgggtgtcgt ctggtggata        40

<210> SEQ ID NO 955
<211> LENGTH: 40
<212> TYPE: DNA
<213> ORGANISM: Artificial
<220> FEATURE:
<223> OTHER INFORMATION: DNA Primer

<400> SEQUENCE: 955
tgttgatgtt ggagtcgacg tatccaccag acgacaccca        40

<210> SEQ ID NO 956
<211> LENGTH: 40
<212> TYPE: DNA
<213> ORGANISM: Artificial
<220> FEATURE:
<223> OTHER INFORMATION: DNA Primer

<400> SEQUENCE: 956
cgtcgactcc aacatcaaca ccaacgaggg caggactggc                                    40

<210> SEQ ID NO 957
<211> LENGTH: 40
<212> TYPE: DNA
<213> ORGANISM: Artificial
<220> FEATURE:
<223> OTHER INFORMATION: DNA Primer

<400> SEQUENCE: 957
aggacggagt tgacatcctt gccagtcctg ccctcgttgg                                    40

<210> SEQ ID NO 958
<211> LENGTH: 40
<212> TYPE: DNA
<213> ORGANISM: Artificial
<220> FEATURE:
<223> OTHER INFORMATION: DNA Primer

<400> SEQUENCE: 958
aaggatgtca actccgtcct gacttccatc cacaccttcg                                    40

<210> SEQ ID NO 959
<211> LENGTH: 40
<212> TYPE: DNA
<213> ORGANISM: Artificial
<220> FEATURE:
<223> OTHER INFORMATION: DNA Primer

<400> SEQUENCE: 959
gtcacagcca aggttgggat cgaaggtgtg gatggaagtc                                    40

<210> SEQ ID NO 960
<211> LENGTH: 40
<212> TYPE: DNA
<213> ORGANISM: Artificial
<220> FEATURE:
<223> OTHER INFORMATION: DNA Primer

<400> SEQUENCE: 960
atcccaacct tggctgtgac gcaggcacct tccagccatg                                    40

<210> SEQ ID NO 961
<211> LENGTH: 40
<212> TYPE: DNA
<213> ORGANISM: Artificial
<220> FEATURE:
<223> OTHER INFORMATION: DNA Primer

<400> SEQUENCE: 961
tggagagcgc tttgtcactg catggctgga aggtgcctgc                                    40

<210> SEQ ID NO 962
<211> LENGTH: 40
<212> TYPE: DNA
<213> ORGANISM: Artificial
<220> FEATURE:
<223> OTHER INFORMATION: DNA Primer

<400> SEQUENCE: 962
cagtgacaaa gcgctctcca acctcaaggt tgttgtcgac                                    40

<210> SEQ ID NO 963
<211> LENGTH: 40
<212> TYPE: DNA

<213> ORGANISM: Artificial
<220> FEATURE:
<223> OTHER INFORMATION: DNA Primer

<400> SEQUENCE: 963
ccgtagatgg agcggaagga gtcgacaaca accttgaggt                    40

<210> SEQ ID NO 964
<211> LENGTH: 40
<212> TYPE: DNA
<213> ORGANISM: Artificial
<220> FEATURE:
<223> OTHER INFORMATION: DNA Primer

<400> SEQUENCE: 964
tccttccgct ccatctacgg cgtgaacaag ggcattcctg                    40

<210> SEQ ID NO 965
<211> LENGTH: 40
<212> TYPE: DNA
<213> ORGANISM: Artificial
<220> FEATURE:
<223> OTHER INFORMATION: DNA Primer

<400> SEQUENCE: 965
aatggcgacg gcagcaccgg caggaatgcc cttgttcacg                    40

<210> SEQ ID NO 966
<211> LENGTH: 40
<212> TYPE: DNA
<213> ORGANISM: Artificial
<220> FEATURE:
<223> OTHER INFORMATION: DNA Primer

<400> SEQUENCE: 966
ccggtgctgc cgtcgccatt ggccggtatg cagaggatgt                    40

<210> SEQ ID NO 967
<211> LENGTH: 40
<212> TYPE: DNA
<213> ORGANISM: Artificial
<220> FEATURE:
<223> OTHER INFORMATION: DNA Primer

<400> SEQUENCE: 967
aagggttgcc gttgtagtac acatcctctg cataccggcc                    40

<210> SEQ ID NO 968
<211> LENGTH: 40
<212> TYPE: DNA
<213> ORGANISM: Artificial
<220> FEATURE:
<223> OTHER INFORMATION: DNA Primer

<400> SEQUENCE: 968
gtactacaac ggcaacccctt ggtatcttgc tacatttgct                   40

<210> SEQ ID NO 969
<211> LENGTH: 40
<212> TYPE: DNA
<213> ORGANISM: Artificial
<220> FEATURE:
<223> OTHER INFORMATION: DNA Primer

<400> SEQUENCE: 969
tcgtacagct gctcggcagc agcaaatgta gcaagatacc                    40

<210> SEQ ID NO 970
<211> LENGTH: 40
<212> TYPE: DNA
<213> ORGANISM: Artificial
<220> FEATURE:
<223> OTHER INFORMATION: DNA Primer

<400> SEQUENCE: 970
gctgccgagc agctgtacga tgccatctac gtctggaaga                                40

<210> SEQ ID NO 971
<211> LENGTH: 40
<212> TYPE: DNA
<213> ORGANISM: Artificial
<220> FEATURE:
<223> OTHER INFORMATION: DNA Primer

<400> SEQUENCE: 971
caccgtgatg agcccgtct tcttccagac gtagatggca                                 40

<210> SEQ ID NO 972
<211> LENGTH: 40
<212> TYPE: DNA
<213> ORGANISM: Artificial
<220> FEATURE:
<223> OTHER INFORMATION: DNA Primer

<400> SEQUENCE: 972
agacgggctc catcacggtg accgccacct ccctggcctt                                40

<210> SEQ ID NO 973
<211> LENGTH: 40
<212> TYPE: DNA
<213> ORGANISM: Artificial
<220> FEATURE:
<223> OTHER INFORMATION: DNA Primer

<400> SEQUENCE: 973
caggaacaag ctcctggaag aaggccaggg aggtggcggt                                40

<210> SEQ ID NO 974
<211> LENGTH: 40
<212> TYPE: DNA
<213> ORGANISM: Artificial
<220> FEATURE:
<223> OTHER INFORMATION: DNA Primer

<400> SEQUENCE: 974
cttccaggag cttgttcctg gcgtgacggc cggacctac                                 40

<210> SEQ ID NO 975
<211> LENGTH: 40
<212> TYPE: DNA
<213> ORGANISM: Artificial
<220> FEATURE:
<223> OTHER INFORMATION: DNA Primer

<400> SEQUENCE: 975
aaggtcgaag agctgctgga gtaggtcccg gccgtcacgc                                40

<210> SEQ ID NO 976
<211> LENGTH: 40
<212> TYPE: DNA
<213> ORGANISM: Artificial
<220> FEATURE:

```
<223> OTHER INFORMATION: DNA Primer

<400> SEQUENCE: 976
tccagcagct cttcgacctt taccaacatc atcaacgccg                    40

<210> SEQ ID NO 977
<211> LENGTH: 40
<212> TYPE: DNA
<213> ORGANISM: Artificial
<220> FEATURE:
<223> OTHER INFORMATION: DNA Primer

<400> SEQUENCE: 977
gccatcggcg tatgtcgaga cggcgttgat gatgttggta                    40

<210> SEQ ID NO 978
<211> LENGTH: 40
<212> TYPE: DNA
<213> ORGANISM: Artificial
<220> FEATURE:
<223> OTHER INFORMATION: DNA Primer

<400> SEQUENCE: 978
tctcgacata cgccgatggc ttcctcagcg aggctgccaa                    40

<210> SEQ ID NO 979
<211> LENGTH: 40
<212> TYPE: DNA
<213> ORGANISM: Artificial
<220> FEATURE:
<223> OTHER INFORMATION: DNA Primer

<400> SEQUENCE: 979
aaccgtcggc ggggacgtac ttggcagcct cgctgaggaa                    40

<210> SEQ ID NO 980
<211> LENGTH: 40
<212> TYPE: DNA
<213> ORGANISM: Artificial
<220> FEATURE:
<223> OTHER INFORMATION: DNA Primer

<400> SEQUENCE: 980
gtacgtcccc gccgacggtt cgctggccga gcagtttgac                    40

<210> SEQ ID NO 981
<211> LENGTH: 40
<212> TYPE: DNA
<213> ORGANISM: Artificial
<220> FEATURE:
<223> OTHER INFORMATION: DNA Primer

<400> SEQUENCE: 981
agcggagtgc cgctgttgcg gtcaaactgc tcggccagcg                    40

<210> SEQ ID NO 982
<211> LENGTH: 40
<212> TYPE: DNA
<213> ORGANISM: Artificial
<220> FEATURE:
<223> OTHER INFORMATION: DNA Primer

<400> SEQUENCE: 982
cgcaacagcg gcactccgct gtctgcgctt cacctgacgt                    40
```

```
<210> SEQ ID NO 983
<211> LENGTH: 40
<212> TYPE: DNA
<213> ORGANISM: Artificial
<220> FEATURE:
<223> OTHER INFORMATION: DNA Primer

<400> SEQUENCE: 983
caagaacgag gcgtacgacc acgtcaggtg aagcgcagac                           40

<210> SEQ ID NO 984
<211> LENGTH: 40
<212> TYPE: DNA
<213> ORGANISM: Artificial
<220> FEATURE:
<223> OTHER INFORMATION: DNA Primer

<400> SEQUENCE: 984
ggtcgtacgc ctcgttcttg acagccacgg cccgtcgggc                           40

<210> SEQ ID NO 985
<211> LENGTH: 40
<212> TYPE: DNA
<213> ORGANISM: Artificial
<220> FEATURE:
<223> OTHER INFORMATION: DNA Primer

<400> SEQUENCE: 985
acgagggggg cacgatgcca gcccgacggg ccgtggctgt                           40

<210> SEQ ID NO 986
<211> LENGTH: 40
<212> TYPE: DNA
<213> ORGANISM: Artificial
<220> FEATURE:
<223> OTHER INFORMATION: DNA Primer

<400> SEQUENCE: 986
tggcatcgtg ccccctcgt gggccaacag cagcgctagc                            40

<210> SEQ ID NO 987
<211> LENGTH: 40
<212> TYPE: DNA
<213> ORGANISM: Artificial
<220> FEATURE:
<223> OTHER INFORMATION: DNA Primer

<400> SEQUENCE: 987
gagcacgtcg aggggatcgt gctagcgctg ctgttggccc                           40

<210> SEQ ID NO 988
<211> LENGTH: 40
<212> TYPE: DNA
<213> ORGANISM: Artificial
<220> FEATURE:
<223> OTHER INFORMATION: DNA Primer

<400> SEQUENCE: 988
acgatcccct cgacgtgctc cggcgcgtcc gtggtcggat                           40

<210> SEQ ID NO 989
<211> LENGTH: 40
<212> TYPE: DNA
<213> ORGANISM: Artificial
<220> FEATURE:
<223> OTHER INFORMATION: DNA Primer
```

<400> SEQUENCE: 989
ggcggtggga cgcgagtagg atccgaccac ggacgcgccg                    40

<210> SEQ ID NO 990
<211> LENGTH: 40
<212> TYPE: DNA
<213> ORGANISM: Artificial
<220> FEATURE:
<223> OTHER INFORMATION: DNA Primer

<400> SEQUENCE: 990
cctactcgcg tcccaccgcc acgtcattcc ctccgtcgca                    40

<210> SEQ ID NO 991
<211> LENGTH: 40
<212> TYPE: DNA
<213> ORGANISM: Artificial
<220> FEATURE:
<223> OTHER INFORMATION: DNA Primer

<400> SEQUENCE: 991
gcacgccagg cttgggcgtc tgcgacggag ggaatgacgt                    40

<210> SEQ ID NO 992
<211> LENGTH: 40
<212> TYPE: DNA
<213> ORGANISM: Artificial
<220> FEATURE:
<223> OTHER INFORMATION: DNA Primer

<400> SEQUENCE: 992
gacgcccaag cctggcgtgc cttccggtac tccctacacg                    40

<210> SEQ ID NO 993
<211> LENGTH: 40
<212> TYPE: DNA
<213> ORGANISM: Artificial
<220> FEATURE:
<223> OTHER INFORMATION: DNA Primer

<400> SEQUENCE: 993
ggggtcgcgc agggcagggg cgtgtaggga gtaccggaag                    40

<210> SEQ ID NO 994
<211> LENGTH: 40
<212> TYPE: DNA
<213> ORGANISM: Artificial
<220> FEATURE:
<223> OTHER INFORMATION: DNA Primer

<400> SEQUENCE: 994
cccctgccct gcgcgacccc aacctccgtg gccgtcacct                    40

<210> SEQ ID NO 995
<211> LENGTH: 40
<212> TYPE: DNA
<213> ORGANISM: Artificial
<220> FEATURE:
<223> OTHER INFORMATION: DNA Primer

<400> SEQUENCE: 995
tgtcgacacg agctcgtgga aggtgacggc cacggaggtt                    40

<210> SEQ ID NO 996
<211> LENGTH: 40

<212> TYPE: DNA
<213> ORGANISM: Artificial
<220> FEATURE:
<223> OTHER INFORMATION: DNA Primer

<400> SEQUENCE: 996
tccacgagct cgtgtcgaca cagtttggcc acacggtcaa        40

<210> SEQ ID NO 997
<211> LENGTH: 40
<212> TYPE: DNA
<213> ORGANISM: Artificial
<220> FEATURE:
<223> OTHER INFORMATION: DNA Primer

<400> SEQUENCE: 997
ccgcggcgtt gcccgccacc ttgaccgtgt ggccaaactg        40

<210> SEQ ID NO 998
<211> LENGTH: 40
<212> TYPE: DNA
<213> ORGANISM: Artificial
<220> FEATURE:
<223> OTHER INFORMATION: DNA Primer

<400> SEQUENCE: 998
ggtggcgggc aacgccgcgg ccctgggcaa ctggagcacg        40

<210> SEQ ID NO 999
<211> LENGTH: 40
<212> TYPE: DNA
<213> ORGANISM: Artificial
<220> FEATURE:
<223> OTHER INFORMATION: DNA Primer

<400> SEQUENCE: 999
tccagagcca cggcggcgct cgtgctccag ttgcccaggg        40

<210> SEQ ID NO 1000
<211> LENGTH: 40
<212> TYPE: DNA
<213> ORGANISM: Artificial
<220> FEATURE:
<223> OTHER INFORMATION: DNA Primer

<400> SEQUENCE: 1000
agcgccgccg tggctctgga cgccgtcaac tatgccgata        40

<210> SEQ ID NO 1001
<211> LENGTH: 40
<212> TYPE: DNA
<213> ORGANISM: Artificial
<220> FEATURE:
<223> OTHER INFORMATION: DNA Primer

<400> SEQUENCE: 1001
cccaatccac aggggggtggt tatcggcata gttgacggcg        40

<210> SEQ ID NO 1002
<211> LENGTH: 40
<212> TYPE: DNA
<213> ORGANISM: Artificial
<220> FEATURE:
<223> OTHER INFORMATION: DNA Primer

<400> SEQUENCE: 1002
accaccccct gtggattggg acggtcaacc tcgaggctgg                    40

<210> SEQ ID NO 1003
<211> LENGTH: 40
<212> TYPE: DNA
<213> ORGANISM: Artificial
<220> FEATURE:
<223> OTHER INFORMATION: DNA Primer

<400> SEQUENCE: 1003
acttgtactc cacgacgtct ccagcctcga ggttgaccgt                    40

<210> SEQ ID NO 1004
<211> LENGTH: 40
<212> TYPE: DNA
<213> ORGANISM: Artificial
<220> FEATURE:
<223> OTHER INFORMATION: DNA Primer

<400> SEQUENCE: 1004
agacgtcgtg gagtacaagt acatcaatgt gggccaagat                    40

<210> SEQ ID NO 1005
<211> LENGTH: 40
<212> TYPE: DNA
<213> ORGANISM: Artificial
<220> FEATURE:
<223> OTHER INFORMATION: DNA Primer

<400> SEQUENCE: 1005
ctctcccagg tcacggagcc atcttggccc acattgatgt                    40

<210> SEQ ID NO 1006
<211> LENGTH: 40
<212> TYPE: DNA
<213> ORGANISM: Artificial
<220> FEATURE:
<223> OTHER INFORMATION: DNA Primer

<400> SEQUENCE: 1006
ggctccgtga cctgggagag tgatcccaac cacacttaca                    40

<210> SEQ ID NO 1007
<211> LENGTH: 40
<212> TYPE: DNA
<213> ORGANISM: Artificial
<220> FEATURE:
<223> OTHER INFORMATION: DNA Primer

<400> SEQUENCE: 1007
acaagccacc gcaggaaccg tgtaagtgtg gttgggatca                    40

<210> SEQ ID NO 1008
<211> LENGTH: 40
<212> TYPE: DNA
<213> ORGANISM: Artificial
<220> FEATURE:
<223> OTHER INFORMATION: DNA Primer

<400> SEQUENCE: 1008
cggttcctgc ggtggcttgt gtgacgcagg ttgtcaagga                    40

<210> SEQ ID NO 1009
<211> LENGTH: 40
<212> TYPE: DNA
<213> ORGANISM: Artificial -continued

```
<220> FEATURE:
<223> OTHER INFORMATION: DNA Primer

<400> SEQUENCE: 1009
tttacgactg ccaggtgtcc tccttgacaa cctgcgtcac                    40

<210> SEQ ID NO 1010
<211> LENGTH: 40
<212> TYPE: DNA
<213> ORGANISM: Artificial
<220> FEATURE:
<223> OTHER INFORMATION: DNA Primer

<400> SEQUENCE: 1010
ggacacctgg cagtcgtaaa cccagctttc ttgtacaaag                    40

<210> SEQ ID NO 1011
<211> LENGTH: 32
<212> TYPE: DNA
<213> ORGANISM: Artificial
<220> FEATURE:
<223> OTHER INFORMATION: DNA Primer

<400> SEQUENCE: 1011
ctctggggac cactttgtac aagaaagctg gg                            32

<210> SEQ ID NO 1012
<211> LENGTH: 40
<212> TYPE: DNA
<213> ORGANISM: Artificial
<220> FEATURE:
<223> OTHER INFORMATION: DNA Primer

<400> SEQUENCE: 1012
ggtgaagcgg tcgatgagga tcttgaagac aagagcgcta                    40

<210> SEQ ID NO 1013
<211> LENGTH: 40
<212> TYPE: DNA
<213> ORGANISM: Artificial
<220> FEATURE:
<223> OTHER INFORMATION: DNA Primer

<400> SEQUENCE: 1013
tcctcatcga ccgcttcacc gaaacgtacg atgcgggcct                    40

<210> SEQ ID NO 1014
<211> LENGTH: 40
<212> TYPE: DNA
<213> ORGANISM: Artificial
<220> FEATURE:
<223> OTHER INFORMATION: DNA Primer

<400> SEQUENCE: 1014
ggtcgtacgc ctcgttcttg acagccgcgg cccgtcgggc                    40

<210> SEQ ID NO 1015
<211> LENGTH: 40
<212> TYPE: DNA
<213> ORGANISM: Artificial
<220> FEATURE:
<223> OTHER INFORMATION: DNA Primer

<400> SEQUENCE: 1015
acgagggggg cacgatgcca gcccgacggg ccgcggctgt                    40
```

<210> SEQ ID NO 1016
<211> LENGTH: 40
<212> TYPE: DNA
<213> ORGANISM: Artificial
<220> FEATURE:
<223> OTHER INFORMATION: DNA Primer

<400> SEQUENCE: 1016
cgcaacagcg gcactccgct gtctgcggtt cacctgacgt        40

<210> SEQ ID NO 1017
<211> LENGTH: 40
<212> TYPE: DNA
<213> ORGANISM: Artificial
<220> FEATURE:
<223> OTHER INFORMATION: DNA Primer

<400> SEQUENCE: 1017
caagaacgag gcgtacgacc acgtcaggtg aaccgcagac        40

<210> SEQ ID NO 1018
<211> LENGTH: 40
<212> TYPE: DNA
<213> ORGANISM: Artificial
<220> FEATURE:
<223> OTHER INFORMATION: DNA Primer

<400> SEQUENCE: 1018
ggtcgtacgc ctcgttcttg acagccgcgg cccgtcgggc        40

<210> SEQ ID NO 1019
<211> LENGTH: 40
<212> TYPE: DNA
<213> ORGANISM: Artificial
<220> FEATURE:
<223> OTHER INFORMATION: DNA Primer

<400> SEQUENCE: 1019 acgaggggggg cacgatgcca gcccgacggg ccgcggctgt        40

<210> SEQ ID NO 1020
<211> LENGTH: 40
<212> TYPE: DNA
<213> ORGANISM: Artificial
<220> FEATURE:
<223> OTHER INFORMATION: DNA Primer

<400> SEQUENCE: 1020
ggtcgtacgc ctcgttcttg acagccgcgc tccgtcgggc        40

<210> SEQ ID NO 1021
<211> LENGTH: 40
<212> TYPE: DNA
<213> ORGANISM: Artificial
<220> FEATURE:
<223> OTHER INFORMATION: DNA Primer

<400> SEQUENCE: 1021 acgaggggggg cacgatgcca gcccgacgga gcgcggctgt        40

<210> SEQ ID NO 1022
<211> LENGTH: 40
<212> TYPE: DNA
<213> ORGANISM: Artificial
<220> FEATURE:
<223> OTHER INFORMATION: DNA Primer

<400> SEQUENCE: 1022
ggtcgtacgc ctcgttcttg acagccgcgg cccgtcgggc                              40

<210> SEQ ID NO 1023
<211> LENGTH: 40
<212> TYPE: DNA
<213> ORGANISM: Artificial
<220> FEATURE:
<223> OTHER INFORMATION: DNA Primer

<400> SEQUENCE: 1023
acgagggggg cacgatgcca gcccgacggg ccgcggctgt                              40

<210> SEQ ID NO 1024
<211> LENGTH: 40
<212> TYPE: DNA
<213> ORGANISM: Artificial
<220> FEATURE:
<223> OTHER INFORMATION: DNA Primer

<400> SEQUENCE: 1024
tgtcgacacg agcgcgtgga aggtgacggc cacggaggtt                              40

<210> SEQ ID NO 1025
<211> LENGTH: 40
<212> TYPE: DNA
<213> ORGANISM: Artificial
<220> FEATURE:
<223> OTHER INFORMATION: DNA Primer

<400> SEQUENCE: 1025
tccacgcgct cgtgtcgaca cagtttggcc acacggtcaa                              40

<210> SEQ ID NO 1026
<211> LENGTH: 40
<212> TYPE: DNA
<213> ORGANISM: Artificial
<220> FEATURE:
<223> OTHER INFORMATION: DNA Primer

<400> SEQUENCE: 1026
ggtcgtacgc ctcgttcttg acagccgcgg cccgtcgggc                              40

<210> SEQ ID NO 1027
<211> LENGTH: 40
<212> TYPE: DNA
<213> ORGANISM: Artificial
<220> FEATURE:
<223> OTHER INFORMATION: DNA Primer

<400> SEQUENCE: 1027
acgagggggg cacgatgcca gcccgacggg ccgcggctgt                              40

<210> SEQ ID NO 1028
<211> LENGTH: 40
<212> TYPE: DNA
<213> ORGANISM: Artificial
<220> FEATURE:
<223> OTHER INFORMATION: DNA Primer

<400> SEQUENCE: 1028
ggtcgtacgc ctcgttcttg acagccgcgg cccgtcgggc                              40

<210> SEQ ID NO 1029

```
<211> LENGTH: 40
<212> TYPE: DNA
<213> ORGANISM: Artificial
<220> FEATURE:
<223> OTHER INFORMATION: DNA Primer

<400> SEQUENCE: 1029
acgagggggg cacgatgcca gcccgacggg ccgcggctgt                              40

<210> SEQ ID NO 1030
<211> LENGTH: 40
<212> TYPE: DNA
<213> ORGANISM: Artificial
<220> FEATURE:
<223> OTHER INFORMATION: DNA Primer

<400> SEQUENCE: 1030
agcgccgccg tggctctgga cgccgtcaac tatcgcgata                              40

<210> SEQ ID NO 1031
<211> LENGTH: 40
<212> TYPE: DNA
<213> ORGANISM: Artificial
<220> FEATURE:
<223> OTHER INFORMATION: DNA Primer

<400> SEQUENCE: 1031
cccaatccac aggggtggt tatcgcgata gttgacggcg                               40

<210> SEQ ID NO 1032
<211> LENGTH: 40
<212> TYPE: DNA
<213> ORGANISM: Artificial
<220> FEATURE:
<223> OTHER INFORMATION: DNA Primer

<400> SEQUENCE: 1032
ggtgaagcgg tcgatgagga tcttgaagac aagagcgcta                              40

<210> SEQ ID NO 1033
<211> LENGTH: 40
<212> TYPE: DNA
<213> ORGANISM: Artificial
<220> FEATURE:
<223> OTHER INFORMATION: DNA Primer

<400> SEQUENCE: 1033
tcctcatcga ccgcttcacc gaaacgtacg atgcgggcct                              40

<210> SEQ ID NO 1034
<211> LENGTH: 40
<212> TYPE: DNA
<220> FEATURE:
<223> OTHER INFORMATION: DNA Primer

<400> SEQUENCE: 1034
ggtcgtacgc ctcgttcttg acagccgcgg cccgtcgggc                              40

<210> SEQ ID NO 1035
<211> LENGTH: 40
<212> TYPE: DNA
<213> ORGANISM: Artificial
<220> FEATURE:
<223> OTHER INFORMATION: DNA Primer

<400> SEQUENCE: 1035
```
acgagggggg cacgatgcca gcccgacggg ccgcggctgt    40

<210> SEQ ID NO 1036
<211> LENGTH: 40
<212> TYPE: DNA
<213> ORGANISM: Artificial
<220> FEATURE:
<223> OTHER INFORMATION: DNA Primer

<400> SEQUENCE: 1036
agcgccgccg tggctctgga cgccgtcaac tatcgcgata    40

<210> SEQ ID NO 1037
<211> LENGTH: 40
<212> TYPE: DNA
<213> ORGANISM: Artificial
<220> FEATURE:
<223> OTHER INFORMATION: DNA Primer

<400> SEQUENCE: 1037
cccaatccac aggggtggt tatcgcgata gttgacggcg    40

<210> SEQ ID NO 1038
<211> LENGTH: 40
<212> TYPE: DNA
<213> ORGANISM: Artificial
<220> FEATURE:
<223> OTHER INFORMATION: DNA Primer

<400> SEQUENCE: 1038
cgcaacagcg gcactccgct gtctgcggtt cacctgacgt    40

<210> SEQ ID NO 1039
<211> LENGTH: 40
<212> TYPE: DNA
<213> ORGANISM: Artificial
<220> FEATURE:
<223> OTHER INFORMATION: DNA Primer

<400> SEQUENCE: 1039
caagaacgag gcgtacgacc acgtcaggtg aaccgcagac    40

<210> SEQ ID NO 1040
<211> LENGTH: 40
<212> TYPE: DNA
<213> ORGANISM: Artificial
<220> FEATURE:
<223> OTHER INFORMATION: DNA Primer

<400> SEQUENCE: 1040
ggtcgtacgc ctcgttcttg acagccgcgg cccgtcgggc    40

<210> SEQ ID NO 1041
<211> LENGTH: 40
<212> TYPE: DNA
<213> ORGANISM: Artificial
<220> FEATURE:
<223> OTHER INFORMATION: DNA Primer

<400> SEQUENCE: 1041
acgagggggg cacgatgcca gcccgacggg ccgcggctgt    40

<210> SEQ ID NO 1042
<211> LENGTH: 40
<212> TYPE: DNA

```
<213> ORGANISM: Artificial
<220> FEATURE:
<223> OTHER INFORMATION: DNA Primer

<400> SEQUENCE: 1042
agcgccgccg tggctctgga cgccgtcaac tatcgcgata                40

<210> SEQ ID NO 1043
<211> LENGTH: 40
<212> TYPE: DNA
<213> ORGANISM: Artificial
<220> FEATURE:
<223> OTHER INFORMATION: DNA Primer

<400> SEQUENCE: 1043
cccaatccac aggggtggt tatcgcgata gttgacggcg                 40

<210> SEQ ID NO 1044
<211> LENGTH: 40
<212> TYPE: DNA
<213> ORGANISM: Artificial
<220> FEATURE:
<223> OTHER INFORMATION: DNA Primer

<400> SEQUENCE: 1044
ggtcgtacgc ctcgttcttg acagccgcgc tccgtcgggc                40

<210> SEQ ID NO 1045
<211> LENGTH: 40
<212> TYPE: DNA
<213> ORGANISM: Artificial
<220> FEATURE:
<223> OTHER INFORMATION: DNA Primer

<400> SEQUENCE: 1045 acgaggggg cacgatgcca gcccgacgga gcgcggctgt                 40

<210> SEQ ID NO 1046
<211> LENGTH: 40
<212> TYPE: DNA
<213> ORGANISM: Artificial
<220> FEATURE:
<223> OTHER INFORMATION: DNA Primer

<400> SEQUENCE: 1046
agcgccgccg tggctctgga cgccgtcaac tatcgcgata                40

<210> SEQ ID NO 1047
<211> LENGTH: 40
<212> TYPE: DNA
<213> ORGANISM: Artificial
<220> FEATURE:
<223> OTHER INFORMATION: DNA Primer

<400> SEQUENCE: 1047
cccaatccac aggggtggt tatcgcgata gttgacggcg                 40

<210> SEQ ID NO 1048
<211> LENGTH: 40
<212> TYPE: DNA
<213> ORGANISM: Artificial
<220> FEATURE:
<223> OTHER INFORMATION: DNA Primer

<400> SEQUENCE: 1048
ggtcgtacgc ctcgttcttg acagccgcgc tccgtcgggc                40
```

<210> SEQ ID NO 1049
<211> LENGTH: 40
<212> TYPE: DNA
<213> ORGANISM: Artificial
<220> FEATURE:
<223> OTHER INFORMATION: DNA Primer

<400> SEQUENCE: 1049 acgaggggggg cacgatgcca gcccgacgga gcgcggctgt                40

<210> SEQ ID NO 1050
<211> LENGTH: 40
<212> TYPE: DNA
<213> ORGANISM: Artificial
<220> FEATURE:
<223> OTHER INFORMATION: DNA Primer

<400> SEQUENCE: 1050
tgtcgacacg agcgcgtgga aggtgacggc cacggaggtt                40

<210> SEQ ID NO 1051
<211> LENGTH: 40
<212> TYPE: DNA
<213> ORGANISM: Artificial
<220> FEATURE:
<223> OTHER INFORMATION: DNA Primer

<400> SEQUENCE: 1051
tccacgcgct cgtgtcgaca cagtttggcc acacggtcaa                40

<210> SEQ ID NO 1052
<211> LENGTH: 40
<212> TYPE: DNA
<213> ORGANISM: Artificial
<220> FEATURE:
<223> OTHER INFORMATION: DNA Primer

<400> SEQUENCE: 1052
ggtgaagcgg tcgatgagga tcttgaagac aagagcgcta                40

<210> SEQ ID NO 1053
<211> LENGTH: 40
<212> TYPE: DNA
<213> ORGANISM: Artificial
<220> FEATURE:
<223> OTHER INFORMATION: DNA Primer

<400> SEQUENCE: 1053
tcctcatcga ccgcttcacc gaaacgtacg atgcgggcct                40

<210> SEQ ID NO 1054
<211> LENGTH: 40
<212> TYPE: DNA
<213> ORGANISM: Artificial
<220> FEATURE:
<223> OTHER INFORMATION: DNA Primer

<400> SEQUENCE: 1054
ggtcgtacgc ctcgttcttg acagccgcgc tccgtcgggc                40

<210> SEQ ID NO 1055
<211> LENGTH: 40
<212> TYPE: DNA
<213> ORGANISM: Artificial
<220> FEATURE:

<223> OTHER INFORMATION: DNA Primer

<400> SEQUENCE: 1055 acgaggggggg cacgatgcca gcccgacgga gcgcggctgt       40

<210> SEQ ID NO 1056
<211> LENGTH: 40
<212> TYPE: DNA
<213> ORGANISM: Artificial
<220> FEATURE:
<223> OTHER INFORMATION: DNA Primer

<400> SEQUENCE: 1056
agcgccgccg tggctctgga cgccgtcaac tatcgcgata       40

<210> SEQ ID NO 1057
<211> LENGTH: 40
<212> TYPE: DNA
<213> ORGANISM: Artificial
<220> FEATURE:
<223> OTHER INFORMATION: DNA Primer

<400> SEQUENCE: 1057
cccaatccac aggggtggt tatcgcgata gttgacggcg       40

<210> SEQ ID NO 1058
<211> LENGTH: 40
<212> TYPE: DNA
<213> ORGANISM: Artificial
<220> FEATURE:
<223> OTHER INFORMATION: DNA Primer

<400> SEQUENCE: 1058
cgcaacagcg gcactccgct gtctgcggtt cacctgacgt       40

<210> SEQ ID NO 1059
<211> LENGTH: 40
<212> TYPE: DNA
<213> ORGANISM: Artificial
<220> FEATURE:
<223> OTHER INFORMATION: DNA Primer

<400> SEQUENCE: 1059
caagaacgag gcgtacgacc acgtcaggtg aaccgcagac       40

<210> SEQ ID NO 1060
<211> LENGTH: 40
<212> TYPE: DNA
<213> ORGANISM: Artificial
<220> FEATURE:
<223> OTHER INFORMATION: DNA Primer

<400> SEQUENCE: 1060
ggtcgtacgc ctcgttcttg acagccgcgc tccgtcgggc       40

<210> SEQ ID NO 1061
<211> LENGTH: 40
<212> TYPE: DNA
<213> ORGANISM: Artificial
<220> FEATURE:
<223> OTHER INFORMATION: DNA Primer

<400> SEQUENCE: 1061 acgaggggggg cacgatgcca gcccgacgga gcgcggctgt       40

<210> SEQ ID NO 1062
<211> LENGTH: 40
<212> TYPE: DNA
<213> ORGANISM: Artificial
<220> FEATURE:
<223> OTHER INFORMATION: DNA Primer

<400> SEQUENCE: 1062
agcgccgccg tggctctgga cgccgtcaac tatcgcgata        40

<210> SEQ ID NO 1063
<211> LENGTH: 40
<212> TYPE: DNA
<213> ORGANISM: Artificial
<220> FEATURE:
<223> OTHER INFORMATION: DNA Primer

<400> SEQUENCE: 1063
cccaatccac aggggtggt tatcgcgata gttgacggcg        40

<210> SEQ ID NO 1064
<211> LENGTH: 40
<212> TYPE: DNA
<213> ORGANISM: Artificial
<220> FEATURE:
<223> OTHER INFORMATION: DNA Primer

<400> SEQUENCE: 1064
ggtgaagcgg tcgatgagga tcttgaagac aagagcgcta        40

<210> SEQ ID NO 1065
<211> LENGTH: 40
<212> TYPE: DNA
<213> ORGANISM: Artificial
<220> FEATURE:
<223> OTHER INFORMATION: DNA Primer

<400> SEQUENCE: 1065
tcctcatcga ccgcttcacc gaaacgtacg atgcgggcct        40

<210> SEQ ID NO 1066
<211> LENGTH: 40
<212> TYPE: DNA
<213> ORGANISM: Artificial
<220> FEATURE:
<223> OTHER INFORMATION: DNA Primer

<400> SEQUENCE: 1066
cgcaacagcg gcactccgct gtctgcggtt cacctgacgt        40

<210> SEQ ID NO 1067
<211> LENGTH: 40
<212> TYPE: DNA
<213> ORGANISM: Artificial
<220> FEATURE:
<223> OTHER INFORMATION: DNA Primer

<400> SEQUENCE: 1067
caagaacgag gcgtacgacc acgtcaggtg aaccgcagac        40

<210> SEQ ID NO 1068
<211> LENGTH: 40
<212> TYPE: DNA
<213> ORGANISM: Artificial
<220> FEATURE:
<223> OTHER INFORMATION: DNA Primer

<400> SEQUENCE: 1068
ggtcgtacgc ctcgttcttg acagccacgc tccgtcgggc                     40

<210> SEQ ID NO 1069
<211> LENGTH: 40
<212> TYPE: DNA
<213> ORGANISM: Artificial
<220> FEATURE:
<223> OTHER INFORMATION: DNA Primer

<400> SEQUENCE: 1069 acgaggggggg cacgatgcca gcccgacgga gcgtggctgt                    40

<210> SEQ ID NO 1070
<211> LENGTH: 40
<212> TYPE: DNA
<213> ORGANISM: Artificial
<220> FEATURE:
<223> OTHER INFORMATION: DNA Primer

<400> SEQUENCE: 1070
agcgccgccg tggctctgga cgccgtcaac tatcgcgata                     40

<210> SEQ ID NO 1071
<211> LENGTH: 40
<212> TYPE: DNA
<213> ORGANISM: Artificial
<220> FEATURE:
<223> OTHER INFORMATION: DNA Primer

<400> SEQUENCE: 1071
cccaatccac aggggggtggt tatcgcgata gttgacggcg                    40

<210> SEQ ID NO 1072
<211> LENGTH: 40
<212> TYPE: DNA
<213> ORGANISM: Artificial
<220> FEATURE:
<223> OTHER INFORMATION: DNA Primer

<400> SEQUENCE: 1072
ggtgaagcgg tcgatgagga tcttgaagac aagagcgcta                     40

<210> SEQ ID NO 1073
<211> LENGTH: 40
<212> TYPE: DNA
<213> ORGANISM: Artificial
<220> FEATURE:
<223> OTHER INFORMATION: DNA Primer

<400> SEQUENCE: 1073
tcctcatcga ccgcttcacc gaaacgtacg atgcgggcct                     40

<210> SEQ ID NO 1074
<211> LENGTH: 40
<212> TYPE: DNA
<213> ORGANISM: Artificial
<220> FEATURE:
<223> OTHER INFORMATION: DNA Primer

<400> SEQUENCE: 1074
agcgccgccg tggctctgga cgccgtcaac tatcgcgata                     40

<210> SEQ ID NO 1075
<211> LENGTH: 40

```
<212> TYPE: DNA
<213> ORGANISM: Artificial
<220> FEATURE:
<223> OTHER INFORMATION: DNA Primer

<400> SEQUENCE: 1075
cccaatccac aggggtggt tatcgcgata gttgacggcg                40

<210> SEQ ID NO 1076
<211> LENGTH: 40
<212> TYPE: DNA
<213> ORGANISM: Artificial
<220> FEATURE:
<223> OTHER INFORMATION: DNA Primer

<400> SEQUENCE: 1076
tgtcgacacg agcgcgtgga aggtgacggc cacggaggtt                40

<210> SEQ ID NO 1077
<211> LENGTH: 40
<212> TYPE: DNA
<213> ORGANISM: Artificial
<220> FEATURE:
<223> OTHER INFORMATION: DNA Primer

<400> SEQUENCE: 1077
tccacgcgct cgtgtcgaca cagtttggcc acacggtcaa                40

<210> SEQ ID NO 1078
<211> LENGTH: 40
<212> TYPE: DNA
<213> ORGANISM: Artificial
<220> FEATURE:
<223> OTHER INFORMATION: DNA Primer

<400> SEQUENCE: 1078
agcgccgccg tggctctgga cgccgtcaac tatcgcgata                40

<210> SEQ ID NO 1079
<211> LENGTH: 40
<212> TYPE: DNA
<213> ORGANISM: Artificial
<220> FEATURE:
<223> OTHER INFORMATION: DNA Primer

<400> SEQUENCE: 1079
cccaatccac aggggtggt tatcgcgata gttgacggcg                40

<210> SEQ ID NO 1080
<211> LENGTH: 40
<212> TYPE: DNA
<213> ORGANISM: Artificial
<220> FEATURE:
<223> OTHER INFORMATION: DNA Primer

<400> SEQUENCE: 1080
ggtcgtacgc ctcgttcttg acagccatgg cccgtcgggc                40

<210> SEQ ID NO 1081
<211> LENGTH: 40
<212> TYPE: DNA
<213> ORGANISM: Artificial
<220> FEATURE:
<223> OTHER INFORMATION: DNA Primer

<400> SEQUENCE: 1081
```
acgagggggg cacgatgcca gcccgacggg ccatggctgt           40

<210> SEQ ID NO 1082
<211> LENGTH: 40
<212> TYPE: DNA
<213> ORGANISM: Artificial
<220> FEATURE:
<223> OTHER INFORMATION: DNA Primer

<400> SEQUENCE: 1082
agcgccgccg tggctctgga cgccgtcaac tatcgcgata           40

<210> SEQ ID NO 1083
<211> LENGTH: 40
<212> TYPE: DNA
<213> ORGANISM: Artificial
<220> FEATURE:
<223> OTHER INFORMATION: DNA Primer

<400> SEQUENCE: 1083
cccaatccac aggggtggt tatcgcgata gttgacggcg            40

<210> SEQ ID NO 1084
<211> LENGTH: 40
<212> TYPE: DNA
<213> ORGANISM: Artificial
<220> FEATURE:
<223> OTHER INFORMATION: DNA Primer

<400> SEQUENCE: 1084
ggtgaagcgg tcgatgagga tcttgaagac aagagcgcta           40

<210> SEQ ID NO 1085
<211> LENGTH: 40
<212> TYPE: DNA
<213> ORGANISM: Artificial
<220> FEATURE:
<223> OTHER INFORMATION: DNA Primer

<400> SEQUENCE: 1085
tcctcatcga ccgcttcacc gaaacgtacg atgcgggcct           40

<210> SEQ ID NO 1086
<211> LENGTH: 40
<212> TYPE: DNA
<213> ORGANISM: Artificial
<220> FEATURE:
<223> OTHER INFORMATION: DNA Primer

<400> SEQUENCE: 1086
ggtcgtacgc ctcgttcttg acagccatgg cccgtcgggc           40

<210> SEQ ID NO 1087
<211> LENGTH: 40
<212> TYPE: DNA
<213> ORGANISM: Artificial
<220> FEATURE:
<223> OTHER INFORMATION: DNA Primer

<400> SEQUENCE: 1087
acgagggggg cacgatgcca gcccgacggg ccatggctgt           40

<210> SEQ ID NO 1088
<211> LENGTH: 40
<212> TYPE: DNA
<213> ORGANISM: Artificial
<220> FEATURE:
<223> OTHER INFORMATION: DNA Primer

<400> SEQUENCE: 1088
agcgccgccg tggctctgga cgccgtcaac tatcgcgata                              40

<210> SEQ ID NO 1089
<211> LENGTH: 40
<212> TYPE: DNA
<213> ORGANISM: Artificial
<220> FEATURE:
<223> OTHER INFORMATION: DNA Primer

<400> SEQUENCE: 1089
cccaatccac aggggtggt tatcgcgata gttgacggcg                               40

<210> SEQ ID NO 1090
<211> LENGTH: 40
<212> TYPE: DNA
<213> ORGANISM: Artificial
<220> FEATURE:
<223> OTHER INFORMATION: DNA Primer

<400> SEQUENCE: 1090
ggtgaagcgg tcgatgagga tcttgaagac aagagcgcta                              40

<210> SEQ ID NO 1091
<211> LENGTH: 40
<212> TYPE: DNA
<213> ORGANISM: Artificial
<220> FEATURE:
<223> OTHER INFORMATION: DNA Primer

<400> SEQUENCE: 1091
tcctcatcga ccgcttcacc gaaacgtacg atgcgggcct                              40

<210> SEQ ID NO 1092
<211> LENGTH: 40
<212> TYPE: DNA
<213> ORGANISM: Artificial
<220> FEATURE:
<223> OTHER INFORMATION: DNA Primer

<400> SEQUENCE: 1092
cgcaacagcg gcactccgct gtctgcggtt cacctgacgt                              40

<210> SEQ ID NO 1093
<211> LENGTH: 40
<212> TYPE: DNA
<213> ORGANISM: Artificial
<220> FEATURE:
<223> OTHER INFORMATION: DNA Primer

<400> SEQUENCE: 1093
caagaacgag gcgtacgacc acgtcaggtg aaccgcagac                              40

<210> SEQ ID NO 1094
<211> LENGTH: 40
<212> TYPE: DNA
<213> ORGANISM: Artificial
<220> FEATURE:
<223> OTHER INFORMATION: DNA Primer

<400> SEQUENCE: 1094
ggtcgtacgc ctcgttcttg acagccatgg cccgtcgggc                              40

<210> SEQ ID NO 1095
<211> LENGTH: 40
<212> TYPE: DNA
<213> ORGANISM: Artificial
<220> FEATURE:
<223> OTHER INFORMATION: DNA Primer

<400> SEQUENCE: 1095
acgagggggg cacgatgcca gcccgacggg ccatggctgt    40

<210> SEQ ID NO 1096
<211> LENGTH: 40
<212> TYPE: DNA
<213> ORGANISM: Artificial
<220> FEATURE:
<223> OTHER INFORMATION: DNA Primer

<400> SEQUENCE: 1096
agcgccgccg tggctctgga cgccgtcaac tatcgcgata    40

<210> SEQ ID NO 1097
<211> LENGTH: 40
<212> TYPE: DNA
<213> ORGANISM: Artificial
<220> FEATURE:
<223> OTHER INFORMATION: DNA Primer

<400> SEQUENCE: 1097
cccaatccac aggggggtggt tatcgcgata gttgacggcg    40

<210> SEQ ID NO 1098
<211> LENGTH: 599
<212> TYPE: PRT
<213> ORGANISM: Trichoderma reesei

<400> SEQUENCE: 1098

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Arg Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

```
His Arg Ala Leu Val Glu Gly Ala Thr Leu Ala Ala Thr Leu Gly Gln
            195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Val Asp Ser
    275                 280                 285

Phe Arg Ser Ile Tyr Gly Val Asn Lys Gly Ile Pro Ala Gly Ala Ala
290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Glu Gln Leu Tyr Asp Ala Ile
            325                 330                 335

Tyr Val Trp Lys Lys Thr Gly Ser Ile Thr Val Thr Ala Thr Ser Leu
                340                 345                 350

Ala Phe Phe Gln Glu Leu Val Pro Gly Val Thr Ala Gly Thr Tyr Ser
            355                 360                 365

Ser Ser Ser Ser Thr Phe Thr Asn Ile Ile Asn Ala Val Ser Thr Tyr
    370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
                435                 440                 445

Ile Pro Ser Thr Cys Ser Gly Ala Ser Val Val Gly Ser Tyr Ser Arg
    450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
                485                 490                 495

Val Ala Val Thr Phe His Glu Leu Val Ser Thr Gln Phe Gly Gln Thr
            500                 505                 510

Val Lys Val Ala Gly Asn Ala Ala Ala Leu Gly Asn Trp Ser Thr Ser
    515                 520                 525

Ala Ala Val Ala Leu Asp Ala Val Asn Tyr Arg Asp Asn His Pro Leu
530                 535                 540

Trp Ile Gly Thr Val Asn Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
            580                 585                 590

Lys Glu Asp Thr Trp Gln Ser
                595
```

<210> SEQ ID NO 1099
<211> LENGTH: 599
<212> TYPE: PRT
<213> ORGANISM: Trichoderma reesei

<400> SEQUENCE: 1099

```
Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Arg Pro Asp Tyr Tyr
        35                  40                  45

Tyr Met Trp Thr Arg Asp Ser Ala Leu Val Phe Lys Ile Leu Ile Asp
    50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Asp Ser
        275                 280                 285

Phe Arg Ser Ile Tyr Gly Val Asn Lys Gly Ile Pro Ala Gly Ala Ala
    290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
        355                 360                 365

Ser Ser Ser Ser Thr Phe Thr Asn Ile Ile Asn Ala Val Ser Thr Tyr
    370                 375                 380
```

```
                                            -continued

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
                420                 425                 430

Arg Ala Gly Ile Val Pro Pro Ser Trp Ala Asn Ser Ser Ala Ser Thr
                435                 440                 445

Ile Pro Ser Thr Cys Ser Gly Ala Ser Val Val Gly Ser Tyr Ser Arg
                450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
                485                 490                 495

Val Ala Val Thr Phe His Glu Leu Val Ser Thr Gln Phe Gly Gln Thr
                500                 505                 510

Val Lys Val Ala Gly Asn Ala Ala Ala Leu Gly Asn Trp Ser Thr Ser
                515                 520                 525

Ala Ala Val Ala Leu Asp Ala Val Asn Tyr Arg Asp Asn His Pro Leu
530                 535                 540

Trp Ile Gly Thr Val Asn Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
                580                 585                 590

Lys Glu Asp Thr Trp Gln Ser
                595
```

The invention claimed is:

1. An enzymatic composition comprising:
   a) at least one glucoamylase variant comprising the following amino acid substitutions:
      i. D44R and A539R; or
      ii. D44R, N61I and A539R,
   the positions corresponding to the respective position in SEQ ID NO: 2, wherein the glucoamylase variant has at least 90% sequence identity to the entire length of the amino acid sequence set forth in SEQ ID NO: 2;
   b) an alpha-amylase; and
   c) a pullulanase;
wherein said enzymatic composition comprises between 0.05-10 PU of pullulanase activity per GAU of said glucoamylase variant and between 0.1-20 SSU of alpha-amylase activity per GAU of said glucoamylase variant.

2. A method for producing a wort for brewing comprising forming a mash from a grist, and contacting the mash with an enzymatic composition according to claim 1.

3. The enzymatic composition of claim 1, wherein said composition comprises between 0.1-5 PU of pullulanase activity per GAU of said glucoamylase variant and between 1-15 SSU of alpha-amylase activity per GAU of said glucoamylase variant.

4. The enzymatic composition of claim 1, wherein said composition comprises between 0.2-2 PU of pullulanase activity per GAU of said glucoamylase variant and between 2-10 SSU of alpha-amylase activity per GAU of said glucoamylase variant.

5. The enzymatic composition of claim 1, wherein said glucoamylase variant has at least 95% sequence identity to SEQ ID NO: 2.

6. The enzymatic composition of claim 1, wherein said glucoamylase comprises SEQ ID NO: 1098 or SEQ ID NO: 1099.

7. The enzymatic composition of claim 1, wherein said glucoamylase variant exhibits a reduced ratio between isomaltose synthesis and starch hydrolysis activity (IS/SH ratio) as compared to the glucoamylase of SEQ ID NO: 2.

8. The enzymatic composition of claim 1, wherein said glucoamylase variant exhibits an enhanced real degree of fermentation as compared to the glucoamylase of SEQ ID NO: 2.

9. The method of claim 2, wherein said enzymatic composition comprises between 0.1-5 PU of pullulanase activity per GAU of said glucoamylase variant and between 1-15 SSU of alpha-amylase activity per GAU of said glucoamylase variant.

10. The method of claim 2, wherein said enzymatic composition comprises between 0.2-2 PU of pullulanase activity per GAU of said glucoamylase variant and between 2-10 SSU of alpha-amylase activity per GAU of said glucoamylase variant.

11. The method of claim 2, wherein said glucoamylase variant has at least 95% sequence identity to SEQ ID NO: 2.

12. The method of claim 2, wherein said glucoamylase comprises SEQ ID NO: 1098 or SEQ ID NO: 1099.

13. The method of claim 2, wherein said glucoamylase variant exhibits a reduced ratio between isomaltose synthesis and starch hydrolysis activity (IS/SH ratio) as compared to the glucoamylase of SEQ ID NO: 2.

14. The method of claim 2, wherein said glucoamylase variant exhibits an enhanced real degree of fermentation as compared to the glucoamylase of SEQ ID NO: 2.

* * * * *